US007897632B2

(12) United States Patent
Kimura et al.

(10) Patent No.: US 7,897,632 B2
(45) Date of Patent: Mar. 1, 2011

(54) MULTI-CYCLIC CINNAMIDE DERIVATIVES

(75) Inventors: Teiji Kimura, Tsukuba (JP); Noritaka Kitazawa, Tsukuba (JP); Toshihiko Kaneko, Tsukuba (JP); Nobuaki Sato, Tsukuba (JP); Koki Kawano, Tsukuba (JP); Koichi Ito, Tsukuba (JP); Eriko Doi, Tsukuba (JP); Mamoru Takaishi, Tsukuba (JP); Takeo Sasaki, Tsukuba (JP); Takehiko Miyagawa, Tsukuba (JP); Hiroaki Hagiwara, Tsukuba (JP); Takashi Doko, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/721,952

(22) Filed: Mar. 11, 2010

(65) Prior Publication Data
US 2010/0168095 A1    Jul. 1, 2010

Related U.S. Application Data

(62) Division of application No. 11/715,440, filed on Mar. 8, 2007, now Pat. No. 7,713,993.

(60) Provisional application No. 60/780,517, filed on Mar. 9, 2006, provisional application No. 60/861,702, filed on Nov. 30, 2006.

(30) Foreign Application Priority Data

Mar. 9, 2006    (JP)    ............... 2006-063562
Nov. 30, 2006   (JP)    ............... 2006-322728

(51) Int. Cl.
C07D 471/04    (2006.01)
C07D 498/04    (2006.01)
A61K 31/5383   (2006.01)
A61K 31/5025   (2006.01)

(52) U.S. Cl. .................. 514/397; 548/312.7; 548/311.1

(58) Field of Classification Search ............. 548/312.7, 548/311.1; 514/397
See application file for complete search history.

(56) References Cited

U.S. PATENT DOCUMENTS

| | | | |
|---|---|---|---|
| 3,470,167 A * | 9/1969 | Sarkar ......................... | 548/217 |
| 3,989,816 A | 11/1976 | Rajadhyaksha | |
| 4,910,200 A | 3/1990 | Curtze et al. | |
| 5,281,626 A | 1/1994 | Oinuma et al. | |
| 5,563,162 A | 10/1996 | Oku et al. | |
| 5,804,577 A | 9/1998 | Hebeisen et al. | |
| 5,985,856 A | 11/1999 | Stella et al. | |
| 6,235,728 B1 | 5/2001 | Golik et al. | |
| 6,306,870 B1 | 10/2001 | Bombrun | |
| 7,053,087 B1 | 5/2006 | Beatch et al. | |
| 7,138,414 B2 | 11/2006 | Schoenafinger et al. | |
| 7,300,936 B2 | 11/2007 | Parker et al. | |
| 7,314,940 B2 | 1/2008 | Graczyk et al. | |
| 7,618,960 B2 | 11/2009 | Kimura et al. | |
| 7,667,041 B2 | 2/2010 | Kimura et al. | |
| 2001/0051642 A1 | 12/2001 | Ahn et al. | |
| 2002/0128263 A1 | 9/2002 | Mutel et al. | |
| 2002/0183324 A1 | 12/2002 | Jacobson et al. | |
| 2003/0195201 A1 | 10/2003 | Bo et al. | |
| 2003/0208082 A1 | 11/2003 | Mutel et al. | |
| 2003/0225070 A1 | 12/2003 | Mutel et al. | |
| 2004/0006062 A1 | 1/2004 | Smallheer et al. | |
| 2004/0034096 A1 | 2/2004 | Jolidon et al. | |
| 2004/0038969 A1 | 2/2004 | Doherty et al. | |
| 2004/0063770 A1 | 4/2004 | Ahn et al. | |
| 2004/0087798 A1 | 5/2004 | Yamada | |
| 2004/0127494 A1 | 7/2004 | Parker et al. | |
| 2004/0127555 A1 | 7/2004 | Snow et al. | |
| 2004/0152743 A1 | 8/2004 | Schoenafinger et al. | |
| 2004/0192743 A1 | 9/2004 | Mjalli et al. | |
| 2004/0235864 A1 | 11/2004 | Graczyk et al. | |
| 2005/0070538 A1 | 3/2005 | Cheng et al. | |
| 2005/0131043 A1 | 6/2005 | Mutel et al. | |
| 2005/0187277 A1 | 8/2005 | Mjalli et al. | |

(Continued)

FOREIGN PATENT DOCUMENTS

DE    3541716 A1    5/1987

(Continued)

OTHER PUBLICATIONS

Eurasian Office Action issued Mar. 12, 2010, in Eurasian Application No. 200870336/28.

(Continued)

*Primary Examiner*—Kahsay T Habte
(74) *Attorney, Agent, or Firm*—Birch, Stewart, Kolasch & Birch, LLP

(57) ABSTRACT

The present invention provides a compound represented by the formula (I):

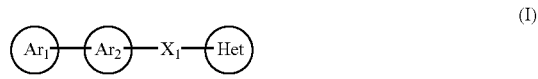

or a pharmacologically acceptable salt thereof, wherein Ar1 represents an imidazolyl group that may be substituted with a C1-6 alkyl group, or the like, Ar2 represents a phenyl group that may be substituted with a C1-6 alkoxy group, or the like, X1 represents a double bond or the like, and Het represents an imidazolyl group that may be substituted with a C1-6 alkyl group, or the like, which is effective as a therapeutic or prophylactic agent for a disease caused by Aβ.

11 Claims, No Drawings

U.S. PATENT DOCUMENTS

| | | |
|---|---|---|
| 2006/0004013 A1 | 1/2006 | Kimura et al. |
| 2007/0117798 A1 | 5/2007 | Kimura et al. |
| 2007/0117839 A1 | 5/2007 | Kimura et al. |
| 2007/0219181 A1 | 9/2007 | Kimura et al. |
| 2007/0249833 A1 | 10/2007 | Cheng et al. |
| 2008/0070902 A1 | 3/2008 | Kimura et al. |
| 2008/0085894 A1 | 4/2008 | Parker et al. |
| 2008/0096892 A1 | 4/2008 | Cheng et al. |
| 2008/0280948 A1 | 11/2008 | Baumann et al. |
| 2009/0048213 A1 | 2/2009 | Kimura et al. |
| 2009/0048448 A1 | 2/2009 | Kushida et al. |
| 2009/0203916 A1 | 8/2009 | Kushida et al. |
| 2009/0270623 A1 | 10/2009 | Shimomura et al. |

FOREIGN PATENT DOCUMENTS

| | | |
|---|---|---|
| EP | 0 219 756 A1 | 4/1987 |
| EP | 1 264 820 A1 | 12/2002 |
| EP | 0 973 768 B1 | 7/2003 |
| EP | 1 757 591 A1 | 2/2007 |
| EP | 1 808 432 A1 | 7/2007 |
| EP | 1 953 151 A1 | 8/2008 |
| EP | 1 953 158 A1 | 8/2008 |
| GE | P 2006 3920 B | 9/2006 |
| GE | P 2008 4571 B | 12/2008 |
| JP | 52-1035 A | 1/1977 |
| JP | 3-206042 A | 9/1991 |
| JP | 7-2780 A | 1/1995 |
| JP | 8-283219 A | 10/1996 |
| JP | 9-132578 A | 5/1997 |
| JP | 10-510512 A | 10/1998 |
| JP | 11-228548 A | 8/1999 |
| JP | 11-513686 A | 11/1999 |
| JP | 3176365 B2 | 4/2001 |
| JP | 2001-508767 A | 7/2001 |
| JP | 2001-527083 A | 12/2001 |
| JP | 2003-206280 A | 7/2003 |
| JP | 2004-520292 A | 7/2004 |
| JP | 2004-531519 A | 10/2004 |
| JP | 2004-536084 A | 12/2004 |
| JP | 2005-518371 A | 6/2005 |
| JP | 2005-526807 A | 9/2005 |
| JP | 2005-531596 A | 10/2005 |
| JP | 2005-533092 A | 11/2005 |
| JP | 2006-502247 A | 1/2006 |
| JP | 2006-518738 A | 8/2006 |
| JP | 2007-504282 A | 3/2007 |
| JP | 2007-523903 A | 8/2007 |
| RU | 2001126135 A | 7/2003 |
| WO | 91/12237 A1 | 8/1991 |
| WO | 95/21832 A1 | 8/1995 |
| WO | 96/10559 A1 | 4/1996 |
| WO | 97/14417 A1 | 4/1997 |
| WO | 97/43287 A1 | 11/1997 |
| WO | 98/03166 A1 | 1/1998 |
| WO | 98/09963 A1 | 3/1998 |
| WO | 98/24785 A1 | 6/1998 |
| WO | WO 99/55693 A2 | 11/1999 |
| WO | 00/07993 A1 | 2/2000 |
| WO | 00/50391 A1 | 8/2000 |
| WO | 00/51981 A1 | 9/2000 |
| WO | 01/68585 A1 | 9/2001 |
| WO | 01/81312 A2 | 11/2001 |
| WO | 03/027081 A2 | 4/2003 |
| WO | 03/053912 A1 | 7/2003 |
| WO | 03/074497 A1 | 9/2003 |
| WO | 03/082292 A1 | 10/2003 |
| WO | 03/101927 A1 | 12/2003 |
| WO | 2004/002478 A1 | 1/2004 |
| WO | 2004/007429 A1 | 1/2004 |
| WO | 2004/007455 A1 | 1/2004 |
| WO | 2004/041776 A2 | 5/2004 |
| WO | 2004/089868 A1 | 10/2004 |
| WO | 2005/020921 A2 | 3/2005 |
| WO | 2005/063754 A1 | 7/2005 |
| WO | 2005/072731 A1 | 8/2005 |
| WO | 2005/087767 A1 | 9/2005 |
| WO | 2005/115990 A1 | 12/2005 |
| WO | 2006/046575 A1 | 5/2006 |
| WO | 2006/112550 A2 | 10/2006 |
| WO | 2007/034282 A2 | 3/2007 |
| WO | 2007/060810 A1 | 5/2007 |
| WO | 2007/102580 A1 | 9/2007 |
| WO | 2008/013213 A1 | 1/2008 |
| WO | 2008/097538 A1 | 8/2008 |
| WO | 2008/137139 A1 | 11/2008 |
| WO | 2008/156580 A1 | 12/2008 |
| WO | 2009/020580 A1 | 2/2009 |

OTHER PUBLICATIONS

Ross et al., "Antiparasitic Nitroimidazoles.3.Synthesis of 2-(4-carboxystyryl)-5-nitro-1-vinylimidazole and Related Compounds", J. of Medicinal Chemistry, vol. 16, No. 4, 1973, pp. 347-352.

Assini et al., "Plasma levels of amyloid β-protein 42 are increased in women with mild cognitive impairment, Neurology," vol. 63, pp. 828-831, Sep. 2004.

Atwood et al., "Cerebrovascular requirement for sealant, anti-coagulant and remodeling molecules that allow for the maintenance of vascular integrity and blood supply," Brain Research Reviews, vol. 43, pp. 164-178, 2003.

Barelli et al., "Characterization of New Polyclonal Antibodies Specific for 40 and 42 Amino Acid-Long Amyloid β Peptides . . . ," Molecular Medicine, vol. 3, No. 10, pp. 695-707, Oct. 1997.

Barrachina et al., "Amyloid-β deposition in the cerebral cortex in Dementia with Lewy bodies is accompanied by a relative increase in AβPP mRNA isoforms containing the Kunitz protease inhibitor," Neurochemistry International, vol. 46, pp. 253-260, 2005.

Blass, "Brain Metabolism and Brain Disease: Is Metabolic Deficiency the Proximate Cause of Alzheimer Dementia?," Journal of Neuroscience Research, vol. 66, pp. 851-856, 2001.

Brocchini et al., "Preparation of piperazinedione-derivative inhibitors of plasminogen activator inhibitor," Database CA [Online] Chemical Abstracts Service, XP002574973, retrieved from STN, Database accession No. 1995:994197, Abstract, (1995).

Calhoun et al., "Neuronal overexpression of mutant amyloid precursor protein results in prominent deposition of cerebrovascular amyloid," Proceedings of the National Academy of Sciences, vol. 96, No. 24, pp. 14088-14093, Nov. 23, 1999.

Catalano et al., "The Role of Amyloid-Beta Derived Diffusible Ligands (ADDLs) in Alzheimer's Disease," Current Topics in Medicinal Chemistry, vol. 6, pp. 597-608, 2006.

Chen et al., "Preparation of cyclosporine A nanoparticles by evaporative precipitation into aqueous solution," International Journal of Pharmaceutics, vol. 242, pp. 3-14, 2002.

Comery et al., "Acute γ-Secretase Inhibition Improves Contextual Fear Conditioning in the Tg2576 Mouse Model of Alzheimer's Disease," The Journal of Neuroscience, vol. 25, No. 39, pp. 8898-8902, Sep. 28, 2005.

Comery et al., "Acute γ-secretase inhibition improves cognition in the TG2576 mouse model of Alzheimer's disease," Society for Neuroscience Annual Meeting, Abstracts, program No. 525.21, 2003.

Cras et al., "Presenile Alzheimer dementia characterized by amyloid angiopathy and large amyloid core type senile plaques in the APP 692Ala→4Gly mutation," Acta Neuropathol, vol. 96, pp. 253-260, 1998.

Crook et al., "A variant of Alzheimer's disease with spastic paraparesis and unusual plaques due to deletion of exon 9 of presenilin 1," Nature Medicine, vol. 4, No. 4, pp. 452-455, Apr. 1998.

Database Crossfire Beilstein, Beilstein Institut Zur Foerderung Der Chemischen Wissenschaften, Frankfurt Am Main, DE, XP002574972, Data accession No. 4617764, Abstract, 2010.

DeMeyer et al., "Platelet Phagocytosis and Processing of β-Amyloid Precursor Protein as a Mechanism of Macrophage Activiation in Atherosclerosis," Circulation Research, pp. 1197-1204, Jun. 14, 2002.

Dermaut et al., "Cerebral amyloid angiopathy is a pathogenic lesion in Alzheimer's disease due to a novel presenilin 1 mutation," Brain, vol. 124, pp. 2383-2392, 2001.

Evert et al., "Inflammatory Genes Are Upregulated in Expanded Atazin-3-Expressing Cell Lines and Spinocerebellar Ataxia Type 3 Brains," The Journal of Neuroscience, vol. 21, No. 15, pp. 5389-5396, Aug. 1, 2001.

Evin et al., "Alternative transcripts of presenilin-1 assoicated with frontotemporal dementia," Molecular Neuroscience, vol. 13, No. 5, pp. 719-723, Apr. 16, 2002.

Extended European Search Report, dated Apr. 24, 2009, for European Application No. 05805284.6.

Extended European Search Report, dated Apr. 7, 2010, for European Application No. 05743758.4.

Extended European Search Report, dated Aug. 4, 2010, for European Application No. 06822806.3.

Forman et al., "Differential Effects of the Swedish Mutant Amyloid Precursor Protein on β-Amyloid Accumulation and Secretion in Neurons and Nonneuronal Cells," The Journal of Biological Chemistry, vol. 272, No. 51, pp. 32247-32253, Dec. 19, 1997.

Gattaz et al., "Platelet phospholipase A2 activity in Alzheimer's disease and mild cognitive impairment," Journal of Neural Transmission, vol. 111, pp. 591-601, 2004.

Gehrmann et al., "Amyloid Precursor Protein (APP) Expression in Multiple Sclerosis Lesions," GLIA, vol. 15, pp. 141-151, 1995.

Georgian Search Report, dated May 27, 2009, for Georgian Application No. AP 2006 010709.

Georgian Search Report, dated Oct. 1, 2009, for Georgian Application No. AP 2007 010893.

Giasson et al., "Interactions of Amyloidogenic Proteins," NeuroMolecular Medicine, vol. 4, pp. 49-58, 2003.

Glenner et al., "Alzheimer's Disease: Initial Report Of The Purification And Characterization Of A Novel Cerebrovascular Amyloid Protein," vol. 120, No. 3, pp. 885-890, May 16, 1984.

Gong et al., "Alzheimer's disease-affected brain: Presense of oligomeric Aβ ligands (ADDLs) suggests a molecular basis for reversible memory loss," PNAS, vol. 100, No. 18, pp. 10417-10422, Sep. 2, 2003.

Gouras et al., "Short Communication Intraneuronal Aβ42 Accumulation in Human Brain," American Journal of Pathology, vol. 156, No. 1, pp. 15-20, Jan. 2000.

Guiroy et al., "Localization of amyloidogenic proteins and sulfated glycosaminoglycans in nontransmissible and transmissible cerebral amyloidoses," Acta Neuropathol, vol. 82, pp. 87-92, 1991.

Hamilton et al., "Alzheimer disease pathology in amyotrophic lateral sclerosis," Acta Neuropathol, vol. 107, pp. 515-522, Mar. 16, 2004.

Hayashi et al., "Evidence for presenilin-1 involvement in amyloid angiopathy in the Alzheimer's disease-affected brain," Brain Research, vol. 789, pp. 307-314, 1998.

Herzig et al., "Aβ is targeted to the vasculature in a mouse model of hereditary cerebral hemorrage with amyloidosis," Nature Neuroscience, vol. 7, No. 9, pp. 954-960, Sep. 2004 (Published online Aug. 15, 2004).

Hock et al., "Antibodies against β-Amyloid Slow Cognitive Decline in Alzheimer's Disease," Neuron, vol. 38, pp. 547-554, May 22, 2003.

International Search Report, dated Jan. 23, 2007, for PCT Application No. PCT/JP2006/322982.

International Search Report, dated Sep. 19, 2008, for PCT Application No. PCT/JP2008/053887.

Ito et al., "Demonstration of β amyloid protein-containing neurofibrillary tangles in parkinsonism-dementia complex on Guam," Neuropathology and Applied Neurobiology, vol. 17, pp. 365-373, 1991.

Japanese Official Action, dated Sep. 28, 2007, for Japanese Application No. 2006-513906.

Jarrett et al., "The Carboxy Terminus of the β Amyloid Protein Is Critical for the Seeding of Amyloid Formation: Implications for the Pathogenesis of Alzheimer's Disease," Biochemistry, vol. 32, No. 18, pp. 4693-4697, May 11, 1993.

Jin et al., "Intracellular Accumulation of Amyloidogenic Fragments of Amyloid-β Precursor Protein in Neurons with Niemann-Pick Type C Defects Is Associated with Endosomal Abnormalities," American Journal of Pathology, vol. 164, No. 3, pp. 975-985, Mar. 2004.

Kajbaf et al., "Rapid and efficient purification of cimetropium bromide and mifentidine drug metabolite mixtures derived from microsomal incubates for analysis by mass spectrometry," Journal of Chromatography, Biomedical Applications, vol. 575, pp. 75-85, 1992.

Kato et al., "New 5-HT3 (Serotonin-3) Receptor Antagonists. I. Synthesis and Structure-Activity Relationships of Pyrido[1,2-α]indoles," Chem. Pharm. Bulletin, vol. 42, No. 12, pp. 2546-2555, 1994.

Kirkitadze et al., "Paradigm Shifts in Alzheimer's Disease and Other Neurodegenerative Disorders: The Emerging Role of Oligomeric Assemblies," Journal of Neuroscience Research, vol. 69, pp. 567-577, Aug. 2, 2002.

Koistinaho et al., "β-Amyloid precursor protein transgenic mice that harbor diffuse Aβ deposits but do not form plaques show increased ischemic vulnerability: Role of inflammation," PNAS, vol. 99, No. 3, pp. 1610-1615, Feb. 5, 2002.

Lanz et al., "Studies of Aβ Pharmacodynamics in the Brain, Cerebrospinal Fluid, and Plasma in Young (Plaque-Free) Tg2576 Mice Using the γ-Secretase Inhibitor . . . ," The Journal of Pharmacology and Experimental Therapeutics, vol. 309, No. 60715/113272, pp. 49-55, 2004.

Laws et al., "Association between the presenilin-1 mutation Glu318Gly and complaints of memory impairment," Neurobiology of Aging, vol. 23, pp. 55-58, 2002.

Levy et al., "Mutation of the Alzheimer's Disease Amyloid Gene in Hereditary Cerebral Hemorrhage, Dutch Type," Science, vol. 248, pp. 1124-1126, 1990.

Lewis et al., "Catalytic Site-Directed γ-Secretase Complex Inhibitors Do Not Discriminate Pharmacologically between Notch S3 and β-APP Cleavages," Biochemistry, vol. 42, pp. 7580-7586, 2003.

Lieberman et al., "Pharmaceutical Dosage Forms," Tablets, Second Edition, Bioavailability in Tablet Technology, vol. 2, pp. 462-465, 1990.

Lipinski, "Solubility in Water and DMSO: Issues and Potential Solutions," Pharmaceutical Profiling in Drug Discovery for Lead Selection, American Association of Pharmaceutical Scientists, pp. 93-125, 2004.

Lowenson et al., "Protein Aging Extracellular Amyloid Formation and Intracellular Repair," TCM, vol. 4, No. 1, pp. 3-8, 1994.

Mann et al., "Deposition of amyloid (A4) protein within the brains of persons with dementing disorders other than Alzheimer's disease and Down's syndrome," Neuroscience Letters, vol. 109, pp. 68-75, 1990.

Marcus et al., "Stimulation of Rauscher Leukemia Virus DNA Polymerase DNA-directed DNA Synthesis by Cationic Trypanocides and Polyamines," Cancer Research, vol. 45, pp. 112-115, Jan. 1985.

Masliah et al., "β-Amyloid peptides enhance α-synuclein accumulation and neuronal deficits in a transgenic mouse model linking Alzheimer's disease and Parkinson's disease," PNAS, vol. 38, No. 21, pp. 12245-12250, Oct. 9, 2001.

Masters et al., "Amyloid plaque core protein in Alzheimer disease and Down syndrome," Proc. Natl. Acad. Sci. USA, vol. 82, pp. 4245-4249, Jun. 1985.

Matsubara-Tsutsui et al., "Molecular Evidence of Presenilin 1 Mutation in Familial Early Onset Dementia," American Journal of Medical Genetics (Neuropsychiatric Genetics), vol. 114, pp. 292-298, 2002.

Moran et al., "Age-related learning deficits in transgenic mice expressing the 751-amino acid isoform of human β-amyloid precursor protein," Proc. Natl. Acad. Sci. USA, vol. 92, pp. 5341-5345, Jun. 1995.

Morgan et al., "Aβ peptide vaccination prevents memory loss in an animal model of Alzheimer's disease," Nature, vol. 408, pp. 982-985, Dec. 2000.

O'Riordan et al., "Presenilin-1 mutation (E280G), spastic paraparesis, and cranial MRI white-matter abnormalities," Neurology, vol. 59, pp. 1108-1110, Oct. 2002.

Pakistani Official Action, dated Apr. 11, 2008, for Pakistani Application No. 1435/2006.

Peruvian Technical Report, dated Jan. 22, 2010, for Peruvian Application No. 001480-2006.

Primavera et al., "Brain Accumulation of Amyloid-β in Non-Alzheimer Neurodegeneration," Journal of Alzheimer's Disease 1, IOS Press, pp. 183-193, 1999.

Reynolds et al., "Myeloperoxidase Polymorphism Is Associated with Gender Specific Risk for Alzheimer's Disease," Experimental Neurology, vol. 155, pp. 31-41, 1999.

Rosso et al., "Coexistent Tau and Amyloid Pathology in Hereditary Frontotemporal Dementia with Tau Mutations," Annals New York Academy of Sciences, vol. 920, pp. 115-119, Dec. 2000.

Russian Official Action, dated Jul. 4, 2008, for Russian Application No. 2006146070/04(050338).

Russian Official Action, dated Jun. 1, 2009, for Russian Application No. 2008125426/04(030920).

Russian Official Action, dated Nov. 14, 2008, for Russian Application No. 2006146070/04(050338).

Sadowski et al., "Links Between the Pathology of Alzheimer's Disease and Vascular Dementia," Neurochemical Research, vol. 29, No. 6, pp. 1257-1266, Jun. 2004.

Sasaki et al., "Immunoreactivity of β-amyloid precursor protein in amyotrophic lateral sclerosis," Acta Neuropathol, vol. 97, pp. 463-468, 1999.

Scheuner et al., "Secreted amyloid β-protein similar to that in the senile plaques of Alzheimer's disease is increased in vivo by the presenilin 1 and 2 and APP mutations linked to familial Alzheimer's disease," Nature Medicine, vol. 2, No. 8, pp. 864-870, Aug. 1996.

Schmidt et al., "Amyloid plaques in Guam amyotrophic lateral sclerosis/parkinsonism-dementia complex contain species of Aβ similar to those found in the amyloid plaques of Alzheimer's disease and pathological aging," Acta Neuropathol, vol. 95, pp. 117-122, 1998.

Shearman et al., "L-685,458, as Aspartyl Protease Transition State Mimic, Is a Potent Inhibitor of Amyloid β-Protein Precursor γ-Secretase Activity," Biochemistry, vol. 39, pp. 8698-8704, Jul. 6, 2000.

Silverberg et al., "Alzheimer's disease, normal-pressure hydrocephalus, and senescent changes in CSF circulatory physiology: a hypothesis," The Lancet Neurology, vol. 2, pp. 506-511, Aug. 2003.

Singapore Written Opinion, dated Feb. 11, 2009, for Singapore Application No. 0803266-6.

Singapore Written Opinion, dated Feb. 24, 2009, for Singapore Application No. 0803192-4.

Singleton et al., "Pathology of early-onset Alzheimer's disease cases bearing the Thr113-114ins presenilin-1 mutation," Brain, vol. 123, pp. 2467-2474, 2000.

Smith et al., "Protein Accumulation in Traumatic Brain Injury," NeuroMolecular Medicine, vol. 4, pp. 59-72, 2003.

Smith et al., "Variable Phenotype of Alzheimer's Disease with Spastic Paraparesis," Ann Neurol, vol. 49, pp. 125-129, 2001.

Stark et al., "Search for novel leads for histamine H3-receptor antagonists: amine derivatives," Pharmazie, vol. 52, No. 6, pp. 419-423, 1997.

Tamaoka et al., "Increased amyloid β protein in the skin of patients with amyotrophic lateral sclerosis," J. Neurol, vol. 247, pp. 633-635, 2000.

Teller et al., "Presence of soluble amyloid β-peptide precedes amyloid plaque formation in Down's syndrome," Nature Medicine, vol. 2, No. 1, pp. 93-95, Jan. 1996.

Tietze et al., "Jikken Manual," Nankodo Co., Ltd., pp. 196-199, Jan. 15, 1995.

Tokada et al, "Plasma Levels of Amyloid β Proteins in Aβ1-40 and Aβ1-42(43) Are Elevated in Down's Syndrome," Ann Neurol, vol. 41, pp. 271-273, 1997.

Tolnay et al., "Low Amyloid (Aβ) plaque load and relative predominance of diffuse plaques distinguish argyrophilic grain disease from Alzheimer's disease," Neuropathology and Applied Neurobiology, vol. 25, pp. 295-305, 1999.

Turner et al., "Brain β-Amyloid Accumulation in Transgenic Mice Expressing Mutant Superoxide Dismutase 1," Neurochemical Research, vol. 29, No. 12, pp. 2281-2286, Dec. 2004.

US Notice of Allowance, dated Aug. 20, 2010, for U.S. Appl. No. 12/200,731.

US Notice of Allowance, dated Sep. 20, 2010, for U.S. Appl. No. 11/596,723.

US Office Action, dated Apr. 1, 2009, for U.S. Appl. No. 12/200,731.
US Office Action, dated Apr. 3, 2009, for U.S. Appl. No. 11/594,130.
US Office Action, dated Jan. 19, 2010, for U.S. Appl. No. 11/596,723.
US Office Action, dated Jul. 11, 2008, for U.S. Appl. No. 11/136,355.
uS Office Action, dated Jul. 16, 2009, for U.S. Appl. No. 11/715,440.
US Office Action, dated Jul. 30, 2009, for U.S. Appl. No. 12/200,731.
US Office Action, dated Mar. 9, 2010, for U.S. Appl. No. 12/200,731.
US Office Action, dated Sep. 16, 2008, for U.S. Appl. No. 11/594,150.

Van Duinen et al., "Hereditary cerebral hemorrage with amyloidosis in patients of Dutch orgin is related to Alzheimer disease," Proc. Natl. Acad. Sci. USA, Neurobiology, vol. 84, pp. 5991-5994, Aug. 1987.

Varnes et al., "Discovery of N-propylurea 3-benzylpiperidines as selective CC chemokine receptor-3 (CCR3) antagonists," Bioorganic & Medicinal Chemistry Letters, vol. 14, pp. 1645-1649, 2004.

Vaucher et al., "Object Recognition Memory and Cholinergic Parameters in Mice Expressing Human Presenilin 1 Transgenes," Experimental Neurology, vol. 175, pp. 398-405, 2002.

Weller et al., "Cerebral Amyloid Angiopathy: Accumulation of Aβ in Interstitial Fluid Drainage Pathways in Alzheimer's Disease," Annals of New York Academy of Sciences, pp. 110-117, 2000.

Weller et al., "Cerebrovascular Disease Is a Major Factor in the Failure of Elimination of Aβ from the Aging Human Brain," Annals New York Academy of Sciences, vol. 977, pp. 162-168, 2002.

Weller, "Pathology of Cerebrospinal Fluid and Interstitial Fluid of the CNS: Significance for Alzheimer Disease, Prion Disorders and Multiple Sclerosis," Journal of Neuropathology and Experimental Neurology, vol. 57, No. 10, pp. 885-894, Oct. 1998.

Wong et al., "Chronic Treatment with the γ-Secretase Inhibitor LY-411,575 Inhibits β-Amyloid Peptide Production and Alters Lymphopoiesis and Intestinal Cell Differentiation," The Journal of Biological Chemistry, vol. 279, No. 13, pp. 12876-12882, Mar. 26, 2004.

Yale et al., "Subsituted s-Triazoles and Related Compounds," Journal of Medicinal Chemistry, vol. 9, No. 1, pp. 42-46, 1966.

Yasuhara et al., "Accumulation of amyloid precursor protein in brain lesions of patients with Pick disease," Neuroscience Letters, vol. 171, pp. 63-66, 1994.

Yow et al., "A role for cerebrovascular disease in determining the pattern of β-amyloid deposition in Alzheimer's disease," Neuropathology and Applied Neurobiology, Abstracts, vol. 28, p. 149, 2002.

Zhang et al., "Increased Susceptibility to Ischemic Brain Damage in Transgenic Mice Overexpressing the Amyloid Precursor Protein," The Journal of Neuroscience, vol. 17, No. 20, pp. 7655-7661, Oct. 16, 1997.

European Search Report issued Oct. 13, 2010, in corresponding European Patent Application No. 07738023.6.

Ono et al., "Synthesis and biological evaluation of (E)-3-styrylpyridine derivatives as amyloid imaging agents for Alzheimer's disease," Nuclear Medicine and Biology, vol. 32 (2005) pp. 329-335.

Zhuang et al., "Structure-Activity Relationship of Imidazol[1,2-a]pyridines as Ligands for Detecting Beta-Amyloid Plaques in the Brain," J. Med. Chem., vol. 46 (2003) pp. 237-243.

Chinese Office Action, dated Nov. 16, 2010, for Chinese Application No. 200780008382.0.

Chinese Office Action, dated Sep. 27, 2010, for Chinese Application No. 200780018255.9.

Extended European Search Report, dated Dec. 7, 2010, for European Application No. 07743623.6.

* cited by examiner

MULTI-CYCLIC CINNAMIDE DERIVATIVES

CROSS-REFERENCE TO RELATED APPLICATIONS

The present application is a 37 CFR §1.53(b) divisional of U.S. application Ser. No. 11/715,440 filed Mar. 8, 2007 now U.S. Pat. No. 7,713,993, which claims priority on U.S. Provisional Application No. 60/780,517 filed on Mar. 9, 2006, U.S. Provisional Application No. 60/861,702 filed on Nov. 30, 2006, Japanese Patent Application No. 2006-063562 filed on Mar. 9, 2006, and from Japanese Patent Application No. 2006-322728 filed on Nov. 30, 2006, each of which is expressly incorporated herein by reference.

BACKGROUND OF THE INVENTION

1. Field of the Invention

The present invention relates to a pharmaceutical, more particularly to a multi-cyclic cinnamide derivative and an amyloid-β (hereinafter referred to as Aβ) production inhibitor comprising the derivative as an active ingredient, which are effective for treatment of a neurodegenerative disease caused by Aβ such as Alzheimer's disease or Down's syndrome.

2. Description of Related Art

Alzheimer's disease is a disease characterized by degeneration and loss of neurons as well as formation of senile plaques and neurofibrillary degeneration. Currently, Alzheimer's disease is treated only with symptomatic treatment using a symptom improving agent typified by an acetylcholinesterase inhibitor, and a fundamental remedy to inhibit progression of the disease has not yet been developed. It is necessary to develop a method for controlling the cause of the onset of pathology in order to create a fundamental remedy for Alzheimer's disease.

It is assumed that Aβ-proteins as metabolites of amyloid precursor proteins (hereinafter referred to as APP) are highly involved in degeneration and loss of neurons and onset of symptoms of dementia (see Klein W L, and seven others, Alzheimer's disease-affected brain: Presence of oligomeric Aβ ligands (ADDLs) suggests a molecular basis for reversible memory loss, Proceeding National Academy of Science USA 2003, Sep. 2; 100(18), p. 10417-10422; and Nitsch R M, and sixteen others, Antibodies against β-amyloid slow cognitive decline in Alzheimer's disease, Neuron, 2003, May 22; 38, p. 547-554, for example). An Aβ-protein has, as main components, Aβ40 consisting of 40 amino acids and Aβ42 in which the number of amino acids is increased by two at the C-terminal. The Aβ40 and Aβ42 are known to have high aggregability (see Jarrett J T, and two others, The carboxy terminus of the β amyloid protein is critical for the seeding of amyloid formation: Implications for the pathogenesis of Alzheimer's disease, Biochemistry, 1993, 32(18), p. 4693-4697, for example) and to be main components of senile plaques (see Jarrett J T, and two others, The carboxy terminus of the β amyloid protein is critical for the seeding of amyloid formation: Implications for the pathogenesis of Alzheimer's disease, Biochemistry, 1993, 32(18), p. 4693-4697; Glenner G G, and one other, Alzheimer's disease: initial report of the purification and characterization of a novel cerebrovascular amyloid protein, Biochemical and biophysical research communications, 1984, May 16, 120(3), p. 885-890; and Masters C L, and five others, Amyloid plaque core protein in Alzheimer disease and Down syndrome, Proceeding National Academy of Science USA, 1985, June, 82(12), p. 4245-4249, for example). Further, it is known that the Aβ40 and Aβ42 are increased by mutation in APP and presenilin genes which is observed in familial Alzheimer's disease (see Gouras G K, and eleven others, Intraneuronal Aβ42 accumulation in human brain, American Journal of Pathology, 2000, January, 156(1), p. 15-20; Scheuner D, and twenty others, Secreted amyloid β-protein similar to that in the senile plaques of Alzheimer's disease is increased in vivo by the presenilin 1 and 2 and APP mutations linked to familial Alzheimer's disease, Nature Medicine, 1996, August, 2(8), p. 864-870; and Forman M S, and four others, Differential effects of the swedish mutant amyloid precursor protein on β-amyloid accumulation and secretion in neurons and nonneuronal cells, The Journal of Biological Chemistry, 1997, Dec. 19, 272(51), p. 32247-32253, for example). Accordingly, a compound that reduces production of Aβ40 and Aβ42 has been expected as a progression inhibitor or prophylactic agent for Alzheimer's disease.

Aβ is produced by cleaving APP by β-secretase and subsequently by γ-secretase. For this reason, attempts have been made to create γ-secretase and β-secretase inhibitors in order to reduce Aβ production. Many of these secretase inhibitors already known are, for example, peptides and peptide mimetics such as L-685,458 (see Shearman M S, and nine others, L-685,458, an Aspartyl Protease Transition State Mimic, Is a Potent Inhibitor of Amyloid β-Protein Precursor γ-Secretase Activity, Biochemistry, 2000, Aug. 1, 39(30), p. 8698-8704, for example) and LY-411575 (see Shearman M S, and six others, Catalytic Site-Directed γ-Secretase Complex Inhibitors Do Not Discriminate Pharmacologically between Notch S3 and β-APP Cleavages, Biochemistry, 2003, Jun. 24, 42(24), p. 7580-7586; Lanz T A, and three others, Studies of Aβ pharmacodynamics in the brain, cerebrospinal fluid, and plasma in young (plaque-free) Tg2576 mice using the γ-secretase inhibitor N2-[(2S)-2-(3,5-difluorophenyl)-2-hydroxyethanoyl]-N1-[(7S)-5-methyl-6-oxo-6,7-dihydro-5H-dibenzo[b,d]azepin-7-yl]-L-alaninamide (LY-411575), The journal of pharmacology and experimental therapeutics, 2004, April, 309(1), p. 49-55; and Wong G T, and twelve others, Chronic treatment with the γ-secretase inhibitor LY-411,575 inhibits β-amyloid peptide production and alters lymphopoiesis and intestinal cell differentiation, The journal of biological chemistry, 2004, Mar. 26, 279(13), p. 12876-12882, for example). WO 2004/110350 describes, as nonpeptide compounds, a group of compounds having multiple aromatic rings, but the compounds of formula (VI) at page 17 of WO 2004/110350 are different from the compounds of the present invention in that they are limited only to a group of compounds having 2-aminothiazolyl group as the main structure.

BRIEF SUMMARY OF THE INVENTION

As described above, a compound that inhibits production of Aβ40 and Aβ42 from APP has been expected as a therapeutic or prophylactic agent for a disease caused by Aβ which is typified by Alzheimer's disease. However, a nonpeptidic compound having high efficacy which inhibits production of Aβ40 and Aβ42 has not yet been known. Accordingly, there is a need for a novel low-molecular-weight compound that inhibits production of Aβ40 and Aβ42.

As a result of extensive studies, the present inventors have found a nonpeptidic cinnamide compound that inhibits production of Aβ40 and Aβ42 from APP for the first time, and thus found a prophylactic or therapeutic agent for a disease caused by Aβ which is typified by Alzheimer's disease. This finding has led to the accomplishment of the present invention.

Specifically, the present invention relates to the following 1) to 42):

1) A compound represented by the formula (I):

[Formula 1]

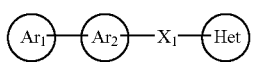
(I)

or a pharmacologically acceptable salt thereof, wherein

Ar$_1$ represents an imidazolyl group, triazolyl group or tetrazolyl group that may be substituted with 1 to 3 substituents selected from Substituent Group A1, Ar$_2$ represents a phenyl group, pyrimidinyl group or pyridinyl group that may be substituted with 1 to 3 substituents selected from Substituent Group A2, X$_1$ represents —C≡C— or —CR$^3$=CR$^4$— or —CR$^5$= (wherein R$^3$, R$^4$ and R$^5$ are the same or different and each represent a substituent selected from Substituent Group A3), and Het is monovalent or divalent and represents (1) a 5-membered aromatic heterocyclic group, (2) a 5-membered aromatic heterocyclic group condensed with a 6- to 14-membered non-aromatic hydrocarbon ring group or (3) a 5-membered aromatic heterocyclic ring group condensed with a 5- to 14-membered non-aromatic heterocyclic group, which may be substituted with 1 to 3 substituents selected from the following Substituent Group A4.

Substituent Group A1: (1) a hydrogen atom, (2) a halogen atom, (3) a cyano group, (4) a nitro group, (5) a C3-8 cycloalkyl group, (6) a C2-6 alkenyl group, (7) a C2-6 alkynyl group, (8) a C1-6 alkoxy group, (9) a C3-8 cycloalkoxy group, (10) a formyl group, (11) a C1-6 alkylcarbonyl group and (12) a C1-6 alkyl group (wherein the C1-6 alkyl group may be substituted with 1 to 3 substituents selected from the group consisting of a halogen atom, a hydroxyl group, a cyano group, a C1-6 alkoxy group, a C3-8 cycloalkyl group and a C1-6 alkylcarbonyl group);

Substituent Group A2: (1) a hydrogen atom, (2) a halogen atom, (3) a hydroxyl group, (4) a cyano group, (5) a C1-6 alkoxy group (wherein the C1-6 alkoxy group may be substituted with 1 to 3 substituents selected from the group consisting of a halogen atom, a cyano group, a C1-6 alkyl group, a C2-6 alkenyl group, a C2-6 alkynyl group and a C3-8 cycloalkyl group), (6) a C3-8 cycloalkoxy group, (7) a C2-6 alkenyloxy group and (8) a C2-6 alkynyloxy group;

Substituent Group A3: (1) a hydrogen atom, (2) a halogen atom, (3) a 6- to 14-membered aromatic hydrocarbon ring group that may be substituted with 1 to 3 substituents selected from Substituent Group A5, (4) a 5- to 14-membered aromatic heterocyclic group that may be substituted with 1 to 3 substituents selected from Substituent Group A5, (5) a C1-6 alkyl group (wherein the C1-6 alkyl group may be substituted with 1 to 3 substituents selected from the group consisting of a formyl group, a halogen atom, a hydroxyl group, a hydroxyl group having a protecting group, a cyano group, a C2-6 alkenyl group, a C2-6 alkynyl group, a C3-8 cycloalkyl group, a C1-6 alkoxy group, a C1-6 alkylthio group, a C1-6 alkylsulfinyl group, a C1-6 alkylsulfonyl group, a C1-6 alkylcarbonyl group, an amino group (wherein the amino group may be substituted with 1 to 2 of a C1-6 alkyl group optionally having 1 to 3 halogen atoms), a 6- to 14-membered aromatic hydrocarbon ring group that may be substituted with 1 to 3 substituents selected from Substituent Group A5, a 5- to 14-membered aromatic heterocyclic group that may be substituted with 1 to 3 substituents selected from Substituent Group A5, a 6- to 14-membered non-aromatic hydrocarbon ring group that may be substituted with 1 to 3 substituents selected from Substituent Group A5, a 5- to 14-membered non-aromatic heterocyclic group that may be substituted with 1 to 3 substituents selected from Substituent Group A5, and —X-A (wherein X represents an imino group, —O— or —S—, and A represents a 6- to 14-membered aromatic hydrocarbon ring group or 5- to 14-membered aromatic heterocyclic group that may be substituted with 1 to 3 substituents selected from Substituent Group A5)) and (6) a C1-6 alkoxy group that may be substituted with 1 to 3 halogen atoms;

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group that may be substituted with 1 to 3 substituents selected from Substituent Group A5, (8) a C2-6 alkynyl group that may be substituted with 1 to 3 substituents selected from Substituent Group A5, (9) a C3-8 cycloalkoxy group, (10) a C3-8 cycloalkylthio group, (11) a formyl group, (12) a C1-6 alkylcarbonyl group that may be substituted with 1 to 3 substituents selected from Substituent Group A5, (13) a C1-6 alkylthio group that may be substituted with 1 to 3 substituents selected from Substituent Group A5, (14) a C1-6 alkylsulfinyl group that may be substituted with 1 to 3 substituents selected from Substituent Group A5, (15) a C1-6 alkylsulfonyl group that may be substituted with 1 to 3 substituents selected from Substituent Group A5, (16) a hydroxyimino group, (17) a C1-6 alkoxyimino group, (18) a C1-6 alkyl group that may be substituted with 1 to 3 substituents selected from Substituent Group A5, (19) a C1-6 alkoxy group that may be substituted with 1 to 3 substituents selected from Substituent Group A5, (20) an amino group that may be substituted with 1 or 2 substituents selected from Substituent Group A5, (21) a carbamoyl group that may be substituted with 1 or 2 substituents selected from Substituent Group A5, (22) a 6- to 14-membered aromatic hydrocarbon ring group that may be substituted with 1 to 3 substituents selected from Substituent Group A5, (23) a 5- to 14-membered aromatic heterocyclic group that may be substituted with 1 to 3 substituents selected from Substituent Group A5, (24) a 6- to 14-membered non-aromatic hydrocarbon ring group that may be substituted with 1 to 3 substituents selected from Substituent Group A5, (25) a 5- to 14-membered non-aromatic heterocyclic group that may be substituted with 1 to 3 substituents selected from Substituent Group A5, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S—, and A represents a 6- to 14-membered aromatic hydrocarbon ring group or 5- to 14-membered aromatic heterocyclic group that may be substituted with 1 to 3 substituents selected from Substituent Group A6), (31) —CO-A (wherein A is as defined above), (32)=CH-A (wherein A is as defined above), (33) a carboxyl group and (34) a C1-6 alkoxycarbonyl group;

Substituent Group A5: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group (wherein the C1-6 alkyl group may be substituted with 1 to 3 substituents selected from Substituent Group A6, a 6- to 14-membered aromatic hydrocarbon ring group (wherein the 6- to 14-membered aromatic hydrocarbon ring group may be substituted with 1 to 3 substituents selected from Substituent Group A6) and a 5- to 14-membered aromatic heterocyclic group (wherein the 5- to 14-membered aromatic heterocyclic group may be substituted with 1 to 3 substituents selected from Substituent Group A6)), (19) a C1-6 alkoxy group (wherein the C1-6 alkoxy group may be substituted with 1 to 3 substituents selected from Substituent Group A6, a 6- to 14-membered aromatic hydrocarbon ring group (wherein the 6- to 14-membered aromatic hydrocarbon ring group may be substituted with 1 to 3 substituents selected from Substituent Group A6) and a 5- to 14-membered aromatic heterocyclic group (wherein the 5- to 14-membered aromatic heterocyclic group may be substituted with 1 to 3 substituents selected from Substituent Group A6)), (20) an amino group that may be substituted with 1 or 2 C1-6 alkyl groups, (21) a carbamoyl group that may be substituted with 1 or 2 C1-6 alkyl groups, (22) a 6- to 14-membered aromatic hydrocarbon ring group that may be substituted with 1 to 3 substituents selected from Substituent Group A6, (23) a 5- to 14-membered aromatic heterocyclic group that may be substituted with 1 to 3 substituents selected from Substituent Group A6, (24) a 6- to 14-membered non-aromatic hydrocarbon ring group that may be substituted with 1 to 3 substituents selected from Substituent Group A6, (25) a 5- to 14-membered non-aromatic heterocyclic group that may be substituted with 1 to 3 substituents selected from Substituent Group A6, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S—, and A represents a 6- to 14-membered aromatic hydrocarbon ring group or 5- to 14-membered aromatic heterocyclic group that may be substituted with 1 to 3 substituents selected from Substituent Group A6), (31) —CO-A (wherein A is as defined above), (32) =CH-A (wherein A is as defined above), (33) a carboxyl group and (34) a C1-6 alkoxycarbonyl group;

Substituent Group A6:

(1) a hydrogen atom, (2) a halogen atom, (3) a hydroxyl group, (4) a cyano group, (5) an amino group that may be substituted with 1 or 2 C1-6 alkyl groups, (6) a C1-6 alkyl group (wherein the C1-6 alkyl group may be substituted with 1 to 3 substituents selected from the group consisting of a halogen atom, a hydroxyl group, a cyano group, an amino group that may be substituted with 1 or 2 C1-6 alkyl groups) and (7) a C1-6 alkoxy group (wherein the C1-6 alkoxy group may be substituted with 1 to 3 substituents selected from the group consisting of a halogen atom, a hydroxyl group, a cyano group, an amino group that may be substituted with 1 or 2 C1-6 alkyl groups).

2) The compound or pharmacologically acceptable salt thereof according to 1), wherein $Ar_1$ is an imidazolyl group or a triazolyl group;

3) The compound or pharmacologically acceptable salt thereof according to 1) or 2), wherein $Ar_1$ is an imidazolyl group;

4) The compound or pharmacologically acceptable salt thereof according to any one of 1) to 3), wherein $Ar_1$ is substituted with 1 or 2 substituents selected from the group consisting of (1) a hydrogen atom, (2) a halogen atom, (3) a C3-8 cycloalkyl group, (4) a C2-6 alkenyl group, (5) a C2-6 alkynyl group and (6) a C1-6 alkyl group (wherein the C1-6 alkyl group may be substituted with 1 to 3 halogen atoms);

5) The compound or pharmacologically acceptable salt thereof according to any one of 1) to 4), wherein $Ar_1$ is substituted with a C1-6 alkyl group;

6) The compound or pharmacologically acceptable salt thereof according to any one of 1) to 5), wherein $Ar_2$ is a pyrimidinyl group, a pyridinyl group or a phenyl group;

7) The compound or pharmacologically acceptable salt thereof according to any one of 1) to 5), wherein $Ar_2$ is a pyridinyl group;

8) The compound or pharmacologically acceptable salt thereof according to any one of 1) to 5), wherein $Ar_2$ is a phenyl group;

9) The compound or pharmacologically acceptable salt thereof according to any one of 1) and 6) to 8), wherein $Ar_2$ is substituted with 1 to 3 substituents selected from the group consisting of (1) a hydrogen atom, (2) a halogen atom, (3) a hydroxyl group, (4) a cyano group, (6) a C1-6 alkoxy group (wherein the C1-6 alkoxy group may be substituted with 1 to 3 substituents selected from the group consisting of a C1-6 alkyl group, a C2-6 alkenyl group, a C2-6 alkynyl group and a C3-8 cycloalkyl group), (7) a C2-6 alkenyloxy group and (8) a C2-6 alkynyloxy group;

10) The compound or pharmacologically acceptable salt thereof according to any one of 1) and 6) to 9), wherein $Ar_2$ is substituted with 1 to 3 substituents selected from the group consisting of (1) a hydrogen atom, (2) a halogen atom, (3) a cyano group and (4) a C1-6 alkoxy group;

11) The compound or pharmacologically acceptable salt thereof according to any one of 1) and 6) to 10), wherein $Ar_2$ is substituted with a C1-6 alkoxy group;

12) The compound or pharmacologically acceptable salt thereof according to 1), wherein $X_1$ is —C≡C— or —CR$^3$=CR$^4$— (wherein R$^3$ and R$^4$ are the same or different and each represent a substituent selected from Substituent Group A3);

13) The compound or pharmacologically acceptable salt thereof according to 1), wherein $X_1$ is —CR$^5$= (wherein R$^5$ represents a substituent selected from Substituent Group A3);

14) The compound or pharmacologically acceptable salt thereof according to 1) or 12), wherein $X_1$ is —C≡C—;

15) The compound or pharmacologically acceptable salt thereof according to 1) or 12), wherein $X_1$ represents —CR$^3$=CR$^4$— (wherein R$^3$ and R$^4$ are the same or different and each represent a substituent selected from Substituent Group A3);

16) The compound or pharmacologically acceptable salt thereof according to 1), 12) or 15), wherein $X_1$ represents —CR$^3$=CR$^4$— (wherein R$^3$ and R$^4$ represent (1) a hydrogen atom, (2) a C1-6 alkyl group, (3) an alkoxy group, or (4) a halogen atom);

17) The compound or pharmacologically acceptable salt thereof according to 1), 12), 15) or 16), wherein $X_1$ is —CH=CH—;

18) The compound or pharmacologically acceptable salt thereof according to 1), wherein Het is monovalent and is (1) a 5-membered aromatic heterocyclic group, (2) a 5-membered aromatic heterocyclic group condensed with a 6- to 14-membered non-aromatic hydrocarbon ring group or (3) a 5-membered aromatic heterocyclic group condensed with a 5- to 14-membered non-aromatic heterocyclic group, which may be substituted with 1 to 3 substituents selected from Substituent Group A4 as described in 1);

19) The compound or pharmacologically acceptable salt thereof according to 1), wherein Het is divalent and is (1) a 5-membered aromatic heterocyclic group, (2) a 5-membered aromatic heterocyclic group condensed with a 5- to 14-membered non-aromatic hydrocarbon ring group or (3) a 5-membered aromatic heterocyclic group condensed with a 6- to 14-membered non-aromatic heterocyclic group, which may be substituted with 1 to 3 substituents selected from Substituent Group A4 described in 1);

20) The compound or pharmacologically acceptable salt thereof according to 1) or 18), wherein Het is a 5-membered aromatic heterocyclic group represented by the formula:

[Formula 2]

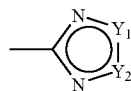

wherein $Y_1$ and $Y_2$ are the same or different and each represent a methine group or a carbon atom, an imino group or a nitrogen atom, an oxygen atom, or a sulfur atom;

21) The compound or pharmacologically acceptable salt thereof according to any one of 1) and 18) to 20), wherein Het is an imidazolyl group, a tetrazolyl group or a triazolyl group;

22) The compound or pharmacologically acceptable salt thereof according to 1), 18), 20) or 21), wherein Het is an imidazolyl group or triazolyl group that may be substituted with 1 or 2 substituents selected from the group consisting of (1) a C1-6 alkyl group (wherein the C1-6 alkyl group may be substituted with 1 to 3 substituents selected from the group consisting of a halogen atom, a hydroxyl group, a C1-6 alkyl group, a C1-6 alkoxy group, a 6- to 14-membered aromatic hydrocarbon ring group (wherein the 6- to 14-membered aromatic hydrocarbon ring group may be substituted with 1 to 3 substituents selected from the group consisting of a halogen atom, a hydroxyl group, a C1-6 alkyl group (wherein the C1-6 alkyl group may be substituted with 1 to 3 substituents selected from the group consisting of a halogen atom, a hydroxyl group and a C1-6 alkoxy group) and a C1-6 alkoxy group (wherein the C1-6 alkoxy group may be substituted with 1 to 3 substituents selected from the group consisting of a halogen atom, a hydroxyl group and a C1-6 alkoxy group)) and a 5- to 14-membered aromatic heterocyclic group (wherein the 5- to 14-membered aromatic heterocyclic group may be substituted with 1 to 3 substituents selected from the group consisting of a halogen atom, a hydroxyl group, a C1-6 alkyl group (wherein the C1-6 alkyl group may be substituted with 1 to 3 substituents selected from the group consisting of a halogen atom, a hydroxyl group and a C1-6 alkoxy group) and a C1-6 alkoxy group (wherein the C1-6 alkoxy group may be substituted with 1 to 3 substituents selected from the group consisting of a halogen atom, a hydroxyl group and a C1-6 alkoxy group))), (2) a C1-6 alkoxycarbonyl group, (3) a carboxyl group, (4) a carbamoyl group that may be substituted with a C1-6 alkyl group optionally having 1 to 3 halogen atoms, (5) a 6- to 14-membered aromatic hydrocarbon ring group (wherein the 6- to 14-membered aromatic hydrocarbon ring group may be substituted with 1 to 3 substituents selected from the group consisting of a halogen atom, a hydroxyl group, a C1-6 alkyl group (wherein the C1-6 alkyl group may be substituted with 1 to 3 substituents selected from the group consisting of a halogen atom, a hydroxyl group and a C1-6 alkoxy group) and a C1-6 alkoxy group (wherein the C1-6 alkoxy group may be substituted with 1 to 3 substituents selected from the group consisting of a halogen atom, a hydroxyl group and a C1-6 alkoxy group)) and (6) a 5- to 14-membered aromatic heterocyclic group (wherein the 5- to 14-membered aromatic heterocyclic group may be substituted with 1 to 3 substituents selected from the group consisting of a halogen atom, a hydroxyl group, a C1-6 alkyl group (wherein the C1-6 alkyl group may be substituted with 1 to 3 substituents selected from the group consisting of a halogen atom, a hydroxyl group and a C1-6 alkoxy group), a C1-6 alkoxy group (wherein the C1-6 alkoxy group may be substituted with 1 to 3 substituents selected from the group consisting of a halogen atom, a hydroxyl group and a C1-6 alkoxy group) and a halogen atom), or a group represented by the formula:

[Formula 3]

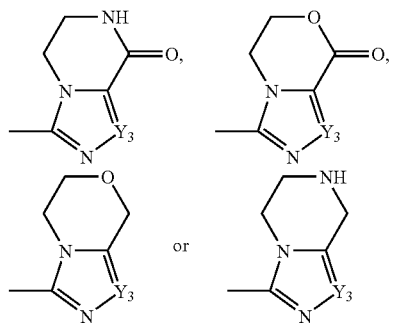

which may be substituted with 1 to 3 substituents selected from Substituent Group A4, wherein $Y_3$ represents a methine group or a nitrogen atom;

23) The compound or pharmacologically acceptable salt thereof according to 1), 19) or 21), wherein Het is represented by the formula:

[Formula 4]

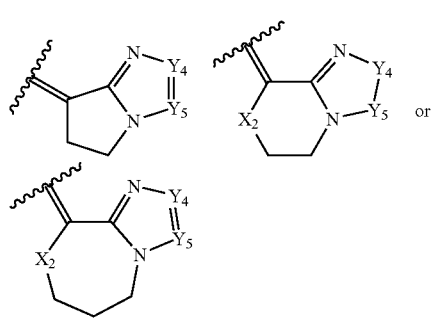

which may be substituted with 1 to 3 substituents selected from Substituent Group A4, wherein $X_2$ represents an oxygen atom or a methylene group, and $Y_4$ and $Y_5$ are the same or different and each represent a methine group or a nitrogen atom;

24) The compound or pharmacologically acceptable salt thereof according to 1), 19), 21) or 23), wherein Het is represented by the formula:

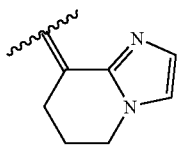

[Formula 5]

which may be substituted with 1 to 3 substituents selected from Substituent Group A4;

25) The compound or pharmacologically acceptable salt thereof according to 1), 19), 21) or 23), wherein Het is a group represented by the formula:

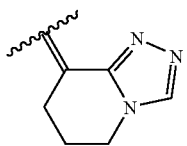

[Formula 6]

which may be substituted with 1 to 3 substituents selected from Substituent Group A4;

26) The compound or pharmacologically acceptable salt thereof according to 1), 19), 21) or 23), wherein Het is represented by the formula:

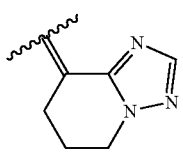

[Formula 7]

which may be substituted with 1 to 3 substituents selected from Substituent Group A4.

27) The compound or pharmacologically acceptable salt thereof according to 1), 18), 20) or 21), wherein Het is a group represented by the formula:

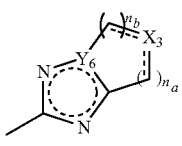

[Formula 8]

which may be substituted with 1 to 3 substituents selected from Substituent Group A4, wherein ⚌ represents a single bond or a double bond, $X_3$ represents a methine group or methylene group, an imino group, an oxygen atom, a sulfur atom or —$SO_2$—, which may be substituted with a substituent selected from Substituent Group A4, $Y_6$ represents a carbon atom or a nitrogen atom, and $n_a$ and $n_b$ independently represent an integer of 0 to 3.

28) The compound or pharmacologically acceptable salt thereof according to 27), wherein Het is a group represented by the formula:

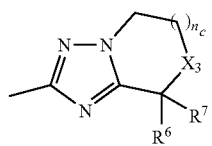

[Formula 9]

which may be substituted with 1 to 3 substituents selected from Substituent Group A4, wherein $R^6$ and $R^7$ are the same or different and each represent a substituent selected from Substituent Group A4, $X_3$ is as defined in claim 27, and $n_c$ represents an integer of 0 to 2.

29) The compound or pharmacologically acceptable salt thereof according to 28), wherein $R^6$ represents a 6- to 14-membered aromatic hydrocarbon ring group or 5- to 14-membered aromatic heterocyclic group that may be substituted with 1 to 3 substituents selected from Substituent Group A4.

30) The compound or pharmacologically acceptable salt thereof according to 28), wherein $R^6$ represents a phenyl group, pyridinyl group or naphthyl group that may be substituted with 1 to 3 substituents selected from the group consisting of (1) a hydrogen atom, (2) a halogen atom, (3) a cyano group, (4) a C1-6 alkoxy group (wherein the C1-6 alkoxy group group may be substituted with 1 to 3 halogen atoms), (5) a C1-6 alkyl group (wherein the C1-6 alkyl group may be substituted with 1 to 3 halogen atoms, and (6) a amino group that may be substituted with 1 to 2 C1-6 alkyl groups.

31) The compound or pharmacologically acceptable salt thereof according to 28), wherein $R^7$ represents a substituent group selected from the group consisting of (1) a hydrogen atom, (2) a halogen atom, (3) a hydroxyl group, (4) a cyano group, (5) a C1-6 alkyl group, (6) a C2-6 alkenyl group, (7) a C2-6 alkynyl group, (8) a C1-6 alkoxy group and (9) an amino group that may be substituted with 1 to 2 C1-6 alkyl groups.

32) The compound or pharmacologically acceptable salt thereof according to 1), 18) or 21), wherein Het is a group represented by the formula:

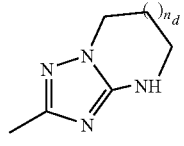

[Formula 10]

which may be substituted with 1 to 3 substituents selected from Substituent Group A4, wherein $n_d$ represents an integer of 0 to 3.

33) The compound or pharmacologically acceptable salt thereof according to 1), 18), 20) or 21), wherein Het is a group represented by the formula:

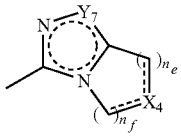

[Formula 11]

which may be substituted with 1 to 3 substituents selected from Substituent Group A4, wherein ═ represents a single bond or a double bond, $X_4$ represents a methine group or methylene group, an imino group, an oxygen atom, a sulfur atom or —$SO_2$—, which may be ═substituted with a substituent selected from Substituent Group A4, $Y_7$ represents a carbon atom or a nitrogen atom, and $n_e$ and $n_f$ independently represent an integer of 0 to 3.

34) The compound or pharmacologically acceptable salt thereof according to 33), wherein Het is a group represented by the formula:

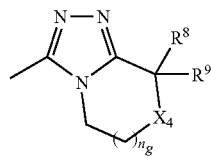

[Formula 12]

which may be substituted with 1 to 3 substituents selected from Substituent Group A4, wherein $R^8$ and $R^9$ are the same or different and each represent a substituent selected from Substituent Group A4, $X_4$ is the same as defined in claim 33, and $n_g$ represent an integer of 0 to 2.

35) The compound or pharmacologically acceptable salt thereof according to 34), wherein $R^8$ represents a 6- to 14-membered aromatic hydrocarbon ring group or 5- to 14-membered aromatic heterocyclic group that may be substituted with 1 to 3 substituents selected from Substituent Group A4.

36) The compound or pharmacologically acceptable salt thereof according to 34), wherein $R^8$ represents a phenyl group, pyridinyl group or naphthyl group that may be substituted with 1 to 3 substituents selected from the group consisting of (1) a hydrogen atom, (2) a halogen atom, (3) a cyano group, (4) a C1-6 alkoxy group (wherein the C1-6 alkoxy group group may be substituted with 1 to 3 halogen atoms), (5) a C1-6 alkyl group (wherein the C1-6 alkyl group may be substituted with 1 to 3 halogen atoms, and (6) a amino group that may be substituted with 1 to 2 C1-6 alkyl groups.

37) The compound or pharmacologically acceptable salt thereof according to 34), wherein $R^9$ represents a substituent group selected from the group consisting of (1) a hydrogen atom, (2) a halogen atom, (3) a hydroxyl group, (4) a cyano group, (5) a C1-6 alkyl group, (6) a C2-6 alkenyl group, (7) a C2-6 alkynyl group, (8) a C1-6 alkoxy group, and (9) an amino group that may be substituted with 1 or 2 C1-6 alkyl groups.

38) The compound or pharmacologically acceptable salt thereof according to any one of 1) to 37)), wherein $Ar_1$ is bonded to $Ar_2$ through an atom in the imidazolyl group, triazolyl group or tetrazolyl group represented by $Ar_1$ which may be substituted with substituents and an atom in the phenyl group, pyrimidinyl group or pyridinyl group represented by $Ar_2$ which may be substituted with substituents; $Ar_2$ is bonded to $X_1$ through an atom in the phenyl group, pyrimidinyl group or pyridinyl group represented by $Ar_2$ which may be substituted with substituents; and monovalent Het is bonded to —C≡C— or —$CR^3$=$CR^4$— of $X_1$, or divalent Het is bonded to —$CR^5$= of $X_1$.

39) The compound or pharmacologically acceptable salt thereof according to 1), wherein the compound is selected from the following group:

1) 4-(4-fluorophenyl)-2-{(E)-2-[3-methoxy-4-(4-methyl-1H-imidazol-1-yl)phenyl]vinyl}-1H-imidazole,
2) 4-(4-fluorophenyl)-2-{(E)-2-[3-methoxy-4-(4-methyl-1H-imidazol-1-yl)phenyl]vinyl}-1-methyl-1H-imidazole,
3) 2-{(E)-2-[3-methoxy-4-(4-methyl-1H-imidazol-1-yl)phenyl]vinyl}-1-methyl-5-phenyl-1H-imidazole,
4) 2-{(E)-2-[3-methoxy-4-(4-methyl-1H-imidazol-1-yl)phenyl]vinyl}-4-phenyl-1H-imidazole,
5) 2-{(E)-2-[3-methoxy-4-(4-methyl-1H-imidazol-1-yl)phenyl]vinyl}-1-methyl-4-phenyl-1H-imidazole,
6) methyl 5-(4-fluorophenyl)-2-{(E)-2-[3-methoxy-4-(4-methyl-1H-imidazol-1-yl)phenyl]vinyl}-1H-imidazole-4-carboxylate,
7) 5-(4-fluorophenyl)-2-{(E)-2-[3-methoxy-4-(4-methyl-1H-imidazol-1-yl)phenyl]vinyl}-(1H-imidazol-4-yl)methanol,
8) 5-(4-fluorophenyl)-2-{(E)-2-[3-methoxy-4-(4-methyl-1H-imidazol-1-yl)phenyl]vinyl}-1H-imidazole-4-carboxylic acid,
9) 5-(4-fluorophenyl)-2-{(E)-2-[3-methoxy-4-(4-methyl-1H-imidazol-1-yl)phenyl]vinyl}-1H-imidazole-4-carboxylic acid (2-chloroethyl)amide,
10) 1-(4-fluorophenyl)-3-{(E)-2-[3-methoxy-4-(4-methyl-1H-imidazol-1-yl)phenyl]vinyl}-6,7-dihydro-5H-imidazo[1,5-a]pyrazin-8-one,
11) 1-(4-fluorophenyl)-3-{(E)-2-[3-methoxy-4-(4-methyl-1H-imidazol-1-yl)phenyl]vinyl}-7-methyl-6,7-dihydro-5H-imidazo[1,5-a]pyrazin-8-one,
12) 1-(4-fluorophenyl)-3-{(E)-2-[3-methoxy-4-(4-methyl-1H-imidazol-1-yl)phenyl]vinyl}-5,6-dihydroimidazo[5,1-c][1,4]oxazin-8-one,
13) 1-(4-fluorophenyl)-3-{(E)-2-[3-methoxy-4-(4-methyl-1H-imidazol-1-yl)phenyl]vinyl}-5,6-dihydro-8H-imidazo[5,1-c][1,4]oxazine,
14) 2-{4-(4-fluorophenyl)-5-methoxymethyl-2-{(E)-2-[3-methoxy-4-(4-methyl-1H-imidazol-1-yl)phenyl]vinyl}imidazol-1-yl}ethanol,
15) 1-(4-fluorophenyl)-3-{(E)-2-[3-methoxy-4-(4-methyl-1H-imidazol-1-yl)phenyl]vinyl}-7-methyl-5,6,7,8-tetrahydroimidazo[1,5-a]pyrazine,
16) 3-(3-fluorophenyl)-5-{(E)-2-[3-methoxy-4-(4-methyl-1H-imidazol-1-yl)phenyl]vinyl}-4H-[1,2,4]triazole,
17) 3-(4-fluorobenzyl)-5-{(E)-2-[3-methoxy-4-(4-methyl-1H-imidazol-1-yl)phenyl]vinyl}-4H-[1,2,4]triazole,
18) 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine,
19) 2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine,
20) 2-(4-fluorophenyl)-8-{1-[3-methoxy-4-(4-methyl-1H-imidazol-1-yl)phenyl]-(E)-methylidene}-5,6,7,8-tetrahydro[1,2,4]triazolo[1,5-a]pyridine, 21) methyl 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylate,
22) methyl 2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-3-carboxylate,
23) {3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridin-2-yl}methanol,
24) {2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridin-3-yl}methanol,
25) 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylic acid,
26) 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylic acid dimethylamide,
27) 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylic acid methylamide,
28) 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylic acid amide,
29) 1-(4-fluorobenzyl)-2-{(E)-2-[3-methoxy-4-(4-methyl-1H-imidazol-1-yl)phenyl]vinyl}-4,5-dimethyl-1H-imidazole,
30) 8-{1-[3-methoxy-4-(4-methyl-1H-imidazol-1-yl)phenyl]-(E)-methylidene}-2-pyridin-4-yl-5,6,7,8-tetrahydroimidazo[1,2-a]pyridine,
31) 3-[1-(4-fluorophenyl)ethyl]-5-{(E)-2-[3-methoxy-4-(4-methyl-1H-imidazol-1-yl)phenyl]vinyl}-4H-[1,2,4]triazole,
32) 3-[2-(4-fluorophenyl)ethyl]-5-{(E)-2-[3-methoxy-4-(4-methyl-1H-imidazol-1-yl)phenyl]vinyl}-4H-[1,2,4]triazole,
33) 4-(4-fluorobenzyl)-2-{(E)-2-[3-methoxy-4-(4-methyl-1H-imidazol-1-yl)phenyl]vinyl}-1H-imidazole,
34) 5-(4-fluorobenzyl)-3-{(E)-2-[3-methoxy-4-(4-methyl-1H-imidazol-1-yl)phenyl]vinyl}-1-methyl-1H-[1,2,4]triazole,
35) 3-(4-fluorobenzyl)-5-{(E)-2-[3-methoxy-4-(4-methyl-1H-imidazol-1-yl)phenyl]vinyl}-1-methyl-1H-[1,2,4]triazole,
36) (+)-3-[1-(4-fluorophenyl)ethyl]-5-{(E)-2-[3-methoxy-4-(4-methyl-1H-imidazol-1-yl)phenyl]vinyl}-4H-[1,2,4]triazole,
37) (−)-3-[1-(4-fluorophenyl)ethyl]-5-{(E)-2-[3-methoxy-4-(4-methyl-1H-imidazol-1-yl)phenyl]vinyl}-4H-[1,2,4]triazole,
38) 5-[1-(4-fluorophenyl)ethyl]-3-{(E)-2-[3-methoxy-4-(4-methyl-1H-imidazol-1-yl)phenyl]vinyl}-1-methyl-1H-[1,2,4]triazole,
39) 3-[1-(4-fluorophenyl)ethyl]-5-{(E)-2-[3-methoxy-4-(4-methyl-1H-imidazol-1-yl)phenyl]vinyl}-1-methyl-1H-[1,2,4]triazole,
40) 5-[1-(4-fluorophenyl)ethyl]-3-{(E)-2-[3-methoxy-4-(4-methyl-1H-imidazol-1-yl)phenyl]vinyl}-1-methyl-1H-[1,2,4]triazole,
41) 3-[1-(4-fluorophenyl)ethyl]-5-{(E)-2-[3-methoxy-4-(4-methyl-1H-imidazol-1-yl)phenyl]vinyl}-1-methyl-1H-[1,2,4]triazole,
42) (+)-3-[1-(4-fluorophenyl)ethyl]-5-{(E)-2-[3-methoxy-4-(4-methyl-1H-imidazol-1-yl)phenyl]vinyl}-4-methyl-4H-[1,2,4]triazole,
43) (−)-3-[1-(4-fluorophenyl)ethyl]-5-{(E)-2-[3-methoxy-4-(4-methyl-1H-imidazol-1-yl)phenyl]vinyl}-4-methyl-4H-[1,2,4]triazole,
44) 3-{(E)-2-[3-methoxy-4-(4-methyl-1H-imidazol-1-yl)phenyl]vinyl}-5-(1-phenylethyl)-4H-[1,2,4]triazole,
45) 3-{(E)-2-[3-methoxy-4-(4-methyl-1H-imidazol-1-yl)phenyl]vinyl}-1-methyl-5-(1-phenylethyl)-1H-[1,2,4]triazole,
46) 5-{(E)-2-[3-methoxy-4-(4-methyl-1H-imidazol-1-yl)phenyl]vinyl}-1-methyl-3-(1-phenylethyl)-1H-[1,2,4]triazole,
47) 3-(4-fluorophenyl)-5-{(E)-2-[3-methoxy-4-(4-methyl-1H-imidazol-1-yl)phenyl]vinyl}-4H-[1,2,4]triazole,
48) 5-(4-fluorophenyl)-2-{(E)-2-[3-methoxy-4-(4-methyl-1H-imidazol-1-yl)phenyl]vinyl}-4-methyl-1H-imidazole,
49) 3-{(E)-2-[3-methoxy-4-(4-methyl-1H-imidazol-1-yl)phenyl]vinyl}-5-(1-methyl-1-phenylethyl)-4H-[1,2,4]triazole,
50) 3-{(E)-2-[3-methoxy-4-(4-methyl-1H-imidazol-1-yl)phenyl]vinyl}-1-phenyl-5,6,7,8-tetrahydroimidazo[1,5-a]pyridine,
51) (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
52) (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
53) (+)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
54) (−)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
55) (+)-5-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
56) (−)-5-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
57) (+)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
58) (−)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
59) (+)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine,
60) (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine,
61) (+)-2-{(E)-2-[3-fluoro-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
62) (−)-2-{(E)-2-[3-fluoro-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
63) (+)-2-{(E)-2-[3-methoxy-4-(4-methyl-1H-imidazol-1-yl)phenyl]vinyl}-8-(2,4,6-trifluorophenyl)-5,6,7,8-tetrahydro[1,2,4]triazolo[1,5-a]pyridine,
64) (−)-2-{(E)-2-[3-methoxy-4-(4-methyl-1H-imidazol-1-yl)phenyl]vinyl}-8-(2,4,6-trifluorophenyl)-5,6,7,8-tetrahydro[1,2,4]triazolo[1,5-a]pyridine,
65) 7-(4-fluorophenyl)-2-{(E)-2-[3-methoxy-4-(4-methyl-1H-imidazol-1-yl)phenyl]vinyl}-6,7-dihydro-5H-pyrrolo[1,2-b][1,2,4]triazol-7-ol, 66) (−)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol,
67) (+)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol,
68) (+)-2-{(E)-2-[2-fluoro-5-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
69) (−)-2-{(E)-2-[2-fluoro-5-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
70) (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol,
71) (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol,
72) (+)-8-fluoro-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
73) (−)-8-fluoro-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
74) 8-(4-fluorophenyl)-2-{(E)-2-[3-methoxy-4-(4-methyl-1H-imidazol-1-yl)phenyl]vinyl}-5,6-dihydro[1,2,4]triazolo[1,5-a]pyridine,
75) (−)-2-{(E)-2-[3-methoxy-4-(4-methyl-1H-imidazol-1-yl)phenyl]vinyl}-8-(4-methoxyphenyl)-5,6,7,8-tetrahydro-[1,2,4]triazolo[1,5-a]pyridine,
76) (+)-2-{(E)-2-[3-methoxy-4-(4-methyl-1H-imidazol-1-yl)phenyl]vinyl}-8-(4-methoxyphenyl)-5,6,7,8-tetrahydro-[1,2,4]triazolo[1,5-a]pyridine,
77) (−)-2-{(E)-2-[3-methoxy-4-(4-methyl-1H-imidazol-1-yl)phenyl]vinyl}-8-(3,4,5-trifluorophenyl)-5,6-dihydro-8H-[1,2,4]triazolo[5,1-c][1,4]oxazine,
78) (+)-2-{(E)-2-[3-methoxy-4-(4-methyl-1H-imidazol-1-yl)phenyl]vinyl}-8-(3,4,5-trifluorophenyl)-5,6-dihydro-8H-[1,2,4]triazolo[5,1-c][1,4]oxazine,
79) (−)-8-(4-fluorophenyl)-2-{(E)-2-[3-methoxy-4-(4-methyl-1H-imidazol-1-yl)phenyl]vinyl}-8-methyl-5,6,7,8-tetrahydro-[1,2,4]triazolo[1,5-a]pyridine,
80) (+)-8-(4-fluorophenyl)-2-{(E)-2-[3-methoxy-4-(4-methyl-1H-imidazol-1-yl)phenyl]vinyl}-8-methyl-5,6,7,8-tetrahydro-[1,2,4]triazolo[1,5-a]pyridine,
81) 2-(4-fluorobenzyl)-8-{1-[3-methoxy-4-(4-methyl-1H-imidazol-1-yl)phenyl]-(E)-methylidene}-5,6,7,8-tetrahydro[1,2,4]triazolo[1,5-a]pyridine and
82) 3-(4-fluorobenzyl)-8-{1-[3-methoxy-4-(4-methyl-1H-imidazol-1-yl)phenyl]-(E)-methylidene}-5,6,7,8-tetrahydro[1,2,4]triazolo[4,3-a]pyridine,
83) 3-{(E)-2-[3-methoxy-4-(4-methyl-1H-imidazol-1-yl)phenyl]vinyl}-5-((S)-1-phenylethyl)-4H-[1,2,4]triazole,
84) 3-{(E)-2-[3-methoxy-4-(4-methyl-1H-imidazol-1-yl)phenyl]vinyl}-5-((R)-1-phenylethyl)-4H-[1,2,4]triazole,
85) (−)-8-(4-fluorophenyl)-8-methoxy-2-{(E)-2-[3-methoxy-4-(4-methyl-1H-imidazol-1-yl)phenyl]vinyl}-5,6,7,8-tetrahydro[1,2,4]triazolo[1,5-a]pyridine,
86) (+)-8-(4-fluorophenyl)-8-methoxy-2-{(E)-2-[3-methoxy-4-(4-methyl-1H-imidazol-1-yl)phenyl]vinyl}-5,6,7,8-tetrahydro[1,2,4]triazolo[1,5-a]pyridine,
87) (−)-8-methoxy-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
88) (+)-8-methoxy-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
89) (−)-8-methoxy-2-{(E)-2-[3-methoxy-4-(4-methyl-1H-imidazol-1-yl)phenyl]vinyl}-8-(4-methoxyphenyl)-5,6,7,8-tetrahydro[1,2,4]triazolo[1,5-a]pyridine,
90) (+)-8-methoxy-2-{(E)-2-[3-methoxy-4-(4-methyl-1H-imidazol-1-yl)phenyl]vinyl}-8-(4-methoxyphenyl)-5,6,7,8-tetrahydro[1,2,4]triazolo[1,5-a]pyridine,
91) 5-[methoxy-(4-methoxyphenyl)methyl]-3-{(E)-2-[3-methoxy-4-(4-methyl-1H-imidazol-1-yl)phenyl]vinyl}-1H-[1,2,4]triazole,
92) 7-(4-fluorophenyl)-7-methoxy-2-{(E)-2-[3-methoxy-4-(4-methyl-1H-imidazol-1-yl)phenyl]vinyl}-6,7-dihydro-5H-pyrrolo[1,2-b][1,2,4]triazole,
93) 4-(4-fluorophenyl)-2-{(E)-2-[3-methoxy-4-(4-methyl-1H-imidazol-1-yl)phenyl]vinyl}-1-(tetrahydrofuran-2-ylmethyl)-1H-imidazole,
94) 4-{5-{(E)-2-[3-methoxy-4-(4-methyl-1H-imidazol-1-yl)phenyl]vinyl}-4H-[1,2,4]triazol-3-yl}-4-(3,4,5-trifluorophenyl)butan-1-ol,
95) (+)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine-8-carbonitrile,
96) (−)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine-8-carbonitrile,
97) (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile,
98) (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile,
99) (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ylamine,
100) (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ylamine,
101) 2-{(E)-2-[3-fluoro-4-(4-methyl-1H-imidazol-1-yl)phenyl]vinyl}-8-(4-fluorophenyl)-5,6,7,8-tetrahydro[1,2,4]triazolo[1,5-a]pyridine,
102) (−)-2-{(E)-2-[3-fluoro-4-(4-methyl-1H-imidazol-1-yl)phenyl]vinyl}-8-(4-fluorophenyl)-5,6,7,8-tetrahydro[1,2,4]triazolo[1,5-a]pyridin-8-ol,
103) (+)-2-{(E)-2-[3-fluoro-4-(4-methyl-1H-imidazol-1-yl)phenyl]vinyl}-8-(4-fluorophenyl)-5,6,7,8-tetrahydro[1,2,4]triazolo[1,5-a]pyridin-8-ol,
104) 2-{(E)-2-[2-fluoro-5-methoxy-4-(4-methyl-1H-imidazol-1-yl)phenyl]vinyl}-8-(4-fluorophenyl)-5,6,7,8-tetrahydro[1,2,4]triazolo[1,5-a]pyridine,
105) (+)-2-{(E)-2-[2-fluoro-5-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol,
106) (−)-2-{(E)-2-[2-fluoro-5-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol,
107) 2-{(Z)-1-fluoro-2-[3-methoxy-4-(4-methyl-1H-imidazol-1-yl)phenyl]vinyl}-8-(4-fluorophenyl)-5,6,7,8-tetrahydro[1,2,4]triazolo[1,5-a]pyridine,
108) (−)-2-{(Z)-1-fluoro-2-[3-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol,
109) (+)-2-{(Z)-1-fluoro-2-[3-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol,
110) (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridin-8-ol, 111) (+)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridin-8-ol, 112) (+)-2-{(E)-2-[3-methoxy-4-(4-methyl-1H-imidazol-1-yl)phenyl]vinyl}-7-(3,4,5-trifluorophenyl)-6,7-dihydro-5H-pyrrolo[1,2-b][1,2,4]triazole, 113) (−)-2-{(E)-2-[3-methoxy-4-(4-methyl-1H-imidazol-1-yl)phenyl]vinyl}-7-(3,4,5-trifluorophenyl)-6,7-dihydro-5H-pyrrolo[1,2-b][1,2,4]triazole, 114) (+)-2-{(E)-2-[3-methoxy-4-(4-methyl-1H-imidazol-1-yl)phenyl]vinyl}-7-(3,4,5-trifluorophenyl)-6,7-dihydro-5H-pyrrolo[1,2-b][1,2,4]triazol-7-ol, 115) (−)-2-{(E)-2-[3-methoxy-4-(4-methyl-1H-imidazol-1-yl)phenyl]vinyl}-7-(3,4,5-trifluorophenyl)-6,7-dihydro-5H-pyrrolo[1,2-b][1,2,4]triazol-7-ol, 116) (+)-8-(3,4-difluorophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine, 117) (−)-8-(3,4-difluorophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine, 118) 4-(4-fluorophenyl)-2-{(E)-2-[3-methoxy-4-(4-methyl-1H-imidazol-1-yl)phenyl]vinyl}-4,5,6,7-tetrahydro[1,2,4]triazolo[1,5-a]pyrimidine, 119) (+)-3-{(E)-2-[3-methoxy-4-(4-methyl-1H-imidazol-1-yl)phenyl]vinyl}-5-phenyl-5,6,7,8-tetrahydro[1,2,4]triazolo[4,3-a]pyridine, 120) (−)-3-{(E)-2-[3-methoxy-4-(4-methyl-1H-imidazol-1-yl)phenyl]vinyl}-5-phenyl-5,6,7,8-tetrahydro[1,2,4]triazolo[4,3-a]pyridine, 121) 4-chloro-2-{(E)-2-[3-methoxy-4-(4-methyl-1H-imidazol-1-yl)phenyl]vinyl}-1H-imidazole, 122) 4-(4-methoxyphenyl)-2-{(E)-2-[3-methoxy-4-(4-methyl-1H-imidazol-1-yl)phenyl]vinyl}-1H-imidazole, 123) 4-(3-methoxyphenyl)-2-{(E)-2-[3-methoxy-4-(4-methyl-1H-imidazol-1-yl)phenyl]vinyl}-1H-imidazole, 124) 4-(2-methoxyphenyl)-2-{(E)-2-[3-methoxy-4-(4-methyl-1H-imidazol-1-yl)phenyl]vinyl}-1H-imidazole, 125) 4-(4-chlorophenyl)-2-{(E)-2-[3-methoxy-4-(4-methyl-1H-imidazol-1-yl)phenyl]vinyl}-1H-imidazole, 126) 4-(4-biphenyl)-2-{(E)-2-[3-methoxy-4-(4-methyl-1H-imidazol-1-yl)phenyl]vinyl}-1H-imidazole, 127) 4-(4-propyl)-2-{(E)-2-[3-methoxy-4-(4-methyl-1H-imidazol-1-yl)phenyl]vinyl}-1H-imidazole, 128) (+)-2-{(E)-2-[3-methoxy-4-(4-methyl-1H-imidazol-1-yl)phenyl]vinyl}-8-(4-trifluoromethoxyphenyl)-5,6,7,8-tetrahydro[1,2,4]triazolo[1,5-a]pyridine, 129) (−)-2-{(E)-2-[3-methoxy-4-(4-methyl-1H-imidazol-1-yl)phenyl]vinyl}-8-(4-trifluoromethoxyphenyl)-5,6,7,8-tetrahydro[1,2,4]triazolo[1,5-a]pyridine, 130) (+)-2-{(E)-2-[3-methoxy-4-(4-methyl-1H-imidazol-1-yl)phenyl]vinyl}-8-naphthalen-1-yl-5,6,7,8-tetrahydro[1,2,4]triazolo[1,5-a]pyridine, 131) (−)-2-{(E)-2-[3-methoxy-4-(4-methyl-1H-imidazol-1-yl)phenyl]vinyl}-8-naphthalen-1-yl-5,6,7,8-tetrahydro[1,2,4]triazolo[1,5-a]pyridine, 132) (+)-2-{(E)-2-[3-methoxy-4-(4-methyl-1H-imidazol-1-yl)phenyl]vinyl}-8-(4-methoxyphenyl)-5,6,7,8-tetrahydro[1,2,4]triazolo[1,5-a]pyridin-8-ol, 133) (−)-2-{(E)-2-[3-methoxy-4-(4-methyl-1H-imidazol-1-yl)phenyl]vinyl}-8-(4-methoxyphenyl)-5,6,7,8-tetrahydro[1,2,4]triazolo[1,5-a]pyridin-8-ol, 134) (+)-2-{(E)-2-[3-methoxy-4-(4-methyl-1H-imidazol-1-yl)phenyl]vinyl}-8-(4-trifluoromethoxyphenyl)-5,6-dihydro-8H-[1,2,4]triazolo[5,1-c][1,4]oxazine, 135) (−)-2-{(E)-2-[3-methoxy-4-(4-methyl-1H-imidazol-1-yl)phenyl]vinyl}-8-(4-trifluoromethoxyphenyl)-5,6-dihydro-8H-[1,2,4]triazolo[5,1-c][1,4]oxazine, 136) (−)-2-{(E)-2-[3-methoxy-4-(4-methyl-1H-imidazol-1-yl)phenyl]vinyl}-8-naphthalen-1-yl-5,6,7,8-tetrahydro[1,2,4]triazolo[1,5-a]pyridin-8-ol, 137) (+)-2-{(E)-2-[3-methoxy-4-(4-methyl-1H-imidazol-1-yl)phenyl]vinyl}-8-naphthalen-1-yl-5,6,7,8-tetrahydro[1,2,4]triazolo[1,5-a]pyridin-8-ol, 138) (−)-2-{(E)-2-[3-methoxy-4-(4-methyl-1H-imidazol-1-yl)phenyl]vinyl}-8-p-tolyl-5,6-dihydro-8H-[1,2,4]triazolo[5,1-c][1,4]oxazine, 139) (+)-2-{(E)-2-[3-methoxy-4-(4-methyl-1H-imidazol-1-yl)phenyl]vinyl}-8-p-tolyl-5,6-dihydro-8H-[1,2,4]triazolo[5,1-c][1,4]oxazine, 140) (+)-2-{(E)-2-[3-methoxy-4-(4-methyl-1H-imidazol-1-yl)phenyl]vinyl}-8-(2,4,6-trifluorophenyl)-5,6-dihydro-8H-[1,2,4]triazolo[5,1-c][1,4]oxazine, 141) (−)-2-{(E)-2-[3-methoxy-4-(4-methyl-1H-imidazol-1-yl)phenyl]vinyl}-8-(2,4,6-trifluorophenyl)-5,6-dihydro-8H-[1,2,4]triazolo[5,1-c][1,4]oxazine, 142) (+)-8-(4-bromophenyl)-2-{(E)-2-[3-methoxy-4-(4-methyl-1H-imidazol-1-yl)phenyl]vinyl}-5,6-dihydro-8H-[1,2,4]triazolo[5,1-c][1,4]oxazine, 143) (−)-8-(4-bromophenyl)-2-{(E)-2-[3-methoxy-4-(4-methyl-1H-imidazol-1-yl)phenyl]vinyl}-5,6-dihydro-8H-[1,2,4]triazolo[5,1-c][1,4]oxazine, 144) (+)-8-(6-chloropyridin-3-yl)-2-{(E)-2-[3-methoxy-4-(4-methyl-1H-imidazol-1-yl)phenyl]vinyl}-5,6-dihydro-8H-[1,2,4]triazolo[5,1-c][1,4]oxazine, 145) (−)-8-(6-chloropyridin-3-yl)-2-{(E)-2-[3-methoxy-4-(4-methyl-1H-imidazol-1-yl)phenyl]vinyl}-5,6-dihydro-8H-[1,2,4]triazolo[5,1-c][1,4]oxazine, 146) (+)-4-(2-{(E)-2-[3-methoxy-4-(4-methyl-1H-imidazol-1-yl)phenyl]vinyl}-5,6-dihydro-8H-[1,2,4]triazolo[5,1-c][1,4]oxazin-8-yl)benzonitrile, 147) (−)-4-(2-{(E)-2-[3-methoxy-4-(4-methyl-1H-imidazol-1-yl)phenyl]vinyl}-5,6-dihydro-8H-[1,2,4]triazolo[5,1-c][1,4]oxazin-8-yl)benzonitrile, 148) (+)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine, 149) (−)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine, 150) (+)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridine, 151) (−)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridine, 152) (+)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol, 153) (−)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol, 154) (+)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridin-8-ol, 155) (−)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridin-8-ol, 156) (+)-4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile, 157) (−)-4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile, 158) (+)-4-{8-hydroxy-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile, 159) (−)-4-{8-hydroxy-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile, 160) {4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}phenyl}dimethylamine, 161) (S)-8-(4-chlorophenyl)-3-{(E)-2-[3-methoxy-4-(4-methyl-1H-imidazol-1-yl)phenyl]vinyl}-5,6,7,8-tetrahydro[1,2,4]triazolo[4,3-a]pyridine, 162) (R)-8-(4-chlorophenyl)-3-{(E)-2-[3-methoxy-4-(4-methyl-1H-imidazol-1-yl)phenyl]vinyl}-5,6,7,8-tetrahydro[1,2,4]triazolo[4,3-a]pyridine, 163) (+)-3-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[4,3-a]pyridine, 164) (−)-3-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[4,3-a]pyridine, 165) (+)-3-{(E)-2-[3-methoxy-4-(4-methyl-1H-imidazol-1-yl)phenyl]vinyl}-7-(3,4,5-trifluorophenyl)-6,7-dihydro-5H-pyrrolo[2,1-c][1,2,4]triazole, 166) (−)-3-{(E)-2-[3-methoxy-4-(4-methyl-1H-imidazol-1-yl)phenyl]vinyl}-7-(3,4,5-trifluorophenyl)-6,7-dihydro-5H-pyrrolo[2,1-c][1,2,4]triazole, 167) (S)-3-{(E)-2-[3-methoxy-4-(4-methyl-1H-imidazol-1-yl)phenyl]vinyl}-9-(3,4,5-trifluorophenyl)-6,7,8,9-tetrahydro-5H-[1,2,4]triazolo[4,3-a]azepine, 168) (R)-3-{(E)-2-[3-methoxy-4-(4-methyl-1H-imidazol-1-yl)phenyl]vinyl}-9-(3,4,5-trifluorophenyl)-6,7,8,9-tetrahydro-5H-[1,2,4]triazolo[4,3-a]azepine, 169) (+)-2-{(E)-2-[3-methoxy-4-(4-methyl-1H-imidazol-1-yl)phenyl]vinyl}-9-(3,4,5-trifluorophenyl)-6,7,8,9-tetrahydro-5H-[1,2,4]triazolo[1,5-a]azepine, 170) (−)-2-{(E)-2-[3-methoxy-4-(4-methyl-1H-imidazol-1-yl)phenyl]vinyl}-9-(3,4,5-trifluorophenyl)-6,7,8,9-tetrahydro-5H-[1,2,4]triazolo[1,5-a]azepine, 171) 3-(4-fluorophenyl)-8-{1-[3-methoxy-4-(4-methyl-1H-imidazol-1-yl)phenyl]-(E)-methylidene}-5,6,7,8-tetrahydro[1,2,4]triazolo[4,3-a]pyridine, 172) (−)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine, 173) (+)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine, 174) (−)-8-(2-bromophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine, 175) (+)-8-(2-bromophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine, 176) 8-(2-bromo-4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine, 177) 8-(2-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine, 178) 2-{(E)-2-[3-methoxy-4-(4-methyl-1H-imidazol-1-yl)phenyl]vinyl}-8-(2-methoxyphenyl)-5,6,7,8-tetrahydro[1,2,4]triazolo[1,5-a]pyridine, 179) 8-(3-bromophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and 180) 2-{(E)-2-[3-methoxy-4-(4-methyl-1H-imidazol-1-yl)phenyl]vinyl}-8-(2-nitrophenyl)-5,6,7,8-tetrahydro[1,2,4]triazolo[1,5-a]pyridine;

40) A medicine comprising the compound or pharmacologically acceptable salt thereof according to any one of 1) to 39) as an active ingredient;

41) The medicine according to 40) for preventing or treating a disease caused by amyloid-β; and 42) The medicine according to 41), wherein the disease caused by amyloid-β is Alzheimer's disease, dementia, Down's syndrome or amyloidosis.

The compound of the general formula (I) or pharmacologically acceptable salt thereof according to the present invention and the prophylactic or therapeutic agent for a disease caused by Aβ according to the present invention are novel inventions that have not yet been described in any documents.

DETAILED DESCRIPTION OF THE INVENTION

Meanings of symbols, terms and the like used in the present specification will be explained, and the present invention will be described in detail below.

In the present specification, a structural formula of a compound may represent a certain isomer for convenience. However, the present invention includes all isomers and isomer mixtures such as geometric isomers which can be generated from the structure of a compound, optical isomers based on asymmetric carbon, stereoisomers and tautomers. The present invention is not limited to the description of a chemical formula for convenience and may include any one of the isomers or mixtures thereof. Accordingly, the compound of the present invention may have an asymmetric carbon atom in the molecule and exist as an optically active compound or racemate, and the present invention includes each of the optically active compound and the racemate without limitations. Although crystal polymorphs of the compound may be present, the compound is not limited thereto as well and may be present as a single crystal form or a mixture of single crystal forms. The compound may be an anhydride or hydrate.

The "disease caused by Aβ" refers to a wide variety of diseases such as Alzheimer's disease (see Klein W L, and seven others, Alzheimer's disease-affected brain: Presence of oligomeric Aβ ligands (ADDLs) suggests a molecular basis for reversible memory loss, Proceeding National Academy of Science USA, 2003, Sep. 2, 100(18), p. 10417-10422; Nitsch R M, and sixteen others, Antibodies against β-amyloid slow cognitive decline in Alzheimer's disease, Neuron, 2003, May 22, 38(4), p. 547-554; Jarrett J T, and two others, The carboxy terminus of the β amyloid protein is critical for the seeding of amyloid formation: Implications for the pathogenesis of Alzheimer's disease, Biochemistry, 1993, May 11, 32(18), p. 4693-4697; Glenner G G, and one other, Alzheimer's disease: initial report of the purification and characterization of a novel cerebrovascular amyloid protein, Biochemical and biophysical research communications, 1984, May 16, 120(3), p. 885-890; Masters C L, and six others, Amyloid plaque core protein in Alzheimer disease and Down syndrome, Proceeding National Academy of Science USA, 1985, June, 82(12), p. 4245-4249; Gouras G K, and eleven others, Intraneuronal Aβ42 accumulation in human brain, American journal of pathology, 2000, January, 156(1), p. 15-20; Scheuner D, and twenty others, Secreted amyloid β-protein similar to that in the senile plaques of Alzheimer's disease is increased in vivo by the presenilin 1 and 2 and APP mutations linked to familial Alzheimer's disease, Nature Medicine, 1996, August, 2(8), p. 864-870; and Forman M S, and four others, Differential effects of the swedish mutant amyloid precursor protein on β-amyloid accumulation and secretion in neurons and non-neuronal cells, The journal of biological chemistry, 1997, Dec. 19, 272(51), p. 32247-32253, for example), senile dementia (see Blass J P, Brain metabolism and brain disease: Is metabolic deficiency the proximate cause of Alzheimer dementia? Journal of Neuroscience Research, 2001, Dec. 1, 66(5), p. 851-856, for example), frontotemporal dementia (see Evin G, and eleven others, Alternative transcripts of presenilin-1 associated with frontotemporal dementia, Neuroreport, 2002, Apr. 16, 13(5), p. 719-723, for example), Pick's disease (see Yasuhara O, and three others, Accumulation of amyloid precursor protein in brain lesions of patients with Pick disease, Neuroscience Letters, 1994, Apr. 25, 171 (1-2), p. 63-66, for example), Down's syndrome (see Teller J K, and ten others, Presence of soluble amyloid β-peptide precedes amyloid plaque formation in Down's syndrome, Nature Medicine, 1996, January, 2(1), p. 93-95; and Tokuda T, and six others, Plasma levels of amyloid β proteins Aβ1-40 and Aβ1-42(43) are elevated in Down's syndrome, Annals of Neurology, 1997, February, 41(2), p. 271-273, for example), cerebral angiopathy (see Hayashi Y, and nine others, Evidence for presenilin-1 involvement in amyloid angiopathy in the Alzheimer's disease-affected brain, Brain Research, 1998, Apr. 13, 789(2), p. 307-314; Barelli H, and fifteen others, Characterization of new polyclonal antibodies specific for 40 and 42 amino acid-long amyloid β peptides: their use to examine the cell biology of presenilins and the immunohistochemistry of sporadic Alzheimer's disease and cerebral amyloid angiopathy cases, Molecular Medicine, 1997, October, 3(10), p. 695-707; Calhoun M E, and ten others, Neuronal overexpression of mutant amyloid precursor protein results in prominent deposition of cerebrovascular amyloid, Proceeding National Academy of Science USA, 1999, Nov. 23, 96(24), p. 14088-14093; and Dermaut B, and ten others, Cerebral amyloid angiopathy is a pathogenic lesion in Alzheimer's Disease due to a novel presenilin-1 mutation, Brain, 2001, December, 124(12), p. 2383-2392, for example), hereditary cerebral hemorrhage with amyloidosis (Dutch type) (see Cras P, and nine others, Presenile Alzheimer dementia characterized by amyloid angiopathy and large amyloid core type senile plaques in the APP 692Ala→Gly mutation, Acta Neuropathologica (Berl), 1998, September, 96(3), p. 253-260; Herzig M C, and fourteen others, Aβ is targeted to the vasculature in a mouse model of hereditary cerebral hemorrhage with amyloidosis, Nature Neuroscience, 2004, September, 7(9), p. 954-960; van Duinen S G, and five others, Hereditary cerebral hemorrhage with amyloidosis in patients of Dutch origin is related to Alzheimer disease, Proceeding National Academy of Science USA, 1987, August, 84(16), p. 5991-5994; and Levy E, and eight others, Mutation of the Alzheimer's disease amyloid gene in hereditary cerebral hemorrhage, Dutch type, Science, 1990, Jun. 1, 248(4959), p. 1124-1126, for example), cognitive impairment (see Laws S M, and seven others, Association between the presenilin-1 mutation Glu318Gly and complaints of memory impairment, Neurobiology of Aging, 2002, January-February, 23(1), p. 55-58, for example), memory disorder and learning disability (see Vaucher E, and five others, Object recognition memory and cholinergic parameters in mice expressing human presenilin 1 transgenes, Experimental Neurology, 2002 June, 175(2), p. 398-406; Morgan D, and fourteen others, Aβ peptide vaccination prevents memory loss in an animal model of Alzheimer's disease, Nature, 2000 Dec. 21-28, 408(6815), p. 982-985; and Moran P M, and three others, Age-related learning deficits in transgenic mice expressing the 751-amino acid isoform of human β-amyloid precursor protein, Proceeding National Academy of Science USA, 1995, June 6, 92(12), p. 5341-5345, for example), amyloidosis, cerebral ischemia (see Laws S M, and seven others, Association between the presenilin-1 mutation Glu318Gly and complaints of memory impairment, Neurobiology of Aging, 2002, January-February, 23(1), p. 55-58; Koistinaho M, and ten others, β-amyloid precursor protein transgenic mice that harbor diffuse Aβ deposits but do not form plaques show increased ischemic vulnerability: Role of inflammation, Proceeding National Academy of Science USA, 2002, Feb. 5, 99(3), p. 1610-1615; and Zhang F, and four others, Increased susceptibility to ischemic brain damage in transgenic mice overexpressing the amyloid precursor protein, The journal of neuroscience, 1997, Oct. 15, 17(20), p. 7655-7661, for example), vascular dementia (see Sadowski M, and six others, Links between the pathology of Alzheimer's disease and vascular dementia, Neurochemical Research, 2004, June, 29(6), p. 1257-1266, for example), opthalmoplegia (see O'Riordan S, and seven others, Presenilin-1 mutation (E280G), spastic paraparesis, and cranial MRI white-matter abnormalities, Neurology, 2002, Oct. 8, 59(7), p. 1108-1110, for example), multiple sclerosis (see Gehrmann J, and four others, Amyloid precursor protein (APP) expression in multiple sclerosis lesions, Glia, 1995, October, 15(2), p. 141-51; and Reynolds W F, and six others, Myeloperoxidase polymorphism is associated with gender specific risk for Alzheimer's disease, Experimental Neurology, 1999, January, 155(1), p. 31-41, for example), head injury, cranial trauma (see Smith D H, and four others, Protein accumulation in traumatic brain injury, NeuroMolecular Medicine, 2003, 4(1-2), p. 59-72, for example), apraxia (see Matsubara-Tsutsui M, and seven others, Molecular evidence of presenilin 1 mutation in familial early onset dementia, American journal of Medical Genetics, 2002, Apr. 8, 114(3), p. 292-298, for example), prion disease, familial amyloid neuropathy, triplet repeat disease (see Kirkitadze M D, and two others, Paradigm shifts in Alzheimer's disease and other neurodegenerative disorders: the emerging role of oligomeric assemblies, Journal of Neuroscience Research, 2002, Sep. 1, 69(5), p. 567-577; Evert B O, and eight others, Inflammatory genes are upreglulated in expanded ataxin-3-expressing cell lines and spinocerebellar ataxia type 3 brains, The Journal of Neuroscience, 2001, Aug. 1, 21(15), p. 5389-5396; and Mann D M, and one other, Deposition of amyloid(A4) protein within the brains of persons with dementing disorders other than Alzheimer's disease and Down's syndrome, Neuroscience Letters, 1990, Feb. 5, 109(1-2), p. 68-75, for example), Parkinson's disease (see Primavera J, and four others, Brain accumulation of amyloid-β in Non-Alzheimer Neurodegeneration, Journal of Alzheimer's Disease, 1999, October, 1(3), p. 183-193, for example), Lewy body dementia (see Giasson B I, and two others, Interactions of amyloidogenic proteins. NeuroMolecular Medicine, 2003, 4(1-2), p. 49-58; Masliah E, and six others, β-amyloid peptides enhance α-synuclein accumulation and neuronal deficits in a transgenic mouse model linking Alzheimer's disease and Parkinson's disease, Proceeding National Academy of Science USA, 2001, Oct. 9, 98(21), p. 12245-12250; Barrachina M, and six others, Amyloid-β deposition in the cerebral cortex in Dementia with Lewy bodies is accompanied by a relative increase in AβPP mRNA isoforms containing the Kunitz protease inhibitor, Neurochemistry International, 2005, February, 46(3), p. 253-260; and Primavera J, and four others, Brain accumulation of amyloid-β in Non-Alzheimer Neurodegeneration, Journal of Alzheimer's Disease, 1999, October, 1(3), p. 183-193, for example), parkinsonism-dementia complex (see Schmidt M L, and six others, Amyloid plaques in Guam amyotrophic lateral sclerosis/parkinsonism-dementia complex contain species of Aβ similar to those found in the amyloid plaques of Alzheimer's disease and pathological aging, Acta Neuropathologica (Berl), 1998, February, 95(2), p. 117-122; and Ito H, and three others, Demonstration of P amyloid protein-containing neurofibrillary tangles in parkinsonism-dementia complex on Guam, Neuropathology and applied neurobiology, 1991, October, 17(5), p. 365-373, for example), frontotemporal dementia and parkinsonism linked to chromosome 17 (see Rosso S M, and three others, Coexistent tau and amyloid pathology in hereditary frontotemporal dementia with tau mutations, Annals of the New York academy of sciences, 2000, 920, p. 115-119, for example), dementia with argyrophilic grains (see Tolnay M, and four others, Low amyloid (Aβ) plaque load and relative predominance of diffuse plaques distinguish argyrophilic grain disease from Alzheimer's disease, Neuropathology and applied neurobiology, 1999, August, 25(4), p. 295-305, for example), Niemann-Pick disease (see Jin L W, and three others, Intracellular accumulation of amyloidogenic fragments of amyloid-β precursor protein in neurons with Niemann-Pick type C defects is associated with endosomal abnormalities, American Journal of Pathology, 2004, March, 164(3), p. 975-985, for example), amyotrophic lateral sclerosis (see Sasaki S, and one other, Immunoreactivity of β-amyloid precursor protein in amyotrophic lateral sclerosis, Acta Neuropathologica (Berl), 1999, May, 97(5), p. 463-468; Tamaoka A, and four others, Increased amyloid β protein in the skin of patients with amyotrophic lateral sclerosis, Journal of neurology, 2000, August, 247(8), p. 633-635; Hamilton R L, and one other, Alzheimer disease pathology in amyotrophic lateral sclerosis, Acta Neuropathologica, 2004, June, 107(6), p. 515-522; and Turner B J, and six others, Brain β-amyloid accumulation in transgenic mice expressing mutant superoxide dismutase 1, Neurochemical Research, 2004, December, 29(12), p. 2281-2286, for example), hydrocephalus (see Weller R O, Pathology of cerebrospinal fluid and interstitial fluid of the CNS: Significance for Alzheimer disease, prion disorders and multiple sclerosis, Journal of Neuropathology and Experimental Neurology, 1998, October, 57(10), p. 885-894; Silverberg G D, and four others, Alzheimer's disease, normal-pressure hydrocephalus, and senescent changes in CSF circulatory physiology: a hypothesis, Lancet neurology, 2003, August, 2(8), p. 506-511; Weller R O, and three others, Cerebral amyloid angiopathy: Accumulation of Aβ in interstitial fluid drainage pathways in Alzheimer's disease, Annals of the New York academy of sciences, 2000, April, 903, p. 110-117; Yow H Y, and one other, A role for cerebrovascular disease in determining the pattern of β-amyloid deposition in Alzheimer's disease, Neurology and applied neurobiology, 2002, 28, p. 149; and Weller R O, and four others, Cerebrovascular disease is a major factor in the failure of elimination of Aβ from the aging human brain, Annals of the New York academy of sciences, 2002, November, 977, p. 162-168, for example), paraparesis (see O'Riordan S, and seven others, Presenilin-1 mutation (E280G), spastic paraparesis, and cranial MRI white-matter abnormalities, Neurology, 2002, Oct. 8, 59(7), p. 1108-1110; Matsubara-Tsutsui M, and seven others, Molecular evidence of presenilin 1 mutation in familial early onset dementia, American journal of Medical Genetics, 2002, Apr. 8, 114(3), p. 292-298; Smith M J, and eleven others, Variable phenotype of Alzheimer's disease with spastic paraparesis, Annals of Neurology, 2001, 49(1), p. 125-129; and Crook R, and seventeen others, A variant of Alzheimer's disease with spastic pararesis and unusual plaques due to deletion of exon 9 of presenilin 1, Nature Medicine, 1998, April; 4(4), p. 452-455, for example), progressive supranuclear palsy (see Barrachina M, and six others, Amyloid-β deposition in the cerebral cortex in Dementia with Lewy bodies is accompanied by a relative increase in AβPP mRNA isoforms containing the Kunitz protease inhibitor, Neurochemistry International, 2005, February, 46(3), p. 253-260; and Primavera J, and four others, Brain accumulation of amyloid-β in Non-Alzheimer Neurodegeneration, Journal of Alzheimer's Disease, 1999, October, 1(3), p. 183-193, for example), intracerebral hemorrhage (see Atwood C S, and three others, Cerebrovascular requirement for sealant, anticoagulant and remodeling molecules that allow for the maintenance of vascular integrity and blood supply, Brain Research Reviews, 2003, September, 43(1), p. 164-78; and Lowenson J D, and two others, Protein aging: Extracellular amyloid formation and intracellular repair, Trends in cardiovascular medicine, 1994, 4(1), p. 3-8, for example), convulsion (see Singleton A B, and thirteen others, Pathology of early-onset Alzheimer's disease cases bearing the Thr113-114ins presenilin-1 mutation, Brain, 2000, December, 123 (Pt12), p. 2467-2474, for example), mild cognitive impairment (see Gattaz W F, and four others, Platelet phospholipase A2 activity in Alzheimer's disease and mild cognitive impairment, Journal of Neural Transmission, 2004, May, 111(5), p. 591-601; and Assini A, and fourteen others, Plasma levels of amyloid β-protein 42 are increased in women with mild cognitive impairment, Neurology, 2004, Sep. 14, 63(5), p. 828-831, for example) and arteriosclerosis (see De Meyer G R, and eight others, Platelet phagocytosis and processing of β-amyloid precursor protein as a mechanism of macrophage activation in atherosclerosis, Circulation Research, 2002, Jun. 14, 90(11), p. 1197-1204, for example).

The "5-membered aromatic heterocyclic group", "6- to 14-membered aromatic hydrocarbon ring group", "5- to 14-membered aromatic heterocyclic group", "6- to 14-membered non-aromatic hydrocarbon ring group" and "5- to 14-membered non-aromatic heterocyclic group" in the above formula (I) which are contained in the therapeutic or prophylactic agent for a disease caused by Aβ according to the present invention are defined as follows.

The "5-membered aromatic heterocyclic group" is a 5-membered aromatic heterocyclic group containing one or more hetero atoms selected from the group consisting of a nitrogen atom, a sulfur atom and an oxygen atom such as

[Formula 13]

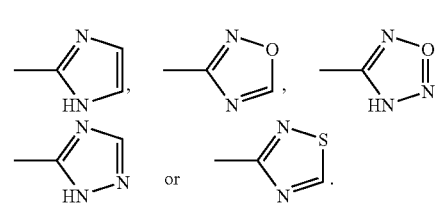

The "6- to 14-membered aromatic hydrocarbon ring group" refers to a monocyclic, bicyclic or tricyclic aromatic hydrocarbon ring group having 6 to 14 carbon atoms. Preferable examples of the group include 6- to 14-membered monocyclic, bicyclic, or tricyclic aromatic hydrocarbon ring groups such as a phenyl group, indenyl group, naphthyl group, azulenyl group, heptalenyl group, biphenyl group, fluorenyl group, phenalenyl group, phenanthrenyl group and anthracenyl group.

The "5- to 14-membered aromatic heterocyclic group" refers to a monocyclic, bicyclic or tricyclic aromatic heterocyclic group having 5 to 14 carbon atoms. Preferable examples of the group include (1) nitrogen-containing aromatic heterocyclic groups such as a pyrrolyl group, pyridyl group, pyridazinyl group, pyrimidinyl group, pyrazinyl group, pyrazolinyl group, imidazolyl group, indolyl group, isoindolyl group, indolizinyl group, purinyl group, indazolyl group, quinolyl group, isoquinolyl group, quinolizinyl group, phthalazinyl group, naphthyridinyl group, quinoxalinyl group, quinazolinyl group, cinnolinyl group, pteridinyl group, imidazotriazinyl group, pyrazinopyridazinyl group, acridinyl group, phenanthridinyl group, carbazolyl group, perimidinyl group, phenanthrolinyl group and phenacyl group, (2) sulfur-containing aromatic heterocyclic groups such as a thienyl group and benzothienyl group, (3) oxygen-containing aromatic heterocyclic groups such as a furyl group, pyranyl group, cyclopentapyranyl group, benzofuranyl group and isobenzofuranyl group and (4) aromatic heterocyclic groups containing two or more hetero atoms selected from the group consisting of a nitrogen atom, sulfur atom and oxygen atom such as a thiazolyl group, isothiazolyl group, benzothiazolinyl group, benzothiadiazolyl group, phenothiazinyl group, isoxazolyl group, furazanyl group, phenoxazinyl group, pyrazoloxazolyl group, imidazothiazolyl group, thienofuryl group, furopyrrolyl group and pyridooxazinyl group.

The "6- to 14-membered non-aromatic hydrocarbon ring group" refers to a cyclic aliphatic hydrocarbon group having 6 to 14 carbon atoms. Examples of the group include cyclic aliphatic hydrocarbon groups having 6 to 14 carbon atoms such as a cyclopropyl group, cyclobutyl group, cyclopentyl group, cyclohexyl group, cycloheptyl group, cyclooctyl group, spiro[3.4]octanyl group, decanyl group, indanyl group, 1-acenaphthenyl group, cyclopentacyclooctenyl group, benzocyclooctenyl group, indenyl group, tetrahydronaphthyl group, 6,7,8,9-tetrahydro-5H-benzocycloheptenyl group and 1,4-dihydronaphthalenyl group.

The "5- to 14-membered non-aromatic heterocyclic group" 1) has 5 to 14 ring-forming atoms, 2) contains 1 to 5 hetero atoms such as a nitrogen atom, —O— or —S— in the ring-forming atoms, and 3) may contain one or more carbonyl groups, double bonds or triple bonds in the ring, and refers not only to a 5- to 14-membered non-aromatic monocyclic heterocyclic group but also to a saturated heterocyclic group condensed with an aromatic hydrocarbon ring group or a saturated hydrocarbon ring group or saturated heterocyclic group condensed with an aromatic heterocyclic group. Specific examples of the 5- to 14-membered non-aromatic heterocyclic group include an azetidinyl ring, pyrrolidinyl ring, piperidinyl ring, azepanyl ring, azocanyl ring, tetrahydrofuranyl ring, tetrahydropyranyl ring, morpholinyl ring, thiomorpholinyl ring, piperazinyl ring, thiazolidinyl ring, dioxanyl ring, imidazolinyl ring, thiazolinyl ring, 1,2-benzopyranyl ring, isochromanyl ring, chromanyl ring, indolinyl ring, isoindolinyl ring, azaindanyl group, azatetrahydronaphthyl group, azachromanyl group, tetrahydrobenzofuranyl group, tetrahydrobenzothienyl group, 2,3,4,5-tetrahydro-benzo[b]thienyl group, 3,4-dihydro-2H-benzo[b][1,4]dioxepinyl group, indan-1-onyl group, 6,7-dihydro-5H-cyclopentapyrazinyl group, 6,7-dihydro-5H-[1]pyridinyl group, 6,7-dihydro-5H-[1]pyridinyl group, 5,6-dihydro-4H-cyclopenta[b]thienyl group, 4,5,6,7-tetrahydro-benzo[b]thienyl group, 3,4-dihydro-2H-naphthale-1-onyl group, 2,3-dihydro-isoindol-1-onyl group, 3,4-dihydro-2H-isoquinolin-1-onyl group and 3,4-dihydro-2H-benzo[1,4]oxapinyl group.

Substituent Group A1, Substituent Group A2, Substituent Group A3, Substituent Group A4, Substituent Group A5 and Substituent Group A6 refer to the following groups.

Substituent Group A1 refers to (1) a hydrogen atom, (2) a halogen atom, (3) a cyano group, (4) a nitro group, (5) a C3-8 cycloalkyl group, (6) a C2-6 alkenyl group, (7) a C2-6 alkynyl group, (8) a C1-6 alkoxy group, (9) a C3-8 cycloalkoxy group, (10) a formyl group, (11) a C1-6 alkylcarbonyl group or (12) a C1-6 alkyl group (wherein the C1-6 alkyl group may be substituted with 1 to 3 substituents selected from the group consisting of a halogen atom, a hydroxyl group, a cyano group, a C1-6 alkoxy group, a C3-8 cycloalkyl group and a C1-6 alkylcarbonyl group).

Substituent Group A2 refers to (1) a hydrogen atom, (2) a halogen atom, (3) a hydroxyl group, (4) a cyano group, (5) a C1-6 alkoxy group (wherein the C1-6 alkoxy group may be substituted with 1 to 3 substituents selected from the group consisting of a halogen atom, a cyano group, a C1-6 alkyl group, a C2-6 alkenyl group, a C2-6 alkynyl group and a C3-8 cycloalkyl group), (6) a C3-8 cycloalkoxy group, (7) a C2-6 alkenyloxy group or (8) a C2-6 alkynyloxy group.

Substituent Group A3 refers to (1) a hydrogen atom, (2) a halogen atom, (3) a 6- to 14-membered aromatic hydrocarbon ring group that may be substituted with 1 to 3 substituents selected from Substituent Group A5, (4) a 5- to 14-membered aromatic heterocyclic group that may be substituted with 1 to 3 substituents selected from Substituent Group A5, (5) a C1-6 alkyl group (wherein the C1-6 alkyl group may be substituted with 1 to 3 substituents selected from the group consisting of a formyl group, a halogen atom, a hydroxyl group, a hydroxyl group having a protecting group, a cyano group, a C2-6 alkenyl group, a C2-6 alkynyl group, a C3-8 cycloalkyl group, a C1-6 alkoxy group, a C1-6 alkylthio group, a C1-6 alkylsulfinyl group, a C1-6 alkylsulfonyl group, a C1-6 alkylcarbonyl group, an amino group (wherein the amino group may be substituted with 1 to 2 of a C1-6 alkyl group optionally having 1 to 5 halogen atoms), a 6- to 14-membered aromatic hydrocarbon ring group that may be substituted with 1 to 3 substituents selected from Substituent Group A5, a 5- to 14-membered aromatic heterocyclic group that may be substituted with 1 to 3 substituents selected from Substituent Group A5, a 6- to 14-membered non-aromatic hydrocarbon ring group that may be substituted with 1 to 3 substituents selected from Substituent Group A5, a 5- to 14-membered non-aromatic heterocyclic group that may be substituted with 1 to 3 substituents selected from Substituent Group A5, and —X-A (wherein X represents an imino group, —O— or —S—, and A represents a 6- to 14-membered aromatic hydrocarbon ring group or 5- to 14-membered aromatic heterocyclic group that may be substituted with 1 to 3 substituents selected from Substituent Group A5)) or (6) a C1-6 alkoxy group that may be substituted with 1 to 3 halogen atoms.

Substituent Group A4 refers to (1) a hydrogen atom, (2) a halogen atom, (3) a hydroxyl group, (4) a cyano group, (5) a nitro group, (6) a C3-8 cycloalkyl group, (7) a C2-6 alkenyl group that may be substituted with 1 to 3 substituents selected from Substituent Group A5, (8) a C2-6 alkynyl group that may be substituted with 1 to 3 substituents selected from Substituent Group A5, (9) a C3-8 cycloalkoxy group, (10) a C3-8 cycloalkylthio group, (11) a formyl group, (12) a C1-6 alkylcarbonyl group that may be substituted with 1 to 3 substituents selected from Substituent Group A5, (13) a C1-6 alkylthio group that may be substituted with 1 to 3 substituents selected from Substituent Group A5, (14) a C1-6 alkylsulfinyl group that may be substituted with 1 to 3 substituents selected from Substituent Group A5, (15) a C1-6 alkylsulfonyl group that may be substituted with 1 to 3 substituents selected from Substituent Group A5, (16) a hydroxyimino group, (17) a C1-6 alkoxyimino group, (18) a C1-6 alkyl group that may be substituted with 1 to 3 substituents selected from Substituent Group A5, (19) a C1-6 alkoxy group that may be substituted with 1 to 3 substituents selected from Substituent Group A5, (20) an amino group that may be substituted with 1 or 2 substituents selected from Substituent Group A5, (21) a carbamoyl group that may be substituted with 1 or 2 substituents selected from Substituent Group A5, (22) a 6- to 14-membered aromatic hydrocarbon ring group that may be substituted with 1 to 3 substituents selected from Substituent Group A5, (23) a 5- to 14-membered aromatic heterocyclic group that may be substituted with 1 to 3 substituents selected from Substituent Group A5, (24) a 6- to 14-membered non-aromatic hydrocarbon ring group that may be substituted with 1 to 3 substituents selected from Substituent Group A5, (25) a 5- to 14-membered non-aromatic heterocyclic group that may be substituted with 1 to 3 substituents selected from Substituent Group A5, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S—, and A represents a 6- to 14-membered aromatic hydrocarbon ring group or 5- to 14-membered aromatic heterocyclic group that may be substituted with 1 to 3 substituents selected from Substituent Group A6), (31) —CO-A (wherein A is as defined above), (32) =CH-A (wherein A is as defined above), (33) a carboxyl group or (34) a C1-6 alkoxycarbonyl group.

Substituent Group A5 refers to (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group (wherein the C1-6 alkyl group may be substituted with 1 to 3 substituents selected from Substituent Group A6, a 6- to 14-membered aromatic hydrocarbon ring group (wherein the 6- to 14-membered aromatic hydrocarbon ring group may be substituted with 1 to 3 substituents selected from Substituent Group A6) and a 5- to 14-membered aromatic heterocyclic group (wherein the 5- to 14-membered aromatic heterocyclic group may be substituted with 1 to 3 substituents selected from Substituent Group A6)), (19) a C1-6 alkoxy group (wherein the C1-6 alkoxy group may be substituted with 1 to 3 substituents selected from Substituent Group A6, a 6- to 14-membered aromatic hydrocarbon ring group (wherein the 6- to 14-membered aromatic hydrocarbon ring group may be substituted with 1 to 3 substituents selected from Substituent Group A6) and a 5- to 14-membered aromatic heterocyclic group (wherein the 5- to 14-membered aromatic heterocyclic group may be substituted with 1 to 3 substituents selected from Substituent Group A6)), (20) an amino group that may be substituted with 1 or 2 C1-6 alkyl groups, (21) a carbamoyl group that may be substituted with 1 or 2 C1-6 alkyl groups, (22) a 6- to 14-membered aromatic hydrocarbon ring group that may be substituted with 1 to 3 substituents selected from Substituent Group A6, (23) a 5- to 14-membered aromatic heterocyclic group that may be substituted with 1 to 3 substituents selected from Substituent Group A6, (24) a 6- to 14-membered non-aromatic hydrocarbon ring group that may be substituted with 1 to 3 substituents selected from Substituent Group A6, (25) a 5- to 14-membered non-aromatic heterocyclic group that may be substituted with 1 to 3 substituents selected from Substituent Group A6, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S—, and A represents a 6- to 14-membered aromatic hydrocarbon ring group or 5- to 14-membered aromatic heterocyclic group that may be substituted with 1 to 3 substituents selected from Substituent Group A6), (31) —CO-A (wherein A is as defined above), (32) =CH-A (wherein A is as defined above), (33) a carboxyl group and (34) a C1-6 alkoxycarbonyl group;

Substituent Group A6 refers to (1) a hydrogen atom, (2) a halogen atom, (3) a hydroxyl group, (4) a cyano group, (5) an amino group that may be substituted with 1 or 2 C1-6 alkyl groups, (6) a C1-6 alkyl group (wherein the C1-6 alkyl group may be substituted with 1 to 3 substituents selected from the group consisting of a halogen atom, a hydroxyl group, a cyano group, an amino group that may be substituted with 1 or 2 C1-6 alkyl groups) and (7) a C1-6 alkoxy group (wherein the C1-6 alkoxy group may be substituted with 1 to 3 substituents selected from the group consisting of a halogen atom, a hydroxyl group, a cyano group, an amino group that may be substituted with 1 or 2 C1-6 alkyl groups).

The "halogen atom" refers to a fluorine atom, chlorine atom, bromine atom, iodine atom or the like, and is preferably a fluorine atom, chlorine atom or bromine atom.

The "C1-6 alkyl group" refers to an alkyl group having 1 to 6 carbon atoms. Preferable examples of the group include linear or branched alkyl groups such as a methyl group, ethyl group, n-propyl group, i-propyl group, n-butyl group, i-butyl group, tert-butyl group, n-pentyl group, i-pentyl group, neopentyl group, n-hexyl group, 1-methylpropyl group, 1,2-dimethylpropyl group, 1-ethylpropyl group, 1-methyl-2-ethylpropyl group, 1-ethyl-2-methylpropyl group, 1,1,2-trimethylpropyl group, 1-methylbutyl group, 2-methylbutyl group, 1,1-dimethylbutyl group, 2,2-dimethylbutyl group, 2-ethylbutyl group, 1,3-dimethylbutyl group, 2-methylpentyl group and 3-methylpentyl group.

The "C2-6 alkenyl group" refers to an alkenyl group having 2 to 6 carbon atoms. Preferable examples of the group include linear or branched alkenyl groups such as a vinyl group, allyl group, 1-propenyl group, isopropenyl group, 1-buten-1-yl group, 1-buten-2-yl group, 1-buten-3-yl group, 2-buten-1-yl group and 2-buten-2-yl group.

The "C2-6 alkynyl group" refers to an alkynyl group having 2 to 6 carbon atoms. Preferable examples of the group include linear or branched alkynyl groups such as an ethynyl group, 1-propynyl group, 2-propynyl group, butynyl group, pentynyl group and hexynyl group.

The "C3-8 cycloalkyl group" refers to a cyclic alkyl group having 3 to 8 carbon atoms. Preferable examples of the group include a cyclopropyl group, cyclobutyl group, cyclopentyl group, cyclohexyl group, cycloheptyl group and cyclooctyl group.

The "C1-6 alkoxy group" refers to an alkyl group having 1 to 6 carbon atoms in which a hydrogen atom is substituted with an oxygen atom. Preferable examples of the group include a methoxy group, ethoxy group, n-propoxy group, i-propoxy group, n-butoxy group, i-butoxy group, sec-butoxy group, tert-butoxy group, n-pentoxy group, i-pentoxy group, sec-pentoxy group, tert-pentoxy group, n-hexoxy group, i-hexoxy group, 1,2-dimethylpropoxy group, 2-ethylpropoxy group, 1-methyl-2-ethylpropoxy group, 1-ethyl-2-methylpropoxy group, 1,1,2-trimethylpropoxy group, 1,1,2-trimethylpropoxy group, 1,1-dimethylbutoxy group, 2,2-dimethylbutoxy group, 2-ethylbutoxy group, 1,3-dimethylbutoxy group, 2-methylpentoxy group, 3-methylpentoxy group and hexyloxy group.

The "C3-8 cycloalkoxy group" refers to a cyclic alkyl group having 3 to 8 carbon atoms in which one hydrogen atom is substituted with an oxygen atom. Preferable examples of the group include a cyclopropoxy group, cyclobutoxy group, cyclopentoxy group, cyclohexoxy group, cycloheptyloxy group and cyclooctyloxy group.

The "C2-6 alkenyloxy group" refers to an alkenyl group having 2 to 6 carbon atoms in which one hydrogen atom is substituted with an oxygen atom. Preferable examples of the group include linear or branched alkenyloxy groups such as a vinyloxy group, allyloxy group, 1-propenyloxy group, isopropenyloxy group, 1-buten-1-yloxy group, 1-buten-2-yloxy group, 1-buten-3-yloxy group, 2-buten-1-yloxy group and 2-buten-2-yloxy group.

The "C2-6 alkynyloxy group" refers to an alkynyl group having 2 to 6 carbon atoms in which one hydrogen atom is substituted with an oxygen atom. Preferable examples of the group include linear or branched alkynyloxy groups such as an ethynyloxy group, 1-propynyloxy group, 2-propynyloxy group, butynyloxy group, pentynyloxy group and hexynyloxy group.

The "C1-6 alkylthio group" refers to an alkyl group having 1 to 6 carbon atoms in which one hydrogen atom is substituted with a sulfur atom. Preferable examples of the group include a methylthio group, ethylthio group, n-propylthio group, i-propylthio group, n-butylthio group, i-butylthio group, tert-butylthio group, n-pentylthio group, i-pentylthio group, neopentylthio group, n-hexylthio group and 1-methylpropylthio group.

The "C1-6 alkylsulfinyl group" refers to an alkyl group having 1 to 6 carbon atoms in which one hydrogen atom is substituted with a sulfinyl group. Preferable examples of the group include a methylsulfinyl group, ethylmethylsulfinyl group, n-propylsulfinyl group, i-propylsulfinyl group, n-butylsulfinyl group, i-butylsulfinyl group, tert-butylsulfinyl group, n-pentylsulfinyl group, i-pentylsulfinyl group, neopentylsulfinyl group, n-hexylsulfinyl group and 1-methylpropylsulfinyl group.

The "C1-6 alkylsulfonyl group" refers to an alkyl group having 1 to 6 carbon atoms in which one hydrogen atom is substituted with a sulfonyl group. Preferable examples of the group include a methanesulfonyl group and ethanesulfonyl group.

The "C3-8 cycloalkylthio group" refers to a cyclic alkyl group having 3 to 8 carbon atoms in which one hydrogen atom is substituted with a sulfur atom. Preferable examples of the group include a cyclopropylthio group, cyclobutylthio group, cyclopentylthio group, cyclohexylthio group, cycloheptylthio group and cyclooctylthio group.

The "C3-8 cycloalkylsulfinyl group" refers to a cyclic alkyl group having 3 to 8 carbon atoms in which one hydrogen atom is substituted with a sulfinyl group. Preferable examples of the group include a cyclopropylsulfinyl group, cyclobutylsulfinyl group, cyclopentylsulfinyl group, cyclohexylsulfinyl group, cycloheptylsulfinyl group and cyclooctylsulfinyl group.

The "C3-8 cycloalkylsulfonyl group" refers to a cyclic alkyl group having 3 to 8 carbon atoms in which one hydrogen atom is substituted with a sulfonyl group. Preferable examples of the group include a cyclopropylsulfonyl group, cyclobutylsulfonyl group, cyclopentylsulfonyl group, cyclohexylsulfonyl group, cycloheptylsulfonyl group and cyclooctylsulfonyl group.

The "amino group that may be substituted with a C1-6 alkyl group" refers to an amino group that may be substituted with an alkyl group having 1 to 6 carbon atoms. Preferable examples of the group include an amino group, methylamino group, ethylamino group, propylamino group and dimethylamino group.

The "C1-6 alkylcarbonyl group" refers to an alkyl group having 1 to 6 carbon atoms in which one hydrogen atom is substituted with a carbonyl group. Preferable examples of the group include an acetyl group, propionyl group and butyryl group.

The "C1-6 alkoxyimino group" refers to an imino group in which a hydrogen atom is substituted with a C1-6 alkoxy group. Preferable examples of the group include a methoxyimino group and ethoxyimino group.

The "C1-6 alkoxycarbonyl group" refers to a carbonyl group in which a hydrogen atom is substituted with a C1-6 alkyl group. Preferable examples of the group include an ethoxycarbonyl group.

Preferable examples of the "hydroxyl group having a protecting group" include a methoxymethyl ether group, tetrahydropyranyl ether group, tert-butyl ether group, allyl ether group, benzoate group, acetate group, formate group, crotonate group, p-phenylbenzoate group, pivaloate group, tert-butyldimethylsilyl group, tert-butyldiphenylsilyl group, trityl group and benzyl group.

The substituent in the "6- to 14-membered aromatic hydrocarbon ring group that may be substituted with 1 to 3 substituents", the "5- to 14-membered aromatic heterocyclic group that may be substituted with 1 to 3 substituents", the "6- to 14-membered non-aromatic hydrocarbon ring group that may be substituted with 1 to 3 substituents" or the "5- to 14-membered non-aromatic heterocyclic group that may be substituted with 1 to 3 substituents" is preferably, for example, (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group (wherein the C1-6 alkyl group may be substituted with 1 to 3 substituents selected from Substituent Group A6, a 6- to 14-membered aromatic hydrocarbon ring group (wherein the 6- to 14-membered aromatic hydrocarbon ring group may be substituted with 1 to 3 substituents selected from Substituent Group A6) and a 5- to 14-membered aromatic heterocyclic group (wherein the 5- to 14-membered aromatic heterocyclic group may be substituted with 1 to 3 substituents selected from Substituent Group A6)), (19) a C1-6 alkoxy group (wherein the C1-6 alkoxy group may be substituted with 1 to 3 substituents selected from Substituent Group A6, a 6- to 14-membered aromatic hydrocarbon ring group (wherein the 6- to 14-membered aromatic hydrocarbon ring group may be substituted with 1 to 3 substituents selected from Substituent Group A6) and a 5- to 14-membered aromatic heterocyclic group (wherein the 5- to 14-membered aromatic heterocyclic group may be substituted with 1 to 3 substituents selected from Substituent Group A6)), (20) an amino group that may be substituted with 1 to 2 C1-6 alkyl groups, (21) a carbamoyl group that may be substituted with 1 to 2 C1-6 alkyl groups, (22) a 6- to 14-membered aromatic hydrocarbon ring group, (23) a 5- to 14-membered aromatic heterocyclic group, (24) a 6- to 14-membered non-aromatic hydrocarbon ring group, (25) a 5- to 14-membered non-aromatic heterocyclic group, (26) a C2-6 alkenyloxy group, (27)

a C2-6 alkynyloxy group, (28) a C3-8 cycloalkylsulfinyl group, (29) a C3-8 cycloalkylsulfonyl group, (30) —X-A (wherein X represents an imino group, —O— or —S—, and A represents a 6- to 14-membered aromatic hydrocarbon ring group or 5- to 14-membered aromatic heterocyclic group that may be substituted with 1 to 3 substituents selected from Substituent Group A6), (31) —CO-A (wherein A is as defined above), (32) =CH-A (wherein A is as defined above), (33) a carboxyl group, or (34) a C1-6 alkoxycarbonyl group.

The "compound wherein Het is monovalent and is a 5-membered aromatic heterocyclic group" is a compound of the formula (I), wherein Het represents a 5-membered aromatic heterocyclic group and is preferably, for example, a group of the formula:

[Formula 14]

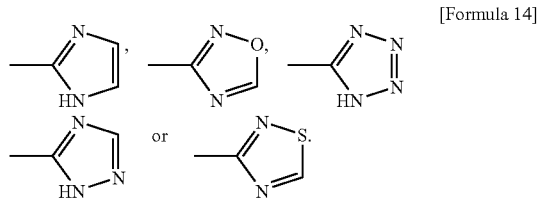

The "compound wherein Het is monovalent and is a 5-membered aromatic heterocyclic group condensed with a 6- to 14-membered non-aromatic hydrocarbon ring group" is a compound of the formula (I), wherein Het represents a 5-membered aromatic heterocyclic group condensed with a 6- to 14-membered non-aromatic hydrocarbon ring group and is preferably, for example, a group of the formula:

[Formula 15]

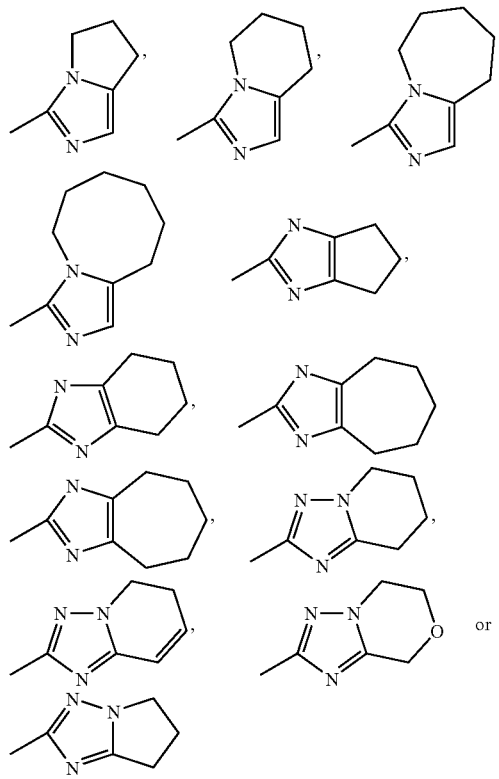

The "compound wherein Het is monovalent and is a 5-membered aromatic heterocyclic group condensed with a 5- to 14-membered non-aromatic heterocyclic group" is a compound of the formula (I), wherein Het represents a 5-membered aromatic heterocyclic group condensed with a 5- to 14-membered non-aromatic heterocyclic group and is preferably, for example, a group of the formula:

[Formula 16]

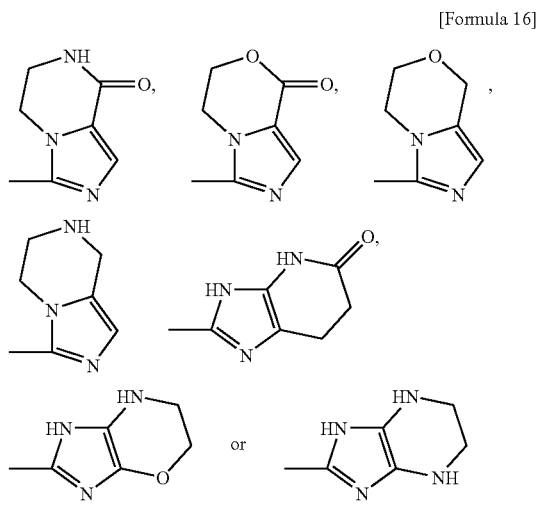

The "Het which is divalent and is a 5-membered aromatic heterocyclic group condensed with a 5- to 14-membered non-aromatic heterocyclic group" is preferably, for example, a group of the formula:

[Formula 17]

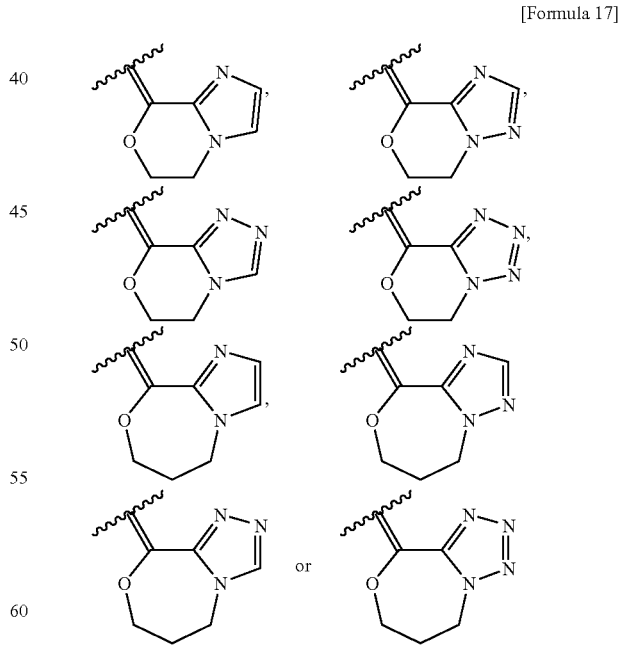

The "Het which is divalent and is a 5-membered aromatic heterocyclic group condensed with a 6- to 14-membered non-aromatic hydrocarbon ring group" is, for example, a group of the formula:

[Formula 18]

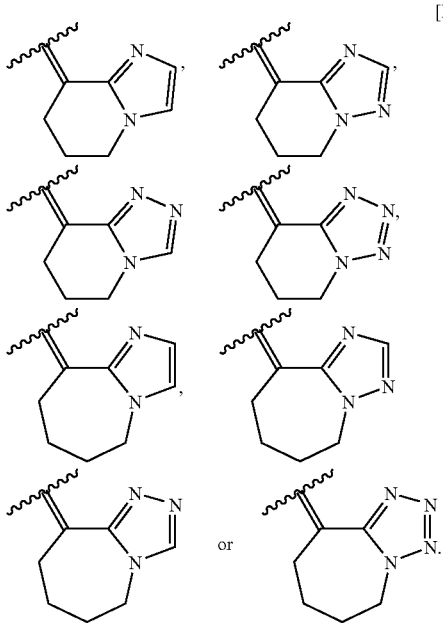

The "Het which is a group represented by the formula:

[Formula 19]

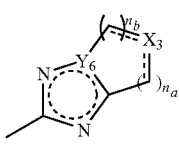

wherein ⁓represents a single bond or a double bond, $X_3$ represents a methine group or methylene group, an imino group, an oxygen atom, a sulfur atom or —$SO_2$—, which may be substituted with a substituent selected from Substituent Group A4, $Y_6$ represents a carbon atom or a nitrogen atom, and $n_a$ and $n_b$ independently represent an integer of 0 to 3", is, for example, a group of the formula:

[Formula 20]

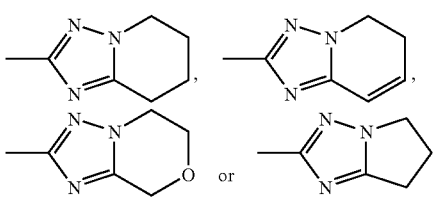

The "Het which is a group represented by the formula:

[Formula 21]

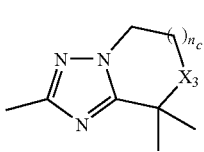

wherein $X_3$ represents a methine group or methylene group, an imino group, an oxygen atom, a sulfur atom or —$SO_2$—, and $n_c$ represents an integer of 0 to 3", is, for example, a group of the formula:

[Formula 22]

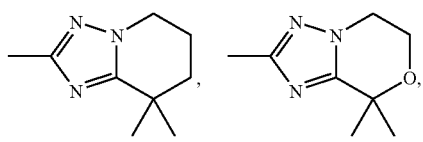

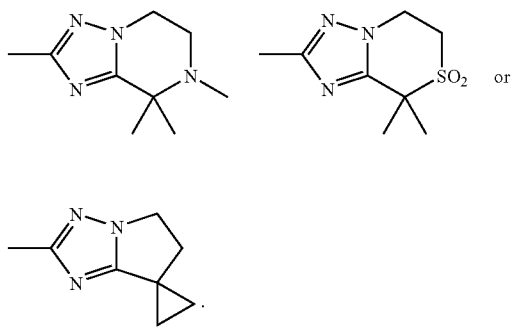

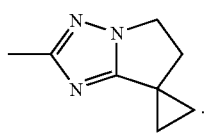

The "Het which is a group represented by the formula:

[Formula 23]

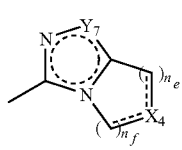

which may be substituted with 1 to 3 substituents selected from Substituent Group A4, wherein ⁓represents a single bond or a double bond, $X_4$ represents a methine group or methylene group, an imino group, an oxygen atom, a sulfur atom or —$SO_2$—, which may be substituted with a substituent selected from Substituent Group A4, $Y_7$ represents a carbon atom or a nitrogen atom, and $n_e$ and $n_f$ independently represent an integer of 0 to 3" is, for example, a group of the formula:

[Formula 24]

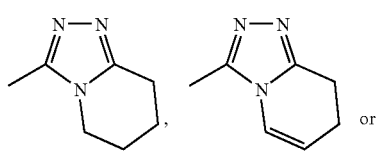

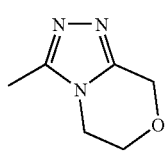

The "Het which is a group represented by the formula:

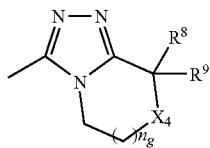

[Formula 25]

which may be substituted with 1 to 3 substituents selected from Substituent Group A4, wherein $R^8$ and $R^9$ are the same or different and each represent a substituent selected from Substituent Group A4, $X_4$ is the same as defined in claim 33, and $n_g$ represent an integer of 0 to 2" is, for example, a group of the formula;

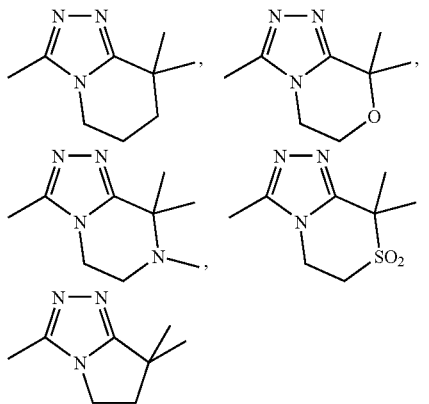

[Formula 26]

In the present invention, there are no specific limitations to the "pharmacologically acceptable salt" insofar as it is a pharmacologically acceptable salt formed with a compound of the general formula (I) that is a prophylactic or therapeutic agent for a disease caused by Aβ. Preferable specific examples of the salt include hydrohalides (such as hydrofluorides, hydrochlorides, hydrobromides and hydroiodides), inorganic acid salts (such as sulfates, nitrates, perchlorates, phosphates, carbonates and bicarbonates), organic carboxylates (such as acetates, oxalates, maleates, tartrates, fumarates and citrates), organic sulfonates (such as methanesulfonates, trifluoromethanesulfonates, ethanesulfonates, benzenesulfonates, toluenesulfonates and camphorsulfonates), amino acid salts (such as aspartates and glutamates), quaternary amine salts, alkali metal salts (such as sodium salts and potassium salts) and alkali earth metal salts (such as magnesium salts and calcium salts).

Next, the compound of the formula (I) of the present invention will be described.

In the compound of the formula (I) or pharmacologically acceptable salt thereof, $Ar_1$ is preferably an imidazolyl group, triazolyl group or tetrazolyl group, $Ar_1$ is more preferably an imidazolyl group or triazolyl group, and $Ar_1$ is most preferably an imidazolyl group.

In the compound of the formula (I) or pharmacologically acceptable salt thereof, $Ar_1$ is preferably substituted with 1 to 3 substituents selected from Substituent Group A1, $Ar_1$ is more preferably substituted with 1 or 2 substituents selected from the group consisting of a hydrogen atom, a halogen atom, a C3-8 cycloalkyl group, a C2-6 alkenyl group, a C2-6 alkynyl group, and a C1-6 alkyl group (wherein the C1-6 alkyl group may be substituted with 1 to 3 halogen atoms), and $Ar_1$ is most preferably substituted with a C1-6 alkyl group.

In the compound of the formula (I) or pharmacologically acceptable salt thereof, $Ar_2$ is preferably a pyrimidinyl group, pyridinyl group or phenyl group, and $Ar_2$ is more preferably a phenyl group or pyridinyl group.

In the compound of the formula (I) or pharmacologically acceptable salt thereof, $Ar_2$ is preferably substituted with 1 to 3 substituents selected from Substituent Group A2, $Ar_2$ is preferably substituted with 1 to 3 substituents selected from the group consisting of a hydrogen atom, a halogen atom, a hydroxyl group, a cyano group, C1-6 alkoxy group (wherein the C1-6 alkoxy group may be substituted with 1 to 3 substituents selected from the group consisting of a C1-6 alkyl group, a C2-6 alkenyl group, a C2-6 alkynyl group and a C3-8 cycloalkyl group), a C2-6 alkenyloxy group and a C2-6 alkynyloxy group, $Ar_2$ is more preferably substituted with 1 to 3 substituents selected from the group consisting of a hydrogen atom, a halogen atom, a cyano group and a C1-6 alkoxy group, and $Ar_2$ is most preferably substituted with a C1-6 alkoxy group.

In the compound of the formula (I) or pharmacologically acceptable salt thereof, $X_1$ is preferably —C≡C—, —$CR^3$=$CR^4$— or —$CR^5$= (wherein $R^3$, $R^4$ and $R^5$ are the same or different and each represent a substituent selected from Substituent Group A3), $X_1$ is more preferably —$CR^3$=$CR^4$— (wherein $R^3$ and $R^4$ represent a hydrogen atom, a C1-6 alkyl group, a C1-6 alkoxy group or a halogen atom), and $X_1$ is most preferably —$CR^3$=$CR^4$— (wherein $R^3$ and $R^4$ represent a hydrogen atom, or a halogen atom).

In the compound of the formula (I) or pharmacologically acceptable salt thereof, preferably, Het is monovalent and is a 5-membered aromatic heterocyclic group, a 5-membered aromatic heterocyclic group condensed with a 5- to 14-membered non-aromatic heterocyclic group or a 5-membered aromatic heterocyclic group condensed with a 6- to 14-membered non-aromatic hydrocarbon ring group, which may be substituted with 1 to 3 substituents selected from Substituent Group A4; preferably, Het is monovalent and is a 5-membered aromatic heterocyclic group represented by the formula:

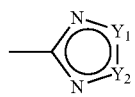

[Formula 27]

which may be substituted with 1 to 3 substituents selected from Substituent Group A4, wherein $Y_1$ and $Y_2$ are the same or different and each represent a methine group, nitrogen atom, oxygen atom or sulfur atom; and more preferably, Het is an imidazolyl group, tetrazolyl group or triazolyl group.

In the compound of the formula (I) or pharmacologically acceptable salt thereof, preferably, Het is monovalent and is a 5-membered aromatic heterocyclic group, a 5-membered aromatic heterocyclic group condensed with a 5- to 14-membered non-aromatic heterocyclic group or a 5-membered aromatic heterocyclic group condensed with a 6- to 14-membered non-aromatic hydrocarbon ring group, which may be substituted with 1 to 3 substituents selected from Substituent Group A4; and more preferably, Het is an imidazolyl group or triazolyl group that may be substituted with 1 or 2 substituents selected from the group consisting of a C1-6 alkyl group (wherein the C1-6 alkyl group may be substituted with 1 to 3 substituents selected from the group consisting of a halogen atom, a hydroxyl group, a C1-6 alkyl group, a C1-6 alkoxy group, a 6- to 14-membered aromatic hydrocarbon ring group (wherein the 6- to 14-membered aromatic hydrocarbon ring group may be substituted with 1 to 3 substituents selected from the group consisting of a halogen atom, a hydroxyl group, a C1-6 alkyl group (wherein the C1-6 alkyl group may be substituted with 1 to 3 substituents selected from the group consisting of a halogen atom, a hydroxyl group and a C1-6 alkoxy group) and a C1-6 alkoxy group (wherein the C1-6 alkoxy group may be substituted with 1 to 3 substituents selected from the group consisting of a halogen atom, a hydroxyl group and a C1-6 alkoxy group)) and a 5- to 14-membered aromatic heterocyclic group (wherein the 5- to 14-membered aromatic heterocyclic group may be substituted with 1 to 3 substituents selected from the group consisting of a halogen atom, a hydroxyl group, a C1-6 alkyl group (wherein the C1-6 alkyl group may be substituted with 1 to 3 substituents selected from the group consisting of a halogen atom, a hydroxyl group and a C1-6 alkoxy group) and a C1-6 alkoxy group (wherein the C1-6 alkoxy group may be substituted with 1 to 3 substituents selected from the group consisting of a halogen atom, a hydroxyl group and a C1-6 alkoxy group))), a C1-6 alkoxycarbonyl group, a carboxyl group, a carbamoyl group that may be substituted with a C1-6 alkyl group optionally having 1 to 3 halogen atoms, a 6- to 14-membered aromatic hydrocarbon ring group (wherein the 6- to 14-membered aromatic hydrocarbon ring group may be substituted with 1 to 3 substituents selected from the group consisting of a halogen atom, a hydroxyl group, a C1-6 alkyl group (wherein the C1-6 alkyl group may be substituted with 1 to 3 substituents selected from the group consisting of a halogen atom, a hydroxyl group and a C1-6 alkoxy group) and a C1-6 alkoxy group (wherein the C1-6 alkoxy group may be substituted with 1 to 3 substituents selected from the group consisting of a halogen atom, a hydroxyl group and a C1-6 alkoxy group)) and a 5- to 14-membered aromatic heterocyclic group (wherein the 5- to 14-membered aromatic heterocyclic group may be substituted with 1 to 3 substituents selected from the group consisting of a halogen atom, a hydroxyl group, a C1-6 alkyl group (wherein the C1-6 alkyl group may be substituted with 1 to 3 substituents selected from the group consisting of a halogen atom, a hydroxyl group and a C1-6 alkoxy group), a C1-6 alkoxy group (wherein the C1-6 alkoxy group may be substituted with 1 to 3 substituents selected from the group consisting of a halogen atom, a hydroxyl group and a C1-6 alkoxy group) and a halogen atom), or Het is monovalent and is a group represented by the formula:

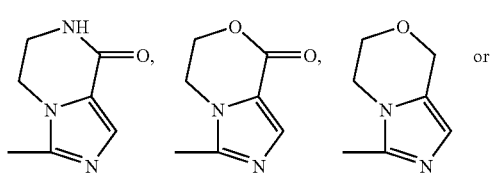

[Formula 28]

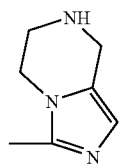

which may be substituted with 1 to 3 substituents selected from Substituent Group A4.

In the compound of the formula (I) or pharmacologically acceptable salt thereof, preferably, Het is divalent and is a 5-membered aromatic heterocyclic group, a 5-membered aromatic heterocyclic group condensed with a 5- to 14-membered non-aromatic heterocyclic group or a 5-membered aromatic heterocyclic group condensed with a 6- to 14-membered non-aromatic hydrocarbon ring group, which may be substituted with 1 to 3 substituents selected from Substituent Group A4; and more preferably, Het is divalent and represented by the formula:

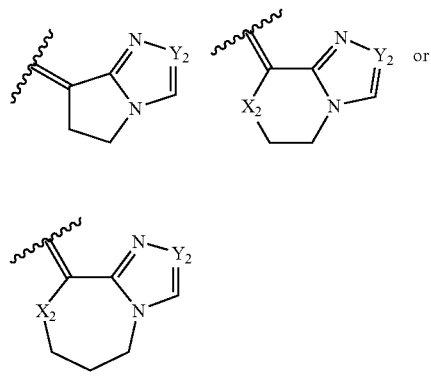

[Formula 29]

which may be substituted with 1 to 3 substituents selected from Substituent Group A4, wherein $X_2$ represents an oxygen atom or a methylene group, and $Y_4$ and $Y_5$ are the same or different and each represent a methine group or a nitrogen atom, Het is divalent and represented by the formula:

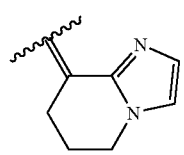

[Formula 30]

which may be substituted with 1 to 3 substituents selected from Substituent Group A4, or Het is divalent and is a group represented by the formula:

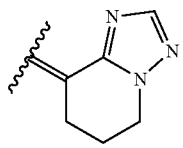

[Formula 31]

which may be substituted with 1 to 3 substituents selected from Substituent Group A4.

In the compound of the formula (I) or pharmacologically acceptable salt thereof, preferably, Het is monovalent and is a group represented by the formula:

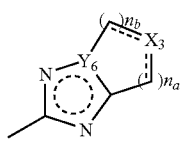

[Formula 32]

which may be substituted with 1 to 3 substituents selected from Substituent Group A4, wherein ⋯ represents a single bond or a double bond, $X_3$ represents a methine group or methylene group, an imino group, an oxygen atom, a sulfur atom or —$SO_2$—, which may be substituted with a substituent selected from Substituent Group A4, $Y_6$ represents a carbon atom or a nitrogen atom, and $n_a$ and $n_b$ independently represent an integer of 0 to 3; and more preferably, Het is monovalent and is a group represented by the formula:

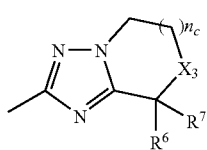

[Formula 33]

which may be substituted with 1 to 3 substituents selected from Substituent Group A4, wherein $R^6$ and $R^7$ are the same or different and each represent a substituent selected from Substituent Group A4, $X_3$ represents a methine group or methylene group, an imino group, an oxygen atom, a sulfur atom or —$SO_2$—, which may be substituted with a substituent selected from Substituent Group A4, and $n_c$ represents an integer of 0 to 3.

In the compound of the formula (I) or pharmacologically acceptable salt thereof, preferably, Het is monovalent and is a group represented by the formula:

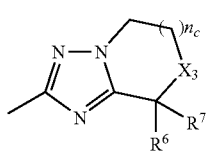

[Formula 34]

wherein $R^6$ and $R^7$ are the same or different and each represent a substituent selected from Substituent Group A4, $X_3$ represents a methine group or methylene group, an imino group, an oxygen atom, a sulfur atom or —$SO_2$—, which may be substituted with a substituent selected from Substituent Group A4, and $n_c$ represents an integer of 0 to 3. More preferably, $R^6$ represents a 6- to 14-membered aromatic hydrocarbon ring group or 5- to 14-membered aromatic heterocyclic group that may be substituted with 1 to 3 substituents selected from Substituent Group A5, and $R^7$ represents a substituent selected from Substituent Group A4. Most preferably, $R^6$ represents a phenyl group, naphthyl group, or pyridinyl group that may be substituted with 1 to 3 substituents selected from the group consisting of a hydrogen atom, a halogen atom, a cyano group, a C1-6 alkoxy group (wherein the C1-6 alkoxy group may be substituted with 1 to 3 halogen atoms), a C1-6 alkyl group (wherein the C1-6 alkyl group may be substituted with 1 to 3 halogen atoms, and an amino group that may be substituted with 1 to 2 C1-6 alkyl groups; and $R^7$ represents a substituent group selected from the group consisting of a hydrogen atom, a halogen atom, a hydroxyl group, a cyano group, a C1-6 alkyl group, a C2-6 alkenyl group, a C2-6 alkynyl group, and an amino group that may be substituted with 1 to 2 C1-6 alkyl groups.

In the compound of the formula (I) or pharmacologically acceptable salt thereof, preferably, Het is monovalent and is a group represented by the formula:

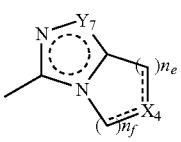

[Formula 35]

which may be substituted with 1 to 3 substituents selected from Substituent Group A4, wherein ⋯ represents a single bond or a double bond, $X_4$ represents a methine group or methylene group, an imino group, an oxygen atom, a sulfur atom or —$SO_2$—, which may be substituted with a substituent selected from Substituent Group A4, $Y_7$ represents a carbon atom or a nitrogen atom, and $n_e$ and $n_f$ independently represent an integer of 0 to 3. More preferably, Het is a group represented by the formula:

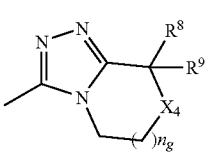

[Formula 36]

which may be substituted with 1 to 3 substituents selected from Substituent Group A4, wherein $R^8$ and $R^9$ are the same or different and each represent a substituent selected from Substituent Group A4, $X_4$ represents a methine group or methylene group, an imino group, an oxygen atom, a sulfur atom or —$SO_2$—, which may be substituted with a substituent selected from Substituent Group A4, and $n_g$ represent an integer of 0 to 2.

In the compound of the formula (I) or pharmacologically acceptable salt thereof, preferably, Het is monovalent and is a group represented by the formula:

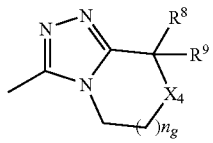

[Formula 37]

which may be substituted with 1 to 3 substituents selected from Substituent Group A4, wherein $R^8$ and $R^9$ are the same or different and each represent a substituent selected from Substituent Group A4, $X_4$ represents a methine group or methylene group, an imino group, an oxygen atom, a sulfur atom or —$SO_2$—, which may be substituted with a substituent selected from Substituent Group A4, and $n_g$ represent an integer of 0 to 2. More preferably, $R^8$ represents a 6- to 14-membered aromatic hydrocarbon ring group or 5- to 14-membered aromatic heterocyclic group that may be substituted with 1 to 3 substituents selected from Substituent Group A5; and $R^9$ is a substituent selected from Substituent Group A4. Most preferably, $R^8$ represents a phenyl group, pyridinyl group or naphtyl group that may be substituted with 1 to 3 substituents selected from the group consisting of a hydrogen atom, a halogen atom, a cyano group, a C1-6 alkoxy group (wherein the C1-6 alkoxy group group may be substituted with 1 to 3 halogen atoms), a C1-6 alkyl group (wherein the C1-6 alkyl group may be substituted with 1 to 3 halogen atoms, and an amino group that may be substituted with 1 to 2 C1-6 alkyl groups; and $R^9$ represents an amine group that may be substituted with a hydrogen atom, a halogen atom, a hydroxyl group, a cyano group, a C1-6 alkyl group, a C2-6 alkenyl group, a C2-6 alkynyl group, or 1 to 2 C1-6 alkyl groups.

In particular, a compound selected from the following group or a pharmacologically acceptable salt thereof according to claim 1 is particularly suitable, for example, and is useful as a therapeutic or prophylactic agent for a disease caused by amyloid-β such as Alzheimer's disease, senile dementia, Down's syndrome or amyloidosis.

1) 4-(4-fluorophenyl)-2-{(E)-2-[3-methoxy-4-(4-methyl-1H-imidazol-1-yl)phenyl]vinyl}-1H-imidazole,
2) 4-(4-fluorophenyl)-2-{(E)-2-[3-methoxy-4-(4-methyl-1H-imidazol-1-yl)phenyl]vinyl}-1-methyl-1H-imidazole,
3) 2-{(E)-2-[3-methoxy-4-(4-methyl-1H-imidazol-1-yl)phenyl]vinyl}-1-methyl-5-phenyl-1H-imidazole,
4) 2-{(E)-2-[3-methoxy-4-(4-methyl-1H-imidazol-1-yl)phenyl]vinyl}-4-phenyl-1H-imidazole,
5) 2-{(E)-2-[3-methoxy-4-(4-methyl-1H-imidazol-1-yl)phenyl]vinyl}-1-methyl-4-phenyl-1H-imidazole,
6) methyl 5-(4-fluorophenyl)-2-{(E)-2-[3-methoxy-4-(4-methyl-1H-imidazol-1-yl)phenyl]vinyl}-1H-imidazole-4-carboxylate,
7) 5-(4-fluorophenyl)-2-{(E)-2-[3-methoxy-4-(4-methyl-1H-imidazol-1-yl)phenyl]vinyl}-(1H-imidazol-4-yl)methanol,
8) 5-(4-fluorophenyl)-2-{(E)-2-[3-methoxy-4-(4-methyl-1H-imidazol-1-yl)phenyl]vinyl}-1H-imidazole-4-carboxylic acid,
9) 5-(4-fluorophenyl)-2-{(E)-2-[3-methoxy-4-(4-methyl-1H-imidazol-1-yl)phenyl]vinyl}-1H-imidazole-4-carboxylic acid (2-chloroethyl)amide,
10) 1-(4-fluorophenyl)-3-{(E)-2-[3-methoxy-4-(4-methyl-1H-imidazol-1-yl)phenyl]vinyl}-6,7-dihydro-5H-imidazo[1,5-a]pyrazin-8-one,
11) 1-(4-fluorophenyl)-3-{(E)-2-[3-methoxy-4-(4-methyl-1H-imidazol-1-yl)phenyl]vinyl}-7-methyl-6,7-dihydro-5H-imidazo[1,5-a]pyrazin-8-one,
12) 1-(4-fluorophenyl)-3-{(E)-2-[3-methoxy-4-(4-methyl-1H-imidazol-1-yl)phenyl]vinyl}-5,6-dihydroimidazo[5,1-c][1,4]oxazin-8-one,
13) 1-(4-fluorophenyl)-3-{(E)-2-[3-methoxy-4-(4-methyl-1H-imidazol-1-yl)phenyl]vinyl}-5,6-dihydro-8H-imidazo[5,1-c][1,4]oxazine,
14) 2-{4-(4-fluorophenyl)-5-methoxymethyl-2-{(E)-2-[3-methoxy-4-(4-methyl-1H-imidazol-1-yl)phenyl]vinyl}imidazol-1-yl}ethanol,
15) 1-(4-fluorophenyl)-3-{(E)-2-[3-methoxy-4-(4-methyl-1H-imidazol-1-yl)phenyl]vinyl}-7-methyl-5,6,7,8-tetrahydroimidazo[1,5-a]pyrazine,
16) 3-(3-fluorophenyl)-5-{(E)-2-[3-methoxy-4-(4-methyl-1H-imidazol-1-yl)phenyl]vinyl}-4H-[1,2,4]triazole,
17) 3-(4-fluorobenzyl)-5-{(E)-2-[3-methoxy-4-(4-methyl-1H-imidazol-1-yl)phenyl]vinyl}-4H-[1,2,4]triazole,
18) 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine,
19) 2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine,
20) 2-(4-fluorophenyl)-8-{1-[3-methoxy-4-(4-methyl-1H-imidazol-1-yl)phenyl]-(E)-methylidene}-5,6,7,8-tetrahydro[1,2,4]triazolo[1,5-a]pyridine,
21) methyl 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylate,
22) methyl 2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-3-carboxylate,
23) {3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridin-2-yl}methanol,
24) {2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridin-3-yl]methanol,
25) 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylic acid,
26) 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylic acid dimethylamide,
27) 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylic acid methylamide,
28) 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylic acid amide,
29) 1-(4-fluorobenzyl)-2-{(E)-2-[3-methoxy-4-(4-methyl-1H-imidazol-1-yl)phenyl]vinyl}-4,5-dimethyl-1H-imidazole,
30) 8-{1-[3-methoxy-4-(4-methyl-1H-imidazol-1-yl)phenyl]-(E)-methylidene}-2-pyridin-4-yl-5,6,7,8-tetrahydroimidazo[1,2-a]pyridine,
31) 3-[1-(4-fluorophenyl)ethyl]-5-{(E)-2-[3-methoxy-4-(4-methyl-1H-imidazol-1-yl)phenyl]vinyl}-4H-[1,2,4]triazole, 32) 3-[2-(4-fluorophenyl)ethyl]-5-{(E)-2-[3-methoxy-4-(4-methyl-1H-imidazol-1-yl)phenyl]vinyl}-4H-[1,2,4]triazole,
33) 4-(4-fluorobenzyl)-2-{(E)-2-[3-methoxy-4-(4-methyl-1H-imidazol-1-yl)phenyl]vinyl}-1H-imidazole,
34) 5-(4-fluorobenzyl)-3-{(E)-2-[3-methoxy-4-(4-methyl-1H-imidazol-1-yl)phenyl]vinyl}-1-methyl-1H-[1,2,4]triazole,
35) 3-(4-fluorobenzyl)-5-{(E)-2-[3-methoxy-4-(4-methyl-1H-imidazol-1-yl)phenyl]vinyl}-1-methyl-1H-[1,2,4]triazole,
36) (+)-3-[1-(4-fluorophenyl)ethyl]-5-{(E)-2-[3-methoxy-4-(4-methyl-1H-imidazol-1-yl)phenyl]vinyl}-4H-[1,2,4]triazole,
37) (−)-3-[1-(4-fluorophenyl)ethyl]-5-{(E)-2-[3-methoxy-4-(4-methyl-1H-imidazol-1-yl)phenyl]vinyl}-4H-[1,2,4]triazole,
38) 5-[1-(4-fluorophenyl)ethyl]-3-{(E)-2-[3-methoxy-4-(4-methyl-1H-imidazol-1-yl)phenyl]vinyl}-1-methyl-1H-[1,2,4]triazole,
39) 3-[1-(4-fluorophenyl)ethyl]-5-{(E)-2-[3-methoxy-4-(4-methyl-1H-imidazol-1-yl)phenyl]vinyl}-1-methyl-1H-[1,2,4]triazole,
40) 5-[1-(4-fluorophenyl)ethyl]-3-{(E)-2-[3-methoxy-4-(4-methyl-1H-imidazol-1-yl)phenyl]vinyl}-1-methyl-1H-[1,2,4]triazole,
41) 3-[1-(4-fluorophenyl)ethyl]-5-{(E)-2-[3-methoxy-4-(4-methyl-1H-imidazol-1-yl)phenyl]vinyl}-1-methyl-1H-[1,2,4]triazole,
42) (+)-3-[1-(4-fluorophenyl)ethyl]-5-{(E)-2-[3-methoxy-4-(4-methyl-1H-imidazol-1-yl)phenyl]vinyl}-4-methyl-4H-[1,2,4]triazole,
43) (−)-3-[1-(4-fluorophenyl)ethyl]-5-{(E)-2-[3-methoxy-4-(4-methyl-1H-imidazol-1-yl)phenyl]vinyl}-4-methyl-4H-[1,2,4]triazole,
44) 3-{(E)-2-[3-methoxy-4-(4-methyl-1H-imidazol-1-yl)phenyl]vinyl}-5-(1-phenylethyl)-4H-[1,2,4]triazole,
45) 3-{(E)-2-[3-methoxy-4-(4-methyl-1H-imidazol-1-yl)phenyl]vinyl}-1-methyl-5-(1-phenylethyl)-1H-[1,2,4]triazole,
46) 5-{(E)-2-[3-methoxy-4-(4-methyl-1H-imidazol-1-yl)phenyl]vinyl}-1-methyl-3-(1-phenylethyl)-1H-[1,2,4]triazole,
47) 3-(4-fluorophenyl)-5-{(E)-2-[3-methoxy-4-(4-methyl-1H-imidazol-1-yl)phenyl]vinyl}-4H-[1,2,4]triazole,
48) 5-(4-fluorophenyl)-2-{(E)-2-[3-methoxy-4-(4-methyl-1H-imidazol-1-yl)phenyl]vinyl}-4-methyl-1H-imidazole,
49) 3-{(E)-2-[3-methoxy-4-(4-methyl-1H-imidazol-1-yl)phenyl]vinyl}-5-(1-methyl-1-phenylethyl)-4H-[1,2,4]triazole,
50) 3-{(E)-2-[3-methoxy-4-(4-methyl-1H-imidazol-1-yl)phenyl]vinyl}-1-phenyl-5,6,7,8-tetrahydroimidazo[1,5-a]pyridine,
51) (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
52) (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
53) (+)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
54) (−)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
55) (+)-5-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
56) (−)-5-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
57) (+)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
58) (−)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
59) (+)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine,
60) (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine,
61) (+)-2-{(E)-2-[3-fluoro-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
62) (−)-2-{(E)-2-[3-fluoro-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
63) (+)-2-{(E)-2-[3-methoxy-4-(4-methyl-1H-imidazol-1-yl)phenyl]vinyl}-8-(2,4,6-trifluorophenyl)-5,6,7,8-tetrahydro[1,2,4]triazolo[1,5-a]pyridine,
64) (−)-2-{(E)-2-[3-methoxy-4-(4-methyl-1H-imidazol-1-yl)phenyl]vinyl}-8-(2,4,6-trifluorophenyl)-5,6,7,8-tetrahydro[1,2,4]triazolo[1,5-a]pyridine,
65) 7-(4-fluorophenyl)-2-{(E)-2-[3-methoxy-4-(4-methyl-1H-imidazol-1-yl)phenyl]vinyl}-6,7-dihydro-5H-pyrrolo[1,2-b][1,2,4]triazol-7-ol,
66) (−)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol,
67) (+)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol,
68) (+)-2-{(E)-2-[2-fluoro-5-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
69) (−)-2-{(E)-2-[2-fluoro-5-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
70) (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol,
71) (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol,
72) (+)-8-fluoro-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
73) (−)-8-fluoro-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
74) 8-(4-fluorophenyl)-2-{(E)-2-[3-methoxy-4-(4-methyl-1H-imidazol-1-yl)phenyl]vinyl}-5,6-dihydro[1,2,4]triazolo[1,5-a]pyridine,
75) (−)-2-{(E)-2-[3-methoxy-4-(4-methyl-1H-imidazol-1-yl)phenyl]vinyl}-8-(4-methoxyphenyl)-5,6,7,8-tetrahydro-[1,2,4]triazolo[1,5-a]pyridine,
76) (+)-2-{(E)-2-[3-methoxy-4-(4-methyl-1H-imidazol-1-yl)phenyl]vinyl}-8-(4-methoxyphenyl)-5,6,7,8-tetrahydro-[1,2,4]triazolo[1,5-a]pyridine, 77) (−)-2-{(E)-2-[3-methoxy-4-(4-methyl-1H-imidazol-1-yl)phenyl]vinyl}-8-(3,4,5-trifluorophenyl)-5,6-dihydro-8H-[1,2,4]triazolo[5,1-c][1,4]oxazine,
78) (+)-2-{(E)-2-[3-methoxy-4-(4-methyl-1H-imidazol-1-yl)phenyl]vinyl}-8-(3,4,5-trifluorophenyl)-5,6-dihydro-8H-[1,2,4]triazolo[5,1-c][1,4]oxazine,
79) (−)-8-(4-fluorophenyl)-2-{(E)-2-[3-methoxy-4-(4-methyl-1H-imidazol-1-yl)phenyl]vinyl}-8-methyl-5,6,7,8-tetrahydro-[1,2,4]triazolo[1,5-a]pyridine,
80) (+)-8-(4-fluorophenyl)-2-{(E)-2-[3-methoxy-4-(4-methyl-1H-imidazol-1-yl)phenyl]vinyl}-8-methyl-5,6,7,8-tetrahydro-[1,2,4]triazolo[1,5-a]pyridine,
81) 2-(4-fluorobenzyl)-8-{1-[3-methoxy-4-(4-methyl-1H-imidazol-1-yl)phenyl]-(E)-methylidene}-5,6,7,8-tetrahydro[1,2,4]triazolo[1,5-a]pyridine,
82) 3-(4-fluorobenzyl)-8-{1-[3-methoxy-4-(4-methyl-1H-imidazol-1-yl)phenyl]-(E)-methylidene}-5,6,7,8-tetrahydro[1,2,4]triazolo[4,3-a]pyridine,
83) 3-{(E)-2-[3-methoxy-4-(4-methyl-1H-imidazol-1-yl)phenyl]vinyl}-5-((S)-1-phenylethyl)-4H-[1,2,4]triazole,
84) 3-{(E)-2-[3-methoxy-4-(4-methyl-1H-imidazol-1-yl)phenyl]vinyl}-5-((R)-1-phenylethyl)-4H-[1,2,4]triazole,
85) (−)-8-(4-fluorophenyl)-8-methoxy-2-{(E)-2-[3-methoxy-4-(4-methyl-1H-imidazol-1-yl)phenyl]vinyl}-5,6,7,8-tetrahydro[1,2,4]triazolo[1,5-a]pyridine,
86) (+)-8-(4-fluorophenyl)-8-methoxy-2-{(E)-2-[3-methoxy-4-(4-methyl-1H-imidazol-1-yl)phenyl]vinyl}-5,6,7,8-tetrahydro[1,2,4]triazolo[1,5-a]pyridine,
87) (−)-8-methoxy-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
88) (+)-8-methoxy-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine,
89) (−)-8-methoxy-2-{(E)-2-[3-methoxy-4-(4-methyl-1H-imidazol-1-yl)phenyl]vinyl}-8-(4-methoxyphenyl)-5,6,7,8-tetrahydro[1,2,4]triazolo[1,5-a]pyridine,
90) (+)-8-methoxy-2-{(E)-2-[3-methoxy-4-(4-methyl-1H-imidazol-1-yl)phenyl]vinyl}-8-(4-methoxyphenyl)-5,6,7,8-tetrahydro[1,2,4]triazolo[1,5-a]pyridine,
91) 5-[methoxy-(4-methoxyphenyl)methyl]-3-{(E)-2-[3-methoxy-4-(4-methyl-1H-imidazol-1-yl)phenyl]vinyl}-1H-[1,2,4]triazole,
92) 7-(4-fluorophenyl)-7-methoxy-2-{(E)-2-[3-methoxy-4-(4-methyl-1H-imidazol-1-yl)phenyl]vinyl}-6,7-dihydro-5H-pyrrolo[1,2-b][1,2,4]triazole,
93) 4-(4-fluorophenyl)-2-{(E)-2-[3-methoxy-4-(4-methyl-1H-imidazol-1-yl)phenyl]vinyl}-1-(tetrahydrofuran-2-ylmethyl)-1H-imidazole,
94) 4-{5-{(E)-2-[3-methoxy-4-(4-methyl-1H-imidazol-1-yl)phenyl]vinyl}-4H-[1,2,4]triazol-3-yl}-4-(3,4,5-trifluorophenyl)butan-1-ol,
95) (+)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine-8-carbonitrile,
96) (−)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine-8-carbonitrile,
97) (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile,
98) (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile,
99) (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ylamine,
100) (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ylamine,
101) 2-{(E)-2-[3-fluoro-4-(4-methyl-1H-imidazol-1-yl)phenyl]vinyl}-8-(4-fluorophenyl)-5,6,7,8-tetrahydro[1,2,4]triazolo[1,5-a]pyridine,
102) (−)-2-{(E)-2-[3-fluoro-4-(4-methyl-1H-imidazol-1-yl)phenyl]vinyl}-8-(4-fluorophenyl)-5,6,7,8-tetrahydro[1,2,4]triazolo[1,5-a]pyridin-8-ol,
103) (+)-2-{(E)-2-[3-fluoro-4-(4-methyl-1H-imidazol-1-yl)phenyl]vinyl}-8-(4-fluorophenyl)-5,6,7,8-tetrahydro[1,2,4]triazolo[1,5-a]pyridin-8-ol,
104) 2-{(E)-2-[2-fluoro-5-methoxy-4-(4-methyl-1H-imidazol-1-yl)phenyl]vinyl}-8-(4-fluorophenyl)-5,6,7,8-tetrahydro[1,2,4]triazolo[1,5-a]pyridine,
105) (+)-2-{(E)-2-[2-fluoro-5-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol,
106) (−)-2-{(E)-2-[2-fluoro-5-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol,
107) 2-{(Z)-1-fluoro-2-[3-methoxy-4-(4-methyl-1H-imidazol-1-yl)phenyl]vinyl}-8-(4-fluorophenyl)-5,6,7,8-tetrahydro[1,2,4]triazolo[1,5-a]pyridine,
108) (−)-2-{(Z)-1-fluoro-2-[3-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol,
109) (+)-2-{(Z)-1-fluoro-2-[3-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol,
110) (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridin-8-ol,
111) (+)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridin-8-ol,
112) (+)-2-{(E)-2-[3-methoxy-4-(4-methyl-1H-imidazol-1-yl)phenyl]vinyl}-7-(3,4,5-trifluorophenyl)-6,7-dihydro-5H-pyrrolo[1,2-b][1,2,4]triazole,
113) (−)-2-{(E)-2-[3-methoxy-4-(4-methyl-1H-imidazol-1-yl)phenyl]vinyl}-7-(3,4,5-trifluorophenyl)-6,7-dihydro-5H-pyrrolo[1,2-b][1,2,4]triazole,
114) (+)-2-{(E)-2-[3-methoxy-4-(4-methyl-1H-imidazol-1-yl)phenyl]vinyl}-7-(3,4,5-trifluorophenyl)-6,7-dihydro-5H-pyrrolo[1,2-b][1,2,4]triazol-7-ol,
115) (−)-2-{(E)-2-[3-methoxy-4-(4-methyl-1H-imidazol-1-yl)phenyl]vinyl}-7-(3,4,5-trifluorophenyl)-6,7-dihydro-5H-pyrrolo[1,2-b][1,2,4]triazol-7-ol,
116) (+)-8-(3,4-difluorophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine,
117) (−)-8-(3,4-difluorophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine,
118) 4-(4-fluorophenyl)-2-{(E)-2-[3-methoxy-4-(4-methyl-1H-imidazol-1-yl)phenyl]vinyl}-4,5,6,7-tetrahydro[1,2,4]triazolo[1,5-a]pyrimidine,
119) (+)-3-{(E)-2-[3-methoxy-4-(4-methyl-1H-imidazol-1-yl)phenyl]vinyl}-5-phenyl-5,6,7,8-tetrahydro[1,2,4]triazolo[4,3-a]pyridine,
120) (−)-3-{(E)-2-[3-methoxy-4-(4-methyl-1H-imidazol-1-yl)phenyl]vinyl}-5-phenyl-5,6,7,8-tetrahydro[1,2,4]triazolo[4,3-a]pyridine,
121) 4-chloro-2-{(E)-2-[3-methoxy-4-(4-methyl-1H-imidazol-1-yl)phenyl]vinyl}-1H-imidazole,
122) 4-(4-methoxyphenyl)-2-{(E)-2-[3-methoxy-4-(4-methyl-1H-imidazol-1-yl)phenyl]vinyl}-1H-imidazole, 123) 4-(3-methoxyphenyl)-2-{(E)-2-[3-methoxy-4-(4-methyl-1H-imidazol-1-yl)phenyl]vinyl}-1H-imidazole,
124) 4-(2-methoxyphenyl)-2-{(E)-2-[3-methoxy-4-(4-methyl-1H-imidazol-1-yl)phenyl]vinyl}-1H-imidazole,
125) 4-(4-chlorophenyl)-2-{(E)-2-[3-methoxy-4-(4-methyl-1H-imidazol-1-yl)phenyl]vinyl}-1H-imidazole,
126) 4-(4-biphenyl)-2-{(E)-2-[3-methoxy-4-(4-methyl-1H-imidazol-1-yl)phenyl]vinyl}-1H-imidazole,
127) 4-(4-propyl)-2-{(E)-2-[3-methoxy-4-(4-methyl-1H-imidazol-1-yl)phenyl]vinyl}-1H-imidazole,
128) (+)-2-{(E)-2-[3-methoxy-4-(4-methyl-1H-imidazol-1-yl)phenyl]vinyl}-8-(4-trifluoromethoxyphenyl)-5,6,7,8-tetrahydro[1,2,4]triazolo[1,5-a]pyridine,
129) (−)-2-{(E)-2-[3-methoxy-4-(4-methyl-1H-imidazol-1-yl)phenyl]vinyl}-8-(4-trifluoromethoxyphenyl)-5,6,7,8-tetrahydro[1,2,4]triazolo[1,5-a]pyridine,
130) (+)-2-{(E)-2-[3-methoxy-4-(4-methyl-1H-imidazol-1-yl)phenyl]vinyl}-8-naphthalen-1-yl-5,6,7,8-tetrahydro[1,2,4]triazolo[1,5-a]pyridine,
131) (−)-2-{(E)-2-[3-methoxy-4-(4-methyl-1H-imidazol-1-yl)phenyl]vinyl}-8-naphthalen-1-yl-5,6,7,8-tetrahydro[1,2,4]triazolo[1,5-a]pyridine,
132) (+)-2-{(E)-2-[3-methoxy-4-(4-methyl-1H-imidazol-1-yl)phenyl]vinyl}-8-(4-methoxyphenyl)-5,6,7,8-tetrahydro[1,2,4]triazolo[1,5-a]pyridin-8-ol,
133) (−)-2-{(E)-2-[3-methoxy-4-(4-methyl-1H-imidazol-1-yl)phenyl]vinyl}-8-(4-methoxyphenyl)-5,6,7,8-tetrahydro[1,2,4]triazolo[1,5-a]pyridin-8-ol,
134) (+)-2-{(E)-2-[3-methoxy-4-(4-methyl-1H-imidazol-1-yl)phenyl]vinyl}-8-(4-trifluoromethoxyphenyl)-5,6-dihydro-8H-[1,2,4]triazolo[5,1-c][1,4]oxazine,
135) (−)-2-{(E)-2-[3-methoxy-4-(4-methyl-1H-imidazol-1-yl)phenyl]vinyl}-8-(4-trifluoromethoxyphenyl)-5,6-dihydro-8H-[1,2,4]triazolo[5,1-c][1,4]oxazine,
136) (−)-2-{(E)-2-[3-methoxy-4-(4-methyl-1H-imidazol-1-yl)phenyl]vinyl}-8-naphthalen-1-yl-5,6,7,8-tetrahydro[1,2,4]triazolo[1,5-a]pyridin-8-ol,
137) (+)-2-{(E)-2-[3-methoxy-4-(4-methyl-1H-imidazol-1-yl)phenyl]vinyl}-8-naphthalen-1-yl-5,6,7,8-tetrahydro[1,2,4]triazolo[1,5-a]pyridin-8-ol,
138) (−)-2-{(E)-2-[3-methoxy-4-(4-methyl-1H-imidazol-1-yl)phenyl]vinyl}-8-p-tolyl-5,6-dihydro-8H-[1,2,4]triazolo[5,1-c][1,4]oxazine,
139) (+)-2-{(E)-2-[3-methoxy-4-(4-methyl-1H-imidazol-1-yl)phenyl]vinyl}-8-p-tolyl-5,6-dihydro-8H-[1,2,4]triazolo[5,1-c][1,4]oxazine,
140) (+)-2-{(E)-2-[3-methoxy-4-(4-methyl-1H-imidazol-1-yl)phenyl]vinyl}-8-(2,4,6-trifluorophenyl)-5,6-dihydro-8H-[1,2,4]triazolo[5,1-c][1,4]oxazine,
141) (−)-2-{(E)-2-[3-methoxy-4-(4-methyl-1H-imidazol-1-yl)phenyl]vinyl}-8-(2,4,6-trifluorophenyl)-5,6-dihydro-8H-[1,2,4]triazolo[5,1-c][1,4]oxazine,
142) (+)-8-(4-bromophenyl)-2-{(E)-2-[3-methoxy-4-(4-methyl-1H-imidazol-1-yl)phenyl]vinyl}-5,6-dihydro-8H-[1,2,4]triazolo[5,1-c][1,4]oxazine,
143) (−)-8-(4-bromophenyl)-2-{(E)-2-[3-methoxy-4-(4-methyl-1H-imidazol-1-yl)phenyl]vinyl}-5,6-dihydro-8H-[1,2,4]triazolo[5,1-c][1,4]oxazine,
144) (+)-8-(6-chloropyridin-3-yl)-2-{(E)-2-[3-methoxy-4-(4-methyl-1H-imidazol-1-yl)phenyl]vinyl}-5,6-dihydro-8H-[1,2,4]triazolo[5,1-c][1,4]oxazine,
145) (−)-8-(6-chloropyridin-3-yl)-2-{(E)-2-[3-methoxy-4-(4-methyl-1H-imidazol-1-yl)phenyl]vinyl}-5,6-dihydro-8H-[1,2,4]triazolo[5,1-c][1,4]oxazine,
146) (+)-4-(2-{(E)-2-[3-methoxy-4-(4-methyl-1H-imidazol-1-yl)phenyl]vinyl}-5,6-dihydro-8H-[1,2,4]triazolo[5,1-c][1,4]oxazin-8-yl)benzonitrile,
147) (−)-4-(2-{(E)-2-[3-methoxy-4-(4-methyl-1H-imidazol-1-yl)phenyl]vinyl}-5,6-dihydro-8H-[1,2,4]triazolo[5,1-c][1,4]oxazin-8-yl)benzonitrile,
148) (+)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
149) (−)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
150) (+)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridine,
151) (−)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridine,
152) (+)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol,
153) (−)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol,
154) (+)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridin-8-ol,
155) (−)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridin-8-ol,
156) (+)-4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile,
157) (−)-4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile,
158) (+)-4-{8-hydroxy-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile,
159) (−)-4-{8-hydroxy-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile,
160) {4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}phenyl}dimethylamine,
161) (S)-8-(4-chlorophenyl)-3-{(E)-2-[3-methoxy-4-(4-methyl-1H-imidazol-1-yl)phenyl]vinyl}-5,6,7,8-tetrahydro[1,2,4]triazolo[4,3-a]pyridine,
162) (R)-8-(4-chlorophenyl)-3-{(E)-2-[3-methoxy-4-(4-methyl-1H-imidazol-1-yl)phenyl]vinyl}-5,6,7,8-tetrahydro[1,2,4]triazolo[4,3-a]pyridine,
163) (+)-3-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[4,3-a]pyridine,
164) (−)-3-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[4,3-a]pyridine,
165) (+)-3-{(E)-2-[3-methoxy-4-(4-methyl-1H-imidazol-1-yl)phenyl]vinyl}-7-(3,4,5-trifluorophenyl)-6,7-dihydro-5H-pyrrolo[2,1-c][1,2,4]triazole,
166) (−)-3-{(E)-2-[3-methoxy-4-(4-methyl-1H-imidazol-1-yl)phenyl]vinyl}-7-(3,4,5-trifluorophenyl)-6,7-dihydro-5H-pyrrolo[2,1-c][1,2,4]triazole,
167) (S)-3-{(E)-2-[3-methoxy-4-(4-methyl-1H-imidazol-1-yl)phenyl]vinyl}-9-(3,4,5-trifluorophenyl)-6,7,8,9-tetrahydro-5H-[1,2,4]triazolo[4,3-a]azepine,
168) (R)-3-{(E)-2-[3-methoxy-4-(4-methyl-1H-imidazol-1-yl)phenyl]vinyl}-9-(3,4,5-trifluorophenyl)-6,7,8,9-tetrahydro-5H-[1,2,4]triazolo[4,3-a]azepine, 169) (+)-2-{(E)-2-[3-methoxy-4-(4-methyl-1H-imidazol-1-yl)phenyl]vinyl}-9-(3,4,5-trifluorophenyl)-6,7,8,9-tetrahydro-5H-[1,2,4]triazolo[1,5-a]azepine, 170) (−)-2-{(E)-2-[3-methoxy-4-(4-methyl-1H-imidazol-1-yl)phenyl]vinyl}-9-(3,4,5-trifluorophenyl)-6,7,8,9-tetrahydro-5H-[1,2,4]triazolo[1,5-a]azepine, 171) 3-(4-fluorophenyl)-8-{1-[3-methoxy-4-(4-methyl-1H-imidazol-1-yl)phenyl]-(E)-methylidene}-5,6,7,8-tetrahydro[1,2,4]triazolo[4,3-a]pyridine, 172) (−)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine, 173) (+)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine, 174) (−)-8-(2-bromophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine, 175) (+)-8-(2-bromophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine, 176) 8-(2-bromo-4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine, 177) 8-(2-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine, 178) 2-{(E)-2-[3-methoxy-4-(4-methyl-1H-imidazol-1-yl)phenyl]vinyl}-8-(2-methoxyphenyl)-5,6,7,8-tetrahydro[1,2,4]triazolo[1,5-a]pyridine, 179) 8-(3-bromophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and 180) 2-{(E)-2-[3-methoxy-4-(4-methyl-1H-imidazol-1-yl)phenyl]vinyl}-8-(2-nitrophenyl)-5,6,7,8-tetrahydro[1,2,4]triazolo[1,5-a]pyridine.

Methods for preparing the compound of the general formula (I) of the present invention will be described below.

The compound represented by the general formula (I):

[Formula 38]

(I)

wherein $Ar_1$, $Ar_2$, $X_1$ and Het are as defined above, is synthesized according to a method such as the following General Preparation Method 1 to General Preparation Method 8, for example.

[General Preparation Method 1]

Typically used General Preparation Method 1 for the compound of the general formula (I) of the present invention will be described below.

[Formula 39]

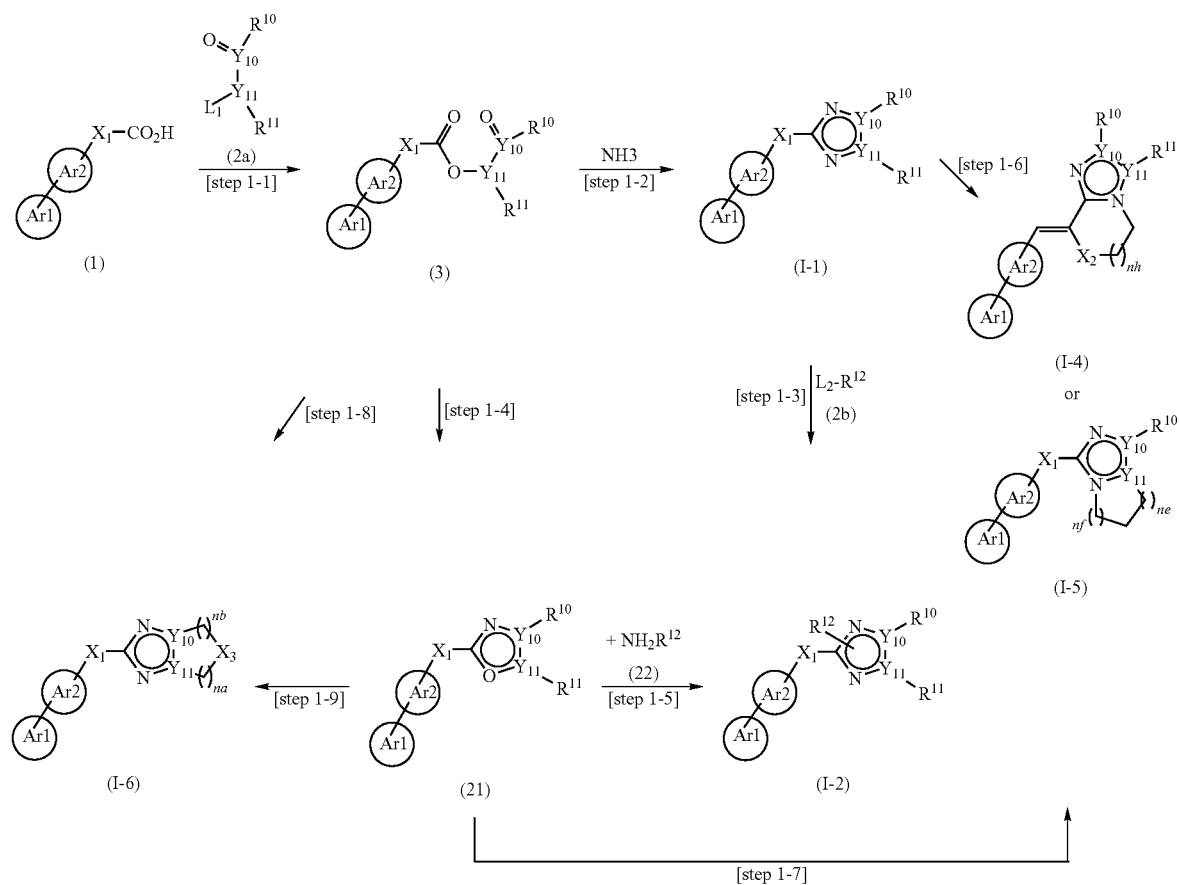

In the formula, $Ar_1$, $Ar_2$, $X_1$, $X_3$, $X_4$, na, nb, ne and nf are as defined above; $Y_{10}$ and $Y_{11}$ are the same or different and each represent a carbon atom, nitrogen atom or sulfur atom; $R_{10}$, $R_{11}$ and $R_{12}$ are the same or different and represent groups selected from the above Substituent Group A4 which may optionally form a ring; $L_1$ represents a halogen atom such as a chlorine atom, bromine atom or iodine atom, a sulfonate group such as a methanesulfonate group, p-toluenesulfonate group or trifluoromethanesulfonate group, or a hydroxyl group; $L_2$ represents a halogen atom such as a chlorine atom, bromine atom or iodine atom, or a sulfonate group such as a methanesulfonate group, p-toluenesulfonate group or trifluoromethanesulfonate group, a boronic acid group or a boronate group such as a pinacol boronate group; $X_2$ represents a methylene group or an oxygen atom; and nh represents an integer of 0 to 2.

The above General Preparation Method 1 includes a method of condensing a carboxylic acid compound (1) with a compound (2a) in Step 1-1 to convert the carboxylic acid compound (1) into an ester compound (3) and reacting the ester compound (3) with ammonia, an ammonium salt or formamide in Step 1-2 to prepare a compound of the general formula (I-1); a method of reacting the compound of the general formula (I-1) with a compound (2b) in Step 1-3 to prepare a compound of the general formula (I-2); a method of reacting the ester compound (3) with ammonia, an ammonium salt or formamide in Step 1-4 to convert the ester compound (3) into an oxazole compound (21) and then reacting the oxazole compound (21) with an amine compound (22) in Step 1-5 to prepare a compound of the general formula (I-2); a method of preparing a compound of the general formula (I-4) or a compound of the general formula (I-5) from the compound of the general formula (I-1) in Step 1-6; a method of preparing a compound of the general formula (I-4) or a compound of the general formula (I-5) from the oxazole compound (21) in Step 1-7; a method of preparing a compound of the general formula (I-6) from the ester compound (3) and ammonia, an ammonium salt or formamide in Step 1-8; and a method of preparing compound of the general formula (I-6) from the oxazole compound (21) in Step 1-9.

[Preparation of Compound of General Formula (I-4) or Compound of General Formula (I-5)]

The compound of the general formula (I-4) or the compound of the general formula (I-5) can be prepared from a compound of the general formula (I-1) by intramolecular cyclization reaction according to Step 1-6. Specifically, Step 1-6 as an intramolecular cyclization reaction may employ a known method described in many documents such as N-alkylation reaction (see The Journal of Organic Chemistry, 1977, vol. 42, p. 3925, for example). The compound of the general formula (I-4) or the compound of the general formula (I-5) can also be prepared from an oxazole compound (21) by intramolecular cyclization reaction according to Step 1-7. Specifically, Step 1-7 may employ a method of forming a triazole or imidazole ring and cyclizing the second ring at the same time in the presence or absence of a nitrogen atom source (see The Chemistry of Heterocyclic Compounds. Imidazole and Derivatives, Part I, p. 33, Inters. Publish. 1953, for example).

Step 1-6 is preferably, for example, a method of stirring a compound of the general formula (I-1), wherein $X_1$ is —$CR^3$=$CR^4$—, and $R^4$ represents a C1-6 alkyl group substituted with a halogen atom or a C1-6 alkoxy group substituted with a halogen atom, or $R^{11}$ represents a C1-6 alkyl group (wherein the C1-6 alkyl group is substituted with a halogen atom, a C1-6 alkoxy group substituted with a halogen atom or a C1-6 alkylamino group substituted with a halogen atom), in a solvent in the presence of 1.0 to 10.0 equivalents of a base with respect to the compound of the general formula (I-1). The base used varies according to the starting material and is not specifically limited. Preferable examples of the base include alkali metal hydrides (such as sodium hydride and lithium hydride), alkali metal salts (such as potassium carbonate, sodium carbonate and cesium carbonate), metal alkoxides (such as sodium methoxide and tert-butyl potassium) and organometallic salts (such as lithium diisopropyl amide and lithium hexamethyldisilazane). The solvent used varies according to the starting material, and is not specifically limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; polar solvents such as N,N-dimethylformamide and N-methylpyrrolidone; nonpolar solvents such as toluene and benzene; and a mixture thereof. The reaction temperature must be a temperature that can complete the reaction without promoting formation of an undesirable by-product, and is preferably −78° C. to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

Step 1-7 is preferably, for example, a method of stirring an oxazole compound (21), wherein $X_1$ is —$CR^3$=$CR^4$—, and $R^4$ represents a C1-6 alkyl group substituted with a halogen atom or a C1-6 alkoxy group substituted with a halogen atom, or R represents a C1-6 alkyl group (wherein the C1-6 alkyl group is substituted with a halogen atom, a C1-6 alkoxy group substituted with a halogen atom or a C1-6 alkylamino group substituted with a halogen atom), in a solvent in the presence of 1.0 to 100 equivalents of ammonia or an ammonium salt such as ammonium acetate with respect to the oxazole compound (21). Step 1-7 may also be a method of stirring an oxazole compound (21), wherein $X_1$ is —$CR^3$=$CR^4$—, and $R^4$ represents a C1-6 alkyl group substituted with an amino group or a C1-6 alkoxy group substituted with an amino group, or $R^{11}$ represents a C1-6 alkyl group (wherein the C1-6 alkyl group is substituted with an amino group, a C1-6 alkoxy group substituted with an amino group or a C1-6 alkylamino group substituted with an amino group), in a solvent. The solvent used is not specifically limited insofar as the solvent does not inhibit the reaction and allows the starting material to be dissolved therein to a certain extent. Preferable examples of the solvent include nonpolar solvents such as toluene and benzene; alcohol solvents such as methanol and ethanol; organic acids such as acetic acid; water; and a mixture thereof. The reaction temperature must be a temperature that can complete the reaction without promoting formation of an undesirable by-product, and is preferably room temperature to 250° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Compound of General Formula (I-6)]

The compound of the general formula (I-6) can be prepared from an ester compound (3) according to Step 1-8 using ammonia, an ammonium salt or formamide as a nitrogen source, for example. The compound of the general formula (I-6) can also be prepared from an oxazole compound (21) according to Step 1-9 using ammonia, an ammonium salt or formamide as a nitrogen source, for example. Specifically, Step 1-8 or Step 1-9 varies according to the starting material and is not specifically limited insofar as the conditions are similar to those in this reaction. A known method described in many documents may be used for the reaction (see The Chemistry of Heterocyclic Compounds. Imidazole and Derivatives, Part I, p. 33, Inters. Publish. 1953, for example). The reaction is preferably a method of stirring an ester compound (3) or an oxazole compound (21) and 1.0 to 100.0 equivalents of ammonia or an ammonium salt such as ammonium acetate with respect to the ester compound (3) or the oxazole compound (21) in a solvent, for example. The solvent used is not specifically limited insofar as the solvent does not inhibit the reaction and allows the starting material to be dissolved therein to a certain extent. Preferable examples of the solvent include nonpolar solvents such as toluene and benzene; alcohol solvents such as methanol and ethanol; organic acids such as acetic acid; water; and a mixture thereof. Formamide may optionally be used as a nitrogen atom source and a solvent. The reaction temperature must be a temperature that can complete the reaction without promoting formation of an undesirable by-product, and is preferably room temperature to 250° C., for example. The yield may be improved when the reaction is performed using a tight container. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Compound of General Formula (I-2)]

The compound of the general formula (I-2) can be prepared by reacting a compound of the general formula (I-1) with a compound of the general formula (2b) according to Step 1-3. Specifically, Step 1-3 may employ a known method described in many documents such as N-alkylation reaction (see The Journal of Organic Chemistry, 1977, vol. 42, p. 3925, for example) or N-arylation reaction (see The Journal of Organic Chemistry, 2001, vol. 66, p. 7892; Journal of Medicinal Chemistry, 1981, vol. 24, p. 1139; or Journal of Medicinal Chemistry, 1991, vol. 39, p. 2671, for example).

N-alkylation reaction is preferably, for example, a method of stirring a compound of the general formula (I-1) and 1.0 to 10.0 equivalents of a compound (2b), wherein $L_2$ represents a halogen atom such as a chlorine atom, bromine atom or iodine atom or a sulfonate group such as a methanesulfonate group, p-toluenesulfonate group or trifluoromethanesulfonate group, with respect to the compound of the general formula (I-1) in a solvent in the presence of 1.0 to 10.0 equivalents of a base with respect to the compound of the general formula (I-1). The base used varies according to the starting material and is not specifically limited. Preferable examples of the base include alkali metal hydrides (such as sodium hydride and lithium hydride), alkali metal salts (such as potassium carbonate, sodium carbonate and cesium carbonate) and metal alkoxides (such as sodium methoxide and potassium tert-butoxide). The solvent used varies according to the starting material, and is not specifically limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; polar solvents such as N,N-dimethylformamide and N-methylpyrrolidone; nonpolar solvents such as toluene and benzene; and a mixture thereof. The reaction temperature must be a temperature that can complete the reaction without promoting formation of an undesirable by-product, and is preferably 0° C. to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

N-arylation reaction may be i) Ullmann reaction, ii) a coupling reaction of an arylboronic acid derivative using a copper compound or iii) nucleophilic substitution reaction.

In the case of i) Ullmann reaction, there are no specific limitations to the reaction conditions. Ullmann reaction is preferably, for example, a method of stirring a compound of the general formula (I-1) and 1.0 to 10.0 equivalents of a compound (2b), wherein $L_2$ represents a halogen atom such as a chlorine atom, bromine atom or iodine atom, with respect to the compound of the general formula (I-1) in a solvent in the presence of 0.01 to 1.0 equivalent of a copper reagent such as copper, copper bromide or copper iodide with respect to the compound of the general formula (I-1) by addition of 1.0 to 10.0 equivalents of a base with respect to the compound of the general formula (I-1). The base used varies according to the starting material and is not specifically limited. Preferable examples of the base include alkali metal salts (such as potassium carbonate, sodium carbonate, potassium acetate, sodium acetate and cesium carbonate) and metal alkoxides (such as sodium methoxide and potassium tert-butoxide). The solvent used varies according to the starting material, the reagent and the like, and is not specifically limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; alcohol solvents such as amyl alcohol and isopropyl alcohol; polar solvents such as N,N-dimethylformamide and N-methylpyrrolidone; nonpolar solvents such as toluene, benzene and dichlorobenzene; and a mixture thereof. The reaction temperature must be a temperature that can complete the reaction without promoting formation of an undesirable by-product, and is preferably room temperature to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

The ii) coupling reaction of an arylboronic acid derivative using a copper compound is preferably, for example, a method of stirring a compound of the general formula (I-1) and 1.0 to 10.0 equivalents of a compound (2b), wherein $L_2$ represents a boronic acid group or a boronate group such as a pinacol boronate group, with respect to the compound of the general formula (I-1) in a solvent in the presence of 0.01 to 1.0 equivalent of a copper reagent such as copper, copper bromide or copper iodide with respect to the compound of the general formula (I-1) by addition of 1.0 to 10.0 equivalents of a base with respect to the compound of the general formula (I-1). The base used varies according to the starting material, the solvent used and the like, and is not specifically limited insofar as the base does not inhibit the reaction. Preferable examples of the base include organic bases such as triethylamine, pyridine and tetramethylethylenediamine; alkali metal salts such as potassium carbonate, sodium carbonate, potassium acetate, sodium acetate and cesium carbonate; and metal alkoxides such as sodium methoxide and potassium tert-butoxide. The copper reagent used varies according to the starting material and is not specifically limited. Preferable examples of the copper reagent include copper acetate and di-t-hydroxo-bis[(N,N,N',N'-tetramethylethylenediamine) copper (II)]chloride. The solvent used varies according to the starting material, the reagent and the like, and is not specifically limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; polar solvents such as ethyl acetate, N,N-dimethylformamide and N-methylpyrrolidone; nonpolar solvents such as toluene, benzene, dichlorobenzene; and a mixture thereof. The reaction temperature must be a temperature that can complete the reaction without promoting formation of an undesirable by-product, and is preferably room temperature to 200° C., for example. Good results such as reduction in the reaction time and improvement of the yield can be achieved when the reaction is performed in an oxygen atmosphere or air stream. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In iii) nucleophilic substitution reaction, a compound of the general formula (I-1) and 2.0 to 5.0 equivalents of a compound (2b), wherein $L_2$ represents a halogen atom such as a chlorine atom, bromine atom or iodine atom or a sulfonate group such as a methanesulfonate group, p-toluenesulfonate group or trifluoromethanesulfonate group, with respect to the compound of the general formula (I-1) are preferably stirred in a solvent in the presence or absence of 1.0 to 5.0 equivalents of a base with respect to the compound of the general formula (I-1), for example. The base used varies according to the starting material and is not specifically limited. Preferable examples of the base include sodium hydride, sodium hydroxide, potassium hydroxide, potassium carbonate, sodium carbonate, cesium carbonate, barium carbonate, pyridine, lutidine and triethylamine. The solvent used varies according to the starting material, and is not specifically limited insofar as the solvent does not inhibit the reaction and allows the starting material to be dissolved therein to a certain extent. Preferable examples of the solvent include acetonitrile, tetrahydrofuran, dimethyl sulfoxide, N,N-dimethylformamide and N-methylpyrrolidine. Optionally, the bases may be used as a solvent. The reaction temperature must be a temperature that can complete the reaction without promoting formation of an undesirable by-product, and is preferably room temperature to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

The compound of the general formula (I-2) can be prepared by reacting an oxazole compound (21) with an amine compound (22) according to Step 1-5. Specifically, Step 1-5 varies according to the starting material and is not specifically limited insofar as the conditions are similar to those in this reaction. A known method described in many documents may be used for the reaction (see Heterocyclic Compounds, vol. 5, Wiley, New York, N.Y. 1950, p. 214, for example). Preferably, an oxazole compound (21) and 1.0 to 100.0 equivalents of an amine compound (22) with respect to the oxazole compound (21) are stirred in a solvent, for example. The solvent used is not specifically limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; alcohol solvents such as amyl alcohol and isopropyl alcohol; polar solvents such as N,N-dimethylformamide and N-methylpyrrolidone; nonpolar solvents such as toluene, benzene and dichlorobenzene; organic acids such as acetic acid; water; and a mixture thereof. The amine compound (22) to be reacted may be used as a solvent. The reaction temperature must be a temperature that can complete the reaction without promoting formation of an undesirable by-product, and is preferably room temperature to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Compound of General Formula (I-1)]

The compound of the general formula (I-1) can be prepared from an ester compound (3) according to Step 1-2 using ammonia, an ammonium salt or formamide as a nitrogen atom source, for example. Specifically, Step 1-2 varies according to the starting material and is not specifically limited insofar as the conditions are similar to those in this reaction. A known method described in many documents may be used for the reaction (see The Chemistry of Heterocyclic Compounds. Imidazole and Derivatives, Part I, p. 33, Inters. Publish. 1953, for example). The reaction is preferably a method of stirring an ester compound (3) and 1.0 to 100.0 equivalents of ammonia or an ammonium salt such as ammonium acetate with respect to the ester compound (3) in a solvent, for example. The solvent used is not specifically limited insofar as the solvent does not inhibit the reaction and allows the starting material to be dissolved therein to a certain extent. Preferable examples of the solvent include nonpolar solvents such as toluene and benzene; alcohol solvents such as methanol and ethanol; organic acids such as acetic acid; water; and a mixture thereof. Formamide may optionally be used as a nitrogen atom source and a solvent. The reaction temperature must be a temperature that can complete the reaction without promoting formation of an undesirable by-product, and is preferably room temperature to 250° C., for example. The yield may be improved when the reaction is performed using a tight container. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Ester Compound (3)]

The ester compound (3) is prepared by condensation reaction of a carboxylic acid compound (1) with a compound (2a) according to Step 1-1. Specifically, Step 1-1 varies according to the starting material and is not specifically limited insofar as the conditions are similar to those in this reaction. A known method described in many documents may be used for the reaction. Preferable examples of the reaction include i) nucleophilic substitution reaction of a carboxylic acid compound (1) with a compound (2a), wherein $L_1$ represents a halogen atom such as a chlorine atom, bromine atom or iodine atom or a sulfonate group such as a methanesulfonate group, p-toluenesulfonate group or trifluoromethanesulfonate group (see Shin Jikken Kagaku Koza (New Courses in Experimental Chemistry), vol. 22, Yuki Gosei (Organic Synthesis) [IV], edited by The Chemical Society of Japan, Maruzen Co., Ltd., November 1992, p. 49-50, for example) and ii) dehydration condensation reaction of a carboxylic acid compound (1) with a compound (2a), wherein $L_1$ represents a hydroxyl group (see Shin Jikken Kagaku Koza (New Courses in Experimental Chemistry), vol. 22, Yuki Gosei (Organic Synthesis) [IV], edited by The Chemical Society of Japan, Maruzen Co., Ltd., November 1992, p. 43-47, for example).

i) Nucleophilic substitution reaction is preferably, for example, a method of stirring a carboxylic acid compound (1) and 1.0 to 10.0 equivalents of a compound (2a) with respect to the carboxylic acid compound (1) in a solvent in the presence of 1.0 to 10.0 equivalents of a base with respect to the carboxylic acid compound (1). The base used varies according to the starting material and is not specifically limited. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; alkali metal hydrides such as sodium hydride; and alkali metal ammonium salts such as sodium amide. The solvent used varies according to the starting material and the base used, and is not specifically limited insofar as the solvent does not inhibit the reaction and allows the starting material to be dissolved therein to a certain extent. Preferable examples of the solvent include polar solvents such as nitromethane, acetonitrile, 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; halogenated solvents such as chloroform and methylene chloride; water; and a mixed solvent thereof. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

ii) Dehydration condensation reaction is preferably, for example, a method of stirring a carboxylic acid compound (1) and 1.0 to 10.0 equivalents of a compound (2a) with respect to the carboxylic acid compound (1) in a solvent in the presence of 0.1 to 10.0 equivalents of a condensing agent with respect to the carboxylic acid compound (1). The condensing agent used varies according to the starting material and is not specifically limited. Preferable examples of the condensing agent include inorganic acids such as hydrochloric acid and sulfuric acid; organic acids such as p-toluenesulfonic acid and methanesulfonic acid; 1,3-dicyclohexylcarbodiimide, 1-ethyl-3-(3'-dimethylaminopropyl)carbodiimide, benzotriazol-1-yloxytris(dimethylamino)phosphonium hexafluorophosphate, diethyl cyanophosphonate, bis(2-oxo-3-oxazolidinyl)phosphonic chloride and diphenyl phosphoryl azide. Preferably, 1.0 to 5.0 equivalents of N-hydroxysuccinimide, N-hydroxybenzotriazole or dimethylaminopyridine may be added in order to make the reaction efficiently proceed, for example. The solvent used varies according to the starting material and the condensing agent used, and is not specifically limited insofar as the solvent does not inhibit the reaction and allows the starting material to be dissolved therein to a certain extent. Preferable examples of the solvent include halogenated solvents such as chloroform, methylene chloride and 1,2-dichloroethane; polar solvents such as tetrahydrofuran and N,N-dimethylformamide; and a mixture thereof. The reaction temperature must be a temperature that can complete the reaction without promoting formation of an undesirable by-product, and is preferably ice-cold temperature to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

[Preparation of Oxazole Compound (21)]

The oxazole compound (21) can be prepared by reacting an ester compound (3) with ammonia, an ammonium salt or formamide as a nitrogen atom source according to Step 1-4, for example. Specifically, Step 1-4 varies according to the starting material and is not specifically limited insofar as the conditions are similar to those in this reaction. A known method described in many documents may be used for the reaction (see Synthesis, 1998, vol. 9, p. 1298, for example). Preferably, an ester compound (3) and 1.0 to 100.0 equivalents of ammonia or an ammonium salt such as ammonium acetate with respect to the ester compound (3) are stirred in a solvent, for example. The solvent used is not specifically limited insofar as the solvent does not inhibit the reaction and allows the starting material to be dissolved therein to a certain extent. Preferable examples of the solvent include nonpolar solvents such as toluene and benzene; alcohol solvents such as methanol and ethanol; organic acids such as acetic acid; water; and a mixture thereof. Formamide may optionally be used as a nitrogen atom source and a solvent. The reaction temperature must be a temperature that can complete the reaction without promoting formation of an undesirable by-product, and is preferably room temperature to 250° C., for example. The yield may be improved when the reaction is performed using a tight container. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Compound (2b)]

The compound (2b) is commercially available or can be prepared by a method known to a person skilled in the art (see Shin Jikken Kagaku Koza (New Courses in Experimental Chemistry), vol. 19, Yuki Gosei (Organic Synthesis) [I], edited by The Chemical Society of Japan, Maruzen Co., Ltd., September 1992, p. 363-482; and Shin Jikken Kagaku Koza (New Courses in Experimental Chemistry), vol. 24, Yuki Gosei (Organic Synthesis) [VI], edited by The Chemical Society of Japan, Maruzen Co., Ltd., June 1992, p. 61-90, for example).

[Preparation of Compound (22)]

The compound (22) is commercially available or can be prepared by a method known to a person skilled in the art (see Shin Jikken Kagaku Koza (New Courses in Experimental Chemistry), vol. 20, Yuki Gosei (Organic Synthesis) [II], edited by The Chemical Society of Japan, Maruzen Co., Ltd., July 1992, p. 279-372, for example).

[Preparation of Compound (2a)]

The compound (2a) is commercially available or can be prepared by a method known to a person skilled in the art (see Shin Jikken Kagaku Koza (New Courses in Experimental Chemistry), vol. 19, Yuki Gosei (Organic Synthesis) [I], edited by The Chemical Society of Japan, Maruzen Co., Ltd., September 1992, p. 363-482; and Shin Jikken Kagaku Koza (New Courses in Experimental Chemistry), vol. 20, Yuki Gosei (Organic Synthesis) [II], edited by The Chemical Society of Japan, Maruzen Co., Ltd., July 1992, p. 1-110, for example).

[Preparation of Carboxylic Acid Compound (1)]

In the formula, $Ar_1$, $Ar_2$ and $X_1$ are as defined above; $V_1$ represents a protecting group for a carboxylic group such as a methyl group, ethyl group, benzyl group, allyl group, triphenylmethyl group, tert-butyl group or tert-butyldimethylsilyl group; $L_3$ and $L_6$ each represent a hydrogen atom, a halogen atom such as a fluorine atom, chlorine atom, bromine atom or iodine atom, a sulfonate group such as a trifluoromethanesulfonate group, a trialkyltin group or a leaving group such as a boronic acid or boronate group; $L_4$ represents a formyl group, an alkanoyl group such as an acetyl group, an alkoxycarbonyl group such as a methyl ester group, a halogen atom such as a fluorine atom, chlorine atom, bromine atom or iodine atom, a sulfonate group such as a trifluoromethanesulfonate group, a trialkyltin group or a boronic acid or boronate group; $L_5$ represents a halogen atom such as a fluorine atom, chlorine atom, bromine atom or iodine atom or a sulfonate group such as a trifluoromethanesulfonate group; W represents a phosphate group such as a diethylphosphonyl group, diphenylphosphonyl group or bis(2,2,2-trifluoroethyl) phosphonyl group, a phosphonium salt such as triphenylphosphonium bromide or a silyl group such as a trimethylsilyl group; and $R_{26}$, $R_{13}$, $R_{14}$ and $R_{15}$ each represent a group selected from the above Substituent Group A3.

[Formula 40]

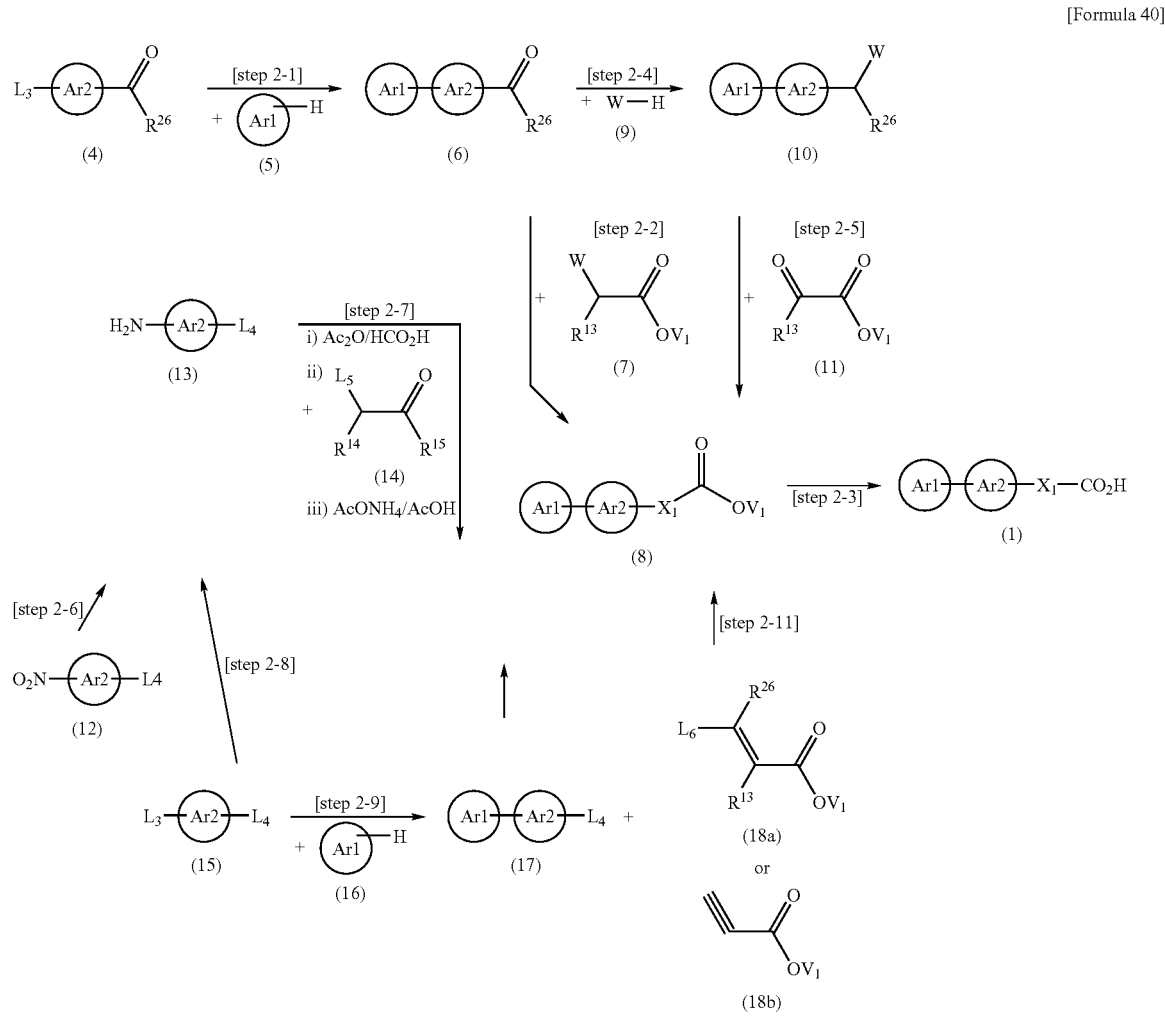

The carboxylic acid compound (1) is prepared by hydrolysis of an ester compound (8) according to Step 2-3. Specifically, Step 2-3 varies according to the starting material and is not specifically limited insofar as the conditions are similar to those in this reaction. A known method described in many documents may be used for the reaction (see Shin Jikken Kagaku Koza (New Courses in Experimental Chemistry), vol. 22, Yuki Gosei (Organic Synthesis) [IV], edited by The Chemical Society of Japan, Maruzen Co., Ltd., November 1992, p. 6-11, for example). Preferably, an ester compound (8) is stirred in a solvent in the presence of 1.0 to 100.0 equivalents of a base or acid with respect to the ester compound (8), for example. The base used varies according to the starting material and is not specifically limited. Preferable examples of the base include sodium hydride, sodium hydroxide, potassium hydroxide, potassium carbonate, sodium carbonate, cesium carbonate and barium carbonate. The acid used varies according to the starting material and is not specifically limited. Preferable examples of the acid include inorganic acids such as hydrochloric acid and sulfuric acid; organic acids such as trifluoroacetic acid and p-toluenesulfonic acid; and Lewis acids such as boron trichloride. The solvent used varies according to the starting material, and is not specifically limited insofar as the solvent does not inhibit the reaction and allows the starting material to be dissolved therein to a certain extent. Preferable examples of the solvent include alcohol solvents such as methanol, ethanol and ethylene glycol; ether solvents such as tetrahydrofuran; water; and a mixture thereof. In the case of acid hydrolysis, an organic acid such as acetic acid or formic acid may be used as a solvent. The reaction temperature must be a temperature that can complete the reaction without promoting formation of an undesirable by-product, and is preferably room temperature to 100° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

[Preparation of Ester Compound (8)]

The ester compound (8) can be prepared as shown by the above reaction formula, but the preparation is not limited thereto. Specifically, the ester compound (8) can be prepared by reacting a compound (4) with a compound (5) in Step 2-1 to obtain a carbonyl compound (6) and then condensing the carbonyl compound (6) by condensation reaction such as Horner-Emmons reaction, Wittig reaction or Peterson reaction in Step 2-2, for example. Alternatively, the ester compound (8) can be prepared by preparing a compound (10) from a carbonyl compound (6) in Step 2-4 and condensing the compound (10) with a compound (11) by condensation reaction such as Horner-Emmons reaction, Wittig reaction or Peterson reaction in Step 2-5. Alternatively, the ester compound (8) can be prepared by forming $Ar_1$ in a compound (17) from an amino compound (13) as a starting material through three-stage reaction in Step 2-7 and then performing coupling reaction of the compound (17) with a compound (18a) or compound (18b) according to Step 2-11. The ester compound (8) can be prepared by converting a compound (15) as a starting material into a compound (17) according to Step 2-9 and then subjecting the compound (17) to Step 2-11.

[Conversion of Carbonyl Compound (6) into Ester Compound (8) and Conversion of Compound (10) into Ester Compound (8)]

A carbonyl compound (6) can be converted into the ester compound (8) and a compound (10) can be converted into the ester compound (8) by a method known to a person skilled in the art. For example, the ester compound (8) can be prepared from a carbonyl compound (6) and a compound (7) according to Step 2-2. Alternatively, the ester compound (8) can be prepared from a compound (10) and a compound (11) according to Step 2-5. Specifically, coupling reaction in Step 2-2 or Step 2-5 varies according to the starting material and is not specifically limited insofar as the conditions are similar to those in this reaction. A method known to a person skilled in the art may be used for the reaction. Preferable examples of the method include Wittig reaction, Horner-Emmons reaction and Peterson reaction (see Shin Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 57-85, for example).

In Wittig reaction, a compound (7) or compound (10), wherein W represents a phosphonium salt, and 0.5 to 2.0 equivalents of a carbonyl compound (6) or a compound (11) with respect to the compound (7) or compound (10) are preferably stirred in a solvent in the presence of 1.0 to 5.0 equivalents of a base with respect to the compound (7) or compound (10), for example. This reaction may be a method of first treating a compound (7) or compound (10) and a base to form a phosphorus ylide and then adding a carbonyl compound (6) or a compound (11) to the ylide; or a method of adding a base in the presence of a compound (7) or compound (10) and a carbonyl compound (6) or a compound (11). This reaction is preferably performed in the presence of a solvent from the viewpoint of operativity and stirring efficiency. The solvent used varies according to the starting material and the base used, and is not specifically limited insofar as the solvent does not inhibit the reaction and allows the starting material to be dissolved therein to a certain extent. Preferable examples of the solvent include polar solvents such as nitromethane, acetonitrile, 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; halogenated solvents such as chloroform and methylene chloride; water; and a mixed solvent thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; and alkali metal hydrides such as sodium hydride. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Horner-Emmons reaction, a compound (7) or compound (10), wherein W represents a phosphite group, and 0.5 to 2.0 equivalents of a carbonyl compound (6) or a compound (11) with respect to the compound (7) or compound (10) are preferably stirred in a solvent in the presence of 1.0 to 5.0 equivalents of a base with respect to the compound (7) or compound (10), for example. This reaction may be a method of first treating a compound (7) or compound (10) and a base to form a carbanion and then adding a carbonyl compound (6) or a compound (11) to the carbanion; or a method of adding a base in the presence of a compound (7) or compound (10) and a carbonyl compound (6) or a compound (11). This reaction is preferably performed in the presence of a solvent from the viewpoint of operativity and stirring efficiency. The solvent used varies according to the starting material and the base used, and is not specifically limited insofar as the solvent does not inhibit the reaction and allows the starting material to be dissolved therein to a certain extent. Preferable examples of the solvent include polar solvents such as 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; water; and a mixed solvent thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; alkali metal hydrides such as sodium hydride; and alkali metal ammonia salts such as sodium amide. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Peterson reaction, a compound (7) or compound (10), wherein W represents a silyl group, and 0.5 to 2.0 equivalents of a carbonyl compound (6) or a compound (11) with respect to the compound (7) or compound (10) are preferably stirred in a solvent in the presence of 1.0 to 5.0 equivalents of a base with respect to the compound (7) or compound (10), for example. This reaction may be a method of first treating a compound (7) or compound (10) and a base to form a carbanion and then adding a carbonyl compound (6) or a compound (11) to the carbanion; or a method of adding a base in the presence of a compound (7) or compound (10) and a carbonyl compound (6) or a compound (11). This reaction is preferably performed in the presence of a solvent from the viewpoint of operativity and stirring efficiency. The solvent used varies according to the starting material and the base used, and is not specifically limited insofar as the solvent does not inhibit the reaction and allows the starting material to be dissolved therein to a certain extent. Preferable examples of the solvent include polar solvents such as 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; water; and a mixed solvent thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclonone; organic metals such as butyl lithium and lithium diisobutylamide; alkali metal hydrides such as sodium hydride; and alkali metal ammonia salts such as sodium amide. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Conversion of Compound (17) into Ester Compound (8)]

A compound (17) can be converted into the ester compound (8) by a method known to a person skilled in the art. The ester compound (8) can be prepared from a compound (17) together with a compound (18a) or compound (18b) according to Step 2-11, for example. Specifically, the coupling reaction in Step 2-11 varies according to the starting material and is not specifically limited insofar as the conditions are similar to those in this reaction. A method known to a person skilled in the art may be used for the reaction. Preferable examples of the method include Mizoroki-Heck reaction (see R. F. Heck, "Org. Reactions.", 1982, vol. 27, p. 345, for example), Suzuki-Miyaura reaction (see A. Suzuki, "Chem. Rev.", 1995, vol. 95, p. 2457, for example), Sonogashira reaction (see K. Sonogashira, "Comprehensive Organic Synthesis", 1991, vol. 3, p. 521) and Stille coupling reaction (see J. K. Stille, "Angew. Chem. Int. Ed. Engl.", 1986, vol. 25, p. 508, for example).

In Mizoroki-Heck reaction, a halogen compound or triflate compound (17), wherein $L_4$ represents a chlorine atom, a bromine atom, an iodine atom or a sulfonate group such as a trifluoromethanesulfonate group, is preferably coupled with 1.0 to 5.0 equivalents of an alkene compound (18a; wherein $L_6$ is a hydrogen atom) with respect to the compound (17) in the presence of 0.01 to 0.2 equivalent of a transition metal catalyst with respect to the compound (17), for example. This reaction is preferably performed in the presence of a solvent from the viewpoint of operativity and stirring efficiency. The solvent used varies according to the starting material and the transition metal catalyst used, and is not specifically limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone and N,N-dimethylformamide. The reaction temperature must be a temperature that can complete the coupling reaction, and is preferably room temperature to 150° C. This reaction is performed preferably in an inert gas atmosphere, and more preferably in a nitrogen or argon atmosphere. The transition metal catalyst is preferably a palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). It is also preferable to appropriately add a phosphorus ligand (preferably triphenylphosphine, tri-o-tolylphosphine, tri-tert-butylphosphine or 2-(di-tert-butylphosphino)biphenyl, for example) in order to make the reaction efficiently proceed. A preferable result may be achieved in the presence of a base. The base used is not specifically limited insofar as the base is used in a coupling reaction similar to this reaction. Preferable examples of the base include triethylamine, N,N-diisopropylethylamine, N,N-dicyclohexylmethylamine and tetrabutylammonium chloride. Under preferable reaction conditions, the reaction is completed in 1 to 24 hours, and the progress of the reaction can be monitored by a known chromatography technique.

In Suzuki-Miyaura reaction, a halogen compound or trifluoromethanesulfonate compound (17), wherein $L_4$ represents a chlorine atom, a bromine atom, an iodine atom or a sulfonate group such as a trifluoromethanesulfonate group, is preferably coupled with 1.0 to 5.0 equivalents of a boronic acid compound or boronate compound (18a; wherein $L_6$ is a boronic acid or boronate group) with respect to the compound (17) in the presence of 0.01 to 0.5 equivalent of a transition metal catalyst with respect to the compound (17), for example. This reaction is preferably performed in the presence of a solvent from the viewpoint of operativity and stirring efficiency. The solvent used varies according to the starting material and the transition metal catalyst used, and is not specifically limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone, N,N-dimethylformamide, water and a mixed solvent thereof. The reaction temperature must be a temperature that can complete the coupling reaction, and is preferably room temperature to 200° C. This reaction is performed preferably in an inert gas atmosphere, and more preferably in a nitrogen or argon atmosphere. Under preferable reaction conditions, the reaction is completed in 1 to 24 hours, and the progress of the reaction can be monitored by a known chromatography technique. The transition metal catalyst is preferably a known palladium complex, and more preferably a known palladium complex such as palladium (II) acetate, dichlorobis(triphenylphosphine)palladium (II), tetrakis(triphenylphosphine)palladium (0), or tris(dibenzylideneacetone)dipalladium (0). A phosphorus ligand (preferably triphenylphosphine, tri-o-tolylphosphine, tricyclohexylphosphine, or tri-tert-butylphosphine, for example) may be appropriately added in order to make the reaction efficiently proceed. A quaternary ammonium salt, preferably tetrabutylammonium chloride or tetrabutylammonium bromide, for example, may also be appropriately added in order to make the reaction efficiently proceed. In this reaction, a preferable result may be achieved in the presence of a base. The base used at this time varies according to the starting material, the solvent used and the like, and is not specifically limited. Preferable examples of the base include sodium hydroxide, barium hydroxide, potassium fluoride, cesium fluoride, sodium carbonate, potassium carbonate, cesium carbonate and potassium phosphate. Under preferable reaction conditions, the reaction is completed in 1 to 24 hours, and the progress of the reaction can be monitored by a known chromatography technique. In this reaction, the desired ester compound (8) can be efficiently obtained even when the compound (18a) is a halide or a trifluoromethanesulfonate compound, wherein $L_6$ is a chlorine atom, bromine atom, iodine atom or trifluoromethanesulfonate group, for example, and the compound (17) is a boronic acid compound or boronate compound, wherein $L_4$ is a boronic acid or boronate group, for example.

The reaction conditions in Sonogashira reaction vary according to the starting material, the solvent and the transition metal catalyst, and are not specifically limited insofar as the conditions are similar to those in this reaction. A method known to a person skilled in the art may be used for the reaction. Preferably, a compound (17), wherein $L_4$ represents a chlorine atom, a bromine atom, an iodine atom or a sulfonate group such as a trifluoromethanesulfonate group, and 1.0 to 5.0 equivalents of an alkyne compound (18b) with respect to the compound (17) are stirred in a solvent, for example. Preferable examples of the solvent used include acetonitrile, tetrahydrofuran, 1,4-dioxane, 1,2-dimethoxyethane, benzene, toluene, xylene, 1-methyl-2-pyrrolidone, N,N-dimethylformamide and dimethyl sulfoxide. More preferable examples of the solvent include tetrahydrofuran, 1,4-dioxane, 1-methyl-2-pyrrolidone and N,N-dimethylformamide. The reaction temperature must be a temperature that can complete the coupling reaction, and is preferably room temperature to 150° C. This reaction is performed preferably in an inert gas atmosphere, and more preferably in a nitrogen or argon atmosphere. Under preferable reaction conditions, the reaction is completed in 1 to 24 hours, and the progress of the reaction can be monitored by a known chromatography technique. The transition metal catalyst is preferably 0.01 to 0.5 equivalent with respect to the compound (17) of a known palladium complex, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand (preferably triphenylphosphine, tri-o-tolylphosphine or tri-tert-butylphosphine, for example) may be appropriately added, for example, in order to make the reaction efficiently proceed. In the reaction, a metal halide or a quaternary ammonium salt, preferably copper (I) iodide, lithium chloride, tetrabutylammonium fluoride or silver (I) oxide, for example, may be added. A preferable result may be achieved in the presence of a base. The base used here is not specifically limited insofar as the base is used in a coupling reaction similar to this reaction. Preferable examples of the base include basic solvents such as diethylamine, triethylamine, N,N-diisopropylethylamine, piperidine and pyridine.

In Stille coupling reaction, a trialkyltin compound (17), wherein $L_4$ represents an alkyltin group, and 1.0 to 5.0 equivalents of a halide or a trifluoromethanesulfonate compound (18a), wherein $L_6$ represents a chlorine atom, bromine atom, iodine atom or trifluoromethanesulfonate group, with respect to the compound (17) are preferably stirred in a solvent in the presence of 0.01 to 0.2 equivalent of a transition metal catalyst with respect to the compound (17), for example. It is preferable to appropriately use 0.1 to 5.0 equivalents of copper (I) halide or/and lithium chloride in order to make the reaction efficiently proceed. Preferable examples of the solvent used in this reaction include toluene, xylene, N,N-dimethylformamide, N,N-dimethylacetamide, 1-methyl-2-pyrrolidone and dimethyl sulfoxide. The reaction temperature must be a temperature that can complete the coupling reaction, and is preferably room temperature to 150° C. The preferable transition metal catalyst is a palladium complex, preferably a known palladium complex such as palladium (II) acetate, dichlorobis(triphenylphosphine)palladium (II), tetrakis(triphenylphosphine)palladium (0) or tris(dibenzylideneacetone)dipalladium (0), for example, and more preferably tetrakis(triphenylphosphine)palladium (0) or tris(dibenzylideneacetone)dipalladium (0), for example. This reaction is performed preferably in an inert gas atmosphere, and more preferably in a nitrogen or argon atmosphere. Under preferable reaction conditions, the reaction is completed in 1 to 24 hours, and the progress of the reaction can be monitored by a known chromatography technique.

[Preparation of Carbonyl Compound (6)]

The carbonyl compound (6) can be prepared from a compound (4) as a starting material according to Step 2-1, for example. Specifically, Step 2-1 varies according to the starting material and is not specifically limited insofar as the conditions are similar to those in this reaction. A method known to a person skilled in the art may be used for the reaction. For example, a compound (4) and 1.0 to 5.0 equivalents of a compound (5) with respect to the compound (4) are stirred in a solvent in the presence or absence of 1.0 to 5.0 equivalents of a base with respect to the compound (4) (see D. D. Davey et al., "J. Med. Chem.", 1991, vol. 39, p. 2671-2677). Preferable examples of the base used include sodium hydride, sodium hydroxide, potassium hydroxide, potassium carbonate, sodium carbonate, cesium carbonate, barium carbonate, pyridine, lutidine and triethylamine. The solvent used varies according to the starting material, and is not specifically limited insofar as the solvent does not inhibit the reaction and allows the starting material to be dissolved therein to a certain extent. Preferable examples of the solvent include acetonitrile, tetrahydrofuran, dimethyl sulfoxide, N,N-dimethylformamide and N-methylpyrrolidine. Optionally, the bases may be used as a solvent. The reaction temperature must be a temperature that can complete the reaction without promoting formation of an undesirable by-product, and is preferably room temperature to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

The carbonyl compound (6) can also be prepared from a compound (17) as a starting material according to Step 2-10, for example. Specifically, Step 2-10 varies according to the starting material and is not specifically limited insofar as the conditions are similar to those in this reaction. A method known to a person skilled in the art may be used for the reaction. For example, it is possible to use a two-stage method of converting a compound (17), wherein $L_4$ represents a chlorine atom, a bromine atom, an iodine atom or a sulfonate group such as a trifluoromethanesulfonate group, into a vinyl compound by Stille coupling reaction using 1.0 to 5.0 equivalents of a vinyltin compound with respect to the compound (17) and then oxidizing the carboxylic acid by ozone oxidation reaction (see S. S. Chandran et al., "Bioorg. Med. Chem. Lett.", 2001, vol. 11, p. 1493-1496, for example). It is also possible to use carbon monoxide insertion reaction using a transition metal catalyst (see T. Okano et al., "Bull. Chem. Soc. Jpn.", 1994, vol. 67, p. 2329-2332, for example).

[Preparation of Compound (4)]

The compound (4) is commercially available or can be obtained by a technique known to a person skilled in the art. If not commercially available, the preferable compound (4), wherein $L_3$ represents a fluorine atom, chlorine atom or bromine atom, can be obtained by oxidizing a corresponding alcohol compound by an oxidation reaction known to a person skilled in the art; or the carbonyl compound can be obtained by reducing a corresponding ester compound by a known reduction reaction.

[Preparation of Compound (5)]

The compound (5) used in this step is commercially available or can be obtained by a technique known to a person skilled in the art. (see M. Komoto et al., "Agr. Biol. Chem.", 1968, vol. 32, p. 983-987; or J. M. Kokosa et al., "J. Org. Chem.", 1983, vol. 48, p. 3605-3607, for example).

[Preparation of Compound (7)]

[Formula 41]

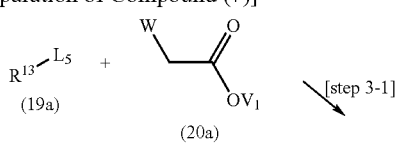

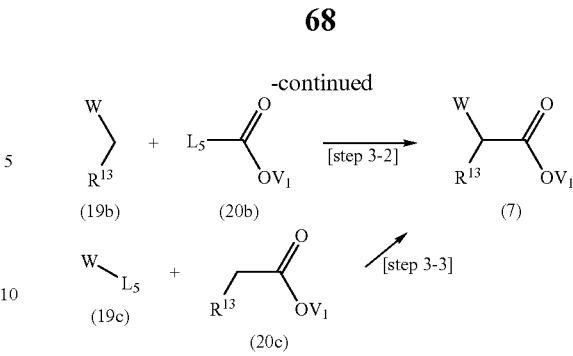

In the formula $R^{13}$, W, $L_5$ and $V_1$ are as defined above.

The above reaction formula shows an example of a method for preparing the phosphonate compound (7). Specifically, the phosphonate compound (7) is commercially available or can be obtained by a method shown in the above Step 3-1 to Step 3-3 and known to a person skilled in the art (see C. Patois et al., "Synth. Commun.", 1991, vol. 22, p. 2391; or J. A. Jackson et al., "J. Org. Chem.", 1989, vol. 20, p. 5556, for example). Step 3-1 is a step of obtaining the desired phosphonate compound (7) by stirring a phosphonate compound (20a) and 1.0 to 2.0 equivalents of an alkyl halide compound (19a) with respect to the phosphonate compound (20a) in a solvent in the presence of 1.0 to 1.5 equivalents of a base with respect to the phosphonate compound (20a) to introduce $R_{13}$, for example. Step 3-2 is a step of obtaining the desired phosphonate compound (7) by stirring a phosphonate compound (19b) and 1.0 to 2.0 equivalents of a halogenated formate compound (20b) with respect to the phosphonate compound (19b) in a solvent in the presence of 1.0 to 1.5 equivalents of a base with respect to the phosphonate compound (19b). Step 3-3 is a step of obtaining the desired phosphonate compound (7) by stirring a phosphonic acid halide compound (19c) and 1.0 to 2.0 equivalents of an ester compound (20c) with respect to the phosphonic acid halide compound (19c) in a solvent in the presence of 1.0 to 1.5 equivalents of a base with respect to the phosphonic acid halide compound (19c). The base used varies according to the starting material and is not specifically limited. Preferable examples of the base include sodium hydride, n-butyl lithium, lithium diisopropylamide, lithium bis(trimethylsilyl)amide and sodium bis(trimethylsilyl) amide. The solvent used varies according to the starting material, and is not specifically limited insofar as the solvent does not inhibit the reaction and allows the starting material to be dissolved therein to a certain extent. Preferable examples of the solvent include hexane, toluene, diethyl ether, tetrahydrofuran, N,N-dimethylformamide, hexamethylphosphoric triamide and a mixed solvent thereof. The reaction temperature must be a temperature that can complete the reaction without promoting formation of an undesirable by-product, and is preferably −78° C. to 100° C. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization. The desired phosphonate compound (7) can be efficiently obtained by modification of $R_{13}$ by a technique known to a person skilled in the art.

The alkyl halide compound (19a), phosphonate compound (19b), phosphonic acid halide compound (19c), phosphonate compound (20a), halogenated formate compound (20b) and ester compound (20c) used in this step are commercially available or can be obtained by a technique known to a person skilled in the art.

[Preparation of Compound (10)]

The compound (10) can be prepared from a compound (6) and a compound (9) according to Step 2-4. Specifically, Step 2-4 varies according to the starting material and is not specifically limited insofar as the conditions are similar to those in this reaction. A method known to a person skilled in the art may be used for the reaction (see Journal of the American Chemistry, 1961, vol. 83, p. 173, for example). Preferably, a compound (6) and 1.0 to 10.0 equivalents of a compound (9) with respect to the compound (6) are stirred in a solvent in the presence of 1.0 to 10.0 equivalents of a base with respect to the compound (6), for example. The base used varies according to the starting material and is not specifically limited. Preferable examples of the base include organic bases such as 1,8-diazabicyclo[5,4,0]-7-undecene and diisopropylamine; and alkali metal salts such as potassium carbonate and sodium carbonate. The solvent used varies according to the starting material, and is not specifically limited insofar as the solvent does not inhibit the reaction and allows the starting material to be dissolved therein to a certain extent. Preferable examples of the solvent include hexane, toluene, diethyl ether, tetrahydrofuran, N,N-dimethylformamide, hexamethylphosphoric triamide and a mixed solvent thereof. The reaction temperature must be a temperature that can complete the reaction without promoting formation of an undesirable by-product, and is preferably −78° C. to 100° C. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

[Preparation of Compound (9)]

The compound (9) used in this step is commercially available or can be obtained by a technique known to a person skilled in the art.

[Preparation of Compound (11)]

The compound (11) used in this step is commercially available or can be obtained by a technique known to a person skilled in the art.

[Preparation of Amine Compound (13)]

The amine compound (13) is commercially available or can be obtained by a technique known to a person skilled in the art. Preferably, the compound can be prepared from a nitro compound (12) as a starting material according to Step 2-6. Specifically, reduction reaction in Step 2-6 varies according to the starting material and is not specifically limited insofar as the conditions are similar to those in this reaction. A method known to a person skilled in the art may be used for the reaction (see Shin Jikken Kagaku Koza (New Courses in Experimental Chemistry), vol. 14, Yuki Kagobutsu No Gosei To Hannou (Synthesis and Reaction of Organic Compounds) [III], edited by The Chemical Society of Japan, Maruzen Co., Ltd., February 1978, p. 1333-1341, for example). The reaction is preferably a catalytic reduction method using a metal catalyst or a reduction method using a metal, for example. The catalytic reduction method is preferably performed in a hydrogen atmosphere at normal pressure to 100 atm. Preferable examples of the metal catalyst used in this reaction include platinum, platinum oxide, platinum black, Raney nickel and palladium-carbon. The solvent used in the present reaction varies according to the starting material, and is not specifically limited insofar as the solvent does not inhibit the reaction and allows the starting material to be dissolved therein to a certain extent. Preferable examples of the solvent include methanol, ethanol, diethyl ether, tetrahydrofuran, methylene chloride, chloroform and ethyl acetate. An acidic substance such as acetic acid or hydrochloric acid may be appropriately added in order to make the reaction efficiently proceed. The reduction method using a metal preferably employs zinc, iron or tin, for example, and is preferably performed under acidic conditions using hydrochloric acid, acetic acid or ammonium chloride, for example. The solvent used in the present reaction varies according to the starting material, and is not specifically limited insofar as the solvent does not inhibit the reaction and allows the starting material to be dissolved therein to a certain extent. Preferable examples of the solvent include methanol, ethanol and 2-propanol. The reaction temperature must be a temperature that can complete the reaction without promoting formation of an undesirable by-product, and is preferably room temperature to 100° C. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

The preferable amine compound (13) can also be prepared from a compound (15) as a starting material which is commercially available or can be obtained by a technique known to a person skilled in the art, according to coupling reaction in Step 2-8. Specifically, the coupling reaction in Step 2-8 varies according to the starting material and is not specifically limited insofar as the conditions are similar to those in this reaction. A method known to a person skilled in the art may be used for the reaction. Preferably, for example, it is possible to use a two-stage method of performing coupling reaction of benzophenone imine using a transition metal catalyst and then performing a known benzophenone removal reaction treatment (see S. L. Buchwald et al., "Tetrahedron Lett.", 1997, vol. 38, p. 6367-6370; or J. F. Hartwig et al., "J. Am. Chem. Soc.", 1998, vol. 120, p. 827-828, for example). In the coupling reaction of benzophenone imine, a compound (15) and 1.0 to 10.0 equivalents of benzophenone imine with respect to the compound (15) are stirred in a solvent in the presence of 0.01 to 0.2 equivalent of a catalyst with respect to the compound (15). Examples of the catalyst that can be used include known palladium complexes such as palladium (II) acetate, dichlorobis(triphenylphosphine)palladium (II), tetrakis(triphenylphosphine)palladium (0) and tris(dibenzylideneacetone)dipalladium (0); and known nickel catalysts such as (1,5-cyclooctadiene)nickel (0). Preferably, a phosphorus ligand such as triphenylphosphine, tri-o-tolylphosphine, tri-tert-butylphosphine, 2-(di-tert-butylphosphino)biphenyl, 2,2'-bis(diphenylphosphino)-1,1'-binaphthyl, 1,2-bis(diphenylphosphino)ethane or 1,1'-bis(diphenylphosphino)ferrocene may be appropriately added in order to make the reaction efficiently proceed, for example. A preferable result may be achieved in the presence of a base. The base used is not specifically limited insofar as the base is used in a coupling reaction similar to this reaction. Preferable examples of the base include sodium hydroxide, barium hydroxide, potassium fluoride, cesium fluoride, sodium carbonate, potassium carbonate, cesium carbonate, potassium phosphate and sodium tert-butoxide. The solvent used varies according to the starting material and the transition metal catalyst used, and is not specifically limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone and N,N-dimethylformamide. The reaction temperature must be a temperature that can complete the coupling reaction, and is preferably room temperature to 100° C., for example. This reaction is performed preferably in an inert gas atmosphere, and more preferably in a nitrogen or argon atmosphere. A method known to a person skilled in the art may be used for the treatment after the second stage (see T. W. Green, "Protective Groups in Organic Synthesis", John Wiley & Sons, Inc., 1981). An undesirable by-product can be removed by a technique known to a person skilled in the art such as a conventional chromatography technique or/and crystallization.

In the preferable amine compound (13), $L_4$ can be modified by a method known to a person skilled in the art, and a hydrogen atom in $L_4$ can be preferably converted into a halogen substituent (see Shin Jikken Kagaku Koza (New Courses in Experimental Chemistry), vol. 14, Yuki Kagobutsu No Gosei To Hannou (Synthesis and Reaction of Organic Compounds) [I], edited by The Chemical Society of Japan, Maruzen Co., Ltd., November 1977, p. 354-360, for example).

[Preparation of Nitro Compound (12)]

The nitro compound (12) is commercially available or can be obtained by a technique known to a person skilled in the art. If not commercially available, the preferable compound (12), wherein $L_4$ represents a fluorine atom, chlorine atom, bromine atom or iodine atom, can be efficiently obtained from a corresponding precursor by a nitration reaction known to a person skilled in the art (see Shin Jikken Kagaku Koza (New Courses in Experimental Chemistry), vol. 14, Yuki Kagobutsu No Gosei To Hannou (Synthesis and Reaction of Organic Compounds) [III], edited by The Chemical Society of Japan, Maruzen Co., Ltd., February 1978, p. 1261-1300, for example).

[Preparation of Compound (17)]

The compound (17) can be obtained by a technique known to a person skilled in the art. Preferably, the compound (17) can be prepared i) from a compound (15) as a starting material according to Step 2-9 or ii) from an amine compound (13) as a starting material according to Step 2-7, for example.

In the case of i), Step 2-9 is performed by the same method as in the above Step 2-1.

In the case of ii), an amine compound (13) can be efficiently converted into the compound (17) in Step 2-7 by treating the amine compound (13) with a mixed solvent of acetic anhydride and formic acid in a first stage, condensing the compound with a compound (14) under basic conditions in a second stage, and heating the condensate with ammonium acetate and acetic acid in a third stage, for example. In the first stage, a compound (13) is stirred in a mixed solvent of 2.0 to 10.0 equivalents of acetic anhydride with respect to the compound (13) and 10.0 to 20.0 equivalents of formic acid with respect to the compound (13) at ice-cold temperature to 50° C. In the second stage, 1.0 to 5.0 equivalents of a base is preferably used with respect to the compound (13). Examples of the base include sodium hydride, sodium hydroxide, potassium hydroxide, lithium hydroxide, n-butyl lithium, lithium diisopropylamide, lithium bis(trimethylsilyl)amide and sodium bis(trimethylsilyl)amide. The solvent used in the present reaction varies according to the starting material, and is not specifically limited insofar as the solvent does not inhibit the reaction and allows the starting material to be dissolved therein to a certain extent. Preferable examples of the solvent include diethyl ether, tetrahydrofuran, dimethyl sulfoxide and N,N-dimethylformamide. Preferably, potassium iodide or sodium iodide may be added, for example, in order to make the reaction efficiently proceed. The reaction temperature must be a temperature that can complete the reaction without promoting formation of an undesirable by-product, and is preferably room temperature to 100° C., for example. In the third stage, the condensate is preferably treated in a mixture of 5.0 to 10.0 equivalents of ammonium acetate with respect to the compound (13) and 10.0 to 20.0 equivalents of acetic acid with respect to the compound (13) at 50 to 100° C. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

The compound (14) used in the second stage of this step is commercially available or can be obtained by a technique known to a person skilled in the art. If not commercially available, the preferable compound (14) can be prepared from a corresponding carbonyl compound by a halogenation reaction known to a person skilled in the art (see Shin Jikken Kagaku Koza (New Courses in Experimental Chemistry), vol. 19, Yuki Gosei (Organic Synthesis) [I], edited by The Chemical Society of Japan, Maruzen Co., Ltd., June 1992, p. 363-482, for example).

$L_4$ in the compound (17) can be modified by a technique known to a person skilled in the art, and can be preferably converted into, for example, an iodine group (see S. L. Buchwald et al., "J. Am. Chem. Soc.", 2002, vol. 124, p. 14844-14845, for example), a lower alkyltin group (see J. Marti et al., "Synth. Commun.", 2000, vol. 30, p. 3023-3030, for example) or a boron group (see N. Miyaura et al., "J. Org. Chem.", 1995, vol. 60, p. 7508-7510, for example). The compounds (18a) and (18b) are commercially available or can be obtained by a technique known to a person skilled in the art.

The compound of the general formula (I-1), general formula (I-2) or general formula (I-4), wherein two of $R^{10}$, $R^{11}$ and $R^{12}$ form a ring, can be prepared from the compound (2a) as a starting material, wherein $R^{10}$ and $R^{11}$ form a ring, by the same method as above. When the method as above is performed using the compound (2a) as a starting material, wherein $R^{10}$ or $R^{11}$ represents an alkyl group substituted with a halogen atom such as a chlorine atom, bromine atom or iodine atom, the compound of the general formula (I-1), general formula (I-2) or general formula (I-4), wherein two of $R^{10}$, $R^{11}$ and $R^{12}$ form a ring, can be prepared in Step 1-2, Step 1-5, Step 1-6 or Step 1-7.

[General Preparation Method 2]

Typically used General Preparation Method 2 for the compound of the general formula (I) of the present invention will be described below.

[Formula 42]
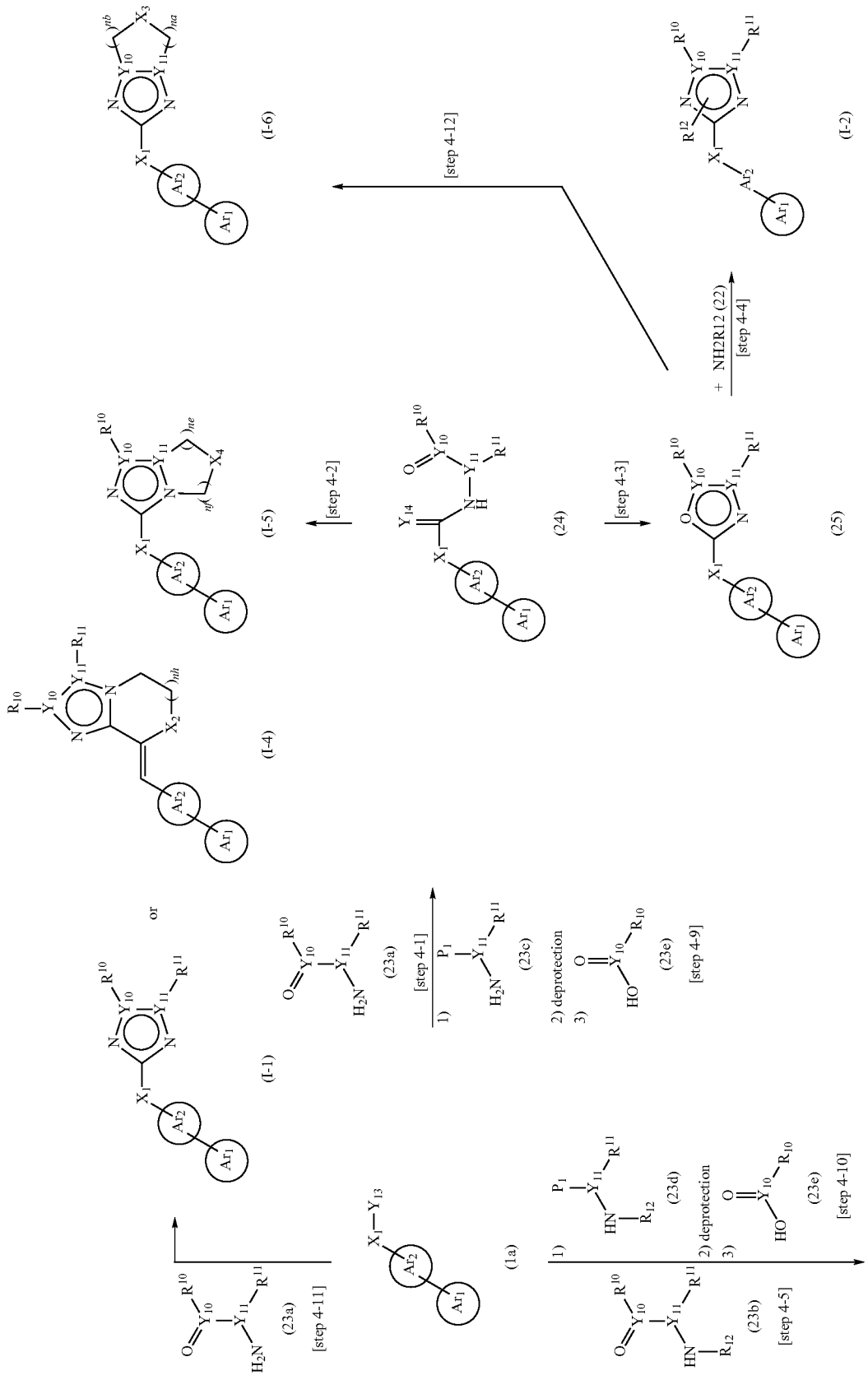

-continued
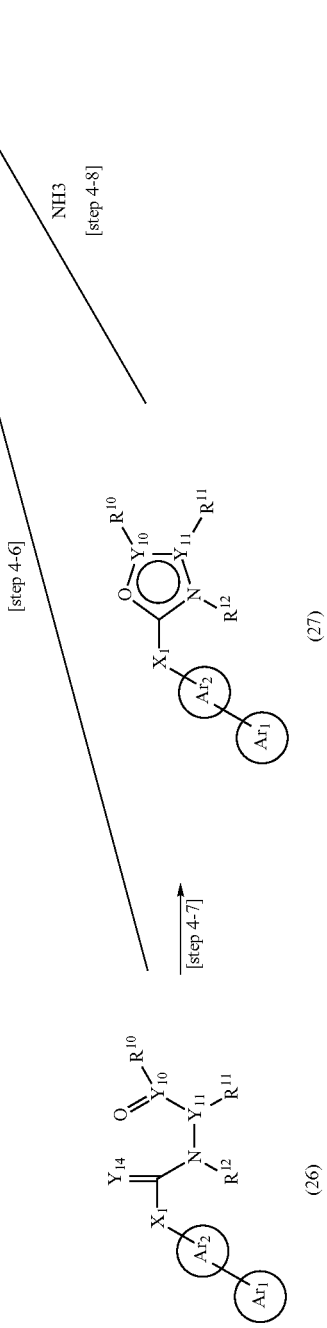

In the formula, $Ar_1$, $Ar_2$, $X_1$, $X_2$, $X_3$, $X_4$, $Y_{10}$, $Y_{11}$, $R^{10}$, $R^{11}$, $R^{12}$, na, nb, nh, nf and ne are as defined above; $Y_{13}$ represents a carboxyl group, ester group, thioester group, dithioester group, nitrile group, thioimino ether group or iminoether group; $Y_{14}$ represents an oxygen atom, nitrogen atom or sulfur atom; and $P_1$ represents a protecting group for an amino group such as a methyl carbamate group, benzyl carbamate group, tert-butyl carbamate group, allyl group, acetyl group or formyl group.

The above General Preparation Method 2 includes a method of reacting a compound (1a) with an amine compound (23a) or amine compound (23b) according to Step 4-1 or Step 4-5 to convert the compound (1a) into a compound (24) or compound (26), or converting a compound (1a) into a compound (24) or compound (26) according to Step 4-9 or Step 4-10 which is a three-stage reaction including deprotection, and further reacting the resulting compound (24) or compound (26) with ammonia, an ammonium salt or formamide in Step 4-2 or Step 4-6 to prepare a compound of the general formula (I-1), the general formula (I-2), the general formula (I-4), the general formula (I-5) or the general formula (I-6); a method of once converting a compound (24) or compound (26) into an oxazole compound (25) or a compound (27) by dehydration reaction in Step 4-3 or Step 4-7, and then reacting the oxazole compound (25) or the compound (27) with ammonia, an ammonium salt, formamide or an amine compound (22) in Step 4-4, Step 4-8 or Step 4-12 to prepare a compound of the general formula (I-1), the general formula (I-2), the general formula (I-4), the general formula (I-5) or the general formula (I-6); and a method of reacting a compound (1a) with an amine compound (23a) according to Step 4-11 to prepare a compound of the general formula (I-1), the general formula (I-4), the general formula (I-5) or the general formula (I-6).

[Preparation of Compound of General Formula (I-2)]

The compound of the general formula (I-2) can be prepared i) by reacting a compound (26) in the presence of an acid or base and optionally in the presence of ammonia, an ammonium salt, formamide or the like according to Step 4-6. The compound of the general formula (I-2) can also be prepared ii) by reacting a compound (25) or compound (27) with an amine compound (22), ammonia, an ammonium salt, formamide or the like according to Step 4-4 or Step 4-8.

The method i), specifically, Step 4-6 varies according to the starting material and is not specifically limited insofar as the conditions are similar to those in this reaction. A known method described in many documents may be used for the reaction (see Heterocyclic Compounds, Vol. 5, Wiley, New York, N.Y. 1957, p. 503; and Journal of Heterocyclic Chemistry, 1982, vol. 19, p. 193, for example). Preferably, a compound (26), wherein $Y_{14}$ represents an oxygen atom or sulfur atom, is stirred in a solvent in the presence of 1.0 to 100.0 equivalents of ammonia, an ammonium salt such as ammonium acetate or ammonium carbonate or formamide with respect to the compound (26), for example. The solvent used is not specifically limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; alcohol solvents such as amyl alcohol and isopropyl alcohol; polar solvents such as N,N-dimethylformamide and N-methylpyrrolidone; nonpolar solvents such as toluene, benzene and dichlorobenzene; organic acids such as acetic acid; water; and a mixture thereof. Formamide may be used as a solvent. The reaction temperature must be a temperature that can complete the reaction without promoting formation of an undesirable by-product, and is preferably room temperature to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

Alternatively, a compound (26), wherein $Y_4$ represents a nitrogen atom, is stirred in a solvent in the presence or absence of 0.1 to 10 equivalents of an acid, base or organic salt with respect to the compound (26). Preferable examples of the acid, base or organic salt used include inorganic acids such as hydrochloric acid and sulfuric acid; organic acids, such as p-toluenesulfonic acid and methanesulfonic acid; organic bases such as pyridine and dimethylamino pyridine; and organic salts such as pyridinium p-toluenesulfonate and tetrabutylammonium hydroxide. The solvent used is not specifically limited insofar as the solvent does not inhibit the reaction and allows the starting material to be dissolved therein to a certain extent. Preferable examples of the solvent that can be used include ether solvents such as tetrahydrofuran, 1,4-dioxane and diethyl ether; halogenated solvents such as methylene chloride, 1,2-dichloroethane and chloroform; alcohol solvents such as methanol, ethanol, amyl alcohol and isopropyl alcohol; polar solvents such as N,N-dimethylformamide and N-methylpyrrolidone; nonpolar solvents such as toluene, benzene and dichlorobenzene; water; and a mixture thereof. The above acid, base or organic salt may be used as a solvent. The reaction temperature must be a temperature that can complete the reaction without promoting formation of an undesirable by-product, and is preferably room temperature to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

The method ii), specifically, Step 4-4 or Step 4-8 varies according to the starting material and is not specifically limited insofar as the conditions are similar to those in this reaction. A known method described in many documents may be used for the reaction (see Heterocyclic Compounds, vol. 5, Wiley, New York, N.Y. 1950, p. 214; and The Journal of Organic Chemistry, 1962, vol. 27, p. 3240, for example). For example, an oxazole compound (25) or a compound (27) and 1.0 to 100.0 equivalents of an amine compound (22), ammonia, an ammonium salt such as ammonium acetate or ammonium carbonate or formamide with respect to the compound (25) or compound (27) are stirred in a solvent. The solvent used is not specifically limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; alcohol solvents such as amyl alcohol and isopropyl alcohol; polar solvents such as N,N-dimethylformamide and N-methylpyrrolidone; nonpolar solvents such as toluene, benzene and dichlorobenzene; organic acids such as acetic acid; water; and a mixture thereof. The amine source to be reacted may be used as a solvent. The reaction temperature must be a temperature that can complete the reaction without promoting formation of an undesirable by-product, and is preferably room temperature to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The amine compound (22) used in this step is commercially available or can be obtained by a technique known to a person skilled in the art.

[Preparation of Compound of General Formula (I-1), General Formula (I-4), General Formula (I-5) and General Formula (I-6)]

The compound of the general formula (I-1), the general formula (I-4), the general formula (I-5) or the general formula (I-6) can be prepared i) by reacting a compound (24) or compound (25) in the presence of ammonia, an ammonium salt, formamide or the like according to Step 4-2 or Step 4-12. The compound of the general formula (I-1), the general formula (I-4), the general formula (I-5) or the general formula (I-6) can also be prepared by reacting a compound (1a) with an amine compound (23a) according to Step 4-11.

The method i), specifically, Step 4-2 or Step 4-12 is the same method as in Step 4-6.

The method ii), specifically, Step 4-11 varies according to the starting material and is not specifically limited insofar as the conditions are similar to those in this reaction. A known method described in many documents may be used for the reaction (see Journal of the Chemical Society, 1962, p. 5149; and Journal of Medicinal Chemistry, 1983, vol. 26, p. 1187, for example). For example, a compound (1a), wherein $Y^{13}$ represents a nitrile group, thioimino ether group or imino ether group, and 1.0 to 5.0 equivalents of an amine compound (23a) with respect to the compound (1a) are stirred in a solvent. The solvent used is not specifically limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; alcohol solvents such as methanol, ethanol, butanol, amyl alcohol and isopropyl alcohol; polar solvents such as N,N-dimethylformamide and N-methylpyrrolidone; nonpolar solvents such as toluene, benzene and dichlorobenzene; organic acids such as acetic acid; water; and a mixture thereof. The yield may be improved when performing reaction in the presence of 1.0 to 10.0 equivalents of an organic amine such as triethylamine, diisopropylamine or pyridine or an alkali metal salt such as potassium carbonate or sodium carbonate with respect to the compound (1a). The reaction temperature must be a temperature that can complete the reaction without promoting formation of an undesirable by-product, and is preferably room temperature to 200° C., for example. Under preferable reaction conditions, the reaction is completed in 1 to 72 hours, and the progress of the reaction can be monitored by a known chromatography technique. An undesirable by-product can be removed by a technique known to a person skilled in the art such as a conventional chromatography technique, extraction or/and crystallization.

[Preparation of Compound (24) and Compound (26)]

The compound (24) or compound (26) can be prepared by reacting a compound (1a) with an amine compound (23a) or amine compound (23b) according to Step 4-1 or Step 4-5. Specifically, Step 4-1 or Step 4-5 varies according to the starting material and is not specifically limited insofar as the conditions are similar to those in this reaction. A known method described in many documents may be used for the reaction (see Shin Jikken Kagaku Koza (New Courses in Experimental Chemistry), vol. 22, Yuki Gosei (Organic Synthesis) [IV], edited by The Chemical Society of Japan, Maruzen Co., Ltd., November 1992, p. 137-163; and Organic Synthesis, 1941, I, p. 5, for example). For example, a compound (1a), wherein $Y_{13}$ represents a carboxyl group, and 1.0 to 10.0 equivalents of a compound (23a) or compound (23b) with respect to the compound (1a) are stirred in a solvent in the presence of 0.1 to 10.0 equivalents of a condensing agent with respect to the compound (1a). The condensing agent used varies according to the starting material and is not specifically limited. Preferable examples of the condensing agent include inorganic acids such as hydrochloric acid and sulfuric acid; organic acids such as p-toluenesulfonic acid and methanesulfonic acid, 1,3-dicyclohexylcarbodiimide, 1-ethyl-3-(3'-dimethylaminopropyl)carbodiimide, benzotriazol-1-yloxytris(dimethylamino)phosphonium hexafluorophosphate, diethyl cyanophosphonate and bis(2-oxo-3-oxazolidinyl)phosphonic chloride. Preferably, 1.0 to 5.0 equivalents of N-hydroxysuccinimide, N-hydroxybenzotriazole or dimethylaminopyridine may be added with respect to the compound (1a) in order to make the reaction efficiently proceed, for example. The solvent used varies according to the starting material and the condensing agent used, and is not specifically limited insofar as the solvent does not inhibit the reaction and allows the starting material to be dissolved therein to a certain extent. Preferable examples of the solvent include halogenated solvents such as chloroform, methylene chloride and 1,2-dichloroethane; and polar solvents such as tetrahydrofuran and N,N-dimethylformamide. The reaction temperature must be a temperature that can complete the reaction without promoting formation of an undesirable by-product, and is preferably ice-cold temperature to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

Alternatively, a compound (1a), wherein $Y_{13}$ represents a cyano group, imino ether group or thioimino ether group, and 1.0 to 100.0 equivalents of an amine compound (23a) or amine compound (23b) with respect to the compound (1a) are stirred in a solvent. The solvent used is not specifically limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; alcohol solvents such as methanol, ethanol and isopropyl alcohol; polar solvents such as N,N-dimethylformamide and N-methylpyrrolidone; nonpolar solvents such as toluene, benzene and dichlorobenzene; organic acids such as acetic acid; organic bases such as pyridine; water; and a mixture thereof. The amine compound (23a) or amine compound (24b) may be used as a solvent. The yield may be improved when using 0.1 to 1.0 equivalent of an inorganic acid such as hydrochloric acid, a Lewis acid such as trifluoroborate or an organic acid such as p-toluenesulfonic acid, or 1.0 to 10.0 equivalent of an organic bases such as triethylamine, pyridine and diisopropylethylamine, with respect to the compound (1a). The reaction temperature must be a temperature that can complete the reaction without promoting formation of an undesirable by-product, and is preferably 0 to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

The compound (24) or compound (26) can also be prepared from a compound (1a) according to Step 4-9 or Step 4-10. Specifically, Step 4-9 or Step 4-10 consists of a three-stage reaction including a deprotection step. In a first stage, a compound (1a) is condensed with a compound (23c) or compound (23d) by dehydration. In a second stage, the protecting group is deprotected. In a third stage, the condensate is condensed with a compound (23e).

The first-stage condensation reaction may be performed by the same method as in Step 4-1. The second-stage deprotection reaction varies according to the starting material and is not specifically limited insofar as the conditions are similar to those in this reaction. A known method described in many documents may be used for the reaction (see T. W. Green, "Protective Groups in Organic Synthesis", John Wiley & Sons, Inc., 1999, p. 615-626). Preferably, the condensation compound in the first stage, wherein $P_1$ represents a tert-butyl carbamate group, is stirred in a solvent in the presence of 1.0 to 100.0 equivalents of an acid with respect to the compound, for example. Examples of the acid used include inorganic acids such as hydrochloric acid and sulfuric acid; and organic acids such as trifluoroacetic acid and methanesulfonic acid. The solvent used is not specifically limited insofar as the solvent does not inhibit the reaction and allows the starting material to be dissolved therein to a certain extent. Preferable examples of the solvent include ethyl acetate, methanol, ethanol, 1,4-dioxane, methylene chloride, chloroform, methanol, isopropyl alcohol, N,N-dimethylformamide and N-methylpyrrolidone. The reaction temperature must be a temperature that can complete the reaction without promoting formation of an undesirable by-product, and is preferably 0 to 100° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

The third-stage condensation reaction may be performed by the same method as in Step 4-1.

[Preparation of Compound (1a)]

The compound (1a) can be prepared from a compound (4) or compound (17) by the same method as in the above Step 2-1 or Step 2-10.

[Preparation of Compound (25) and Compound (27)]

The compound (25) or compound (27) can be prepared from the compound (24) or compound (26) by dehydration reaction according to Step 4-3 or Step 4-7. Specifically, Step 4-3 or Step 4-7 varies according to the starting material and is not specifically limited insofar as the conditions are similar to those in this reaction. A known method described in many documents may be used for the reaction (see The Chemistry of Heterocyclic Compounds, 45; Wiley, New York, 1986, p. 1, for example). For example, the compound (24) or compound (26) is stirred in a solvent in the presence of 1.0 to 100.0 equivalents of a dehydration reagent with respect to the compound (24) or compound (26). The dehydration reagent used varies according to the starting material and is not specifically limited. Preferable examples of the dehydration reagent include phosphorus oxychloride, thionyl chloride, phosgene, triphosgene, carbonyldiimidazole, hydrochloric acid, sulfuric acid, p-toluenesulfonic acid, methanesulfonic acid, triphenylphosphine-carbon tetrachloride, and triphenylphosphine-carbon tetrabromide. The solvent used is not specifically limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; polar solvents such as N,N-dimethylformamide and N-methylpyrrolidone; nonpolar solvents such as toluene, benzene and dichlorobenzene; and a mixture thereof. The dehydration reagent may be used as a solvent. The reaction temperature must be a temperature that can complete the reaction without promoting formation of an undesirable by-product, and is preferably 0 to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Compound (23a), Compound (23b), Compound (23c), Compound (23d) and Compound (23e)]

The compound (23a), compound (23b), compound (23c), compound (23d) and compound (23e) are commercially available or can be obtained by a technique known to a person skilled in the art.

[General Preparation Method 3]

Typically used General Preparation Method 3 for the compound of the general formula (I) of the present invention will be described below.

[Formula 43]

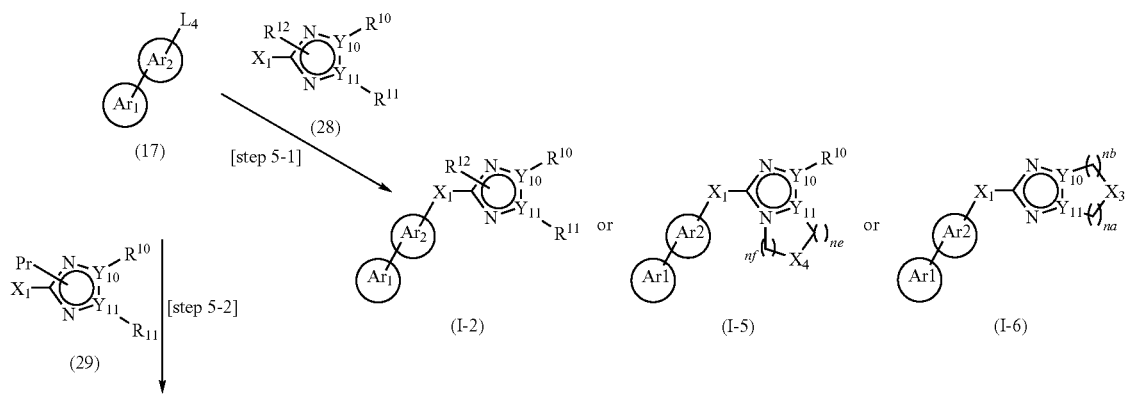

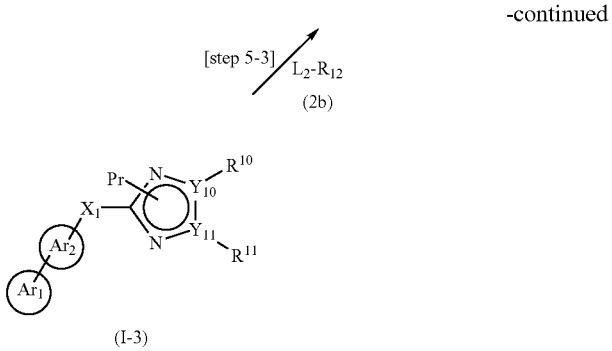

(I-3)

In the formula, $Ar_1$, $Ar_2$, $X_1$, $X_3$, $X_4$, $Y_{10}$, $Y_{11}$, $R^{10}$, $R^{11}$, $R^{12}$, $L_2$, $L_4$, na, nb, nf and ne are as defined above; and Pr represents a protecting group for a heterocycle nitrogen atom such as a trityl group, methoxymethyl group, benzyl group or methanesulfonic acid group.

The above General Preparation Method 3 includes a method of reacting a compound (17) with a heterocyclic compound (28) in Step 5-1 to prepare a compound of the general formula (I-2), the general formula (I-5) or the general formula (I-6); and a method of reacting a compound (17) with a heterocyclic compound (29) having a protecting group in Step 5-2 to once convert the compound (17) into a compound of the general formula (I-3) having a protecting group, and deprotecting the protecting group of the compound of the general formula (I-3) and reacting the compound with a compound (2b) in Step 5-3 to prepare a compound of the general formula (I-2), the general formula (I-5) or the general formula (I-6).

[Preparation of Compounds of General Formula (I-2) and (I-3)]

The compound of the general formula (I-2) or (I-3) can be prepared by i) reacting a compound (17) with a compound (28) or compound (29) according to Step 5-1 or Step 5-2. The compound of the general formula (I-2) can also be prepared by ii) deprotecting the protecting group of the compound of the general formula (I-3) and then reacting the compound with a compound (2b) according to Step 5-3.

The method i), specifically, Step 5-1 or Step 5-2 varies according to the starting material and is not specifically limited insofar as the conditions are similar to those in this reaction. A known method described in many documents such as Mizoroki-Heck reaction (see R. F. Heck, "Org. Reactions.", 1982, vol. 27, p. 345, for example) or Sonogashira reaction (see K. Sonogashira, "Comprehensive Organic Synthesis", 1991, vol. 3, p. 521, for example) may be used for the reaction.

In Mizoroki-Heck reaction, a compound (17), wherein $L_4$ represents a chlorine atom, a bromine atom, an iodine atom or a sulfonate group such as a trifluoromethanesulfonate group, and 1.0 to 5.0 equivalents of a compound (28) or compound (29), wherein $X_1$ represents an alkenyl group, with respect to the compound (17) are stirred in a solvent in the presence of 0.01 to 0.5 equivalent of a transition metal catalyst with respect to the compound (17), for example. The transition metal catalyst used is preferably a palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine, tri-tert-butylphosphine or 2-(di-tert-butylphosphino)biphenyl may be preferably added, for example, in order to make the reaction efficiently proceed. A preferable result may be achieved in the presence of a base. The base used is not specifically limited insofar as the base is used in a coupling reaction similar to this reaction. Preferable examples of the base include triethylamine, N,N-diisopropylethylamine, N,N-dicyclohexylmethylamine and tetrabutylammonium chloride. The solvent used varies according to the starting material and the transition metal catalyst used, and is not specifically limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Sonogashira reaction, a compound (17), wherein $L_4$ represents a chlorine atom, a bromine atom, an iodine atom or a sulfonate group such as a trifluoromethanesulfonate group, and 1.0 to 5.0 equivalents of a compound (28) or compound (29), wherein $X_1$ represents an alkynyl group, with respect to the compound (17) are stirred in a solvent in the presence of 0.01 to 0.5 equivalent of a transition metal catalyst with respect to the compound (17), for example. The transition metal catalyst used is preferably a known palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine or tri-tert-butylphosphine may be preferably added, for example, in order to make the reaction efficiently proceed. In the reaction, a good result may be achieved when adding a metal halide or a quaternary ammonium salt, preferably copper (I) iodide, lithium chloride, tetrabutylammonium fluoride or silver (I) oxide, for example. A preferable result may be achieved in the presence of a base. The base used here is not specifically limited insofar as the base is used in a coupling reaction similar to this reaction. Preferable examples of the base include diethylamine, triethylamine, N,N-diisopropylethylamine, a piperidine and pyridine. Preferable examples of the solvent used include acetonitrile, tetrahydrofuran, 1,4-dioxane, 1,2-dimethoxyethane, benzene, toluene, xylene, 1-methyl-2-pyrrolidone, N,N-dimethylformamide and dimethyl sulfoxide. More preferable examples of the solvent include tetrahydrofuran, 1,4-dioxane, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

The method ii), specifically, Step 5-3 consists of first-stage deprotection reaction and second-stage reaction with a compound (2b). The first-stage deprotection reaction varies according to the starting material and is not specifically limited insofar as the conditions are similar to those in this reaction. A known method described in many documents may be used for the reaction (see T. W. Green, "Protective Groups in Organic Synthesis", John Wiley & Sons, Inc., 1999, p. 615-626). Preferably, the compound of the general formula (I-3) is stirred in a solvent in the presence of 1.0 to 100.0 equivalents of an acid or base with respect to the compound of the general formula (I-3), for example. Preferable Examples of the acid used include inorganic acids such as hydrochloric acid and sulfuric acid; and organic acids such as trifluoroacetic acid, methanesulfonic acid and p-toluenesulfonic acid. Preferable examples of the base used include alkali metal hydroxides such as sodium hydroxide and potassium hydroxide; alkali metal carbonates such as potassium carbonate and sodium carbonate; and organic amines such as ammonia and methylamine. The solvent used is not specifically limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, ethyl acetate, methanol, ethanol, benzene, toluene, xylene, chloroform, methylene chloride, water; and a mixture thereof. An acid or base may be used as a solvent. The reaction temperature must be a temperature that can complete the deprotection reaction, and is preferably room temperature to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The second stage reaction of the compound (1-3) with the compound (2b) may be performed by the same method as in Step 1-3.

[Preparation of Compound (28)]

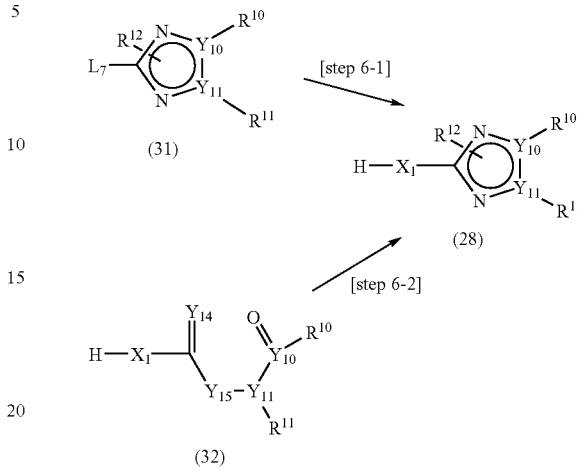

[Formula 44]

In the formula, $X_1$, $Y_{10}$, $Y_{11}$, $Y_{14}$, $R^{10}$, $R^{11}$ and $R^{12}$ are as defined above; $L_7$ represents a hydrogen atom, a halogen atom such as a chlorine atom, bromine atom or iodine atom, a sulfonate group such as a trifluoromethanesulfonate group, a trialkyltin group or a leaving group such as a boronic acid or boronate group; and $Y_{15}$ represents an oxygen atom, or a nitrogen atom that may be substituted with a substituent selected from the above Substituent Group A4.

The compound (28) can be prepared by i) condensing a compound (31) with an alkene or alkyne compound according to Step 6-1. The compound (28) can also be prepared by ii) cyclizing a compound (32) according to Step 6-2.

The method i), specifically, Step 6-1 varies according to the starting material and is not specifically limited insofar as the conditions are similar to those in this reaction. A known method described in many documents such as Mizoroki-Heck reaction (see R. F. Heck, "Org. Reactions.", 1982, vol. 27, p. 345, for example), Suzuki-Miyaura reaction (see A. Suzuki, "Chem. Rev.", 1995, vol. 95, p. 2457, for example), Sonogashira reaction (see K. Sonogashira, "Comprehensive Organic Synthesis", 1991, vol. 3, p. 521) or Stille coupling reaction (see J. K. Stille, "Angew. Chem. Int. Ed. Engl.", 1986, vol. 25, p. 508, for example) may be used for the reaction.

In Mizoroki-Heck reaction, a compound (31), wherein $L_7$ represents a chlorine atom, a bromine atom, an iodine atom or a sulfonate group such as a trifluoromethanesulfonate group, and 1.0 to 5.0 equivalents of an alkene compound, wherein the alkene compound refers to a compound having a double bond in the molecule, with respect to the compound (31) are stirred in a solvent in the presence of 0.01 to 0.2 equivalent of a transition metal catalyst with respect to the compound (31), for example. The transition metal catalyst used is preferably a palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine, tri-tert-butylphosphine or 2-(di-tert-butylphosphino)biphenyl may be preferably added, for example, in order to make the reaction efficiently proceed. A preferable result may be achieved in the presence of a base. The base used is not specifically limited insofar as the base is used in a coupling reaction similar to this reaction. Preferable examples of the base include triethylamine, N,N-diisopropylethylamine, N,N-dicyclohexylmethylamine and tetrabutylammonium chloride. The solvent used varies according to the starting material and the transition metal catalyst used, and is not specifically limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Suzuki-Miyaura reaction, a compound (31), wherein $L_7$ represents a chlorine atom, a bromine atom, an iodine atom or a sulfonate group such as a trifluoromethanesulfonate group, and 1.0 to 5.0 equivalents of an alkene or alkyne boronic acid or boronate compound, wherein the boronic acid or boronate compound refers to a boronic acid or boronate compound directly bonded to a double bond or triple bond, with respect to the compound (31) are stirred in a solvent in the presence of 0.01 to 0.5 equivalent of a transition metal catalyst with respect to the compound (31), for example. The transition metal catalyst used is preferably a known palladium complex, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine, tricyclohexylphosphine or tri-tert-butylphosphine may be preferably added, for example, in order to make the reaction efficiently proceed. A quaternary ammonium salt, preferably tetrabutylammonium chloride or tetrabutylammonium bromide, for example, may also be added in order to make the reaction efficiently proceed. In this reaction, a preferable result may be achieved in the presence of a base. The base used at this time varies according to the starting material, the solvent used and the like, and is not specifically limited. Preferable examples of the base include sodium hydroxide, barium hydroxide, potassium fluoride, cesium fluoride, sodium carbonate, potassium carbonate, cesium carbonate and potassium phosphate. The solvent used varies according to the starting material and the transition metal catalyst used, and is not specifically limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone, N,N-dimethylformamide, water and a mixed solvent thereof. The reaction temperature must be a temperature that can complete the coupling reaction, and is preferably room temperature to 200° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The desired compound (28) can also be obtained from a combination of the boronic acid compound or boronate compound (31), wherein $L_7$ represents a boronic acid group or boronate group, with a halogenated alkene compound or enol trifluoromethanesulfonate compound by the same method as above.

In Sonogashira reaction, a compound (31), wherein $L_7$ represents a chlorine atom, a bromine atom, an iodine atom or a sulfonate group such as a trifluoromethanesulfonate group, and 1.0 to 5.0 equivalents of an alkyne compound, wherein the alkyne compound refers to a compound having HC≡C— in the molecule, with respect to the compound (31) are stirred in a solvent in the presence of 0.01 to 0.5 equivalent of a transition metal catalyst with respect to the compound (31), for example. The transition metal catalyst used is preferably a known palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine or tri-tert-butylphosphine may be preferably added, for example, in order to make the reaction efficiently proceed. In the reaction, a good result may be achieved when adding a metal halide or a quaternary ammonium salt, preferably copper (I) iodide, lithium chloride, tetrabutylammonium fluoride or silver (I) oxide, for example. A preferable result may be achieved in the presence of a base. The base used here is not specifically limited insofar as the base is used in a coupling reaction similar to this reaction. Preferable examples of the base include diethylamine, triethylamine, N,N-diisopropylethylamine, a piperidine and pyridine. Preferable examples of the solvent used include acetonitrile, tetrahydrofuran, 1,4-dioxane, 1,2-dimethoxyethane, benzene, toluene, xylene, 1-methyl-2-pyrrolidone, N,N-dimethylformamide and dimethyl sulfoxide. More preferable examples of the solvent include tetrahydrofuran, 1,4-dioxane, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Stille coupling reaction, a compound (31), wherein $L_7$ represents a chlorine atom, bromine atom, iodine atom or trifluoromethanesulfonate group, and 1.0 equivalent or more of a trialkyltin compound, wherein the trialkyltin compound refers to an alkyltin compound directly bonded to a double bond or triple bond, with respect to the compound (31) are stirred in a solvent in the presence of 0.01 to 0.2 equivalent of a transition metal catalyst with respect to the compound (31), for example. The transition metal catalyst used is preferably a palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). 0.1 to 5.0 equivalents of copper (I) halide or/and lithium chloride may be added in order to make the reaction efficiently proceed. Preferable examples of the solvent used include toluene, xylene, N,N-dimethylformamide, N,N-dimethylacetamide, 1-methyl-2-pyrrolidone and dimethyl sulfoxide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The desired compound (28) can also be obtained from a combination of the tin compound (31), wherein $L_7$ represents a trialkyltin group, with a halogenated alkene compound or enol trifluoromethanesulfonate compound by the same method as above. The halogenated alkene compound refers to a compound of which the hydrogen atom bonded to the double bond in the molecule is substituted with a halogen atom. The enol trifluoromethanesulfonate compound refers to a compound of which the hydrogen atom of the enol ester group in the molecule is substituted with a trifluoromethanesulfonyl group.

The method ii), specifically, Step 6-2 may be performed by the same method as in Step 4-2 or Step 4-6.

[Preparation of Compound (31)]

The compound (31) is commercially available or prepared by a method known to a person skilled in the art. If not commercially available, the compound (31), wherein $L_7$ is a boronic acid group or boronate group, can be prepared by a method known to a person skilled in the art, for example, although the method varies according to the starting material (see Shin Jikken Kagaku Koza (New Courses in Experimental Chemistry), vol. 22, Yuki Gosei (Organic Synthesis) [VI], edited by The Chemical Society of Japan, Maruzen Co., Ltd., September 1992, p. 61-90, for example). The compound (31), wherein $L_7$ is a trialkyltin group, can be prepared by a method known to a person skilled in the art, although the method varies according to the starting material (see Shin Jikken Kagaku Koza (New Courses in Experimental Chemistry), vol. 22, Yuki Gosei (Organic Synthesis) [VI], edited by The Chemical Society of Japan, Maruzen Co., Ltd., September 1992, p. 179-201, for example).

[Preparation of Compound (32)]

The compound (32) is commercially available or prepared by a method known to a person skilled in the art. If not commercially available, the compound (32) can be prepared by the same method as in Step 1-1 or Step 4-1, for example.

[Preparation of Compound (29)]

The compound (29) is commercially available or can be prepared by the same method as in the case of the compound (28) if not commercially available.

The compound of the general formula (I-5) or the general formula (I-6) can be prepared from the compound (28) or compound (29), wherein two of $R^{10}$, $R^{11}$ and $R^{12}$ form a ring, as a starting material by the same method as above.

[General Preparation Method 4]

Typically used General Preparation Method 4 for the compound of the general formula (I) of the present invention will be described below.

[Formula 45]

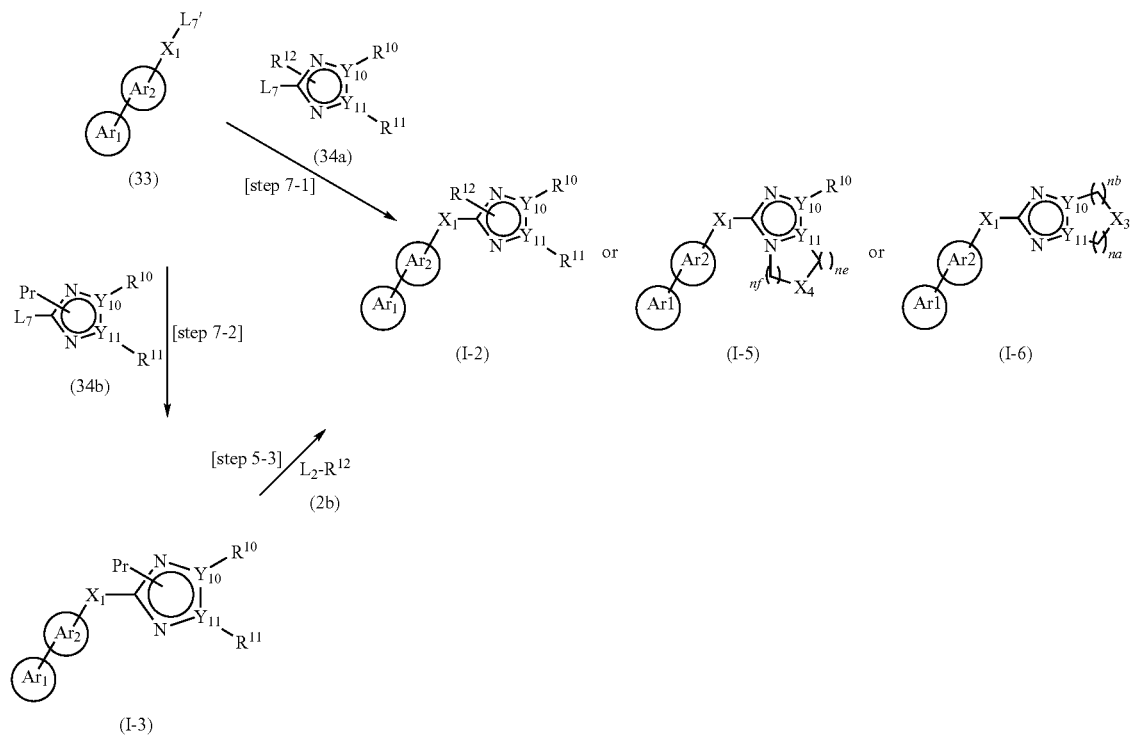

In the formula, $Ar_1$, $Ar_2$, $X_1$, $X_3$, $X_4$, $Y_{10}$, $Y_{11}$, $R^{10}$, $R^{11}$, $R^{12}$, $L_2$, $L_7$, Pr, na, nb, nf and ne are as defined above; and $L_7'$ represents a hydrogen atom, a halogen atom such as a chlorine atom, bromine atom or iodine atom, a sulfonate group such as a trifluoromethanesulfonate group, a trialkyltin group or a leaving group such as a boronic acid or boronate group.

The above General Preparation Method 4 includes a method of condensing a compound (33) with a heterocyclic compound (34a) in Step 7-1 to prepare a compound of the general formula (I-2), the general formula (I-5) or the general formula (I-6); and a method of condensing a compound (33) with a heterocyclic compound (34b) having a protecting group in Step 7-2 to convert the compound (33) into a compound of the general formula (I-3) having a protecting group, and deprotecting the protecting group of the compound of the general formula (I-3) and subsequently reacting the compound with a compound (2b) in Step 5-3 to prepare a compound of the general formula (I-2), the general formula (I-5) or the general formula (I-6).

[Preparation of Compound of General Formula (I-2) and Compound of General Formula (I-3)]

The compound of the general formula (I-2) or the compound of the general formula (I-3) can be prepared by reacting a compound (33) with a compound (34a) or compound (34b) according to Step 7-1 or Step 7-2. Specifically, Step 7-1 or Step 7-2 varies according to the starting material and is not specifically limited insofar as the conditions are similar to those in this reaction. A known method described in many documents may be used for the reaction. Preferable examples of the method include Mizoroki-Heck reaction (see R. F. Heck, "Org. Reactions.", 1982, vol. 27, p. 345, for example), Suzuki-Miyaura reaction (see A. Suzuki, "Chem. Rev.", 1995, vol. 95, p. 2457, for example), Sonogashira reaction (see K. Sonogashira, "Comprehensive Organic Synthesis", 1991, vol. 3, p. 521) and Stille coupling reaction (see J. K. Stille, "Angew. Chem. Int. Ed. Engl.", 1986, vol. 25, p. 508, for example).

In Mizoroki-Heck reaction, a compound (33), wherein $L_7'$ represents a hydrogen atom, and $X_1$ represents an alkenyl group, and 0.5 to 5.0 equivalents of a compound (34a) or compound (34b), wherein $L_7$ represents a chlorine atom, a bromine atom, an iodine atom or a sulfonate group such as a trifluoromethanesulfonate group, with respect to the compound (33) are stirred in a solvent in the presence of 0.01 to 1.0 equivalent of a transition metal catalyst with respect to the compound (33), for example. The transition metal catalyst used is preferably a palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine, tri-tert-butylphosphine or 2-(di-tert-butylphosphino)biphenyl may be preferably added, for example, in order to make the reaction efficiently proceed. A preferable result may be achieved in the presence of a base. The base used is not specifically limited insofar as the base is used in a coupling reaction similar to this reaction. Preferable examples of the base include triethylamine, N,N-diisopropylethylamine, N,N-dicyclohexylmethylamine and tetrabutylammonium chloride. The solvent used varies according to the starting material and the transition metal catalyst used, and is not specifically limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Suzuki-Miyaura reaction, a compound (33), wherein $L_7'$ represents a boronic acid or boronate group, and 0.5 to 5.0 equivalents of a compound (34a) or compound (34b), wherein $L_7$ represents a chlorine atom, a bromine atom, an iodine atom or a sulfonate group such as a trifluoromethanesulfonate group, with respect to the compound (33) are stirred in a solvent in the presence of 0.01 to 1.0 equivalent of a transition metal catalyst with respect to the compound (33), for example. The transition metal catalyst used is preferably a known palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine, tricyclohexylphosphine or tri-tert-butylphosphine may be preferably added, for example, in order to make the reaction efficiently proceed. A good result may be achieved when appropriately adding a quaternary ammonium salt, preferably tetrabutylammonium chloride or tetrabutylammonium bromide, for example. In this reaction, a preferable result may be achieved in the presence of a base. The base used at this time varies according to the starting material, the solvent used and the like, and is not specifically limited. Preferable examples of the base include sodium hydroxide, barium hydroxide, potassium fluoride, cesium fluoride, sodium carbonate, potassium carbonate, cesium carbonate and potassium phosphate. The solvent used varies according to the starting material and the transition metal catalyst used, and is not specifically limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone, N,N-dimethylformamide, water and a mixed solvent thereof. The reaction temperature must be a temperature that can complete the coupling reaction, and is preferably room temperature to 200° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The desired compound of the general formula (I-2) or general formula (I-3) can also be obtained from a combination of the compound (33), wherein $L_7$ represents a chlorine atom, a bromine atom, an iodine atom or a sulfonate group such as a trifluoromethanesulfonate group, with the compound (34a) or compound (34b), wherein $L_7$ represents a boronic acid or boronate group, by the same method as above.

In Sonogashira reaction, an alkyne compound (33), wherein $L_7'$ represents a hydrogen atom, and $X_1$ represents an alkynyl group, and 0.5 to 5.0 equivalents of a compound (34a) or compound (34b), wherein $L_7$ represents a chlorine atom, a bromine atom, an iodine atom or a sulfonate group such as a trifluoromethanesulfonate group, with respect to the compound (33) are stirred in a solvent in the presence of 0.01 to 1.0 equivalent of a transition metal with respect to the compound (33), for example. The transition metal catalyst used is preferably a known palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine or tri-tert-butylphosphine may be preferably added, for example, in order to make the reaction efficiently proceed. In the reaction, a good result may be achieved when adding a metal halide or a quaternary ammonium salt such as preferably copper (I) iodide, lithium chloride, tetrabutylammonium fluoride or silver (I) oxide, for example. A preferable result may be achieved in the presence of a base. The base used here is not specifically limited insofar as the base is used in a coupling reaction similar to this reaction. Preferable examples of the base include diethylamine, triethylamine, N,N-diisopropylethylamine, a piperidine and pyridine. Preferable examples of the solvent used include acetonitrile, tetrahydrofuran, 1,4-dioxane, 1,2-dimethoxyethane, benzene, toluene, xylene, 1-methyl-2-pyrrolidone, N,N-dimethylformamide, dimethyl sulfoxide and a mixture thereof. More preferable examples of the solvent include tetrahydrofuran, 1,4-dioxane, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Stille coupling reaction, a compound (33), wherein $L_7'$ represents a chlorine atom, bromine atom, iodine atom or trifluoromethanesulfonate group, and 0.5 to 5.0 equivalents of a compound (34a) or compound (34b), wherein $L_7$ represents an alkyltin group, with respect to the compound (33) are stirred in a solvent in the presence of 0.01 to 1.0 equivalent of a transition metal catalyst with respect to the compound (33), for example. The transition metal catalyst used is preferably a known palladium complex such as palladium (II) acetate, dichlorobis(triphenylphosphine)palladium (II), tetrakis(triphenylphosphine)palladium (0) or tris(dibenzylideneacetone)dipalladium (0), for example, and more preferably tetrakis(triphenylphosphine)palladium (0) or tris(dibenzylideneacetone)dipalladium (0), for example. 0.1 to 5.0 equivalents of copper (I) halide or/and lithium chloride may be appropriately used in order to make the reaction efficiently proceed. Preferable examples of the solvent used include toluene, xylene, N,N-dimethylformamide, N,N-dimethylacetamide, 1-methyl-2-pyrrolidone, dimethyl sulfoxide and a mixture thereof. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The desired compound of the general formula (I-2) or general formula (I-3) can also be obtained from a combination of the compound (33), wherein $L_7$ represents a trialkyltin group, with the compound (34a) or compound (35b), wherein $L_3$ represents a chlorine atom, bromine atom, iodine atom or trifluoromethanesulfonate group, by the same method as above.

[Preparation of Compound (34a) and Compound (34b)]

The compound (34a) or compound (34b) can be prepared by the same method as in the case of the compound (31).

[Preparation of Compound (33)]

The compound (33) can be prepared from a compound (13) or compound (15) by the same method as in Step 2-7 or Step 2-9.

The compound of the general formula (I-5) or the general formula (I-6) can be prepared from the compound (34a) or compound (34b), wherein two of $R^{10}$, $R^{11}$ and $R^{12}$ form a ring, as a starting material by the same method as above.

[General Preparation Method 5]

Typically used General Preparation Method 5 for the compound of the general formula (I) of the present invention will be described below.

[Formula 46]

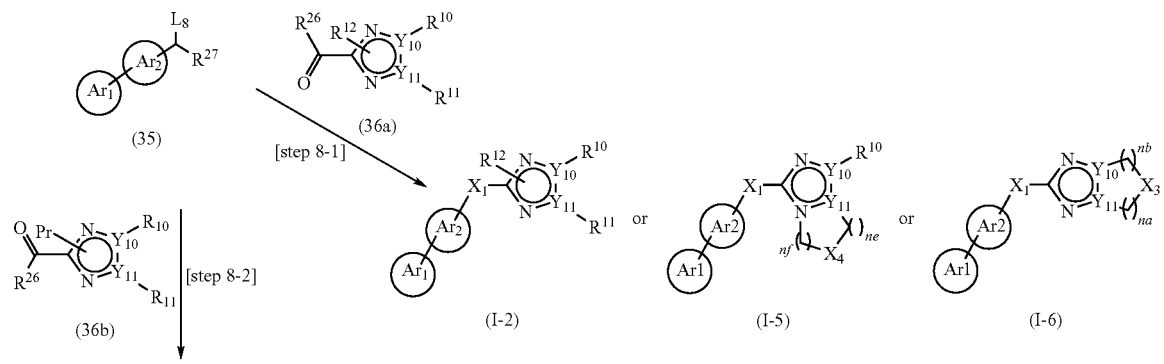

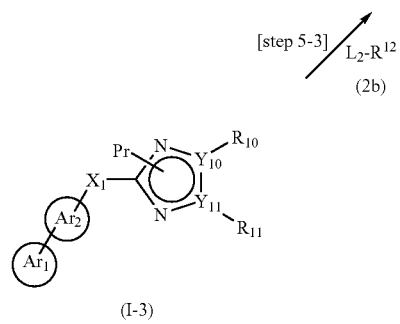

(I-3)

In the formula, $Ar_1$, $Ar_2$, $X_1$, $X_3$, $X_4$, $Y_{10}$, $Y_{11}$, $R^{26}$, $R^{10}$, $R^{11}$, $R^{12}$, Pr, na, nb, nf, ne and $L_2$ are as defined above; $L_8$ represents a phosphite group such as a diethylphosphonyl group, a phosphonium salt such as triphenylphosphonium bromide, a silyl group such as a trimethylsilyl group, or a carboxyl group; and R27 represents a group selected from the above Substituent Group A3.

The above General Preparation Method 5 is an example of a method of condensing a compound (35) with a heterocyclic compound (36a) in Step 8-1 to prepare a compound of the general formula (I-2), the general formula (I-5) or the general formula (I-6); or a method of reacting a compound (35) with a heterocyclic compound (36b) having a protecting group in Step 8-2 to once convert the compound (35) into a compound of the general formula (I-3) having a protecting group, and deprotecting the protecting group of the compound of the general formula (I-3) and subsequently reacting the compound with a compound (2b) in Step 5-3 to prepare a compound of the general formula (I-2), the general formula (I-5) or the general formula (I-6).

[Preparation of Compound of General Formula (I-2) and Compound of General Formula (I-3)]

The compound of the general formula (I-2) or the compound of the general formula (I-3) can be prepared by reacting a compound (35) with a compound (36a) or (36b) according to Step 8-1 or Step 8-2. Specifically, Step 8-1 or Step 8-2 varies according to the starting material and is not specifically limited insofar as the conditions are similar to those in this reaction. A known method described in many documents such as Wittig reaction, Horner-Emmons reaction or Peterson reaction (see Shin Jikken Kagaku Koza (new Courses in Experimental Chemistry), vol. 19, Yuki Gosei (Organic Synthesis) [I], edited by The Chemical Society of Japan, Maruzen Co., Ltd., June 1992, p. 57-85, for example) may be used.

In Wittig reaction, a compound (35), wherein $L_8$ represents a phosphonium salt, and 0.5 to 2.0 equivalents of a carbonyl compound (36a) or a compound (36b) with respect to the compound (35) are stirred in a solvent in the presence of 1.0 to 5.0 equivalents of a base with respect to the compound (35), for example. This reaction may be a method of first reacting a compound (35) with a base to form a phosphorus ylide and then adding a carbonyl compound (36a) or a compound (36b) to the ylide; or a method of adding a base in the presence of a compound (35) and a carbonyl compound (36a) or a compound (36b). The base used varies according to the starting material and the solvent and is not specifically limited. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; and alkali metal hydrides such as sodium hydride. The solvent used varies according to the starting material and the base used, and is not specifically limited insofar as the solvent does not inhibit the reaction and allows the starting material to be dissolved therein to a certain extent. Preferable examples of the solvent used include polar solvents such as nitromethane, acetonitrile, 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; halogenated solvents such as chloroform and methylene chloride; water; and a mixed solvent thereof. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Horner-Emmons reaction, a compound (35), wherein $L_8$ represents a phosphite group, is reacted with 0.5 to 2.0 equivalents of a carbonyl compound (36a) or a compound (36b) with respect to the compound (35) in a solvent in the presence of 1.0 to 5.0 equivalents of a base with respect to the compound (35), for example. This reaction may be a method of first treating a compound (35) and a base to form a carbanion and then adding a carbonyl compound (36a) or a compound (36b) to the carbanion; or a method of adding a base in the presence of a compound (35) and a carbonyl compound (36a) or a compound (36b). The base used varies according to the starting material and the solvent and is not specifically limited. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; alkali metal hydrides such as sodium hydride; and alkali metal ammonia salts such as sodium amide. The solvent used varies according to the starting material and the base used, and is not specifically limited insofar as the solvent does not inhibit the reaction and allows the starting material to be dissolved therein to a certain extent. Preferable examples of the solvent include polar solvents such as 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; water; and a mixed solvent thereof. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Peterson reaction, a compound (35), wherein $L_8$ represents a silyl group, is reacted with 0.5 to 2.0 equivalents of a carbonyl compound (36a) or a compound (36b) with respect to the compound (35) in a solvent in the presence of 1.0 to 5.0 equivalents of a base with respect to the compound (35), for example. This reaction may be a method of first treating a compound (35) and a base to form a carbanion and then adding a carbonyl compound (36a) or a compound (36b) to the carbanion; or a method of adding a base in the presence of a compound (35) and a carbonyl compound (36a) or a compound (36b). The base used varies according to the starting material and the solvent and is not specifically limited. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; alkali metal hydrides such as sodium hydride; and alkali metal ammonia salts such as sodium amide. The solvent used varies according to the starting material and the base used, and is not specifically limited insofar as the solvent does not inhibit the reaction and allows the starting material to be dissolved therein to a certain extent. Preferable examples of the solvent include polar solvents such as 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; water; and a mixed solvent thereof. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Compound (36a) and Compound (36b)]

The compound (36a) and the compound (36b) are commercially available or can be prepared by a technique known to a person skilled in the art. If not commercially available, the compounds can be prepared by acylation of a compound (31), for example (see Shin Jikken Kagaku Koza (New Courses in Experimental Chemistry), vol. 21, Yuki Gosei (Organic Synthesis) [III], edited by The Chemical Society of Japan, Maruzen Co., Ltd., February 1991, p. 184-194, for example).

[Preparation of Compound (35)]

The compound (35) can be prepared from a compound (6) or compound (17) as a starting material by a known method described in many documents. Preferably, for example, i) the compound (35) as a Wittig reagent, wherein $L_8$ represents a phosphonium salt, can be prepared by halogenating a corresponding alcohol compound by a method known to a person skilled in the art (see Shin Jikken Kagaku Koza (New Courses in Experimental Chemistry), vol. 19, Yuki Gosei (Organic Synthesis) [I], edited by The Chemical Society of Japan, Maruzen Co., Ltd., June 1992, p. 430-438, for example), and then reacting the compound with an organophosphorus compound such as triphenylphosphine (see Organic Reaction, 1965, vol. 14, p. 270, for example). ii) The compound (35) as a Horner-Emmons reagent, wherein $L_8$ represents a phosphite, can be prepared by halogenating a corresponding alcohol compound by a method known to a person skilled in the art (see Shin Jikken Kagaku Koza (New Courses in Experimental Chemistry), vol. 19, Yuki Gosei (Organic Synthesis) [I], edited by The Chemical Society of Japan, Maruzen Co., Ltd., June 1992, p. 430-438, for example), and then reacting the compound with an alkyl phosphinite by Arbuzov reaction (see Chemical Review, 1981, vol. 81, p. 415, for example) or with a metal phosphonite by Becker reaction (see Journal of the American Chemical Society, 1945, vol. 67, p. 1180, for example). Alternatively, the Horner-Emmons reagent can be prepared from a corresponding carbonyl compound and a chlorophosphate in the presence of a base (see The Journal of Organic Chemistry, 1989, vol. 54, p. 4750, for example). iii) The compound (35) as a Peterson reagent, wherein $L_9$ represents a silyl group, can be prepared from a corresponding halogen compound and a trialkylsilyl chloride in the presence of a base (see Journal of Organometallic Chemistry, 1983, vol. 248, p. 51, for example).

The compound of the general formula (I-5) or the compound of the general formula (I-6) can be prepared from the compound (36a) or compound (36b), wherein two of $R^{10}$, $R^{11}$ and $R^{12}$ form a ring, as a starting material by the same method as above.

[General Preparation Method 6]

Typically used General Preparation Method 6 for the compound of the general formula (I) of the present invention will be described below.

[Formula 47]

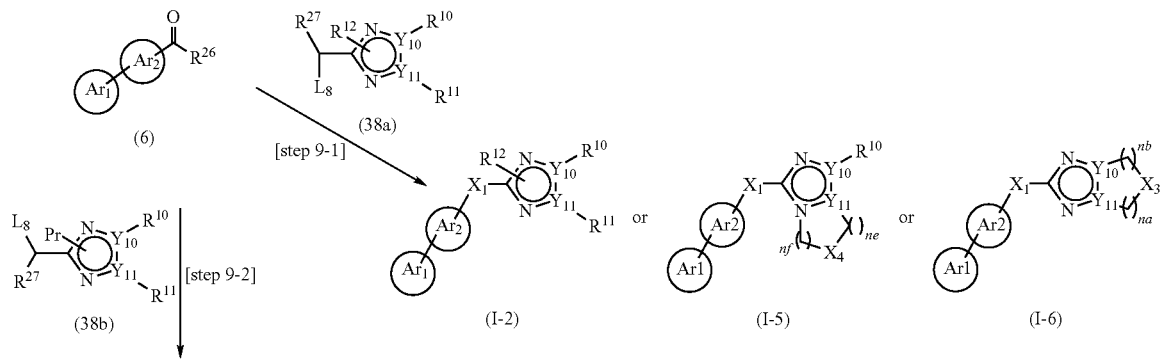

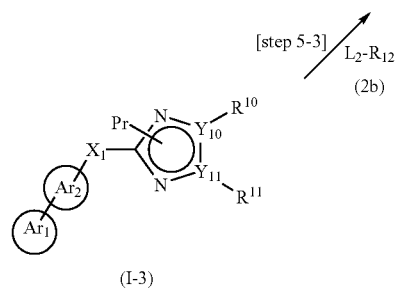

(I-3)

In the formula, $Ar_1$, $Ar_2$, $X_1$, $X_3$, $X_4$, $Y_{10}$, $Y_{11}$, $L_2$, $L_8$, $R^{26}$, $R^{27}$, $R^{10}$, $R^{11}$, $R^{12}$, Pr, na, nb, nf and ne are as defined above.

The above General Preparation Method 6 is an example of a method of condensing a compound (6) with a heterocyclic compound (38a) in Step 9-1 to prepare a compound of the general formula (I-2), the general formula (I-5) or the general formula (I-6); or a method of condensing a compound (6) with a heterocyclic compound (38b) having a protecting group in Step 9-2 to convert the compound (6) into a compound of the general formula (I-3) having a protecting group, and deprotecting the protecting group of the compound of the general formula (I-3) and subsequently reacting the compound with a compound (2b) in Step 5-3 to prepare a compound of the general formula (I-2), the general formula (I-5) or the general formula (I-6).

[Preparation of Compound of General Formula (I-2) and Compound of General Formula (I-3)]

The compound of the general formula (I-2) or general formula (I-3) can be prepared by reacting a compound (6) with a compound (38a) or compound (36b) according to Step 9-1 or Step 9-2. Specifically, Step 9-1 or Step 9-2 varies according to the starting material and is not specifically limited insofar as the conditions are similar to those in this reaction. A known method described in many documents such as Wittig reaction, Horner-Emmons reaction or Peterson reaction may be used for the reaction (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 57-85, for example).

In Wittig reaction, a carbonyl compound (6) and 0.5 to 2.0 equivalents of a compound (38a) or compound (38b), wherein $L_8$ represents a phosphonium salt, with respect to the carbonyl compound (6) are stirred in a solvent in the presence of 1.0 to 5.0 equivalents of a base with respect to the carbonyl compound (6), for example. This reaction may be a method of first reacting a compound (38a) or compound (38b) with a base to form a phosphorus ylide and then adding a carbonyl compound (6) to the ylide; or a method of adding a base in the presence of a carbonyl compound (6) and a compound (38a) or compound (38b). The base used varies according to the starting material and the solvent and is not specifically limited. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; and alkali metal hydrides such as sodium hydride. The solvent used varies according to the starting material and the base used, and is not specifically limited insofar as the solvent does not inhibit the reaction and allows the starting material to be dissolved therein to a certain extent. Preferable examples of the solvent used include polar solvents such as nitromethane, acetonitrile, 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; halogenated solvents such as chloroform and methylene chloride; water; and a mixed solvent thereof. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Horner-Emmons reaction, a carbonyl compound (6) and 0.5 to 2.0 equivalents of a compound (38a) or compound (38b), wherein $L_8$ represents a phosphite group, with respect to the carbonyl compound (6) are stirred in a solvent in the presence of 1.0 to 5.0 equivalents of a base with respect to the carbonyl compound (6), for example. This reaction may be a method of first treating a compound (38a) or compound (38b) and a base to form a carbanion and then adding a carbonyl compound (6) to the carbanion; or a method of adding a base in the presence of a carbonyl compound (6) and a compound (38a) or compound (38b). The base used varies according to the starting material and the solvent and is not specifically limited. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; alkali metal hydrides such as sodium hydride; and alkali metal ammonia salts such as sodium amide. The solvent used varies according to the starting material and the base used, and is not specifically limited insofar as the solvent does not inhibit the reaction and allows the starting material to be dissolved therein to a certain extent. Preferable examples of the solvent include polar solvents such as 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; water; and a mixed solvent thereof. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Peterson reaction, a carbonyl compound (6) and 0.5 to 2.0 equivalents of a compound (38a) or compound (38b), wherein $L_8$ represents a silyl group, with respect to the carbonyl compound (6) are stirred in a solvent in the presence of 1.0 to 5.0 equivalents of a base with respect to the carbonyl compound (6), for example. This reaction may be a method of first treating a compound (38a) or compound (38b) and a base to form a carbanion and then adding a carbonyl compound (6) to the carbanion; or a method of adding a base in the presence of a carbonyl compound (6) and a compound (38a) or compound (38b). The base used varies according to the starting material and the solvent and is not specifically limited. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; alkali metal hydrides such as sodium hydride; and alkali metal ammonia salts such as sodium amide. The solvent used varies according to the starting material and the base used, and is not specifically limited insofar as the solvent does not inhibit the reaction and allows the starting material to be dissolved therein to a certain extent. Preferable examples of the solvent include polar solvents such as 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; water; and a mixed solvent thereof. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Compound (38a) and Compound (38b)]

The compound (38a) and the compound (38b) are commercially available or prepared by a technique known to a person skilled in the art. If not commercially available, for example, i) the compound (38a) or compound (38b) as a Wittig reagent, wherein $L_8$ represents a phosphonium salt, can be prepared by halogenating a corresponding alcohol compound by a method known to a person skilled in the art (see Shin Jikken Kagaku Koza (New Courses in Experimental Chemistry), vol. 19, Yuki Gosei (Organic Synthesis) [I], edited by The Chemical Society of Japan, Maruzen Co., Ltd., June 1992, p. 430-438, for example), and then reacting the compound with an organophosphorus compound such as triphenylphosphine (see Organic Reaction, 1965, vol. 14, p. 270, for example). ii) The compound (38a) or compound (38b) as a Horner-Emmons reagent, wherein $L_8$ represents a phosphite, can be prepared by halogenating a corresponding alcohol compound by a method known to a person skilled in the art (see Shin Jikken Kagaku Koza (New Courses in Experimental Chemistry), vol. 19, Yuki Gosei (Organic Synthesis) [I], edited by The Chemical Society of Japan, Maruzen Co., Ltd., June 1992, p. 430-438, for example), and then reacting the compound with an alkyl phosphinite by Arbuzov reaction (see Chemical Review, 1981, vol. 81, p. 415, for example) or with a metal phosphonite by Becker reaction (see Journal of the American Chemical Society, 1945, vol. 67, p. 1180, for example). Alternatively, the compound can be prepared from a corresponding carbonyl compound and a chlorophosphate in the presence of a base (see Journal of Organic Chemistry, 1989, vol. 54, p. 4750, for example). iii) The compound (38a) or compound (38b) as a Peterson reagent, wherein $L_9$ represents a silyl group, can be prepared from a corresponding halogen compound and a trialkylsilyl chloride (see Journal of Organometallic Chemistry, 1983, vol. 248, p. 51, for example).

The compound of the general formula (I-5) or the compound of the general formula (I-6) can be prepared from the compound (38a) or compound (38b), wherein two of $R^{10}$, $R^{11}$ and $R^{12}$ form a ring, as a starting material by the same method as above.

[General Preparation Method 7]

Typically used General Preparation Method 7 for the compound of the general formula (I) of the present invention will be described below.

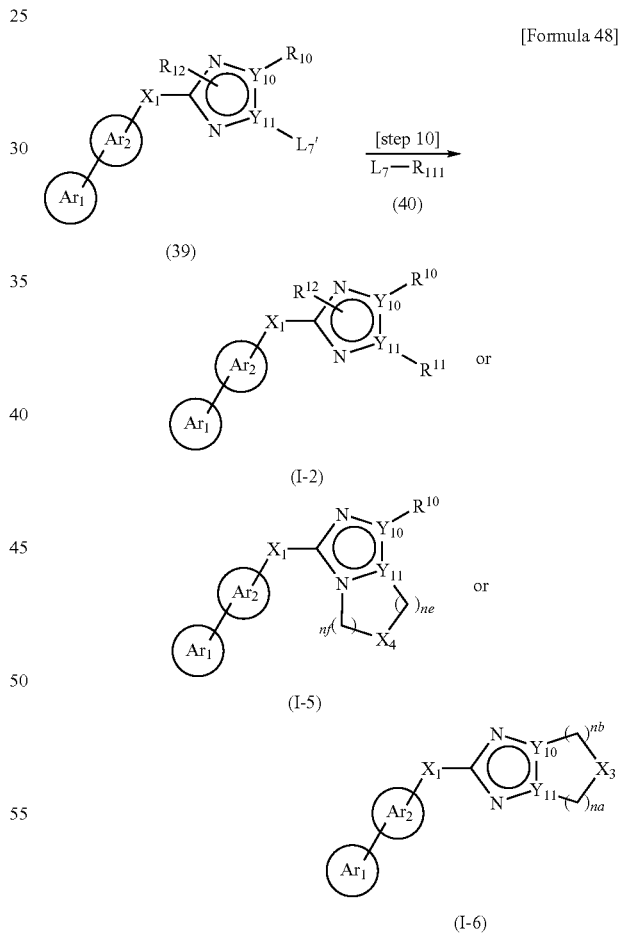

[Formula 48]

In the formula, $Ar_1$, $Ar_2$, $X_1$, $X_3$, $X_4$, $Y_{10}$, $Y_{11}$, $R^{10}$, $R^{11}$, $R^{12}$, $L_7$, $L_7'$, na, nb, nf and ne are as defined above; and R111 represents group selected from the above Substituent Group A4.

The above General Preparation Method 7 is an example of a method of condensing a compound (39) with a compound

(40) in Step 10 to prepare a compound of the general formula (I-2), the general formula (I-5) or the general formula (I-6).

[Preparation of Compound of General Formula (I-2)]

The compound of the general formula (I-2) can be prepared by reacting a compound (39) with a compound (40) according to Step 10. Specifically, Step 10 varies according to the starting material and is not specifically limited insofar as the conditions are similar to those in this reaction. A known method described in many documents such as Mizoroki-Heck reaction (see R. F. Heck, "Org. Reactions.", 1982, vol. 27, p. 345, for example), Suzuki-Miyaura reaction (see A. Suzuki, "Chem. Rev.", 1995, vol. 95, p. 2457, for example), Sonogashira reaction (see K. Sonogashira, "Comprehensive Organic Synthesis", 1991, vol. 3, p. 521) or Stille coupling reaction (see J. K. Stille, "Angew. Chem. Int. Ed. Engl.", 1986, vol. 25, p. 508, for example) may be used for the reaction.

In Mizoroki-Heck reaction, a compound (39), wherein $L_7'$ represents a chlorine atom, a bromine atom, an iodine atom or a sulfonate group such as a trifluoromethanesulfonate group, and 1.0 to 5.0 equivalents of an alkene compound (40), wherein $L_7$ represents a hydrogen atom, and $R^{111}$ represents a C1-6 alkenyl group which may be substituted with 1 to 3 substituents selected from the above Substituent Group A4, with respect to the compound (39) are stirred in a solvent in the presence of 0.01 to 0.2 equivalent of a transition metal catalyst with respect to the compound (39), for example. The transition metal catalyst used is preferably a palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine, tri-tert-butylphosphine or 2-(di-tert-butylphosphino)biphenyl may be preferably added, for example, in order to make the reaction efficiently proceed. A preferable result may be achieved in the presence of a base. The base used is not specifically limited insofar as the base is used in a coupling reaction similar to this reaction. Preferable examples of the base include triethylamine, N,N-diisopropylethylamine, N,N-dicyclohexylmethylamine and tetrabutylammonium chloride. The solvent used varies according to the starting material and the transition metal catalyst used, and is not specifically limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Suzuki-Miyaura reaction, a compound (39), wherein $L_7'$ represents a chlorine atom, a bromine atom, an iodine atom or a sulfonate group such as a trifluoromethanesulfonate group, and 1.0 to 10.0 equivalents of a compound (40), wherein $L_7$ represents a boronic acid group or boronate group, with respect to the compound (39) are stirred in a solvent in the presence of 0.01 to 0.5 equivalent of a transition metal catalyst with respect to the compound (39), for example. The transition metal catalyst used is preferably a known palladium complex, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine, tricyclohexylphosphine or tri-tert-butylphosphine may be preferably added, for example, in order to make the reaction efficiently proceed. A quaternary ammonium salt, preferably tetrabutylammonium chloride or tetrabutylammonium bromide, for example, may also be added in order to make the reaction efficiently proceed. In this reaction, a preferable result may be achieved in the presence of a base. The base used at this time varies according to the starting material, the solvent used and the like, and is not specifically limited. Preferable examples of the base include sodium hydroxide, barium hydroxide, potassium fluoride, cesium fluoride, sodium carbonate, potassium carbonate, cesium carbonate and potassium phosphate. The solvent used varies according to the starting material and the transition metal catalyst used, and is not specifically limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone, N,N-dimethylformamide, water and a mixed solvent thereof. The reaction temperature must be a temperature that can complete the coupling reaction, and is preferably room temperature to 200° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The desired compound of the general formula (I-2) can also be obtained from a combination of the compound (39), wherein $L_7$ represents a boronic acid group or boronate group, with the compound (40), wherein $L_7$ represents a chlorine atom, a bromine atom, an iodine atom or a sulfonate group such as a trifluoromethanesulfonate group, by the same method as above.

In Sonogashira reaction, a compound (39), wherein $L_7'$ represents a chlorine atom, a bromine atom, an iodine atom or a sulfonate group such as a trifluoromethanesulfonate group, and 1.0 to 10 equivalents of an alkyne compound (40), wherein $L_7$ represents a hydrogen atom, and $R^{111}$ represents a C1-6 alkynyl group which may be substituted with 1 to 3 substituents selected from the above Substituent Group A4, with respect to the compound (39) are stirred in a solvent in the presence of 0.01 to 0.5 equivalent of a transition metal catalyst with respect to the compound (39), for example. The transition metal catalyst used is preferably a known palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine or tri-tert-butylphosphine may be preferably added, for example, in order to make the reaction efficiently proceed. In the reaction, a good result may be achieved when adding a metal halide or a quaternary ammonium salt, preferably copper (I) iodide, lithium chloride, tetrabutylammonium fluoride or silver (I) oxide, for example. A preferable result may be achieved in the presence of a base. The base used here is not specifically limited insofar as the base is used in a coupling reaction similar to this reaction. Preferable examples of the base include diethylamine, triethylamine, N,N-diisopropylethylamine, a piperidine and pyridine. Preferable examples of the solvent used include acetonitrile, tetrahydrofuran, 1,4-dioxane, 1,2-dimethoxyethane, benzene, toluene, xylene, 1-methyl-2-pyrrolidone, N,N-dimethylformamide and dimethyl sulfoxide. More preferable examples of the solvent include tetrahydrofuran, 1,4-dioxane, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

trialkyltin group, with the compound (40), wherein $L_7'$ represents a chlorine atom, bromine atom, iodine atom or trifluoromethanesulfonate group, by the same method as above. The compound (40) is commercially available or can be prepared by a method known to a person skilled in the art.

[Preparation of Compound (39)]

The compound (39) can be prepared by a method in the above General Preparation Methods 1 to 6.

The compound of the general formula (I-5) or the general formula (I-6) can be prepared by the same method as above using, as a starting material, the compound (39), wherein $R^{10}$ and $R^{12}$ each represent an alkyl group substituted with an alkenyl group or alkynyl group, or an alkenyl group, alkynyl group or alkyl group substituted with a halogen atom, and $L_7'$ represents a chlorine atom, a bromine atom, an iodine atom, a sulfonate group such as a trifluoromethanesulfonate group, or a trialkyltin group, instead of the compound (40).

[General Preparation Method 8]

Typically used General Preparation Method 8 for the compound of the general formula (I) of the present invention will be described below.

[Formula 49]

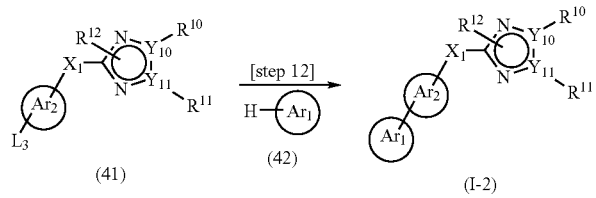 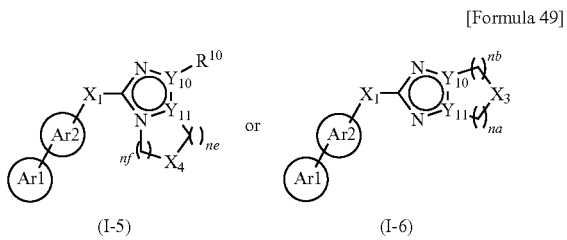

In the formula, $Ar_1$, $Ar_2$, $X_1$, $X_3$, $X_4$, $Y_{10}$, $Y_{11}$, $R^{10}$, $R^{11}$, $R^{12}$, $L_3$, na, nb, nf and ne are as defined above.

The above General Preparation Method 8 is an example of a method of condensing a compound (41) with a compound (42) in Step 12 to prepare a compound of the general formula (I-2), the general formula (I-5) or the general formula (I-6).

[Preparation of Compound of General Formula (I-2)]

The compound of the general formula (I-2) can be prepared by condensing a compound (41) with a compound (42) according to Step 12. Specifically, Step 12 varies according to the starting material and is not specifically limited insofar as the conditions are similar to those in this reaction. For example, a known method described in many documents such as coupling reaction of an arylboronic acid derivative using a copper compound (see The Journal of Organic Chemistry, 2001, vol. 66, p. 7892, for example), Ullmann reaction (see Journal of Medicinal Chemistry, 1981, vol. 24, p. 1139, for example) or nucleophilic substitution reaction (see Journal of Medicinal Chemistry, 1991, vol. 39, p. 2671-2677, for example) may be used for the reaction.

The coupling reaction of an arylboronic acid derivative using a copper compound is, for example, a method of stirring a compound (41), wherein $L_3$ represents a boronic acid group or boronate group, and 1.0 to 10.0 equivalents of a compound (42) with respect to the compound (41) in a solvent in the presence of 0.01 to 1.0 equivalent of a copper reagent such as copper, copper bromide or copper iodide with respect to the compound (41) by addition of 1.0 to 10.0 equivalents of a base with respect to the compound (41). The base used varies according to the starting material, the solvent used and the In Stille coupling reaction, a compound (39), wherein $L_7$ represents a chlorine atom, bromine atom, iodine atom or trifluoromethanesulfonate group, and 1.0 equivalent or more of a compound (40), wherein $L_7$ represents a trialkyltin group, with respect to the compound (39) are stirred in a solvent in the presence of 0.01 to 0.2 equivalent of a transition metal catalyst with respect to the compound (39), for example. The transition metal catalyst used is preferably a palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). 0.1 to 5.0 equivalents of copper (I) halide or/and lithium chloride may be added in order to make the reaction efficiently proceed. Preferable examples of the solvent used include toluene, xylene, N,N-dimethylformamide, N,N-dimethylacetamide, 1-methyl-2-pyrrolidone and dimethyl sulfoxide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The desired compound of the general formula (I-2) can also be obtained from a combination of the compound (39), wherein $L_7$ represents a like, and is not specifically limited insofar as the base does not inhibit the reaction. Preferable examples of the base include organic bases such as triethylamine, pyridine and tetramethylethylenediamine; alkali metal salts such as potassium carbonate, sodium carbonate, potassium acetate, sodium acetate and cesium carbonate; and metal alkoxides such as sodium methoxide and potassium tert-butoxide. The copper reagent used varies according to the starting material and is not specifically limited. Preferable examples of the copper reagent include copper acetate and di-μ-hydroxo-bis[(N,N,N',N'-tetramethylethylenediamine)copper (II)]chloride. The solvent used varies according to the starting material, the reagent and the like, and is not specifically limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; polar solvents such as ethyl acetate, N,N-dimethylformamide and N-methylpyrrolidone; nonpolar solvents such as toluene, benzene and dichlorobenzene; and a mixture thereof. The reaction temperature must be a temperature that can complete the reaction without promoting formation of an undesirable by-product, and is preferably room temperature to 200° C., for example. Good results such as reduction in the reaction time and improvement of the yield may be achieved when the reaction is performed in an oxygen atmosphere or air stream. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Ullmann reaction, a compound (41), wherein $L_3$ represents a halogen atom such as a chlorine atom, bromine atom or iodine atom, and 1.0 to 10.0 equivalents of a compound (42) with respect to the compound (41) are stirred in a solvent in the presence of 0.01 to 1.0 equivalent of a copper reagent such as copper, copper bromide or copper iodide with respect to the compound (41) by addition of 1.0 to 10.0 equivalents of a base with respect to the compound (41), for example. The base used varies according to the starting material and is not specifically limited. Preferable examples of the base include alkali metal salts such as potassium carbonate, sodium carbonate, potassium acetate, sodium acetate and cesium carbonate; and metal alkoxides such as sodium methoxide and potassium tert-butoxide. The solvent used varies according to the starting material, the reagent and the like, and is not specifically limited insofar as the solvent does not inhibit the reaction and allows the starting material to be dissolved therein to a certain extent. Preferable examples of the solvent that can be used include ether solvents such as tetrahydrofuran, 1,4-dioxane and diethyl ether; halogenated solvents such as methylene chloride, 1,2-dichloroethane and chloroform; alcohol solvents such as amyl alcohol and isopropyl alcohol; polar solvents such as N,N-dimethylformamide and N-methylpyrrolidone; nonpolar solvents such as toluene, benzene and dichlorobenzene; and a mixture thereof. The reaction temperature must be a temperature that can complete the reaction without promoting formation of an undesirable by-product, and is preferably room temperature to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In nucleophilic substitution reaction, a compound (41), wherein $L_3$ represents a halogen atom such as a chlorine atom, bromine atom or iodine atom or a sulfonate group such as a methanesulfonate group, p-toluenesulfonate group or trifluoromethanesulfonate group, and 2.0 to 5.0 equivalents of a compound (42) with respect to the compound (41) are stirred in a solvent in the presence or absence of 1.0 to 5.0 equivalents of a base with respect to the compound (41), for example. The base used varies according to the starting material and is not specifically limited. Preferable examples of the base include sodium hydride, sodium hydroxide, potassium hydroxide, potassium carbonate, sodium carbonate, cesium carbonate, barium carbonate, pyridine, lutidine and triethylamine. The solvent used varies according to the starting material, and is not specifically limited insofar as the solvent does not inhibit the reaction and allows the starting material to be dissolved therein to a certain extent. Preferable examples of the solvent include acetonitrile, tetrahydrofuran, dimethyl sulfoxide, N,N-dimethylformamide and N-methylpyrrolidine. Optionally, the bases may be used as a solvent. The reaction temperature must be a temperature that can complete the reaction without promoting formation of an undesirable by-product, and is preferably room temperature to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

[Preparation of Compound (41)]

The compound (41) is prepared by the same method as in the above General Preparation Methods 1 to 7.

[Preparation of Compound (42)]

The compound (42) is commercially available or prepared by a method known to a person skilled in the art.

The compound of the general formula (I-5) or the general formula (I-6) can be prepared from the compound (41), wherein two of $R^{10}$, $R^{11}$ and $R^{12}$ form a ring, as a starting material by the same method as above.

General Preparation Methods 1 to 8 for the compound of the present invention described above in detail are methods for preparing a compound represented by the general formula (I-1), the general formula (I-2), the general formula (I-3), the general formula (I-4), the general formula (I-5) or the general formula (I-6), wherein Het falls within a part of the definition of Het in the general formula (I). The compound of the general formula (I), wherein Het falls within another part of the definition of Het, can be prepared almost in the same manner as in the above General Preparation Methods 1 to 8, or can be prepared by another method itself known to a person skilled in the art. The examples described later will provide reference to these Preparation Methods, and the compound of the general formula (I) can be easily prepared by a method itself known to a person skilled in the art based on these examples.

A prophylactic or therapeutic agent for a disease caused by Aβ comprising the compound of the formula (I) or pharmacologically acceptable salt thereof according to the present invention as an active ingredient can be prepared by a conventional method. Preferable examples of the dosage form include tablets, powders, fine granules, granules, coated tablets, capsules, syrups, troches, inhalants, suppositories, injections, ointments, ophthalmic solutions, ophthalmic ointments, nasal drops, ear drops, cataplasms and lotions. The prophylactic or therapeutic agent can be prepared by using ingredients typically used such as an excipient, a binder, a lubricant, a colorant and a corrective, and ingredients used where necessary such as a stabilizer, an emulsifier, an absorbefacient, a surfactant, a pH adjuster, a preservative and an antioxidant, and can be prepared by blending ingredients generally used as materials for a pharmaceutical preparation. Examples of such ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; a silicone resin; silicone oil; surfactants such as polyoxyethylene fatty acid ester, sorbitan fatty acid ester, glycerin fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrytic acid, a carboxyvinyl polymer, polyethylene glycol, polyvinylpyrrolidone and methylcellulose; lower alcohols such as ethanol and isopropanol; polyhydric alcohols such as glycerin, propylene glycol, dipropylene glycol and sorbitol; sugars such as glucose and sucrose; inorganic powders such as silicic anhydride, magnesium aluminum silicate and aluminum silicate; and purified water. Examples of the excipient used include lactose, corn starch, saccharose, glucose, mannitol, sorbitol, crystalline cellulose and silicon dioxide. Examples of the binder used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, a polypropylene glycol-polyoxyethylene block copolymer and meglumine. Examples of the disintegrator used include starch, agar, gelatin powder, crystalline cellulose, calcium carbonate, sodium bicarbonate, calcium citrate, dextrin, pectin and carboxymethylcellulose calcium. Examples of the lubricant used include magnesium stearate, talc, polyethylene glycol, silica and hydrogenated vegetable oil. Examples of the colorant used include those that are permitted to be added to pharmaceuticals. Examples of the corrective used include cocoa powder, menthol, empasm, mentha oil, borneol and cinnamon powder.

For example, an oral preparation is prepared by adding an active ingredient compound or a salt thereof or a hydrate of the compound or salt, an excipient, and, where necessary, a binder, a disintegrator, a lubricant, a colorant and a corrective, for example, and then forming the mixture into powder, fine granules, granules, tablets, coated tablets or capsules, for example, by a conventional method. It is obvious that tablets or granules may be appropriately coated, for example, sugar coated, where necessary. A syrup or an injection preparation is prepared by adding a pH adjuster, a solubilizer and an isotonizing agent, for example, and a solubilizing aid, a stabilizer and the like where necessary by a conventional method. An external preparation may be prepared by any conventional method without specific limitations. As a base material, any of various materials usually used for a pharmaceutical, a quasi drug, a cosmetic or the like may be used. Examples of the base material include materials such as animal and vegetable oils, mineral oils, ester oils, waxes, higher alcohols, fatty acids, silicone oils, surfactants, phospholipids, alcohols, polyhydric alcohols, water-soluble polymers, clay minerals and purified water. A pH adjuster, an antioxidant, a chelator, a preservative and fungicide, a colorant, a flavor or the like may be added where necessary. Further, an ingredient having a differentiation inducing effect such as a blood flow enhancer, a bactericide, an antiphlogistic, a cell activator, vitamin, amino acid, a humectant or a keratolytic agent may be blended where necessary.

The dose of the therapeutic or prophylactic agent of the present invention varies according to the degree of symptoms, age, sex, body weight, mode of administration, type of salt and specific type of disease, for example. Typically, the compound of the formula (I) or pharmacologically acceptable salt thereof is orally administered to an adult at about 30 µg to g, preferably 100 µg to 5 g, and more preferably 100 µg to 100 mg per day, or is administered to an adult by injection at about 30 µg to 1 g, preferably 100 µg to 500 mg, and more preferably 100 µg to 30 mg per day, in a single dose or multiple doses, respectively.

EXAMPLES

The present invention will now be described in detail with reference to examples. However, the examples are provided only for illustration purposes. The prophylactic or therapeutic agent for a disease caused by Aβ according to the present invention is not limited to the following specific examples in any case. A person skilled in the art can fully implement the present invention by making various modifications to not only the following reference examples and examples but also the claims of the present specification, and such modifications are within the scope of the claims of the present specification.

The following abbreviations are used in the following examples.

DMF: N,N-dimethylformamide

THF: Tetrahydrofuran

LAH: Lithium aluminum hydride

EDC: 1-Ethyl-3-(3-dimethylaminopropyl)carbodiimide hydrochloride

HOBT: 1-Hydroxybenzotriazole

IPEA: Diisopropylethylamine

DCC: 1,3-Dicyclohexylcarbodiimide

DMAP: 4-(Dimethylamino)pyridine

TEA: Triethylamine

DPPA: Diphenylphosphoryl azide

CDI: Carbonyldiimidazole

TBAF: Tetrabutylammonium fluoride

PYBOP: Benzotriazol-1-yloxytris(pyrrolidino)phosphonium hexafluorophosphate

DBU: 1,8-Diazabicyclo[5.4.0]undec-7-ene t: Tertiary

BOPCl: Bis(2-oxo-3-oxazolidinyl)phosphonic chloride

DIBAL-H: Diisobutylaluminum hydride

DAST: Diethylaminosulfur trifluoride

Chromatography was performed using BW-300 manufactured by Fuji Silysia Chemical Ltd. as a carrier unless otherwise specified.

LC-MS: High performance liquid chromatography for preparative isolation of a target compound using mass spectroscopy. As an elution solvent, a 10% to 99% linear gradient system of water containing 0.1% trifluoroacetic acid and acetonitrile containing 0.1% trifluoroacetic acid was used.

Example 1

Synthesis of 4-(4-fluorophenyl)-2-{(E)-2-[3-methoxy-4-(4-methyl-1H-imidazol-1-yl)phenyl]vinyl}-1H-imidazole

[Formula 50]

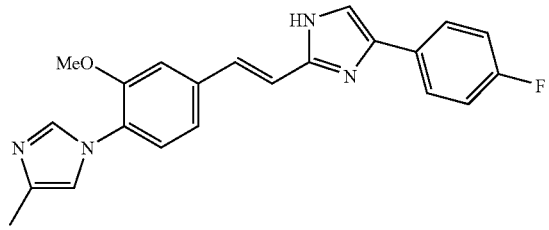

(1) Synthesis of 3-methoxy-4-(4-methyl-1H-imidazol-1-yl)benzaldehyde (1-1) Synthesis of methyl 3-methoxy-4-nitrobenzoate Methyl iodide (463 g) was added dropwise to a mixture of 3-hydroxy-4-nitrobenzoic acid (199 g) with potassium carbonate (450 g) in DMF (1 L) at room temperature. The reaction solution was stirred at room temperature overnight, and then methyl iodide (230 g) was added to the reaction solution. The reaction solution was further stirred at room temperature for six hours. The reaction solution was added to ice water, and the precipitated solid was collected by filtration. The resulting solid was dried at 50° C. overnight to obtain 178 g of the title compound. The property values corresponded to the reported values (CAS #5081-37-8).

(1-2) Synthesis of methyl 4-amino-3-methoxybenzoate

10% palladium-carbon (containing 50% water, 15 g) was added to a solution of methyl 3-methoxy-4-nitrobenzoate (150 g) in methanol (600 mL) and THF (300 mL), and the reaction solution was stirred at a hydrogen pressure of 0.9 MPa at 50° C. to 64° C. for 6.5 hours. The reaction solution was left to cool to room temperature and then filtered through celite. The resulting filtrate was concentrated under reduced pressure to obtain 134 g of the title compound. The property values corresponded to the reported values (CAS #41608-64-4).

(1-3) Synthesis of methyl 4-formylamino-3-methoxybenzoate

Acetic anhydride (268 mL) was added dropwise to formic acid (401 mL) at room temperature, and the reaction solution was stirred at room temperature for 40 minutes. A solution of methyl 4-amino-3-methoxybenzoate (134 g) in THF (600 mL) was added dropwise to the reaction solution at room temperature, and the reaction solution was stirred for one hour. 3.8 L of ice water was added to the reaction solution, and the precipitated solid was filtered and further washed with water (2 L). The resulting solid was dried at 50° C. overnight to obtain 111 g of the title compound. The property values corresponded to the reported values (CAS #700834-18-0).

(1-4) Synthesis of methyl 4-[formyl-(2-oxopropyl)amino]-3-methoxybenzoate

Chloroacetone (84.5 mL) was added dropwise to a mixture of methyl 4-formylamino-3-methoxybenzoate (111 g), cesium carbonate (346 g), and potassium iodide (8.78 g) in DMF (497 mL) at room temperature, and the reaction solution was stirred for three hours. Cesium carbonate (173 g) and chloroacetone (42.0 mL) were added to the reaction solution, which was then stirred at room temperature for two hours. Ice water and ethyl acetate were added to the reaction solution, and the organic layer was separated. Ethyl acetate was added to the aqueous layer, and the organic layer was separated. The organic layers were combined and washed with water and brine in this order. The resulting organic layers were dried over anhydrous magnesium sulfate and then concentrated under reduced pressure. The residue was diluted with toluene, and the solution was concentrated under reduced pressure. tert-Butyl methyl ether and heptane were added to the resulting residue, and the precipitated solid was collected by filtration and washed with a solution of 50% tert-butyl methyl ether in heptane. The resulting solid was air-dried overnight to obtain 118 g of the title compound.

$^1$H-NMR (CDCl$_3$) δ (ppm): 2.19 (s, 3H), 3.91 (s, 3H), 3.94 (s, 3H), 4.49 (s, 2H), 7.31 (d, J=8.0 Hz, 1H), 7.63 (d, J=2.0 Hz, 1H), 7.69 (dd, J=8.0, 2.0 Hz, 1H), 8.33 (s, 1H).

(1-5) Synthesis of methyl 3-methoxy-4-(4-methyl-1H-imidazol-1-yl)benzoate

A solution of methyl 4-[formyl-(2-oxopropyl)amino]-3-methoxybenzoate (118 g) and ammonium acetate (172 g) in acetic acid (255 mL) was heated and stirred at 140° C. for one hour. After the reaction was completed, the reaction solution was neutralized with aqueous ammonia under ice-cooling. Ethyl acetate was added to the reaction solution, and the organic layer was separated. The resulting organic layer was dried over anhydrous magnesium sulfate and then filtered on a silica gel pad, and the filtrate was concentrated under reduced pressure. tert-Butyl methyl ether and heptane were added to the residue, and the precipitated solid was collected by filtration and washed with a solution of 50% tert-butyl methyl ether in heptane. The resulting solid was air-dried overnight to obtain 68.4 g of the title compound. Further, the crystallization mother liquor was concentrated under reduced pressure, and the residue was purified by silica gel column chromatography (elution solvent: heptane-ethyl acetate system) to obtain 22.3 g of the title compound.

$^1$H-NMR (CDCl$_3$) δ (ppm): 2.30 (s, 3H), 3.94 (s, 3H), 3.96 (s, 3H), 6.98 (brs, 1H), 7.32 (d, J=8.4 Hz, 1H), 7.71-7.73 (m, 2H), 7.79 (brs, 1H).

(1-6) Synthesis of 3-methoxy-4-(4-methyl-1H-imidazol-1-yl)benzaldehyde

A solution of pyrrolidine (18 mL) in THF (45 mL) was added dropwise to a solution of sodium bis(2-methoxyethoxy)aluminum hydride (65% solution in toluene, 56 mL) in THF (60 mL) at −5° C. or less over 15 minutes. The reaction solution was stirred at room temperature for one hour. Then, a suspension of tert-butoxide (2.10 g) in THF (15 mL) was added dropwise to the reaction solution at room temperature, and the reaction solution was stirred for 15 minutes. The above reaction solution was added dropwise to a solution of methyl 3-methoxy-4-(4-methyl-1H-imidazol-1-yl)benzoate (20 g) in THF (50 mL) under ice-cooling over 30 minutes. The reaction solution was stirred at room temperature for two hours, and then a 5 N sodium hydroxide solution (150 mL) was added dropwise to the reaction solution. Ethyl acetate was added to the reaction solution, and the organic layer was separated. The organic layer was washed with a saturated ammonium chloride solution and brine in this order. The organic layer was dried over anhydrous magnesium sulfate and filtered on a silica gel pad, and then the filtrate was concentrated under reduced pressure. The residue was diluted with ethyl acetate, and the precipitated solid was collected by filtration. The resulting solid was air-dried overnight to obtain 7.10 g of the title compound. Further, the crystallization mother liquor was concentrated under reduced pressure, and the residue was purified by silica gel column chromatography (elution solvent: heptane-ethyl acetate-2-propanol system) to obtain 2.65 g of the title compound.

$^1$H-NMR (CDCl$_3$) δ (ppm): 2.31 (s, 3H), 3.97 (s, 3H), 7.02 (brs, 1H), 7.44 (d, J=8.0 Hz, 1H), 7.55 (dd, J=1.6 Hz, 8.0 Hz, 1H), 7.58 (d, J=1.6 Hz, 1H), 7.84 (brs, 1H), 10.00 (s, 1H).

(2) Synthesis of (E)-3-[3-methoxy-4-(4-methyl-1H-imidazol-1-yl)phenyl]acrylic acid Ethyl diethylphosphonoacetate (5.7 g) and lithium hydroxide monohydrate (1.3 g) were sequentially added to a mixed solution of 3-methoxy-4-(4-methyl-1H-imidazol-1-yl)benzaldehyde (5.0 g) in THF (20 mL) and ethanol (5 mL), and the reaction solution was stirred at room temperature for nine hours. A 2 N sodium hydroxide solution (20 mL) was added to the reaction solution, and the reaction solution was stirred at room temperature for 12 hours. The reaction solution was cooled to 0° C., and 2 N hydrochloric acid (20 mL) was added to the reaction solution. The resulting precipitate was collected by filtration. The resulting precipitate was washed with water and ethyl acetate to obtain 5.1 g of the title compound. The property values of the compound are as follows.

$^1$H-NMR (DMSO-d$_6$) δ (ppm): 2.15 (s, 3H), 3.88 (s, 3H), 6.66 (d, J=16.0 Hz, 1H), 7.16 (s, 1H), 7.35 (d, J=8.0 Hz, 1H), 7.39 (d, J=8.0 Hz, 1H), 7.56 (s, 1H), 7.60 (d, J=16.0 Hz, 1H), 7.81 (s, 1H).

(3) Synthesis of 2-(4-fluorophenyl)-2-oxoethyl (E)-3-[3-methoxy-4-(4-methyl-1H-imidazol-1-yl)phenyl]acrylate IPEA (0.28 mL) was added to a solution of (E)-3-[3-methoxy-4-(4-methyl-1H-imidazol-1-yl)phenyl]acrylic acid (200 mg) and 4-fluorophenacyl bromide (185 mg) in DMF (3 mL), and the reaction solution was stirred at room temperature for one hour. Ethyl acetate and saturated sodium bicarbonate water were added to the reaction solution, and the organic layer was separated. The resulting organic layer was dried over anhydrous magnesium sulfate and then concentrated under reduced pressure. The residue was suspended in diethyl ether, and the solid was collected by filtration to obtain 230 mg of the title compound. The property values of the compound are as follows.

$^1$H-NMR (CDCl$_3$) δ (ppm): 2.34 (s, 3H), 3.92 (s, 3H), 5.47 (s, 2H), 6.63 (d, J=16.0 Hz, 1H), 6.97 (brs, 1H), 7.20 (t, J=8.8 Hz, 2H), 7.22 (d, J=1.6 Hz, 1H), 7.23 (dd, J=9.6, 1.6 Hz, 1H), 7.30 (d, J=9.6 Hz, 1H), 7.81 (d, J=16.0 Hz, 1H), 7.85 (brs, 1H), 8.00 (dd, J=8.8, 5.6 Hz, 2H).

(4) Synthesis of 4-(4-fluorophenyl)-2-{(E)-2-[3-methoxy-4-(4-methyl-1H-imidazol-1-yl)phenyl]vinyl}-1H-imidazole A solution of 2-(4-fluorophenyl)-2-oxoethyl(E)-3-[3-methoxy-4-(4-methyl-1H-imidazol-1-yl)phenyl]acrylate (230 mg) and ammonium acetate (899 mg) in acetic acid (3 mL) was heated under reflux for five hours. The reaction solution was left to cool to room temperature and concentrated under reduced pressure. Then, ethyl acetate and saturated sodium bicarbonate water were added to the residue, and the organic layer was separated. The resulting organic layer was dried over anhydrous magnesium sulfate and then concentrated under reduced pressure. The residue was purified by silica gel column chromatography (carrier: Chromatorex™ NH; elution solvent: ethyl acetate→ethyl acetate:methanol=5:1). The resulting solid was suspended in ethyl acetate-diethyl ether and collected by filtration to obtain 104 mg of the title compound. The property values of the compound are as follows.

$^1$H-NMR (CDCl$_3$) δ (ppm): 2.32 (s, 3H), 3.87 (s, 3H), 6.95 (brs, 1H), 7.05 (d, J=16.4 Hz, 1H), 7.09 (t, J=8.8 Hz, 2H), 7.11 (brd, J=8.0 Hz, 1H), 7.15 (brs, 1H), 7.21 (d, J=8.0 Hz, 1H), 7.32 (s, 1H), 7.40 (d, J=16.4 Hz, 1H), 7.75 (dd, J=8.8, 5.6 Hz, 2H), 7.83 (brs, 1H).

Example 2

Synthesis of 4-(4-fluorophenyl)-2-{(E)-2-[3-methoxy-4-(4-methyl-1H-imidazol-1-yl)phenyl]vinyl}-3-methyl-1H-imidazole

[Formula 51]

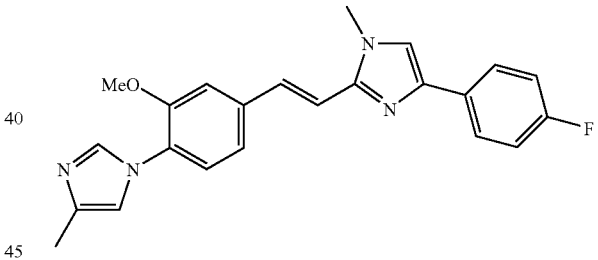

Sodium borohydride (containing mineral oil at 60%, 8 mg) was added to a solution of 5-(4-fluorophenyl)-2-{(E)-2-[3-methoxy-4-(4-methyl-1H-imidazol-1-yl)phenyl]vinyl}-1H-imidazole (50 mg) in THF (5 mL), and the reaction solution was stirred at room temperature for one hour. Methyl iodide (23 mg) was added to the reaction solution, and the reaction solution was stirred at room temperature for 12 hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex™ NH; elution solvent: heptane:ethyl acetate=1:1→ethyl acetate) to obtain 15 mg of the title compound. The property values of the compound are as follows.

ESI-MS; m/z 389 [M$^+$+H]. $^1$H-NMR (CDCl$_3$) δ (ppm): 2.32 (s, 3H), 3.79 (s, 3H), 3.90 (s, 3H), 6.92 (d, J=15.6 Hz, 1H), 6.93 (brs, 1H), 7.08 (t, J=8.8 Hz, 2H), 7.14 (s, 1H), 7.16 (brs, 1H), 7.23-7.26 (m, 2H), 7.65 (d, J=15.6 Hz, 1H), 7.74 (brs, 1H), 7.77 (dd, J=8.8, 5.6 Hz, 2H).

Example 3

Synthesis of 2-{(E)-2-[3-methoxy-4-(4-methyl-1H-imidazol-1-yl)phenyl]vinyl}-1-methyl-5-phenyl-1H-imidazole

[Formula 52]

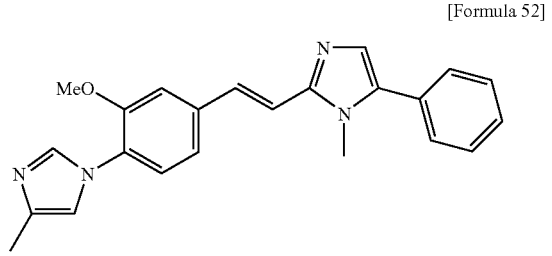

(1) Synthesis of (E)-3-[3-methoxy-4-(4-methyl-1H-imidazol-1-yl)phenyl]-N-(2-oxo-2-phenylethyl)acrylic acid amide Diethyl cyanophosphonate (0.12 mL) was added to a solution of (E)-3-[3-methoxy-4-(4-methyl-1H-imidazol-1-yl)phenyl]acrylic acid (200 mg) and triethylamine (0.22 mL) in DMF (1 mL) at 0° C. The reaction solution was stirred at 0° C. for 30 minutes, and then α-aminoacetophenone hydrochloride (133 mg) was added in small portions to the reaction solution over 30 minutes. The reaction solution was stirred at 0° C. for 2.5 hours. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex™ NH; elution solvent: ethyl acetate→ethyl acetate:methanol=5:1) to obtain 200 mg of the title compound. The property values of the compound are as follows.

$^1$H-NMR (CDCl$_3$) δ (ppm): 2.30 (s, 3H), 3.91 (s, 3H), 4.92 (d, J=4.0 Hz, 2H), 6.57 (d, J=15.2 Hz, 1H), 6.80 (brt, J=4.0 Hz, 1H), 6.93 (t, J=1.2 Hz, 1H), 7.16 (d, J=1.2 Hz, 1H), 7.21 (dd, J=8.0, 1.2 Hz, 1H), 7.26 (d, J=8.0 Hz, 1H), 7.52 (t, J=7.2 Hz, 2H), 7.65 (t, J=7.2 Hz, 1H), 7.66 (d, J=15.2 Hz, 1H), 7.73 (d, J=1.2 Hz, 1H), 8.02 (d, J=7.2 Hz, 2H).

(2) Synthesis of 2-{(E)-2-[3-methoxy-4-(4-methyl-1H-imidazol-1-yl)phenyl]vinyl}-1-methyl-5-phenyl-1H-imidazole A solution of methylamine (2 M solution in methanol, 2.7 mL) in acetic acid (5 mL) was added to a solution of (E)-3-[3-methoxy-4-(4-methyl-1H-imidazol-1-yl)phenyl]-N-(2-oxo-2-phenylethyl)acrylic acid amide (100 mg) in xylene (10 mL), and the reaction solution was heated under reflux for 3.5 hours while evaporating methanol. The reaction solution was left to cool to room temperature and then concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. The residue was purified by silica gel column chromatography (carrier: Chromatorex™ NH; elution solvent: heptane:ethyl acetate=1:1→ethyl acetate→ethyl acetate:methanol=5:1) to obtain 11 mg of the title compound. The property values of the compound are as follows.

ESI-MS; m/z 371 [M$^+$+H]. $^1$H-NMR (CDCl$_3$) δ (ppm): 2.30 (s, 3H), 3.71 (s, 3H), 3.90 (s, 3H), 6.93 (brs, 1H), 6.97 (d, J=16.0 Hz, 1H), 7.15 (brs, 1H), 7.17 (s, 1H), 7.23-7.26 (m, 2H), 7.37-7.42 (m, 3H), 7.46 (t, J=6.4 Hz, 2H), 7.63 (d, J=16.0 Hz, 1H), 7, 71 (d, J=1.6 Hz, 1H).

Example 4

Synthesis of 2-{(E)-2-[3-methoxy-4-(4-methyl-1H-imidazol-1-yl)phenyl]vinyl}-4-phenyl-1H-imidazole

[Formula 53]

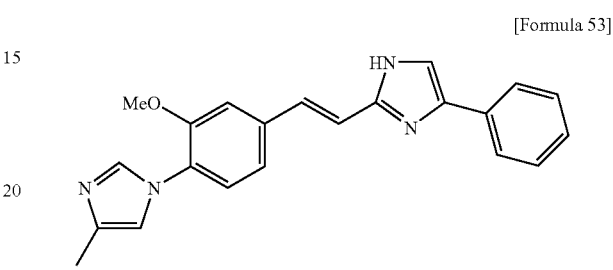

A solution of (E)-3-[3-methoxy-4-(4-methyl-1H-imidazol-1-yl)phenyl]-N-(2-oxo-2-phenylethyl)acrylic acid amide (100 mg) and ammonium acetate (410 mg) in acetic acid (5 mL) was heated under reflux for 10 hours. The reaction solution was left to cool to room temperature and then concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. The residue was purified by silica gel column chromatography (carrier: Chromatorex™ NH; elution solvent: heptane:ethyl acetate=1:1→ethyl acetate→ethyl acetate:methanol=5:1) to obtain 34 mg of the title compound. The property values of the compound are as follows.

ESI-MS; m/z 357 [M$^+$+H]. $^1$H-NMR (CDCl$_3$) δ (ppm): 2.29 (s, 3H), 3.72 (s, 3H), 6.91 (brs, 1H), 6.94 (dd, J=9.6, 1.6 Hz, 1H), 6.98 (brs, 1H), 7.04 (d, J=16.4 Hz, 1H), 7.11 (d, J=9.6 Hz, 1H), 7.25 (t, J=7.2 Hz, 1H), 7.32 (d, J=16.4 Hz, 1H), 7.38 (t, J=7.2 Hz, 2H), 7.46 (brs, 1H), 7.70 (brs, 1H), 7.79 (d, J=7.2 Hz, 2H).

Example 5

Synthesis of 2-{(E)-2-[3-methoxy-4-(4-methyl-1H-imidazol-1-yl)phenyl]vinyl}-1-methyl-4-phenyl-1H-imidazole

[Formula 54]

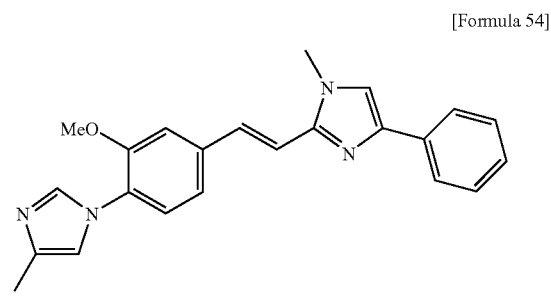

2 mg of the title compound was obtained from 2-{(E)-2-[3-methoxy-4-(4-methyl-1H-imidazol-1-yl)phenyl]vinyl}-

4-phenyl-1H-imidazole (30 mg) by the same method as in Example 2. The property values of the compound are as follows.

ESI-MS; m/z 371 [M$^+$+H]. $^1$H-NMR (CDCl$_3$) δ (ppm): 2.30 (s, 3H), 3.80 (s, 3H), 3.90 (s, 3H), 6.93 (brs, 1H), 6.94 (d, J=15.6 Hz, 1H), 7.16 (brs, 1H), 7.19 (s, 1H), 7.22-7.28 (m, 4H), 7.38 (t, J=7.2 Hz, 1H), 7.65 (d, J=15.6 Hz, 1H), 7.71 (d, J=1.2 Hz, 1H) 7.80 (d, J=7.2 Hz, 2H).

Example 6

Synthesis of methyl 5-(4-fluorophenyl)-2-{(E)-2-[3-methoxy-4-(4-methyl-1H-imidazol-1-yl)phenyl]vinyl}-1H-imidazole-4-carboxylate

[Formula 55]

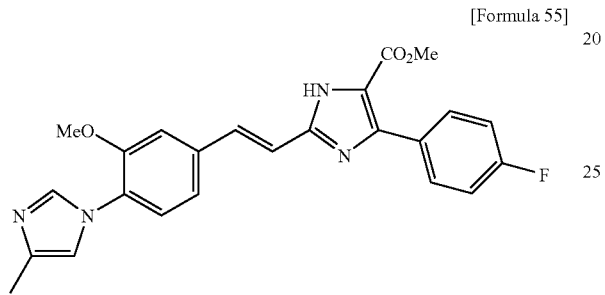

(1) Synthesis of 2-(4-fluorophenyl)-1-methoxycarbonyl-2-oxoethyl(E)-3-[3-methoxy-4-(4-methyl-1H-imidazol-1-yl)phenyl]acrylate IPEA (3 mL) was added to a solution of (E)-3-[3-methoxy-4-(4-methyl-1H-imidazol-1-yl)phenyl]acrylic acid (1 g) and methyl 2-chloro-3-(4-fluorophenyl)-3-oxopropionate (CAS #160727-96-8, 1.1 g) in DMF (10 mL), and the reaction solution was stirred at room temperature for two hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex™ NH; elution solvent: ethyl acetate→ethyl acetate:methanol=5:1) to obtain 792 mg of the title compound. The property values of the compound are as follows.

$^1$H-NMR (CD$_3$OD) δ (ppm): 2.32 (s, 3H), 3.83 (s, 3H), 3.90 (s, 3H), 6.47 (s, 1H), 6.60 (d, J=16.0 Hz, 1H), 6.95 (brs, 1H), 7.16-7.22 (m, 4H), 7.28 (d, J=8.0 Hz, 1H), 7.78 (d, J=16.0 Hz, 1H), 7.82 (d, J=1.2 Hz, 1H), 8.10 (dd, J=8.4, 5.2 Hz, 2H).

(2) Synthesis of methyl 5-(4-fluorophenyl)-2-{(E)-2-[3-methoxy-4-(4-methyl-1H-imidazol-1-yl)phenyl]vinyl}-1H-imidazole-4-carboxylate A solution of 2-(4-fluorophenyl)-1-methoxycarbonyl-2-oxoethyl(E)-3-[3-methoxy-4-(4-methyl-1H-imidazol-1-yl)phenyl]acrylate (792 mg) and ammonium acetate (2.7 g) in acetic acid (10 mL) was heated under reflux for 10 hours. The reaction solution was left to cool to room temperature and concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. The residue was purified by silica gel column chromatography (carrier: Chromatorex™ NH; elution solvent: ethyl acetate→ethyl acetate:methanol=5:1). The resulting solid was suspended in diethyl ether and collected by filtration to obtain 417 mg of the title compound. The property values of the compound are as follows.

$^1$H-NMR (DMSO-d$_6$) δ (ppm): 2.32 (s, 3H), 3.87 (s, 3H), 3.96 (s, 3H), 7.05 (d, J=16.8 Hz, 1H), 7.08 (brs, 1H), 7.14 (t, J=8.8 Hz, 2H), 7.27 (brd, J=9.6 Hz, 1H), 7.29 (brs, 1H), 7.32 (d, J=9.6 Hz, 1H), 7.56 (brd, J=16.8 Hz, 1H), 7.70-7.85 (m, 2H), 8.01 (brs, 1H).

Example 7

Synthesis of 5-(4-fluorophenyl)-2-{(E)-2-[3-methoxy-4-(4-methyl-1H-imidazol-1-yl)phenyl]vinyl}-(1H-imidazol-4-yl)methanol

[Formula 56]

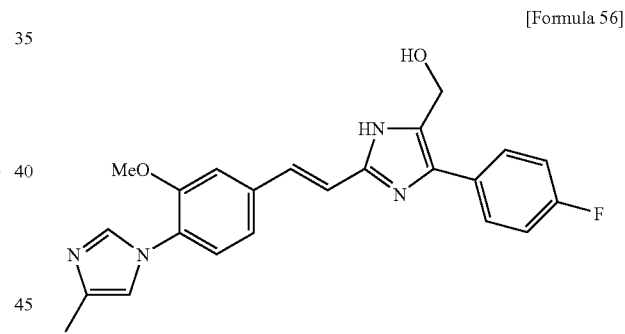

LAH (18 mg) was added to a solution of methyl 5-(4-fluorophenyl)-2-{(E)-2-[3-methoxy-4-(4-methyl-1H-imidazol-1-yl)phenyl]vinyl}-1H-imidazole-4-carboxylate (50 mg) in THF (5 mL), and the reaction solution was stirred at room temperature for 1.5 hours. Ethyl acetate and brine were added to the reaction solution, and the organic layer was separated. The resulting organic layer was dried over anhydrous magnesium sulfate and then concentrated under reduced pressure. The residue was purified by silica gel column chromatography (elution solvent: ethyl acetate→ethyl acetate:methanol=5:1). The resulting solid was suspended in diethyl ether and collected by filtration to obtain 36 mg of the title compound. The property values of the compound are as follows.

$^1$H-NMR (CD$_3$OD) δ (ppm): 2.27 (s, 3H), 3.93 (s, 3H), 4.65 (s, 2H), 7.03 (d, J=16.8 Hz, 1H), 7.06 (brs, 1H), 7.13 (t, J=8.8 Hz, 2H), 7.23 (brd, J=8.0 Hz, 1H), 7.29 (brs, 1H), 7.30 (d, J=8.0 Hz, 1H), 7.38 (d, J=16.8 Hz, 1H), 7.64 (dd, J=8.8, 4.8 Hz, 2H), 7.95 (brs, 1H).

Example 8

Synthesis of 5-(4-fluorophenyl)-2-{(E)-2-[3-methoxy-4-(4-methyl-1H-imidazol-1-yl)phenyl]vinyl}-1H-imidazole-4-carboxylic acid

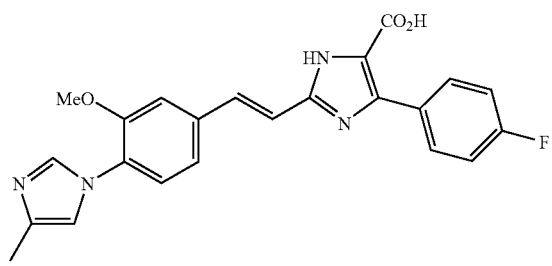

[Formula 57]

A 2 N sodium hydroxide solution (1 mL) was added to a solution of methyl 5-(4-fluorophenyl)-2-{(E)-2-[3-methoxy-4-(4-methyl-1H-imidazol-1-yl)phenyl]vinyl}-1H-imidazole-4-carboxylate (143 mg) in methanol (1 mL), and the reaction solution was stirred at room temperature for 1.5 hours and at 80° C. for 17 hours. The reaction solution was left to cool to room temperature. Then, 2 N hydrochloric acid (1 mL) was added to the reaction solution, which was then stirred at room temperature for 30 minutes. The solid precipitated from the reaction solution was collected by filtration to obtain 139 mg of the title compound.

The property values of the compound are as follows.

$^1$H-NMR (CD$_3$OD) δ (ppm): 2.18 (s, 3H), 3.91 (s, 3H), 7.18 (d, J=16.4 Hz, 1H), 7.22-7.29 (m, 4H), 7.42 (d, J=8.0 Hz, 1H), 7.46 (brs, 1H), 7.69 (brd, J=16.4 Hz, 1H), 8.00-8.10 (m, 3H).

Example 9

Synthesis of 5-(4-fluorophenyl)-2-{(E)-2-[3-methoxy-4-(4-methyl-1H-imidazol-1-yl)phenyl]vinyl}-1H-imidazole-4-carboxylic acid (2-chloroethyl) amide

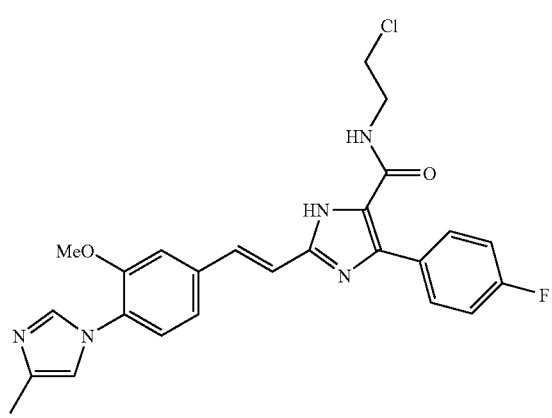

[Formula 58]

HOBT (65 mg) and EDC (92 mg) were sequentially added to a solution of 5-(4-fluorophenyl)-2-{(E)-2-[3-methoxy-4-(4-methyl-1H-imidazol-1-yl)phenyl]vinyl}-1H-imidazole-4-carboxylic acid (100 mg), 2-chloroethylamine hydrochloride (56 mg) and IPEA (0.25 mL) in DMF (3 mL). The reaction solution was stirred at room temperature for two hours. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex™ NH; elution solvent: ethyl acetate→ethyl acetate:methanol=5:1) to obtain 19 mg of the title compound. The property values of the compound are as follows.

ESI-MS; m/z 480 [M$^+$+H]. $^1$H-NMR (CDCl$_3$) δ (ppm): 2.23 (s, 3H), 3.62-3.77 (m, 4H), 3.82 (s, 3H), 6.92 (brs, 1H), 6.93 (d, J=16.4 Hz, 1H), 6.98-7.06 (m, 3H), 7.07 (d, J=1.2 Hz, 1H), 7.15 (d, J=8.0 Hz, 1H), 7.40 (d, J=16.4 Hz, 1H), 7.69 (d, J=0.8 Hz, 1H), 7.78 (dd, J=8.4, 5.6 Hz, 2H).

Example 10

Synthesis of 1-(4-fluorophenyl)-3-{(E)-2-[3-methoxy-4-(4-methyl-1H-imidazol-1-yl)phenyl]vinyl}-6,7-dihydro-5H-imidazo[1,5-a]pyrazin-8-one

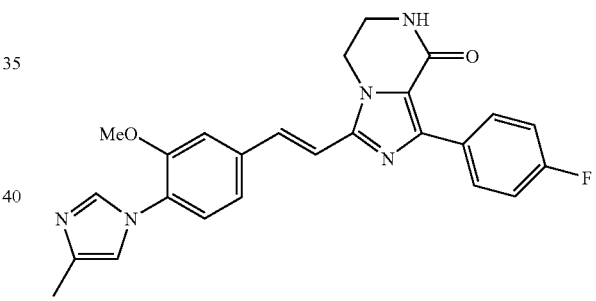

[Formula 59]

Sodium hydride (containing mineral oil at 60%, 3 mg) was added to a solution of 5-(4-fluorophenyl)-2-{(E)-2-[3-methoxy-4-(4-methyl-1H-imidazol-1-yl)phenyl]vinyl}-1H-imidazole-4-carboxylic acid (2-chloroethyl)amide (15 mg) in DMF (2 mL) at room temperature, and the reaction solution was stirred at room temperature for 30 minutes. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex™ NH; elution solvent: ethyl acetate→ethyl acetate:methanol=5:1) to obtain 10 mg of the title compound. The property values of the compound are as follows.

ESI-MS; m/z 444 [M$^+$+H]. $^1$H-NMR (CDCl$_3$) δ (ppm): 2.30 (s, 3H), 3.87 (s, 3H), 4.05 (t, J=9.2 Hz, 2H), 4.44 (t, J=9.2 Hz, 2H), 6.93 (brs, 1H), 6.99 (d, J=16.0 Hz, 1H), 7.06-7.15 (m, 4H), 7.22 (d, J=8.4 Hz, 1H), 7.47 (d, J=16.0 Hz, 1H), 7.75 (brs, 1H), 7.90 (dd, J=9.2, 5.6 Hz, 2H).

Example 11

Synthesis of 1-(4-fluorophenyl)-3-{(E)-2-[3-methoxy-4-(4-methyl-1H-imidazol-1-yl)phenyl]vinyl}-7-methyl-6,7-dihydro-5H-imidazo[1,5-a]pyrazin-8-one

[Formula 60]

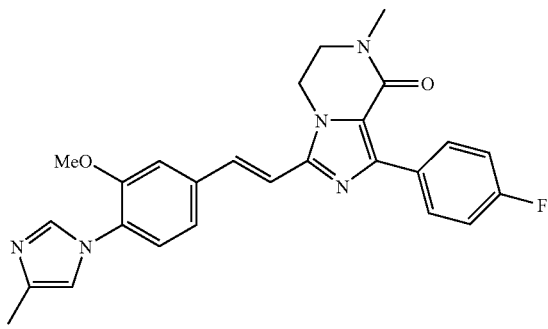

Sodium hydride (containing mineral oil at 60%, 8 mg) was added to a solution of 1-(4-fluorophenyl)-3-{(E)-2-[3-methoxy-4-(4-methyl-1H-imidazol-1-yl)phenyl]vinyl}-6,7-dihydro-5H-imidazo[1,5-a]pyrazin-8-one (42 mg) in THF (3 mL), and the reaction solution was stirred at room temperature for 20 minutes. Methyl iodide (20 mg) was added to the reaction solution, and the reaction solution was stirred at room temperature for two hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex™ NH; elution solvent: ethyl acetate→ethyl acetate:methanol=5:1) to obtain 10 mg of the title compound. The property values of the compound are as follows.

$^1$H-NMR (CDCl$_3$) δ (ppm): 2.36 (s, 3H), 3.54 (s, 3H), 3.90 (s, 3H), 3.94 (t, J=9.6 Hz, 2H), 4.27 (t, J=9.4 Hz, 2H), 6.93 (d, J=16.0 Hz, 1H), 6.95 (brs, 1H), 7.14-7.19 (m, 3H), 7.23-7.28 (m, 2H), 7.37 (dd, J=8.8, 5.6 Hz, 2H), 7.86 (d, J=16.0 Hz, 1H), 7.88 (brs, 1H).

Example 12

Synthesis of 1-(4-fluorophenyl)-3-{(E)-2-[3-methoxy-4-(4-methyl-1H-imidazol-1-yl)phenyl]vinyl}-5,6-dihydroimidazo[5,1-c][1,4]oxazin-8-one

[Formula 61]

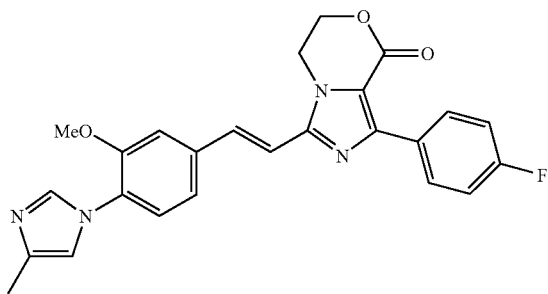

(1) Synthesis of 2-bromoethyl 5-(4-fluorophenyl)-2-{(E)-2-[3-methoxy-4-(4-methyl-1H-imidazol-1-yl)phenyl]vinyl}-1H-imidazole-4-carboxylate DCC (47 mg) was added to a solution of 5-(4-fluorophenyl)-2-{(E)-2-[3-methoxy-4-(4-methyl-1H-imidazol-1-yl)phenyl]vinyl}-1H-imidazole-4-carboxylic acid (80 mg) and 2-bromoethanol (0.27 mL), DMAP (5 mg) in DMF (3 mL), and the reaction solution was stirred at room temperature for 15 hours. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: ethyl acetate→ethyl acetate:methanol=5:1) to obtain 27 mg of the title compound. The property values of the compound are as follows.

$^1$H-NMR (CDCl$_3$) δ (ppm): 2.28 (s, 3H), 3.56 (t, J=5.6 Hz, 2H), 3.84 (s, 3H), 4.58 (t, J=5.6 Hz, 2H), 6.93 (brs, 1H), 7.01 (d, J=16.4 Hz, 1H), 7.08-7.15 (m, 4H), 7.20 (d, J=7.6 Hz, 1H), 7.56 (d, J=16.4 Hz, 1H), 7.74 (brs, 1H), 7.86-7.95 (m, 2H).

(2) Synthesis of 1-(4-fluorophenyl)-3-{(E)-2-[3-methoxy-4-(4-methyl-1H-imidazol-1-yl)phenyl]vinyl}-5,6-dihydroimidazo[5,1-c][1,4]oxazin-8-one Sodium hydride (containing mineral oil at 60%, 3 mg) was added to a solution of 2-bromoethyl 5-(4-fluorophenyl)-2-{(E)-2-[3-methoxy-4-(4-methyl-1H-imidazol-1-yl)phenyl]vinyl}-1H-imidazole-4-carboxylate (27 mg) in DMF (2 mL), and the reaction solution was stirred at room temperature for three hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex™ NH; elution solvent: ethyl acetate→ethyl acetate:methanol=5:1) to obtain 27 mg of the title compound. The property values of the compound are as follows.

$^1$H-NMR (CD$_3$OD) δ (ppm): 2.30 (s, 3H), 3.97 (s, 3H), 4.48 (t, J=5.6 Hz, 2H), 4.71 (t, J=5.6 Hz, 2H), 7.03 (brs, 1H), 7.12 (d, J=16.0 Hz, 1H), 7.16 (t, J=8.8 Hz, 2H), 7.24-7.36 (m, 3H), 7.84 (brs, 1H), 7.85 (d, J=16.0 Hz, 1H), 8.14 (dd, J=8.8, 5.2 Hz, 2H).

Examples 13 and 14

Synthesis of 1-(4-fluorophenyl)-3-{(E)-2-[3-methoxy-4-(4-methyl-1H-imidazol-1-yl)phenyl]vinyl}-5,6-dihydro-8H-imidazo[5,1-c][1,4]oxazine and 2-{4-(4-fluorophenyl)-5-methoxymethyl-2-{(E)-2-[3-methoxy-4-(4-methyl-1H-imidazol-1-yl)phenyl]vinyl}imidazol-1-yl}ethanol

[Formula 62]

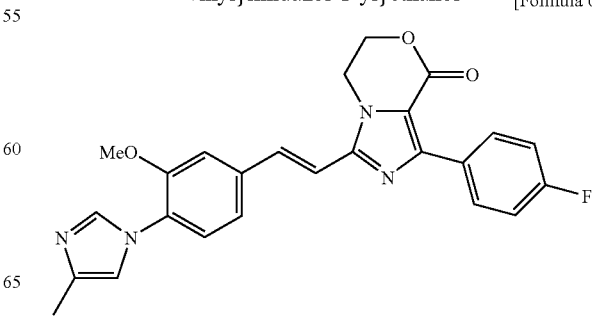

-continued

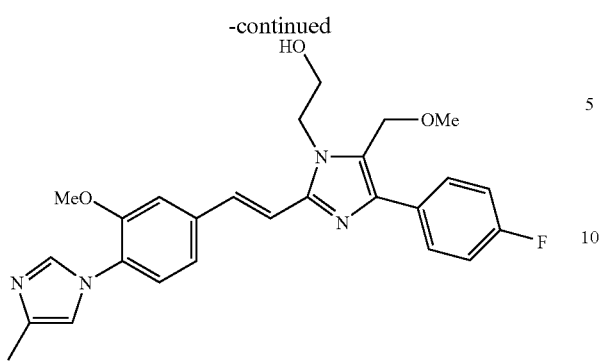

LAH (1 mg) was added to a solution of 1-(4-fluorophenyl)-3-{(E)-2-[3-methoxy-4-(4-methyl-1H-imidazol-1-yl)phenyl]vinyl}-5,6-dihydroimidazo[5,1-c][1,4]oxazin-8-one (5 mg) in THF (1 mL), and the reaction solution was stirred at room temperature for 30 minutes. Water (0.01 mL), a 5 N sodium hydroxide solution (0.01 mL), water (0.03 mL) and methanol (5 mL) were sequentially added to the reaction solution. The suspension was filtered through celite, and the filtrate was concentrated under reduced pressure. p-Toluenesulfonic acid monohydrate (6 mg) was added to a solution of the resulting residue in toluene (5 mL) and DMF (1 mL), and the reaction solution was stirred at 120° C. for 2.5 hours. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex™ NH; elution solvent: ethyl acetate→ethyl acetate:methanol=5:1) to obtain 1 mg of 1-(4-fluorophenyl)-3-{(E)-2-[3-methoxy-4-(4-methyl-1H-imidazol-1-yl)phenyl]vinyl}-5,6-dihydro-8H-imidazo[5,1-c][1,4]oxazine and 2 mg of 2-{4-(4-fluorophenyl)-5-methoxymethyl-2-{(E)-2-[3-methoxy-4-(4-methyl-1H-imidazol-1-yl)phenyl]vinyl}imidazol-1-yl}ethanol.

The property values of 1-(4-fluorophenyl)-3-{(E)-2-[3-methoxy-4-(4-methyl-1H-imidazol-1-yl)phenyl]vinyl}-5,6-dihydro-8H-imidazo[5,1-c][1,4]oxazine are as follows.

ESI-MS; m/z 431 [M$^+$+H]. $^1$H-NMR (CDCl$_3$) δ (ppm): 2.41 (s, 3H), 3.92 (s, 3H), 4.11-4.20 (m, 4H), 5.07 (s, 2H), 6.92 (d, J=16.4 Hz, 1H), 6.98 (brs, 1H), 7.11 (t, J=8.4 Hz, 2H), 7.18 (brs, 1H), 7.23-7.29 (m, 2H), 7.56 (dd, J=8.4, 4.8 Hz, 2H), 7.66 (d, J=16.4 Hz, 1H), 8.01 (brs, 1H).

The property values of 2-{4-(4-fluorophenyl)-5-methoxymethyl-2-{(E)-2-[3-methoxy-4-(4-methyl-1H-imidazol-1-yl)phenyl]vinyl}imidazol-1-yl}ethanol are as follows.

ESI-MS; m/z 463 [M$^+$+H]. $^1$H-NMR (CDCl$_3$) δ (ppm): 2.38 (s, 3H), 3.44 (s, 3H), 3.91 (s, 3H), 4.01 (t, J=4.4 Hz, 2H), 4.32 (t, J=4.4 Hz, 2H), 4.49 (s, 2H), 6.96 (brs, 1H), 7.08 (d, J=16.0 Hz, 1H), 7.14 (t, J=8.8 Hz, 2H), 7.21 (brs, 1H), 7.23 (d, J=6.4 Hz, 1H), 7.25 (brd, J=6.4 Hz, 1H), 7.63 (dd, J=8.8, 5.2 Hz, 2H) 7.79 (d, J=16.0 Hz, 1H), 8.00 (brs, 1H).

Example 15

Synthesis of 1-(4-fluorophenyl)-3-{(E)-2-[3-methoxy-4-(4-methyl-1H-imidazol-1-yl)phenyl]vinyl}-7-methyl-5,6,7,8-tetrahydroimidazo[1,5-a]pyrazine

[Formula 63]

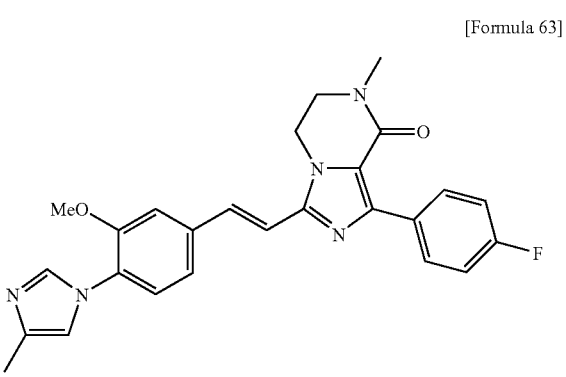

(1) Synthesis of 2-{4-(4-fluorophenyl)-5-hydroxymethyl-2-{(E)-2-[3-methoxy-4-(4-methyl-1H-imidazol-1-yl)phenyl]vinyl}imidazol-1-yl}ethanol LAH (10 mg) was added to a solution of 1-(4-fluorophenyl)-3-{(E)-2-[3-methoxy-4-(4-methyl-1H-imidazol-1-yl)phenyl]vinyl}-5,6-dihydroimidazo[5,1-c][1,4]oxazin-8-one (56 mg) in THF (3 mL), and the reaction solution was stirred at room temperature for 40 minutes. Ethyl acetate and saturated sodium bicarbonate water were added to the reaction solution, and the organic layer was separated. The resulting organic layer was dried over anhydrous magnesium sulfate and then concentrated under reduced pressure to obtain 59 mg of the title crude product. The property value of the compound is as follows.

ESI-MS; m/z 449 [M$^+$+H].

(2) Synthesis of 1-(4-fluorophenyl)-3-{(E)-2-[3-methoxy-4-(4-methyl-1H-imidazol-1-yl)phenyl]vinyl}-7-methyl-5,6,7,8-tetrahydroimidazo[1,5-a]pyrazine Dess-Martin periodinane (280 mg) was added to a solution of 2-{4-(4-fluorophenyl)-5-hydroxymethyl-2-{(E)-2-[3-methoxy-4-(4-methyl-1H-imidazol-1-yl)phenyl]vinyl}imidazol-1-yl}ethanol (59 mg) in methylene chloride (3 mL), and the reaction solution was stirred at room temperature for 1.5 hours. A 1 N sodium hydroxide solution was added to the reaction solution, and the organic layer was separated. Methylamine (2 M solution in methanol, 0.7 mL), acetic acid (0.08 mL) and sodium triacetoxyborohydride (280 mg) were added to the resulting organic layer, and the reaction solution was stirred at room temperature for 1.5 hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex™ NH; elution solvent: ethyl acetate→ethyl acetate:methanol=5:1) to obtain 1 mg of the title compound. The property values of the compound are as follows.

ESI-MS; m/z 444 [M$^+$+H]. $^1$H-NMR (CDCl$_3$) δ (ppm): 2.37 (s, 3H), 2.56 (s, 3H), 2.91 (t, J=5.6 Hz, 2H), 3.83 (s, 2H), 3.91 (s, 3H), 4.19 (t, J=5.6 Hz, 2H), 6.91 (d, J=16.0 Hz, 1H), 6.96 (brs, 1H), 7.11 (t, J=8.8 Hz, 2H), 7.17 (brs, 1H), 7.21-7.28 (m, 2H), 7.61 (dd, J=8.8, 5.6 Hz, 2H), 7.66 (d, J=16.0 Hz, 1H), 7.93 (brs, 1H).

Example 16

Synthesis of 3-(3-fluorophenyl)-5-{(E)-2-[3-methoxy-4-(4-methyl-1H-imidazol-1-yl)phenyl]vinyl}-4H-[1,2,4]triazole

[Formula 64]

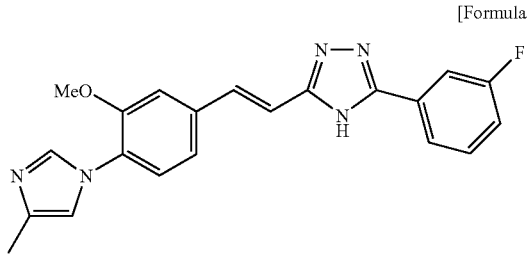

(1) Synthesis of tert-butyl N'-{(E)-3-[3-methoxy-4-(4-methyl-1H-imidazol-1-yl)phenyl]acryloyl}hydrazinecarboxylate HOBT (420 mg) and EDC (590 mg) were sequentially added to a solution of (E)-3-[3-methoxy-4-(4-methyl-1H-imidazol-1-yl)phenyl]acrylic acid (530 mg), tert-butyl carbazate (271 mg) and IPEA (0.71 mL) in DMF (10 mL), and the reaction solution was stirred at room temperature for 15 hours. Ethyl acetate and saturated sodium bicarbonate water were added to the reaction solution, and the organic layer was separated. The resulting organic layer was dried over anhydrous magnesium sulfate and then concentrated under reduced pressure. The resulting solid was recrystallized from a mixed solution of ethyl acetate and ethanol to obtain 668 mg of the title compound. The property values of the compound are as follows.

$^1$H-NMR (CDCl$_3$) δ (ppm): 1.51 (s, 9H), 2.30 (s, 3H), 3.88 (s, 3H), 6.45 (d, J=15.6 Hz, 1H), 6.76 (brs, 1H), 6.93 (s, 1H), 7.09 (brs, 1H), 7.11 (brd, J=8.0 Hz, 1H), 7.25 (d, J=8.0 Hz, 1H), 7.65 (d, J=15.6 Hz, 1H), 7.73 (s, 1H), 8.80 (brs, 1H).

(2) Synthesis of (E)-3-[3-methoxy-4-(4-methyl-1H-imidazol-1-yl)phenyl]acrylic acid hydrazide dihydrochloride A solution of 4 N hydrochloric acid in ethyl acetate (3 mL) was added to a solution of tert-butyl N'-{(E)-3-[3-methoxy-4-(4-methyl-1H-imidazol-1-yl)phenyl]acryloyl}hydrazinecarboxylate (668 mg) in ethyl acetate (5 mL) and methanol (1 mL), and the reaction solution was stirred at room temperature for two hours. The solid precipitated in the reaction solution was collected by filtration and washed with diethyl ether to obtain 658 mg of the title compound. The property value of the compound is as follows.

ESI-MS; m/z 273 [M$^+$+H].

(3) Synthesis of 3-fluorobenzoic acid N'-{(E)-3-[3-methoxy-4-(4-methyl-1H-imidazol-1-yl)phenyl]acryloyl}hydrazide HOBT (70 mg) and EDC (100 mg) were added to a solution of (E)-3-[3-methoxy-4-(4-methyl-1H-imidazol-1-yl)phenyl]acrylic acid hydrazide dihydrochloride (120 mg), 3-fluorobenzoic acid (49 mg) and IPEA (0.37 mL) in DMF, and the reaction solution was stirred at room temperature for 12 hours. Ethyl acetate and water were added to the reaction solution, and the precipitated solid was collected by filtration to obtain 86 mg of the title compound. The property value of the compound is as follows.

ESI-MS; m/z 395 [M$^+$+H].

(4) Synthesis of 2-(3-fluorophenyl)-5-{(E)-2-[3-methoxy-4-(4-methyl-1H-imidazol-1-yl)phenyl]vinyl}-[1,3,4]oxadiazole A solution of 3-fluorobenzoic acid N'-{(E)-3-[3-methoxy-4-(4-methyl-1H-imidazol-1-yl)phenyl]acryloyl}hydrazide (86 mg) in phosphorus oxychloride (2 mL) was stirred at 120° C. for one hour. The reaction solution was left to cool to room temperature and concentrated under reduced pressure. Methylene chloride and a 1 N sodium hydroxide solution were added to the residue, and the organic layer was separated. The resulting organic layer was dried over anhydrous magnesium sulfate and then concentrated under reduced pressure. The residue was purified by silica gel column chromatography (carrier: Chromatorex™ NH; elution solvent: heptane:ethyl acetate=1:1→ethyl acetate) to obtain 65 mg of the title compound. The property values of the compound are as follows.

ESI-MS; m/z 377 [M$^+$+H]. $^1$H-NMR (CDCl$_3$) δ (ppm): 2.31 (s, 3H), 3.94 (s, 3H), 6.96 (brs, 1H), 7.12 (d, J=16.4 Hz, 1H), 7.22-7.30 (m, 3H), 7.31 (d, J=8.4 Hz, 1H), 7.51 (td, J=8.0, 6.0 Hz, 1H), 7.63 (d, J=16.4 Hz, 1H), 7.75 (d, J=1.6 Hz, 1H), 7.79-7.84 (m, 1H), 7.92-7.95 (m, 1H).

(5) Synthesis of 3-(3-fluorophenyl)-5-{(E)-2-[3-methoxy-4-(4-methyl-1H-imidazol-1-yl)phenyl]vinyl}-4H-[1,2,4]triazole A solution of 2-(3-fluorophenyl)-5-{(E)-2-[3-methoxy-4-(4-methyl-1H-imidazol-1-yl)phenyl]vinyl}-[1,3,4]oxadiazole (50 mg) and ammonium acetate (205 mg) in acetic acid (3 mL) was heated under reflux at 150° C. for 1.5 hours. The reaction solution was left to cool to room temperature and concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. The residue was purified by silica gel column chromatography (elution solvent: ethyl acetate→ethyl acetate:methanol=5:1) to obtain 29 mg of the title compound. The property value of the compound is as follows.

ESI-MS; m/z 376 [M$^+$+H].

Example 17

Synthesis of 3-(4-fluorobenzyl)-5-{(E)-2-[3-methoxy-4-(4-methyl-1H-imidazol-1-yl)phenyl]vinyl}-4H-[1,2,4]triazole

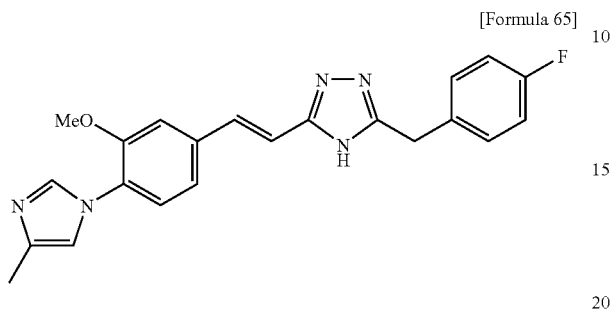

[Formula 65]

(1) Synthesis of 2-(4-fluorobenzyl)-5-{(E)-2-[3-methoxy-4-(4-methyl-1H-imidazol-1-yl)phenyl]vinyl}-[1,3,4]oxadiazole 65 mg of the title compound was obtained from (E)-3-[3-methoxy-4-(4-methyl-1H-imidazol-1-yl)phenyl]acrylic acid hydrazide dihydrochloride (100 mg) and 4-fluorophenylacetic acid (45 mg) by the same method as in Example 16. The property values of the compound are as follows.

$^1$H-NMR (CDCl$_3$) δ (ppm): 2.30 (s, 3H), 3.90 (s, 3H), 4.22 (s, 2H), 6.93 (brs, 1H), 6.99 (d, J=16.0 Hz, 1H), 7.05 (t, J=8.4 Hz, 2H), 7.15 (d, J=2.0 Hz, 1H), 7.17 (dd, J=8.0, 2.0 Hz, 1H), 7.27 (d, J=8.0 Hz, 1H), 7.32 (dd, J=8.4, 5.2 Hz, 2H), 7.45 (d, J=16.0 Hz, 1H), 7.72 (d, J=1.2 Hz, 1H).

(2) Synthesis of 3-(4-fluorobenzyl)-5-{(E)-2-[3-methoxy-4-(4-methyl-1H-imidazol-1-yl)phenyl]vinyl}-4H-[1,2,4]triazole A solution of 2-(4-fluorobenzyl)-5-{(E)-2-[3-methoxy-4-(4-methyl-1H-imidazol-1-yl)phenyl]vinyl}-[1,3,4]oxadiazole (65 mg) and ammonium acetate (256 mg) in acetic acid (1 mL) was stirred at 150° C. for four hours. The reaction solution was left to cool to room temperature and concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. The residue was purified by silica gel column chromatography (elution solvent: ethyl acetate→ethyl acetate:methanol=5:1). The resulting solid was suspended in diethyl ether and collected by filtration to obtain 40 mg of the title compound. The property values of the compound are as follows.

ESI-MS; m/z 390 [M$^+$+H]. $^1$H-NMR (CDCl$_3$) δ (ppm): 2.30 (s, 3H), 3.89 (s, 3H), 4.18 (s, 2H), 6.94 (brs, 1H), 7.05 (t, J=8.8 Hz, 2H), 7.06 (d, J=16.4 Hz, 1H), 7.18 (brd, J=6.0 Hz, 1H), 7.19 (brs, 1H), 7.25 (d, J=6.0 Hz, 1H), 7.30 (dd, J=8.8, 5.6 Hz, 2H), 7.59 (d, J=16.4 Hz, 1H), 7.72 (brs, 1H).

Examples 18 and 19

Synthesis of 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine and 2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine

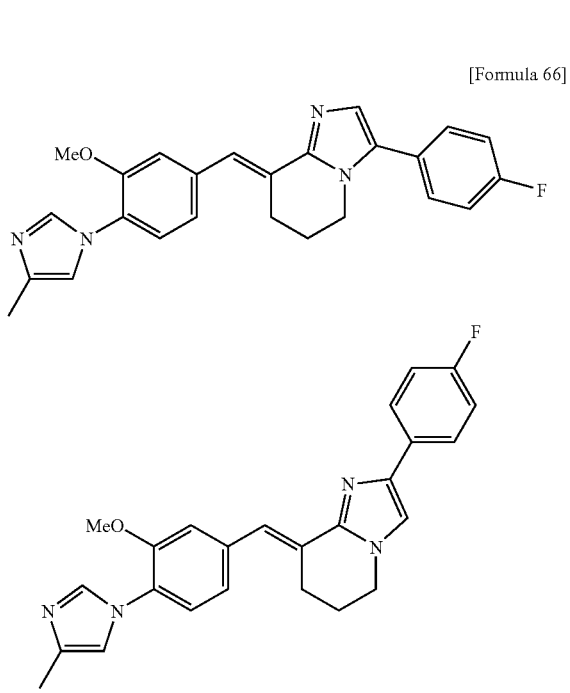

[Formula 66]

(1) Synthesis of tert-butyl 5-chloro-2-(diethoxyphosphoryl)valerate

Sodium hydride (containing mineral oil at 40%, 17.4 g) was washed with hexane (100 mL) three times to remove the oily substance. A solution tert-butyl diethylphosphonoacetate (100 g) in THF (100 mL) was added dropwise to a suspension of the sodium hydride in THF (500 mL) at 0° C. over 30 minutes. Then, the reaction solution was heated to room temperature and further stirred for one hour. A solution of 1-bromo-3-chloropropane (125 g) in THF (100 mL) was added dropwise to the reaction solution over 30 minutes. After completion of the dropwise addition, the reaction solution was heated under reflux for 15 hours. The reaction solution was left to cool to room temperature. Ethyl acetate (1 L) and saturated aqueous ammonium chloride solution (1 L) were added, and the organic layer was separated. The resulting organic layer was dried over anhydrous magnesium sulfate and concentrated under reduced pressure to obtain 113.4 g of the title compound. The property values of the compound are as follows.

$^1$H-NMR (CDCl$_3$) δ (ppm): 1.31-1.48 (m, 6H), 1.48 (s, 9H), 1.79-2.14 (m, 4H), 2.73-2.91 (m, 1H), 3.55 (t, J=6.4 Hz, 2H), 4.10-4.19 (m, 4H).

(2) Synthesis of tert-butyl 5-chloro-2-{1-[3-methoxy-4-(4-methyl-1H-imidazol-1-yl)phenyl-(E)-methylidene]valerate tert-Butyl 5-chloro-2-(diethoxyphosphoryl)valerate (83.5 g) and lithium hydroxide monohydrate (29.1 g) were sequentially added to a solution of 3-methoxy-4-(4-methyl-1H-imidazol-1-yl)benzaldehyde (50 g) in THF (600 mL) and ethanol (200 mL), and the reaction solution was stirred at room temperature overnight. After confirming that the raw materials disappeared, water and ethyl acetate were added to the reaction solution, and the organic layer was separated. The resulting organic layer was washed with brine, and then dried over anhydrous magnesium sulfate and concentrated under reduced pressure. The residue was purified by silica gel chromatography (elution solvent: heptane:ethyl acetate=1:1), and the resulting solid was recrystallized from a mixed solution of ethyl acetate and hexane to obtain 54.9 g of the title compound. The property values of the compound are as follows.

$^1$H-NMR (CDCl$_3$) δ (ppm): 1.55 (s, 9H), 1.99-2.08 (m, 2H), 2.30 (s, 3H), 2.63-2.71 (m, 2H), 3.59 (t, J=6.4 Hz, 2H), 3.87 (s, 3H), 6.93 (m, 1H), 7.00 (d, J=1.2 Hz, 1H), 7.09 (dd, J=8.4, 1.2 Hz, 1H), 7.27 (d, J=8.4 Hz, 1H), 7.58 (s, 1H), 7.72 (m, 1H).

(3) Synthesis of 5-chloro-2-{1-[3-methoxy-4-(4-methyl-1H-imidazol-1-yl)phenyl]-(E)-methylidene}valeric acid trifluoroacetic acid salt Trifluoroacetic acid (10 mL) was added to a solution of tert-butyl 5-chloro-2-{1-[3-methoxy-4-(4-methyl-1H-imidazol-1-yl)phenyl-(E)-methylidene]valerate (5 g) in methylene chloride (20 mL), and the reaction solution was stirred at room temperature for two hours. After confirming that the raw materials disappeared, the reaction solution was concentrated under reduced pressure. The resulting solid was collected by filtration and washed with ethyl acetate to obtain 5.7 g of the title compound. The property values of the compound are as follows.

$^1$H-NMR (DMSO-d$_6$) δ (ppm): 1.93-2.03 (m, 2H), 2.35 (s, 3H), 2.58-2.66 (m, 2H), 3.70 (t, J=6.4 Hz, 2H), 3.91 (s, 3H), 7.24 (dd, J=8.4, 1.2 Hz, 1H), 7.37 (d, J=1.2 Hz, 1H), 7.64 (d, J=8.4, 1H), 7.66 (m, 1H), 7.76 (s, 1H), 9.36 (m, 1H).

(4) Synthesis of 2-(4-fluorophenyl)-2-oxoethyl 5-chloro-2-{1-[3-methoxy-4-(4-methyl-1H-imidazol-1-yl)phenyl]-(E)-methylidene}valerate IPEA (0.14 mL) was added to a solution of 5-chloro-2-{1-[3-methoxy-4-(4-methyl-1H-imidazol-1-yl)phenyl]-(E)-methylidene}valeric acid trifluoroacetic acid salt (110 mg) and 4-fluorophenacyl bromide (85 mg) in DMF (3 mL), and the reaction solution was stirred at room temperature for 30 minutes. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: heptane:ethyl acetate=1:1→ethyl acetate) to obtain 47 mg of the title compound. The property values of the compound are as follows.

$^1$H-NMR (CDCl$_3$) δ (ppm): 2.09-2.20 (m, 2H), 2.31 (s, 3H), 2.78-2.85 (m, 2H), 3.63 (t, J=6.4 Hz, 2H), 3.89 (s, 3H), 5.47 (s, 2H), 6.95 (brs, 1H), 7.07 (d, J=1.6 Hz, 1H), 7.10 (dd, J=8.0, 1.6 Hz, 1H), 7.18 (t, J=8.4 Hz, 2H), 7.29 (d, J=8.0 Hz, 1H), 7.77 (brs, 1H), 7.85 (s, 1H), 7.99 (dd, J=8.4, 5.2 Hz, 2H).

(5) Synthesis of 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine and 2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine A solution of 2-(4-fluorophenyl)-2-oxoethyl 5-chloro-2-{1-[3-methoxy-4-(4-methyl-1H-imidazol-1-yl)phenyl]-(E)-methylidene}valerate (47 mg) and ammonium acetate (154 mg) in acetic acid (1 mL) was stirred at 120° C. for six hours. The reaction solution was left to cool to room temperature and concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. The residue was purified by silica gel column chromatography (elution solvent: heptane:ethyl acetate=1:1→ethyl acetate→ethyl acetate:methanol=9:1) to obtain 14 mg of 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine and 2 mg of 2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine.

The property values of 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine are as follows.

ESI-MS; m/z 415 [M$^+$+H]. $^1$H-NMR (CDCl$_3$) δ (ppm): 2.09-2.17 (m, 2H), 2.39 (s, 3H), 2.92-2.99 (m, 2H), 3.89 (s, 3H), 4.12 (t, J=5.6 Hz, 2H), 6.97 (brs, 1H), 7.07 (t, J=8.8 Hz, 2H), 7.09 (d, J=1.6 Hz, 1H), 7.10 (dd, J=6.0, 1.6 Hz, 1H), 7.15 (s, 1H), 7.26 (d, J=6.0 Hz, 1H), 7.79 (dd, J=8.8, 5.2 Hz, 2H), 7.81 (brs, 1H), 7.96 (brs, 1H).

The property values of 2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine are as follows.

ESI-MS; m/z 415 [M$^+$+H]. $^1$H-NMR (CDCl$_3$) δ (ppm): 2.03-2.11 (m, 2H), 2.32 (s, 3H), 2.90-3.01 (m, 2H), 3.86 (s, 3H), 4.04 (t, J=5.6 Hz, 2H), 6.93 (d, J=1.2 Hz, 1H), 7.07 (brs, 1H), 7.08 (brd, J=8.4 Hz, 1H), 7.14 (t, J=8.4 Hz, 2H), 7.18 (d, J=1.2 Hz, 1H), 7.24 (d, J=8.4 Hz, 1H), 7.38 (dd, J=8.4, 5.6 Hz, 2H), 7.74 (brs, 1H), 7.77 (brs, 1H).

Example 20

Synthesis of 2-(4-fluorophenyl)-8-{1-[3-methoxy-4-(4-methyl-1H-imidazol-1-yl)phenyl]-(E)-methylidene}-5,6,7,8-tetrahydro[1,2,4]triazolo[1,5-a]pyridine

[Formula 67]

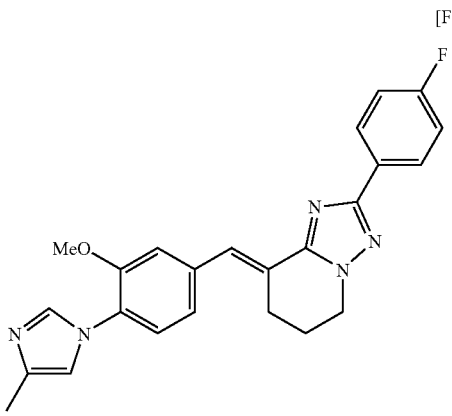

(1) Synthesis of tert-butyl N'-{5-chloro-2-{1-[3-methoxy-4-(4-methyl-1H-imidazol-1-yl)phenyl]-(E)-methylidene}pentanoyl}hydrazinecarboxylate HOBT (108 mg) and EDC (153 mg) were sequentially added to a solution of 5-chloro-2-{1-[3-methoxy-4-(4-methyl-1H-imidazol-1-yl)phenyl]-(E)-methylidene}valeric acid trifluoroacetic acid salt (300 mg), tert-butyl carbazate (71 mg) and IPEA (0.38 mL) in DMF (5 mL), and the reaction solution was stirred at room temperature for three hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex™ NH; elution solvent: heptane:ethyl acetate=1:1→ethyl acetate) to obtain 222 mg of the title compound. The property value of the compound is as follows.

ESI-MS; m/z 449 [M++H].

(2) Synthesis of 5-chloro-2-{1-[3-methoxy-4-(4-methyl-1H-imidazol-1-yl)phenyl]-(E)-methylidene}valeric acid hydrazide dihydrochloride A solution of 4 N hydrochloric acid in ethyl acetate (1 mL) was added to a solution of tert-butyl N'-{5-chloro-2-{1-[3-methoxy-4-(4-methyl-1H-imidazol-1-yl)phenyl]-(E)-methylidene}pentanoyl}hydrazinecarboxylate (222 mg) in ethyl acetate (1 mL), and the reaction solution was stirred at room temperature for two hours. The reaction solution was concentrated under reduced pressure to obtain 208 mg of the title compound. The property values of the compound are as follows.

$^1$H-NMR (CD$_3$OD) δ (ppm): 1.98-2.06 (m, 2H), 2.44 (s, 3H), 2.75-2.80 (m, 2H), 3.61 (t, J=6.4 Hz, 2H), 3.97 (s, 3H), 7.21 (dd, J=8.0, 1.6 Hz, 1H), 7.29 (d, J=1.6 Hz, 1H), 7.37 (s, 1H), 7.60 (s, 1H), 7.61 (d, J=8.0 Hz, 1H), 9.16 (d, J=1.2 Hz, 1H).

(3) Synthesis of 4-fluorobenzoic acid N'-{5-chloro-2-{1-[3-methoxy-4-(4-methyl-1H-imidazol-1-yl)phenyl]-(E)-methylidene}valeric acid}hydrazide A 5 N sodium hydroxide solution (3 mL) was added to a solution of 5-chloro-2-{1-[3-methoxy-4-(4-methyl-1H-imidazol-1-yl)phenyl]-(E)-methylidene}valeric acid hydrazide dihydrochloride (208 mg) and 4-fluorobenzoic acid chloride (0.07 mL) in methylene chloride (5 mL) at 0° C., and the reaction solution was stirred at room temperature for one hour. The organic layer was separated from the reaction solution and washed with brine. The resulting organic layer was dried over anhydrous magnesium sulfate and then concentrated under reduced pressure. The residue was purified by silica gel column chromatography (carrier: Chromatorex™ NH; elution solvent: ethyl acetate→ethyl acetate:methanol=5:1) to obtain 84 mg of the title compound. The property values of the compound are as follows.

ESI-MS; m/z 471 [M++H]. $^1$H-NMR (CDCl$_3$) δ (ppm): 1.99-2.08 (m, 2H), 2.29 (s, 3H), 2.74-2.80 (m, 2H), 3.57 (t, J=5.6 Hz, 2H), 3.84 (s, 3H), 6.93 (brs, 1H), 6.96 (s, 1H), 6.98 (brd, J=8.0 Hz, 1H), 7.09 (t, J=8.8 Hz, 2H), 7.23 (d, J=8.0 Hz, 1H), 7.37 (brs, 1H), 7.74 (d, J=1.2 Hz, 1H), 7.89 (dd, J=8.8, 5.6 Hz, 2H).

(4) Synthesis of 2-{4-chloro-1-{1-[3-methoxy-4-(4-methyl-1H-imidazol-1-yl)phenyl]-(E)-methylidene}butyl}-5-(4-fluorophenyl)-[1,3,4]oxadiazole A solution of 4-fluorobenzoic acid N'-{5-chloro-2-{1-[3-methoxy-4-(4-methyl-1H-imidazol-1-yl)phenyl]-(E)-methylidene}valeric acid}hydrazide (84 mg) in phosphorus oxychloride (2 mL) was stirred at 100° C. for 30 minutes. The reaction solution was left to cool to room temperature and concentrated under reduced pressure. Chloroform and a 1 N sodium hydroxide solution were added to the residue, and the organic layer was separated. The resulting organic layer was washed with brine, and then dried over anhydrous magnesium sulfate and concentrated under reduced pressure to obtain 85 mg of the title compound. The property values of the compound are as follows.

ESI-MS; m/z 453 [M++H]. $^1$H-NMR (CDCl$_3$) δ (ppm): 2.22-2.31 (m, 2H), 2.42 (s, 3H), 3.05-3.11 (m, 2H), 3.70 (t, J=6.0 Hz, 2H), 3.95 (s, 3H), 7.03 (brs, 1H), 7.14 (d, J=1.6 Hz, 1H), 7.18 (dd, J=8.0, 1.6 Hz, 1H), 7.23 (t, J=8.4 Hz, 2H), 7.37 (d, J=8.0 Hz, 1H), 7.60 (s, 1H), 8.13 (dd, J=8.4, 4.8 Hz, 2H), 8.20 (brs, 1H).

(5) Synthesis of 2-(4-fluorophenyl)-8-{1-[3-methoxy-4-(4-methyl-1H-imidazol-1-yl)phenyl]-(E)-methylidene}-5,6,7,8-tetrahydro[1,2,4]triazolo[1,5-a]pyridine A solution of 2-{4-chloro-1-{1-[3-methoxy-4-(4-methyl-1H-imidazol-1-yl)phenyl]-(E)-methylidene}butyl}-5-(4-fluorophenyl)-[1,3,4]oxadiazole (85 mg) and ammonium acetate (290 mg) in acetic acid (3 mL) was heated under reflux for 10 hours. The reaction solution was left to cool to room temperature and concentrated under reduced pressure. Methylene chloride and a 1 N sodium hydroxide solution were added to the residue, and the organic layer was separated. The resulting organic layer was washed with brine, dried over anhydrous magnesium sulfate, and then concentrated under reduced pressure. The resulting residue was purified by silica gel column chromatography (carrier: Chromatorex™ NH;

elution solvent: heptane:ethyl acetate=1:1→ethyl acetate) to obtain 34 mg of the title compound. The property values of the compound are as follows.

ESI-MS; m/z 416 [M⁺+H]. ¹H-NMR (CDCl₃) δ (ppm): 2.17-2.25 (m, 2H), 2.35 (s, 3H), 2.96-3.03 (m, 2H), 3.89 (s, 3H), 4.33 (t, J=6.0 Hz, 2H), 6.95 (brs, 1H), 7.04-7.16 (m, 4H), 7.28 (dd, J=8.4 Hz, 1H), 7.80 (brs, 1H), 7.83 (brs, 1H), 8.11 (dd, J=8.4, 5.6 Hz, 2H).

Examples 21 and 22

Synthesis of methyl 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylate and methyl 2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-3-carboxylate

[Formula 68]

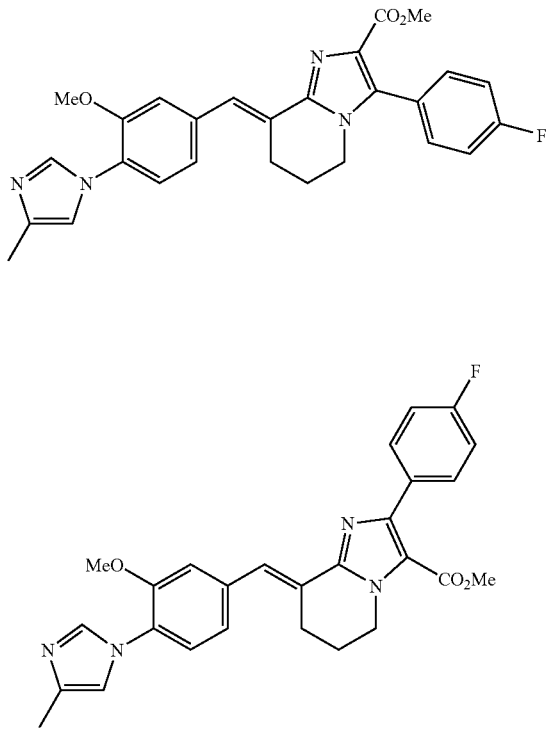

(1) Synthesis of 2-(4-fluorophenyl)-1-methoxycarbonyl-2-oxoethyl 5-chloro-2-{1-[3-methoxy-4-(4-methyl-1H-imidazol-1-yl)phenyl]-(E)-methylidene}valerate IPEA (1.9 mL) was added to a solution of 5-chloro-2-{1-[3-methoxy-4-(4-methyl-1H-imidazol-1-yl)phenyl]-(E)-methylidene}valeric acid trifluoroacetic acid salt (1.53 g) and methyl 2-chloro-3-(4-fluorophenyl)-3-oxopropionate (CAS #160727-96-8, 624 mg) in DMF (5 mL), and the reaction solution was stirred at room temperature for four hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: heptane:ethyl acetate=1:1→ethyl acetate) to obtain 817 mg of the title compound. The property values of the compound are as follows.

ESI-MS; m/z 529 [M⁺+H]. ¹H-NMR (CDCl₃) δ (ppm): 2.02-2.11 (m, 2H), 2.32 (s, 3H), 2.77 (t, J=7.6 Hz, 2H), 3.59 (t, J=6.4 Hz, 2H), 3.83 (s, 3H), 3.89 (s, 3H), 6.44 (s, 1H), 6.95 (brs, 1H), 7.04 (d, J=1.6 Hz, 1H), 7.07 (dd, J=8.0, 1.6 Hz, 1H), 7.20 (t, J=8.8 Hz, 2H), 7.28 (d, J=8.0 Hz, 1H), 7.78 (d, J=1.2 Hz, 1H), 7.83 (s, 1H), 8.09 (dd, J=8.8, 5.2 Hz, 2H).

(2) Synthesis of methyl 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylate and methyl 2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-3-carboxylate A solution of 2-(4-fluorophenyl)-1-methoxycarbonyl-2-oxoethyl 5-chloro-2-{1-[3-methoxy-4-(4-methyl-1H-imidazol-1-yl)phenyl]-(E)-methylidene}valerate (817 mg) and ammonium acetate (2.37 g) in acetic acid (5 mL) was stirred at 120° C. for 11 hours. The reaction solution was left to cool to room temperature and concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. The resulting residue was purified by silica gel column chromatography (elution solvent: heptane:ethyl acetate=1:1→ethyl acetate→ethyl acetate:methanol=9:1) to obtain 258 mg of methyl 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylate and 193 mg of methyl 2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-3-carboxylate.

The property values of methyl 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylate are as follows.

ESI-MS; m/z 473 [M⁺+H]. ¹H-NMR (CDCl₃) δ (ppm): 2.08-2.17 (m, 2H), 2.33 (s, 3H), 2.92-2.98 (m, 2H), 3.75 (s, 3H), 3.86 (s, 3H), 4.46 (t, J=6.0 Hz, 2H), 6.94 (brs, 1H), 7.05-7.12 (m, 4H), 7.26 (d, J=7.6 Hz, 1H), 7.66 (dd, J=8.8, 5.6 Hz, 2H), 7.80 (brs, 1H), 7.85 (brs, 1H).

The property values of methyl 2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-3-carboxylate are as follows.

ESI-MS; m/z 473 [M⁺+H]. ¹H-NMR (CDCl₃) δ (ppm): 2.00-2.10 (m, 2H), 2.33 (s, 3H), 2.95-3.02 (m, 2H), 3.80-3.90 (m, 8H), 6.94 (brs, 1H), 7.08 (brs, 1H), 7.09 (brd, J=6.8 Hz, 1H), 7.17 (t, J=8.4 Hz, 2H), 7.26 (d, J=6.8 Hz, 1H), 7.40 (dd, J=8.4, 5.6 Hz, 2H), 7.78 (brs, 1H), 7.90 (brs, 1H).

Example 23

Synthesis of {3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridin-2-yl}methanol

[Formula 69]

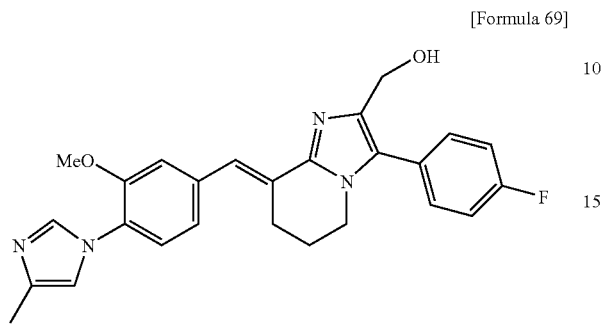

LAH (7 mg) was added to a solution of methyl 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylate (86 mg) in THF (3 mL), and the reaction solution was stirred at 0° C. for one hour. Ethyl acetate and water were added to the reaction solution, and the organic layer was separated. The resulting organic layer was dried over anhydrous magnesium sulfate and then concentrated under reduced pressure. The residue was purified by silica gel column chromatography (elution solvent: ethyl acetate→ethyl acetate:methanol=5:1) to obtain 25 mg of the title compound. The property values of the compound are as follows.

$^1$H-NMR (CDCl$_3$) δ (ppm): 2.10-2.19 (m, 2H), 2.33 (s, 3H), 2.92-2.99 (m, 2H), 3.86 (s, 3H), 4.16 (t, J=5.2 Hz, 2H), 4.76 (s, 2H), 6.94 (brs, 1H), 7.04-7.15 (m, 4H), 7.23 (d, J=8.0 Hz, 1H), 7.66 (dd, J=8.4, 5.2 Hz, 2H), 7.77 (brs, 1H), 7.78 (brs, 1H).

Example 24

Synthesis of {2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridin-3-yl]methanol

[Formula 70]

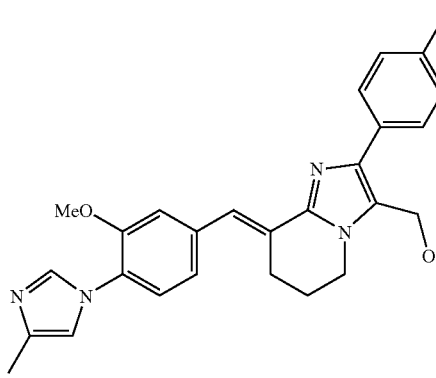

15 mg of the title compound was obtained from methyl 2-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-3-carboxylate (44 mg) by the same method as in Example 23. The property values of the compound are as follows.

$^1$H-NMR (CDCl$_3$) δ (ppm): 2.01-2.10 (m, 2H), 2.31 (s, 3H), 2.94-3.00 (m, 2H), 3.86 (s, 3H), 3.92 (t, J=6.0 Hz, 2H), 4.59 (s, 2H), 6.93 (brs, 1H), 7.06 (d, J=1.6 Hz, 1H), 7.07 (dd, J=7.2, 1.6 Hz, 1H), 7.17 (t, J=8.8 Hz, 2H), 7.24 (d, J=7.2 Hz, 1H), 7.38 (dd, J=8.8, 5.2 Hz, 2H), 7.72 (brs, 1H), 7.73 (brs, 1H).

Example 25

Synthesis of 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylic acid

[Formula 71]

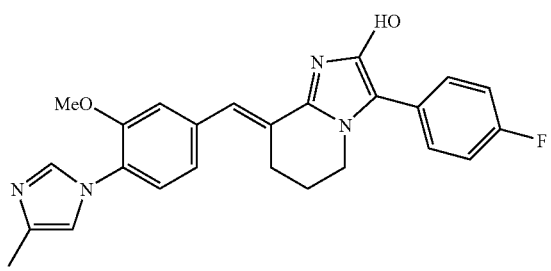

A 2 N sodium hydroxide solution (1 mL) was added to a solution of methyl 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylate (172 mg) in methanol (4 mL), and the reaction solution was heated under reflux for nine hours. The reaction solution was left to cool to room temperature, and 2 N hydrochloric acid (1 mL) was added to the reaction solution. The solid precipitated in the reaction solution was collected by filtration and washed with diethyl ether to obtain 167 mg of the title compound. The property value of the compound is as follows.

ESI-MS; m/z 459 [M$^+$+H].

Example 26

Synthesis of 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylic acid dimethylamide ditrifluoroacetic acid salt

[Formula 72]

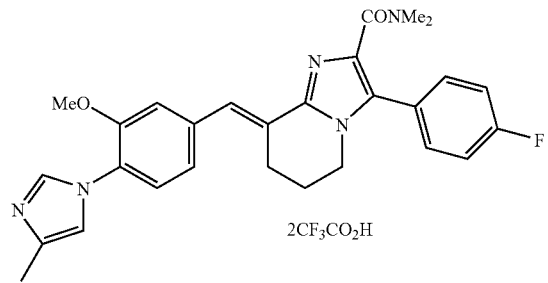

HOBT (9 mg) and EDC (13 mg) were added to a solution of 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylic acid (20 mg) and dimethylamine (2 M solution in methanol, 0.1 mL) in DMF (1 mL), and the reaction solution was stirred at room temperature for nine hours. The reaction solution was purified by LC-MS to obtain 25 mg of the title compound.

The property value of the compound is as follows.
ESI-MS; m/z 486 [M$^+$+H].

Example 27

Synthesis of 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylic acid methylamide ditrifluoroacetic acid salt

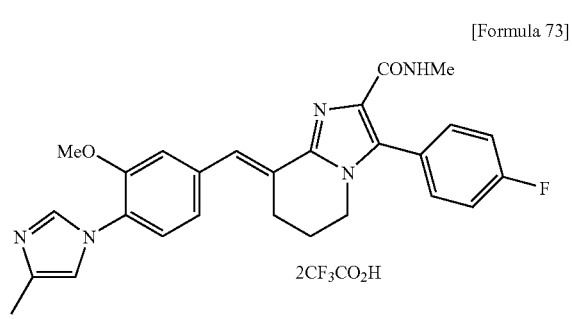

[Formula 73]

HOBT (5 mg) and EDC (7 mg) were added to a solution of 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylic acid (8.7 mg) and methylamine (2 M solution in methanol, 0.1 mL) in DMF (1 mL), and the reaction solution was stirred at room temperature for 11 hours. The reaction solution was purified by LC-MS to obtain 9 mg of the title compound.

The property value of the compound is as follows.
ESI-MS; m/z 472 [M$^+$+H].

Example 28

Synthesis of 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylic acid amide ditrifluoroacetic acid salt

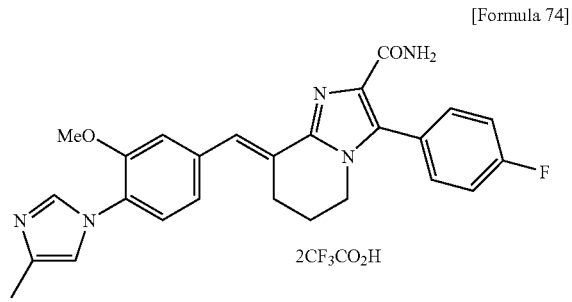

[Formula 74]

HOBT (5 mg) and EDC (7 mg) were added to a solution of 3-(4-fluorophenyl)-8-{1-[3-methoxy-4-(4-methyl-1H-imidazol-1-yl)phenyl]-(E)-methylidene}-5,6,7,8-tetrahydroimidazo[1,2-a]pyridine-2-carboxylic acid (9 mg) and concentrated aqueous ammonia (0.2 mL) in DMF (1 mL), and the reaction solution was stirred at room temperature for 11 hours. The reaction solution was purified by LC-MS to obtain 4 mg of the title compound.

The property value of the compound is as follows.
ESI-MS; m/z 458 [M$^+$+H].

Example 29

Synthesis of 1-(4-fluorobenzyl)-2-{(E)-2-[3-methoxy-4-(4-methyl-1H-imidazol-1-yl)phenyl]vinyl}-4,5-dimethyl-1H-imidazole

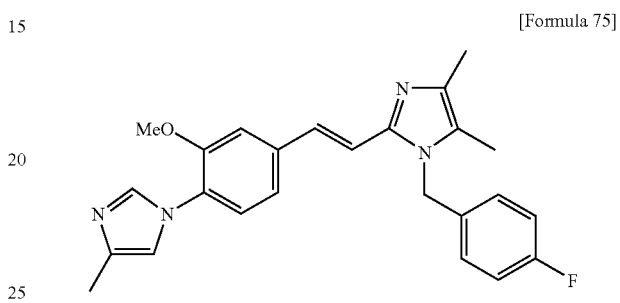

[Formula 75]

(1) Synthesis of 1-methyl-2-oxopropyl(E)-3-[3-methoxy-4-(4-methyl-1H-imidazol-1-yl)phenyl]acrylate IPEA (2.1 mL) was added to a solution of (E)-3-[3-methoxy-4-(4-methyl-1H-imidazol-1-yl)phenyl]acrylic acid (1 g) and 3-chloro-2-butanone (0.39 mL) in DMF (10 mL), and the reaction solution was stirred at room temperature for 19 hours. Ethyl acetate and water were added to the reaction solution, and the organic layer was separated. The resulting organic layer was dried over anhydrous magnesium sulfate and then concentrated under reduced pressure. The residue was purified by silica gel column chromatography (elution solvent: ethyl acetate→ethyl acetate:methanol=5:1) to obtain 1.3 g of the title compound.

The property values of the compound are as follows.
ESI-MS; m/z 329 [M$^+$+H]. $^1$H-NMR (CDCl$_3$) δ (ppm): 1.50 (d, J=7.2 Hz, 3H), 2.23 (s, 3H), 2.32 (s, 3H), 3.91 (s, 3H), 5.24 (q, J=7.2 Hz, 1H), 6.52 (d, J=16.4 Hz, 1H), 6.95 (brs, 1H), 7.18 (d, J=1.6 Hz, 1H), 7.22 (dd, J=8.0, 1.6 Hz, 1H), 7.28 (d, J=8.0 Hz, 1H), 7.72 (d, J=16.4 Hz, 1H), 7.79 (brs, 1H).

(2) Synthesis of 1-(4-fluorobenzyl)-2-{(E)-2-[3-methoxy-4-(4-methyl-1H-imidazol-1-yl)phenyl]vinyl]-4,5-dimethyl-1H-imidazole A solution of 1-methyl-2-oxopropyl(E)-3-[3-methoxy-4-(4-methyl-1H-imidazol-1-yl)phenyl]acrylate (1.31 g) and ammonium acetate (6.1 g) in acetic acid (10 mL) was stirred at 120° C. for six hours and further stirred at 150° C. for 12 hours. The reaction solution was left to cool to room temperature and concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. The residue was purified by silica gel column chromatography (carrier: Chromatorex™ NH; elution solvent: ethyl acetate→ethyl acetate:methanol=5:1) to obtain 256 mg of a crude product of 2-{(E)-2-[3-methoxy-4-(4-methyl-1H-imidazol-1-yl)phenyl]vinyl}-4,5-dimethyl-1H-imidazole. Sodium hydride (containing mineral oil at 60%, 33 mg) was added to a solution of the crude product in DMF (5 mL), and the reaction solution was stirred at room temperature for 20 minutes. 4-Fluorobenzyl bromide (0.1 mL) was added to the reaction solution, and the reaction solution was stirred at room temperature for one hour. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex™ NH; elution solvent: ethyl acetate→ethyl acetate:methanol=5:1) to obtain 49 mg of the title compound. The property values of the compound are as follows.

$^1$H-NMR (CDCl$_3$) δ (ppm): 2.09 (s, 3H), 2.26 (s, 3H), 2.28 (s, 3H), 3.83 (s, 3H), 5.13 (s, 2H), 6.76 (d, J=16.4 Hz, 1H), 6.88 (brs, 1H), 6.97-7.04 (m, 5H), 7.08 (dd, J=8.0, 1.6 Hz, 1H), 7.16 (d, J=8.0, 1H), 7.54 (d, J=16.4 Hz, 1H), 7.66 (d, J=1.2 Hz, 1H).

Example 30

Synthesis of 8-{1-[3-methoxy-4-(4-methyl-1H-imidazol-1-yl)phenyl]-(E)-methylidene}-2-pyridin-4-yl-5,6,7,8-tetrahydroimidazo[1,2-a]pyridine

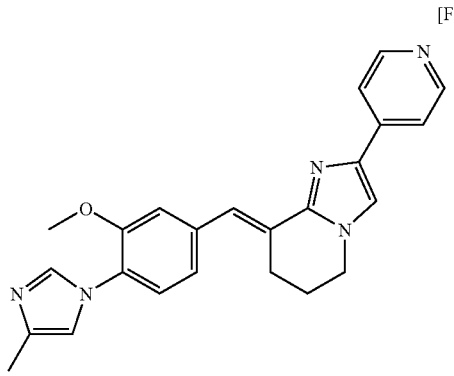

[Formula 76]

(1) Synthesis of 2,2-dimethoxy-2-pyridin-4-ylethyl 5-chloro-2-{1-[3-methoxy-4-(4-methyl-1H-imidazol-1-yl)phenyl]-(E)-methylidene}valerate EDC (1.28 g), HOBT (902 mg) and IPEA (2.33 mL) were sequentially added to a solution of 5-chloro-2-{1-[3-methoxy-4-(4-methylimidazol-1-yl)phenyl]-(E)-methylidene}valeric acid trifluoroacetic acid salt (1 g) and β,β-dimethoxy-4-pyridineethaneamine dihydrochloride (740 mg) as a known compound (CAS #167897-36-1) in DMF (15 mL), and the reaction solution was stirred at room temperature for 12 hours. Ethyl acetate and water were added to the reaction solution, and the organic layer was separated. The resulting organic layer was washed with brine and then dried over anhydrous sodium sulfate and concentrated under reduced pressure. The residue was purified by silica gel column chromatography (carrier: Chromatorex™ NH; elution solvent: heptane:ethyl acetate=1:2) to obtain 822 mg of the title compound. The property values of the compound are as follows.

$^1$H-NMR (CDCl$_3$) δ (ppm): 1.70-1.78 (m, 2H), 2.35 (s, 3H), 2.54-2.59 (m, 2H), 3.26 (s, 6H), 3.45-3.49 (m, 2H), 3.81-3.89 (m, 2H), 3.85 (s, 3H), 5.59 (m, 1H), 6.88-6.94 (m, 3H), 7.46 (dd, J=4.8, 2.0 Hz, 2H), 7.88 (s, 1H), 8.66 (dd, J=4.8, 2.0 Hz, 2H).

(2) Synthesis of 1-(2,2-dimethoxy-2-pyridin-4-ylethyl)-3-{1-[3-methoxy-4-(4-methyl-1H-imidazol-1-yl)phenyl]-(E)-methylidene}piperidin-2-one A solution of 2,2-dimethoxy-2-pyridin-4-ylethyl 5-chloro-2-{1-[3-methoxy-4-(4-methyl-1H-imidazol-1-yl)phenyl]-(E)-methylidene}valerate (800 mg) in DMF (8 mL) was cooled to 0° C. Sodium hydride (containing mineral oil at 60%, 96 mg) was added to the reaction solution, and the reaction solution was stirred at room temperature for one hour. Water and ethyl acetate were added to the reaction solution, and the organic layer was separated. The resulting organic layer was washed with brine, dried over anhydrous sodium sulfate, and then concentrated under reduced pressure. The residue was purified by silica gel column chromatography (carrier: Chromatorex™ NH, elution solvent: heptane:ethyl acetate=1:2) to obtain 586.9 mg of the title compound. The property values of the compound are as follows.

$^1$H-NMR (CDCl$_3$) δ (ppm): 1.63-1.67 (m, 2H), 2.31 (s, 3H), 2.61-2.65 (m, 2H), 3.14-3.18 (m, 2H), 3.29 (s, 6H), 3.83 (s, 3H), 4.00 (s, 2H), 6.90-6.96 (m, 3H), 7.21 (d, J=8.0 Hz, 1H), 7.45 (dd, J=4.8, 2.0 Hz, 2H), 7.54 (s, 1H), 7.74 (s, 1H), 8.60 (dd, J=4.8, 2.0 Hz, 2H).

(3) Synthesis of 3-{1-[3-methoxy-4-(4-methyl-1H-imidazol-1-yl)phenyl]-(E)-methylidene}-1-(2-oxo-2-pyridin-4-ylethyl)piperidin-2-one Concentrated hydrochloric acid (10 mL) was added to 1-(2,2-dimethoxy-2-pyridin-4-ylethyl)-3-{1-[3-methoxy-4-(4-methyl-1H-imidazol-1-yl)phenyl]-(E)-methylidene}piperidin-2-one (580 mg), and the mixture was stirred at 50° C. for four hours. After confirming that the raw materials disappeared, the reaction solution was concentrated under reduced pressure. Saturated sodium bicarbonate water and ethyl acetate were added to the resulting residue, and the organic layer was separated. The resulting organic layer was washed with brine, and then dried over anhydrous sodium sulfate and concentrated under reduced pressure. The residue was purified by silica gel column chromatography (carrier: Chromatorex™ NH, elution solvent: heptane:ethyl acetate=1:2) to obtain 346.2 mg of the title compound. The property values of the compound are as follows.

$^1$H-NMR (CDCl$_3$) δ (ppm): 1.98-2.05 (m, 2H), 2.34 (s, 3H), 2.88-2.93 (m, 2H), 3.52-3.56 (m, 2H), 3.87 (s, 3H), 4.91 (s, 2H), 6.95 (s, 1H), 7.02-7.06 (m, 2H), 7.27 (s, 1H), 7.77 (dd, J=4.8, 2.0 Hz, 2H), 7.79 (s, 1H), 7.84 (s, 1H), 8.84 (dd, J=4.8, 2.0 Hz, 2H).

(4) Synthesis of 8-{1-[3-methoxy-4-(4-methylimidazol-1-yl)phenyl]-(E)-methylidene}-2-pyridin-4-yl-5,6,7,8-tetrahydroimidazo[1,2-a]pyridine A solution of 3-{1-[3-methoxy-4-(4-methyl-1H-imidazol-1-yl)phenyl]-(E)-methylidene}-1-(2-oxo-2-pyridin-4-ylethyl)piperidin-2-one (150 mg) and ammonium acetate (555 mg) in acetic acid (2 mL) was stirred at 120° C. for five hours. The reaction solution was left to cool to room temperature and concentrated under reduced pressure. Ethyl acetate and saturated sodium bicarbonate water were added to the residue, and the organic layer was separated. The resulting organic layer was washed with brine, and then dried over anhydrous sodium sulfate and concentrated under reduced pressure. The residue was purified by silica gel column chromatography (carrier: Chromatorex™ NH; elution solvent: heptane-ethyl acetate system→ethyl acetate-2-propanol) to obtain 121.5 mg of the title compound. The property values of the compound are as follows.

ESI-MS; m/z 398 [M$^+$+H]. $^1$H-NMR (CDCl$_3$) δ (ppm): 2.02-2.17 (m, 2H), 2.33 (s, 3H), 2.95-2.99 (m, 2H), 3.88 (s, 3H), 4.13-4.17 (m, 2H), 6.95 (s, 1H), 7.08-7.11 (m, 2H), 7.25-7.28 (m, 1H), 7.39 (s, 1H), 7.71 (dd, J=4.8, 2.0 Hz, 2H), 7.78 (s, 1H), 7.80 (s, 1H), 8.59 (dd, J=4.8, 2.0 Hz, 2H).

Example 31

Synthesis of 3-[1-(4-fluorophenyl)ethyl]-5-{(E)-2-[3-methoxy-4-(4-methyl-1H-imidazol-1-yl)phenyl]vinyl}-4H-[1,2,4]triazole

[Formula 77]

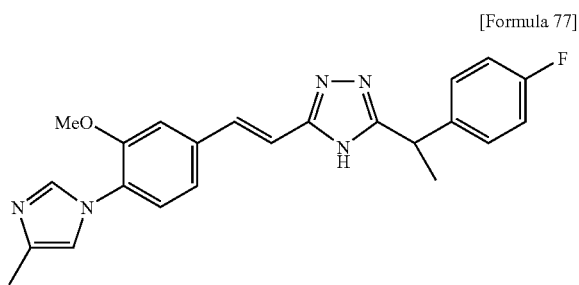

(1) Synthesis of 2-[1-(4-fluorophenyl)ethyl]-5-{(E)-2-[3-methoxy-4-(4-methyl-1H-imidazol-1-yl)phenyl]vinyl}-[1,3,4]oxadiazole 23 mg of the title compound was obtained from (E)-3-[3-methoxy-4-(4-methyl-1H-imidazol-1-yl)phenyl]acrylic acid hydrazide dihydrochloride (100 mg) and 4-fluoro-α-methylphenylacetic acid (33 mg) by the same method as in Example 16. The property value of the compound is as follows.

ESI-MS; m/z 405 [M$^+$+H].

(2) Synthesis of 3-[1-(4-fluorophenyl)ethyl]-5-{(E)-2-[3-methoxy-4-(4-methyl-1H-imidazol-1-yl)phenyl]vinyl}-4H-[1,2,4]triazole A solution of 2-[1-(4-fluorophenyl)ethyl]-5-{(E)-2-[3-methoxy-4-(4-methyl-1H-imidazol-1-yl)phenyl]vinyl}-[1,3,4]oxadiazole (23 mg) and ammonium acetate (88 mg) in acetic acid (1 mL) was stirred at 150° C. for 10 hours. The reaction solution was left to cool to room temperature and concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. The residue was purified by silica gel column chromatography (elution solvent: ethyl acetate→ethyl acetate:methanol=5:1) to obtain 8 mg of the title compound. The property values of the compound are as follows.

ESI-MS; m/z 404 [M$^+$+H]. $^1$H-NMR (CDCl$_3$) δ (ppm): 1.77 (d, J=7.2 Hz, 3H), 2.29 (s, 3H), 3.87 (s, 3H), 4.31 (q, J=7.2 Hz, 1H), 6.92 (brs, 1H), 7.01 (t, J=8.8 Hz, 2H), 7.05 (d, J=16.0 Hz, 1H), 7.15 (brd, J=8.0 Hz, 1H), 7.16 (brs, 1H), 7.22 (d, J=8.0 Hz, 1H), 7.29 (dd, J=8.8, 4.8 Hz, 2H), 7.56 (d, J=16.0 Hz, 1H), 7.71 (brs, 1H).

Example 32

Synthesis of 3-[2-(4-fluorophenyl)ethyl]-5-{(E)-2-[3-methoxy-4-(4-methyl-1H-imidazol-1-yl)phenyl]vinyl}-4H-[1,2,4]triazole

[Formula 78]

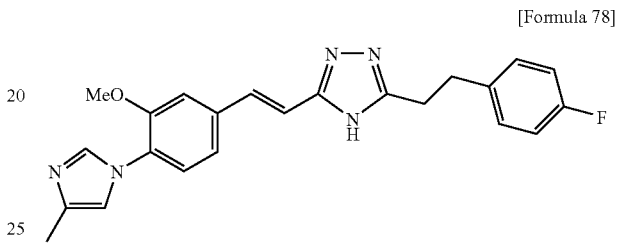

(1) Synthesis of 2-[2-(4-fluorophenyl)ethyl]-5-{(E)-2-[3-methoxy-4-(4-methyl-1H-imidazol-1-yl)phenyl]vinyl}-[1,3,4]oxadiazole 33 mg of the title compound was obtained from (E)-3-[3-methoxy-4-(4-methyl-1H-imidazol-1-yl)phenyl]acrylic acid hydrazide dihydrochloride (100 mg) and 3-(4-fluorophenyl)propionic acid (33 mg) by the same method as in Example 16. The property value of the compound is as follows.

ESI-MS; m/z 405 [M$^+$+H].

(2) Synthesis of 3-[2-(4-fluorophenyl)ethyl]-5-{(E)-2-[3-methoxy-4-(4-methyl-1H-imidazol-1-yl)phenyl]vinyl}-4H-[1,2,4]triazole A solution of 2-[2-(4-fluorophenyl)ethyl]-5-{(E)-2-[3-methoxy-4-(4-methyl-1H-imidazol-1-yl)phenyl]vinyl}-[1,3,4]oxadiazole (33 mg) and ammonium acetate (126 mg) in acetic acid (1 mL) was stirred at 150° C. for 10 hours. The reaction solution was left to cool to room temperature and concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. The residue was purified by silica gel column chromatography (elution solvent: ethyl acetate→ethyl acetate:methanol=5:1) to obtain 8 mg of the title compound. The property values of the compound are as follows.

ESI-MS; m/z 404 [M$^+$+H]. $^1$H-NMR (CDCl$_3$) δ (ppm): 2.31 (s, 3H), 3.11 (s, 4H), 3.88 (s, 3H), 6.94 (brs, 1H), 6.96 (t, J=8.8 Hz, 2H), 7.07 (d, J=16.0 Hz, 1H), 7.13 (dd, J=8.8, 5.6 Hz, 2H), 7.17 (brd, J=8.8 Hz, 1H), 7.18 (brs, 1H), 7.23 (d, J=8.8 Hz, 1H), 7.57 (d, J=16.0 Hz, 1H), 7.74 (brs, 1H).

Example 33

Synthesis of 4-(4-fluorobenzyl)-2-{(E)-2-[3-methoxy-4-(4-methyl-1H-imidazol-1-yl)phenyl]vinyl}-1H-imidazole

[Formula 79]

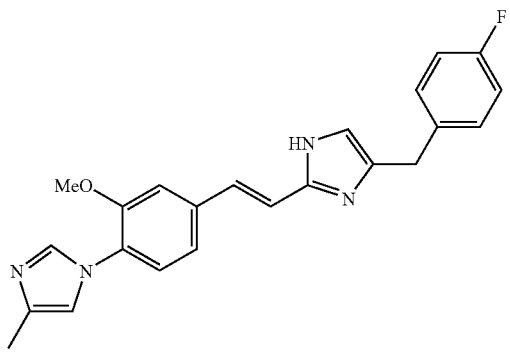

(1) Synthesis of (E)-N-[3-(4-fluorophenyl)-2-oxopropyl]-3-[3-methoxy-4-(4-methyl-1H-imidazol-1-yl)phenyl]acrylamide Diethyl cyanophosphonate (0.12 mL) was added to a solution of (E)-3-[3-methoxy-4-(4-methyl-1H-imidazol-1-yl)phenyl]acrylic acid (200 mg) and triethylamine (0.54 mL) in DMF (2 mL), and the reaction solution was stirred at 0° C. for 30 minutes. A solution of 1-amino-3-(4-fluorophenyl)propan-2-one hydrochloride (CAS #93102-98-8, 158 mg) in DMF (1 mL) was added dropwise to the reaction solution over 20 minutes, and the reaction solution was stirred at 0° C. for 1.5 hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex™ NH; elution solvent: ethyl acetate→ethyl acetate:methanol=5:1) to obtain 43 mg of the title compound. The property values of the compound are as follows.

ESI-MS; m/z 408 [M++H]. $^1$H-NMR (CDCl$_3$) δ (ppm): 2.30 (s, 3H), 3.77 (s, 2H), 3.89 (s, 3H), 4.34 (d, J=4.4 Hz, 2H), 6.35 (brt, J=4.4 Hz, 1H), 6.46 (d, J=15.6 Hz, 1H), 6.92 (brs, 1H), 7.05 (t, J=8.4 Hz, 2H), 7.13 (brs, 1H), 7.15-7.26 (m, 4H), 7.60 (d, J=15.6 Hz, 1H), 7.71 (brs, 1H).

(2) Synthesis of 4-(4-fluorobenzyl)-2-{(E)-2-[3-methoxy-4-(4-methyl-1H-imidazol-1-yl)phenyl]vinyl}-1H-imidazole A solution of (E)-N-[3-(4-fluorophenyl)-2-oxopropyl]-3-[3-methoxy-4-(4-methyl-1H-imidazol-1-yl)phenyl]acrylamide (43 mg) and ammonium acetate (163 mg) in acetic acid (1 mL) and xylene (5 mL) was heated under reflux for 16 hours. The reaction solution was left to cool to room temperature. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex™ NH; elution solvent: ethyl acetate→ethyl acetate:methanol=5:1) to obtain 13 mg of the title compound. The property values of the compound are as follows.

ESI-MS; m/z 389 [M++H]. $^1$H-NMR (CDCl$_3$) δ (ppm): 2.28 (s, 3H), 3.80 (s, 3H), 3.96 (s, 2H), 6.75 (brs, 1H), 6.90 (brs, 1H), 6.94 (d, J=16.4 Hz, 1H), 6.96 (t, J=8.8 Hz, 2H), 7.01 (dd, J=8.0, 1.6 Hz, 1H), 7.04 (d, J=1.6 Hz, 1H), 7.15 (d, J=8.8 Hz, 1H), 7.18-7.24 (m, 3H), 7.66 (s, 1H).

Examples 34 and 35

Synthesis of 5-(4-fluorobenzyl)-3-{(E)-2-[3-methoxy-4-(4-methyl-1H-imidazol-1-yl)phenyl]vinyl}-1-methyl-1H-[1,2,4]triazole and 3-(4-fluorobenzyl)-5-{(E)-2-[3-methoxy-4-(4-methyl-1H-imidazol-1-yl)phenyl]vinyl}-1-methyl-1H-[1,2,4]triazole

[Formula 80]

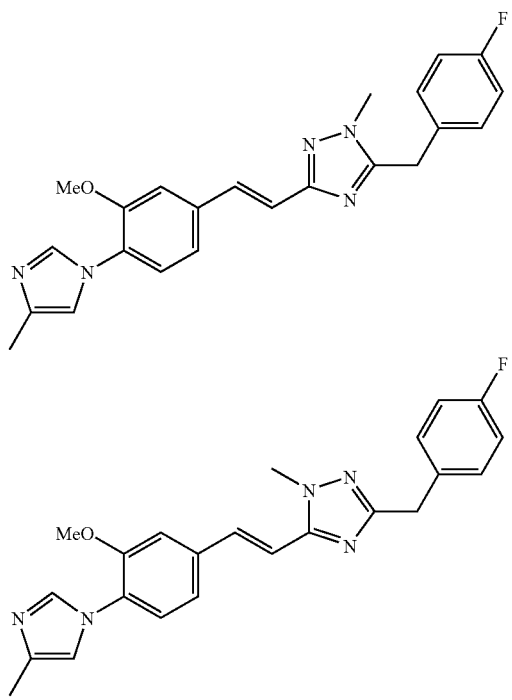

Sodium hydrate (containing mineral oil at 60%, 6 mg) was added to a solution of 3-(4-fluorobenzyl)-5-{(E)-2-[3-methoxy-4-(4-methyl-1H-imidazol-1-yl)phenyl]vinyl}-4H-[1,2,4]triazole (18 mg) in THF (1 mL), and the reaction solution was stirred at room temperature for 30 minutes. Iodomethane (20 mg) was added to the reaction solution, and the reaction solution was then stirred at room temperature for 1.5 hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: ethyl acetate:ethanol=9:1) to obtain 6 mg of 5-(4-fluorobenzyl)-3-{(E)-2-[3-methoxy-4-(4-methyl-1H-imidazol-1-yl)phenyl]vinyl}-1-methyl-1H-[1,2,4]triazole and 2 mg of 3-(4-fluorobenzyl)-5-{(E)-2-[3-methoxy-4-(4-methyl-1H-imidazol-1-yl)phenyl]vinyl}-1-methyl-1H-[1,2,4]triazole.

The property values of 5-(4-fluorobenzyl)-3-{(E)-2-[3-methoxy-4-(4-methyl-1H-imidazol-1-yl)phenyl]vinyl}-1-methyl-1H-[1,2,4]triazole are as follows.

¹H-NMR (CDCl₃) δ (ppm): 2.30 (s, 3H), 3.72 (s, 3H), 3.88 (s, 3H), 4.16 (s, 2H), 6.92 (brs, 1H), 7.02 (t, J=8.4 Hz, 2H), 7.04 (d, J=16.0 Hz, 1H), 7.15-7.26 (m, 5H), 7.53 (d, J=16.0 Hz, 1H), 7.71 (brs, 1H).

The property values of 3-(4-fluorobenzyl)-5-{(E)-2-[3-methoxy-4-(4-methyl-1H-imidazol-1-yl)phenyl]vinyl}-1-methyl-1H-[1,2,4]triazole are as follows.

¹H-NMR (CDCl₃) δ (ppm): 2.31 (s, 3H), 3.90 (s, 3H), 3.92 (s, 3H), 4.04 (s, 2H), 6.85 (d, J=15.6 Hz, 1H), 6.93 (brs, 1H), 6.98 (t, J=8.4 Hz, 2H), 7.14 (d, J=1.6 Hz, 1H), 7.22 (dd, J=8.4, 1.6 Hz, 1H), 7.26 (d, J=8.4 Hz, 1H), 7.32 (dd, J=8.4, 5.6 Hz, 2H), 7.65 (d, J=15.6 Hz, 1H), 7.74 (brs, 1H).

Examples 36 and 37

Synthesis of (+)-3-[1-(4-fluorophenyl)ethyl]-5-{(E)-2-[3-methoxy-4-(4-methyl-1H-imidazol-1-yl)phenyl]vinyl}-4H-[1,2,4]triazole and (−)-3-[1-(4-fluorophenyl)ethyl]-5-{(E)-2-[3-methoxy-4-(4-methyl-1H-imidazol-1-yl)phenyl]vinyl}-4H-[1,2,4]triazole The property values of the title optically active compound with a retention time of 11 minutes (Example 36) are as follows.

¹H-NMR (CDCl₃) δ (ppm): 1.77 (d, J=7.2 Hz, 3H), 2.29 (s, 3H), 3.87 (s, 3H), 4.31 (q, J=7.2 Hz, 1H), 6.92 (brs, 1H), 7.01 (t, J=8.8 Hz, 2H), 7.05 (d, J=16.0 Hz, 1H), 7.15 (brd, J=8.0 Hz, 1H), 7.16 (brs, 1H), 7.22 (d, J=8.0 Hz, 1H), 7.29 (dd, J=8.8, 4.8 Hz, 2H), 7.56 (d, J=16.0 Hz, 1H), 7.71 (brs, 1H).

The property values of the title optically active compound with a retention time of 14 minutes (Example 37) are as follows.

¹H-NMR (CDCl₃) δ (ppm): 1.77 (d, J=7.2 Hz, 3H), 2.29 (s, 3H), 3.87 (s, 3H), 4.31 (q, J=7.2 Hz, 1H), 6.92 (brs, 1H), 7.01 (t, J=8.8 Hz, 2H), 7.05 (d, J=16.0 Hz, 1H), 7.15 (brd, J=8.0 Hz, 1H), 7.16 (brs, 1H), 7.22 (d, J=8.0 Hz, 1H), 7.29 (dd, J=8.8, 4.8 Hz, 2H), 7.56 (d, J=16.0 Hz, 1H), 7.71 (brs, 1H).

Examples 38 and 39

Synthesis of 5-[1-(4-fluorophenyl)ethyl]-3-{(E)-2-[3-methoxy-4-(4-methyl-1H-imidazol-1-yl)phenyl]vinyl}-1-methyl-1H-[1,2,4]triazole and 3-[1-(4-fluorophenyl)ethyl]-5-{(E)-2-[3-methoxy-4-(4-methyl-1H-imidazol-1-yl)phenyl]vinyl}-1-methyl-1H-[1,2,4]triazole

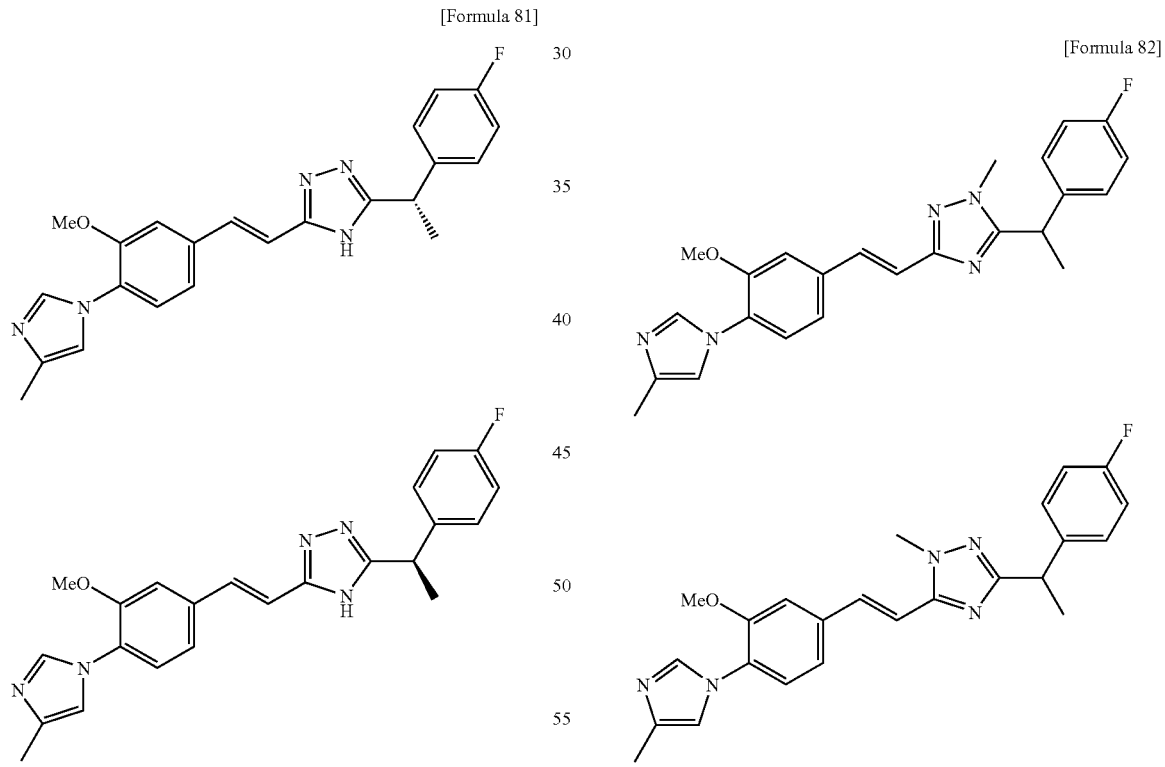

[Formula 81]

[Formula 82]

The racemate synthesized by the method in Example 31, 3-[1-(4-fluorophenyl)ethyl]-5-{(E)-2-[3-methoxy-4-(4-methyl-1H-imidazol-1-yl)phenyl]vinyl}-4H-[1,2,4]triazole (72 mg), was separated by CHIRALCEL™ OD-H manufactured by Daicel Chemical Industries, Ltd. (2 cm×25 cm; mobile phase: hexane:ethanol=8:2) to obtain the title optically active compound with a retention time of 11 minutes (25 mg, >99% ee) and the title optically active compound with a retention time of 14 minutes (26 mg, >99% ee).

4 mg of 5-[1-(4-fluorophenyl)ethyl]-3-{(E)-2-[3-methoxy-4-(4-methyl-1H-imidazol-1-yl)phenyl]vinyl}-1-methyl-1H-[1,2,4]triazole and 2 mg of 3-[1-(4-fluorophenyl)ethyl]-5-{(E)-2-[3-methoxy-4-(4-methyl-1H-imidazol-1-yl)phenyl]vinyl}-1-methyl-1H-[1,2,4]triazole were obtained by the same method as in Examples 34 and 35 from (+)-3-[1-(4-fluorophenyl)ethyl]-5-{(E)-2-[3-methoxy-4-(4-methyl-1H-imidazol-1-yl)phenyl]vinyl}-4H-[1,2,4]triazole (25 mg) obtained in Example 36.

The property values of 5-[1-(4-fluorophenyl)ethyl]-3-{(E)-2-[3-methoxy-4-(4-methyl-1H-imidazol-1-yl)phenyl]vinyl}-1-methyl-1H-[1,2,4]triazole are as follows.

ESI-MS; m/z 418 [M$^+$+H]. $^1$H-NMR (CDCl$_3$) δ (ppm): 1.76 (d, J=7.6 Hz, 3H), 2.30 (s, 3H), 3.61 (s, 3H), 3.88 (s, 3H), 4.20 (q, J=7.6 Hz, 1H), 6.93 (brs, 1H), 7.01 (t, J=8.8 Hz, 2H), 7.07 (d, J=16.4 Hz, 1H), 7.16-7.21 (m, 4H), 7.23 (d, J=8.0 Hz, 1H), 7.57 (d, J=16.4 Hz, 1H), 7.71 (brs, 1H).

The property values of 3-[1-(4-fluorophenyl)ethyl]-5-{(E)-2-[3-methoxy-4-(4-methyl-1H-imidazol-1-yl)phenyl]vinyl}-1-methyl-1H-[1,2,4]triazole are as follows.

$^1$H-NMR (CDCl$_3$) δ (ppm): 1.70 (d, J=7.6 Hz, 3H), 2.30 (s, 3H), 3.89 (s, 3H), 3.92 (s, 3H), 4.25 (q, J=7.6 Hz, 1H), 6.85 (d, J=15.6 Hz, 1H), 6.93 (brs, 1H), 6.98 (t, J=8.8 Hz, 2H), 7.13 (d, J=1.6 Hz, 1H), 7.21 (dd, J=8.0, 1.6 Hz, 1H), 7.25 (d, J=8.0 Hz, 1H), 7.32-7.37 (m, 2H), 7.64 (d, J=15.6 Hz, 1H), 7.72 (brs, 1H).

The property values of 5-[1-(4-fluorophenyl)ethyl]-3-{(E)-2-[3-methoxy-4-(4-methyl-1H-imidazol-1-yl)phenyl]vinyl}-1-methyl-1H-[1,2,4]triazole are as follows.

$^1$H-NMR (CDCl$_3$) δ (ppm): 1.76 (d, J=7.6 Hz, 3H), 2.30 (s, 3H), 3.61 (s, 3H), 3.88 (s, 3H), 4.20 (q, J=7.6 Hz, 1H), 6.93 (brs, 1H), 7.01 (t, J=8.8 Hz, 2H), 7.07 (d, J=16.4 Hz, 1H), 7.16-7.21 (m, 4H), 7.23 (d, J=8.0 Hz, 1H), 7.57 (d, J=16.4 Hz, 1H), 7.71 (brs, 1H).

The property values of 3-[1-(4-fluorophenyl)ethyl]-5-{(E)-2-[3-methoxy-4-(4-methyl-1H-imidazol-1-yl)phenyl]vinyl}-1-methyl-1H-[1,2,4]triazole are as follows.

$^1$H-NMR (CDCl$_3$) δ (ppm): 1.70 (d, J=7.6 Hz, 3H), 2.30 (s, 3H), 3.89 (s, 3H), 3.92 (s, 3H), 4.25 (q, J=7.6 Hz, 1H), 6.85 (d, J=15.6 Hz, 1H), 6.93 (brs, 1H), 6.98 (t, J=8.8 Hz, 2H), 7.13 (d, J=1.6 Hz, 1H), 7.21 (dd, J=8.0, 1.6 Hz, 1H), 7.25 (d, J=8.0 Hz, 1H), 7.32-7.37 (m, 2H), 7.64 (d, J=15.6 Hz, 1H), 7.72 (brs, 1H).

Examples 40 and 41

Synthesis of 5-[1-(4-fluorophenyl)ethyl]-3-{(E)-2-[3-methoxy-4-(4-methyl-1H-imidazol-1-yl)phenyl]vinyl}-1-methyl-1H-[1,2,4]triazole and 3-[1-(4-fluorophenyl)ethyl]-5-{(E)-2-[3-methoxy-4-(4-methyl-1H-imidazol-1-yl)phenyl]vinyl}-1-methyl-1H-[1,2,4]triazole Examples 42 and 43

Synthesis of (+)-3-[1-(4-fluorophenyl)ethyl]-5-{(E)-2-[3-methoxy-4-(4-methyl-1H-imidazol-1-yl)phenyl]vinyl}-4-methyl-4H-[1,2,4]triazole and (−)-3-[1-(4-fluorophenyl)ethyl]-5-{(E)-2-[3-methoxy-4-(4-methyl-1H-imidazol-1-yl)phenyl]vinyl}-4-methyl-4H-[1,2,4]triazole

[Formula 83]

[Formula 84]

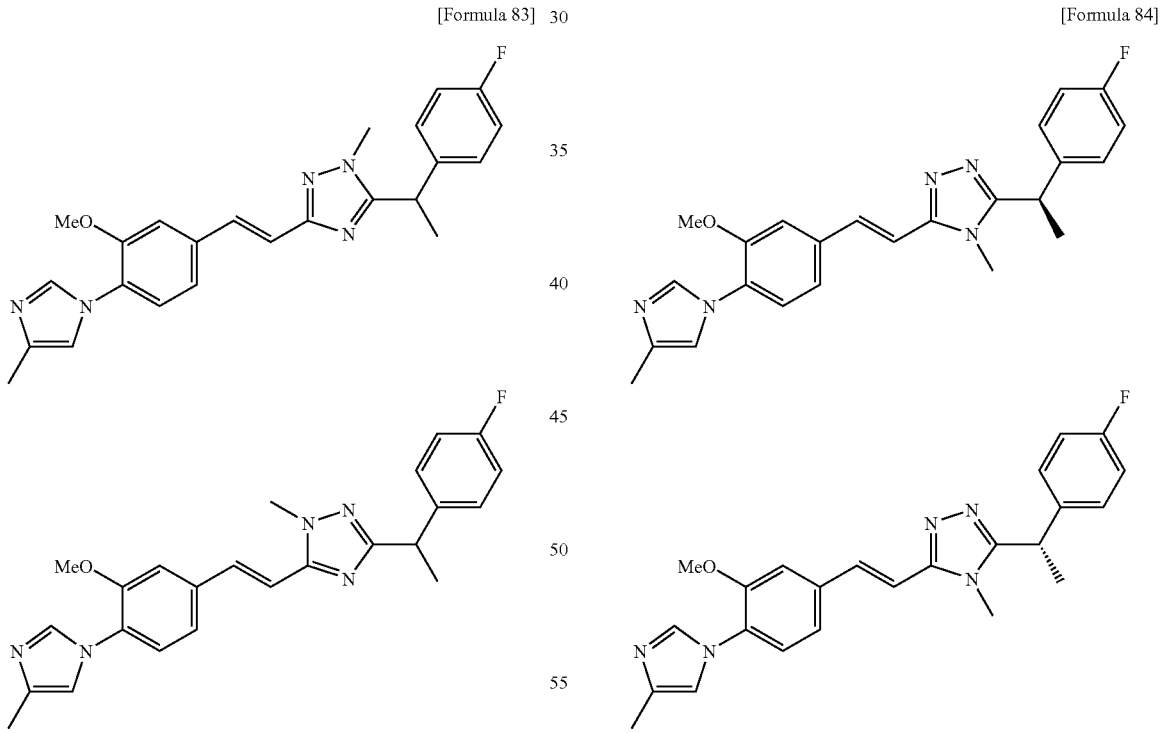

6 mg of 5-[1-(4-fluorophenyl)ethyl]-3-{(E)-2-[3-methoxy-4-(4-methyl-1H-imidazol-1-yl)phenyl]vinyl}-1-methyl-1H-[1,2,4]triazole and 2 mg of 3-[1-(4-fluorophenyl)ethyl]-5-{(E)-2-[3-methoxy-4-(4-methyl-1H-imidazol-1-yl)phenyl]vinyl}-1-methyl-1H-[1,2,4]triazole were obtained by the same method as in Examples 34 and 35 from (−)-3-[1-(4-fluorophenyl)ethyl]-5-{(E)-2-[3-methoxy-4-(4-methyl-1H-imidazol-1-yl)phenyl]vinyl}-4H-[1,2,4]triazole (26 mg) obtained in Example 37.

A solution of 40% methylamine in acetic acid (1 mL) was added to a solution of 2-[1-(4-fluorophenyl)ethyl]-5-{(E)-2-[3-methoxy-4-(4-methyl-1H-imidazol-1-yl)phenyl]vinyl}-[1,3,4]oxadiazole (85 mg) synthesized by the method in Example 31 in xylene (20 mL), and the reaction solution was heated under reflux for 12 hours while azeotropic removing water by a Dean-Stark apparatus. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by LC-MS to obtain a trifluoroacetate of a racemate of the title compound. The resulting trifluoroacetate of the racemate of the title compound was diluted with ethyl acetate. Saturated sodium bicarbonate water was added to the solution, and the organic layer was separated. The resulting organic layer was dried over anhydrous magnesium sulfate and then concentrated under reduced pressure. The residue was separated by CHIRALCEL™ OD-H manufactured by Daicel Chemical Industries, Ltd. (2 cm×25 cm; mobile phase: hexane:ethanol=8:2) to obtain the title optically active compound with a retention time of 13 minutes (13 mg, >99% ee) and the title optically active compound with a retention time of 19 minutes (11 mg, >99% ee).

The property values of (+)-3-[1-(4-fluorophenyl)ethyl]-5-{(E)-2-[3-methoxy-4-(4-methyl-1H-imidazol-1-yl)phenyl]vinyl}-4-methyl-4H-[1,2,4]triazole are as follows.

ESI-MS; m/z 418 [M$^+$+H]. $^1$H-NMR (CDCl$_3$) δ (ppm): 1.83 (d, J=7.2 Hz, 3H), 2.30 (s, 3H), 3.36 (s, 3H), 3.89 (s, 3H), 4.16 (q, J=7.2 Hz, 1H), 6.77 (d, J=16.0 Hz, 1H), 6.92 (brs, 1H), 7.00 (t, J=8.4 Hz, 2H), 7.13 (d, J=1.6 Hz, 1H), 7.14-7.26 (m, 4H), 7.71 (d, J=16.0 Hz, 1H), 7.72 (brs, 1H).

The property values of (−)-3-[1-(4-fluorophenyl)ethyl]-5-{(E)-2-[3-methoxy-4-(4-methyl-1H-imidazol-1-yl)phenyl]vinyl}-4-methyl-4H-[1,2,4]triazole are as follows.

ESI-MS; m/z 418 [M$^+$+H]. $^1$H-NMR (CDCl$_3$) δ (ppm): 1.83 (d, J=7.2 Hz, 3H), 2.30 (s, 3H), 3.36 (s, 3H), 3.89 (s, 3H), 4.16 (q, J=7.2 Hz, 1H), 6.77 (d, J=16.0 Hz, 1H), 6.92 (brs, 1H), 7.00 (t, J=8.4 Hz, 2H), 7.13 (d, J=1.6 Hz, 1H), 7.14-7.26 (m, 4H), 7.71 (d, J=16.0 Hz, 1H), 7.72 (brs, 1H).

Example 44

Synthesis of 3-{(E)-2-[3-methoxy-4-(4-methyl-1H-imidazol-1-yl)phenyl]vinyl}-5-(1-phenylethyl)-4H-[1,2,4]triazole

[Formula 85]

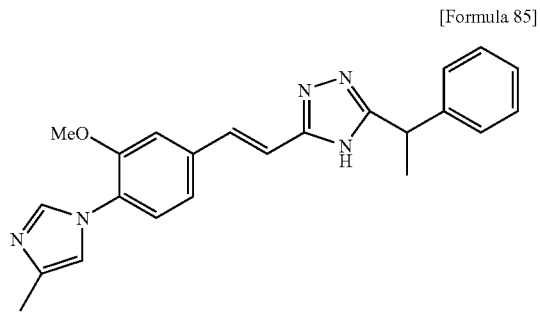

80 mg of the title compound was obtained from (E)-3-[3-methoxy-4-(4-methyl-1H-imidazol-1-yl)phenyl]acrylic acid hydrazide dihydrochloride (200 mg) and 2-phenylpropionic acid (87 mg) by the same method as in Example 16. The property values of the compound are as follows.

$^1$H-NMR (CDCl$_3$) δ (ppm): 1.80 (d, J=7.2 Hz, 3H), 2.29 (s, 3H), 3.87 (s, 3H), 4.32 (q, J=7.2 Hz, 1H), 6.92 (brs, 1H), 7.08 (d, J=16.0 Hz, 1H), 7.17 (brd, J=7.6 Hz, 1H), 7.18 (brs, 1H), 7.22 (d, J=7.6 Hz, 1H), 7.28-7.39 (m, 5H), 7.57 (d, J=16.0 Hz, 1H), 7.69 (d, J=0.8 Hz, 1H).

Examples 45 and 46

Synthesis of 3-{(E)-2-[3-methoxy-4-(4-methyl-1H-imidazol-1-yl)phenyl]vinyl}-1-methyl-5-(1-phenylethyl)-1H-[1,2,4]triazole and 5-{(E)-2-[3-methoxy-4-(4-methyl-1H-imidazol-1-yl)phenyl]vinyl}-1-methyl-3-(1-phenylethyl)-1H-[1,2,4]triazole

[Formula 86]

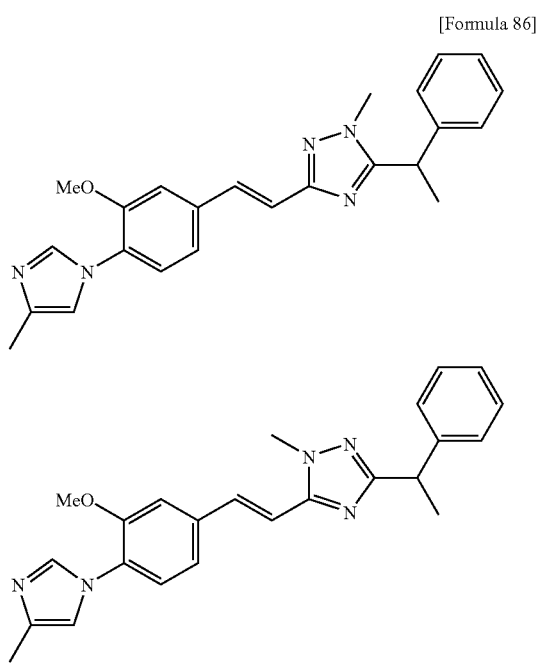

5 mg of 3-{(E)-2-[3-methoxy-4-(4-methyl-1H-imidazol-1-yl)phenyl]vinyl}-1-methyl-5-(1-phenylethyl)-1H-[1,2,4]triazole and 10 mg of 5-{(E)-2-[3-methoxy-4-(4-methyl-1H-imidazol-1-yl)phenyl]vinyl}-1-methyl-3-(1-phenylethyl)-1H-[1,2,4]triazole were obtained by the same method as in Examples 34 and 35 from 3-{(E)-2-[3-methoxy-4-(4-methyl-1H-imidazol-1-yl)phenyl]vinyl}-5-(1-phenylethyl)-4H-[1,2,4]triazole (80 mg) obtained in Example 44.

The property values of 3-{(E)-2-[3-methoxy-4-(4-methyl-1H-imidazol-1-yl)phenyl]vinyl}-1-methyl-5-(1-phenylethyl)-1H-[1,2,4]triazole are as follows.

$^1$H-NMR (CDCl$_3$) δ (ppm): 1.79 (d, J=7.2 Hz, 3H), 2.30 (s, 3H), 3.59 (s, 3H), 3.88 (s, 3H), 4.20 (q, J=7.2 Hz, 1H), 6.92 (brs, 1H), 7.08 (d, J=16.0 Hz, 1H), 7.16-7.23 (m, 5H), 7.23-7.27 (m, 1H), 7.32 (t, J=6.8 Hz, 2H), 7.58 (d, J=16.0 Hz, 1H), 7.70 (d, J=0.8 Hz, 1H).

The property values of 5-{(E)-2-[3-methoxy-4-(4-methyl-1H-imidazol-1-yl)phenyl]vinyl}-1-methyl-3-(1-phenylethyl)-1H-[1,2,4]triazole are as follows.

$^1$H-NMR (CDCl$_3$) δ (ppm): 1.72 (d, J=7.2 Hz, 3H), 2.30 (s, 3H), 3.90 (s, 3H), 3.93 (s, 3H), 4.27 (q, J=7.2 Hz, 1H), 6.86 (d, J=16.0 Hz, 1H), 6.94 (brs, 1H), 7.15 (d, J=1.6 Hz, 1H), 7.18-7.28 (m, 3H), 7.31 (t, J=7.6 Hz, 2H), 7.40 (dd, J=7.6, 0.8 Hz, 2H), 7.65 (d, J=16.0 Hz, 1H), 7.73 (brs, 1H).

Example 47

Synthesis of 3-(4-fluorophenyl)-5-{(E)-2-[3-methoxy-4-(4-methyl-1H-imidazol-1-yl)phenyl]vinyl}-4H-[1,2,4]triazole

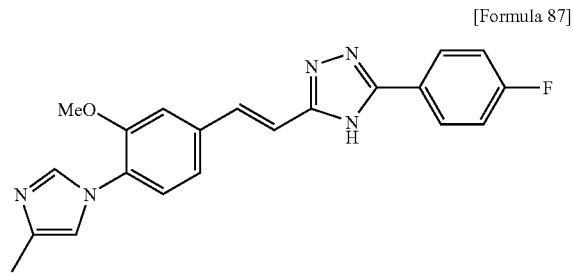

[Formula 87]

7 mg of the title compound was obtained from (E)-3-[3-methoxy-4-(4-methyl-1H-imidazol-1-yl)phenyl]acrylic acid hydrazide dihydrochloride (58 mg) and 4-fluorobenzoic acid (35 mg) by the same method as in Example 16. The property values of the compound are as follows.

ESI-MS; m/z 376 [M$^+$+H]. $^1$H-NMR (CD$_3$OD) δ (ppm): 2.28 (s, 3H), 3.95 (s, 3H), 6.98 (brs, 1H), 7.10 (d, J=16.0 Hz, 1H), 7.16-7.23 (m, 2H), 7.27 (brd, J=8.0 Hz, 1H), 7.30 (brs, 1H), 7.31 (d, J=8.0 Hz, 1H), 7.64 (d, J=16.0 Hz, 1H), 7.74 (d, J=1.2 Hz, 1H), 8.02-8.08 (m, 2H).

Example 48

Synthesis of 5-(4-fluorophenyl)-2-{(E)-2-[3-methoxy-4-(4-methyl-1H-imidazol-1-yl)phenyl]vinyl}-4-methyl-1H-imidazole

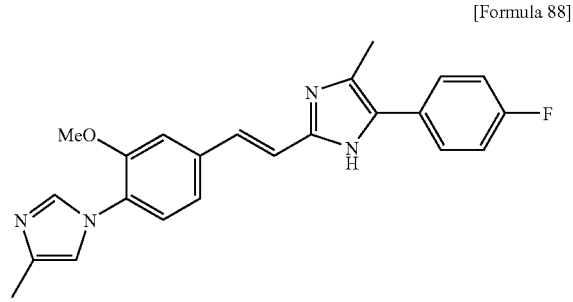

[Formula 88]

16 mg of the title compound was obtained from (E)-3-[3-methoxy-4-(4-methyl-1H-imidazol-1-yl)phenyl]acrylic acid (100 mg) and α-bromopropiophenone (98 mg) by the same method as in Example 6. The property values of the compound are as follows.

$^1$H-NMR (CDCl$_3$) δ (ppm): 2.29 (s, 3H), 2.50 (s, 3H), 3.79 (s, 3H), 6.91 (brs, 1H), 6.99 (d, J=16.4 Hz, 1H), 7.00 (dd, J=8.0, 2.0 Hz, 1H), 7.05 (d, J=2.0 Hz, 1H), 7.14 (d, J=8.0 Hz, 1H), 7.25 (d, J=16.4 Hz, 1H), 7.25-7.30 (m, 1H), 7.41 (t, J=7.2 Hz, 2H), 7.59-7.66 (m, 2H), 7.68 (d, J=1.2 Hz, 1H).

Example 49

Synthesis of 3-{(E)-2-[3-methoxy-4-(4-methyl-1H-imidazol-1-yl)phenyl]vinyl}-5-(1-methyl-1-phenylethyl)-4H-[1,2,4]triazole

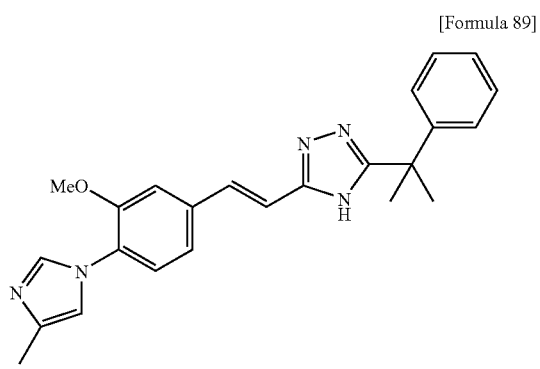

[Formula 89]

16 mg of the title compound was obtained from (E)-3-[3-methoxy-4-(4-methyl-1H-imidazol-1-yl)phenyl]acrylic acid (66 mg) and α,α-dimethylphenylacetic acid (47 mg) by the same method as in Example 16. The property values of the compound are as follows.

ESI-MS; m/z 400 [M$^+$+H]. $^1$H-NMR (CDCl$_3$) δ (ppm): 1.85 (s, 6H), 2.29 (s, 3H), 3.88 (s, 3H), 6.92 (brs, 1H), 7.10 (d, J=16.0 Hz, 1H), 7.14 (dd, J=8.0, 2.4 Hz, 1H), 7.19 (d, J=2.4 Hz, 1H), 7.22 (d, J=8.0 Hz, 1H), 7.25-7.28 (m, 1H), 7.32-7.36 (m, 4H), 7.58 (d, J=16.0 Hz, 1H), 7.66 (d, J=1.2 Hz, 1H).

Example 50

Synthesis of 3-{(E)-2-[3-methoxy-4-(4-methyl-1H-imidazol-1-yl)phenyl]vinyl}-1-phenyl-5,6,7,8-tetrahydroimidazo[1,5-a]pyridine

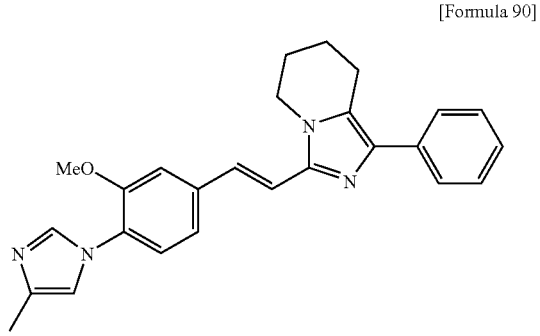

[Formula 90]

Synthesis of (E)-1-[2-(hydroxyphenylmethyl)piperidin-1-yl]-3-[3-methoxy-4-(4-methyl-1H-imidazol-1-yl)phenyl]propenone IPEA (0.2 mL), HOBT (78 mg) and EDC (111 mg) were added to a solution of (E)-3-[3-methoxy-4-(4-methyl-1H-imidazol-1-yl)phenyl]acrylic acid (100 mg) and phenylpiperidin-2-ylmethanol (CAS No. 23702-98-9, 74 mg) in DMF (3 mL), and the reaction solution was stirred at room temperature for 14 hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: ethyl acetate→ethyl acetate:methanol=5:1) to obtain 126 mg of the title compound. The property values of the compound are as follows.

ESI-MS; m/z 432 [M$^+$+H].

Synthesis of (E)-1-[2-benzoylpiperidin-1-yl]-3-[3-methoxy-4-(4-methyl-1H-imidazol-1-yl)phenyl]propenone Dess-Martin periodinane (248 mg) was added to a solution of (E)-1-[2-(hydroxyphenylmethyl)piperidin-1-yl]-3-[3-methoxy-4-(4-methyl-1H-imidazol-1-yl)phenyl]propenone (126 mg) in chloroform (5 mL), and the reaction solution was stirred at room temperature for one hour. The reaction solution was purified as is by silica gel column chromatography (elution solvent: ethyl acetate:heptane=1:1→ethyl acetate→ethyl acetate:methanol=9:1) to obtain 90 mg of the title compound. The property values of the compound are as follows.

$^1$H-NMR (CDCl$_3$) δ (ppm): 1.50-1.92 (m, 5H), 2.21-2.30 (m, 1H), 2.30 (s, 3H), 3.49-3.58 (m, 1H), 3.90 (s, 3H), 3.97-4.05 (m, 1H), 6.22 (brd, J=6.0 Hz, 1H), 6.93 (d, J=15.6 Hz, 1H), 6.94 (brs, 1H), 7.13 (brs, 1H), 7.20 (brd, J=8.0 Hz, 1H), 7.25 (d, J=8.0 Hz, 1H), 7.47 (t, J=7.2 Hz, 2H), 7.57 (t, J=7.2 Hz, 1H), 7.65 (d, J=15.6 Hz, 1H), 7.74 (s, 1H), 7.97 (d, J=7.2 Hz, 2H).

Synthesis of 3-{(E)-2-[3-methoxy-4-(4-methyl-1H-imidazol-1-yl)phenyl]vinyl}-1-phenyl-5,6,7,8-tetrahydroimidazo[1,5-a]pyridine A solution of (E)-1-[2-benzoylpiperidin-1-yl]-3-[3-methoxy-4-(4-methyl-1H-imidazol-1-yl)phenyl]propenone (90 mg) and ammonium acetate (324 mg) in acetic acid (1 mL) was stirred at 150° C. for four hours. The reaction solution was left to cool to room temperature. Then, ethyl acetate and saturated sodium bicarbonate water were added to the reaction solution, and the organic layer was separated. The resulting organic layer was washed with brine, dried over anhydrous magnesium sulfate and then concentrated under reduced pressure. The residue was purified by silica gel column chromatography (carrier: Chromatorex NH; elution solvent: heptane:ethyl acetate=1:1→ethyl acetate→ethyl acetate:methanol=9:1) to obtain 52 mg of the title compound. The property values of the compound are as follows.

ESI-MS; m/z 411 [M$^+$+H]. $^1$H-NMR (CDCl$_3$) δ (ppm): 1.86-1.94 (m, 2H), 2.04-2.10 (m, 2H), 2.30 (s, 3H), 3.05 (t, J=6.8 Hz, 2H), 3.89 (s, 3H), 4.12 (t, J=6.4 Hz, 2H), 6.92 (brs, 1H), 6.93 (d, J=16.0 Hz, 1H), 7.14 (d, J=1.2 Hz, 1H), 7.19 (dd, J=8.4, 1.2 Hz, 1H), 7.22 (d, J=8.4 Hz, 1H), 7.23-7.26 (m, 1H), 7.40 (t, J=7.6 Hz, 2H), 7.60 (d, J=16.0 Hz, 1H), 7.70 (d, J=1.6 Hz, 1H), 7.74 (dd, J=7.6, 1.2 Hz, 2H).

Examples 51 and 52

Synthesis of (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 91]

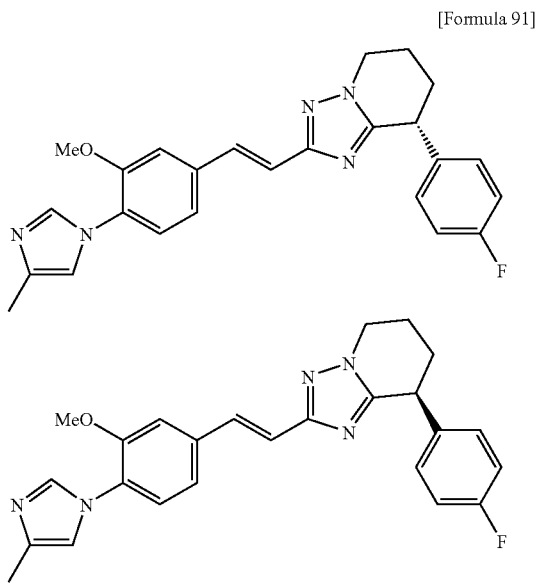

Synthesis of tert-butyl N'-[5-chloro-2-(4-fluorophenyl)pentanoyl]hydrazinecarboxylate IPEA (2.22 mL), HOBT (573 mg) and EDC (813 mg) were added to a solution of 5-chloro-2-(4-fluorophenyl)pentanoic acid (490 mg) synthesized according to the method described in Tetrahedron Letters, 2003, vol. 44, p. 365 and tert-butyl carbazate (420 mg) in DMF (5 mL), and the reaction solution was stirred at room temperature for 12 hours. Ethyl acetate and 1 N aqueous hydrochloric acid were added to the reaction solution, and the organic layer was separated. The resulting organic layer was washed with saturated sodium bicarbonate water, dried over anhydrous magnesium sulfate and then concentrated under reduced pressure. The residue was purified by silica gel column chromatography (elution solvent: heptane→heptane:ethyl acetate=1:1) to obtain 517 mg of the title compound. The property values of the compound are as follows.

ESI-MS; m/z 367 [M$^+$+Na]. $^1$H-NMR (CDCl$_3$) δ (ppm): 1.44 (s, 9H), 1.61-1.85 (m, 2H), 1.90-2.00 (m, 1H), 2.22-2.32 (m, 1H), 3.38 (t, J=7.2 Hz, 1H), 3.46-3.57 (m, 2H), 7.03 (t, J=8.4 Hz, 2H), 7.11 (brs, 1H), 7.28 (dd, J=8.4, 5.6 Hz, 2H).

Synthesis of 5-chloro-2-(4-fluorophenyl)pentanoic acid hydrazide hydrochloride A solution of 4 N hydrochloric acid in ethyl acetate (2 mL) was added to a solution of tert-butyl N'-[5-chloro-2-(4-fluorophenyl)pentanoyl]hydrazinecarboxylate (517 mg) in ethyl acetate (2 mL), and the reaction solution was stirred at room temperature for four hours. The reaction solution was concentrated under reduced pressure to obtain 342 mg of the title compound. The property values of the compound are as follows.

$^1$H-NMR (CD$_3$OD) δ (ppm): 1.64-1.81 (m, 2H), 1.90-2.00 (m, 1H), 2.15-2.25 (m, 1H), 3.53-3.60 (m, 3H), 7.07 (t, J=8.4 Hz, 2H), 7.39 (dd, J=8.4, 4.8 Hz, 2H).

Synthesis of 5-chloro-2-(4-fluorophenyl)pentanoic acid N'-{(E)-3-[3-methoxy-4-(4-methyl-1H-imidazol-1-yl)phenyl]acryloyl}hydrazide IPEA (1.28 mL), HOBT (330 mg) and EDC (468 mg) were added to a solution of 5-chloro-2-(4-fluorophenyl)pentanoic acid hydrazide hydrochloride (342 mg) and (E)-3-[3-methoxy-4-(4-methyl-1H-imidazol-1-yl)phenyl]acrylic acid (315 mg) in DMF (5 mL), and the reaction solution was stirred at room temperature for 14 hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: ethyl acetate→ethyl acetate:methanol=5:1) to obtain 427 mg of the title compound. The property value of the compound is as follows.

ESI-MS; m/z 485 [M$^+$+H].

Synthesis of 2-[4-chloro-1-(4-fluorophenyl)butyl]-5-{(E)-2-[3-methoxy-4-(4-methyl-1H-imidazol-1-yl)phenyl]vinyl}-[1,3,4]oxadiazole Imidazole (211 mg), carbon tetrabromide (1.0 g) and triphenylphosphine (244 mg) were added to a solution of 5-chloro-2-(4-fluorophenyl)pentanoic acid N'-{(E)-3-[3-methoxy-4-(4-methyl-1H-imidazol-1-yl)phenyl]acryloyl}hydrazide (300 mg) in methylene chloride (5 mL), and the reaction solution was stirred at room temperature for 14 hours. The reaction solution was purified as is by silica gel column chromatography (carrier: Chromatorex NH; elution solvent: heptane:ethyl acetate=1:1→ethyl acetate) to obtain 264 mg of the title compound. The property value of the compound is as follows.

ESI-MS; m/z 467 [M$^+$+H].

Synthesis of (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine A solution of 2-[4-chloro-1-(4-fluorophenyl)butyl]-5-{(E)-2-[3-methoxy-4-(4-methyl-1H-imidazol-1-yl)phenyl]vinyl}-[1,3,4]oxadiazole (264 mg) and ammonium acetate (871 mg) in acetic acid (2 mL) was stirred at 150° C. for 5.5 hours. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: ethyl acetate→ethyl acetate:methanol=4:1) to obtain 120 mg of a racemate of the title compound. The resulting racemate was separated by CHIRALPAK™ IA manufactured by Daicel Chemical Industries, Ltd. (2 cm×25 cm; mobile phase: hexane:ethanol=1:1) to obtain the title optically active compound with a retention time of 14 minutes (43 mg, >99% ee) and the title optically active compound with a retention time of 17 minutes (41 mg, >99% ee).

The property values of (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

ESI-MS; m/z 430 [M$^+$+H]. $^1$H-NMR (CDCl$_3$) δ (ppm): 2.00-2.25 (m, 3H), 2.29 (s, 3H), 2.30-2.40 (m, 1H), 3.85 (s, 3H), 4.25-4.35 (m, 3H), 6.90 (brs, 1H), 7.02 (t, J=8.8 Hz, 2H), 7.05 (d, J=16.0 Hz, 1H), 7.10 (dd, J=8.8, 4.8 Hz, 2H), 7.13 (brd, J=7.6 Hz, 1H), 7.14 (brs, 1H), 7.20 (d, J=7.6 Hz, 1H), 7.51 (d, J=16.0 Hz, 1H), 7.69 (d, J=0.8 Hz, 1H).

The property values of (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

ESI-MS; m/z 430 [M$^+$+H]. $^1$H-NMR (CDCl$_3$) δ (ppm): 2.00-2.25 (m, 3H), 2.29 (s, 3H), 2.30-2.40 (m, 1H), 3.85 (s, 3H), 4.25-4.35 (m, 3H), 6.90 (brs, 1H), 7.02 (t, J=8.8 Hz, 2H), 7.05 (d, J=16.0 Hz, 1H), 7.10 (dd, J=8.8, 4.8 Hz, 2H), 7.13 (brd, J=7.6 Hz, 1H), 7.14 (brs, 1H), 7.20 (d, J=7.6 Hz, 1H), 7.51 (d, J=16.0 Hz, 1H), 7.69 (d, J=0.8 Hz, 1H).

Examples 53 and 54

Synthesis of (+)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine and (−)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine

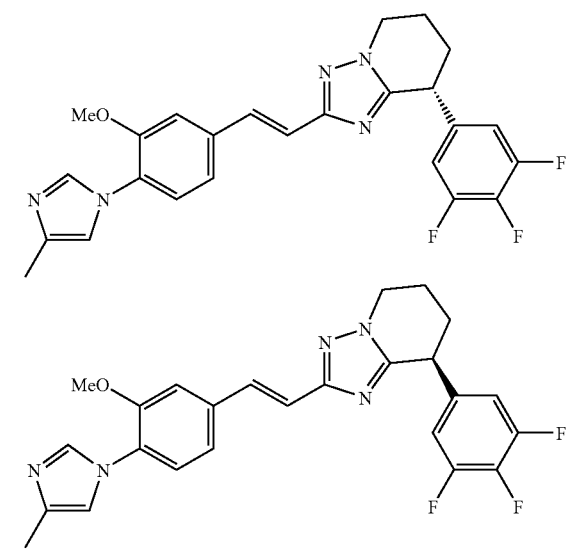

[Formula 92]

Synthesis of tert-butyl N'-[5-chloro-2-(3,4,5-trifluorophenyl)pentanoyl]hydrazinecarboxylate and tert-butyl N'-[5-(benzotriazol-1-yloxy)-2-(3,4,5-trifluorophenyl)pentanoyl]hydrazinecarboxylate IPEA (1.7 mL), HOBT (851 mg) and EDC (1.2 g) were added to a solution of 5-chloro-2-(3,4,5-trifluorophenyl)pentanoic acid (840 mg) synthesized according to the method described in Tetrahedron Letters, 2003, vol. 44, p. 365 and tert-butyl carbazate (500 mg) in DMF (5 mL), and the reaction solution was stirred at room temperature for 23 hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: heptane→heptane:ethyl acetate=1:1) to obtain 718 mg of tert-butyl N'-[5-chloro-2-(3,4,5-trifluorophenyl)pentanoyl]hydrazinecarboxylate and 420 mg of tert-butyl N'-[5-(benzotriazol-1-yloxy)-2-(3,4,5-trifluorophenyl)pentanoyl]hydrazinecarboxylate.

The property values of tert-butyl N'-[5-chloro-2-(3,4,5-trifluorophenyl)pentanoyl]hydrazinecarboxylate are as follows.

ESI-MS; m/z 403 [M$^+$+Na]. $^1$H-NMR (CDCl$_3$) δ (ppm): 1.45 (s, 9H), 1.64-2.00 (m, 3H), 2.15-2.26 (m, 1H), 3.30 (t, J=7.2 Hz, 1H), 3.47-3.60 (m, 2H), 6.99 (dd, J=8.4, 6.4 Hz, 2H).

The property value of tert-butyl N'-[5-(benzotriazol-1-yloxy)-2-(3,4,5-trifluorophenyl)pentanoyl]hydrazinecarboxylate is as follows.

ESI-MS; m/z 480 [M$^+$+H].

Synthesis of tert-butyl[2-oxo-3-(3,4,5-trifluorophenyl)piperidin-1-yl]carbamate

Sodium iodide (131 mg) and sodium hydride (containing mineral oil at 40%, 70 mg) were added to a solution of tert-butyl N'-[5-(benzotriazol-1-yloxy)-2-(3,4,5-trifluorophenyl)pentanoyl]hydrazinecarboxylate (420 mg) in DMF (3 mL), and the reaction solution was stirred at 100° C. for 19 hours. The reaction solution was left to cool to room temperature. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: heptane→ethyl acetate) to obtain 134 mg of the title compound. The property values of the compound are as follows.

$^1$H-NMR (CD$_3$OD) δ (ppm): 1.50 (s, 9H), 1.90-2.05 (m, 3H), 2.15-2.23 (m, 1H), 3.61-3.80 (m, 3H), 6.70 (brs, 1H), 6.90 (t, J=8.0, 6.8 Hz, 2H).

Synthesis of 1-amino-3-(3,4,5-trifluorophenyl)piperidin-2-one hydrochloride

A solution of 4 N hydrochloric acid in ethyl acetate (1 mL) was added to a solution of tert-butyl[2-oxo-3-(3,4,5-trifluorophenyl)piperidin-1-yl]carbamate (134 mg) in chloroform (1 mL), and the reaction solution was stirred at room temperature for three hours. The reaction solution was concentrated under reduced pressure to obtain 109 mg of the title compound. The property value of the compound is as follows.

ESI-MS; m/z 245 [M$^+$+H].

Synthesis of (E)-3-[3-methoxy-4-(4-methyl-1H-imidazol-1-yl)phenyl]-N-[2-oxo-3-(3,4,5-trifluorophenyl)piperidin-1-v]acrylamide IPEA (0.41 mL), HOBT (105 mg) and EDC (149 mg) were added to a solution of 1-amino-3-(3,4,5-trifluorophenyl)piperidin-2-one hydrochloride (109 mg) and (E)-3-[3-methoxy-4-(4-methyl-1H-imidazol-1-yl)phenyl]acrylic acid (100 mg) in DMF (2 mL), and the reaction solution was stirred at room temperature for three hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: ethyl acetate→ethyl acetate:methanol=5:1) to obtain 95 mg of the title compound. The property values of the compound are as follows.

ESI-MS; m/z 485 [M$^+$+H]. $^1$H-NMR (CD$_3$OD) δ (ppm): 1.94-2.10 (m, 3H), 2.22-2.30 (m, 1H), 2.31 (s, 3H), 3.64-3.72 (m, 1H), 3.78-3.82 (m, 2H), 3.84 (s, 3H), 6.41 (d, J=16.0 Hz, 1H), 6.88 (brd, J=8.0 Hz, 1H), 6.90 (brs, 1H), 6.93 (s, 1H), 7.00 (dd, J=6.8, 3.6 Hz, 2H), 7.14 (d, J=8.0 Hz, 1H), 7.44 (d, J=16.0 Hz, 1H), 7.74 (d, J=1.2 Hz, 1H), 9.87 (brs, 1H).

Synthesis of (+)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine and (−)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine A solution of (E)-3-[3-methoxy-4-(4-methyl-1H-imidazol-1-yl)phenyl]-N-[2-oxo-3-(3,4,5-trifluorophenyl)piperidin-1-yl]acrylamide (95 mg) in phosphorus oxychloride (2 mL) was stirred at 120° C. for one hour. The reaction solution was left to cool to room temperature and then concentrated under reduced pressure. Ammonium acetate (302 mg) was added to a solution of the residue in acetic acid (1 mL), and the reaction solution was stirred at 150° C. for three hours. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1→ethyl acetate) to obtain 50 mg of a racemate of the title compound. The resulting racemate was separated by CHIRALPAK™ IA manufactured by Daicel Chemical Industries, Ltd. (2 cm×25 cm; mobile phase: ethanol) to obtain the title optically active compound with a retention time of 19 minutes (25 mg, >99% ee) and the title optically active compound with a retention time of 33 minutes (22 mg, >99% ee).

The property values of (+)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine are as follows.

ESI-MS; m/z 466 [M$^+$+H]. $^1$H-NMR (CDCl$_3$) δ (ppm): 1.97-2.25 (m, 3H), 2.30 (s, 3H), 2.32-2.42 (m, 1H), 3.86 (s, 3H), 4.24-4.30 (m, 3H), 6.82 (dd, J=8.0, 6.0 Hz, 2H), 6.91 (brs, 1H), 7.05 (d, J=16.8 Hz, 1H), 7.14 (dd, J=8.4, 1.6 Hz, 1H), 7.16 (s, 1H), 7.21 (d, J=8.4 Hz, 1H), 7.50 (d, J=16.8 Hz, 1H), 7.69 (d, J=1.2 Hz, 1H).

The property values of (−)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine are as follows.

ESI-MS; m/z 466 [M$^+$+H]. $^1$H-NMR (CDCl$_3$) δ (ppm): 1.97-2.25 (m, 3H), 2.30 (s, 3H), 2.32-2.42 (m, 1H), 3.86 (s, 3H), 4.24-4.30 (m, 3H), 6.82 (dd, J=8.0, 6.0 Hz, 2H), 6.91

(brs, 1H), 7.05 (d, J=16.8 Hz, 1H), 7.14 (dd, J=8.4, 1.6 Hz, 1H), 7.16 (s, 1H), 7.21 (d, J=8.4 Hz, 1H), 7.50 (d, J=16.8 Hz, 1H), 7.69 (d, J=1.2 Hz, 1H).

Examples 55 and 56

Synthesis of (+)-5-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and (−)-5-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 93]

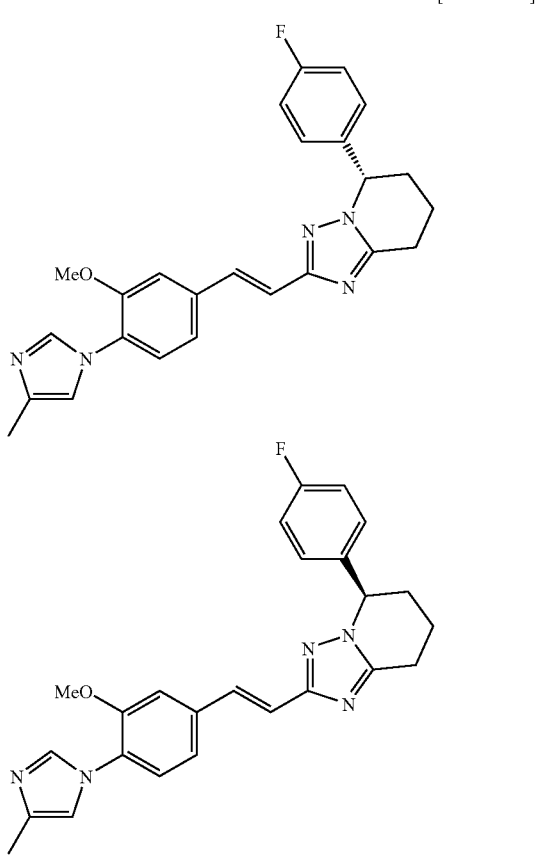

Synthesis of methyl 5-(N'-tert-butoxycarbonylhydrazino)-5-(4-fluorophenyl)pentanoate A solution of methyl 5-(4-fluorophenyl)-5-oxopentanoate (CAS No. 149437-67-2, 116 mg) and tert-butyl carbazate (73 mg) in 2-propanol (3 mL) was heated under reflux for six hours. The reaction solution was left to cool to room temperature, and then platinum oxide (10 mg) was added to the reaction solution. The reaction solution was stirred at room temperature in an hydrogen atmosphere at 3.5 atm for eight hours. The reaction solution was filtered through celite, and the filtrate was concentrated under reduced pressure. The residue was purified by silica gel column chromatography (elution solvent: heptane:ethyl acetate=9:1→heptane:ethyl acetate=1:1) to obtain 81 mg of the title compound. The property value of the compound is as follows.
ESI-MS; m/z 363 [M$^+$+Na].

Synthesis of tert-butyl[2-(4-fluorophenyl)-6-oxopiperidin-1-yl]carbamate

A 1 N sodium hydroxide solution (0.6 mL) was added to a solution of methyl 5-(N'-tert-butoxycarbonylhydrazino)-5-(4-fluorophenyl)pentanoate (81 mg) in methanol (1 mL), and the reaction solution was stirred at room temperature for two hours. 2 N aqueous hydrochloric acid (0.3 mL) was added to the reaction solution, and the reaction solution was concentrated under reduced pressure. HOBT (64 mg) and EDC (91 mg) were added to a solution of the residue in DMF (1 mL), and the reaction solution was stirred at room temperature for two hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: heptane:ethyl acetate=9:1→ethyl acetate) to obtain 50 mg of the title compound. The property values of the compound are as follows.
ESI-MS; m/z 331 [M$^+$+Na]. $^1$H-NMR (CDCl$_3$) δ (ppm): 1.43 (s, 9H), 1.78-1.91 (m, 3H), 2.25-2.34 (m, 1H), 2.52-2.70 (m, 2H), 4.90 (brs, 1H), 6.42 (brs, 1H), 7.04 (t, J=8.8 Hz, 2H), 7.16 (dd, J=8.8, 4.8 Hz, 2H).

Synthesis of (E)-N-[2-(4-fluorophenyl)-6-oxopiperidin-1-yl]-3-[3-methoxy-4-(4-methyl-1H-imidazol-1-yl)phenyl]acrylamide Trifluoroacetic acid (1 mL) was added to a solution of tert-butyl[2-(4-fluorophenyl)-6-oxopiperidin-1-yl]carbamate (50 mg) in chloroform (1 mL). The reaction solution was stirred at room temperature for one hour and then concentrated under reduced pressure. IPEA (0.14 mL), HOBT (65 mg) and EDC (93 mg) were added to a solution of the residue and (E)-3-[3-methoxy-4-(4-methyl-1H-imidazol-1-yl)phenyl]acrylic acid (42 mg) in DMF (2 mL), and the reaction solution was stirred at room temperature for 5.5 hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: ethyl acetate→ethyl acetate:methanol=5:1) to obtain 42 mg of the title compound. The property values of the compound are as follows.
$^1$H-NMR (CDCl$_3$) δ (ppm): 1.75-2.00 (m, 3H), 2.27 (s, 3H), 2.35-2.46 (m, 1H), 2.58-2.77 (m, 2H), 3.80 (s, 3H), 5.09 (t, J=6.4 Hz, 1H), 6.28 (d, J=15.6 Hz, 1H), 6.88 (brs, 2H), 6.91 (brd, J=8.0 Hz, 1H), 7.05 (t, J=8.8 Hz, 2H), 7.15 (d, J=8.0 Hz, 1H), 7.19 (dd, J=8.8, 5.2 Hz, 2H), 7.41 (d, J=15.6 Hz, 1H), 7.69 (s, 1H), 8.92 (brs, 1H).

Synthesis of (+)-5-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and (−)-5-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine A solution of (E)-N-[2-(4-fluorophenyl)-6-oxopiperidin-1-yl]-3-[3-methoxy-4-(4-methyl-1H-imidazol-1-yl)phenyl]acrylamide (42 mg) in phosphorus oxychloride (1 mL) was stirred at 120° C. for one hour. The reaction solution was left to cool to room temperature and then concentrated under reduced pressure. Ammonium acetate (144 mg) was added to a solution of the residue in acetic acid (1 mL), and the reaction solution was stirred at 150° C. for four hours. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1→ethyl acetate→ethyl acetate:methanol=5:1) to obtain 14 mg of a racemate of the title compound. The resulting racemate was separated by CHIRALPAK™ IA manufactured by Daicel Chemical Industries, Ltd. (2 cm×25 cm; mobile phase: ethanol) to obtain the title optically active compound with a retention time of minutes (4 mg, >99% ee) and the title optically active compound with a retention time of 29 minutes (4 mg, >99% ee).

The property values of (+)-5-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

ESI-MS; m/z 430 [M$^+$+H]. $^1$H-NMR (CDCl$_3$) δ (ppm): 1.87-2.05 (m, 2H), 2.06-2.15 (m, 1H), 2.29 (s, 3H), 2.40-2.49 (m, 1H), 3.00-3.09 (m, 2H), 3.85 (s, 3H), 5.43 (t, J=5.6 Hz, 1H), 6.91 (brs, 1H), 6.91 (brs, 1H), 6.98-7.08 (m, 5H), 7.12 (dd, J=8.0, 1.6 Hz, 1H), 7.16 (d, J=1.6 Hz, 1H), 7.21 (d, J=8.0 Hz, 1H), 7.54 (d, J=16.4 Hz, 1H), 7.69 (brs, 1H).

The property values of (−)-5-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

ESI-MS; m/z 430 [M$^+$+H]. $^1$H-NMR (CDCl$_3$) δ (ppm): 1.87-2.05 (m, 2H), 2.06-2.15 (m, 1H), 2.29 (s, 3H), 2.40-2.49 (m, 1H), 3.00-3.09 (m, 2H), 3.85 (s, 3H), 5.43 (t, J=5.6 Hz, 1H), 6.91 (brs, 1H), 6.91 (brs, 1H), 6.98-7.08 (m, 5H), 7.12 (dd, J=8.0, 1.6 Hz, 1H), 7.16 (d, J=1.6 Hz, 1H), 7.21 (d, J=8.0 Hz, 1H), 7.54 (d, J=16.4 Hz, 1H), 7.69 (brs, 1H).

Examples 57 and 58

Synthesis of (+)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine and (−)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine

[Formula 94]

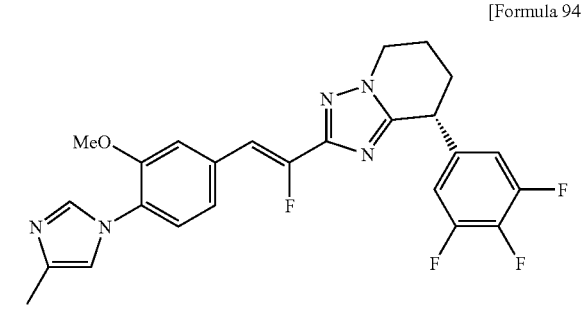

-continued

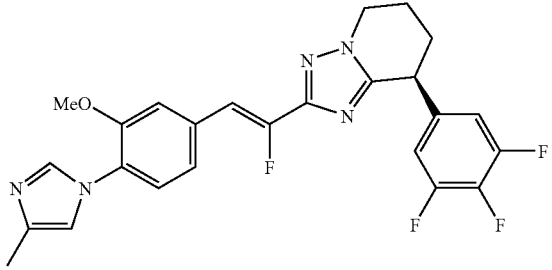

Synthesis of 5-chloro-2-(3,4,5-trifluorophenyl)pentanoic acid hydrazide hydrochloride A solution of 4 N hydrochloric acid in acetic acid (2 mL) was added to a solution of tert-butyl N'-[5-chloro-2-(3,4,5-trifluorophenyl)pentanoyl]hydrazinecarboxylate (300 mg) in ethyl acetate (2 mL), and the reaction solution was stirred at room temperature for one hour. The reaction solution was concentrated under reduced pressure to obtain 250 mg of the title compound. The property value of the compound is as follows.

ESI-MS; m/z 281 [M$^+$+H].

Synthesis of 5-chloro-2-(3,4,5-trifluorophenyl)pentanoic acid N'-{(Z)-2-fluoro-3-[3-methoxy-4-(4-methyl-1H-imidazol-1-yl)phenyl]acryloyl}hydrazide IPEA (0.14 mL) and BOPCl (100 mg) were added to a solution of 5-chloro-2-(3,4,5-trifluorophenyl)pentanoic acid hydrazide hydrochloride (83 mg) and (Z)-2-fluoro-3-[3-methoxy-4-(4-methyl-1H-imidazol-1-yl)phenyl]acrylic acid (CAS No. 870838-71-4, 72 mg) in methylene chloride (5 mL), and the reaction solution was stirred at room temperature for 13 hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: heptane:ethyl acetate=1:1→ethyl acetate→ethyl acetate:methanol=9:1) to obtain 84 mg of the title compound. The property value of the compound is as follows.

ESI-MS; m/z 539 [M$^+$+H].

Synthesis of 2-[4-chloro-1-(3,4,5-trifluorophenyl)butyl]-5-{(Z)-1-fluoro-2-[3-methoxy-4-(4-methyl-1H-imidazol-1-yl)phenyl]vinyl}-[1,3,4]oxadiazole A solution of 5-chloro-2-(3,4,5-trifluorophenyl)pentanoic acid N'-{(Z)-2-fluoro-3-[3-methoxy-4-(4-methyl-1H-imidazol-1-yl)phenyl]acryloyl}hydrazide (84 mg) in phosphorus oxychloride (1 mL) was stirred at 120° C. for 7.5 hours. The reaction solution was left to cool to room temperature and then concentrated under reduced pressure to obtain 81 mg of the title compound. The property value of the compound is as follows.

ESI-MS; m/z 521 [M$^+$+H].

Synthesis of (+)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine and (−)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine A solution of 2-[4-chloro-1-(3,4,5-trifluorophenyl)butyl]-5-{(Z)-1-fluoro-2-[3-methoxy-4-(4-methyl-1H-imidazol-1-yl)phenyl]vinyl}-[1,3,4]oxadiazole (81 mg) and ammonium acetate (358 mg) in acetic acid (2 mL) was stirred at 150° C. for three hours. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1→ethyl acetate) to obtain a racemate of the title compound. The resulting racemate was separated by CHIRALPAK™ IA manufactured by Daicel Chemical Industries, Ltd. (2 cm×25 cm; mobile phase: ethanol) to obtain the title optically active compound with a retention time of 12 minutes (4 mg, >99% ee) and the title optically active compound with a retention time of 20 minutes (4 mg, >99% ee).

The property values of (+)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine are as follows.

$^1$H-NMR (CDCl$_3$) δ (ppm): 1.99-2.08 (m, 1H), 2.09-2.28 (m, 2H), 2.31 (s, 3H), 2.35-2.44 (m, 1H), 3.87 (s, 3H), 4.28 (t, J=7.2 Hz, 1H), 4.34 (t, J=5.2 Hz, 2H), 6.74 (d, J=38.4 Hz, 1H), 6.82 (dd, J=8.0, 6.4 Hz, 2H), 6.94 (brs, 1H), 7.25 (d, J=8.4 Hz, 1H), 7.28 (dd, J=8.4, 1.6 Hz, 1H), 7.36 (brs, 1H), 7.73 (d, J=0.8 Hz, 1H).

The property values of (−)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine are as follows.

$^1$H-NMR (CDCl$_3$) δ (ppm): 1.99-2.08 (m, 1H), 2.09-2.28 (m, 2H), 2.31 (s, 3H), 2.35-2.44 (m, 1H), 3.87 (s, 3H), 4.28 (t, J=7.2 Hz, 1H), 4.34 (t, J=5.2 Hz, 2H), 6.74 (d, J=38.4 Hz, 1H), 6.82 (dd, J=8.0, 6.4 Hz, 2H), 6.94 (brs, 1H), 7.25 (d, J=8.4 Hz, 1H), 7.28 (dd, J=8.4, 1.6 Hz, 1H), 7.36 (brs, 1H), 7.73 (d, J=0.8 Hz, 1H).

Examples 59 and 60

Synthesis of (+)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine and (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine

[Formula 95]

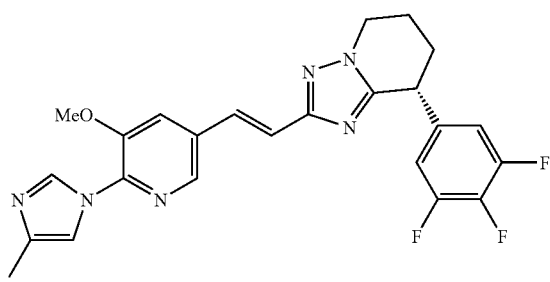

-continued

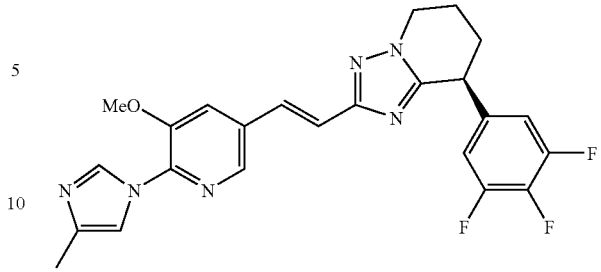

Synthesis of 5-chloro-2-(3,4,5-trifluorophenyl)pentanoic acid N'-{(E)-3-[5-methoxy-6-(4-methyl-1H-imidazol-1-yl)pyridin-3-yl]acryloyl}hydrazide IPEA (0.14 mL) and BOPCl (100 mg) were added to a solution of 5-chloro-2-(3,4,5-trifluorophenyl)pentanoic acid hydrazide hydrochloride (83 mg) and (E)-3-[5-methoxy-6-(4-methyl-1H-imidazol-1-yl)pyridin-3-yl]acrylic acid (CAS No. 870837-77-7, 68 mg) in methylene chloride (5 mL), and the reaction solution was stirred at room temperature for 18 hours. Ethyl acetate and saturated sodium bicarbonate water were added to the reaction solution, and the organic layer was separated. The resulting organic layer was dried over anhydrous magnesium sulfate and concentrated under reduced pressure to obtain 112 mg of the title compound. The property value of the compound is as follows.

ESI-MS; m/z 522 [M$^+$+H].

Synthesis of 5-{(E)-2-{5-[4-chloro-1-(3,4,5-trifluorophenyl)butyl]-[1,3,4]oxadiazol-2-yl}vinyl}-3-methoxy-2-(4-methyl-1H-imidazol-1-yl)pyridine A solution of 5-chloro-2-(3,4,5-trifluorophenyl)pentanoic acid N'-{(E)-3-[5-methoxy-6-(4-methyl-1H-imidazol-1-yl)pyridin-3-yl]acryloyl}hydrazide (112 mg) in phosphorus oxychloride (2 mL) was stirred at 120° C. for 3.5 hours. The reaction solution was left to cool to room temperature and then concentrated under reduced pressure to obtain 108 mg of the title compound. The property value of the compound is as follows.

ESI-MS; m/z 504 [M$^+$+H].

Synthesis of (+)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine and (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine A solution of 5-{(E)-2-{5-[4-chloro-1-(3,4,5-trifluorophenyl)butyl]-[1,3,4]oxadiazol-2-yl}vinyl}-3-methoxy-2-(4-methyl-1H-imidazol-1-yl)pyridine (495 mg) in acetic acid (2 mL) was stirred at 150° C. for 25 hours. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1→ethyl acetate) to obtain a racemate of the title compound. The resulting racemate was separated by CHIRALPAK™ IA manufactured by Daicel Chemical Industries, Ltd. (2 cm×25 cm; mobile phase: ethanol) to obtain the title optically active compound with a retention time of 20 minutes (11 mg, >99% ee) and the title optically active compound with a retention time of 25 minutes (12 mg, >99% ee).

The property values of (+)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine are as follows.

$^1$H-NMR (CDCl$_3$) δ (ppm): 1.97-2.06 (m, 1H), 2.07-2.25 (m, 2H), 2.29 (s, 3H), 2.34-2.42 (m, 1H), 3.97 (s, 3H), 4.23-4.30 (m, 3H), 6.81 (dd, J=8.0, 6.4 Hz, 2H), 7.08 (d, J=16.0 Hz, 1H), 7.46 (d, J=2.0 Hz, 1H), 7.49 (d, J=16.0 Hz, 1H), 7.52 (brs, 1H), 8.14 (d, J=2.0 Hz, 1H), 8.34 (brs, 1H).

The property values of (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine are as follows.

$^1$H-NMR (CDCl$_3$) δ (ppm): 1.97-2.06 (m, 1H), 2.07-2.25 (m, 2H), 2.29 (s, 3H), 2.34-2.42 (m, 1H), 3.97 (s, 3H), 4.23-4.30 (m, 3H), 6.81 (dd, J=8.0, 6.4 Hz, 2H), 7.08 (d, J=16.0 Hz, 1H), 7.46 (d, J=2.0 Hz, 1H), 7.49 (d, J=16.0 Hz, 1H), 7.52 (brs, 1H), 8.14 (d, J=2.0 Hz, 1H), 8.34 (brs, 1H).

Examples 61 and 62

Synthesis of (+)-2-{(E)-2-[3-fluoro-4-(4-methyl-1H-imidazol-1-yl)phenyl]vinyl}-8-(3,4,5-trifluorophenyl)-5,6,7,8-tetrahydro[1,2,4]triazolo[1,5-a]pyridine and (−)-2-{(E)-2-[3-fluoro-4-(4-methyl-1H-imidazol-1-yl)phenyl]vinyl}-8-(3,4,5-trifluorophenyl)-5,6,7,8-tetrahydro[1,2,4]triazolo[1,5-a]pyridine

[Formula 96]

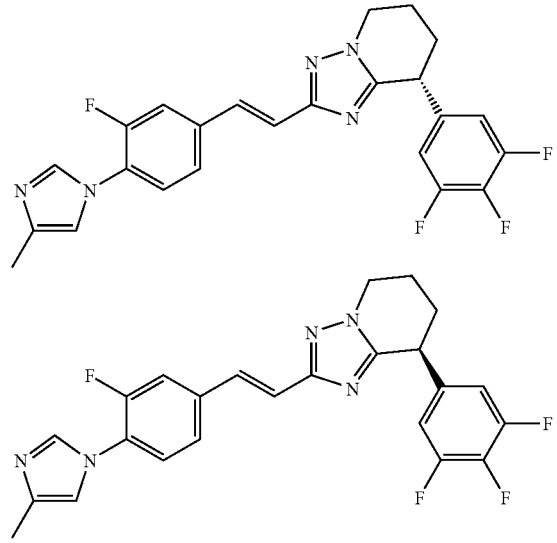

Synthesis of 5-chloro-2-(3,4,5-trifluorophenyl)pentanoic acid N'-{(E)-3-[3-fluoro-4-(4-methyl-1H-imidazol-1-yl)phenyl]acryloyl}hydrazide IPEA (0.14 mL) and BOPCl (100 mg) were added to a solution of 5-chloro-2-(3,4,5-trifluorophenyl)pentanoic acid hydrazide hydrochloride (83 mg) and (E)-3-[3-fluoro-4-(4-methyl-1H-imidazol-1-yl)phenyl]acrylic acid (CAS No. 870839-63-7, 65 mg) in methylene chloride (5 mL), and the reaction solution was stirred at room temperature for 18 hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: heptane:ethyl acetate=1:1→ethyl acetate→ethyl acetate:methanol=9:1) to obtain 103 mg of the title compound. The property value of the compound is as follows.

ESI-MS; m/z 509 [M$^+$+H].

Synthesis of 2-[4-chloro-1-(3,4,5-trifluorophenyl)butyl]-5-{(E)-2-[3-fluoro-4-(4-methyl-1H-imidazol-1-yl)phenyl]vinyl}-[1,3,4]oxadiazole A solution of 5-chloro-2-(3,4,5-trifluorophenyl)pentanoic acid N'-{(E)-3-[3-fluoro-4-(4-methyl-H-imidazol-1-yl)phenyl]acryloyl}hydrazide (103 mg) in phosphorus oxychloride (2 mL) was stirred at 120° C. for 3.5 hours. The reaction solution was left to cool to room temperature and then concentrated under reduced pressure to obtain 99 mg of the title compound. The property value of the compound is as follows.

ESI-MS; m/z 491 [M$^+$+H].

Synthesis of (+)-2-{(E)-2-[3-fluoro-4-(4-methyl-1H-imidazol-1-yl)phenyl]vinyl}-8-(3,4,5-trifluorophenyl)-5,6,7,8-tetrahydro[1,2,4]triazolo[1,5-a]pyridine and (−)-2-{(E)-2-[3-fluoro-4-(4-methyl-1H-imidazol-1-yl)phenyl]vinyl}-8-(3,4,5-trifluorophenyl)-5,6,7,8-tetrahydro[1,2,4]triazolo[1,5-a]pyridine A solution of 2-[4-chloro-1-(3,4,5-trifluorophenyl)butyl]-5-{(E)-2-[3-fluoro-4-(4-methyl-1H-imidazol-1-yl)phenyl]vinyl}-[1,3,4]oxadiazole (99 mg) and ammonium acetate (467 mg) in acetic acid (2 mL) was stirred at 150° C. for 25 hours. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1→ethyl acetate) to obtain a racemate of the title compound. The resulting racemate was separated by CHIRALPAK™ IA manufactured by Daicel Chemical Industries, Ltd. (2 cm×25 cm; mobile phase: ethanol) to obtain the title optically active compound with a retention time of 17 minutes (14 mg, >99% ee) and the title optically active compound with a retention time of 24 minutes (11 mg, >99% ee).

The property values of (+)-2-{(E)-2-[3-fluoro-4-(4-methyl-1H-imidazol-1-yl)phenyl]vinyl}-8-(3,4,5-trifluorophenyl)-5,6,7,8-tetrahydro[1,2,4]triazolo[1,5-a]pyridine are as follows.

ESI-MS; m/z 454 [M$^+$+H]. $^1$H-NMR (CDCl$_3$) δ (ppm): 1.97-2.06 (m, 1H), 2.06-2.25 (m, 2H), 2.30 (s, 3H), 2.32-2.42 (m, 1H), 4.23-4.30 (m, 3H), 6.81 (dd, J=8.0, 6.4 Hz, 2H), 6.97 (brs, 1H), 7.03 (d, J=16.8 Hz, 1H), 7.29-7.38 (m, 3H), 7.46 (d, J=16.8 Hz, 1H), 7.73 (brs, 1H).

The property values of (−)-2-{(E)-2-[3-fluoro-4-(4-methyl-1H-imidazol-1-yl)phenyl]vinyl}-8-(3,4,5-trifluorophenyl)-5,6,7,8-tetrahydro[1,2,4]triazolo[1,5-a]pyridine are as follows.

ESI-MS; m/z 454 [M++H]. $^1$H-NMR (CDCl$_3$) δ (ppm): 1.97-2.06 (m, 1H), 2.06-2.25 (m, 2H), 2.30 (s, 3H), 2.32-2.42 (m, 1H), 4.23-4.30 (m, 3H), 6.81 (dd, J=8.0, 6.4 Hz, 2H), 6.97 (brs, 1H), 7.03 (d, J=16.8 Hz, 1H), 7.29-7.38 (m, 3H), 7.46 (d, J=16.8 Hz, 1H), 7.73 (brs, 1H).

Examples 63 and 64

Synthesis of (+)-2-{(E)-2-[3-methoxy-4-(4-methyl-1H-imidazol-1-yl)phenyl]vinyl}-8-(2,4,6-trifluorophenyl)-5,6,7,8-tetrahydro[1,2,4]triazolo[1,5-a]pyridine and (−)-2-{(E)-2-[3-methoxy-4-(4-methyl-1H-imidazol-1-yl)phenyl]vinyl}-8-(2,4,6-trifluorophenyl)-5,6,7,8-tetrahydro[1,2,4]triazolo[1,5-a]pyridine

[Formula 97]

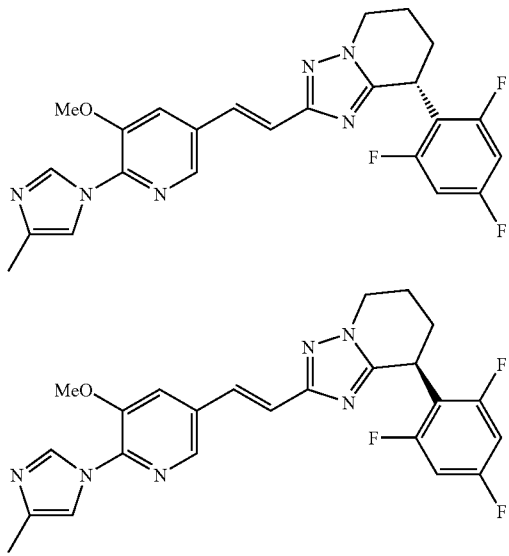

Synthesis of tert-butyl N'-[5-chloro-2-(2,4,6-trifluorophenyl)pentanoyl]hydrazinecarboxylate IPEA (1.1 mL) and BOPCl (798 mg) were added to a solution of 5-chloro-2-(2,4,6-trifluorophenyl)pentanoic acid (560 mg) synthesized according to the method described in Tetrahedron Letters, 2003, vol. 44, p. 365 and tert-butyl carbazate (276 mg) in methylene chloride (5 mL), and the reaction solution was stirred at room temperature for one hour. Ethyl acetate and 1 N aqueous hydrochloric acid were added to the reaction solution, and the organic layer was separated. The resulting organic layer was washed with saturated sodium bicarbonate water, dried over anhydrous magnesium sulfate and then concentrated under reduced pressure. The residue was purified by silica gel column chromatography (elution solvent: heptane→heptane:ethyl acetate=1:1) to obtain 333 mg of the title compound. The property values of the compound are as follows.

ESI-MS; m/z 403 [M++Na]. $^1$H-NMR (CDCl$_3$) δ (ppm): 1.45 (s, 9H), 1.59-1.71 (m, 1H), 1.75-1.87 (m, 1H), 1.97-2.08 (m, 1H), 2.36-2.47 (m, 1H), 3.47-3.58 (m, 2H), 3.87 (t, J=7.6 Hz, 1H), 6.73 (t, J=8.4 Hz, 2H), 7.11 (brs, 1H).

Synthesis of 5-chloro-2-(2,4,6-trifluorophenyl)pentanoic acid hydrazide hydrochloride A solution of 4 N hydrochloric acid in acetic acid (3 mL) was added to a solution of tert-butyl N'-[5-chloro-2-(2,4,6-trifluorophenyl)pentanoyl]hydrazinecarboxylate (333 mg) in ethyl acetate (3 mL), and the reaction solution was stirred at room temperature for 15 hours. The reaction solution was concentrated under reduced pressure to obtain 277 mg of the title compound. The property value of the compound is as follows.

ESI-MS; m/z 281 [M++H].

Synthesis of 5-chloro-2-(2,4,6-trifluorophenyl)pentanoic acid N'-{(E)-3-[3-methoxy-4-(4-methyl-1H-imidazol-1-yl)phenyl]acryloyl}hydrazide IPEA (0.46 mL) and BOPCl (333 mg) were added to a solution of 5-chloro-2-(2,4,6-trifluorophenyl)pentanoic acid hydrazide hydrochloride (277 mg) and (E)-3-[3-methoxy-4-(4-methyl-1H-imidazol-1-yl)phenyl]acrylic acid (225 mg) in methylene chloride (10 mL), and the reaction solution was stirred at room temperature for two hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: heptane:ethyl acetate=1:1→ethyl acetate→ethyl acetate:methanol=9:1) to obtain 286 mg of the title compound. The property value of the compound is as follows.

ESI-MS; m/z 521 [M++H].

Synthesis of (+)-2-{(E)-2-[3-methoxy-4-(4-methyl-1H-imidazol-1-yl)phenyl]vinyl}-8-(2,4,6-trifluorophenyl)-5,6,7,8-tetrahydro[1,2,4]triazolo[1,5-a]pyridine and (−)-2-{(E)-2-[3-methoxy-4-(4-methyl-1H-imidazol-1-yl)phenyl]vinyl}-8-(2,4,6-trifluorophenyl)-5,6,7,8-tetrahydro[1,2,4]triazolo[1,5-a]pyridine A solution of 5-chloro-2-(2,4,6-trifluorophenyl)pentanoic acid N'-{(E)-3-[3-methoxy-4-(4-methyl-1H-imidazol-1-yl)phenyl]acryloyl}hydrazide (286 mg) in phosphorus oxychloride (2 mL) was stirred at 120° C. for two hours. The reaction solution was left to cool to room temperature and then concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. Ammonium acetate (1.27 g) was added to a solution of the residue in acetic acid (5 mL), and the reaction solution was stirred at 150° C. for 12 hours. The reaction solution was left to cool to room temperature. Then, ethyl acetate and saturated sodium bicarbonate water were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane: ethyl acetate=1:1→ethyl acetate→ethyl acetate:methanol=9: 1) to obtain a racemate of the title compound. The resulting racemate was separated by CHIRALCEL™ OD-H manufactured by Daicel Chemical Industries, Ltd. (2 cm×25 cm; mobile phase: hexane:ethanol=1:1) to obtain the title optically active compound with a retention time of 14 minutes (57 mg, >99% ee) and the title optically active compound with a retention time of 24 minutes (50 mg, >99% ee).

The property values of (+)-2-{(E)-2-[3-methoxy-4-(4-methyl-1H-imidazol-1-yl)phenyl]vinyl}-8-(2,4,6-trifluorophenyl)-5,6,7,8-tetrahydro[1,2,4]triazolo[1,5-a]pyridine are as follows.

ESI-MS; m/z 466 [M$^+$+H]. $^1$H-NMR (CDCl$_3$) δ (ppm): 2.02-2.22 (m, 2H), 2.25-2.38 (m, 5H), 3.84 (s, 3H), 4.18-4.26 (m, 1H), 4.32-4.40 (m, 1H), 4.52-4.38 (m, 1H), 6.68 (t, J=8.4 Hz, 2H), 6.90 (brs, 1H), 7.02 (d, J=16.0 Hz, 1H), 7.11 (dd, J=7.6, 2.4 Hz, 1H), 7.13 (d, J=2.4 Hz, 1H), 7.19 (d, J=7.6 Hz, 1H), 7.44 (d, J=16.0 Hz, 1H), 7.68 (brs, 1H).

The property values of (−)-2-{(E)-2-[3-methoxy-4-(4-methyl-1H-imidazol-1-yl)phenyl]vinyl}-8-(2,4,6-trifluorophenyl)-5,6,7,8-tetrahydro[1,2,4]triazolo[1,5-a]pyridine are as follows.

ESI-MS; m/z 466 [M$^+$+H]. $^1$H-NMR (CDCl$_3$) δ (ppm): 2.02-2.22 (m, 2H), 2.25-2.38 (m, 5H), 3.84 (s, 3H), 4.18-4.26 (m, 1H), 4.32-4.40 (m, 1H), 4.52-4.38 (m, 1H), 6.68 (t, J=8.4 Hz, 2H), 6.90 (brs, 1H), 7.02 (d, J=16.0 Hz, 1H), 7.11 (dd, J=7.6, 2.4 Hz, 1H), 7.13 (d, J=2.4 Hz, 1H), 7.19 (d, J=7.6 Hz, 1H), 7.44 (d, J=16.0 Hz, 1H), 7.68 (brs, 1H).

Example 65

Synthesis of 7-(4-fluorophenyl)-2-{(E)-2-[3-methoxy-4-(4-methyl-1H-imidazol-1-yl)phenyl]vinyl}-6,7-dihydro-5H-pyrrolo[1,2-b][1,2,4]triazol-7-ol

[Formula 98]

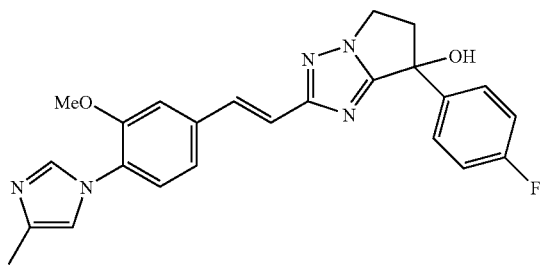

Synthesis of 2-(4-fluorophenyl)-4-hydroxybutyric acid hydrazide

Acetic acid (1 mL) was added to a solution of 3-(4-fluorophenyl)dihydrofuran-2-one (393 mg) and hydrazine (699 mg) in methanol (10 mL), and the reaction solution was heated to reflux for two hours. The reaction solution was left to cool to room temperature. Then, ethyl acetate and concentrated aqueous ammonia were added to the reaction solution, and the organic layer was separated. The resulting organic layer was dried over anhydrous magnesium sulfate and then concentrated under reduced pressure. Chloroform was added to the residue, and the precipitated solid was collected by filtration to obtain 147 mg of the title compound. The property values of the compound are as follows.

ESI-MS; m/z 213 [M$^+$+H]. $^1$H-NMR (CD$_3$OD) δ (ppm): 1.87-1.98 (m, 1H), 2.17-2.28 (m, 1H), 3.43-3.50 (m, 2H), 3.58-3.66 (m, 1H), 6.97-7.04 (m, 2H), 7.32-7.39 (m, 2H).

Synthesis of 2-(4-fluorophenyl)-4-hydroxybutyric acid N'-{(E)-3-[3-methoxy-4-(4-methyl-1H-imidazol-1-yl)phenyl]acryloyl}hydrazide IPEA (0.17 mL), HOBT (134 mg) and EDC (190 mg) were added to a solution of 2-(4-fluorophenyl)-4-hydroxybutyric acid hydrazide (105 mg) and (E)-3-[3-methoxy-4-(4-methyl-1H-imidazol-1-yl)phenyl]acrylic acid (153 mg) in DMF (3 mL), and the reaction solution was stirred at room temperature for 14 hours. Ethyl acetate and brine were added to the reaction solution, and the organic layer was separated. The resulting organic layer was dried over anhydrous magnesium sulfate and concentrated under reduced pressure to obtain 224 mg of the title compound. The property value of the compound is as follows.

ESI-MS; m/z 453 [M$^+$+H].

Synthesis of 2-[3-chloro-1-(4-fluorophenyl)propyl]-5-{(E)-2-[3-methoxy-4-(4-methyl-1H-imidazol-1-yl)phenyl]vinyl}-[1,3,4]oxadiazole A solution of 2-(4-fluorophenyl)-4-hydroxybutyric acid N'-{(E)-3-[3-methoxy-4-(4-methyl-1H-imidazol-1-yl)phenyl]acryloyl}hydrazide (224 mg) in phosphorus oxychloride (1 mL) was stirred at 120° C. for two hours. The reaction solution was left to cool to room temperature and then concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. The residue was purified by silica gel column chromatography (eluent solvent: ethyl acetate→ethyl acetate:methanol=3:1) to obtain 87 mg of the title compound. The property value of the compound is as follows.

ESI-MS; m/z 453 [M$^+$+H].

Synthesis of 3-(4-fluorophenyl)-3-{5-{(E)-2-[3-methoxy-4-(4-methyl-1H-imidazol-1-yl)phenyl]vinyl}-4H-[1,2,4]triazol-3-yl}propan-1-ol A solution of 2-[3-chloro-1-(4-fluorophenyl)propyl]-5-{(E)-2-[3-methoxy-4-(4-methyl-1H-imidazol-1-yl)phenyl]vinyl}-[1,3,4]oxadiazole (87 mg) and ammonium acetate (444 mg) in acetic acid (1 mL) was stirred at 150° C. for 17 hours. The reaction solution was left to cool to room temperature and then concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. Potassium carbonate (100 mg) was added to a solution of the residue in methanol (1 mL), and the reaction solution was stirred at room temperature for one hour. Ethyl acetate and brine were added to the reaction solution, and the organic layer was separated. The resulting organic layer was dried over anhydrous magnesium sulfate and then concentrated under reduced pressure to obtain 83 mg of the title compound. The property value of the compound is as follows.

ESI-MS; m/z 434 [M$^+$+H].

Synthesis of 3-[3-chloro-1-(4-fluorophenyl)propyl]-5-{(E)-2-[3-methoxy-4-(4-methyl-1H-imidazol-1-yl)phenyl]vinyl}-4H-[1,2,4]triazole A solution of 3-(4-fluorophenyl)-3-{5-{(E)-2-[3-methoxy-4-(4-methyl-1H-imidazol-1-yl)phenyl]vinyl}-4H-[1,2, 4]triazol-3-yl}propan-1-ol (83 mg) in phosphorus oxychloride (1 mL) was stirred at 120° C. for one hour. The reaction solution was left to cool to room temperature and then concentrated under reduced pressure. Ethyl acetate and saturated sodium bicarbonate water were added to the residue, and the organic layer was separated. The resulting organic layer was dried over anhydrous magnesium sulfate and concentrated under reduced pressure to obtain 86 mg of the title compound. The property value of the compound is as follows.

ESI-MS; m/z 452 [M$^+$+H].

Synthesis of 7-(4-fluorophenyl)-2-{(E)-2-[3-methoxy-4-(4-methyl-1H-imidazol-1-yl)phenyl]vinyl}-6,7-dihydro-5H-pyrrolo[1,2-b][1,2,4]triazol-7-ol Sodium hydrate (containing mineral oil at 40%, 15 mg) was added to a solution of 3-[3-chloro-1-(4-fluorophenyl)propyl]-5-{(E)-2-[3-methoxy-4-(4-methyl-1H-imidazol-1-yl)phenyl]vinyl}-4H-[1,2,4]triazole (86 mg) in DMF (1 mL), and the reaction solution was stirred at room temperature for 13 hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: ethyl acetate) to obtain 3 mg of the title compound. The property values of the compound are as follows.

ESI-MS; m/z 432 [M$^+$+H]. $^1$H-NMR (CDCl$_3$) δ (ppm): 2.27 (s, 3H), 2.90-3.00 (m, 1H), 3.10-3.17 (m, 1H), 3.81 (s, 3H), 4.21-4.27 (m, 1H), 4.36-4.43 (m, 1H), 6.90 (brs, 1H), 6.99 (dd, J=8.0, 2.0 Hz, 1H), 7.06 (d, J=2.0 Hz, 1H), 7.07 (t, J=8.4 Hz, 2H), 7.08 (d, J=16.0 Hz, 1H), 7.18 (d, J=8.0 Hz, 1H), 7.51 (d, J=16.0 Hz, 1H), 7.52-7.58 (m, 2H), 7.81 (brs, 1H).

Examples 66 and 67

Synthesis of (−)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol and (+)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol

[Formula 99]

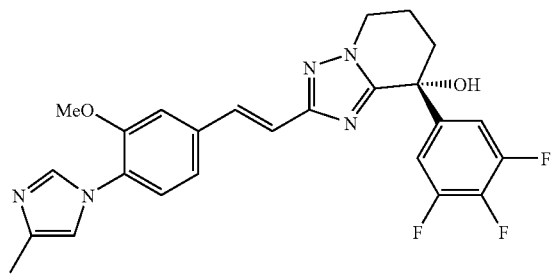

-continued

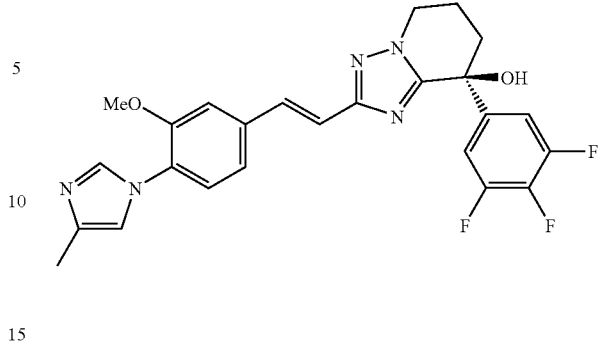

Sodium hydride (containing mineral oil at 40%, 3 mg) was added to a solution of 2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine (12 mg) obtained by the method in Examples 53 and 54 in DMF (3 mL) at 0° C., and the reaction solution was stirred at room temperature for one hour. To the reaction solution was added mcpba (5 mg), and the reaction solution was stirred at room temperature for 30 minutes. Ethyl acetate and saturated sodium bicarbonate water were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane:ethyl acetate=1:1→ethyl acetate→ethyl acetate:methanol=9:1) to obtain a racemate of the title compound. The resulting racemate was separated by CHIRALPAK™ AD-H manufactured by Daicel Chemical Industries, Ltd. (2 cm×25 cm; mobile phase: hexane:ethanol=1:1) to obtain the title optically active compound with a retention time of 12 minutes (1.8 mg, >99% ee) and the title optically active compound with a retention time of 15 minutes (1.8 mg, >99% ee).

The property values of (−)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol are as follows.

ESI-MS; m/z 482 [M$^+$+H]. $^1$H-NMR (CDCl$_3$) δ (ppm): 2.03-2.12 (m, 2H), 2.28 (s, 3H), 2.30-2,37 (m, 1H), 2.48-2.61 (m, 1H), 3.70 (d, J=2.4 Hz, 3H), 4.17-4.26 (m, 1H), 4.31-4.38 (m, 1H), 6.85 (brs, 1H), 6.86 (d, J=7.2 Hz, 1H), 6.90 (brs, 1H), 7.00 (dd, J=16.0, 1.2 Hz, 1H), 7.05-7.11 (m, 3H), 7.35 (d, J=16.0 Hz, 1H), 7.77 (dd, J=2.8, 1.6 Hz, 1H).

The property values of (+)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol are as follows.

ESI-MS; m/z 482 [M$^+$+H]. $^1$H-NMR (CDCl$_3$) δ (ppm): 2.03-2.12 (m, 2H), 2.28 (s, 3H), 2.30-2,37 (m, 1H), 2.48-2.61 (m, 1H), 3.70 (d, J=2.4 Hz, 3H), 4.17-4.26 (m, 1H), 4.31-4.38 (m, 1H), 6.85 (brs, 1H), 6.86 (d, J=7.2 Hz, 1H), 6.90 (brs, 1H), 7.00 (dd, J=16.0, 1.2 Hz, 1H), 7.05-7.11 (m, 3H), 7.35 (d, J=16.0 Hz, 1H), 7.77 (dd, J=2.8, 1.6 Hz, 1H).

Examples 68 and 69

Synthesis of (+)-2-{(E)-2-[2-fluoro-5-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine and (−)-2-{(E)-2-[2-fluoro-5-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine

[Formula 100]

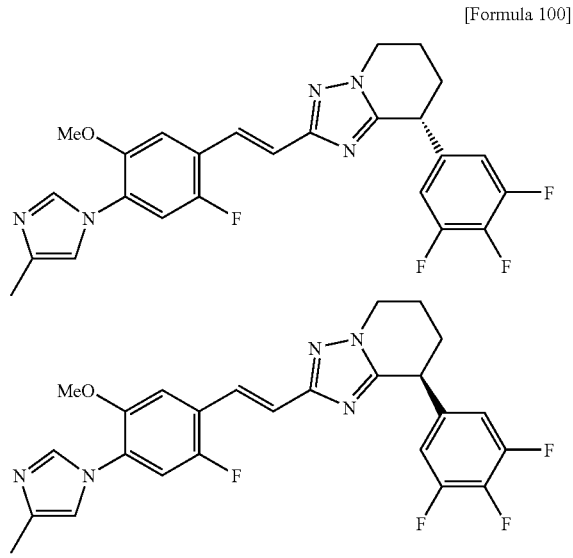

Synthesis of (E)-3-[2-fluoro-5-methoxy-4-(4-methyl-1H-imidazol-1-yl)phenyl]acrylic acid Lithium hydroxide monohydrate (240 mg) was added to a mixed solution of 2-fluoro-5-methoxy-4-(4-methyl-1H-imidazol-1-yl)benzaldehyde (CAS No. 870851-52-8, 1.03 g) and triethyl phosphonoacetate (1.09 g) in THF (4 mL) and ethanol (1 mL), and the reaction solution was stirred at room temperature for five hours. A 2 N sodium hydroxide solution (4 mL) was added to the reaction solution, and the reaction solution was stirred for 17 hours. 2 N aqueous hydrochloric acid (4 mL) was added to the reaction solution, and the reaction solution was stirred at room temperature for 30 minutes. Then, the precipitated solid was collected by filtration and washed with water and an ether. The resulting solid was air-dried to obtain 1.03 g of the title compound. The property value of the compound is as follows.

ESI-MS; m/z 277 [M++H].

Synthesis of 5-chloro-2-(3,4,5-trifluorophenyl)pentanoic acid N'-{(E)-3-[2-fluoro-5-methoxy-4-(4-methyl-1H-imidazol-1-yl)phenyl]acryloyl}hydrazide IPEA (0.31 mL) and BOPCl (119 mg) were added to a solution of 5-chloro-2-(3,4,5-trifluorophenyl)pentanoic acid hydrazide hydrochloride (114 mg) and (E)-3-[2-fluoro-5-methoxy-4-(4-methyl-1H-imidazol-1-yl)phenyl]acrylic acid (99 mg) in methylene chloride (5 mL), and the reaction solution was stirred at room temperature for one hour. Ethyl acetate and saturated aqueous ammonium chloride solution were added to the reaction solution, and the organic layer was separated. The resulting organic layer was dried over anhydrous magnesium sulfate and concentrated under reduced pressure to obtain 200 mg of the title compound. The property value of the compound is as follows.

ESI-MS; m/z 539 [M++H].

Synthesis of 2-[4-chloro-1-(3,4,5-trifluorophenyl)butyl]-5-{(E)-2-[2-fluoro-5-methoxy-4-(4-methyl-1H-imidazol-1-yl)phenyl]vinyl}-[1,3,4]oxadiazole A solution of 5-chloro-2-(3,4,5-trifluorophenyl)pentanoic acid N'-{(E)-3-[2-fluoro-5-methoxy-4-(4-methyl-1H-imidazol-1-yl)phenyl]acryloyl}hydrazide (200 mg) in phosphorus oxychloride (2 mL) was stirred at 120° C. for 5.5 hours. The reaction solution was left to cool to room temperature and then concentrated under reduced pressure. Ethyl acetate and saturated sodium bicarbonate water were added to the residue, and the organic layer was separated. The resulting organic layer was dried over anhydrous magnesium sulfate and concentrated under reduced pressure to obtain 180 mg of the title compound. The property value of the compound is as follows.

ESI-MS; m/z 521 [M++H].

Synthesis of (+)-2-{(E)-2-[2-fluoro-5-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine and (−)-2-{(E)-2-[2-fluoro-5-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine A solution of 2-[4-chloro-1-(3,4,5-trifluorophenyl)butyl]-5-{(E)-2-[2-fluoro-5-methoxy-4-(4-methyl-1H-imidazol-1-yl)phenyl]vinyl}-[1,3,4]oxadiazole (180 mg) and ammonium acetate (533 mg) in acetic acid (2 mL) was stirred at 150° C. for 24 hours. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: heptane:ethyl acetate=1:1→ethyl acetate→ethyl acetate:methanol=4:1) to obtain a racemate of the title compound. The resulting racemate was separated by CHIRALPAK™ AD-H manufactured by Daicel Chemical Industries, Ltd. (2 cm×25 cm; mobile phase: hexane:ethanol=1:1) to obtain the title optically active compound with a retention time of 12 minutes (19 mg, >99% ee) and the title optically active compound with a retention time of 26 minutes (17 mg, >99% ee).

The property values of (+)-2-{(E)-2-[2-fluoro-5-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine are as follows.

ESI-MS; m/z 484 [M++H]. $^1$H-NMR (CDCl$_3$) δ (ppm): 1.97-2.25 (m, 3H), 2.29 (s, 3H), 2.34-2.42 (m, 1H), 3.85 (s, 3H), 4.24-4.31 (m, 3H), 6.82 (dd, J=8.0, 6.4 Hz, 2H), 6.92 (brs, 1H), 7.02 (d, J=10.4 Hz, 1H), 7.15 (d, J=5.6 Hz, 1H), 7.16 (d, J=16.4 Hz, 1H), 7.60 (d, J=16.4 Hz, 1H), 7.75 (brs, 1H).

The property values of (−)-2-{(E)-2-[2-fluoro-5-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine are as follows.

ESI-MS; m/z 484 [M++H]. $^1$H-NMR (CDCl$_3$) δ (ppm): 1.97-2.25 (m, 3H), 2.29 (s, 3H), 2.34-2.42 (m, 1H), 3.85 (s, 3H), 4.24-4.31 (m, 3H), 6.82 (dd, J=8.0, 6.4 Hz, 2H), 6.92

(brs, 1H), 7.02 (d, J=10.4 Hz, 1H), 7.15 (d, J=5.6 Hz, 1H), 7.16 (d, J=16.4 Hz, 1H), 7.60 (d, J=16.4 Hz, 1H), 7.75 (brs, 1H).

Examples 70 and 71

Synthesis of (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol and (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol

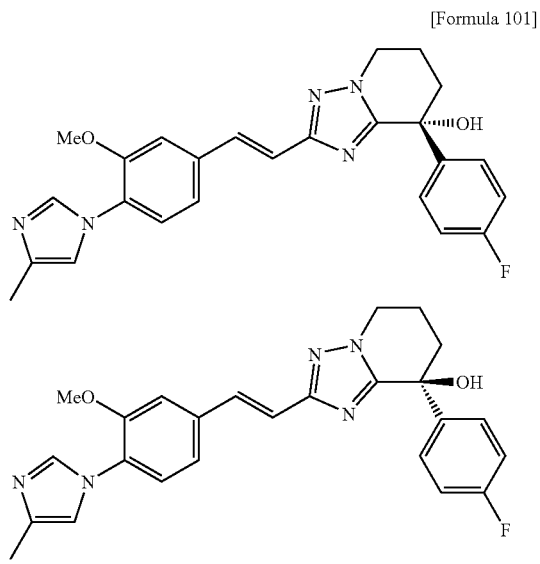

[Formula 101]

Sodium hydride (containing mineral oil at 40%, 21 mg) was added to a solution of (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine synthesized by the method in Example 51 (115 mg) in DMF (1 mL), and the reaction solution was stirred at room temperature for one hour under oxygen bubbling. A saturated sodium bisulfite solution was added to the reaction solution, and the reaction solution was stirred at room temperature for 10 minutes. Ethyl acetate and saturated sodium bicarbonate water were added to the reaction solution, and the organic layer was separated. The resulting organic layer was dried over anhydrous magnesium sulfate and then concentrated under reduced pressure. The residue was separated by CHIRALPAK™ AD-H manufactured by Daicel Chemical Industries, Ltd. (2 cm×25 cm; mobile phase: hexane:ethanol=1:1) to obtain the title optically active compound with a retention time of 15 minutes (35 mg, >99% ee) and the title optically active compound with a retention time of 25 minutes (35 mg, >99% ee).

The property values of (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol are as follows.
$^1$H-NMR (CDCl$_3$) δ (ppm): 1.93-2.04 (m, 1H), 2.14-2.24 (m, 1H), 2.28 (s, 3H), 2.29-2.44 (m, 2H), 3.80 (s, 3H), 4.19-4.31 (m, 2H), 6.88 (brs, 1H), 6.94-7.06 (m, 5H), 7.14 (d, J=8.4 Hz, 1H), 7.31 (dd, J=8.4, 5.2 Hz, 2H), 7.44 (d, J=16.4 Hz, 1H), 7.71 (brs, 1H).

The property values of (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol are as follows.
$^1$H-NMR (CDCl$_3$) δ (ppm): 1.93-2.04 (m, 1H), 2.14-2.24 (m, 1H), 2.28 (s, 3H), 2.29-2.44 (m, 2H), 3.80 (s, 3H), 4.19-4.31 (m, 2H), 6.88 (brs, 1H), 6.94-7.06 (m, 5H), 7.14 (d, J=8.4 Hz, 1H), 7.31 (dd, J=8.4, 5.2 Hz, 2H), 7.44 (d, J=16.4 Hz, 1H), 7.71 (brs, 1H).

Examples 72, 73 and 74

Synthesis of (+)-8-fluoro-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine, (−)-8-fluoro-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and 8-(4-fluorophenyl)-2-{(E)-2-[3-methoxy-4-(4-methyl-1H-imidazol-1-yl)phenyl]vinyl}-5,6-dihydro[1,2,4]triazolo[1,5-a]pyridine

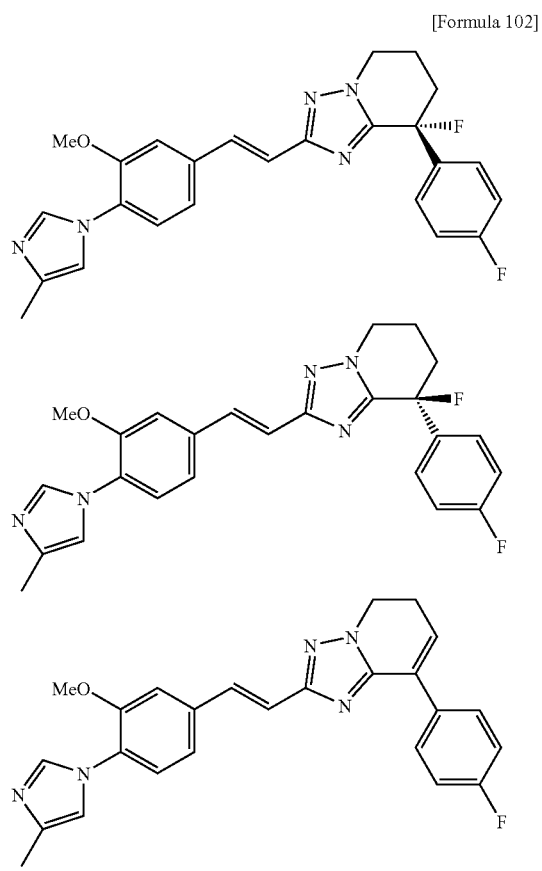

[Formula 102]

DAST (0.04 mL) was added to a solution of (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine synthesized by the method in Example 51 (51 mg) in methylene chloride (2 mL) at 0° C., and the reaction solution was stirred at 0° C. for one hour. Ethyl acetate and saturated sodium bicarbonate water were added to the reaction solution, and the organic layer was separated. The resulting organic layer was dried over anhydrous magnesium sulfate and then concentrated under reduced pressure. The residue was separated by CHIRALPAK™ IA manufactured by Daicel Chemical Industries, Ltd. (2 cm×25 cm; mobile phase: hexane:ethanol=1:1) to obtain (+)-8-fluoro-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine with a retention time of 11 minutes (6 mg, >99% ee), (−)-8-fluoro-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine with a retention time of 12 minutes (5 mg, >99% ee) and 8-(4-fluorophenyl)-2-{(E)-2-[3-methoxy-4-(4-methyl-1H-imidazol-1-yl)phenyl]vinyl}-5,6-dihydro[1,2,4]triazolo[1,5-a]pyridine with a retention time of 14 minutes (2 mg).

The property values of (+)-8-fluoro-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

$^1$H-NMR (CDCl$_3$) δ (ppm): 2.12-2.24 (m, 1H), 2.25-2.38 (m, 4H), 2.46-2.64 (m, 2H), 3.86 (s, 3H), 4.21-4.32 (m, 1H), 4.43-4.50 (m, 1H), 6.92 (brs, 1H), 7.07 (d, J=16.4 Hz, 1H), 7.11 (t, J=7.6 Hz, 2H), 7.15 (dd, J=8.4, 2.4 Hz, 1H), 7.16 (brs, 1H), 7.22 (d, J=8.4 Hz, 1H), 7.39 (dd, J=8.8, 5.6 Hz, 2H), 7.56 (d, J=16.4 Hz, 1H), 7.71 (brs, 1H).

The property values of (−)-8-fluoro-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

$^1$H-NMR (CDCl$_3$) δ (ppm): 2.12-2.24 (m, 1H), 2.25-2.38 (m, 4H), 2.46-2.64 (m, 2H), 3.86 (s, 3H), 4.21-4.32 (m, 1H), 4.43-4.50 (m, 1H), 6.92 (brs, 1H), 7.07 (d, J=16.4 Hz, 1H), 7.11 (t, J=7.6 Hz, 2H), 7.15 (dd, J=8.4, 2.4 Hz, 1H), 7.16 (brs, 1H), 7.22 (d, J=8.4 Hz, 1H), 7.39 (dd, J=8.8, 5.6 Hz, 2H), 7.56 (d, J=16.4 Hz, 1H), 7.71 (brs, 1H).

The property values of 8-(4-fluorophenyl)-2-{(E)-2-[3-methoxy-4-(4-methyl-1H-imidazol-1-yl)phenyl]vinyl}-5,6-dihydro[1,2,4]triazolo[1,5-a]pyridine are as follows.

$^1$H-NMR (CDCl$_3$) δ (ppm): 2.30 (s, 3H), 2.87-2.95 (m, 2H), 3.89 (s, 3H), 4.40 (t, J=8.0 Hz, 2H), 6.44 (t, J=4.8 Hz, 1H), 6.93 (brs, 1H), 7.11 (d, J=16.4 Hz, 1H), 7.13 (t, J=8.4 Hz, 2H), 7.18 (d, J=8.4 Hz, 1H), 7.20 (brs, 1H), 7.25 (d, J=8.4 Hz, 1H), 7.58 (d, J=16.4 Hz, 1H), 7.72 (s, 1H), 7.75 (dd, J=8.4, 5.6 Hz, 2H).

Examples 75 and 76

Synthesis of (−)-2-{(E)-2-[3-methoxy-4-(4-methyl-1H-imidazol-1-yl)phenyl]vinyl}-8-(4-methoxyphenyl)-5,6,7,8-tetrahydro-[1,2,4]triazolo[1,5-a]pyridine and (+)-2-{(E)-2-[3-methoxy-4-(4-methyl-1H-imidazol-1-yl)phenyl]vinyl}-8-(4-methoxyphenyl)-5,6,7,8-tetrahydro-[1,2,4]triazolo[1,5-a]pyridine

[Formula 103]

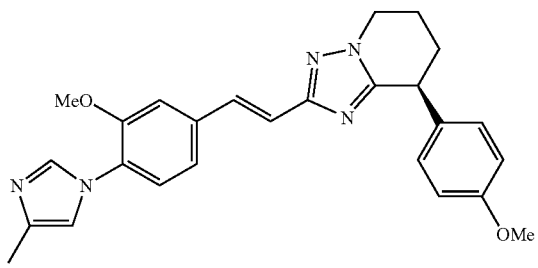

-continued

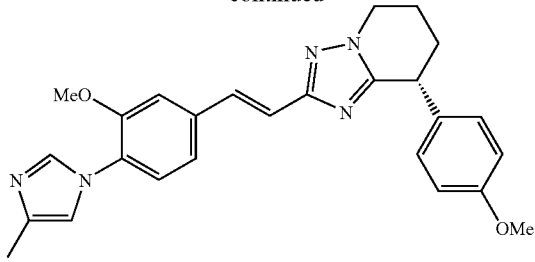

292.3 mg of a racemate of the title compound was obtained from 5-chloro-2-(4-methoxyphenyl)pentanoic acid (970 mg) by the same method as in Examples 51 and 52. The racemate was separated by CHIRALCEL™ OJ-H manufactured by Daicel Chemical Industries, Ltd. (2 cm×25 cm; mobile phase: hexane:ethanol=80:20) to obtain the title optically active compound with a retention time of 17.9 minutes (10.0 mg; >99% ee) and the title optically active compound with a retention time of 27.4 minutes (10.1 mg; >99% ee).

The property values of the title optically active compound with a retention time of 17.9 minutes are as follows.

ESI-MS; m/z 442 [M$^+$+H]. $^1$H-NMR (CDCl$_3$) δ (ppm): 2.02-2.09 (m, 2H), 2.10-2.19 (m, 1H), 2.29 (s, 3H), 2.29-2.44 (m, 1H), 3.79 (s, 3H), 3.85 (s, 3H), 4.24-4.31 (m, 3H), 6.85-6.91 (m, 3H), 7.03-7.08 (m, 3H), 7.13 (d, J=7.6 Hz, 1H), 7.14 (s, 1H), 7.21 (d, J=7.6 Hz, 1H), 7.51 (d, J=16.4 Hz, 1H), 7.68 (s, 1H).

The property values of the title optically active compound with a retention time of 27.4 minutes are as follows.

ESI-MS; m/z 442 [M$^+$+H]. $^1$H-NMR (CDCl$_3$) δ (ppm): 2.02-2.09 (m, 2H), 2.10-2.19 (m, 1H), 2.29 (s, 3H), 2.29-2.44 (m, 1H), 3.79 (s, 3H), 3.85 (s, 3H), 4.24-4.31 (m, 3H), 6.85-6.91 (m, 3H), 7.03-7.08 (m, 3H), 7.13 (d, J=7.6 Hz, 1H), 7.14 (s, 1H), 7.21 (d, J=7.6 Hz, 1H), 7.51 (d, J=16.4 Hz, 1H), 7.68 (s, 1H).

Examples 77 and 78

Synthesis of (−)-2-{(E)-2-[3-methoxy-4-(4-methyl-1H-imidazol-1-yl)phenyl]vinyl}-8-(3,4,5-trifluorophenyl)-5,6-dihydro-8H-[1,2,4]triazolo[5,1-c][1,4]oxazine and (+)-2-{(E)-2-[3-methoxy-4-(4-methyl-1H-imidazol-1-yl)phenyl]vinyl}-8-(3,4,5-trifluorophenyl)-5,6-dihydro-8H-[1,2,4]triazolo[5,1-c][1,4]oxazine

[Formula 104]

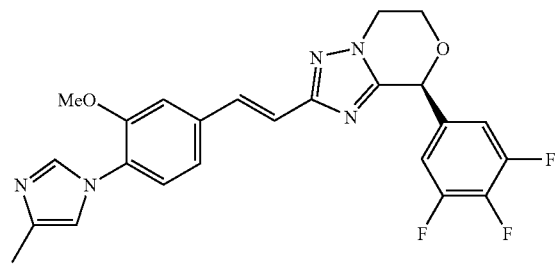

-continued

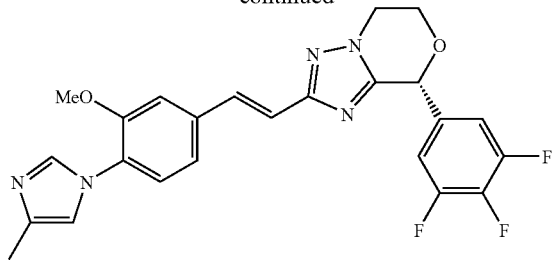

Synthesis of 5-[bis-(2-chloroethoxy)methyl]-1,2,3-trifluorobenzene p-Toluenesulfonic acid monohydrate (593 mg) was added to a solution of 3,4,5-trifluorobenzaldehyde (5 g) and 2-chloroethanol (10 mL) in benzene (100 mL), and the reaction solution was heated under reflux for 48 hours using a Dean-Stark reflux tube. The reaction solution was returned to room temperature and then concentrated under reduced pressure. Ethyl acetate and saturated sodium bicarbonate solution were added to the resulting residue, and the organic layer was separated. The resulting organic layer was washed with brine, and then dried over anhydrous magnesium sulfate and concentrated under reduced pressure. The residue was purified by silica gel column chromatography (carrier: Chromatorex NH; elution solvent: heptane:ethyl acetate=20:1) to obtain 9.3 g of the title compound. The property values of the compound are as follows.

$^1$H-NMR (CDCl$_3$) δ (ppm): 3.68 (t, J=5.6 Hz, 4H), 3.79 (t, J=5.6 Hz, 4H), 5.63 (s, 1H), 7.16 (t, J=7.2 Hz, 2H).

Synthesis of (2-chloroethoxy)-(3,4,5-trifluorophenyl)acetonitrile

5-[bis-(2-chloroethoxy)methyl]-1,2,3-trifluorobenzene (9.3 g) was added dropwise to a mixed solution of acetyl chloride (4.8 mL) with thionyl chloride (0.112 mL). The reaction solution was stirred at 60° C. for 24 hours, and then left to cool to room temperature and concentrated under reduced pressure. Toluene (20 mL) and copper cyanide (3.57 g) were added to the resulting residue, and the mixed solution was heated under reflux for three hours and left to cool to room temperature. A saturated sodium bicarbonate solution and ethyl acetate were added to the reaction solution. The resulting precipitate was removed by filtration through celite, and then the organic layer was separated. The resulting organic layer was washed with brine, dried over anhydrous magnesium sulfate and then concentrated under reduced pressure. The residue was purified by silica gel column chromatography (carrier: Chromatorex NH; elution solvent: heptane:ethyl acetate=20:1) to obtain 6.1 g of the title compound. The property values of the compound are as follows.

$^1$H-NMR (CDCl$_3$) δ (ppm): 3.72 (dd, J=5.6, 5.2 Hz, 2H), (dt, J=10.4, 5.6 Hz, 1H), 3.83 (dt, J=10.4, 5.2 Hz, 1H), 5.33 (s, 1H), 7.20 (t, J=7.2 Hz, 2H).

Synthesis of (2-chloroethoxy)-(3,4,5-trifluorophenyl)acetic acid

Concentrated hydrochloric acid (20 mL) was added to (2-chloroethoxy)-(3,4,5-trifluorophenyl)acetonitrile (2 g), and the reaction solution was heated under reflux for 24 hours. The reaction solution was left to cool to room temperature and then concentrated under reduced pressure. A 1 N sodium hydroxide solution and diethyl ether were added to the resulting residue, and the aqueous layer was separated. A 5 N hydrochloric acid solution was added to the resulting aqueous layer to make the layer acidic, followed by extraction with ethyl acetate. The resulting organic layer was washed with brine, dried over anhydrous sodium sulfate and then concentrated under reduced pressure to obtain 1.9 g of the title compound. The property values of the compound are as follows.

$^1$H-NMR (CDCl$_3$) δ (ppm): 3.69-3.80 (m, 3H), 3.89 (dq, J=10.8, 5.6 Hz, 1H), 4.91 (s, 1H), 7.14 (t, J=7.2 Hz, 2H).

Synthesis of tert-butyl N'-[2-(2-chloroethoxy)-2-(3,4,5-trifluorophenyl)acetyl]hydrazinecarboxylate HOBT (1.91 g), IPEA (4.31 mL) and EDC (2.71 g) were sequentially added to a solution of (2-chloroethoxy)-(3,4,5-trifluorophenyl)acetic acid (1.9 g) and tert-butyl carbazate (1.03 g) in DMF (30 mL), and the reaction solution was stirred at room temperature for five hours. Ethyl acetate and water were added to the reaction solution, and the organic layer was separated. The resulting organic layer was washed with brine, dried over anhydrous sodium sulfate and then concentrated under reduced pressure. The residue was purified by silica gel column chromatography (elution solvent: heptane-ethyl acetate system) to obtain 1.75 g of the title compound. The property values of the compound are as follows.

$^1$H-NMR (CDCl$_3$) δ (ppm): 1.46 (s, 9H), 3.72 (t, J=5.2 Hz, 2H), 3.84 (t, J=5.2 Hz, 2H), 4.86 (s, 1H), 6.34 (bs, 1H), 7.14 (t, J=7.2 Hz, 2H), 8.35 (s, 1H).

Synthesis of (2-chloroethoxy)-(3,4,5-trifluorophenyl) acetic acid N'-{(E)-3-[3-methoxy-4-(4-methyl-1H-imidazol-1-yl)phenyl]acryloyl}hydrazide A solution of 4 N hydrochloric acid in ethyl acetate (10 mL) was added to tert-butyl N'-[2-(2-chloroethoxy)-2-(3,4,5-trifluorophenyl)acetyl]hydrazinecarboxylate (700 mg). The reaction solution was stirred at room temperature for one hour and then concentrated under reduced pressure. (E)-3-[3-methoxy-4-(4-methyl-1H-imidazol-1-yl)phenyl]acrylic acid (473 mg), BOPCl (606 mg) and IPEA (1.59 mL) were sequentially added to a solution of the resulting residue in methylene chloride (15 mL), and the reaction solution was stirred at room temperature for two hours. Ethyl acetate and a saturated ammonium chloride solution were added to the reaction solution, and the organic layer was separated. The resulting organic layer was washed with brine, dried over anhydrous sodium sulfate and then concentrated under reduced pressure. The residue was purified by silica gel column chromatography (carrier: Chromatorex NH; elution solvent: ethyl acetate-methanol system) to obtain 344.9 mg of the title compound. The property values of the compound are as follows.

$^1$H-NMR (CDCl$_3$) δ (ppm): 2.29 (s, 3H), 3.75 (t, J=5.6 Hz, 2H), 3.84-3.86 (m, 5H), 4.91 (s, 1H), 6.45 (d, J=15.6 Hz, 1H), 6.92 (s, 1H), 7.09-7.23 (m, 4H), 7.23 (s, 1H), 7.68 (d, J=15.6 Hz, 1H), 7.73 (s, 1H).

Synthesis of (−)-2-{(E)-2-[3-methoxy-4-(4-methyl-1H-imidazol-1-yl)phenyl]vinyl}-8-(3,4,5-trifluorophenyl)-5,6-dihydro-8H-[1,2,4]triazolo[5,1-c][1,4]oxazine and (+)-2-{(E)-2-[3-methoxy-4-(4-methyl-1H-imidazol-1-yl)phenyl]vinyl}-8-(3,4,5-trifluorophenyl)-5,6-dihydro-8H-[1,2,4]triazolo[5,1-c][1,4]oxazine A solution of (2-chloroethoxy)-(3,4,5-trifluorophenyl)acetic acid N'-{(E)-3-[3-methoxy-4-(4-methyl-1H-imidazol-1-yl)phenyl]acryloyl}hydrazide (340 mg) in phosphorus oxychloride (4 mL) was stirred at 120° C. for five hours. The reaction solution was left to cool to room temperature and then concentrated under reduced pressure. A saturated sodium bicarbonate solution and ethyl acetate were added to the resulting residue, and the organic layer was separated. The resulting organic layer was washed with brine, dried over anhydrous magnesium sulfate and then concentrated under reduced pressure. Acetic acid (5 mL) and ammonium acetate (1 g) were added to the residue, and the reaction solution was stirred at 150° C. for 15 hours. The reaction solution was left to cool to room temperature and concentrated under reduced pressure. A saturated sodium bicarbonate solution and ethyl acetate were added to the resulting residue, and the organic layer was separated. The resulting organic layer was washed with brine, dried over anhydrous magnesium sulfate and then concentrated under reduced pressure. The residue was purified by silica gel column chromatography (carrier: Chromatorex NH; elution solvent: heptane-ethyl acetate system) to obtain 15.8 mg of a racemate of the title compound. The racemate was separated by CHIRALCEL™ OJ-H manufactured by Daicel Chemical Industries, Ltd. (2 cm×25 cm; mobile phase: hexane:ethanol=80:20) to obtain the title optically active compound with a retention time of 18.7 minutes (5.1 mg; >99% ee) and the title optically active compound with a retention time of 23.2 minutes (3.9 mg; >99% ee).

The property values of the title optically active compound with a retention time of 18.7 minutes are as follows.

ESI-MS; m/z 468 [M$^+$+H]. $^1$H-NMR (CDCl$_3$) δ (ppm): 2.30 (s, 3H), 3.88 (s, 3H), 4.15-4.21 (m, 1H), 4.27-4.37 (m, 3H), 5.85 (s, 1H), 6.92 (s, 1H), 7.06 (d, J=16.0 Hz, 1H), 7.17-7.27 (m, 5H), 7.55 (d, J=16.0 Hz, 1H), 7.71 (s, 1H).

The property values of the title optically active compound with a retention time of 23.2 minutes are as follows.

ESI-MS; m/z 468 [M$^+$+H]. $^1$H-NMR (CDCl$_3$) δ (ppm): 2.30 (s, 3H), 3.88 (s, 3H), 4.15-4.21 (m, 1H), 4.27-4.37 (m, 3H), 5.85 (s, 1H), 6.92 (s, 1H), 7.06 (d, J=16.0 Hz, 1H), 7.17-7.27 (m, 5H), 7.55 (d, J=16.0 Hz, 1H), 7.71 (s, 1H).

Examples 79 and 80

Synthesis of (−)-8-(4-fluorophenyl)-2-{(E)-2-[3-methoxy-4-(4-methyl-1H-imidazol-1-yl)phenyl]vinyl}-8-methyl-5,6,7,8-tetrahydro-[1,2,4]triazolo[1,5-a]pyridine and (+)-8-(4-fluorophenyl)-2-{(E)-2-[3-methoxy-4-(4-methyl-1H-imidazol-1-yl)phenyl]vinyl}-8-methyl-5,6,7,8-tetrahydro-[1,2,4]triazolo[1,5-a]pyridine

[Formula 105]

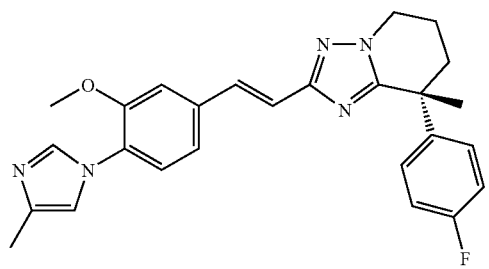

[Formula 106]

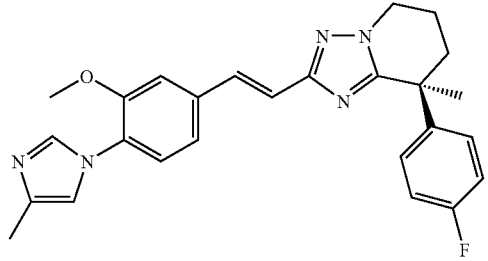

142.1 mg of a racemate of the title compound was obtained from 5-chloro-2-(4-fluorophenyl)-2-methylpentanoic acid (870 mg) by the same method as in Examples 51 and 52. The racemate was separated by CHIRALCEL™ OD-H manufactured by Daicel Chemical Industries, Ltd. (2 cm×25 cm; mobile phase: hexane:ethanol=80:20) to obtain the title optically active compound with a retention time of 7.9 minutes (8.8 mg; >99% ee) and the title optically active compound with a retention time of 11.4 minutes (8.7 mg; >99% ee).

The property values of the title optically active compound with a retention time of 7.9 minutes are as follows.

ESI-MS; m/z 444 [M$^+$+H]. $^1$H-NMR (CDCl$_3$) δ (ppm): 1.83 (s, 3H), 1.84-1.92 (m, 1H), 1.99-2.07 (m, 2H), 2.30 (s, 3H), 2.29-2.37 (m, 1H), 3.87 (s, 3H), 4.14 (ddd, J=15.6, 10.4, 5.2 Hz, 1H), 4.27 (ddd, J=15.6, 8.8, 6.0 Hz, 1H), 6.92 (s, 1H), 6.95-7.01 (m, 2H), 7.04-7.09 (m, 2H), 7.13 (s, 1H), 7.16-7.24 (m, 3H), 7.58 (d, J=16.8 Hz, 1H), 7.70 (s, 1H).

The property values of the title optically active compound with a retention time of 11.4 minutes are as follows.

ESI-MS; m/z 444 [M$^+$+H]. $^1$H-NMR (CDCl$_3$) δ (ppm): 1.83 (s, 3H), 1.84-1.92 (m, 1H), 1.99-2.07 (m, 2H), 2.30 (s, 3H), 2.29-2.37 (m, 1H), 3.87 (s, 3H), 4.14 (ddd, J=15.6, 10.4, 5.2 Hz, 1H), 4.27 (ddd, J=15.6, 8.8, 6.0 Hz, 1H), 6.92 (s, 1H), 6.95-7.01 (m, 2H), 7.04-7.09 (m, 2H), 7.13 (s, 1H), 7.16-7.24 (m, 3H), 7.58 (d, J=16.8 Hz, 1H), 7.70 (s, 1H).

Example 81

Synthesis of 2-(4-fluorobenzyl)-8-{1-[3-methoxy-4-(4-methyl-1H-imidazol-1-yl)phenyl]-(E)-methylidene}-5,6,7,8-tetrahydro[1,2,4]triazolo[1,5-a]pyridine

[Formula 106]

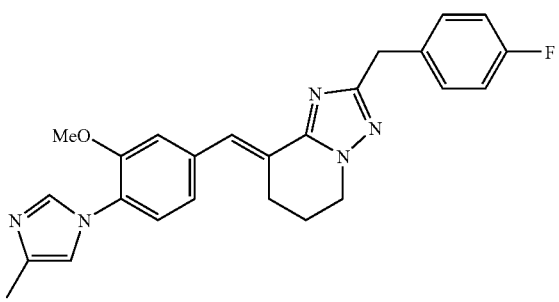

Synthesis of 2-(4-fluorophenyl)-N-{3-{1-[3-methoxy-4-(4-methyl-1H-imidazol-1-yl)phenyl]-(E)-methylidene}-2-oxopiperidin-1-yl}acetamide and (4-fluorophenyl)acetic acid N'-{5-chloro-2-{1-[3-methoxy-4-(4-methyl-1H-imidazol-1-yl)phenyl]-(E)-methylidene}pentanoyl}hydrazide IPEA (0.5 mL), HOBT (128 mg) and EDC (182 mg) were added to a solution of 5-chloro-2-{1-[3-methoxy-4-(4-methyl-1H-imidazol-1-yl)phenyl]-(E)-methylidene}valeric acid hydrazide dihydrochloride (200 mg) and 4-fluorophenylacetic acid (73 mg) in DMF (3 mL), and the reaction solution was stirred at room temperature for six hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: ethyl acetate→ethyl acetate:methanol=5:1) to obtain 75 mg of 2-(4-fluorophenyl)-N-{3-{1-[3-methoxy-4-(4-methyl-1H-imidazol-1-yl)phenyl]-(E)-methylidene}-2-oxopiperidin-1-yl}acetamide and 217 mg of (4-fluorophenyl)acetic acid N'-{5-chloro-2-{1-[3-methoxy-4-(4-methyl-1H-imidazol-1-yl)phenyl]-(E)-methylidene}pentanoyl}hydrazide.

The property value of 2-(4-fluorophenyl)-N-{3-{1-[3-methoxy-4-(4-methyl-1H-imidazol-1-yl)phenyl]-(E)-methylidene}-2-oxopiperidin-1-yl}acetamide is as follows.

ESI-MS; m/z 449 [M++H].

The property value of (4-fluorophenyl)acetic acid N'-{5-chloro-2-{1-[3-methoxy-4-(4-methyl-1H-imidazol-1-yl)phenyl]-(E)-methylidene}pentanoyl}hydrazide is as follows.

ESI-MS; m/z 485 [M++H].

Synthesis of 2-(4-fluorobenzyl)-8-{1-[3-methoxy-4-(4-methyl-1H-imidazol-1-yl)phenyl]-(E)-methylidene}-5,6,7,8-tetrahydro[1,2,4]triazolo[1,5-a]pyridine A solution of 2-(4-fluorophenyl)-N-{3-{1-[3-methoxy-4-(4-methyl-1H-imidazol-1-yl)phenyl]-(E)-methylidene}-2-oxopiperidin-1-yl}acetamide (75 mg) in phosphorus oxychloride (2 mL) was stirred at 120° C. for one hour. The reaction solution was left to cool to room temperature and then concentrated under reduced pressure. Ammonium acetate (257 mg) was added to a solution of the residue in acetic acid (2 mL), and the reaction solution was stirred at 150° C. for one hour. The reaction solution was left to cool to room temperature. Then, ethyl acetate and saturated sodium bicarbonate water were added to the reaction solution, and the organic layer was separated. The resulting organic layer was washed with brine, dried over anhydrous magnesium sulfate and then concentrated under reduced pressure. The residue was purified by silica gel column chromatography (carrier: Chromatorex NH; elution solvent: heptane:ethyl acetate=1:1→ethyl acetate) to obtain 40 mg of the title compound. The property values of the compound are as follows.

ESI-MS; m/z 430 [M++H]. $^1$H-NMR (CDCl$_3$) δ (ppm): 2.10-2.18 (m, 2H), 2.30 (s, 3H), 2.90-2.96 (m, 2H), 3.84 (s, 3H), 4.06 (s, 2H), 4.20-4.25 (m, 2H), 6.92 (brs, 1H), 6.98 (t, J=8.8 Hz, 2H), 7.02 (d, J=2.8 Hz, 1H), 7.05 (dd, J=8.0, 2.8 Hz, 1H), 7.25 (d, J=8.0 Hz, 1H), 7.33 (dd, J=8.8, 5.6 Hz, 2H), 7.66 (brs, 1H), 7.71 (d, J=1.2 Hz, 1H).

Example 82

Synthesis of 3-(4-fluorobenzyl)-8-{1-[3-methoxy-4-(4-methyl-1H-imidazol-1-yl)phenyl]-(E)-methylidene}-5,6,7,8-tetrahydro[1,2,4]triazolo[4,3-a]pyridine

[Formula 107]

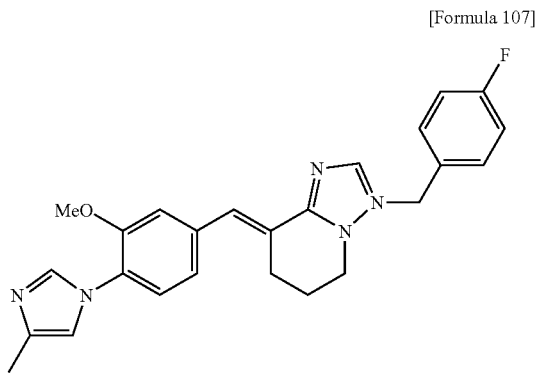

Synthesis of 2-{4-chloro-1-{1-[3-methoxy-4-(4-methyl-1H-imidazol-1-yl)phenyl]-(E)-methylidene}butyl}-5-(4-fluorobenzyl) [1,3,4]oxadiazole A solution of N'-{5-chloro-2-{1-[3-methoxy-4-(4-methyl-1H-imidazol-1-yl)phenyl]-(E)-methylidene}pentanoyl}hydrazide (217 mg) in phosphorus oxychloride (1 mL) was stirred at 120° C. for two hours. The reaction solution was left to cool to room temperature and concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1→ethyl acetate) to obtain 97 mg of the title compound. The property values of the compound are as follows.

ESI-MS; m/z 467 [M++H]. $^1$H-NMR (CDCl$_3$) δ (ppm): 2.15-2.24 (m, 2H), 2.30 (s, 3H), 2.96-3.01 (m, 2H), 3.65 (t, J=6.0 Hz, 2H), 3.89 (s, 3H), 4.22 (s, 2H), 6.94 (brs, 1H), 7.02-7.09 (m, 4H), 7.28 (d, J=8.0 Hz, 1H), 7.33 (dd, J=8.4, 5.2 Hz, 2H), 7.41 (s, 1H), 7.73 (d, J=1.6 Hz, 1H).

Synthesis of 2-{4-azido-1-{1-[3-methoxy-4-(4-methyl-1H-imidazol-1-yl)phenyl]-(E)-methylidene}butyl}-5-(4-fluorobenzyl)[1,3,4]oxadiazole Sodium iodide (35 mg) and sodium azide (20 mg) were added to a solution of 2-{4-chloro-1-{1-[3-methoxy-4-(4-methyl-1H-imidazol-1-yl)phenyl]-(E)-methylidene}butyl}-5-(4-fluorobenzyl)[1,3,4]oxadiazole (72 mg) in DMF (2 mL), and the reaction solution was stirred at 80° C. for five hours. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=3:1→ethyl acetate) to obtain 50 mg of the title compound. The property values of the compound are as follows.

ESI-MS; m/z 474 [M++H]. $^1$H-NMR (CDCl$_3$) δ (ppm): 1.93-2.02 (m, 2H), 2.30 (s, 3H), 2.87-2.94 (m, 2H), 3.41 (t, J=6.4 Hz, 2H), 3.89 (s, 3H), 4.22 (s, 2H), 6.94 (brs, 1H), 7.02-7.09 (m, 4H), 7.28 (d, J=8.0 Hz, 1H), 7.30-7.35 (m, 2H), 7.41 (s, 1H), 7.74 (brs, 1H).

Synthesis of 3-(4-fluorobenzyl)-8-{1-[3-methoxy-4-(4-methyl-1H-imidazol-1-yl)phenyl]-(E)-methylidene}-5,6,7,8-tetrahydro[1,2,4]triazolo[4,3-a]pyridine Triphenylphosphine (28 mg) and water (0.3 mL) were added to a solution of 2-{4-azido-1-{1-[3-methoxy-4-(4-methyl-1H-imidazol-1-yl)phenyl]-(E)-methylidene}butyl}-5-(4-fluorobenzyl)[1,3,4]oxadiazole (50 mg) in THF (5 mL), and the reaction solution was heated under reflux for four hours. The reaction solution was left to cool to room temperature and then concentrated under reduced pressure. A solution of the residue in acetic acid (2 mL) was heated under reflux for three hours. The reaction solution was left to cool to room temperature and then concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. The residue was purified by silica gel column chromatography (carrier: Chromatorex NH; elution solvent: ethyl acetate→ethyl acetate:methanol=5:1) to obtain 40 mg of the title compound. The property values of the compound are as follows.

$^1$H-NMR (CDCl$_3$) δ (ppm): 1.95-2.02 (m, 2H), 2.30 (s, 3H), 2.84-2.90 (m, 2H), 3.71 (t, J=6.0 Hz, 2H), 3.86 (s, 3H), 4.21 (s, 2H), 6.93 (brs, 1H), 7.01 (t, J=8.4 Hz, 2H), 7.04 (d, J=2.0 Hz, 1H), 7.05 (dd, J=8.0, 2.0 Hz, 1H), 7.20 (dd, J=8.4, 5.2 Hz, 2H), 7.25 (d, J=8.0 Hz, 1H), 7.71 (d, J=1.6 Hz, 1H), 7.88 (brs, 1H).

Example 83

Synthesis of 3-{(E)-2-[3-methoxy-4-(4-methyl-1H-imidazol-1-yl)phenyl]vinyl}-5-((S)-1-phenylethyl)-4H-[1,2,4]triazole

[Formula 108]

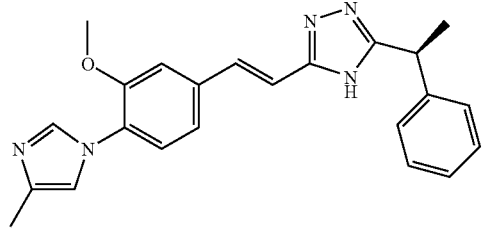

Synthesis of (E)-3-[3-methoxy-4-(4-methyl-1H-imidazol-1-yl)phenyl]acrylonitrile

A lithium hydroxide monohydrate powder (2.23 g) was added to a suspension of 3-methoxy-4-(4-methyl-1H-imidazol-1-yl)benzaldehyde (10 g) and diethyl cyanomethylphosphonate (8.2 g) in THF (50 ml) under ice-cooling, and the reaction solution was stirred at the same temperature for one hour. Ethyl acetate (200 mL) and water were added to the reaction solution, and the organic layer was separated. The organic layer was washed with brine, dried over anhydrous magnesium sulfate and then filtered through a silica gel pad (carrier: Chromatorex™ NH). The filtrate was concentrated under reduced pressure. The resulting residue was crystallized from ethyl acetate and hexane, and the crystals were collected by filtration. The resulting crystals were dried under reduced pressure to obtain 7.49 g of the title compound. The property values of the compound are as follows.

$^1$H-NMR (CDCl$_3$) δ (ppm): 2.30 (s, 3H), 3.91 (s, 3H), 5.90 (d, J=16.8 Hz, 1H), 6.93 (d, J=0.8 Hz, 1H), 7.06 (d, J=1.6 Hz, 1H), 7.13 (dd, J=8.0, 1.6 Hz, 1H), 7.29 (d, J=8.0 Hz, 1H), 7.39 (d, J=16.8 Hz, 1H), 7.74 (d, J=0.8 Hz, 1H).

Synthesis of ethyl(E)-3-[3-methoxy-4-(4-methyl-1H-imidazol-1-yl)phenyl]acrylimidate A suspension of (E)-3-[3-methoxy-4-(4-methyl-1H-imidazol-1-yl)phenyl]acrylonitrile (700 mg) in ethanol (6 mL) was saturated with hydrogen chloride gas under ice-cooling, and then the reaction solution was stirred at 0° C. overnight. Diethyl ether (10 mL) was added to the reaction solution. The precipitate was removed by filtration, and the filtrate was concentrated under reduced pressure. Ethyl acetate and a saturated sodium bicarbonate solution were added to the resulting residue, and the organic layer was separated. The organic layer was washed with brine, dried over anhydrous magnesium sulfate and then concentrated under reduced pressure. The resulting residue was purified by silica gel column chromatography (elution solvent: heptane-ethyl acetate-ethanol system) to obtain 127 mg of the title compound. The property values of the compound are as follows.

$^1$H-NMR (DMSO-D$_6$) δ (ppm): 1.29 (t, J=6.8 Hz, 3H), 2.14 (s, 3H), 3.87 (s, 3H), 4.17 (q, J=6.8 Hz, 2H), 6.74 (d, J=16.4 Hz, 1H), 7.14 (s, 1H), 7.21 (d, J=16.4 Hz, 1H), 7.23 (d, J=8.0 Hz, 1H), 7.38 (d, J=8.0 Hz, 1H), 7.41 (s, 1H), 7.78 (s, 1H), 8.32 (s, 1H).

Synthesis of tert-butyl N'-((S)-2-phenylpropionyl)hydrazinecarboxylate

EDC (734 mg) was added to a solution of (S)-(+)-2-phenylpropionic acid (CAS #7782-24-3, 500 mg), tert-butyl carbazate (CAS #870-46-2, 440 mg) and HOBT (517 mg) in DMF (7.5 ml), and the reaction solution was stirred at room temperature for eight hours. Ethyl acetate and a sodium bicarbonate solution were added to the reaction solution, and the organic layer was separated. The organic layer was washed with water and brine, dried over anhydrous magnesium sulfate and then concentrated under reduced pressure. Ethyl acetate and heptane were added to the resulting residue, and the precipitated solid was collected by filtration to obtain 482 mg of the title compound. The property values of the compound are as follows.

$^1$H-NMR (DMSO-D$_6$) δ (ppm): 1.33 (d, J=6.8 Hz, 3H), 1.38 (s, 9H), 3.59 (q, J=6.8 Hz, 1H), 7.17-7.35 (m, 5H), 8.69 (s, 1H), 9.71 (s, 1H).

Synthesis of (S)-2-phenylpropionic acid hydrazide monohydrochloride

4 N hydrogen chloride-ethyl acetate (2 mL) was added to a suspension of tert-butyl N'-((S)-2-phenylpropionyl)hydrazinecarboxylate (470 mg) in ethyl acetate (4 mL), and the reaction solution was stirred at room temperature overnight. Diethyl ether (6 mL) was added to the reaction solution, and the precipitated powder was collected by filtration. The resulting solid was dried under reduced pressure to obtain 280 mg of the title compound. The property values of the compound are as follows.

$^1$H-NMR (DMSO-D$_6$) δ (ppm): 1.39 (d, J=7.2 Hz, 3H), 3.79 (q, J=7.2 Hz, 1H), 7.21-7.37 (m, 5H), 10.29 (brs, 3H), 11.22 (s, 1H).

Synthesis of 3-{(E)-2-[3-methoxy-4-(4-methyl-1H-imidazol-1-yl)phenyl]vinyl}-5-((S)-1-phenylethyl)-4H-[1,2,4]triazole A solution of ethyl(E)-3-[3-methoxy-4-(4-methyl-1H-imidazol-1-yl)phenyl]acrylimidate (30 mg) and TEA (35 ul) in ethanol (0.5 ml) was added to a solution of (S)-2-phenylpropionic acid hydrazide monohydrochloride (37 mg) and TEA (35 uL) in ethanol (0.5 mL), and the reaction solution was stirred at 75° C. for 19 hours. The reaction solution was left to cool to room temperature. Then, ethyl acetate and water were added to the reaction solution, and the organic layer was separated. The organic layer was washed with brine, dried over anhydrous magnesium sulfate and then concentrated under reduced pressure. The resulting residue was purified by silica gel column chromatography (elution solvent: ethyl acetate-ethanol system) to obtain 13.5 mg of the title compound with positive optical rotation. The property values of the compound are as follows.

ESI-MS; m/z 386 [M$^+$+H]. $^1$H-NMR (CDCl$_3$) δ (ppm): 1.80 (d, J=7.2 Hz, 3H), 2.29 (s, 3H), 3.87 (s, 3H), 4.32 (q, J=7.2 Hz, 1H), 6.92 (brs, 1H), 7.08 (d, J=16.0 Hz, 1H), 7.17 (brd, J=7.6 Hz, 1H), 7.18 (brs, 1H), 7.22 (d, J=7.6 Hz, 1H), 7.28-7.39 (m, 5H), 7.57 (d, J=16.0 Hz, 1H), 7.69 (d, J=0.8 Hz, 1H).

Example 84

Synthesis of 3-{(E)-2-[3-methoxy-4-(4-methyl-1H-imidazol-1-yl)phenyl]vinyl}-5-((R)-1-phenylethyl)-4H-[1,2,4]triazole

[Formula 109]

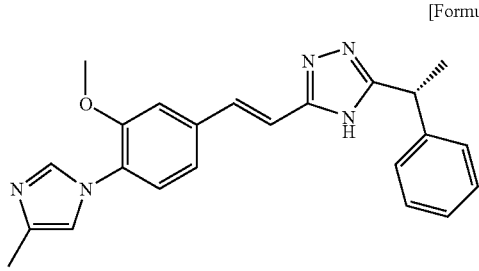

Synthesis of (R)-2-phenylpropionic acid hydrazide monohydrochloride 272 mg of the title compound was obtained from (R)-(−)-2-phenylpropionic acid (CAS #7782-26-5, 500 mg) and tert-butyl carbazate (440 mg) by the same method as in Example 83. The property values of the compound are as follows.

$^1$H-NMR (DMSO-D$_6$) δ (ppm): 1.39 (d, J=7.2 Hz, 3H), 3.79 (q, J=7.2 Hz, 1H), 7.21-7.37 (m, 5H), 10.32 (brs, 3H), 11.24 (s, 1H).

Synthesis of 3-{(E)-2-[3-methoxy-4-(4-methyl-1H-imidazol-1-yl)phenyl]vinyl}-5-((R)-1-phenylethyl)-4H-[1,2,4]triazole 17.6 mg of the title compound with negative optical rotation was obtained from (R)-2-phenylpropionic acid hydrazide monohydrochloride (22.5 mg) and ethyl(E)-3-[3-methoxy-4-(4-methyl-1H-imidazol-1-yl)phenyl]acrylimidate (29 mg) by the same method as in Example 83. The property values of the compound are as follows.

ESI-MS; m/z 386 [M$^+$+H]. $^1$H-NMR (CDCl$_3$) δ (ppm): 1.80 (d, J=7.2 Hz, 3H), 2.29 (s, 3H), 3.87 (s, 3H), 4.32 (q, J=7.2 Hz, 1H), 6.92 (brs, 1H), 7.08 (d, J=16.0 Hz, 1H), 7.17 (brd, J=7.6 Hz, 1H), 7.18 (brs, 1H), 7.22 (d, J=7.6 Hz, 1H), 7.28-7.39 (m, 5H), 7.57 (d, J=16.0 Hz, 1H), 7.69 (d, J=0.8 Hz, 1H).

Examples 85 and 86

Synthesis of (−) and (+)-8-(4-fluorophenyl)-8-methoxy-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 110]

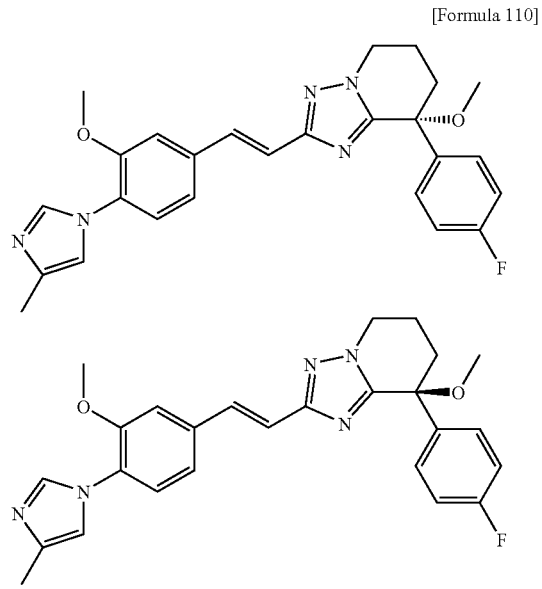

Synthesis of ethyl(E)-3-[3-methoxy-4-(4-methyl-1H-imidazol-1-yl)phenyl]acrylimidate dihydrochloride A suspension of (E)-3-[3-methoxy-4-(4-methyl-1H-imidazol-1-yl)phenyl]acrylonitrile (7.45 g) in ethanol (75 mL) was bubbled with hydrogen chloride gas under ice-cooling for 10 minutes and at room temperature for 15 minutes, and then the reaction solution was stirred at room temperature overnight. The reaction solution was concentrated under reduced pressure. Then, ethanol and diethyl ether were added to the residue, and the precipitated powder was collected by filtration. The resulting powder was crystallized from ethanol and diethyl ether to obtain 9.22 g of the title compound. The property values of the compound are as follows.

ESI-MS; m/z 286 [M$^+$+H−2HCl]. $^1$H-NMR (DMSO-D$_6$) δ (ppm): 1.46 (t, J=6.8 Hz, 3H), 2.35 (s, 3H), 3.93 (s, 3H), 4.54

(q, J=6.8 Hz, 2H), 7.18 (d, J=16.0 Hz, 1H), 7.50 (dd, J=8.0, 1.2 Hz, 1H), 7.68-7.77 (m, 3H), 8.01 (d, J=16.0 Hz, 1H), 9.35 (s, 1H).

Synthesis of methyl (4-fluorophenyl)methoxyacetate

Cesium carbonate (6.5 g) was added to a solution of 4-fluoromandelic acid (CAS #395-33-5, 1.7 g) and methyl iodide (1.9 mL) in DMF (15 ml), and the reaction solution was stirred at room temperature for 11 hours. Ethyl acetate and water were added to the reaction solution, and the organic layer was separated. The organic layer was washed with water and brine, dried over anhydrous magnesium sulfate and then concentrated under reduced pressure. The residue was purified by silica gel column chromatography (elution solvent: heptane-ethyl acetate system) to obtain 1.22 g of the title compound. The property values of the compound are as follows.
$^1$H-NMR (CDCl$_3$) δ (ppm): 3.40 (s, 3H), 3.72 (s, 3H), 4.75 (s, 1H), 7.02-7.70 (m, 2H), 7.39-7.43 (m, 2H).

Synthesis of methyl 5-chloro-2-(4-fluorophenyl)-2-methoxyvalerate

A solution of methyl (4-fluorophenyl)methoxyacetate (300 mg) in THF (1.5 mL) was added dropwise at −78° C. to a solution in THF (7 mL) of lithium diisopropylamide prepared from diisopropylamine (0.26 mL) and n-butyl lithium (2.66 M solution in hexane, 0.63 mL). Then, the reaction solution was gradually heated to −30° C. 1-chloro-3-iodopropane (0.25 ml) was added dropwise to the reaction solution at −30° C. Then, the reaction solution was gradually heated to 0° C. and stirred at the same temperature for one hour. A saturated ammonium chloride solution and ethyl acetate were sequentially added to the reaction solution, and the organic layer was separated. The resulting organic layer was sequentially washed with water, 1 N hydrochloric acid, water, a saturated sodium bicarbonate solution and brine. The resulting organic layer was dried over anhydrous magnesium sulfate and then concentrated under reduced pressure. The resulting residue was purified by silica gel column chromatography (elution solvent: heptane-ethyl acetate system) to obtain 152 mg of the title compound. The property values of the compound are as follows.
$^1$H-NMR (CDCl$_3$) δ (ppm): 1.60-1.70 (m, 2H), 2.24-2.31 (m, 1H), 2.42-2.51 (m, 1H), 3.24 (s, 3H), 3.50-3.58 (m, 2H), 3.72 (s, 3H), 7.00-7.08 (m, 2H), 7.40-7.47 (m, 2H).

Synthesis of 5-chloro-2-(4-fluorophenyl)-2-methoxyvaleric acid

A 4 N sodium hydroxide solution (0.2 mL) was added to a mixed solution of methyl 5-chloro-2-(4-fluorophenyl)-2-methoxyvalerate (141 mg) in THF (1 mL) and methanol (0.5 mL), and the reaction solution was stirred at room temperature for 3.5 hours. Methanol (0.5 mL) and a 4 N sodium hydroxide solution (0.1 mL) were added to the reaction solution, and the reaction solution was further stirred at room temperature for 1.5 hours. Water was added to the reaction solution which was then washed with diethyl ether. 1 N hydrochloric acid (1.4 mL) and ethyl acetate were added to the resulting aqueous layer, and the organic layer was separated. The resulting ethyl acetate layer was washed with brine and dried over anhydrous magnesium sulfate. The resulting ethyl acetate layer was concentrated under reduced pressure to obtain 109 mg of the title compound. The property values of the compound are as follows.
$^1$H-NMR (CDCl$_3$) δ (ppm): 1.75-1.85 (m, 2H), 2.31-2.40 (m, 1H), 2.50-2.59 (m, 1H), 3.24 (s, 3H), 3.51-3.73 (m, 2H), 7.05-7.11 (m, 2H), 7.40-7.47 (m, 2H).

Synthesis of tert-butyl N'-[5-chloro-2-(4-fluorophenyl)-2-methoxypentanoyl]hydrazinecarboxylate Oxalyl chloride (44 μL) was added a mixed solution of 5-chloro-2-(4-fluorophenyl)-2-methoxyvaleric acid (108 mg) in methylene chloride (1 mL) and DMF (1 drop) under ice-cooling, and then the reaction solution was stirred at room temperature for 30 minutes. The acid chloride solution was added dropwise to a solution of tert-butyl carbazate (82 mg) and TEA (0.3 mL) in methylene chloride (2 mL) under ice-cooling, and the reaction solution was stirred at the same temperature for 10 minutes and at room temperature for 30 minutes. Water and ethyl acetate were added to the reaction solution, and the organic layer was separated. The organic layer was sequentially washed with 1 N hydrochloric acid, water, a saturated sodium bicarbonate solution and brine. The resulting organic layer was dried over anhydrous magnesium sulfate and then concentrated under reduced pressure. The resulting residue was purified by silica gel column chromatography (elution solvent: heptane-ethyl acetate system) to obtain 90 mg of the title compound. The property values of the compound are as follows.
ESI-MS; m/z 397 [M$^+$+Na]. $^1$H-NMR (CDCl$_3$) δ (ppm): 1.45 (s, 9H), 1.72-1.92 (m, 2H), 2.27-2.36 (m, 1H), 2.49-2.58 (m, 1H), 3.18 (s, 3H), 3.51-3.58 (m, 1H), 3.62-3.69 (m, 1H), 6.31 (brs, 1H), 7.01-7.08 (m, 2H), 7.42-7.47 (m, 2H), 8.42 (s, 1H).

Synthesis of 5-chloro-2-(4-fluorophenyl)-2-methoxyvaleric acid hydrazide monohydrochloride tert-Butyl N'-[5-chloro-2-(4-fluorophenyl)-2-methoxypentanoyl]hydrazinecarboxylate (90 mg) was dissolved in a solution of 4 N hydrogen chloride in dioxane (1 mL), and the reaction solution was stirred at room temperature for 70 minutes. The reaction solution was concentrated under reduced pressure to obtain 81 mg of the title compound. The property value of the compound is as follows.
ESI-MS; m/z 297 [M$^+$-HCl+Na].

Synthesis of (−) and (+)-8-(4-fluorophenyl)-8-methoxy-2-{(E)-2-[3-methoxy-4-(4-methyl-1H-imidazol-1-yl)phenyl]vinyl}-5,6,7,8-tetrahydro[1,2,4]triazolo[1,5-a]pyridine A solution of 5-chloro-2-(4-fluorophenyl)-2-methoxyvaleric acid hydrazide monohydrochloride (81 mg) and TEA (0.16 ml) in ethanol (1 ml) was added to a solution of ethyl (E)-3-[3-methoxy-4-(4-methyl-1H-imidazol-1-yl)phenyl]acrylimidate dihydrochloride (94 mg) and TEA (0.16 ml) in ethanol (1 ml), and the reaction solution was stirred at 75° C. for 24 hours. The reaction solution was left to cool to room temperature. Then, ethyl acetate and water were added to the reaction solution, and the organic layer was separated. The organic layer was washed with brine, dried over anhydrous magnesium sulfate and then concentrated under reduced pressure. The resulting residue was purified by silica gel column chromatography (carrier: Chromatorex™ NH; elution solvent: heptane-ethyl acetate system) and again purified by silica gel column chromatography (elution solvent: ethyl acetate-methanol system) to obtain 36 mg of 8-(4-fluorophenyl)-8-methoxy-2-{(E)-2-[3-methoxy-4-(4-methyl-1H-imidazol-1-yl)phenyl]vinyl}-5,6,7,8-tetrahydro[1,2,4]triazolo[1,5-a]pyridine as a racemate. Then, the racemate was separated by CHIRALPAK™ AD-H manufactured by Daicel Chemical Industries, Ltd. (2 cm×25 cm; mobile phase: ethanol) to obtain the title optically active compound with a retention time of 15 minutes and negative optical rotation (14.2 mg, 100% ee) and the title optically active compound with a retention time of 18 minutes and positive optical rotation (14.3 mg, >99% ee).

The property values of the title optically active compound with a retention time of 15 minutes are as follows.

ESI-MS; m/z 460 [M$^+$+H]. $^1$H-NMR (CDCl$_3$) δ (ppm): 1.96-2.07 (m, 2H), 2.30 (s, 3H), 2.33-2.40 (m, 1H), 2.43-2.55 (m, 1H), 3.31 (s, 3H), 3.87 (s, 3H), 4.14-4.22 (m, 1H), 4.33-4.40 (m, 1H), 6.92 (d, J=1.2 Hz, 1H), 7.03-7.09 (m, 2H), 7.12 (d, J=16.4 Hz, 1H), 7.17 (d, J=8.0 Hz, 1H), 7.18 (s, 1H), 7.22 (d, J=8.0 Hz, 1H), 7.32-7.38 (m, 2H), 7.57 (d, J=16.4 Hz, 1H), 7.70 (d, J=1.2 Hz, 1H).

The property values of the title optically active compound with a retention time of 18 minutes are as follows.

ESI-MS; m/z 460 [M$^+$+H]. $^1$H-NMR (CDCl$_3$) δ (ppm): 1.96-2.07 (m, 2H), 2.30 (s, 3H), 2.33-2.40 (m, 1H), 2.43-2.55 (m, 1H), 3.31 (s, 3H), 3.87 (s, 3H), 4.14-4.22 (m, 1H), 4.33-4.40 (m, 1H), 6.92 (d, J=1.2 Hz, 1H), 7.03-7.09 (m, 2H), 7.12 (d, J=16.4 Hz, 1H), 7.17 (d, J=8.0 Hz, 1H), 7.18 (s, 1H), 7.22 (d, J=8.0 Hz, 1H), 7.32-7.38 (m, 2H), 7.57 (d, J=16.4 Hz, 1H), 7.70 (d, J=1.2 Hz, 1H).

Examples 87 and 88

Synthesis of (−) and (+)-8-methoxy-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine

[Formula 111]

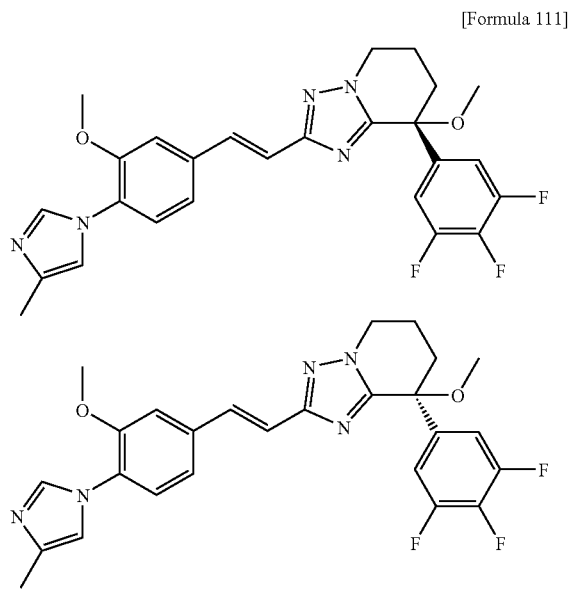

Synthesis of methyl hydroxy-(3,4,5-trifluorophenyl)acetate

Trimethyl cyanide (3.2 mL) was added dropwise to a suspension of 3,4,5-trifluorobenzaldehyde (3.2 g) and Zinc iodide (0.64 g) in methylene chloride (30 mL), and the reaction solution was stirred at room temperature for 3.5 hours. The insoluble matter was removed by filtration, and the filtrate was concentrated. A mixed solution of the resulting residue in methanol (30 mL) and concentrated hydrochloric acid (20 mL) was heated under reflux for two hours. The reaction solution was cooled with ice, and a sodium bicarbonate powder (19 g) was added to the reaction solution while stirring. The reaction solution was concentrated under reduced pressure. Water and diethyl ether were added to the resulting residue, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system), and the resulting yellow crystals were recrystallized from heptane to obtain 3.11 g of the title compound. The property values of the compound are as follows.

$^1$H-NMR (CDCl$_3$) δ (ppm): 3.53 (d, J=5.2 Hz, 1H), 3.80 (s, 3H), 5.11 (d, J=5.2 Hz, 1H), 7.06-7.14 (m, 2H).

Synthesis of tert-butyl N'-[5-chloro-2-methoxy-2-(3,4,5-trifluorophenyl)pentanoyl]hydrazinecarboxylate Methyl hydroxy-(3,4,5-trifluorophenyl)acetate (1.6 g) was methyl-etherified, alkylated, hydrolyzed and then amidated with tert-butyl carbazate by the same method as in Examples 85 and 86 to obtain 15 mg of the title compound. The property values of the compound are as follows.

$^1$H-NMR (CDCl$_3$) δ (ppm): 1.45 (s, 9H), 1.66-1.92 (m, 2H), 2.23-2.32 (m, 1H), 2.43-2.51 (m, 1H), 3.24 (s, 3H), 3.51-3.56 (m, 1H), 3.61-3.68 (m, 1H), 6.29 (brs, 1H), 7.08-7.17 (m, 2H), 8.34 (d, J=2.8 Hz, 1H).

Synthesis of 5-chloro-2-methoxy-2-(3,4,5-trifluorophenyl)valeric acid hydrazide monohydrochloride 13 mg of the title compound was obtained from tert-butyl N'-[5-chloro-2-methoxy-2-(3,4,5-trifluorophenyl)pentanoyl]hydrazinecarboxylate (15 mg) by the same method as in Examples 85 and 86. The property value of the compound is as follows.

ESI-MS; m/z 311 [M$^+$-HCl+H].

Synthesis of (−) and (+)-8-methoxy-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine 3.1 mg of 8-methoxy-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine as a racemate was obtained from ethyl(E)-3-[3-methoxy-4-(4-methyl-1H-imidazol-1-yl)phenyl]acrylimidate dihydrochloride (17 mg) and 5-chloro-2-methoxy-2-(3,4,5-trifluorophenyl)valeric acid hydrazide monohydrochloride (13 mg) by the same method as in Examples 85 and 86. Then, the racemate was separated by CHIRALPAK™ AD-H manufactured by Daicel Chemical Industries, Ltd. (2 cm×25 cm; mobile phase: ethanol) to obtain the title optically active compound with a retention time of 14.5 minutes and negative optical rotation (1.16 mg, 100% ee) and the title optically active compound with a retention time of 17.5 minutes and positive optical rotation (1.19 mg, >98% ee).

The property values of the title optically active compound with a retention time of 14.5 minutes are as follows.

ESI-MS; m/z 496 [M$^+$+H]. $^1$H-NMR (CDCl$_3$) δ (ppm): 1.91-2.08 (m, 2H), 2.30 (s, 3H), 2.30-2.37 (m, 1H), 2.45-2.58 (m, 1H), 3.27 (s, 3H), 3.88 (s, 3H), 4.13-4.21 (m, 1H), 4.35-4.42 (m, 1H), 6.92 (s, 1H), 7.02-7.08 (m, 2H), 7.10 (d, J=16.4 Hz, 1H), 7.16-7.26 (m, 3H), 7.56 (d, J=16.4 Hz, 1H), 7.71 (s, 1H).

The property values of the title optically active compound with a retention time of 17.5 minutes are as follows.

ESI-MS; m/z 496 [M$^+$+H]. $^1$H-NMR (CDCl$_3$) δ (ppm): 1.91-2.08 (m, 2H), 2.30 (s, 3H), 2.30-2.37 (m, 1H), 2.45-2.58 (m, 1H), 3.27 (s, 3H), 3.88 (s, 3H), 4.13-4.21 (m, 1H), 4.35-4.42 (m, 1H), 6.92 (s, 1H), 7.02-7.08 (m, 2H), 7.10 (d, J=16.4 Hz, 1H), 7.16-7.26 (m, 3H), 7.56 (d, J=16.4 Hz, 1H), 7.71 (s, 1H).

Examples 89 and 90

Synthesis of (−) and (+)-8-methoxy-2-{(E)-2-[3-methoxy-4-(4-methyl-1H-imidazol-1-yl)phenyl]vinyl}-8-(4-methoxyphenyl)-5,6,7,8-tetrahydro[1,2,4]triazolo[1,5-a]pyridine

[Formula 112]

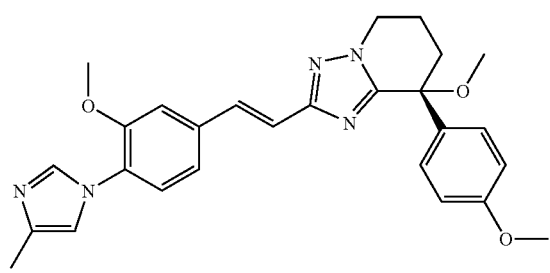

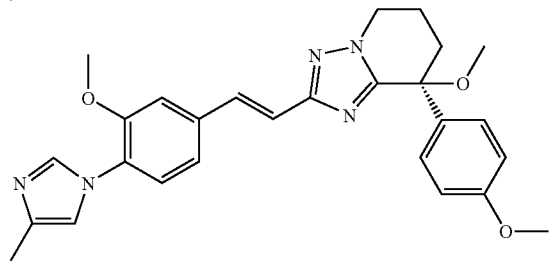

Synthesis of methyl methoxy-(4-methoxyphenyl)acetate

A 28% solution of sodium methoxide in methanol (12.8 g) and iodobenzene diacetate (7.15 g) were added to a solution of methyl 4-methoxyphenylacetate (4.0 g) in methanol (60 mL), and the reaction solution was stirred at room temperature for five days. 1 N hydrochloric acid (67 ml) was added dropwise to the reaction solution under ice-cooling, and methanol was evaporated from the reaction solution under reduced pressure. Ethyl acetate was added to the remaining aqueous layer, and the organic layer was separated. The resulting organic layer was sequentially washed with a saturated sodium bicarbonate solution and brine, dried over anhydrous magnesium sulfate and then concentrated under reduced pressure. The resulting residue was purified by silica gel column chromatography (eluting solvent: heptane-ethyl acetate system) to obtain 725 mg of the title compound. The property values of the compound are as follows.

$^1$H-NMR (CDCl$_3$) δ (ppm): 3.37 (s, 3H), 3.72 (s, 3H), 3.80 (s, 3H), 4.72 (s, 1H), 6.89 (dd, J=6.8, 2.0 Hz, 2H), 7.34 (dd, J=6.8, 2.0 Hz, 2H).

Synthesis of tert-butyl N'-[5-chloro-2-methoxy-2-(4-methoxyphenyl)pentanoyl]hydrazinecarboxylate and tert-butyl N'-[2-methoxy-2-(4-methoxyphenyl)acetyl]hydrazinecarboxylate 246 mg of a mixture of methyl 5-chloro-2-methoxy-2-(4-methoxyphenyl)valerate with methyl methoxy-(4-methoxyphenyl)acetate was obtained from methyl hydroxy-(4-methoxyphenyl)acetate (724 mg) and 1-chloro-3-iodopropane (0.56 ml) by the same method as in Examples 85 and 86. Then, the ester mixture was hydrolyzed and amidated with tert-butyl carbazate according to the method in Examples 85 and 86 to obtain 32 mg of tert-butyl N'-[5-chloro-2-methoxy-2-(4-methoxyphenyl)pentanoyl]hydrazinecarboxylate and 122 mg of tert-butyl N'-[2-methoxy-2-(4-methoxyphenyl)acetyl]hydrazinecarboxylate.

The property values of tert-butyl N'-[5-chloro-2-methoxy-2-(4-methoxyphenyl)pentanoyl]hydrazinecarboxylate are as follows.

$^1$H-NMR (CDCl$_3$) δ (ppm): 1.45 (s, 9H), 1.70-1.92 (m, 2H), 2.25-2.36 (m, 1H), 2.47-2.55 (m, 1H), 3.16 (s, 3H), 3.51-3.57 (m, 1H), 3.61-3.69 (m, 1H), 3.79 (s, 3H), 6.33 (brs, 1H), 6.87 (d, J=8.8 Hz, 2H), 7.37 (d, J=8.8 Hz, 2H), 8.44 (s, 1H).

The property values of tert-butyl N'-[2-methoxy-2-(4-methoxyphenyl)acetyl]hydrazinecarboxylate are as follows.

$^1$H-NMR (CDCl$_3$) δ (ppm): 1.46 (s, 9H), 3.36 (s, 3H), 3.80 (s, 3H), 4.69 (s, 1H), 6.38 (brs, 1H), 6.89 (d, J=8.4 Hz, 2H), 7.33 (d, J=8.4 Hz, 2H), 8.31 (brs, 1H).

Synthesis of 5-chloro-2-methoxy-2-(4-methoxyphenyl)valeric acid hydrazide monohydrochloride 29 mg of the title compound was obtained from tert-butyl N'-[5-chloro-2-methoxy-2-(4-methoxyphenyl)pentanoyl]hydrazinecarboxylate (32 mg) by the same method as in Examples 85 and 86. The property value of the compound is as follows.

ESI-MS; m/z 309 [M$^+$-HCl+Na].

Synthesis of (−) and (+)-8-methoxy-2-{(E)-2-[3-methoxy-4-(4-methyl-1H-imidazol-1-yl)phenyl]vinyl}-8-(4-methoxyphenyl)-5,6,7,8-tetrahydro-[1,2,4]triazolo[1,5-a]pyridine 2.6 mg of 8-methoxy-2-{(E)-2-[3-methoxy-4-(4-methyl-1H-imidazol-1-yl)phenyl]vinyl}-8-(4-methoxyphenyl)-5,6,7,8-tetrahydro[1,2,4]triazolo[1,5-a]pyridine as a racemate was obtained from ethyl(E)-3-[3-methoxy-4-(4-methyl-1H-imidazol-1-yl)phenyl]acrylimidate dihydrochloride (36 mg) and 5-chloro-2-methoxy-2-(4-methoxyphenyl)valeric acid hydrazide monohydrochloride (29 mg) by the same method as in Examples 85 and 86. Then, the racemate was separated by CHIRALPAK™ OJ-H manufactured by Daicel Chemical Industries, Ltd. (2 cm×25 cm; mobile phase: 30% ethanol-hexane) to obtain the title optically active compound with a retention time of 13 minutes and negative optical rotation (1.25 mg, 100% ee) and the title optically active compound with a retention time of 18.5 minutes and positive optical rotation (0.93 mg, >90% ee).

The property values of the title optically active compound with a retention time of 13 minutes are as follows.

ESI-MS; m/z 472 [M++H]. ¹H-NMR (CDCl₃) δ (ppm): 1.93-2.12 (m, 2H), 2.30 (s, 3H), 2.33-2.50 (m, 2H), 3.32 (s, 3H), 3.81 (s, 3H), 3.87 (s, 3H), 4.13-4.22 (m, 1H), 4.30-4.38 (m, 1H), 6.91 (d, J=8.8 Hz, 2H), 6.92 (s, 1H), 7.13 (d, J=16.4 Hz, 1H), 7.17 (d, J=8.0 Hz, 1H), 7.18 (s, 1H), 7.22 (d, J=8.0 Hz, 1H), 7.28 (d, J=8.8 Hz, 2H), 7.59 (d, J=16.4 Hz, 1H), 7.70 (s, 1H).

The property values of the title optically active compound with a retention time of 18.5 minutes are as follows.

ESI-MS; m/z 472 [M++H]. ¹H-NMR (CDCl₃) δ (ppm): 1.93-2.12 (m, 2H), 2.30 (s, 3H), 2.33-2.50 (m, 2H), 3.32 (s, 3H), 3.81 (s, 3H), 3.87 (s, 3H), 4.13-4.22 (m, 1H), 4.30-4.38 (m, 1H), 6.91 (d, J=8.8 Hz, 2H), 6.92 (s, 1H), 7.13 (d, J=16.4 Hz, 1H), 7.17 (d, J=8.0 Hz, 1H), 7.18 (s, 1H), 7.22 (d, J=8.0 Hz, 1H), 7.28 (d, J=8.8 Hz, 2H), 7.59 (d, J=16.4 Hz, 1H), 7.70 (s, 1H).

Example 91

Synthesis of 5-[methoxy-(4-methoxyphenyl)methyl]-3-{(E)-2-[3-methoxy-4-(4-methyl-1H-imidazol-1-yl)phenyl]vinyl}-1H-[1,2,4]triazole

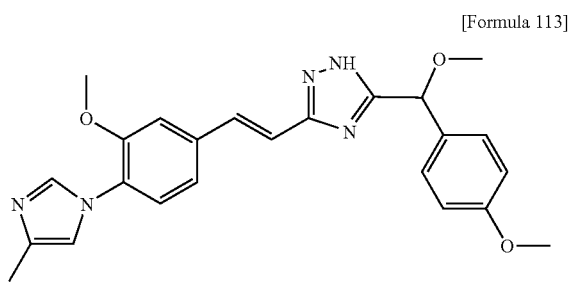

[Formula 113]

Synthesis of 2-methoxy-2-(4-methoxyphenyl)acetic acid hydrazide monohydrochloride 100 mg of the title compound was obtained from tert-butyl N'-[2-methoxy-2-(4-methoxyphenyl)acetyl]hydrazinecarboxylate (120 mg) by the same method as in Examples 85 and 86. The property value of the compound is as follows.

ESI-MS; m/z 233 [M+-HCl+Na].

Synthesis of 5-[methoxy-(4-methoxyphenyl)methyl]-3-{(E)-2-[3-methoxy-4-(4-methylimidazol-1-yl)phenyl]vinyl}-1H-[1,2,4]triazole 23.6 mg of the title compound was obtained from ethyl(E)-3-[3-methoxy-4-(4-methyl-1H-imidazol-1-yl)phenyl]acrylimidate dihydrochloride (110 mg) and 2-methoxy-2-(4-methoxyphenyl)acetic acid hydrazide monohydrochloride (100 mg) by the same method as in Examples 85 and 86. The property values of the compound are as follows.

ESI-MS; m/z 432 [M++H] ¹H-NMR (CDCl₃) δ (ppm): 2.30 (s, 3H), 3.42 (s, 3H), 3.81 (s, 3H), 3.86 (s, 3H), 5.44 (s, 1H), 6.91 (s, 1H), 6.92 (d, J=8.8 Hz, 2H), 7.05 (d, J=16.0 Hz, 1H), 7.13 (d, J=8.0 Hz, 1H), 7.15 (s, 1H), 7.21 (d, J=8.0 Hz, 1H), 7.34 (d, J=8.8 Hz, 2H), 7.54 (d, J=16.0 Hz, 1H), 7.70 (d, J=1.2 Hz, 1H).

Example 92

Synthesis of 7-(4-fluorophenyl)-7-methoxy-2-{(E)-2-[3-methoxy-4-(4-methyl-1H-imidazol-1-yl)phenyl]vinyl}-6,7-dihydro-5H-pyrrolo[1,2-b][1,2,4]triazole

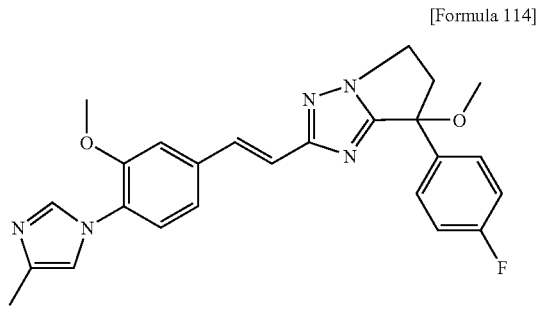

[Formula 114]

Synthesis of methyl 4-chloro-2-(4-fluorophenyl)-2-methoxybutyrate 113 mg of the title compound was obtained from methyl (4-fluorophenyl)methoxyacetate (900 mg) and 1-chloro-2-iodoethane (1.3 g) according to the method in Examples 85 and 86. The property values of the compound are as follows.

¹H-NMR (CDCl₃) δ (ppm): 2.65 (ddd, J=16.4, 10.8, 4.8 Hz, 1H), 2.79 (ddd, J=16.4, 10.8, 5.6 Hz, 1H), 3.27 (s, 3H), 3.27-3.41 (m, 2H), 3.74 (s, 3H), 7.00-7.10 (m, 2H), 7.38-7.48 (m, 2H).

Synthesis of 3-(4-fluorophenyl)-3-methoxydihydrofuran-2-one

A 5 N sodium hydroxide solution (0.5 mL) was added to a solution of methyl 4-chloro-2-(4-fluorophenyl)-2-methoxybutyrate (113 mg) in methanol (1 mL), and the reaction solution was stirred at room temperature for two hours. Water was added to the reaction solution which was then washed with diethyl ether. 1 N hydrochloric acid (2.6 mL) and ethyl acetate were added to the resulting aqueous layer, and the organic layer was separated. The resulting ethyl acetate layer was washed with brine, dried over anhydrous magnesium sulfate and concentrated under reduced pressure to obtain 90 mg of a carboxylic acid compound. Oxalyl chloride (38 μL) was added a mixed solution of the resulting carboxylic acid compound (90 mg) in methylene chloride (1 mL) and DMF (1 drop) under ice-cooling, and then the reaction solution was stirred at room temperature for 30 minutes. The acid chloride solution was added dropwise to a solution of tert-butyl carbazate (73 mg) and TEA (0.25 mL) in methylene chloride (1.5 mL) under ice-cooling, and the reaction solution was stirred at the same temperature for five minutes and at room temperature for 50 minutes. Water and ethyl acetate were added to the reaction solution, and the organic layer was separated. The organic layer was sequentially washed with 1 N hydrochloric acid, water, a saturated sodium bicarbonate solution and brine, dried over anhydrous magnesium sulfate and then concentrated under reduced pressure. The resulting residue was purified by silica gel column chromatography (elution solvent: heptane-ethyl acetate system) to obtain 37 mg of the title compound. The property values of the compound are as follows.

1H-NMR (CDCl3) δ (ppm): 2.47 (dt, J=14.0, 6.8 Hz, 1H), 2.66 (ddd, J=14.0, 6.8, 4.8 Hz, 1H), 3.24 (s, 3H), 4.23 (ddd, J=8.8, 6.8, 4.8 Hz, 1H), 4.46 (dt, J=8.8, 6.8 Hz, 1H), 7.06-7.14 (m, 2H), 7.43-7.49 (m, 2H).

Synthesis of 2-(4-fluorophenyl)-4-hydroxy-2-methoxybutyric acid hydrazide

A solution of hydrazine (29 mg) in ethanol (0.5 mL) was added to a solution of 3-(4-fluorophenyl)-3-methoxydihydrofuran-2-one (37 mg) in ethanol (1.2 mL), and the reaction solution was stirred at room temperature for 2.5 hours. The reaction solution was concentrated under reduced pressure to obtain 41 mg of the title compound. The property values of the compound are as follows.

ESI-MS; m/z 265 [M++Na]. 1H-NMR (CDCl3) δ (ppm): 1.80 (brs, 1H), 2.40 (dt, J=14.4, 6.4 Hz, 1H), 2.76 (dt, J=14.4, 6.4 Hz, 1H), 3.15 (s, 3H), 3.72 (brs, 2H), 3.83 (brs, 2H), 7.02-7.09 (m, 2H), 7.36-7.42 (m, 2H), 8.01 (brs, 1H).

Synthesis of 3-(4-fluorophenyl)-3-methoxy-3-(5-{(E)-2-[3-methoxy-4-(4-methyl-1H-imidazol-1-yl)phenyl]vinyl}-2H-[1,2,4]triazol-3-yl)propan-1-ol A solution of 2-(4-fluorophenyl)-4-hydroxy-2-methoxybutyric acid hydrazide (40 mg) in ethanol (1.6 mL) was added to a solution of ethyl(E)-3-[3-methoxy-4-(4-methyl-1H-imidazol-1-yl)phenyl]acrylimidate dihydrochloride (65 mg) and TEA (0.12 mL) in ethanol (0.7 mL), and the reaction solution was stirred at 75° C. for two days. The reaction solution was left to cool to room temperature. Then, ethyl acetate and water were added to the reaction solution, and the organic layer was separated. The organic layer was washed with brine, dried over anhydrous magnesium sulfate and then concentrated under reduced pressure. The resulting residue was purified by silica gel column chromatography (elution solvent: heptane-ethyl acetate-methanol system) to obtain 38 mg of the title compound. The property value of the compound is as follows.

ESI-MS; m/z 464 [M++H].

Synthesis of 7-(4-fluorophenyl)-7-methoxy-2-{(E)-2-[3-methoxy-4-(4-methyl-1H-imidazol-1-yl)phenyl]vinyl}-6,7-dihydro-5H-pyrrolo[1,2-b][1,2,4]triazole Triphenylphosphine (22 mg) was added to a suspension of 3-(4-fluorophenyl)-3-methoxy-3-(5-{(E)-2-[3-methoxy-4-(4-methyl-1H-imidazol-1-yl)phenyl]vinyl}-2H-[1,2,4]triazol-3-yl)propan-1-ol (38 mg) in carbon tetrachloride (2 mL) and THF (2 mL), and the reaction solution was heated under reflux for seven hours. The reaction solution was left to cool to room temperature and concentrated under reduced pressure. Ethyl acetate and a saturated sodium bicarbonate solution were added to the resulting residue, and the organic layer was separated. The organic layer was washed with brine, dried over anhydrous magnesium sulfate and then concentrated under reduced pressure. The resulting residue was purified by silica gel column chromatography (carrier: Chromatorex™ NH; elution solvent: heptane-ethyl acetate system), again purified with silica gel column chromatography (elution solvent: ethyl acetate-methanol system) and then purified by LC-MS. After concentrating the target fraction, ethyl acetate and a saturated sodium bicarbonate solution were added to the residue, and the organic layer was separated. The organic layer was washed with brine, dried over anhydrous magnesium sulfate and then concentrated under reduced pressure to obtain 0.69 mg of the title compound. The property values of the compound are as follows.

ESI-MS; m/z 446 [M++H]. 1H-NMR (CDCl3) δ (ppm): 2.30 (s, 3H), 2.87 (dt, J=13.6, 8.0 Hz, 1H), 3.12 (dd, J=13.6, 8.0, 2.4 Hz, 1H), 3.21 (s, 3H), 3.89 (s, 3H), 4.20 (ddd, J=11.2, 8.0, 2.4 Hz, 1H), 4.36 (dt, J=11.2, 8.0 Hz, 1H), 6.93 (s, 1H), 7.07-7.13 (m, 2H), 7.15 (d, J=16.4 Hz, 1H), 7.18-7.26 (m, 3H), 7.51-7.58 (m, 2H), 7.65 (d, J=16.4 Hz, 1H), 7.74 (s, 1H).

Example 93

Synthesis of 4-(4-fluorophenyl)-2-{(E)-2-[3-methoxy-4-(4-methyl-1H-imidazol-1-yl)phenyl]vinyl}-1-(tetrahydrofuran-2-ylmethyl)-1H-imidazole

[Formula 115]

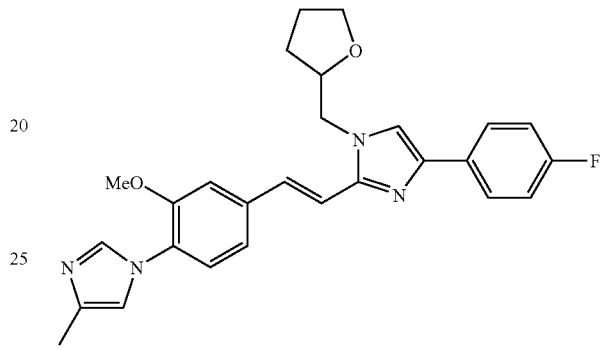

14 mg of the title compound was obtained from 5-(4-fluorophenyl)-2-{(E)-2-[3-methoxy-4-(4-methyl-1H-imidazol-1-yl)phenyl]vinyl}-1H-imidazole (50 mg) and tetrahydrofurfuryl bromide (0.03 mL) by the same method as in Example 2. The property values of the compound are as follows.

1H-NMR (CDCl3) δ (ppm): 1.58-1.67 (m, 1H), 1.75-1.96 (m, 2H), 2.01-2.10 (m, 1H), 2.31 (s, 3H), 3.75-3.89 (m, 2H), 3.90 (s, 3H), 4.06-4.26 (m, 3H), 6.93 (brs, 1H), 6.98 (d, J=16.0 Hz, 1H), 7.06 (t, J=8.8 Hz, 2H), 7.15 (brs, 1H), 7.21-7.28 (m, 3H), 7.69 (d, J=16.0 Hz, 1H), 7.71 (brs, 1H), 7.78 (dd, J=8.8, 5.2 Hz, 2H).

Example 94

Synthesis of 4-{5-{(E)-2-[3-methoxy-4-(4-methyl-1H-imidazol-1-yl)phenyl]vinyl}-4H-[1,2,4]triazol-3-yl}-4-(3,4,5-trifluorophenyl)butan-1-ol

[Formula 116]

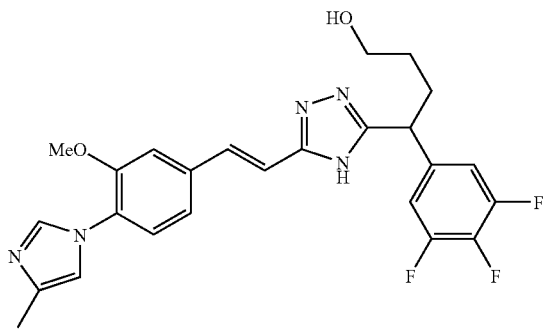

Synthesis of 4-{5-{(E)-2-[3-methoxy-4-(4-methyl-1H-imidazol-1-yl)phenyl]vinyl}-4H-[1,2,4]triazol-3-yl}-4-(3,4,5-trifluorophenyl)butyl acetate A solution of 5-chloro-2-(3,4,5-trifluorophenyl)pentanoic acid N'-{(E)-3-[3-methoxy-4-(4-methyl-1H-imidazol-1-yl)

phenyl]acryloyl}hydrazide (2.84 g) in phosphorus oxychloride (5 mL) was stirred at 120° C. for one hour. The reaction solution was left to cool to room temperature and then concentrated under reduced pressure. Ammonium acetate (5.72 g) was added to a solution of the residue in acetic acid (5 mL), and the reaction solution was stirred at 150° C. for 12 hours. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1→ethyl acetate→ethyl acetate:methanol=5:1) to obtain 400 mg of the title compound. The property value of the compound is as follows.

ESI-MS; m/z 526 [M$^+$+H].

Synthesis of 4-{5-{(E)-2-[3-methoxy-4-(4-methyl-1H-imidazol-1-yl)phenyl]vinyl}-4H-[1,2,4]triazol-3-yl}-4-(3,4,5-trifluorophenyl)butan-1-ol Potassium carbonate (210 mg) was added to a solution of 4-{5-{(E)-2-[3-methoxy-4-(4-methyl-1H-imidazol-1-yl)phenyl]vinyl}-4H-[1,2,4]triazol-3-yl}-4-(3,4,5-trifluorophenyl)butyl acetate (400 mg) in methanol (3 mL), and the reaction solution was stirred at room temperature for three hours. Ethyl acetate and brine were added to the reaction solution, and the organic layer was separated. The resulting organic layer was dried over anhydrous magnesium sulfate and concentrated under reduced pressure to obtain 325 mg of the title compound. The property values of the compound are as follows.

$^1$H-NMR (CDCl$_3$) δ (ppm): 1.54-1.66 (m, 2H), 2.04-2.14 (m, 1H), 2.29 (s, 3H), 2.33-2.43 (m, 1H), 3.67-3.72 (m, 2H), 3.86 (s, 3H), 4.14 (dd, J=8.4, 6.8 Hz, 1H), 6.93 (brs, 1H), 6.98-7.04 (m, 3H), 7.13 (brd, J=8.4 Hz, 1H), 7.14 (brs, 1H), 7.21 (d, J=8.4 Hz, 1H), 7.53 (d, J=16.0 Hz, 1H), 7.72 (brs, 1H).

Examples 95 and 96

Synthesis of (+)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine-8-carbonitrile and (−)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine-8-carbonitrile

[Formula 117]

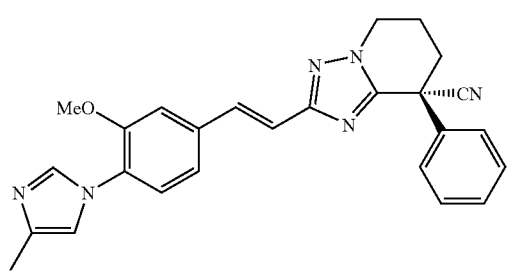

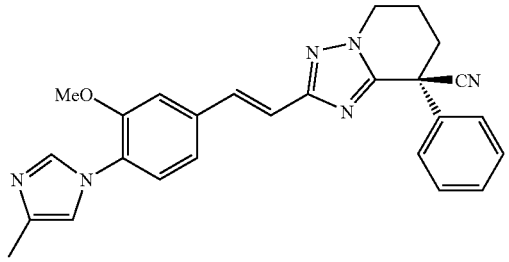

Synthesis of (E)-N-(3-cyano-2-oxo-3-phenylpiperidin-1-yl)-3-[3-methoxy-4-(4-methyl-1H-imidazol-1-yl)phenyl]acrylamide Hydrazine (1.2 g) was added to a solution of ethyl 5-chloro-2-cyano-2-phenylpentanoate (CAS No. 52370-87-3, 1 g) in ethanol (5 mL), and the reaction solution was stirred at room temperature for one hour. Ethyl acetate and saturated sodium bicarbonate water were added to the reaction solution, and the organic layer was separated. The resulting organic layer was filtered through a silica gel, and the filtrate was concentrated under reduced pressure to obtain a crude product of 5-chloro-2-cyano-2-phenylpentanoic acid hydrazide.

BOPCl (1.43 g) was added to a solution of (E)-3-[3-methoxy-4-(4-methyl-1H-imidazol-1-yl)phenyl]acrylic acid (973 mg) and IPEA (1.97 mL) in methylene chloride (10 mL), and the reaction solution was stirred at room temperature for 30 minutes. A solution of the previously obtained crude product of 5-chloro-2-cyano-2-phenylpentanoic acid hydrazide in methylene chloride (5 mL) was added dropwise to the solution, and the reaction solution was stirred at room temperature for 30 minutes. Ethyl acetate and saturated sodium bicarbonate water were added to the reaction solution, and the organic layer was separated. The resulting organic layer was washed with brine, dried over anhydrous magnesium sulfate and then concentrated under reduced pressure. The residue was purified by silica gel column chromatography (carrier: Chromatorex NH; elution solvent: ethyl acetate→ethyl acetate: methanol=4:1) to obtain 300 mg of the title compound. The property values of the compound are as follows.

ESI-MS; m/z 456 [M$^+$+H]. $^1$H-NMR (CDCl$_3$) δ (ppm): 1.96-2.16 (m, 2H), 2.29 (s, 3H), 2.37-2.46 (m, 1H), 2.64-2.74 (m, 1H), 3.78 (s, 3H), 3.83-3.88 (m, 2H), 6.48 (d, J=15.6 Hz, 1H), 6.84 (brs, 1H), 6.93 (brs, 1H), 6.95 (brd, J=8.0 Hz, 1H), 7.08 (d, J=8.0 Hz, 1H), 7.35-7.42 (m, 1H), 7.48 (t, J=7.6 Hz, 2H), 7.57 (d, J=15.6 Hz, 1H), 7.65 (d, J=7.6 Hz, 2H), 7.68 (brs, 1H), 9.42 (brs, 1H).

Synthesis of 2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine-8-carbonitrile A solution of (E)-N-(3-cyano-2-oxo-3-phenylpiperidin-1-yl)-3-[3-methoxy-4-(4-methyl-1H-imidazol-1-yl)phenyl]acrylamide (300 mg) in phosphorus oxychloride (2 mL) was stirred at 120° C. for one hour. The reaction solution was left to cool to room temperature and concentrated under reduced pressure. Ammonium acetate (1.52 g) was added to a solution of the residue in acetic acid (2 mL), and the reaction solution was stirred at 150° C. for three hours. The reaction solution was left to cool to room temperature. Ethyl acetate and saturated sodium bicarbonate water were added to the reaction solution, and the organic layer was separated. The resulting organic layer was washed with brine, dried over anhydrous magnesium sulfate and then concentrated under reduced pressure. The residue was purified by silica gel column chromatography (carrier: Chromatorex NH; elution solvent: heptane:ethyl acetate=1:1→ethyl acetate→ethyl acetate:methanol=4:1) to obtain 58 mg of the title compound. The property values of the compound are as follows.

ESI-MS; m/z 437 [M$^+$+H]. $^1$H-NMR (CDCl$_3$) δ (ppm): 2.12-2.24 (m, 1H), 2.30 (s, 3H), 2.30-2.42 (m, 1H), 2.45-2.53 (m, 1H), 2.68-2.76 (m, 1H), 3.87 (s, 3H), 4.30-4.38 (m, 2H), 6.92 (brs, 1H), 7.07 (d, J=16.4 Hz, 1H), 7.16 (d, J=1.6 Hz, 1H), 7.17 (dd, J=8.4, 1.6 Hz, 1H), 7.23 (d, J=8.4 Hz, 1H), 7.28-7.32 (m, 2H), 7.38-7.45 (m, 3H), 7.58 (d, J=16.4 Hz, 1H), 7.74 (brs, 1H).

Synthesis of (+)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine-8-carbonitrile and (−)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine-8-carbonitrile 2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine-8-carbonitrile as a racemate obtained by repeating the above method (82 mg) was separated by CHIRALPAK™ IA manufactured by Daicel Chemical Industries, Ltd. (2 cm×25 cm; mobile phase: ethanol) to obtain the title optically active compound with a retention time of 14 minutes and positive optical rotation (20 mg, >99% ee) and the title optically active compound with a retention time of 17 minutes and negative optical rotation (24 mg, >99% ee).

Examples 97 and 98

Synthesis of (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile and (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile

[Formula 118]

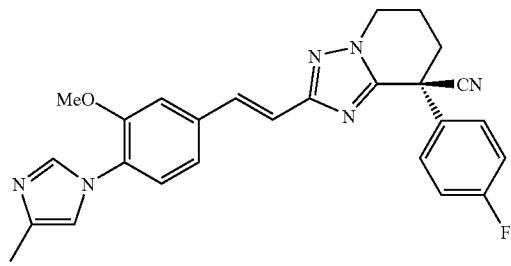

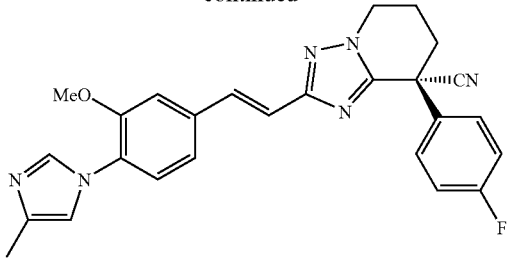

Synthesis of (E)-N-[3-cyano-3-(4-fluorophenyl)-2-oxopiperidin-1-yl]-3-[3-methoxy-4-(4-methyl-1H-imidazol-1-yl)phenyl]acrylamide Hydrazine (340 mg) was added to a solution of ethyl 5-chloro-2-cyano-2-(4-fluorophenyl)pentanoate (300 mg) in ethanol (3 mL), and the reaction solution was stirred at room temperature for 40 minutes. Ethyl acetate and saturated sodium bicarbonate water were added to the reaction solution, and the organic layer was separated. The resulting organic layer was filtered through a silica gel, and the filtrate was concentrated under reduced pressure to obtain a crude product of 5-chloro-2-cyano-2-(4-fluorophenyl)pentanoic acid hydrazide.

BOPCl (270 mg) was added to a solution of (E)-3-[3-methoxy-4-(4-methyl-1H-imidazol-1-yl)phenyl]acrylic acid (274 mg) and IPEA (0.37 mL) in methylene chloride (4 mL), and the reaction solution was stirred at room temperature for one hour. A solution of the previously obtained crude product of 5-chloro-2-cyano-2-(4-fluorophenyl)pentanoic acid hydrazide in methylene chloride (1 mL) was added dropwise to the solution, and the reaction solution was stirred at room temperature for eight hours. Ethyl acetate and saturated sodium bicarbonate water were added to the reaction solution, and the organic layer was separated. The resulting organic layer was washed with brine, dried over anhydrous magnesium sulfate and then concentrated under reduced pressure. The residue was purified by silica gel column chromatography (carrier: Chromatorex NH; elution solvent: ethyl acetate:heptane=1:1→ethyl acetate→ethyl acetate:methanol=4:1) to obtain 74 mg of the title compound. The property value of the compound is as follows.

ESI-MS; m/z 474 [M$^+$+H].

Synthesis of (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile and (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile A solution of (E)-N-[3-cyano-3-(4-fluorophenyl)-2-oxopiperidin-1-yl]-3-[3-methoxy-4-(4-methyl-1H-imidazol-1-yl)phenyl]acrylamide (74 mg) in phosphorus oxychloride (3 mL) was stirred at 120° C. for 12 hours. The reaction solution was left to cool to room temperature and concentrated under reduced pressure. Ammonium acetate (361 mg) was added to a solution of the residue in acetic acid (3 mL), and the reaction solution was stirred at 150° C. for three hours. The reaction solution was left to cool to room temperature. Ethyl acetate and saturated sodium bicarbonate water were added to the reaction solution, and the organic layer was separated. The resulting organic layer was washed with brine, dried over anhydrous magnesium sulfate and then concentrated under reduced pressure. The residue was purified by silica gel column chromatography (carrier: Chromatorex NH; elution solvent: ethyl acetate→ethyl acetate:methanol=9:1) to obtain 29 mg of a racemate of the title compound. The racemate obtained by repeating the above step (54 mg) was separated by CHIRALPAK™ AD-H manufactured by Daicel Chemical Industries, Ltd. (2 cm×25 cm; mobile phase: ethanol) to obtain the title optically active compound with a retention time of 15 minutes and negative optical rotation (16 mg, >99% ee) and the title optically active compound with a retention time of 22 minutes and positive optical rotation (12 mg, >99% ee).

The property values of (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile are as follows.

ESI-MS; m/z 455 [M$^+$+H]. $^1$H-NMR (CDCl$_3$) δ (ppm): 2.13-2.20 (m, 1H), 2.29 (s, 3H), 2.32-2.48 (m, 2H), 2.67-2.74 (m, 1H), 3.87 (s, 3H), 4.27-4.40 (m, 2H), 6.91 (brs, 1H), 7.05 (d, J=16.0 Hz, 1H), 7.11 (t, J=8.8 Hz, 2H), 7.15 (d, J=1.6 Hz, 1H), 7.16 (dd, J=8.4, 1.6 Hz, 1H), 7.22 (d, J=8.4 Hz, 1H), 7.30 (dd, J=8.8, 4.8 Hz, 2H), 7.57 (d, J=16.0 Hz, 1H), 7.70 (d, J=1.2 Hz, 1H).

The property values of (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile are as follows.

ESI-MS; m/z 455 [M$^+$+H]. $^1$H-NMR (CDCl$_3$) δ (ppm): 2.13-2.20 (m, 1H), 2.29 (s, 3H), 2.32-2.48 (m, 2H), 2.67-2.74 (m, 1H), 3.87 (s, 3H), 4.27-4.40 (m, 2H), 6.91 (brs, 1H), 7.05 (d, J=16.0 Hz, 1H), 7.11 (t, J=8.8 Hz, 2H), 7.15 (d, J=1.6 Hz, 1H), 7.16 (dd, J=8.4, 1.6 Hz, 1H), 7.22 (d, J=8.4 Hz, 1H), 7.30 (dd, J=8.8, 4.8 Hz, 2H), 7.57 (d, J=16.0 Hz, 1H), 7.70 (d, J=1.2 Hz, 1H).

Examples 99 and 100

Synthesis of (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ylamine and (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ylamine

[Formula 119]

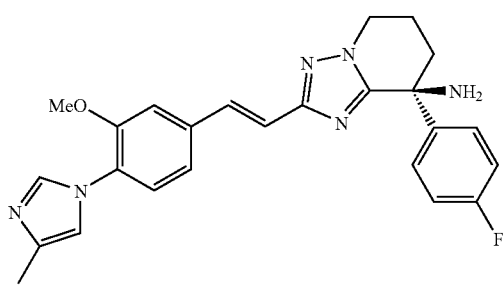

-continued

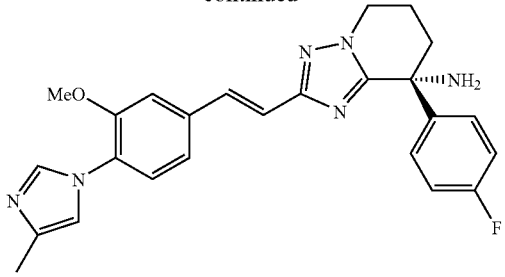

Synthesis of 8-azido-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine Methanesulfonic acid (0.3 mL) was added to a solution of 8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol synthesized by the method in Examples 70 and 71 (45 mg) and sodium azide (66 mg) in TFA (1 mL), and the reaction solution was stirred at room temperature for 16 hours. The reaction solution was diluted with ethyl acetate. The solution was added to saturated sodium bicarbonate water, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1→ethyl acetate) to obtain 28 mg of the title compound. The property values of the compound are as follows.

ESI-MS; m/z 471 [M$^+$+H]. $^1$H-NMR (CDCl$_3$) δ (ppm): 1.94-2.04 (m, 1H), 2.17-2.29 (m, 3H), 2.30 (s, 3H), 3.87 (s, 3H), 4.20-4.33 (m, 2H), 6.92 (brs, 1H), 7.10 (t, J=8.4 Hz, 2H), 7.11 (d, J=16.4 Hz, 1H), 7.18 (dd, J=8.8, 1.2 Hz, 1H), 7.19 (d, J=1.2 Hz, 1H), 7.23 (d, J=8.8 Hz, 1H), 7.33 (dd, J=8.4, 4.8 Hz, 2H), 7.59 (d, J=16.4 Hz, 1H), 7.70 (d, J=0.8 Hz, 1H).

Synthesis of (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ylamine and (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ylamine Indium (64 mg) was added to a solution of 8-azido-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine (26 mg) and concentrated hydrochloric acid (0.09 mL) in THF (1 mL), and the reaction solution was stirred at room temperature for two hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: ethyl acetate) to obtain 10 mg of a racemate of the title compound. The resulting racemate (10 mg) was separated by CHIRALPAK™ IA manufactured by Daicel Chemical Industries, Ltd. (2 cm×25 cm; mobile phase: hexane:ethanol=1:1) to obtain the title optically active compound with a retention time of 17 minutes and positive optical rotation (2.4 mg, >99% ee) and the title optically active compound with a retention time of 23 minutes and negative optical rotation (2.4 mg, >99% ee).

The property values of (+)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ylamine are as follows.

ESI-MS; m/z 445 [M$^+$+H]. $^1$H-NMR (CDCl$_3$) δ (ppm): 1.83-1.96 (m, 1H), 2.02-2.11 (m, 2H), 2.30 (s, 3H), 2.30-2.38 (m, 1H), 3.87 (s, 3H), 4.14-4.21 (m, 1H), 4.26-4.35 (m, 1H), 6.92 (brs, 1H), 7.00 (t, J=8.4 Hz, 2H), 7.09 (d, J=16.0 Hz, 1H), 7.16 (brd, J=8.4 Hz, 1H), 7.17 (brs, 1H), 7.20-7.25 (m, 3H), 7.55 (d, J=16.0 Hz, 1H), 7.71 (brs, 1H).

The property values of (−)-8-(4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ylamine are as follows.

ESI-MS; m/z 445 [M$^+$+H]. $^1$H-NMR (CDCl$_3$) δ (ppm): 1.83-1.96 (m, 1H), 2.02-2.11 (m, 2H), 2.30 (s, 3H), 2.30-2.38 (m, 1H), 3.87 (s, 3H), 4.14-4.21 (m, 1H), 4.26-4.35 (m, 1H), 6.92 (brs, 1H), 7.00 (t, J=8.4 Hz, 2H), 7.09 (d, J=16.0 Hz, 1H), 7.16 (brd, J=8.4 Hz, 1H), 7.17 (brs, 1H), 7.20-7.25 (m, 3H), 7.55 (d, J=16.0 Hz, 1H), 7.71 (brs, 1H).

Example 101

Synthesis of 2-{(E)-2-[3-fluoro-4-(4-methyl-1H-imidazol-1-yl)phenyl]vinyl}-8-(4-fluorophenyl)-5,6,7,8-tetrahydro[1,2,4]triazolo[1,5-a]pyridine

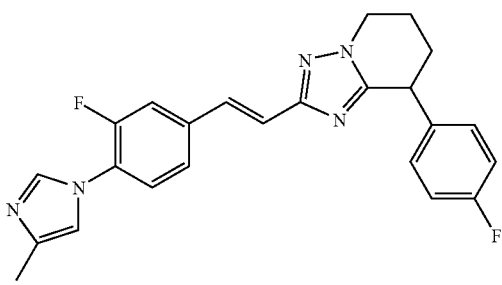

[Formula 120]

108 mg of the title compound was obtained from 5-chloro-2-(4-fluorophenyl)pentanoic acid hydrazide (500 mg) and (E)-3-[3-fluoro-4-(4-methyl-1H-imidazol-1-yl)phenyl]acrylic acid (502 mg) by the same method as in Examples 61 and 62. The property values of the compound are as follows.

ESI-MS; m/z 418 [M$^+$+H]. $^1$H-NMR (CDCl$_3$) δ (ppm): 1.99-2.14 (m, 2H), 2.15-2.25 (m, 1H), 2.30 (s, 3H), 2.30-2.40 (m, 1H), 4.25-4.36 (m, 3H), 6.96 (brs, 1H), 7.02 (t, J=8.8 Hz, 2H), 7.04 (d, J=16.4 Hz, 1H), 7.09 (dd, J=8.8, 5.6 Hz, 2H), 7.30-7.37 (m, 3H), 7.46 (d, J=16.4 Hz, 1H), 7.72 (brs, 1H).

Examples 102 and 103

Synthesis of (−)-2-{(E)-2-[3-fluoro-4-(4-methyl-1H-imidazol-1-yl)phenyl]vinyl}-8-(4-fluorophenyl)-5,6,7,8-tetrahydro[1,2,4]triazolo[1,5-a]pyridin-8-ol and (+)-2-{(E)-2-[3-fluoro-4-(4-methyl-1H-imidazol-1-yl)phenyl]vinyl}-8-(4-fluorophenyl)-5,6,7,8-tetrahydro[1,2,4]triazolo[1,5-a]pyridin-8-ol

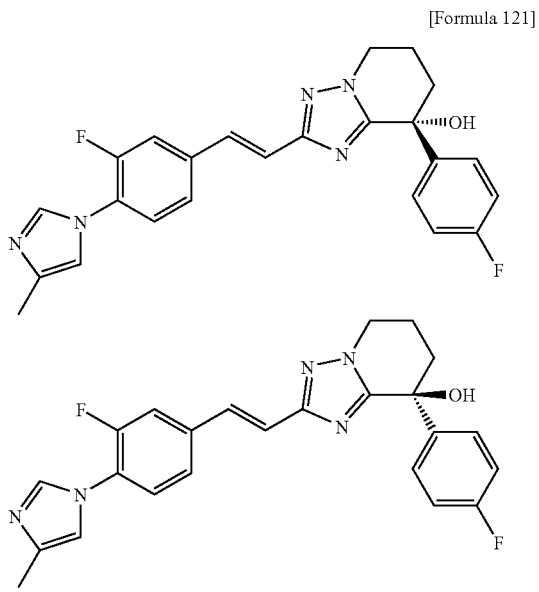

[Formula 121]

Sodium hydride (containing mineral oil at 40%, 20 mg) was added to a solution of 2-{(E)-2-[3-fluoro-4-(4-methyl-1H-imidazol-1-yl)phenyl]vinyl}-8-(4-fluorophenyl)-5,6,7,8-tetrahydro[1,2,4]triazolo[1,5-a]pyridine (100 mg) in DMF (2 mL), and the reaction solution was stirred at room temperature for one hour while bubbling with oxygen gas. Ethyl acetate and saturated sodium bicarbonate water were added to the reaction solution, and the organic layer was separated. The resulting organic layer was dried over anhydrous magnesium sulfate and then concentrated under reduced pressure. 37 mg of the resulting racemate crude product of the title compound was separated by CHIRALPAK™ IA manufactured by Daicel Chemical Industries, Ltd. (2 cm×25 cm; mobile phase: ethanol) to obtain the title optically active compound with a retention time of 14 minutes and negative optical rotation (25 mg, >99% ee) and the title optically active compound with a retention time of 37 minutes and positive optical rotation (19 mg, >99% ee).

The property values of (−)-2-{(E)-2-[3-fluoro-4-(4-methyl-1H-imidazol-1-yl)phenyl]vinyl}-8-(4-fluorophenyl)-5,6,7,8-tetrahydro[1,2,4]triazolo[1,5-a]pyridin-8-ol are as follows.

ESI-MS; m/z 434 [M$^+$+H]. $^1$H-NMR (CDCl$_3$) δ (ppm): 1.92-2.05 (m, 1H), 2.16-2.24 (m, 1H), 2.29 (s, 3H), 2.30-2.38 (m, 2H), 4.20-4.31 (m, 2H), 4.56 (brs, 1H), 6.94 (brs, 1H), 7.02 (d, J=16.4 Hz, 1H), 7.03 (t, J=8.4 Hz, 2H), 7.21 (brd, J=8.4 Hz, 1H), 7.25-7.32 (m, 4H), 7.42 (d, J=16.4 Hz, 1H), 7.74 (brs, 1H).

The property values of (+)-2-{(E)-2-[3-fluoro-4-(4-methyl-1H-imidazol-1-yl)phenyl]vinyl}-8-(4-fluorophenyl)-5,6,7,8-tetrahydro[1,2,4]triazolo[1,5-a]pyridin-8-ol are as follows.

ESI-MS; m/z 434 [M$^+$+H]. $^1$H-NMR (CDCl$_3$) δ (ppm): 1.92-2.05 (m, 1H), 2.16-2.24 (m, 1H), 2.29 (s, 3H), 2.30-2.38 (m, 2H), 4.20-4.31 (m, 2H), 4.56 (brs, 1H), 6.94 (brs, 1H), 7.02 (d, J=16.4 Hz, 1H), 7.03 (t, J=8.4 Hz, 2H), 7.21 (brd, J=8.4 Hz, 1H), 7.25-7.32 (m, 4H), 7.42 (d, J=16.4 Hz, 1H), 7.74 (brs, 1H).

Example 104

Synthesis of 2-{(E)-2-[2-fluoro-5-methoxy-4-(4-methyl-1H-imidazol-1-yl)phenyl]vinyl}-8-(4-fluorophenyl)-5,6,7,8-tetrahydro[1,2,4]triazolo[1,5-a]pyridine

[Formula 122]

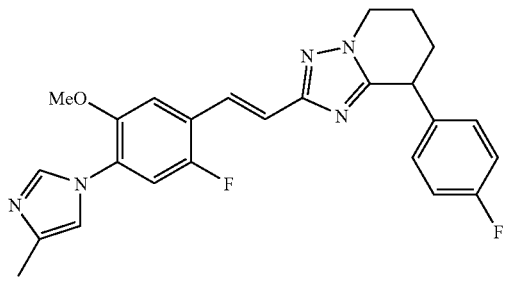

92 mg of the title compound was obtained from 5-chloro-2-(4-fluorophenyl)pentanoic acid hydrazide (525 mg) and (E)-3-[2-fluoro-5-methoxy-4-(4-methyl-1H-imidazol-1-yl)phenyl]acrylic acid (591 mg) by the same method as in Examples 68 and 69. The property values of the compound are as follows.

ESI-MS; m/z 448 [M$^+$+H]. $^1$H-NMR (CDCl$_3$) δ (ppm): 1.99-2.14 (m, 2H), 2.15-2.25 (m, 1H), 2.29 (s, 3H), 2.31-2.40 (m, 1H), 3.83 (s, 3H), 4.25-4.37 (m, 3H), 6.90 (brs, 1H), 6.99 (d, J=10.8 Hz, 1H), 7.02 (t, J=8.4 Hz, 2H), 7.10 (dd, J=8.4, 4.8 Hz, 2H), 7.13 (d, J=6.8 Hz, 1H), 7.16 (d, J=16.4 Hz, 1H), 7.59 (d, J=16.4 Hz, 1H), 7.72 (brs, 1H).

Examples 105 and 106

Synthesis of (+)-2-{(E)-2-[2-fluoro-5-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol and (−)-2-{(E)-2-[2-fluoro-5-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol

[Formula 123]

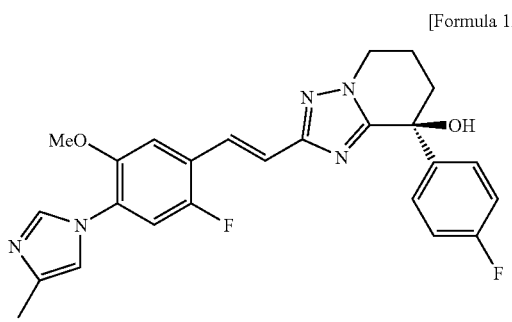

-continued

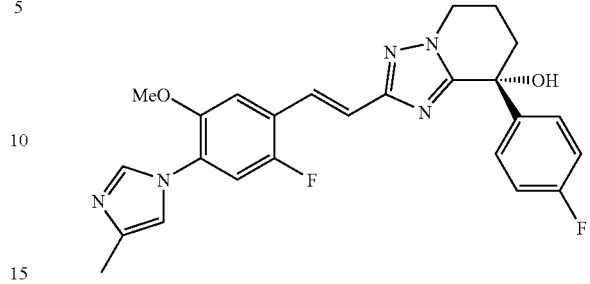

Sodium hydride (containing mineral oil at 40%, 17 mg) was added to a solution of 2-{(E)-2-[2-fluoro-5-methoxy-4-(4-methyl-1H-imidazol-1-yl)phenyl]vinyl}-8-(4-fluorophenyl)-5,6,7,8-tetrahydro[1,2,4]triazolo[1,5-a]pyridine (90 mg) in DMF (2 mL), and the reaction solution was stirred at room temperature for 30 minutes while bubbling with oxygen gas. Ethyl acetate and saturated aqueous ammonium chloride were added to the reaction solution, and the organic layer was separated. The resulting organic layer was dried over anhydrous magnesium sulfate and then concentrated under reduced pressure. The resulting racemate crude product of the title compound was separated by CHIRALPAK™ AD-H manufactured by Daicel Chemical Industries, Ltd. (2 cm×25 cm; mobile phase: hexane:ethanol=1:1) to obtain the title optically active compound with a retention time of 11 minutes and positive optical rotation (30 mg, >99% ee) and the title optically active compound with a retention time of 12 minutes and negative optical rotation (25 mg, >99% ee).

The property values of (+)-2-{(E)-2-[2-fluoro-5-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol are as follows.

ESI-MS; m/z 464 [M$^+$+H]. $^1$H-NMR (CDCl$_3$) δ (ppm): 1.94-2.04 (m, 1H), 2.15-2.23 (m, 1H), 2.28 (s, 3H), 2.30-2.45 (m, 2H), 3.79 (s, 3H), 4.20-4.33 (m, 2H), 6.87 (brs, 1H), 6.95 (d, J=10.4 Hz, 1H), 7.01 (d, J=5.6 Hz, 1H), 7.03 (t, J=8.8 Hz, 2H), 7.12 (d, J=16.4 Hz, 1H), 7.32 (dd, J=8.8, 5.2 Hz, 2H), 7.53 (d, J=16.4 Hz, 1H), 7.73 (brs, 1H).

The property values of (−)-2-{(E)-2-[2-fluoro-5-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol are as follows.

ESI-MS; m/z 464 [M$^+$+H]. $^1$H-NMR (CDCl$_3$) δ (ppm): 1.94-2.04 (m, 1H), 2.15-2.23 (m, 1H), 2.28 (s, 3H), 2.30-2.45 (m, 2H), 3.79 (s, 3H), 4.20-4.33 (m, 2H), 6.87 (brs, 1H), 6.95 (d, J=10.4 Hz, 1H), 7.01 (d, J=5.6 Hz, 1H), 7.03 (t, J=8.8 Hz, 2H), 7.12 (d, J=16.4 Hz, 1H), 7.32 (dd, J=8.8, 5.2 Hz, 2H), 7.53 (d, J=16.4 Hz, 1H), 7.73 (brs, 1H).

Example 107

Synthesis of 2-{(Z)-1-fluoro-2-[3-methoxy-4-(4-methyl-1H-imidazol-1-yl)phenyl]vinyl}-8-(4-fluorophenyl)-5,6,7,8-tetrahydro[1,2,4]triazolo[1,5-a]pyridine

[Formula 124]

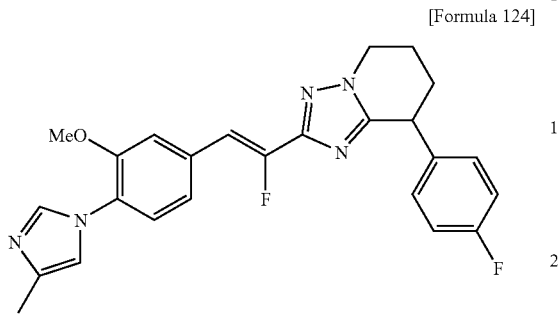

100 mg of the title compound was obtained from 5-chloro-2-(4-fluorophenyl)pentanoic acid hydrazide (683 mg) and (Z)-2-fluoro-3-[3-methoxy-4-(4-methyl-1H-imidazol-1-yl)phenyl]acrylic acid (770 mg) by the same method as in Examples 57 and 58. The property values of the compound are as follows.

ESI-MS; m/z 448 [M$^+$+H]. $^1$H-NMR (CDCl$_3$) δ (ppm): 2.00-2.15 (m, 2H), 2.16-2.26 (m, 1H), 2.29 (s, 3H), 2.31-2.41 (m, 1H), 3.85 (s, 3H), 4.29-4.37 (m, 3H), 6.71 (d, J=38.4 Hz, 1H), 6.92 (brs, 1H), 7.03 (t, J=8.4 Hz, 2H), 7.10 (dd, J=8.4, 5.2 Hz, 2H), 7.20-7.26 (m, 2H), 7.33 (brs, 1H), 7.70 (brs, 1H).

Examples 108 and 109

Synthesis of (−)-2-{(Z)-1-fluoro-2-[3-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol and (+)-2-{(Z)-1-fluoro-2-[3-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol

[Formula 125]

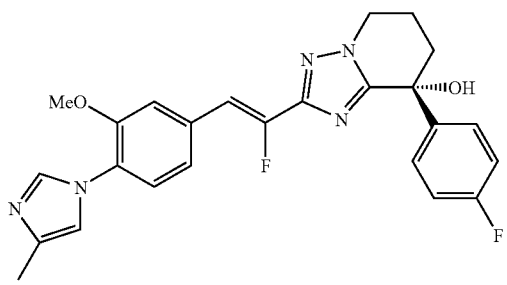

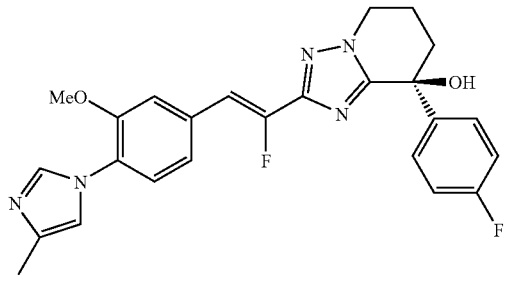

Sodium hydride (containing mineral oil at 40%, 18 mg) was added to a solution of 2-{(Z)-1-fluoro-2-[3-methoxy-4-(4-methyl-1H-imidazol-1-yl)phenyl]vinyl}-8-(4-fluorophenyl)-5,6,7,8-tetrahydro[1,2,4]triazolo[1,5-a]pyridine (98 mg) in DMF (2 mL), and the reaction solution was stirred at room temperature for 30 minutes while bubbling with oxygen gas. Ethyl acetate and saturated aqueous ammonium chloride were added to the reaction solution, and the organic layer was separated. The resulting organic layer was dried over anhydrous magnesium sulfate and then concentrated under reduced pressure. The resulting racemate crude product of the title compound was separated by CHIRALPAK™ AD-H manufactured by Daicel Chemical Industries, Ltd. (2 cm×25 cm; mobile phase: hexane:ethanol=1:1) to obtain the title optically active compound with a retention time of 9 minutes and negative optical rotation (22 mg, >99% ee) and the title optically active compound with a retention time of 10 minutes and positive optical rotation (19 mg, >99% ee).

The property values of (−)-2-{(Z)-1-fluoro-2-[3-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol are as follows.

ESI-MS; m/z 464 [M$^+$+H]. $^1$H-NMR (CDCl$_3$) δ (ppm): 1.96-2.07 (m, 1H), 2.36-2.25 (m, 1H), 2.27 (s, 3H), 2.32-2.48 (m, 2H), 3.77 (s, 3H), 4.23-4.33 (m, 2H), 6.62 (d, J=38.4 Hz, 1H), 6.87 (brs, 1H), 7.00 (dd, J=18.0, 1.6 Hz, 1H), 7.03 (t, J=8.4 Hz, 2H), 7.13 (d, J=8.4 Hz, 1H), 7.18 (brs, 1H), 7.33 (dd, J=8.4, 5.2 Hz, 2H), 7.72 (d, J=1.2 Hz, 1H).

The property values of (+)-2-{(Z)-1-fluoro-2-[3-methoxy-4-(4-methyl-1H-imidazol-1-yl)phenyl]vinyl}-8-(4-fluorophenyl)-5,6,7,8-tetrahydro[1,2,4]triazolo[1,5-a]pyridin-8-ol are as follows.

ESI-MS; m/z 464 [M$^+$+H]. $^1$H-NMR (CDCl$_3$) δ (ppm): 1.96-2.07 (m, 1H), 2.36-2.25 (m, 1H), 2.27 (s, 3H), 2.32-2.48 (m, 2H), 3.77 (s, 3H), 4.23-4.33 (m, 2H), 6.62 (d, J=38.4 Hz, 1H), 6.87 (brs, 1H), 7.00 (dd, J=18.0, 1.6 Hz, 1H), 7.03 (t, J=8.4 Hz, 2H), 7.13 (d, J=8.4 Hz, 1H), 7.18 (brs, 1H), 7.33 (dd, J=8.4, 5.2 Hz, 2H), 7.72 (d, J=1.2 Hz, 1H).

Examples 110 and 111

Synthesis of (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridin-8-ol and (+)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridin-8-ol

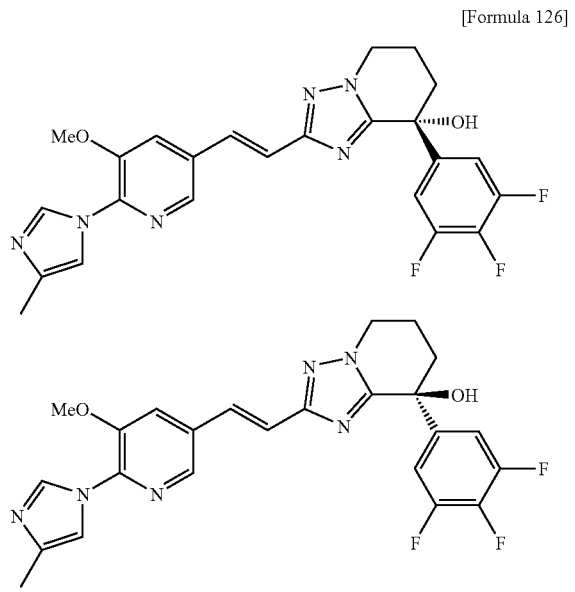

[Formula 126]

Sodium hydride (containing mineral oil at 40%, 4 mg) was added to a solution of 2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine (21 mg) synthesized by the method in Examples 59 and 60 in DMF (2 mL), and the reaction solution was stirred at room temperature for 30 minutes while bubbling with oxygen gas. Ethyl acetate and saturated aqueous ammonium chloride were added to the reaction solution, and the organic layer was separated. The resulting organic layer was dried over anhydrous magnesium sulfate and then concentrated under reduced pressure. The resulting racemate crude product of the title compound was separated by CHIRALPAK™ AD-H manufactured by Daicel Chemical Industries, Ltd. (2 cm×25 cm; mobile phase: hexane:ethanol=1:1) to obtain the title optically active compound with a retention time of 7 minutes and negative optical rotation (3.7 mg, >99% ee) and the title optically active compound with a retention time of 10 minutes and positive optical rotation (3.2 mg, >99% ee).

The property values of (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridin-8-ol are as follows.

ESI-MS; m/z 483 [M$^+$+H]. $^1$H-NMR (CDCl$_3$) δ (ppm): 2.01-2.16 (m, 2H), 2.28 (s, 3H), 2.30-2.39 (m, 1H), 2.40-2.53 (m, 1H), 3.91 (s, 3H), 4.19-4.28 (m, 1H), 4.29-4.36 (m, 1H), 7.00-7.05 (m, 3H), 7.33 (d, J=1.6 Hz, 1H), 7.41 (d, J=16.8 Hz, 1H), 7.46 (brs, 1H), 8.02 (d, J=1.6 Hz, 1H), 8.28 (brs, 1H).

The property values of (+)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridin-8-ol are as follows.

ESI-MS; m/z 483 [M$^+$+H]. $^1$H-NMR (CDCl$_3$) δ (ppm): 2.01-2.16 (m, 2H), 2.28 (s, 3H), 2.30-2.39 (m, 1H), 2.40-2.53 (m, 1H), 3.91 (s, 3H), 4.19-4.28 (m, 1H), 4.29-4.36 (m, 1H), 7.00-7.05 (m, 3H), 7.33 (d, J=1.6 Hz, 1H), 7.41 (d, J=16.8 Hz, 1H), 7.46 (brs, 1H), 8.02 (d, J=1.6 Hz, 1H), 8.28 (brs, 1H).

Examples 112 and 113

Synthesis of (+)-2-{(E)-2-[3-methoxy-4-(4-methyl-1H-imidazol-1-yl)phenyl]vinyl}-7-(3,4,5-trifluorophenyl)-6,7-dihydro-5H-pyrrolo[1,2-b][1,2,4]triazole and (−)-2-{(E)-2-[3-methoxy-4-(4-methyl-1H-imidazol-1-yl)phenyl]vinyl}-7-(3,4,5-trifluorophenyl)-6,7-dihydro-5H-pyrrolo[1,2-b][1,2,4]triazole

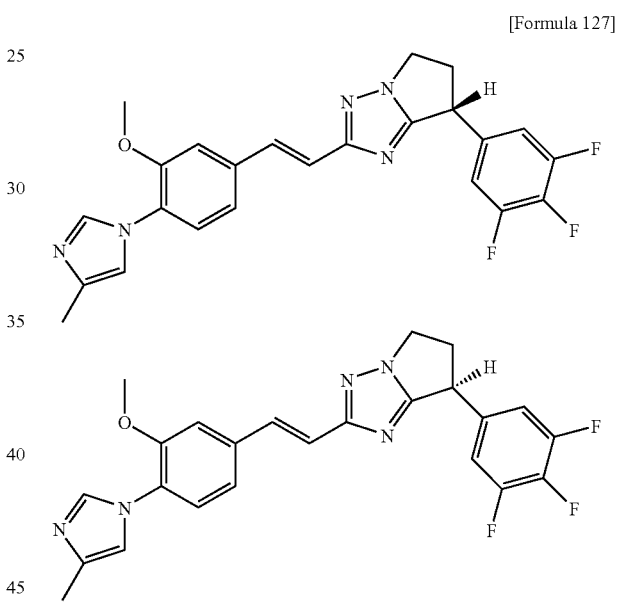

[Formula 127]

Synthesis of 4-chloro-2-(3,4,5-trifluorophenyl)butyric acid

A 2.66 M solution of butyl lithium in hexane (20 mL) was added to a solution of 3,4,5-trifluorophenylacetic acid (5.00 g) in THF (150 mL) in a nitrogen atmosphere at −78° C., and the reaction solution was stirred at −78° C. for 20 minutes. The reaction solution was further stirred at 0° C. for one hour. Then, 1-bromo-2-chloroethane (2.2 mL) was added at 0° C., and the reaction solution was stirred at room temperature for 14 hours. Ethyl acetate and 1 N hydrochloric acid were added to the reaction solution, and the organic layer was separated. The resulting organic layer was washed with a saturated sodium chloride solution. The resulting organic layer was dried over magnesium sulfate and then concentrated under reduced pressure. The residue was purified by silica gel column chromatography (elution solvent: heptane-ethyl acetate system) to obtain 4.54 g of the title compound. The property values of the compound are as follows.

$^1$H-NMR (CDCl$_3$) δ (ppm): 2.13-2.22 (m, 1H), 2.45-2.54 (m, 1H), 3.36 (ddd, J=11.6, 8.4, 4.8 Hz, 1H), 3.58 (ddd, J=11.6, 6.4, 5.2 Hz, 1H), 3.89 (dd, J=7.6, 7.6 Hz, 1H), 6.94-7.02 (m, 2H).

Synthesis of tert-butyl N'-[4-chloro-2-(3,4,5-trifluorophenyl)butyryl]hydrazinecarboxylate oxalyl chloride (0.63 mL) and DMF (1 drop) were added to a solution of 4-chloro-2-(3,4,5-trifluorophenyl)butyric acid (1.17 g) in methylene chloride (30 mL) at 0° C., and the reaction solution was stirred at room temperature for one hour. The reaction solution was concentrated under reduced pressure to obtain 4-chloro-2-(3,4,5-trifluorophenyl)butyryl chloride. A solution of 4-chloro-2-(3,4,5-trifluorophenyl)butyryl chloride in THF (5 mL) was added to a solution of tert-butyl carbazate (600 mg) and triethylamine (3.1 mL) in THF (20 mL) at 0° C., and the reaction solution was stirred at room temperature for one hour. The reaction solution was added to a saturated sodium bicarbonate solution, followed by extraction with ethyl acetate. The resulting extract was dried over magnesium sulfate and then concentrated under reduced pressure. The residue was purified by silica gel column chromatography (elution solvent: heptane-ethyl acetate system) to obtain 1.35 g of the title compound. The property value of the compound is as follows.
ESI-MS; m/z 389 [M$^+$+Na]

Synthesis of (+)-2-{(E)-2-[3-methoxy-4-(4-methyl-1H-imidazol-1-yl)phenyl]vinyl}-7-(3,4,5-trifluorophenyl)-6,7-dihydro-5H-pyrrolo[1,2-b][1,2,4]triazole and (−)-2-{(E)-2-[3-methoxy-4-(4-methyl-1H-imidazol-1-yl)phenyl]vinyl}-7-(3,4,5-trifluorophenyl)-6,7-dihydro-5H-pyrrolo[1,2-b][1,2,4]triazole A solution of 4 N hydrogen chloride in ethyl acetate (20 mL) was added to tert-butyl N'-[4-chloro-2-(3,4,5-trifluorophenyl)butyryl]hydrazinecarboxylate (1.35 g). The reaction solution was stirred at room temperature for one hour and then concentrated under reduced pressure to obtain 4-chloro-2-(3,4,5-trifluorophenyl)butyric acid hydrazide hydrochloride (1.18 g). A solution of 4-chloro-2-(3,4,5-trifluorophenyl) butyric acid hydrazide hydrochloride (552 mg) and triethylamine (0.95 mL) in ethanol (10 mL) was added to a solution of ethyl(E)-3-[3-methoxy-4-(4-methyl-1H-imidazol-1-yl)phenyl]acrylimidate dihydrochloride (500 mg) and triethylamine (1 mL) in ethanol (10 mL) at room temperature, and the reaction solution was stirred at 80° C. for 21 hours. The reaction solution was left to cool to room temperature and concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system) to obtain 131 mg of the title compound as a racemate. The property values of the compound are as follows.
ESI-MS; m/z 452 [M$^+$+H]. $^1$H-NMR (CDCl$_3$) δ (ppm): 2.30 (s, 3H), 2.61-2.72 (m, 1H), 3.22-3.32 (m, 1H), 3.89 (s, 3H), 4.17-4.27 (m, 1H), 4.30-4.48 (m, 1H), 4.41 (t, J=7.6 Hz, 1H), 6.93 (s, 1H), 6.94-7.02 (m, 2H), 7.08 (d, J=16.4 Hz, 1H), 7.16-7.21 (m, 2H), 7.22-7.27 (m, 1H), 7.58 (d, J=16.4 Hz, 1H), 7.71 (s, 1H).
The title compound as a racemate obtained above (131 mg) was separated by CHIRALPAK™ IA manufactured by Daicel Chemical Industries, Ltd. (2 cm×25 cm; mobile phase: ethanol) to obtain the title optically active compound with a retention time of 23 minutes and positive optical rotation (52 mg) and the title optically active compound with a retention time of 32 minutes and negative optical rotation (55 mg).

Examples 114 and 115

Synthesis of (+)-2-{(E)-2-[3-methoxy-4-(4-methyl-1H-imidazol-1-yl)phenyl]vinyl}-7-(3,4,5-trifluorophenyl)-6,7-dihydro-5H-pyrrolo[1,2-b][1,2,4]triazol-7-ol and (−)-2-{(E)-2-[3-methoxy-4-(4-methyl-1H-imidazol-1-yl)phenyl]vinyl}-7-(3,4,5-trifluorophenyl)-6,7-dihydro-5H-pyrrolo[1,2-b][1,2,4]triazol-7-ol

[Formula 128]

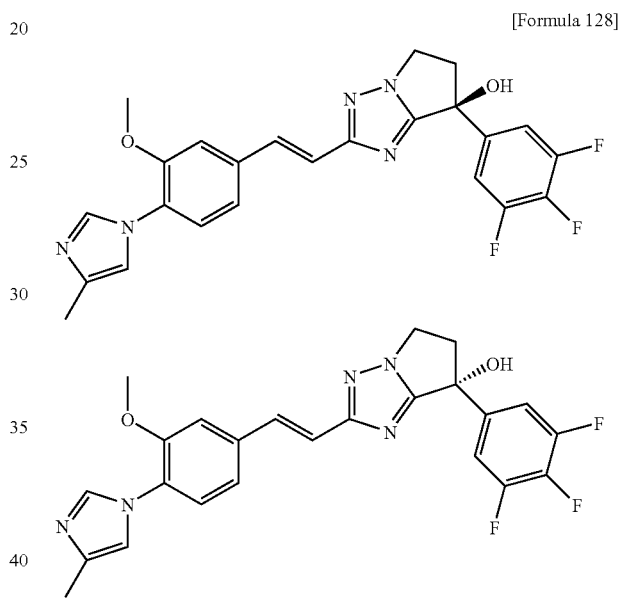

Sodium hydride (containing mineral oil at 40%, 9 mg) was added to a solution of the optically active compound obtained in Examples 112 and 113 with a retention time of 23 minutes and positive optical rotation, 2-{(E)-2-[3-methoxy-4-(4-methylimidazol-1-yl)phenyl]vinyl}-7-(3,4,5-trifluorophenyl)-6,7-dihydro-5H-pyrrolo[1,2-b][1,2,4]triazole (50 mg) in DMF (2 mL) at room temperature. The reaction solution was stirred at room temperature for 30 minutes while bubbling with oxygen gas and further stirred at room temperature in an oxygen atmosphere for one hour. A sodium thiosulfate solution was added to the reaction solution, followed by extraction with ethyl acetate. The resulting extract was washed with a saturated sodium chloride solution. The resulting organic layer was dried over magnesium sulfate and then concentrated under reduced pressure. The residue was purified by silica gel column chromatography (carrier: Chromatorex NH; elution solvent: heptane-ethyl acetate system, then ethyl acetate-methanol system) to obtain 32 mg of the title compound as a racemate. The property values of the compound are as follows.
ESI-MS; m/z 468 [M$^+$+H]. $^1$H-NMR (CDCl$_3$) δ (ppm): 2.25 (s, 3H), 2.86-2.95 (m, 1H), 3.05-3.13 (m, 1H), 3.75 (s, 3H), 4.22-4.30 (m, 1H), 4.36-4.44 (m, 1H), 6.81-6.85 (m, 1H), 6.88 (s, 1H), 6.95 (brs, 1H), 7.05 (d, J=16.0 Hz, 1H), 7.12 (d, J=8.0 Hz, 1H), 7.20-7.30 (m, 2H), 7.43 (d, J=16.0 Hz, 1H), 7.86 (d, J=0.8 Hz, 1H).

The title compound as a racemate obtained above (32 mg) was separated by CHIRALCEL™ OJ-H manufactured by Daicel Chemical Industries, Ltd. (2 cm×25 cm; mobile phase: hexane:ethanol=4:1) to obtain the title optically active compound with a retention time of 21 minutes and positive optical rotation (14 mg) and the title optically active compound with a retention time of 32 minutes and negative optical rotation (14 mg).

Examples 116 and 117

Synthesis of (+)-8-(3,4-difluorophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine and (−)-8-(3,4-difluorophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine

[Formula 129]

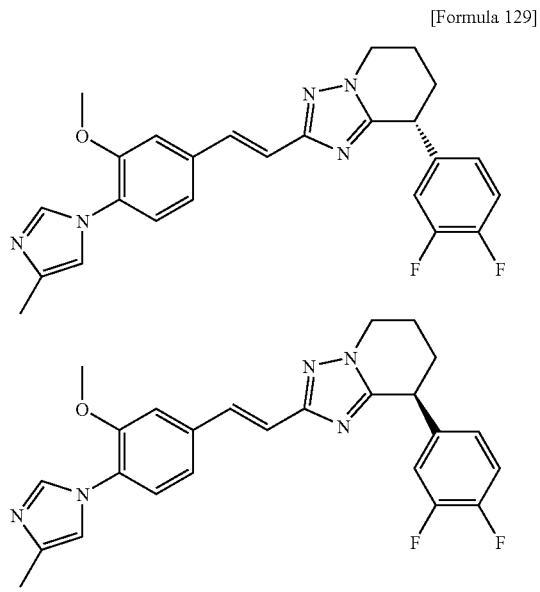

Synthesis of 1-amino-3-(3,4-difluorophenyl)piperidin-2-one

Sodium hydride (containing mineral oil at 40%, 0.48 g) was added to a solution of methyl (3,4-difluorophenyl)acetate (CAS #210530-71-5, 2.04 g) in DMF (30 mL) at 0° C., and the reaction solution was stirred at room temperature for 10 minutes. 1-chloro-3-iodopropane (1.3 mL) was added to the reaction solution at 0° C., and the reaction solution was stirred at room temperature for two hours. A saturated ammonium chloride solution was added to the reaction solution, followed by extraction with ethyl acetate. The resulting extract was washed with a saturated sodium chloride solution. The resulting organic layer was dried over magnesium sulfate and then concentrated under reduced pressure. Hydrazine monohydrate (5.5 g) was added to a solution of the resulting residue in ethanol (50 mL) at room temperature, and the reaction solution was stirred at 80° C. for seven hours. The reaction solution was left to cool to room temperature and concentrated under reduced pressure. A saturated sodium bicarbonate solution was added to the residue, followed by extraction with chloroform. The resulting extract was dried over magnesium sulfate and then concentrated under reduced pressure. The residue was purified by silica gel column chromatography (elution solvent: heptane-ethyl acetate system, then ethyl acetate-methanol system) to obtain 1.42 g of the title compound. The property values of the compound are as follows.

ESI-MS; m/z 227 [M⁺+H]. ¹H-NMR (CDCl₃) δ (ppm): 1.84-2.06 (m, 3H), 2.10-2.21 (m, 1H), 3.53-3.71 (m, 3H), 4.59 (brs, 2H), 6.89-6.95 (m, 1H), 6.97-7.05 (m, 1H), 7.06-7.26 (m, 1H).

Synthesis of (E)-N-[3-(3,4-difluorophenyl)-2-oxopiperidin-1-yl]-3-[3-methoxy-4-(4-methyl-1H-imidazol-1-yl)phenyl]acrylamide IPEA (1.5 mL), 1-amino-3-(3,4-difluorophenyl)piperidin-2-one (420 mg) and BOPCl (0.53 g) were added to a solution of (E)-3-[3-methoxy-4-(4-methyl-1H-imidazol-1-yl)phenyl]acrylic acid (450 mg) in methylene chloride (15 mL) at room temperature, and the reaction solution was stirred at room temperature for three hours. Water was added to the reaction solution, followed by extraction with chloroform. The resulting extract was washed with a saturated sodium chloride solution. The resulting organic layer was dried over magnesium sulfate and then concentrated under reduced pressure. The residue was purified by silica gel column chromatography (carrier: Chromatorex NH; elution solvent: heptane-ethyl acetate system, then ethyl acetate-methanol system) to obtain 572 mg of the title compound. The property value of the compound is as follows.

ESI-MS; m/z 467 [M⁺+H].

Synthesis of (+)-8-(3,4-difluorophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine and (−)-8-(3,4-difluorophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine A solution of (E)-N-[3-(3,4-difluorophenyl)-2-oxopiperidin-1-yl]-3-[3-methoxy-4-(4-methyl-1H-imidazol-1-yl)phenyl]acrylamide (572 mg) in phosphorus oxychloride (8 mL) was heated under reflux for one hour. The reaction solution was left to cool to room temperature and concentrated under reduced pressure. Acetic acid (5 mL) and ammonium acetate (4.7 g) were added to the resulting residue, and the reaction solution was stirred at 150° C. for two hours. The reaction solution was left to cool to room temperature and concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system) to obtain 373 mg of the title compound as a racemate. The property values of the compound are as follows.

ESI-MS; m/z 448 [M⁺+H]. ¹H-NMR (CDCl₃) δ (ppm): 1.93-2.27 (m, 3H), 2.30 (s, 3H), 2.32-2.42 (m, 1H), 3.86 (s, 3H), 4.25-4.33 (m, 3H), 6.87-6.94 (m, 2H), 6.95-7.02 (m, 1H), 7.06 (d, J=16.4 Hz, 1H), 7.11-7.18 (m, 3H), 7.20-7.25 (m, 1H), 7.51 (d, J=16.4 Hz, 1H), 7.70 (d, J=0.8 Hz, 1H).

The title compound as a racemate (16 mg) was separated by CHIRALPAK™ IA manufactured by Daicel Chemical Industries, Ltd. (2 cm×25 cm; mobile phase: ethanol) to obtain the title optically active compound with a retention time of 17 minutes and positive optical rotation (7.6 mg) and the title optically active compound with a retention time of 23 minutes and negative optical rotation (7.7 mg).

Example 118

Synthesis of 4-(4-fluorophenyl)-2-{(E)-2-[3-methoxy-4-(4-methyl-1H-imidazol-1-yl)phenyl]vinyl}-4,5,6,7-tetrahydro[1,2,4]triazolo[1,5-a]pyrimidine

[Formula 130]

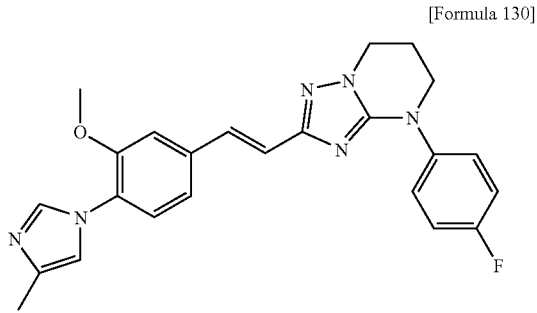

Synthesis of 3-(4-fluorophenylamino)propan-1-ol 4-fluoroaniline (3.82 g) and lithium tetrafluoroborate (3.32 g) were added to a solution of oxetane (1.00 g) in acetonitrile (20 mL) at room temperature, and the reaction solution was stirred at room temperature for 64 hours. A saturated sodium bicarbonate solution was added to the reaction solution, followed by extraction with chloroform. The resulting extract was dried over magnesium sulfate and then concentrated under reduced pressure. The residue was purified by silica gel column chromatography (elution solvent: heptane-ethyl acetate system) to obtain 2.37 g of the title compound. The property values of the compound are as follows.

ESI-MS; m/z 170 [M$^+$+H]. $^1$H-NMR (CDCl$_3$) δ (ppm): 1.88 (tt, J=6.4, 6.0 Hz, 2H), 3.25 (t, J=6.4 Hz, 2H), 3.83 (t, J=6.0 Hz, 2H), 6.55-6.62 (m, 2H), 6.86-6.93 (m, 2H).

Synthesis of 1-amino-3-(4-fluorophenyl)tetrahydropyrimidin-2-one

Thionyl chloride (5.3 mL) was added to a solution of 3-(4-fluorophenylamino)propan-1-ol (2.37 g) in toluene (30 mL) at room temperature, and the reaction solution was stirred at 60° C. for five hours. The reaction solution was left to cool to room temperature and concentrated under reduced pressure. Ice and a saturated sodium bicarbonate solution were added to the residue, followed by extraction with ethyl acetate (100 mL). Heptane (100 mL) was added to the resulting extract, and the solution was purified by silica gel column chromatography (elution solvent: heptane:ethyl acetate=1:1) to obtain (3-chloropropyl)-(4-fluorophenyl)amine. Triethylamine (5.4 mL) and phenyl chlorocarbonate (1.9 mL) were added to a solution of (3-chloropropyl)-(4-fluorophenyl) amine (2.40 g) in THF (40 mL) at 0° C., and the reaction solution was stirred at room temperature for 12 hours. Water was added to the reaction solution, followed by extraction with ethyl acetate. The resulting extract was dried over magnesium sulfate and then concentrated under reduced pressure. The residue was purified by silica gel column chromatography (elution solvent: heptane-ethyl acetate system) to obtain phenyl (3-chloropropyl)-(4-fluorophenyl)carbamate (3.93 g). Hydrazine monohydrate (0.40 mL) was added to a solution of phenyl (3-chloropropyl)-(4-fluorophenyl)carbamate (500 mg) in ethanol (10 mL) at room temperature. The reaction solution was stirred at room temperature for one hour, stirred at 60° C. for one hour and heated under reflux for seven hours. Hydrazine monohydrate (0.40 mL) was added to the reaction solution, and the reaction solution was heated under reflux for 13 hours. The reaction solution was left to cool to room temperature and concentrated under reduced pressure. A saturated sodium bicarbonate solution was added to the residue, followed by extraction with chloroform. The resulting extract was dried over magnesium sulfate and then concentrated under reduced pressure. The residue was purified by silica gel column chromatography (elution solvent: heptane-ethyl acetate system, then ethyl acetate-methanol system) to obtain 265 mg of the title compound. The property values of the compound are as follows.

ESI-MS; m/z 210 [M$^+$+H]. $^1$H-NMR (CDCl$_3$) δ (ppm): 2.15 (tt, J=6.4, 5.6 Hz, 2H), 3.58-3.67 (m, 4H), 4.31 (brs, 2H), 6.98-7.05 (m, 2H), 7.18-7.24 (m, 2H).

Synthesis of (E)-N-[3-(4-fluorophenyl)-2-oxotetrahydropyrimidin-1-yl]-3-[3-methoxy-4-(4-methyl-1H-imidazol-1-yl)phenyl]acrylamide IPEA (0.51 mL), (E)-3-[3-methoxy-4-(4-methylimidazol-1-yl)phenyl]acrylic acid (150 mg) and BOPCl (0.18 g) were added to a solution of 1-amino-3-(4-fluorophenyl)tetrahydropyrimidin-2-one (132 mg) in methylene chloride (5 mL) at room temperature, and the reaction solution was stirred at room temperature for 13 hours. Water was added to the reaction solution, followed by extraction with chloroform. The resulting extract was washed with a saturated sodium bicarbonate solution. The resulting organic layer was dried over magnesium sulfate and then concentrated under reduced pressure. The residue was purified by silica gel column chromatography (carrier: Chromatorex NH; elution solvent: heptane-ethyl acetate system, then ethyl acetate-methanol system) to obtain 261 mg of the title compound. The property value of the compound is as follows.

ESI-MS; m/z 450 [M$^+$+H].

Synthesis of 4-(4-fluorophenyl)-2-{(E)-2-[3-methoxy-4-(4-methyl-1H-imidazol-1-yl)phenyl]vinyl}-4,5,6,7-tetrahydro[1,2,4]triazolo[1,5-a]pyrimidine A solution of (E)-N-[3-(4-fluorophenyl)-2-oxotetrahydropyrimidin-1-yl]-3-[3-methoxy-4-(4-methyl-1H-imidazol-1-yl)phenyl]acrylamide (261 mg) in phosphorus oxychloride (3 mL) was heated under reflux for one hour. The reaction solution was left to cool to room temperature and concentrated under reduced pressure. Acetic acid (2 mL) and ammonium acetate (2.2 g) were added to the resulting residue, and the reaction solution was stirred at 150° C. for two hours. The reaction solution was left to cool to room temperature and concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system) to obtain 179 mg of the title compound. The property values of the compound are as follows.

ESI-MS; m/z 431 [M$^+$+H]. $^1$H-NMR (CDCl$_3$) δ (ppm): 2.30 (s, 3H), 2.37 (tt, J=6.4, 5.6 Hz, 2H), 3.83 (t, J=5.6 Hz, 2H), 3.87 (s, 3H), 4.23 (t, J=6.4 Hz, 2H), 6.92 (brs, 1H), 6.95 (d, J=16.4 Hz, 1H), 7.07-7.18 (m, 4H), 7.22 (d, J=8.0 Hz, 1H), 7.43 (d, J=16.4 Hz, 1H) 7.47-7.54 (m, 2H), 7.70 (d, J=1.2 Hz, 1H).

Examples 119 and 120

Synthesis of (+)-3-{(E)-2-[3-methoxy-4-(4-methyl-1H-imidazol-1-yl)phenyl]vinyl}-5-phenyl-5,6,7,8-tetrahydro[1,2,4]triazolo[4,3-a]pyridine and (−)-3-{(E)-2-[3-methoxy-4-(4-methyl-1H-imidazol-1-yl)phenyl]vinyl}-5-phenyl-5,6,7,8-tetrahydro[1,2,4]triazolo[4,3-a]pyridine

[Formula 131]

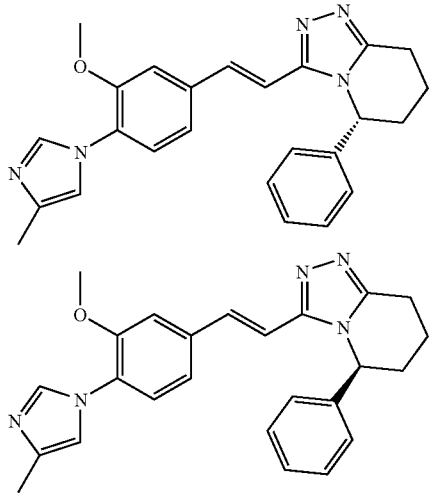

Synthesis of 4-{5-{(E)-2-[3-methoxy-4-(4-methyl-1H-imidazol-1-yl)phenyl]vinyl}[1,3,4]oxadiazol-2-yl}-1-phenylbuten-1-one IPEA (2.5 mL) was added to a suspension of (E)-3-[3-methoxy-4-(4-methyl-1H-imidazol-1-yl)phenyl]acrylic acid hydrazide (500 mg) in methylene chloride (12 mL) at room temperature, and the reaction solution was stirred at room temperature for 10 minutes. 4-benzoylbutyric acid (334 mg) and BOPCl (442 mg) were added to the reaction solution at room temperature, and the reaction solution was stirred at room temperature for four hours. A saturated sodium bicarbonate solution was added to the reaction solution, followed by extraction with chloroform. The resulting extract was dried over magnesium sulfate and then concentrated under reduced pressure to obtain 5-oxo-5-phenylpentanoic acid N'-{(E)-3-[3-methoxy-4-(4-methyl-1H-imidazol-1-yl)phenyl]acryloyl}hydrazide (692 mg). Imidazole (494 mg), carbon tetrabromide (2.36 g) and triphenylphosphine (559 mg) were added to a suspension of 5-oxo-5-phenylpentanoic acid N'-{(E)-3-[3-methoxy-4-(4-methyl-1H-imidazol-1-yl)phenyl]acryloyl}hydrazide (634 mg) in methylene chloride (15 mL) at room temperature, and the reaction solution was stirred at room temperature for 12 hours. The reaction solution was concentrated under reduced pressure, and the residue was purified by silica gel column chromatography (elution solvent: heptane-ethyl acetate system, then ethyl acetate-methanol system) to obtain 515 mg of the title compound. The property value of the compound is as follows.

ESI-MS; m/z 429 [M$^+$+H].

Synthesis of (+)-3-{(E)-2-[3-methoxy-4-(4-methyl-1H-imidazol-1-yl)phenyl]vinyl}-5-phenyl-5,6,7,8-tetrahydro[1,2,4]triazolo[4,3-a]pyridine and (−)-3-{(E)-2-[3-methoxy-4-(4-methyl-1H-imidazol-1-yl)phenyl]vinyl}-5-phenyl-5,6,7,8-tetrahydro[1,2,4]triazolo[4,3-a]pyridine Sodium borohydride (96 mg) was added to a solution of 4-{5-{(E)-2-[3-methoxy-4-(4-methyl-1H-imidazol-1-yl)phenyl]vinyl}[1,3,4]oxadiazol-2-yl}-1-phenylbuten-1-one (515 mg) in methanol (10 mL) at 0° C., and the reaction solution was stirred at room temperature for one hour. The reaction solution was concentrated under reduced pressure. A saturated sodium bicarbonate solution was added to the residue, followed by extraction with ethyl acetate. The resulting extract was washed with a saturated sodium chloride solution. The organic layer was dried over magnesium sulfate and then concentrated under reduced pressure. Triethylamine (0.43 mL) and methanesulfonic acid chloride (0.12 mL) were added to a solution of the resulting residue in methylene chloride (10 mL) at 0° C., and the reaction solution was stirred at room temperature for 30 minutes. Ethyl acetate was added to the reaction solution, and the reaction solution was sequentially washed with a saturated sodium bicarbonate solution and a saturated sodium chloride solution. The resulting organic layer was dried over magnesium sulfate and then concentrated under reduced pressure. Sodium azide (134 mg) was added to a solution of the resulting residue in DMF (10 mL), and the reaction solution was stirred at room temperature for one hour. Water and ethyl acetate were added to the reaction solution, and the organic layer was separated. The resulting organic layer was washed with a saturated sodium chloride solution, dried over magnesium sulfate and then concentrated under reduced pressure. Triphenylphosphine (405 mg) was added to a mixed solution of the resulting residue in THF (10 mL) and water (0.5 mL) at room temperature, and the reaction solution was stirred at 60° C. for one hour. Water (0.5 mL) was added to the reaction solution, and then the reaction solution was stirred at 60° C. for 4.5 hours. The reaction solution was left to cool to room temperature and concentrated under reduced pressure. THF and toluene were added to the residue, and the solution was again concentrated under reduced pressure. A solution of the resulting residue in acetic acid (5 mL) was heated under reflux for one hour. The reaction solution was left to cool to room temperature and concentrated under reduced pressure. A saturated sodium bicarbonate solution was added to the residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system, then ethyl acetate-methanol system) to obtain 270 mg of the title compound as a racemate. The property values of the compound are as follows.

ESI-MS; m/z 412 [M$^+$+H]. $^1$H-NMR (CDCl$_3$) δ (ppm): 1.83-1.95 (m, 2H), 2.07-2.18 (m, 1H), 2.28 (s, 3H), 2.34-2.45 (m, 1H), 3.00-3.12 (m, 1H), 3.15-3.24 (m, 1H), 3.78 (s, 3H), 5.40 (t, J=5.2 Hz, 1H), 6.29 (d, J=16.4 Hz, 1H), 6.79 (s, 1H), 6.83-6.88 (m, 2H), 7.00-7.05 (m, 2H), 7.25 (d, J=7.6 Hz, 1H), 7.30-7.41 (m, 3H), 7.54 (d, J=16.4 Hz, 1H), 7.64 (s, 1H).

The title compound as a racemate (12 mg) was separated by CHIRALCEL™ OD-H manufactured by Daicel Chemical Industries, Ltd. (2 cm×25 cm; mobile phase: ethanol) to obtain the title optically active compound with a retention time of 15 minutes and positive optical rotation (4.6 mg) and the title optically active compound with a retention time of 20 minutes and negative optical rotation (4.7 mg).

Example 121

Synthesis of 4-chloro-2-{(E)-2-[3-methoxy-4-(4-methyl-1H-imidazol-1-yl)phenyl]vinyl}-1H-imidazole

[Formula 132]

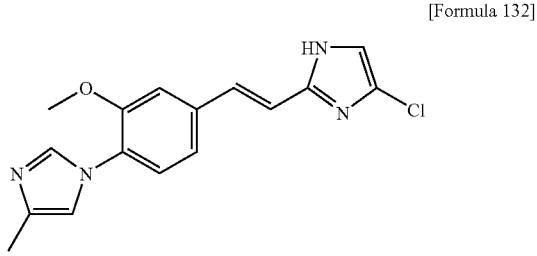

Synthesis of (E)-N-cyanomethyl-3-[3-methoxy-4-(4-methyl-1H-imidazol-1-yl)phenyl]acrylamide EDC (4.48 g), HOBT (3.14 g) and IPEA (6.76 mL) were sequentially added to a solution of (E)-3-[3-methoxy-4-(4-methyl-1H-imidazol-1-yl)phenyl]acrylic acid (2 g) and aminoacetonitrile hydrochloride (1.08 g) in DMF (25 mL), and the reaction solution was stirred at room temperature for five hours. Ethyl acetate and water were added to the reaction solution, and the organic layer was separated. The resulting organic layer was washed with brine and then dried over anhydrous sodium sulfate and filtered through a silica gel pad (Chromatorex NH). The filtrate was concentrated under reduced pressure. The residue was crystallized (heptane-ethyl acetate-methanol system) to obtain 1.24 g of the title compound. The property values of the compound are as follows.

$^1$H-NMR (CD$_3$OD) δ (ppm): 2.24 (s, 3H), 3.93 (s, 3H), 4.29 (s, 2H), 6.66 (d, J=15.6 Hz, 1H), 7.10 (s, 1H), 7.30 (dd, J=8.0, 2.0 Hz, 1H), 7.38-7.40 (m, 2H), 7.63 (d, J=15.6 Hz, 1H), 7.82 (s, 1H).

Synthesis of 4-chloro-2-{(E)-2-[3-methoxy-4-(4-methyl-1H-imidazol-1-yl)phenyl]vinyl}-1H-imidazole Carbon tetrachloride (0.326 mL) was added to a solution of (E)-N-cyanomethyl-3-[3-methoxy-4-(4-methyl-1H-imidazol-1-yl)phenyl]acrylamide (400 mg) and triphenylphosphine (888 mg) in acetonitrile (20 mL), and the reaction solution was stirred at 45° C. for 12 hours. The reaction solution was concentrated under reduced pressure. Ethyl acetate and saturated sodium bicarbonate water were added to the resulting residue, and the organic layer was separated. The resulting organic layer was sequentially washed with water and brine, dried over anhydrous sodium sulfate and then concentrated under reduced pressure. The residue was purified by silica gel column chromatography (carrier: Chromatorex NH; elution solvent: ethyl acetate) to obtain 76 mg of the title compound. The property values of the compound are as follows.

ESI-MS; m/z 315 [M$^+$+H]. $^1$H-NMR (CDCl$_3$) δ (ppm): 2.29 (s, 3H), 3.78 (s, 3H), 6.89 (d, J=16.4 Hz, 1H), 6.92 (s, 1H), 6.98-7.01 (m, 3H), 7.12 (d, J=8.4 Hz, 1H), 7.34 (d, J=16.4 Hz, 1H), 7.70 (s, 1H).

Example 122

Synthesis of 4-(4-methoxyphenyl)-2-{(E)-2-[3-methoxy-4-(4-methyl-1H-imidazol-1-yl)phenyl]vinyl}-1H-imidazole

[Formula 133]

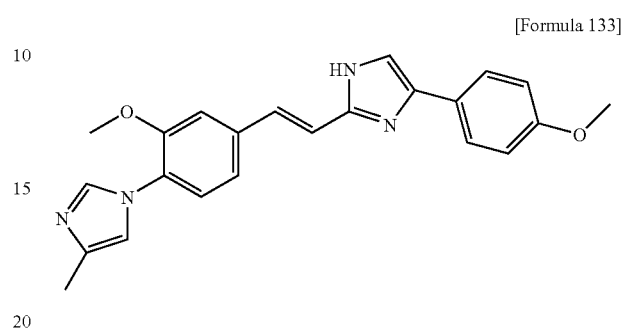

Synthesis of (E)-3-[3-methoxy-4-(4-methyl-1H-imidazol-1-yl)phenyl]-N-[2-(4-methoxyphenyl)-2-oxoethyl]acrylamide EDC (223 mg), HOBT (157 mg) and IPEA (0.337 mL) were sequentially added to a solution of (E)-3-[3-methoxy-4-(4-methyl-1H-imidazol-1-yl)phenyl]acrylic acid (100 mg) and 2-amino-1-(4-methoxyphenyl)ethanone hydrochloride (CAS No. 3883-94-1, 117 mg) in DMF (3 mL), and the reaction solution was stirred at room temperature for three hours. Ethyl acetate and water were added to the reaction solution, and the organic layer was separated. The resulting organic layer was washed with brine and then dried over anhydrous sodium sulfate and concentrated under reduced pressure. The residue was purified by silica gel column chromatography (carrier: Chromatorex NH; elution solvent: ethyl acetate) to obtain 104.7 mg of the title compound. The property values of the compound are as follows.

$^1$H-NMR (CDCl$_3$) δ (ppm): 2.30 (s, 3H), 3.90 (s, 3H), 3.91 (s, 3H), 4.77 (d, J=4.4 Hz, 2H), 6.57 (d, J=15.6 Hz, 1H), 6.84 (t, J=4.4 Hz, 1H), 6.93 (s, 1H), 6.99 (dd, J=5.2, 2.8 Hz, 2H), 7.16-7.27 (m, 3H), 7.65 (d, J=15.6 Hz, 1H), 7.72 (s, 1H), 8.00 (dd, J=5.2, 2.8 Hz, 1H).

Synthesis of 4-(4-methoxyphenyl)-2-{(E)-2-[3-methoxy-4-(4-methyl-1H-imidazol-1-yl)phenyl]vinyl}-1H-imidazole Ammonium acetate (379 mg) was added to a solution of (E)-3-[3-methoxy-4-(4-methyl-1H-imidazol-1-yl)phenyl]-N-[2-(4-methoxyphenyl)-2-oxoethyl]acrylamide (100 mg) in acetic acid (3 mL), and the reaction solution was stirred at 120° C. for 12 hours. The reaction solution was concentrated. Ethyl acetate and saturated sodium bicarbonate water were added to the resulting residue, and the organic layer was separated. The resulting organic layer was washed with brine, dried over anhydrous sodium sulfate and then concentrated under reduced pressure. The residue was purified by silica gel column chromatography (carrier: Chromatorex NH; elution solvent: ethyl acetate:2-propanol=20:1) to obtain 15 mg of the title compound. The property values of the compound are as follows.

$^1$H-NMR (CDCl$_3$) δ (ppm): 2.29 (s, 3H), 3.78 (s, 3H), 3.82 (s, 3H), 6.90-7.03 (m, 6H), 7.13 (d, J=8.0 Hz, 1H), 7.28 (d, J=16.4 Hz, 1H), 7.32 (s, 1H), 7.67 (s, 1H), 7.69 (m, 2H).

Example 123

Synthesis of 4-(3-methoxyphenyl)-2-{(E)-2-[3-methoxy-4-(4-methyl-1H-imidazol-1-yl)phenyl]vinyl}-1H-imidazole

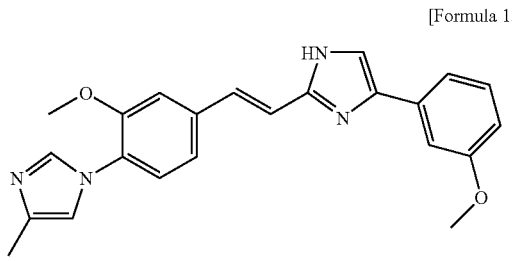

[Formula 134]

6.0 mg of the title compound was obtained from (E)-3-[3-methoxy-4-(4-methylimidazol-1-yl)phenyl]acrylic acid (100 mg) and 2-amino-1-(3-methoxyphenyl)ethanone hydrochloride (CAS No. 24037-72-7, 117 mg) by the same method as in Example 122. The property values of the compound are as follows.

$^1$H-NMR (CDCl$_3$) δ (ppm): 2.30 (s, 3H), 3.83 (s, 3H), 3.85 (s, 3H), 6.82 (dd, J=9.2, 2.4 Hz, 1H), 6.92 (s, 1H), 7.05-7.09 (m, 3H), 7.18 (d, J=8.0 Hz, 1H), 7.26-7.33 (m, 4H), 7.39 (s, 1H), 7.71 (s, 1H).

Example 124

Synthesis of 4-(2-methoxyphenyl)-2-{(E)-2-[3-methoxy-4-(4-methyl-1H-imidazol-1-yl)phenyl]vinyl}-1H-imidazole

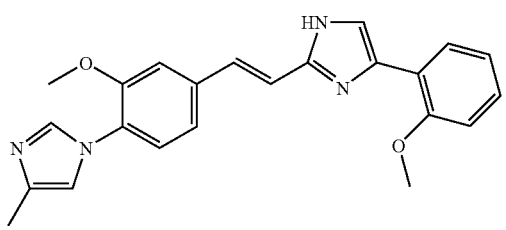

[Formula 135]

23.8 mg of the title compound was obtained from (E)-3-[3-methoxy-4-(4-methyl-1H-imidazol-1-yl)phenyl]acrylic acid (100 mg) and 2-amino-1-(2-methoxyphenyl)ethanone hydrochloride (CAS No. 34589-97-4, 117 mg) by the same method as in Example 122. The property values of the compound are as follows.

$^1$H-NMR (CDCl$_3$) δ (ppm): 2.30 (s, 3H), 3.86 (s, 3H), 4.00 (s, 3H), 6.91 (s, 1H), 6.99-7.12 (m, 5H), 7.19-7.31 (m, 4H), 7.59 (s, 1H), 7.71 (s, 1H).

Example 125

Synthesis of 4-(4-chlorophenyl)-2-{(E)-2-[3-methoxy-4-(4-methyl-1H-imidazol-1-yl)phenyl]vinyl}-1H-imidazole ditrifluoroacetate

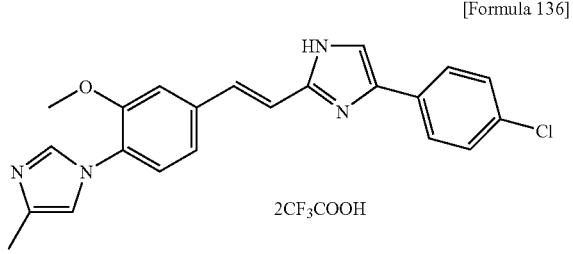

[Formula 136]

2CF$_3$COOH

A crude product of the title compound was obtained from (E)-3-[3-methoxy-4-(4-methyl-1H-imidazol-1-yl)phenyl]acrylic acid (150 mg) and 2-amino-1-(4-chlorophenyl)ethanone hydrochloride (CAS No. 5467-71-0, 144 mg) by the same method as in Example 33. The crude product was purified by LC-MS to obtain 3.5 mg of the title compound. The property values of the compound are as follows.

ESI-MS; m/z 391 [M$^+$+H], $^1$H-NMR (CD$_3$OD) δ (ppm): 2.44 (s, 3H), 4.03 (s, 3H), 7.30 (d, J=16.4 Hz, 1H), 7.47 (dd, J=8.4, 2.0 Hz, 1H), 7.52-7.57 (m, 2H), 7.61-7.65 (m, 2H), 7.75-7.81 (m, 4H), 7.97 (s, 1H), 9.18 (s, 1H).

Example 126

Synthesis of 4-(4-biphenyl)-2-{(E)-2-[3-methoxy-4-(4-methyl-1H-imidazol-1-yl)phenyl]vinyl}-1H-imidazole

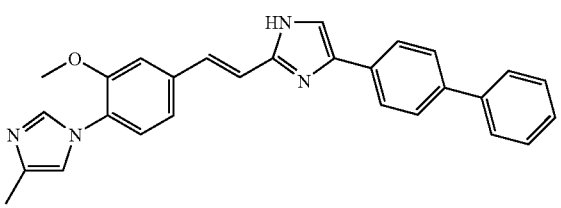

[Formula 137]

6.6 mg of the title compound was obtained from (E)-3-[3-methoxy-4-(4-methyl-1H-imidazol-1-yl)phenyl]acrylic acid (150 mg) and 2-amino-1-(4-biphenyl)ethanone hydrochloride (CAS No. 71350-68-0, 173 mg) by the same method as in Example 33. The property value of the compound is as follows.

ESI-MS; m/z 433 [M$^+$+H].

Example 127

Synthesis of 4-(4-propyl)-2-{(E)-2-[3-methoxy-4-(4-methyl-1H-imidazol-1-yl)phenyl]vinyl}-1H-imidazole ditrifluoroacetate

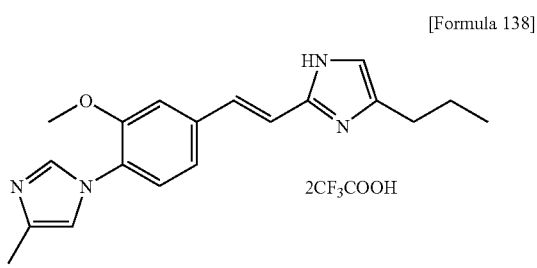

[Formula 138]

A crude product of the title compound was obtained from (E)-3-[3-methoxy-4-(4-methyl-1H-imidazol-1-yl)phenyl]acrylic acid (150 mg) and 1-aminopentan-2-one hydrochloride (CAS No. 41172-98-9, 88.2 mg) by the same method as in Example 33. The crude product was purified by LC-MS to obtain 1.7 mg of the title compound. The property value of the compound is as follows.

ESI-MS; m/z 323 [M$^+$+H].

Examples 128 and 129

Synthesis of (+)-2-{(E)-2-[3-methoxy-4-(4-methyl-1H-imidazol-1-yl)phenyl]vinyl}-8-(4-trifluoromethoxyphenyl)-5,6,7,8-tetrahydro[1,2,4]triazolo[1,5-a]pyridine and (−)-2-{(E)-2-[3-methoxy-4-(4-methyl-1H-imidazol-1-yl)phenyl]vinyl}-8-(4-trifluoromethoxyphenyl)-5,6,7,8-tetrahydro[1,2,4]triazolo[1,5-a]pyridine

[Formula 139]

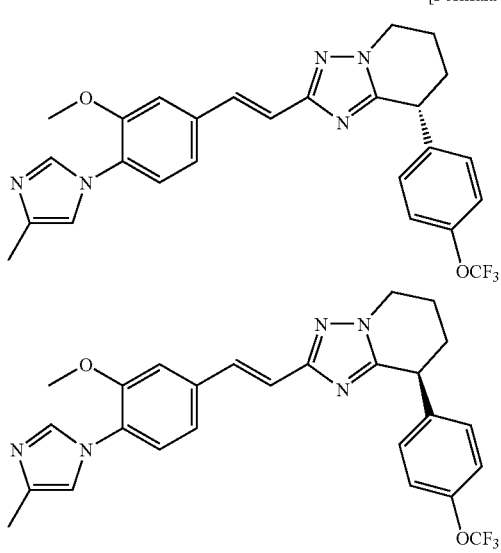

A racemate of the title compound was obtained from 5-chloro-2-(4-trifluoromethoxyphenyl)pentanoic acid (1.1 g) by the same method as in Examples 51 and 52. The resulting racemate was separated by CHIRALPAK™ AD-H manufactured by Daicel Chemical Industries, Ltd. (2 cm×25 cm; mobile phase: ethanol) to obtain the title optically active compound with a retention time of 7.7 minutes and positive optical rotation (9.2 mg, >99% ee) and the title optically active compound with a retention time of 12.9 minutes and negative optical rotation (9.1 mg, >99% ee).

The property values of the title optically active compound with a retention time of 7.7 minutes are as follows.

ESI-MS; m/z 496 [M$^+$+H], $^1$H-NMR (CDCl$_3$) δ (ppm): 2.02-2.21 (m, 3H), 2.29 (s, 3H), 2.33-2.39 (m, 1H), 3.85 (s, 3H), 4.27-4.37 (m, 3H), 6.90 (d, J=1.6 Hz, 1H), 7.05 (d, J=16.0 Hz, 1H), 7.12-7.22 (m, 7H), 7.50 (d, J=16.0 Hz, 1H) 7.68 (d, J=1.6 Hz, 1H).

The property values of the title optically active compound with a retention time of 12.9 minutes are as follows.

ESI-MS; m/z 496 [M$^+$+H], $^1$H-NMR (CDCl$_3$) δ (ppm): 2.02-2.21 (m, 3H), 2.29 (s, 3H), 2.33-2.39 (m, 1H), 3.85 (s, 3H), 4.27-4.37 (m, 3H), 6.90 (d, J=1.6 Hz, 1H), 7.05 (d, J=16.0 Hz, 1H), 7.12-7.22 (m, 7H), 7.50 (d, J=16.0 Hz, 1H) 7.68 (d, J=1.6 Hz, 1H).

Examples 130 and 131

Synthesis of (+)-2-{(E)-2-[3-methoxy-4-(4-methyl-1H-imidazol-1-yl)phenyl]vinyl}-8-naphthalen-1-yl-5,6,7,8-tetrahydro[1,2,4]triazolo[1,5-a]pyridine and (−)-2-{(E)-2-[3-methoxy-4-(4-methyl-1H-imidazol-1-yl)phenyl]vinyl}-8-naphthalen-1-yl-5,6,7,8-tetrahydro[1,2,4]triazolo[1,5-a]pyridine

[Formula 140]

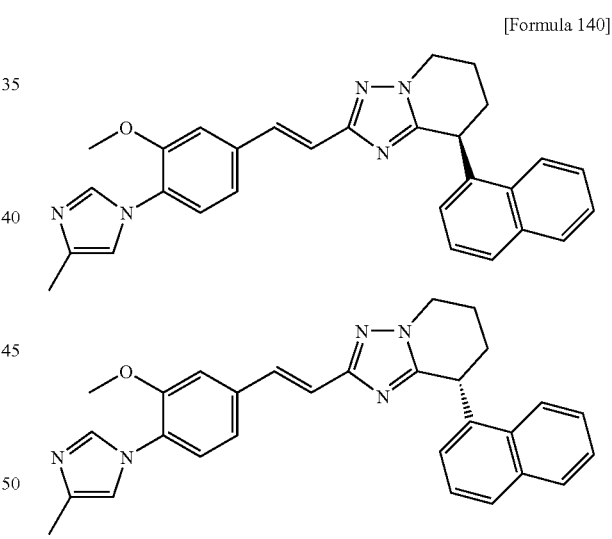

Synthesis of 5-chloro-2-naphthalen-1-ylpentanoic acid N'-{(E)-3-[3-methoxy-4-(4-methyl-1H-imidazol-1-yl)phenyl]acryloylhydrazide IPEA (6.05 mL) and BOPCl (2.78 g) were added to a solution of 5-chloro-2-naphthalen-1-ylpentanoic acid (2.4 g) synthesized according to the method described in Tetrahedron Letters, 2003, vol. 44, p. 365 and (E)-3-[3-methoxy-4-(4-methyl-1H-imidazol-1-yl)phenyl]acrylic acid hydrazide dihydrochloride (2.4 g) in methylene chloride (50 mL), and the reaction solution was stirred at room temperature for 12 hours. Ethyl acetate and 1 N aqueous hydrochloric acid were added to the reaction solution, and the organic layer was separated. The resulting organic layer was sequentially washed with a 1 N sodium hydroxide solution and brine, dried over anhydrous sodium sulfate and then concentrated under reduced pressure. The residue was purified by silica gel column chromatography (carrier: Chromatorex NH; elution solvent: ethyl acetate:methanol=20:1) and then solidified with tert-butyl methyl ether. Thereafter, the solid was collected by filtration to obtain 2.2 g of the title compound. The property values of the compound are as follows.

$^1$H-NMR (CDCl$_3$) δ (ppm): 1.72-1.81 (m, 1H), 1.84-1.93 (m, 1H), 2.14-2.22 (m, 1H), 2.28 (s, 3H), 2.43-2.50 (m, 1H), 3.46-3.57 (m, 2H), 3.83 (s, 3H), 4.36 (t, J=7.6 Hz, 1H), 6.40 (d, J=16.0 Hz, 1H), 6.90 (s, 1H), 7.05 (d, J=8.0 Hz, 1H), 7.09 (d, J=16.0 Hz, 1H), 7.20 (d, J=8.0 Hz, 1H), 7.43-7.60 (m, 5H), 7.70 (s, 1H), 7.81 (d, J=8.4 Hz, 1H), 7.88 (d, J=7.2 Hz, 1H), 8.05 (d, J=8.0 Hz, 1H), 8.60 (brs, 1H), 8.73 (brs, 1H).

Synthesis of (+)-2-{(E)-2-[3-methoxy-4-(4-methyl-1H-imidazol-1-yl)phenyl]vinyl}-8-naphthalen-1-yl-5,6,7,8-tetrahydro[1,2,4]triazolo[1,5-a]pyridine and (−)-2-{(E)-2-[3-methoxy-4-(4-methyl-1H-imidazol-1-yl)phenyl]vinyl}-8-naphthalen-1-yl-5,6,7,8-tetrahydro[1,2,4]triazolo[1,5-a]pyridine A solution of 5-chloro-2-naphthalen-1-ylpentanoic acid N'-{(E)-3-[3-methoxy-4-(4-methyl-1H-imidazol-1-yl)phenyl]acryloylhydrazide (2.2 g) in phosphorus oxychloride (15 mL) was stirred at 120° C. for four hours. The reaction solution was left to cool to room temperature and then concentrated under reduced pressure. Ammonium acetate (6.79 g) was added to a solution of the residue in acetic acid (5 mL), and the reaction solution was stirred at 150° C. for 15 hours. The reaction solution was left to cool to room temperature. Then, ethyl acetate and saturated sodium bicarbonate water were added to the reaction solution, and the organic layer was separated. The resulting organic layer was washed with brine, dried over anhydrous magnesium sulfate and then concentrated under reduced pressure. The residue was purified by silica gel column chromatography (carrier: Chromatorex NH; elution solvent: heptane:ethyl acetate=1:3) to obtain a racemate of the title compound. The resulting racemate was separated by CHIRALPAK™ IA manufactured by Daicel Chemical Industries, Ltd. (2 cm×25 cm; mobile phase: ethanol) to obtain the title optically active compound with a retention time of 8.6 minutes and positive optical rotation (55.8 mg, >99% ee) and the title optically active compound with a retention time of 10.8 minutes and negative optical rotation (51.4 mg, >99% ee).

The property values of the title optically active compound with a retention time of 8.6 minutes are as follows.

ESI-MS; m/z 462 [M$^+$+H], $^1$H-NMR (CDCl$_3$) δ (ppm): 2.04-2.28 (m, 3H), 2.29 (s, 3H), 2.40-2.47 (m, 1H), 3.84 (s, 3H), 4.24-4.31 (m, 1H), 4.38-4.40 (m, 1H), 5.20 (t, J=5.6 Hz, 1H), 6.86 (d, J=7.2 Hz, 1H), 6.90 (s, 1H), 7.09 (d, J=16.0 Hz, 1H), 7.13 (d, J=8.8 Hz, 1H), 7.14 (s, 1H), 7.20 (d, J=8.8 Hz, 1H), 7.36 (t, J=7.2 Hz, 1H), 7.49-7.57 (m, 3H), 7.68 (s, 1H), 7.77 (d, J=8.4 Hz, 1H), 7.89 (d, J=7.6 Hz, 1H), 7.99 (d, J=8.4 Hz, 1H).

The property values of the title optically active compound with a retention time of 10.8 minutes are as follows.

ESI-MS; m/z 462 [M$^+$+H], $^1$H-NMR (CDCl$_3$) δ (ppm): 2.04-2.28 (m, 3H), 2.29 (s, 3H), 2.40-2.47 (m, 1H), 3.84 (s, 3H), 4.24-4.31 (m, 1H), 4.38-4.40 (m, 1H), 5.20 (t, J=5.6 Hz, 1H), 6.86 (d, J=7.2 Hz, 1H), 6.90 (s, 1H), 7.09 (d, J=16.0 Hz, 1H), 7.13 (d, J=8.8 Hz, 1H), 7.14 (s, 1H), 7.20 (d, J=8.8 Hz, 1H), 7.36 (t, J=7.2 Hz, 1H), 7.49-7.57 (m, 3H), 7.68 (s, 1H), 7.77 (d, J=8.4 Hz, 1H), 7.89 (d, J=7.6 Hz, 1H), 7.99 (d, J=8.4 Hz, 1H).

Examples 132 and 133

Synthesis of (+)-2-{(E)-2-[3-methoxy-4-(4-methyl-1H-imidazol-1-yl)phenyl]vinyl}-8-(4-methoxyphenyl)-5,6,7,8-tetrahydro[1,2,4]triazolo[1,5-a]pyridin-8-ol and (−)-2-{(E)-2-[3-methoxy-4-(4-methyl-1H-imidazol-1-yl)phenyl]vinyl}-8-(4-methoxyphenyl)-5,6,7,8-tetrahydro[1,2,4]triazolo[1,5-a]pyridin-8-ol

[Formula 141]

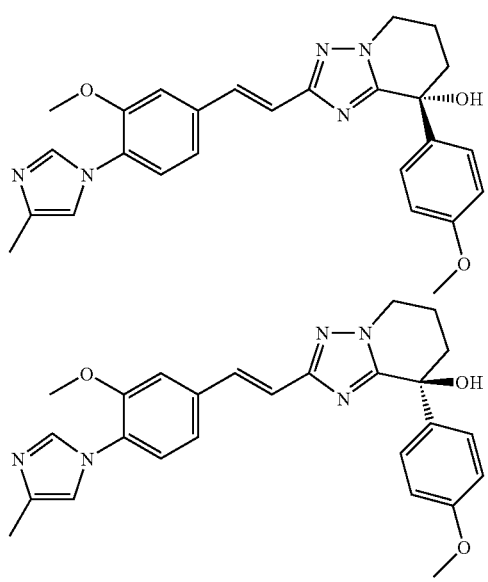

A racemate of the title compound (83.8 mg) was obtained from 2-{(E)-2-[3-methoxy-4-(4-methyl-1H-imidazol-1-yl)phenyl]vinyl}-8-(4-methoxyphenyl)-5,6,7,8-tetrahydro-[1,2,4]triazolo[1,5-a]pyridine (120 mg) by the same method as in Examples 70 and 71. The racemate was separated by CHIRALPAK™ AD-H manufactured by Daicel Chemical Industries, Ltd. (2 cm×25 cm; mobile phase: ethanol) to obtain the title optically active compound with a retention time of 8.7 minutes and negative optical rotation (24.5 mg; >99% ee) and the title optically active compound with a retention time of 10.7 minutes and positive optical rotation (18.8 mg; >99% ee).

The property values of the title optically active compound with a retention time of 8.7 minutes are as follows.

ESI-MS; m/z 458 [M$^+$+H]. $^1$H-NMR (CDCl$_3$) δ (ppm): 1.95-2.00 (m, 1H), 2.20-2.26 (m, 1H), 2.28 (s, 3H), 2.28-2.36 (m, 2H), 3.79 (s, 3H), 3.80 (s, 3H), 4.22-4.27 (m, 2H), 6.84 (s, 1H), 6.86 (d, J=8.4 Hz, 2H), 6.97 (m, 1H), 6.99 (s, 1H), 7.00 (d, J=16.0 Hz, 1H), 7.14 (d, J=8.0 Hz, 1H), 7.25 (d, J=8.4 Hz, 2H), 7.44 (d, J=16.0 Hz, 1H), 7.75 (s, 1H).

The property values of the title optically active compound with a retention time of 10.7 minutes are as follows.

ESI-MS; m/z 458 [M$^+$+H]. $^1$H-NMR (CDCl$_3$) δ (ppm): 1.95-2.00 (m, 1H), 2.20-2.26 (m, 1H), 2.28 (s, 3H), 2.28-2.36 (m, 2H), 3.79 (s, 3H), 3.80 (s, 3H), 4.22-4.27 (m, 2H), 6.84 (s, 1H), 6.86 (d, J=8.4 Hz, 2H), 6.97 (m, 1H), 6.99 (s, 1H), 7.00 (d, J=16.0 Hz, 1H), 7.14 (d, J=8.0 Hz, 1H), 7.25 (d, J=8.4 Hz, 2H), 7.44 (d, J=16.0 Hz, 1H), 7.75 (s, 1H).

Examples 134 and 135

Synthesis of (+)-2-{(E)-2-[3-methoxy-4-(4-methyl-1H-imidazol-1-yl)phenyl]vinyl}-8-(4-trifluoromethoxyphenyl)-5,6-dihydro-8H-[1,2,4]triazolo[5,1-c][1,4]oxazine and (−)-2-{(E)-2-[3-methoxy-4-(4-methyl-1H-imidazol-1-yl)phenyl]vinyl}-8-(4-trifluoromethoxyphenyl)-5,6-dihydro-8H-[1,2,4]triazolo[5,1-c][1,4]oxazine

[Formula 142]

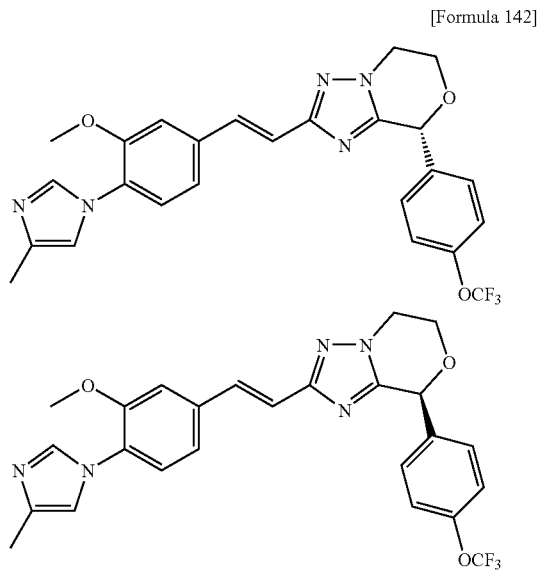

Synthesis of tert-butyl N'-[2-(2-chloroethoxy)-2-(4-trifluoromethoxyphenyl)acetyl]hydrazinecarboxylate The title compound (4.84 g) was obtained from 4-(trifluoromethoxy)benzaldehyde (5.3 g) by the same method as in Examples 77 and 78. The property values of the compound are as follows.

$^1$H-NMR (CDCl$_3$) δ (ppm): 1.45 (s, 9H), 3.68-2.71 (m, 2H), 3.80-3.83 (m, 2H), 4.94 (s, 1H), 6.38 (brs, 1H), 7.22 (d, J=8.4 Hz, 2H), 7.50 (d, J=8.4 Hz, 2H), 8.40 (brs, 1H).

Synthesis of (+)-2-{(E)-2-[3-methoxy-4-(4-methyl-1H-imidazol-1-yl)phenyl]vinyl}-8-(4-trifluoromethoxyphenyl)-5,6-dihydro-8H-[1,2,4]triazolo[5,1-c][1,4]oxazine and (−)-2-{(E)-2-[3-methoxy-4-(4-methyl-1H-imidazol-1-yl)phenyl]vinyl}-8-(4-trifluoromethoxyphenyl)-5,6-dihydro-8H-[1,2,4]triazolo[5,1-c][1,4]oxazine A solution of 4 N hydrochloric acid in ethyl acetate (5 mL) was added to tert-butyl N'-[2-(2-chloroethoxy)-2-(4-trifluoromethoxyphenyl)acetyl]hydrazinecarboxylate (438 mg). The reaction solution was stirred at room temperature for two hours and then concentrated under reduced pressure. Triethylamine (0.5 mL) was added to a solution of the resulting residue in ethanol (5 mL), and the reaction solution was stirred at room temperature for five minutes. A solution of ethyl(E)-3-[3-methoxy-4-(4-methyl-1H-imidazol-1-yl)phenyl]acrylimidate dihydrochloride (290 mg) and triethylamine (0.613 mL) in ethanol (5 mL) was added dropwise to the solution, and the reaction solution was stirred at 80° C. for 12 hours. The reaction solution was returned to room temperature and concentrated under reduced pressure. Ethyl acetate and water were added to the resulting residue, and the organic layer was separated. The resulting organic layer was washed with saturated sodium bicarbonate water and brine, dried over anhydrous magnesium sulfate and then concentrated under reduced pressure. The residue was purified by silica gel column chromatography (carrier: Chromatorex NH; elution solvent: heptane:ethyl acetate=1:3) and then purified by silica gel column chromatography (elution solvent: ethyl acetate: methanol=20:1) to obtain a racemate of the title compound. The resulting racemate was separated by CHIRALPAK™ AD-H manufactured by Daicel Chemical Industries, Ltd. (2 cm×25 cm; mobile phase: ethanol) to obtain the title optically active compound with a retention time of 10.4 minutes and positive optical rotation (68.5 mg, >99% ee) and the title optically active compound with a retention time of 15.2 minutes and negative optical rotation (70.9 mg, >99% ee).

The property values of the title optically active compound with a retention time of 8.7 minutes are as follows.
ESI-MS; m/z 498 [M$^+$+H]. $^1$H-NMR (CDCl$_3$) δ (ppm): 2.29 (s, 3H), 3.87 (s, 3H), 4.14-4.20 (m, 1H), 4.29-4.41 (m, 3H), 5.94 (s, 1H), 6.91 (s, 1H), 7.06 (d, J=16.0 Hz, 1H), 7.14-7.16 (m, 2H), 7.21-7.27 (m, 3H), 7.51-7.56 (m, 3H), 7.69 (d, J=1.2 Hz, 1H).

The property values of the title optically active compound with a retention time of 15.2 minutes are as follows.
ESI-MS; m/z 498 [M$^+$+H]. $^1$H-NMR (CDCl$_3$) δ (ppm): 2.29 (s, 3H), 3.87 (s, 3H), 4.14-4.20 (m, 1H), 4.29-4.41 (m, 3H), 5.94 (s, 1H), 6.91 (s, 1H), 7.06 (d, J=16.0 Hz, 1H), 7.14-7.16 (m, 2H), 7.21-7.27 (m, 3H), 7.51-7.56 (m, 3H), 7.69 (d, J=1.2 Hz, 1H).

Examples 136 and 137

Synthesis of (−)-2-{(E)-2-[3-methoxy-4-(4-methyl-1H-imidazol-1-yl)phenyl]vinyl}-8-naphthalen-1-yl-5,6,7,8-tetrahydro[1,2,4]triazolo[1,5-a]pyridin-8-ol and (+)-2-{(E)-2-[3-methoxy-4-(4-methyl-1H-imidazol-1-yl)phenyl]vinyl}-8-naphthalen-1-yl-5,6,7,8-tetrahydro[1,2,4]triazolo[1,5-a]pyridin-8-ol

[Formula 143]

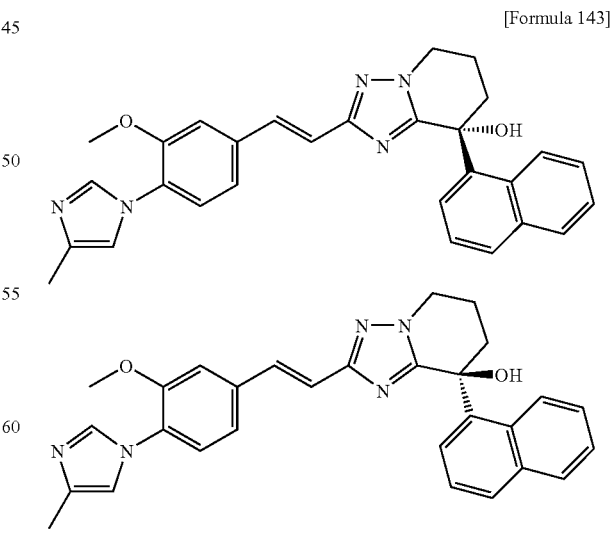

A racemate of the title compound (154 mg) was obtained from 2-{(E)-2-[3-methoxy-4-(4-methyl-1H-imidazol-1-yl)

phenyl]vinyl}-8-naphthalen-1-yl-5,6,7,8-tetrahydro[1,2,4]triazolo[1,5-a]pyridine (124 mg) by the same method as in Examples 70 and 71. The racemate was separated by CHIRALCEL™ OD-H manufactured by Daicel Chemical Industries, Ltd. (2 cm×25 cm; mobile phase: hexane:ethanol=8:2) to obtain the title optically active compound with a retention time of 11.2 minutes and negative optical rotation (2.5 mg; >99% ee) and the title optically active compound with a retention time of 14 minutes and positive optical rotation (2.4 mg; >99% ee).

The property values of the title optically active compound with a retention time of 11.2 minutes are as follows.

ESI-MS; m/z 478 [M$^+$+H]. $^1$H-NMR (CDCl$_3$) δ (ppm): 1.95-2.00 (m, 1H), 1.90-2.03 (m, 1H), 2.28 (s, 3H), 2.35-2.40 (m, 2H), 2.80-2.90 (m, 1H), 3.78 (s, 3H), 4.33-4.38 (m, 2H), 6.87 (s, 1H), 7.03 (s, 1H), 7.04 (d, J=8.0 Hz, 1H), 7.05 (d, J=16.4 Hz, 1H), 7.15 (d, J=8.4 Hz, 1H), 7.30-7.46 (m, 5H), 7.70 (s, 1H), 7.81 (d, J=8.4 Hz, 1H), 7.87 (d, J=8.0 Hz, 1H), 7.90 (brs, 1H).

The property values of the title optically active compound with a retention time of 14 minutes are as follows.

ESI-MS; m/z 478 [M$^+$+H]. $^1$H-NMR (CDCl$_3$) δ (ppm): 1.95-2.00 (m, 1H), 1.90-2.03 (m, 1H), 2.28 (s, 3H), 2.35-2.40 (m, 2H), 2.80-2.90 (m, 1H), 3.78 (s, 3H), 4.33-4.38 (m, 2H), 6.87 (s, 1H), 7.03 (s, 1H), 7.04 (d, J=8.0 Hz, 1H), 7.05 (d, J=16.4 Hz, 1H), 7.15 (d, J=8.4 Hz, 1H), 7.30-7.46 (m, 5H), 7.70 (s, 1H), 7.81 (d, J=8.4 Hz, 1H), 7.87 (d, J=8.0 Hz, 1H), 7.90 (brs, 1H).

Examples 138 and 139

Synthesis of (−)-2-{(E)-2-[3-methoxy-4-(4-methyl-1H-imidazol-1-yl)phenyl]vinyl}-8-p-tolyl-5,6-dihydro-8H-[1,2,4]triazolo[5,1-c][1,4]oxazine and (+)-2-{(E)-2-[3-methoxy-4-(4-methyl-1H-imidazol-1-yl)phenyl]vinyl}-8-p-tolyl-5,6-dihydro-8H-[1,2,4]triazolo[5,1-c][1,4]oxazine

[Formula 144]

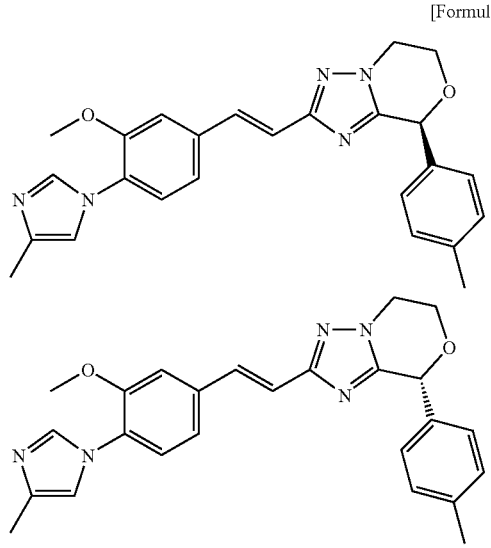

A racemate of the title compound (65.5 mg) was obtained from 4-methylbenzaldehyde (4 g) by the same method as in Examples 77 and 78. The racemate was separated by CHIRALCEL™ OJ-H manufactured by Daicel Chemical Industries, Ltd. (2 cm×25 cm; mobile phase: ethanol) to obtain the title optically active compound with a retention time of 6.5 minutes and negative optical rotation (26.3 mg) and the title optically active compound with a retention time of 8.6 minutes and positive optical rotation (26.8 mg).

The property values of the title optically active compound with a retention time of 6.5 minutes are as follows.

ESI-MS; m/z 428 [M$^+$+H]. $^1$H-NMR (CDCl$_3$) δ (ppm): 2.29 (s, 3H), 2.36 (s, 3H), 3.86 (s, 3H), 4.09-4.15 (m, 1H), 4.26-4.39 (m, 3H), 5.90 (s, 1H), 6.91 (s, 1H), 7.07 (d, J=16.0 Hz, 1H), 7.14 (d, J=8.4 Hz, 1H), 7.15 (s, 1H), 7.20 (s, 1H), 7.21 (d, J=8.0 Hz, 2H), 7.31 (d, J=8.0 Hz, 2H), 7.53 (d, J=16.0 Hz, 1H), 7.69 (s, 1H).

The property values of the title optically active compound with a retention time of 8.6 minutes are as follows.

ESI-MS; m/z 428 [M$^+$+H]. $^1$H-NMR (CDCl$_3$) δ (ppm): 2.29 (s, 3H), 2.36 (s, 3H), 3.86 (s, 3H), 4.09-4.15 (m, 1H), 4.26-4.39 (m, 3H), 5.90 (s, 1H), 6.91 (s, 1H), 7.07 (d, J=16.0 Hz, 1H), 7.14 (d, J=8.4 Hz, 1H), 7.15 (s, 1H), 7.20 (s, 1H), 7.21 (d, J=8.0 Hz, 2H), 7.31 (d, J=8.0 Hz, 2H), 7.53 (d, J=16.0 Hz, 1H), 7.69 (s, 1H).

Examples 140 and 141

Synthesis of (+)-2-{(E)-2-[3-methoxy-4-(4-methyl-1H-imidazol-1-yl)phenyl]vinyl}-8-(2,4,6-trifluorophenyl)-5,6-dihydro-8H-[1,2,4]triazolo[5,1-c][1,4]oxazine and (−)-2-{(E)-2-[3-methoxy-4-(4-methyl-1H-imidazol-1-yl)phenyl]vinyl}-8-(2,4,6-trifluorophenyl)-5,6-dihydro-8H-[1,2,4]triazolo[5,1-c][1,4]oxazine

[Formula 145]

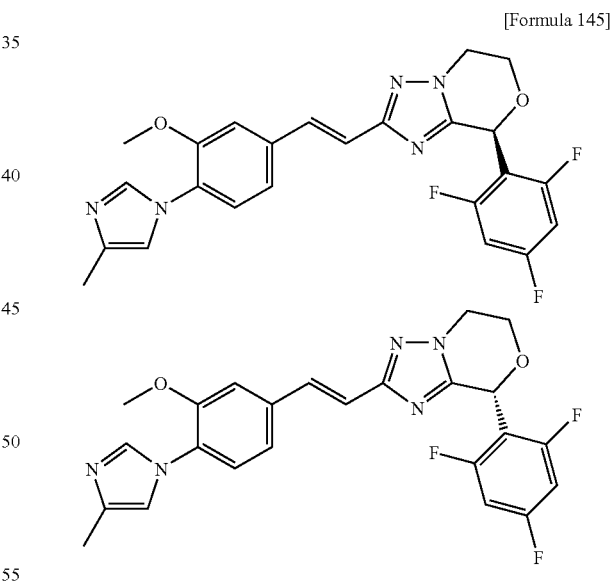

A racemate of the title compound (179.6 mg) was obtained from 2,4,6-trifluorobenzaldehyde (3 g) by the same method as in Examples 77 and 78. The racemate was separated by CHIRALPAK™ AD-H manufactured by Daicel Chemical Industries, Ltd. (2 cm×25 cm; mobile phase: ethanol) to obtain the title optically active compound with a retention time of 4.4 minutes and negative optical rotation (30.4 mg) and the title optically active compound with a retention time of 5.8 minutes and positive optical rotation (32.3 mg).

The property values of the title optically active compound with a retention time of 4.4 minutes are as follows.

ESI-MS; m/z 468 [M+ +H]. $^1$H-NMR (CDCl$_3$) δ (ppm): 2.29 (s, 3H), 3.85 (s, 3H), 4.10-4.19 (m, 1H), 4.28-4.32 (m, 1H), 4.38-4.45 (m, 2H), 6.18 (s, 1H), 6.72 (t, J=8.4 Hz, 2H), 6.91 (d, J=1.2 Hz, 1H), 7.04 (d, J=16.4 Hz, 1H), 7.12 (d, J=8.8 Hz, 1H), 7.14 (s, 1H), 7.21 (d, J=8.8 Hz, 1H), 7.48 (d, J=16.4 Hz, 1H), 7.69 (d, J=1.2 Hz, 1H).

The property values of the title optically active compound with a retention time of 5.8 minutes are as follows.

ESI-MS; m/z 468 [M+ +H]. $^1$H-NMR (CDCl$_3$) δ (ppm): 2.29 (s, 3H), 3.85 (s, 3H), 4.10-4.19 (m, 1H), 4.28-4.32 (m, 1H), 4.38-4.45 (m, 2H), 6.18 (s, 1H), 6.72 (t, J=8.4 Hz, 2H), 6.91 (d, J=1.2 Hz, 1H), 7.04 (d, J=16.4 Hz, 1H), 7.12 (d, J=8.8 Hz, 1H), 7.14 (s, 1H), 7.21 (d, J=8.8 Hz, 1H), 7.48 (d, J=16.4 Hz, 1H), 7.69 (d, J=1.2 Hz, 1H).

Examples 142 and 143

Synthesis of (+)-8-(4-bromophenyl)-2-{(E)-2-[3-methoxy-4-(4-methyl-1H-imidazol-1-yl)phenyl]vinyl}-5,6-dihydro-8H-[[1,2,4]triazolo-5,1-c][1,4]oxazine and (−)-8-(4-bromophenyl)-2-{(E)-2-[3-methoxy-4-(4-methyl-1H-imidazol-1-yl)phenyl]vinyl}-5,6-dihydro-8H-[1,2,4]triazolo[5,1-c][1,4]oxazine

[Formula 146]

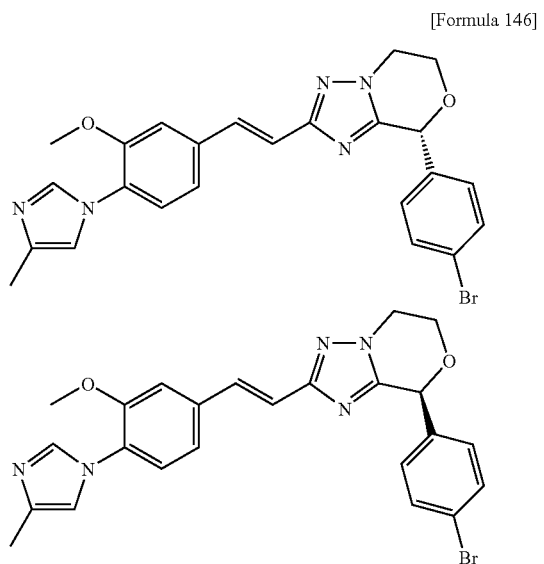

A racemate of the title compound (352.2 mg) was obtained from 4-bromobenzaldehyde (6 g) by the same method as in Examples 77 and 78. The racemate was separated by CHIRALPAK™ AD-H manufactured by Daicel Chemical Industries, Ltd. (2 cm×25 cm; mobile phase: ethanol) to obtain the title optically active compound with a retention time of 10.9 minutes and positive optical rotation (6.2 mg) and the title optically active compound with a retention time of 15.7 minutes and negative optical rotation (4.8 mg).

The property values of the title optically active compound with a retention time of 10.9 minutes are as follows.

$^1$H-NMR (CDCl$_3$) δ (ppm): 2.29 (s, 3H), 3.87 (s, 3H), 4.13-4.19 (m, 1H), 4.29-4.38 (m, 3H), 5.89 (s, 1H), 6.91 (s, 1H), 7.06 (d, J=16.4 Hz, 1H), 7.14-7.16 (m, 2H), 7.22 (d, J=8.4 Hz, 1H), 7.36 (d, J=8.0 Hz, 2H), 7.52 (d, J=8.0 Hz, 2H), 7.53 (d, J=16.4 Hz, 1H), 7.69 (s, 1H).

The property values of the title optically active compound with a retention time of 15.7 minutes are as follows.

$^1$H-NMR (CDCl$_3$) δ (ppm): 2.29 (s, 3H), 3.87 (s, 3H), 4.13-4.19 (m, 1H), 4.29-4.38 (m, 3H), 5.89 (s, 1H), 6.91 (s, 1H), 7.06 (d, J=16.4 Hz, 1H), 7.14-7.16 (m, 2H), 7.22 (d, J=8.4 Hz, 1H), 7.36 (d, J=8.0 Hz, 2H), 7.52 (d, J=8.0 Hz, 2H), 7.53 (d, J=16.4 Hz, 1H), 7.69 (s, 1H).

Examples 144 and 145

Synthesis of (+)-8-(6-chloropyridin-3-yl)-2-{(E)-2-[3-methoxy-4-(4-methyl-1H-imidazol-1-yl)phenyl]vinyl}-5,6-dihydro-8H-[1,2,4]triazolo[5,1-c][1,4]oxazine and (−)-8-(6-chloropyridin-3-yl)-2-{(E)-2-[3-methoxy-4-(4-methyl-1H-imidazol-1-yl)phenyl]vinyl}-5,6-dihydro-8H-[1,2,4]triazolo[5,1-c][1,4]oxazine

[Formula 147]

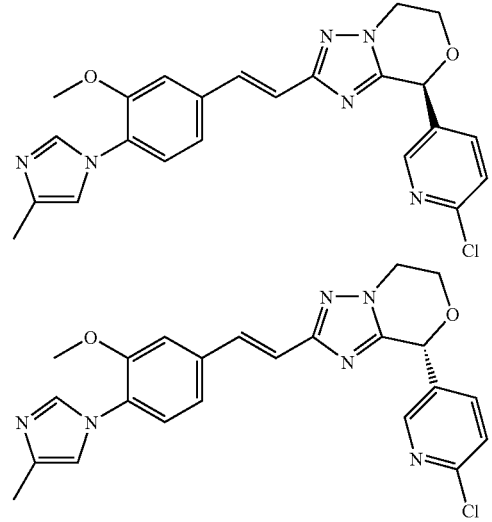

Synthesis of 5-[bis-(2-chloroethoxy)methyl]-2-chloropyridine p-Toluenesulfonic acid monohydrate (268 mg) was added to a solution of 6-chloropyridine-3-carboxyaldehyde (2 g) and 2-chloroethanol (9.45 mL) in toluene (100 mL), and the reaction solution was heated under reflux for 15 hours using a Dean-Stark reflux tube. The reaction solution was returned to room temperature, and then the solvent was evaporated from the reaction solution under reduced pressure. Ethyl acetate and a saturated sodium bicarbonate solution were added to the resulting residue, and the organic layer was separated. The resulting organic layer was washed with brine and then dried over anhydrous magnesium sulfate and concentrated under reduced pressure. The residue was purified by silica gel column chromatography (carrier: Chromatorex NH; elution solvent: heptane:ethyl acetate=10:1) to obtain 3.07 g of the title compound. The property values of the compound are as follows.

$^1$H-NMR (CDCl$_3$) δ (ppm): 3.68 (t, J=5.6 Hz, 4H), 3.81 (t, J=5.6 Hz, 4H), 5.75 (s, 1H), 7.44 (d, J=8.4 Hz, 1H), 7.79 (dd, J=8.4, 2.8 Hz, 1H), 8.51 (d, J=2.8 Hz, 1H).

235

Synthesis of (2-chloroethoxy)-(6-chloropyridin-3-yl)acetonitrile

Trimethylsilyl cyanide (1.88 mL) and tetracyanoethylene (240 mg) were added to a solution of 5-[bis-(2-chloroethoxy)methyl]-2-chloropyridine (2.67 g) in acetonitrile (50 mL), and the reaction solution was heated under reflux for five hours. The reaction solution was left to cool to room temperature, and the solvent was evaporated under reduced pressure. Ethyl acetate was added to the resulting residue. The organic layer was washed with brine and then dried over anhydrous magnesium sulfate and concentrated under reduced pressure. The residue was purified by silica gel column chromatography (carrier: Chromatorex NH; elution solvent: heptane:ethyl acetate=8:1) to obtain 2.04 g of the title compound. The property values of the compound are as follows.

$^1$H-NMR (CDCl$_3$) δ (ppm): 3.72 (dd, J=5.6, 5.2 Hz, 2H), 3.90 (dt, J=10.4, 5.6 Hz, 1H), 4.09 (dt, J=10.4, 5.2 Hz, 1H), 5.40 (s, 1H), 7.44 (d, J=8.0 Hz, 1H), 7.84 (dd, J=8.0, 2.0 Hz, 1H), 8.53 (d, J=2.0 Hz, 1H).

Synthesis of (2-chloroethoxy)-(6-chloropyridin-3-yl)acetic acid

A 5 N hydrochloric acid solution (5 mL) was added to a solution of (2-chloroethoxy)-(6-chloropyridin-3-yl)acetonitrile (1.3 g) in THF (5 mL), and the reaction solution was stirred at 130° C. for two hours using a microwave reactor. The reaction solution was left to cool to room temperature. Then, a 5 N sodium hydroxide solution (10 mL) and diethyl ether were added to the reaction solution, and the aqueous layer was separated. A 5 N hydrochloric acid solution (5 mL) was added to the resulting aqueous layer to make the reaction solution neutral again, followed by extraction with methylene chloride twice. The resulting organic layer was dried over anhydrous sodium sulfate and concentrated under reduced pressure to obtain 565.1 mg of the title compound. The property value of the compound is as follows.

ESI-MS; m/z 250 [M$^+$+H].

Synthesis of tert-butyl N'-[2-(2-chloroethoxy)-2-(6-chloropyridin-3-yl)acetyl]hydrazinecarboxylate HOBT (681 mg), IPEA (1.98 mL) and EDC (966 mg) were sequentially added to a solution of (2-chloroethoxy)-(6-chloropyridin-3-yl)acetic acid (630 mg) and tert-butyl carbazate (400 mg) in DMF (15 mL), and the reaction solution was stirred at room temperature for three hours. Ethyl acetate and water were added to the reaction solution, and the organic layer was separated. The resulting organic layer was washed with brine, dried over anhydrous sodium sulfate and then concentrated under reduced pressure. The residue was purified by silica gel column chromatography (eluent solvent: heptane:ethyl acetate=1:2) to obtain 666 mg of the title compound. The property value of the compound is as follows.

ESI-MS; m/z 386 [M$^+$+H].

236

Synthesis of (+)-8-(6-chloropyridin-3-yl)-2-{(E)-2-[3-methoxy-4-(4-methyl-1H-imidazol-1-yl)phenyl]vinyl}-5,6-dihydro-8H-[1,2,4]triazolo[5,1-c][1,4]oxazine and (−)-8-(6-chloropyridin-3-yl)-2-{(E)-2-[3-methoxy-4-(4-methyl-1H-imidazol-1-yl)phenyl]vinyl}-5,6-dihydro-8H-[1,2,4]triazolo[5,1-c][1,4]oxazine A solution of 4 N hydrochloric acid in ethyl acetate (10 mL) was added to tert-butyl N'-[2-(2-chloroethoxy)-2-(6-chloropyridin-3-yl)acetyl]hydrazinecarboxylate (666 mg). The reaction solution was stirred at room temperature for two hours and then concentrated under reduced pressure. Triethylamine (1.03 mL) was added to a solution of the resulting residue in ethanol (15 mL), and the reaction solution was stirred at room temperature for five minutes. A solution of ethyl(E)-3-[3-methoxy-4-(4-methyl-1H-imidazol-1-yl)phenyl]acrylimidate dihydrochloride (530 mg) and triethylamine (1.03 mL) in ethanol (15 mL) was added dropwise to the solution, and the reaction solution was stirred at 80° C. for 12 hours. The reaction solution was returned to room temperature and concentrated under reduced pressure. Ethyl acetate and water were added to the resulting residue, and the organic layer was separated. The resulting organic layer was sequentially washed with saturated sodium bicarbonate water and brine, dried over anhydrous magnesium sulfate and then concentrated under reduced pressure. The residue was purified by silica gel column chromatography (carrier: Chromatorex NH; elution solvent: ethyl acetate) and then purified by silica gel column chromatography (elution solvent: ethyl acetate:methanol=20:1) to obtain a racemate of the title compound. The resulting racemate was separated by CHIRALPAK™ AD-H manufactured by Daicel Chemical Industries, Ltd. (2 cm×25 cm; mobile phase: ethanol) to obtain the title optically active compound with a retention time of 15.5 minutes and positive optical rotation (10.5 mg) and the title optically active compound with a retention time of 22.3 minutes and negative optical rotation (8.2 mg).

The property values of the title optically active compound with a retention time of 15.5 minutes are as follows.

ESI-MS; m/z 449 [M$^+$+H]. $^1$H-NMR (CDCl$_3$) δ (ppm): 2.30 (s, 3H), 3.88 (s, 3H), 4.17-4.24 (m, 1H), 4.31-4.44 (m, 3H), 5.94 (s, 1H), 6.92 (d, J=1.2 Hz, 1H), 7.05 (d, J=16.0 Hz, 1H), 7.15-7.18 (m, 2H), 7.23 (d, J=8.4 Hz, 1H), 7.38 (d, J=8.8 Hz, 1H), 7.53 (d, J=16.0 Hz, 1H), 7.70 (d, J=1.2 Hz, 1H), 7.80 (dd, J=8.8, 2.0 Hz, 1H), 8.60 (d, J=2.0 Hz, 1H).

The property values of the title optically active compound with a retention time of 22.3 minutes are as follows.

ESI-MS; m/z 449 [M$^+$+H]. $^1$H-NMR (CDCl$_3$) δ (ppm): 2.30 (s, 3H), 3.88 (s, 3H), 4.17-4.24 (m, 1H), 4.31-4.44 (m, 3H), 5.94 (s, 1H), 6.92 (d, J=1.2 Hz, 1H), 7.05 (d, J=16.0 Hz, 1H), 7.15-7.18 (m, 2H), 7.23 (d, J=8.4 Hz, 1H), 7.38 (d, J=8.8 Hz, 1H), 7.53 (d, J=16.0 Hz, 1H), 7.70 (d, J=1.2 Hz, 1H), 7.80 (dd, J=8.8, 2.0 Hz, 1H), 8.60 (d, J=2.0 Hz, 1H).

Examples 146 and 147

Synthesis of (+)-4-(2-{(E)-2-[3-methoxy-4-(4-methyl-1H-imidazol-1-yl)phenyl]vinyl}-5,6-dihydro-8H-[1,2,4]triazolo[5,1-c][1,4]oxazin-8-yl)benzonitrile and (−)-4-(2-{(E)-2-[3-methoxy-4-(4-methyl-1H-imidazol-1-yl)phenyl]vinyl}-5,6-dihydro-8H-[1,2,4]triazolo[5,1-c][1,4]oxazin-8-yl)benzonitrile

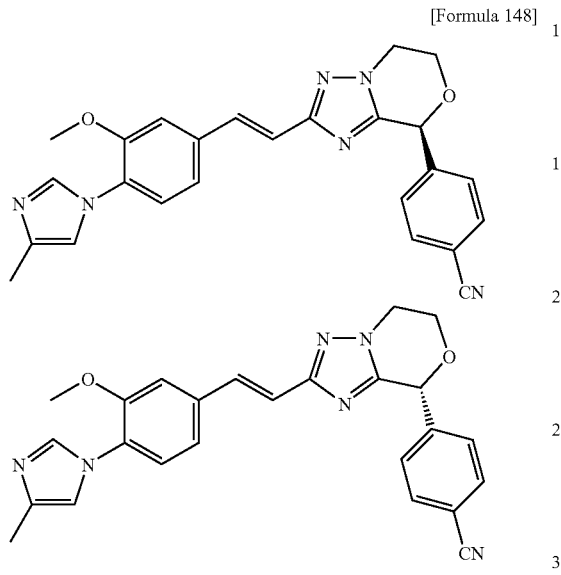

[Formula 148]

Zinc cyanide (26.2 mg) and tetrakistriphenylphosphine palladium (11.7 mg) were added to a solution of 8-(4-bromophenyl)-2-{(E)-2-[3-methoxy-4-(4-methyl-1H-imidazol-1-yl)phenyl]vinyl}-5,6-dihydro-8H-[1,2,4]triazolo[5,1-c][1,4]oxazine (100 mg) in DMF (1 mL), and the reaction solution was stirred at 130° C. for 30 minutes using a microwave reactor. The reaction solution was left to cool to room temperature. Then, water and ethyl acetate were added to the reaction solution, and the organic layer was separated. The resulting organic layer was washed with brine, dried over anhydrous magnesium sulfate and then concentrated under reduced pressure. The residue was purified by silica gel column chromatography (carrier: Chromatorex NH; elution solvent: ethyl acetate) to obtain a racemate of the title compound (22.5 mg). The resulting racemate was separated by CHIRALPAK™ IA manufactured by Daicel Chemical Industries, Ltd. (2 cm×25 cm; mobile phase: ethanol) to obtain the title optically active compound with a retention time of 11.5 minutes and positive optical rotation (10.1 mg) and the title optically active compound with a retention time of 16.1 minutes and negative optical rotation (9.4 mg).

The property values of the title optically active compound with a retention time of 11.5 minutes are as follows.

ESI-MS; m/z 439 [M+ +H]. $^1$H-NMR (CDCl$_3$) δ (ppm): 2.30 (s, 3H), 3.87 (s, 3H), 4.17-4.24 (m, 1H), 4.31-4.40 (m, 3H), 5.96 (s, 1H), 6.91 (s, 1H), 7.05 (d, J=16.0 Hz, 1H), 7.15-7.17 (m, 2H), 7.23 (d, J=8.4 Hz, 1H), 7.53 (d, J=16.0 Hz, 1H), 7.66-7.73 (m, 5H).

The property values of the title optically active compound with a retention time of 16.1 minutes are as follows.

ESI-MS; m/z 439 [M+ +H]. $^1$H-NMR (CDCl$_3$) δ (ppm): 2.30 (s, 3H), 3.87 (s, 3H), 4.17-4.24 (m, 1H), 4.31-4.40 (m, 3H), 5.96 (s, 1H), 6.91 (s, 1H), 7.05 (d, J=16.0 Hz, 1H), 7.15-7.17 (m, 2H), 7.23 (d, J=8.4 Hz, 1H), 7.53 (d, J=16.0 Hz, 1H), 7.66-7.73 (m, 5H).

Examples 148 and 149

Synthesis of (+)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and (−)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

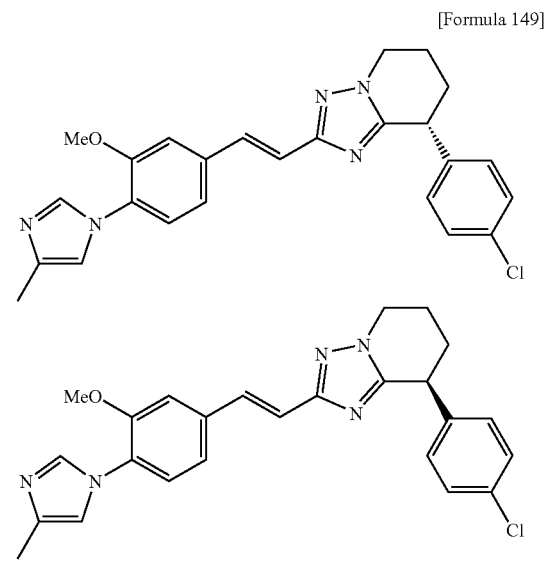

[Formula 149]

Synthesis of 5-chloro-2-(4-chlorophenyl)pentanoic acid

A solution of 4-chlorophenylacetic acid (1 g) in THF (30 mL) was stirred at −78° C. for 20 minutes. n-Butyl lithium (2.66 M solution in hexane, 4.41 mL) was added to the solution, and the reaction solution was stirred at −78° C. for one hour. Thereafter, the reaction solution was stirred at 0° C. for one hour, 1-bromo-3-chloropropane (0.638 mL) was added to the reaction solution, and the reaction solution was stirred at room temperature for 18 hours. Thereafter, ethyl acetate and 1 N aqueous 2hydrochloric acid were added to the reaction solution, and the organic layer was separated. The resulting organic layer was dried over anhydrous magnesium sulfate and concentrated under reduced pressure to obtain 1.55 g of the title compound. The property values of the compound are as follows.

$^1$H-NMR (CDCl$_3$) δ (ppm): 1.62-2.00 (m, 3H), 2.14-2.32 (m, 1H), 3.46-3.59 (m, 3H), 7.24 (d, J=8.4 Hz, 2H), 7.30 (d, J=8.4 Hz, 2H).

Synthesis of 5-chloro-2-(4-chlorophenyl)pentanoic acid N'-{(E)-3-[3-methoxy-4-(4-methyl-1H-imidazol-1-yl)phenyl]acryloyl}hydrazide IPEA (6.02 mL) and BOPCl (1.79 g) were added to a solution of 5-chloro-2-(4-chlorophenyl)pentanoic acid (1.55 g) and (E)-3-[3-methoxy-4-(4-methyl-1H-imidazol-1-yl)phenyl]acrylic acid hydrazide dihydrochloride (2.03 g) in methylene chloride (80 mL), and the reaction solution was stirred at room temperature for two hours. Dichloromethane and saturated sodium bicarbonate water were added to the reaction solution, and the organic layer was separated. The resulting organic layer was dried over anhydrous magnesium sulfate and then concentrated under reduced pressure to obtain 4.67 g of the title compound in an unrefined state. The property value of the compound is as follows.

ESI-MS; m/z 501 [M$^+$+H].

Synthesis of 2-[4-chloro-1-(4-chlorophenyl)butyl]-5-{(E)-2-[3-methoxy-4-(4-methyl-1H-imidazol-1-yl)phenyl]vinyl}-[1,3,4]oxadiazole A solution of 5-chloro-2-(4-chlorophenyl)pentanoic acid N'-{(E)-3-[3-methoxy-4-(4-methyl-1H-imidazol-1-yl)phenyl]acryloyl}hydrazide (4.67 g) in phosphorus oxychloride (15 mL) was stirred at 120° C. for 3.5 hours. The reaction solution was left to cool to room temperature and then concentrated under reduced pressure. Ethyl acetate and saturated sodium bicarbonate water were added to the resulting residue, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate) to obtain 1.90 g of the title compound. The property value of the compound is as follows. ESI-MS; m/z 483 [M$^+$+H].

Synthesis of (+)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and (−)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine A solution of 2-[4-chloro-1-(4-chlorophenyl)butyl]-5-{(E)-2-[3-methoxy-4-(4-methyl-1H-imidazol-1-yl)phenyl]vinyl}-[1,3,4]oxadiazole (1.9 g) and ammonium acetate (9.06 g) in acetic acid (12 mL) was stirred at 150° C. for three hours. The reaction solution was left to cool to room temperature, and then acetic acid was evaporated from the reaction solution under reduced pressure. Ethyl acetate and saturated sodium bicarbonate water were added to the resulting residue, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1→ethyl acetate→ethyl acetate:methanol=9:1) to obtain 654 mg of a racemate of the title compound. The resulting racemate (200 mg) was separated by CHIRALPAK™ IA manufactured by Daicel Chemical Industries, Ltd. (2 cm×25 cm; mobile phase: hexane:THF=3:7) to obtain a crude purified product (61.1 mg) of the title optically active compound with a retention time of 10 minutes and positive optical rotation and a crude purified product of the title optically active compound with a retention time of 15 minutes and negative optical rotation. The crude purified product of the title optically active compound with a retention time of 15 minutes was further purified by silica gel column chromatography (elution solvent: ethyl acetate→ethyl acetate:methanol=9:1) to obtain 34.5 mg of the title optically active compound with negative optical rotation.

The property values of (−)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

$^1$H-NMR (CDCl$_3$) δ (ppm): 1.97-2.24 (m, 3H), 2.28-2.40 (m, 4H), 3.85 (s, 3H), 4.23-4.34 (m, 3H), 6.90 (brs, 1H), 7.05 (d, J=16.0 Hz, 1H), 7.08 (d, J=8.4 Hz, 2H), 7.11-7.16 (m, 2H), 7.21 (brd, J=8.0 Hz, 1H), 7.31 (d, J=8.4 Hz, 2H), 7.50 (d, J=16.0 Hz, 1H), 7.69 (d, J=0.8 Hz, 1H).

Examples 150 and 151

Synthesis of (+)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridine and (−)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridine

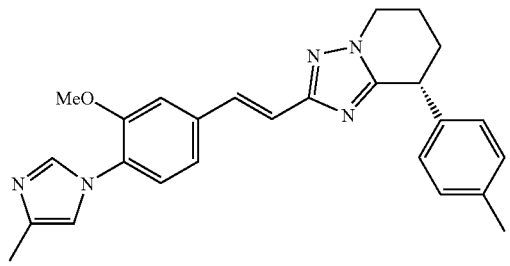

[Formula 150]

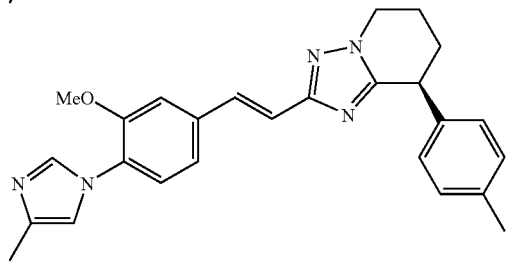

Synthesis of 5-chloro-2-p-tolylpentanoic acid

A solution of p-tolylacetic acid (1 g) in THF (30 mL) was stirred at −78° C. for 30 minutes. n-Butyl lithium (2.66 M solution in hexane, 5.01 mL) was added to the solution, and the reaction solution was stirred at −78° C. for three hours. Thereafter, the reaction solution was stirred at 0° C. for 30 minutes, 1-bromo-3-chloropropane (0.725 mL) was added to the reaction solution, and the reaction solution was stirred at room temperature for 24 hours. Thereafter, ethyl acetate and 1 N aqueous hydrochloric acid were added to the reaction solution, and the organic layer was separated. The resulting organic layer was dried over anhydrous magnesium sulfate and concentrated under reduced pressure to obtain 1.53 g of the title compound. The property values corresponded to the reported values (CAS #2856-76-0).

Synthesis of tert-butyl N'-(5-chloro-2-p-tolylpentanoyl)hydrazinecarboxylate

IPEA (4.04 mL), HOBt (1.82 g) and EDC (2.59 g) were added to a solution of 5-chloro-2-p-tolylpentanoic acid (1.53 g) and tert-butyl carbazate (1.07 g) in DMF (25 mL), and the reaction solution was stirred at room temperature overnight. Ethyl acetate and water were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 1.77 g of the title compound. The property values of the compound are as follows.

$^1$H-NMR (CDCl$_3$) δ (ppm): 1.42 (s, 9H), 1.55-2.06 (m, 3H), 2.11-2.45 (m, 4H), 3.36-3.56 (m, 3H), 6.69 (brs, 1H), 7.13 (d, J=8.4 Hz, 2H), 7.20 (d, J=8.4 Hz, 2H), 7.94 (brs, 1H).

Synthesis of (+)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridine and (−)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridine A solution of 4 N hydrochloric acid in ethyl acetate (10 mL) was added to tert-butyl N'-(5-chloro-2-p-tolylpentanoyl)hydrazinecarboxylate (600 mg), and the reaction solution was stirred at room temperature for two hours. The reaction solution was concentrated under reduced pressure to obtain a crude product of 5-chloro-2-p-tolylpentanoic acid hydrazide hydrochloride. A solution of ethyl(E)-3-[3-methoxy-4-(4-methyl-1H-imidazol-1-yl)phenyl]acrylimidate dihydrochloride (2.03 g) and triethylamine (1 mL) in ethanol (8 mL) was added to a solution of the resulting crude product of 5-chloro-2-p-tolylpentanoic acid hydrazide 2hydrochloride and triethylamine (0.87 mL) in ethanol (8 mL), and the reaction solution was stirred at 80° C. in a nitrogen atmosphere for 19.5 hours. The reaction solution was cooled to room temperature, and then the solvent was evaporated from the reaction solution under reduced pressure. Ethyl acetate and saturated sodium bicarbonate water were added to the resulting residue, and the organic layer was separated. The resulting organic layer was washed with brine, dried over anhydrous magnesium sulfate and then concentrated under reduced pressure. The residue was purified by silica gel column chromatography (carrier: Chromatorex NH; elution solvent: heptane:ethyl acetate=1:1→ethyl acetate→ethyl acetate:methanol=9:1) and further purified by silica gel column chromatography (elution solvent: ethyl acetate→ethyl acetate:methanol=9:1) to obtain 221 mg of a racemate of the title compound. The resulting racemate (100 mg) was separated by CHIRALPAK™ AD-H manufactured by Daicel Chemical Industries, Ltd. (2 cm×25 cm; mobile phase: hexane:ethanol=1:1) to obtain the title optically active compound with a retention time of 17 minutes and positive optical rotation (48.6 mg) and the title optically active compound with a retention time of 23 minutes and negative optical rotation (48 mg).

The property values of (+)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridine are as follows.

$^1$H-NMR (CDCl$_3$) δ (ppm): 2.00-2.40 (m, 10H), 3.85 (s, 3H), 4.21-4.35 (m, 3H), 6.91 (brs, 1H), 7.02 (d, J=8.0 Hz, 2H), 7.07 (d, J=16.0 Hz, 1H), 7.10-7.18 (m, 4H), 7.21 (d, J=8.0 Hz, 1H), 7.52 (d, J=16.0 Hz, 1H), 7.70 (d, J=1.6 Hz, 1H).

The property values of (−)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridine are as follows.

$^1$H-NMR (CDCl$_3$) δ (ppm): 2.00-2.40 (m, 10H), 3.85 (s, 3H), 4.21-4.35 (m, 3H), 6.91 (brs, 1H), 7.02 (d, J=8.0 Hz, 2H), 7.07 (d, J=16.0 Hz, 1H), 7.10-7.18 (m, 4H), 7.21 (d, J=8.0 Hz, 1H), 7.52 (d, J=16.0 Hz, 1H), 7.70 (d, J=1.6 Hz, 1H).

Examples 152 and 153

Synthesis of (+)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol and (−)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol

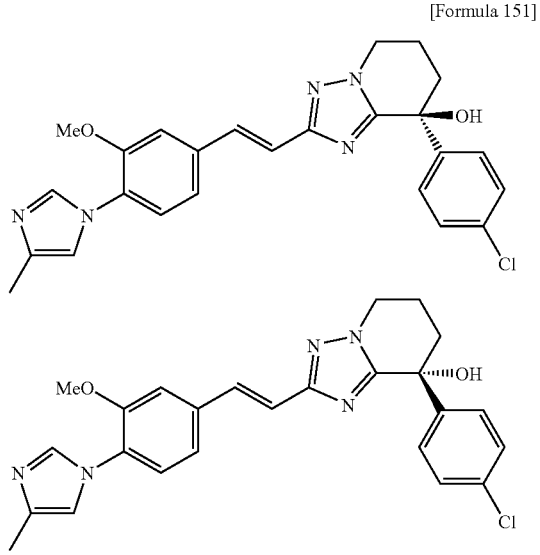

[Formula 151]

Sodium hydride (containing mineral oil at 40%, 36 mg) was added to a solution of 8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine synthesized by the method in Example 148 and 149 (200 mg) in DMF (2 mL), and the reaction solution was stirred at room temperature for 5.5 hours under oxygen bubbling. Sodium thiosulfate pentahydride was added to the reaction solution, and the reaction solution was stirred at room temperature for several minutes. Ethyl acetate and a saturated ammonium chloride solution were added to the reaction solution, and the organic layer was separated. The resulting organic layer was dried over anhydrous magnesium sulfate and concentrated under reduced pressure to obtain the title compound as a racemate. The racemate was separated by CHIRALPAK™ IA manufactured by Daicel Chemical Industries, Ltd. (2 cm×25 cm; mobile phase: hexane:ethanol=1:1) to obtain a crude purified product of the title optically active compound with a retention time of 14 minutes and positive optical rotation and a crude purified product of the title optically active compound with a retention time of 19 minutes and negative optical rotation. The respective crude purified products were further purified by silica gel column chromatography (elution solvent: ethyl acetate→ethyl acetate:methanol=9:1) to obtain 51.4 mg of the title optically active compound with positive optical rotation and 49.8 mg of the title optically active compound with negative optical rotation.

The property values of (+)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol are as follows.

$^1$H-NMR (CDCl$_3$) δ (ppm): 1.93-2.06 (m, 1H), 2.10-2.20 (m, 1H), 2.24-2.48 (m, 5H), 3.78 (s, 3H), 4.16-4.35 (m, 2H), 6.86-6.93 (m, 2H), 6.99 (d, J=16.4 Hz, 1H), 7.00 (d, J=1.6 Hz, 1H), 7.13 (d, J=8.0 Hz, 1H), 7.28-7.34 (m, 4H), 7.42 (d, J=16.4 Hz, 1H), 7.72 (d, J=1.6 Hz, 1H).

The property values of (−)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol are as follows.

$^1$H-NMR (CDCl$_3$) δ (ppm): 1.93-2.06 (m, 1H), 2.10-2.20 (m, 1H), 2.24-2.48 (m, 5H), 3.78 (s, 3H), 4.16-4.35 (m, 2H), 6.86-6.93 (m, 2H), 6.99 (d, J=16.4 Hz, 1H), 7.00 (d, J=1.6 Hz, 1H), 7.13 (d, J=8.0 Hz, 1H), 7.28-7.34 (m, 4H), 7.42 (d, J=16.4 Hz, 1H), 7.72 (d, J=1.6 Hz, 1H).

Examples 154 and 155

Synthesis of (+)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridin-8-ol and (−)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridin-8-ol

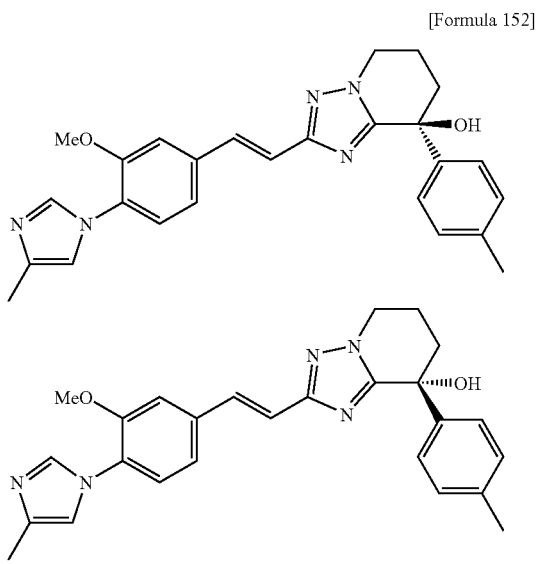

[Formula 152]

The title compound as a racemate was obtained from 2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridine (121 mg) by the same method as in Examples 152 and 153. The racemate was separated by CHIRALPAK™ AD-H manufactured by Daicel Chemical Industries, Ltd. (2 cm×25 cm; mobile phase: ethanol) to obtain the title optically active compound with a retention time of 18 minutes and negative optical rotation (34.2 mg; >99% ee) and the title optically active compound with a retention time of 20 minutes and positive optical rotation (36.6 mg).

The property values of (+)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridin-8-ol are as follows.

$^1$H-NMR (CDCl$_3$) δ (ppm): 1.91-2.05 (m, 1H), 2.16-2.40 (m, 9H), 3.81 (s, 3H), 4.24 (t, J=5.6 Hz, 2H), 6.88 (brs, 1H), 6.98-7.23 (m, 8H), 7.47 (d, J=16.4 Hz, 1H), 7.70 (d, J=1.2 Hz, 1H).

The property values of (−)-2-{(E)-2-[3-methoxy-4-(4-methyl-1H-imidazol-1-yl)phenyl]vinyl}-8-p-tolyl-5,6,7,8-tetrahydro[1,2,4]triazolo[1,5-a]pyridin-8-ol are as follows.

ESI-MS; m/z 442 [M$^+$+H]. $^1$H-NMR (CDCl$_3$) δ (ppm): 1.91-2.05 (m, 1H), 2.16-2.40 (m, 9H), 3.81 (s, 3H), 4.24 (t, J=5.6 Hz, 2H), 6.88 (brs, 1H), 6.98-7.23 (m, 8H), 7.47 (d, J=16.4 Hz, 1H), 7.70 (d, J=1.2 Hz, 1H).

Examples 156 and 157

Synthesis of (+)-4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile and (−)-4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile

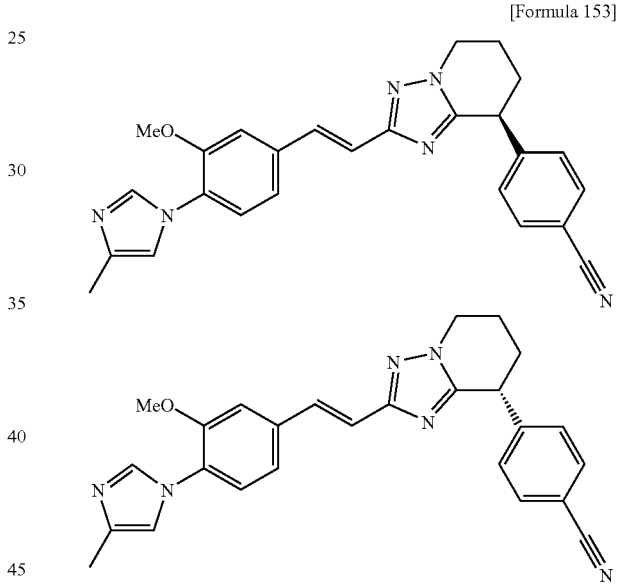

[Formula 153]

357.4 mg of a racemate of the title compound was obtained from 4-cyanophenylacetic acid (1 g) by the same method as in Examples 150 and 151. The resulting racemate (154 mg) was separated by CHIRALPAK™ IB manufactured by Daicel Chemical Industries, Ltd. (2 cm×25 cm; mobile phase: hexane:ethanol=1:1) to obtain the title optically active compound with a retention time of 27 minutes and negative optical rotation (81.3 mg; >99% ee) and the title optically active compound with a retention time of 41 minutes and positive optical rotation (76.5 mg; 93% ee).

The property values of (+)-4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile are as follows.

ESI-MS; m/z 437 [M$^+$+H]. $^1$H-NMR (CDCl$_3$) δ (ppm): 1.97-2.34 (m, 6H), 2.35-2.47 (m, 1H), 3.85 (s, 3H), 4.30 (t, J=6.0 Hz, 2H), 4.38 (t, J=6.8 Hz, 1H), 6.91 (brs, 1H), 7.05 (d, J=16.4 Hz, 1H), 7.10-7.18 (m, 2H), 7.21 (d, J=8.4 Hz, 1H), 7.28 (d, J=8.4 Hz, 2H), 7.48 (d, J=16.4 Hz, 1H), 7.64 (d, J=8.4 Hz, 2H), 7.71 (brs, 1H).

The property values of (−)-4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile are as follows.

ESI-MS; m/z 437 [M$^+$+H]. $^1$H-NMR (CDCl$_3$) δ (ppm): 1.97-2.34 (m, 6H), 2.35-2.47 (m, 1H), 3.85 (s, 3H), 4.30 (t, J=6.0 Hz, 2H), 4.38 (t, J=6.8 Hz, 1H), 6.91 (brs, 1H), 7.05 (d, J=16.4 Hz, 1H), 7.10-7.18 (m, 2H), 7.21 (d, J=8.4 Hz, 1H), 7.28 (d, J=8.4 Hz, 2H), 7.48 (d, J=16.4 Hz, 1H), 7.64 (d, J=8.4 Hz, 2H), 7.71 (brs, 1H).

Examples 158 and 159

Synthesis of (+)-4-{8-hydroxy-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile and (−)-4-{8-hydroxy-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile

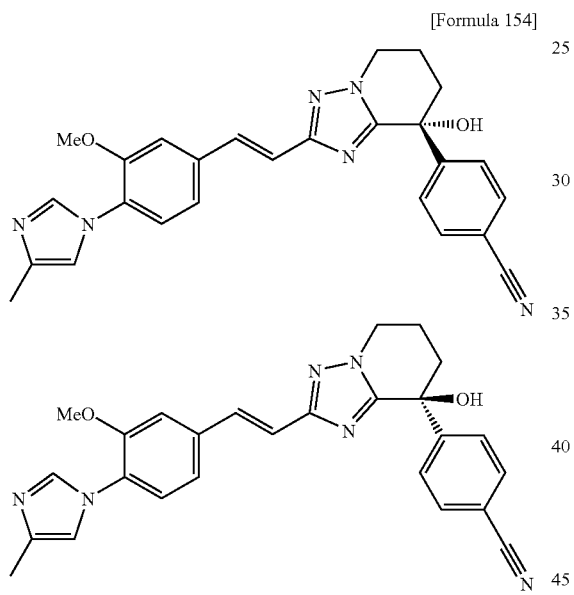

[Formula 154]

The title compound as a racemate was obtained from 4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile (203.4 mg) by the same method as in Examples 152 and 153. The resulting racemate was separated by CHIRALPAK™ IA manufactured by Daicel Chemical Industries, Ltd. (2 cm×25 cm; mobile phase: hexane:ethanol=1:1) to obtain the title optically active compound with a retention time of 14 minutes and negative optical rotation (75.1 mg; >99% ee) and the title optically active compound with a retention time of 22 minutes and positive optical rotation (72.5 mg; >99% ee).

The property values of (+)-4-{8-hydroxy-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile are as follows.

ESI-MS; m/z 453 [M$^+$+H]. $^1$H-NMR (CDCl$_3$) δ (ppm): 1.96-2.23 (m, 2H), 2.27 (s, 3H), 2.31-2.44 (m, 1H), 2.47-2.64 (m, 1H), 3.75 (s, 3H), 4.17-4.39 (m, 2H), 6.79 (d, J=8.0 Hz, 1H), 6.86 (brs, 1H), 6.93 (brs, 1H), 6.96 (d, J=16.4 Hz, 1H), 7.08 (d, J=8.0 Hz, 1H), 7.34 (d, J=16.4 Hz, 1H), 7.56 (d, J=8.4 Hz, 2H), 7.65 (d, J=8.4 Hz, 2H), 7.69 (brs, 1H).

The property values of (−)-4-{8-hydroxy-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}benzonitrile are as follows.

ESI-MS; m/z 453 [M$^+$+H]. $^1$H-NMR (CDCl$_3$) δ (ppm): 1.96-2.23 (m, 2H), 2.27 (s, 3H), 2.31-2.44 (m, 1H), 2.47-2.64 (m, 1H), 3.75 (s, 3H), 4.17-4.39 (m, 2H), 6.79 (d, J=8.0 Hz, 1H), 6.86 (brs, 1H), 6.93 (brs, 1H), 6.96 (d, J=16.4 Hz, 1H), 7.08 (d, J=8.0 Hz, 1H), 7.34 (d, J=16.4 Hz, 1H), 7.56 (d, J=8.4 Hz, 2H), 7.65 (d, J=8.4 Hz, 2H), 7.69 (brs, 1H).

Example 160

Synthesis of {4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}phenyl}dimethylamine

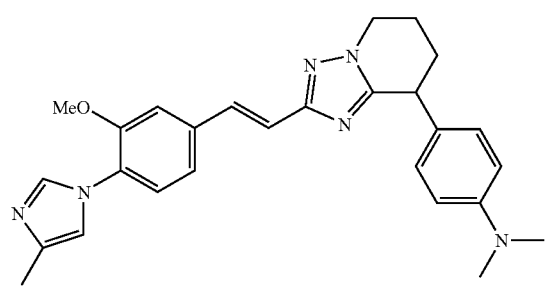

[Formula 155]

Synthesis of methyl (4-dimethylaminophenyl)acetate

Iodomethane (0.382 mL) and potassium carbonate (848 mg) were added to a solution of (4-dimethylaminophenyl)acetic acid (1 g) in DMF (10 mL), and the reaction solution was stirred at room temperature for 71 hours. Thereafter, ethyl acetate and water were added to the reaction solution, and the organic layer was separated. The resulting organic layer was washed with brine, dried over anhydrous magnesium sulfate and then concentrated under reduced pressure to obtain 468 mg of the title compound. The property values of the compound are as follows.

$^1$H-NMR (CDCl$_3$) δ (ppm): 2.92 (s, 6H), 3.52 (s, 2H), 3.67 (s, 3H), 6.69 (d, J=8.4 Hz, 2H), 7.13 (d, J=8.4 Hz, 2H).

Synthesis of methyl 5-chloro-2-(4-dimethylaminophenyl)pentanoate

A solution of diisopropylamine (0.391 mL) in THF (10 mL) was stirred at −30° C. for 30 minutes. n-Butyl lithium (2.66 M solution in hexane, 1 mL) was added to the solution, and the reaction solution was stirred for one hour. Thereafter, the reaction solution was stirred at −78° C. for 30 minutes. Then, a solution of methyl (4-dimethylaminophenyl)acetate (468 mg) in THF (5 mL) was added dropwise to the solution, and the reaction solution was stirred at the same temperature for two hours. To the reaction solution was added 1-bromo-3-chloropropane at −78° C., and the reaction solution was stirred for one hour. Then, the reaction solution was stirred for 42 hours while gradually heating the solution to room temperature. Thereafter, ethyl acetate and saturated sodium bicarbonate water were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane+ethyl acetate) to obtain 174.7 mg of the title compound. The property values of the compound are as follows.

ESI-MS; m/z 270 [M$^+$+H]. $^1$H-NMR (CDCl$_3$) δ (ppm): 1.62-1.81 (m, 2H), 1.83-1.98 (m, 1H), 2.09-2.22 (m, 1H), 2.93 (s, 6H), 3.42-3.56 (m, 3H), 3.64 (s, 3H), 6.69 (d, J=8.8 Hz, 2H), 7.15 (d, J=8.8 Hz, 2H).

Synthesis of
5-chloro-2-(4-dimethylaminophenyl)pentanoic acid

A 5 N sodium hydroxide solution (0.5 mL) was added to a solution of methyl 5-chloro-2-(4-dimethylaminophenyl)pentanoate (175 mg) in methanol (2 mL), and the reaction solution was stirred at room temperature for 23.5 hours. Thereafter, 1 N aqueous hydrochloric acid (2.5 mL) was added to the reaction solution, and the reaction solution was concentrated under reduced pressure to obtain 317 mg of the title compound. The property value of the compound is as follows.

ESI-MS; m/z 256 [M$^+$+H].

Synthesis of tert-butyl N'-[5-chloro-2-(4-dimethylaminophenyl)pentanoyl]hydrazinecarboxylate IPEA (0.555 mL), HOBt (175 mg) and EDC (249 mg) were added to a solution of 5-chloro-2-(4-dimethylaminophenyl) pentanoic acid (317 mg) and tert-butyl carbazate (103 mg) in DMF (2.5 mL), and the reaction solution was stirred at room temperature for five hours. Ethyl acetate and water were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane+ ethyl acetate) to obtain 106.9 mg of the title compound. The property values of the compound are as follows.

ESI-MS; m/z 370 [M$^+$+H]. $^1$H-NMR (CDCl$_3$) δ (ppm): 1.44 (s, 9H), 1.58-1.84 (m, 2H), 1.87-2.00 (m, 1H), 2.20-2.33 (m, 1H), 2.94 (s, 6H), 3.33 (t, J=7.6 Hz, 1H), 3.43-3.57 (m, 2H), 6.42 (brs, 1H), 6.70 (d, J=8.8 Hz, 2H), 7.15 (d, J=8.8 Hz, 2H), 7.24 (brs, 1H).

Synthesis of {4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}phenyl}dimethylamine A solution of 4 N hydrochloric acid in ethyl acetate (2.64 mL) was added to tert-butyl N'-[5-chloro-2-(4-dimethylaminophenyl)pentanoyl]hydrazinecarboxylate (106.9 mg), and the reaction solution was stirred at room temperature for four hours. The reaction solution was concentrated under reduced pressure to obtain 5-chloro-2-(4-dimethylaminophenyl)pentanoic acid hydrazide hydrochloride. A solution of ethyl(E)-3-[3-methoxy-4-(4-methyl-1H-imidazol-1-yl)phenyl] acrylimidate hydrochloride (77.6 mg) and triethylamine (0.16 mL) in ethanol (1.25 mL) was added to a solution of the resulting 5-chloro-2-(4-dimethylaminophenyl)pentanoic acid hydrazide hydrochloride and triethylamine (0.291 mL) in ethanol (1.25 mL), and the reaction solution was stirred at 80° C. in a nitrogen atmosphere for 22 hours. The reaction solution was cooled to room temperature, and then the solvent was evaporated from the reaction solution under reduced pressure. Ethyl acetate and saturated sodium bicarbonate water were added to the resulting residue, and the organic layer was separated. The resulting organic layer was washed with brine, dried over anhydrous magnesium sulfate and then concentrated under reduced pressure. The residue was purified by silica gel column chromatography (carrier: Chromatorex NH; elution solvent: heptane:ethyl acetate=1:1→ethyl acetate→ethyl acetate:methanol=9:1) and further purified by silica gel column chromatography (elution solvent: ethyl acetate→ethyl acetate:methanol=9:1) to obtain 26.6 mg of the title compound. The property values of the compound are as follows.

ESI-MS; m/z 455 [M$^+$+H]. $^1$H-NMR (CDCl$_3$) δ (ppm): 1.70-2.36 (m, 7H), 2.93 (s, 6H), 3.85 (s, 3H), 4.18-4.34 (m, 3H), 6.71 (d, J=8.8 Hz, 2H), 6.91 (brs, 1H), 7.00 (d, J=8.8 Hz, 2H), 7.07 (d, J=16.0 Hz, 1H), 7.10-7.18 (m, 2H), 7.21 (d, J=8.0 Hz, 1H), 7.53 (d, J=16.0 Hz, 1H), 7.70 (brs, 1H).

Examples 161 and 162

Synthesis of (S)-8-(4-chlorophenyl)-3-{(E)-2-[3-methoxy-4-(4-methyl-1H-imidazol-1-yl)phenyl]vinyl}-5,6,7,8-tetrahydro[1,2,4]triazolo[4,3-a]pyridine and (R)-8-(4-chlorophenyl)-3-{(E)-2-[3-methoxy-4-(4-methyl-1H-imidazol-1-yl)phenyl]vinyl}-5,6,7,8-tetrahydro[1,2,4]triazolo[4,3-a]pyridine

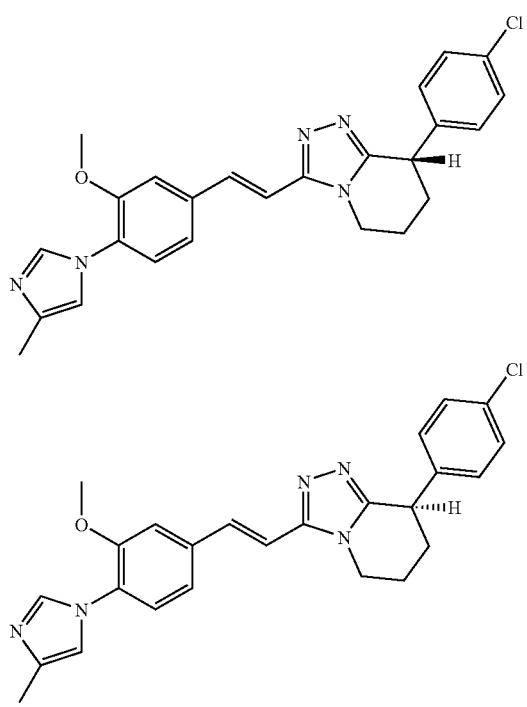

[Formula 156]

Synthesis of 2-[4-chloro-1-(4-chlorophenyl)butyl]-5-{(E)-2-[3-methoxy-4-(4-methyl-1H-imidazol-1-yl)phenyl]vinyl}[1,3,4]oxadiazole IPEA (2.5 mL), 5-chloro-2-(4-chlorophenyl)pentanoic acid (430 mg) and BOPCl (0.44 g) were added to a suspension of (E)-3-[3-methoxy-4-(4-methylimidazol-1-yl)phenyl]

acrylic acid hydrazide dihydrochloride (500 mg) in methylene chloride (15 mL) at room temperature, and the reaction solution was stirred at room temperature for 14 hours. Water was added to the reaction solution, followed by extraction with chloroform. The resulting extract was washed with a saturated sodium chloride solution, dried over magnesium sulfate and then concentrated under reduced pressure. A solution of the residue in phosphorus oxychloride (4 mL) was heated under reflux for five hours. The reaction solution was left to cool to room temperature and concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system) to obtain 366 mg of the title compound. The property value of the compound is as follows.

ESI-MS; m/z 483 [M$^+$+H].

Synthesis of (S)-8-(4-chlorophenyl)-3-{(E)-2-[3-methoxy-4-(4-methyl-1H-imidazol-1-yl)phenyl]vinyl}-5,6,7,8-tetrahydro[1,2,4]triazolo[4,3-a]pyridine and (R)-8-(4-chlorophenyl)-3-{(E)-2-[3-methoxy-4-(4-methyl-1H-imidazol-1-yl)phenyl]vinyl}-5,6,7,8-tetrahydro[1,2,4]triazolo[4,3-a]pyridine Sodium azide (0.15 g) was added to a solution of 2-[4-chloro-1-(4-chlorophenyl)butyl]-5-{(E)-2-[3-methoxy-4-(4-methyl-1H-imidazol-1-yl)phenyl]vinyl}[1,3,4]oxadiazole (366 mg) in DMSO (10 mL) at room temperature, and the reaction solution was stirred at 70° C. for six hours. The reaction solution was left to cool to room temperature. Then, ethyl acetate and a saturated sodium bicarbonate solution were added to the reaction solution, and the organic layer was separated. The resulting organic layer was washed with a saturated sodium chloride solution, dried over magnesium sulfate and then concentrated under reduced pressure. Triphenylphosphine (0.30 g) was added to a mixed solution of the resulting residue in THF (10 mL) and water (0.5 mL) at room temperature, and the reaction solution was stirred at 60° C. for three hours. The reaction solution was left to cool to room temperature and concentrated under reduced pressure. THF and toluene were added to the residue, and the solution was again concentrated under reduced pressure. A solution of the resulting residue in acetic acid (5 mL) was stirred at 150° C. for 1.5 hours. The reaction solution was left to cool to room temperature and concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system, then ethyl acetate-methanol system) to obtain 240 mg of the title compound as a racemate. The property values of the compound are as follows.

ESI-MS; m/z 446 [M$^+$+H]. $^1$H-NMR (CDCl$_3$) δ (ppm): 1.97-2.12 (m, 2H), 2.13-2.23 (m, 1H), 2.28-2.37 (m, 1H), 2.31 (d, J=0.8 Hz, 3H), 3.91 (s, 3H), 4.08-4.18 (m, 2H), 4.40 (dd, J=7.6, 5.2 Hz, 1H), 6.90 (d, J=16.4 Hz, 1H), 6.95 (dd, J=1.2, 1.2 Hz, 1H), 7.11-7.15 (m, 2H), 7.17 (d, J=1.6 Hz, 1H), 7.21-7.33 (m, 4H), 7.74 (d, J=16.4 Hz, 1H), 7.73 (d, J=1.6 Hz, 1H).

The title compound as a racemate (13 mg) was separated by CHIRALPAK™ IB manufactured by Daicel Chemical Industries, Ltd. (2 cm×25 cm; mobile phase: ethanol) to obtain the title optically active compound with a retention time of 11 minutes (5.2 mg) and the title optically active compound with a retention time of 15 minutes (5.3 mg).

Examples 163 and 164

Synthesis of (+)-3-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[4,3-a]pyridine and (−)-3-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[4,3-a]pyridine

[Formula 157]

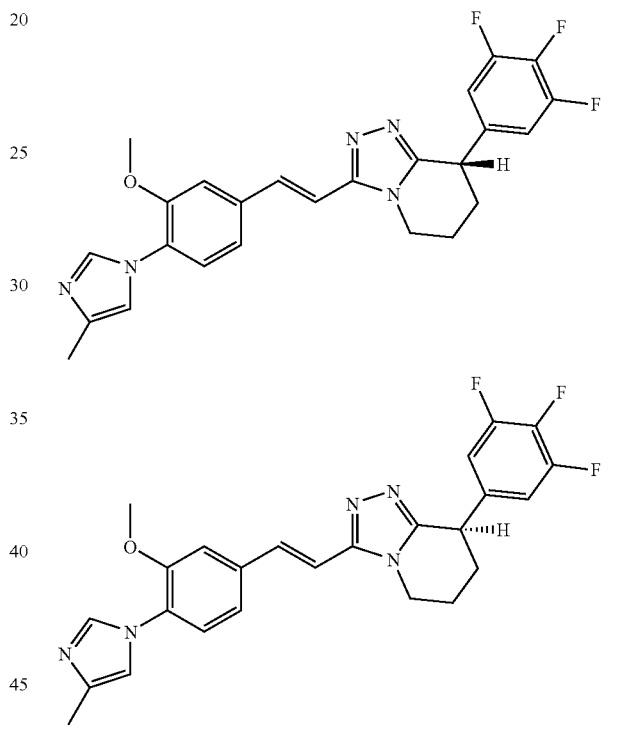

489 mg of the title compound as a racemate was obtained from (E)-3-[3-methoxy-4-(4-methyl-1H-imidazol-1-yl)phenyl]acrylic acid hydrazide dihydrochloride (1.00 g) and 5-chloro-2-(3,4,5-trifluorophenyl)pentanoic acid (0.93 g) by the same method as in Examples 161 and 162. The property values of the compound are as follows.

ESI-MS; m/z 466 [M$^+$+H]. $^1$H-NMR (CDCl$_3$) δ (ppm): 1.95-2.25 (m, 3H), 2.28-2.39 (m, 1H), 2.31 (d, J=0.8 Hz, 3H), 3.92 (s, 3H), 4.06-4.20 (m, 2H), 4.35 (dd, J=8.4, 5.6 Hz, 1H), 6.83-6.90 (m, 2H), 6.88 (d, J=16.4 Hz, 1H), 6.95 (dd, J=1.2, 1.2 Hz, 1H), 7.17 (d, J=1.6 Hz, 1H), 7.22-7.30 (m, 2H), 7.72-7.75 (m, 1H), 7.75 (d, J=16.4 Hz, 1H).

The title compound as a racemate (10 mg) was separated by CHIRALPAK™ IB manufactured by Daicel Chemical Industries, Ltd. (2 cm×25 cm; mobile phase: ethanol) to obtain the title optically active compound with a retention time of 19 minutes and positive optical rotation (4.5 mg) and the title optically active compound with a retention time of 24 minutes and negative optical rotation (4.6 mg).

Examples 165 and 166

Synthesis of (+)-3-{(E)-2-[3-methoxy-4-(4-methyl-1H-imidazol-1-yl)phenyl]vinyl}-7-(3,4,5-trifluorophenyl)-6,7-dihydro-5H-pyrrolo[2,1-c][1,2,4]triazole and (−)-3-{(E)-2-[3-methoxy-4-(4-methyl-1H-imidazol-1-yl)phenyl]vinyl}-7-(3,4,5-trifluorophenyl)-6,7-dihydro-5H-pyrrolo[2,1-c][1,2,4]triazole

[Formula 158]

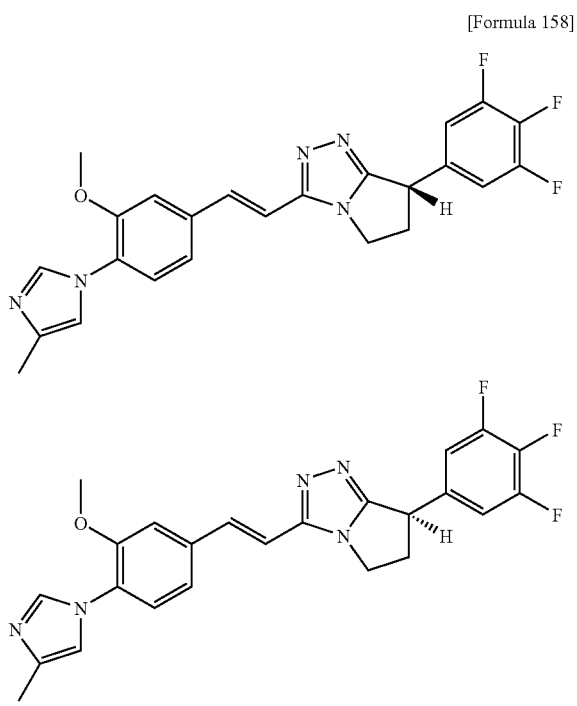

Synthesis of 4-chloro-2-(3,4,5-trifluorophenyl)butyric acid N'-{(E)-3-[3-methoxy-4-(4-methyl-1H-imidazol-1-yl)phenyl]acryloyl}hydrazide oxalyl chloride (0.39 mL) and DMF (1 drop) were added to a solution of 4-chloro-2-(3,4,5-trifluorophenyl)butyric acid (730 mg) in methylene chloride (20 mL) at 0° C., and the reaction solution was stirred at room temperature for one hour. The reaction solution was concentrated under reduced pressure to obtain 4-chloro-2-(3,4,5-trifluorophenyl)butyric acid chloride. Triethylamine (4.1 mL), methylene chloride (20 mL) and DMF (5 mL) were added to a suspension of (E)-3-[3-methoxy-4-(4-methyl-1H-imidazol-1-yl)phenyl]acrylic acid hydrazide dihydrochloride (1.00 g) in THF (25 mL) at room temperature, and the reaction solution was stirred at room temperature for 10 minutes. A solution of 4-chloro-2-(3,4,5-trifluorophenyl)butyric acid chloride obtained above in THF (5 mL) was added to the reaction solution at 0° C., and the reaction solution was stirred at room temperature for one hour. The reaction solution was added to a saturated sodium bicarbonate solution, followed by extraction with ethyl acetate. The resulting extract was dried over magnesium sulfate and then concentrated under reduced pressure. The residue was purified by silica gel column chromatography (carrier: Chromatorex NH; elution solvent: ethyl acetate-methanol system) to obtain the title compound. The property value of the compound is as follows.

ESI-MS; m/z 507 [M$^+$+H].

Synthesis of 2-[3-chloro-1-(3,4,5-trifluorophenyl)propyl]-5-{(E)-2-[3-methoxy-4-(4-methyl-1H-imidazol-1-yl)phenyl]vinyl}[1,3,4]oxadiazole A solution of 4-chloro-2-(3,4,5-trifluorophenyl)butyric acid N'-{(E)-3-[3-methoxy-4-(4-methyl-1H-imidazol-1-yl)phenyl]acryloyl}hydrazide obtained above in phosphorus oxychloride (8 mL) was heated under reflux for five hours. The reaction solution was left to cool to room temperature and concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system) to obtain the title compound. The property value of the compound is as follows.

ESI-MS; m/z 489 [M$^+$+H].

Synthesis of (S)-3-{(E)-2-[3-methoxy-4-(4-methyl-1H-imidazol-1-yl)phenyl]vinyl}-7-(3,4,5-trifluorophenyl)-6,7-dihydro-5H-pyrrolo[2,1-c][1,2,4]triazole and (R)-3-{(E)-2-[3-methoxy-4-(4-methyl-1H-imidazol-1-yl)phenyl]vinyl}-7-(3,4,5-trifluorophenyl)-6,7-dihydro-5H-pyrrolo[2,1-c][1,2,4]triazole Sodium azide (0.27 g) was added to a solution of 2-[3-chloro-1-(3,4,5-trifluorophenyl)propyl]-5-{(E)-2-[3-methoxy-4-(4-methyl-1H-imidazol-1-yl)phenyl]vinyl}[1,3,4]oxadiazole obtained above in DMSO (15 mL) at room temperature, and the reaction solution was stirred at 70° C. for nine hours. The reaction solution was left to cool to room temperature. Then, ethyl acetate and a saturated sodium bicarbonate solution were added to the reaction solution, and the organic layer was separated. The resulting organic layer was washed with a saturated sodium chloride solution, dried over magnesium sulfate and then concentrated under reduced pressure. The resulting solid was washed with a mixed solvent of diethyl ether and heptane. Triphenylphosphine (0.36 g) was added to a mixed solution of the resulting solid in THF (10 mL) and water (0.5 mL) at room temperature, and the reaction solution was stirred at 60° C. for three hours. The reaction solution was left to cool to room temperature and concentrated under reduced pressure. THF and toluene were added to the residue, and the solution was again concentrated under reduced pressure. A solution of the resulting residue in acetic acid (5 mL) was stirred at 150° C. for five hours. The reaction solution was left to cool to room temperature and concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system, then ethyl acetate-methanol system) to obtain 166 mg of the title compound as a racemate. The property values of the compound are as follows.

ESI-MS; m/z 452 [M$^+$+H]. $^1$H-NMR (CDCl$_3$) δ (ppm): 2.31 (d, J=1.2 Hz, 3H), 2.75-2.86 (m, 1H), 3.29-3.38 (m, 1H), 3.92 (s, 3H), 4.18-4.26 (m, 1H), 4.27-4.35 (m, 1H), 4.50 (t, J=8.0 Hz, 1H), 6.95 (dd, J=1.2, 1.2 Hz, 1H), 7.04-7.09 (m, 2H), 7.09 (d, J=16.4 Hz, 1H), 7.15-7.20 (m, 2H), 7.26-7.30 (m, 1H), 7.33 (d, J=16.4 Hz, 1H), 7.73 (d, J=1.2 Hz, 1H).

The title compound as a racemate (12 mg) was separated by CHIRALPAK™ IB manufactured by Daicel Chemical Industries, Ltd. (2 cm×25 cm; mobile phase: ethanol) to obtain the title optically active compound with a retention time of 21 minutes and positive optical rotation (5.4 mg) and the title optically active compound with a retention time of 26 minutes and negative optical rotation (5.5 mg).

Examples 167 and 168

Synthesis of (S)-3-{(E)-2-[3-methoxy-4-(4-methyl-1H-imidazol-1-yl)phenyl]vinyl}-9-(3,4,5-trifluorophenyl)-6,7,8,9-tetrahydro-5H-[1,2,4]triazolo[4,3-a]azepine and (R)-3-{(E)-2-[3-methoxy-4-(4-methyl-1H-imidazol-1-yl)phenyl]vinyl}-9-(3,4,5-trifluorophenyl)-6,7,8,9-tetrahydro-5H-[1,2,4]triazolo[4,3-a]azepine

[Formula 159]

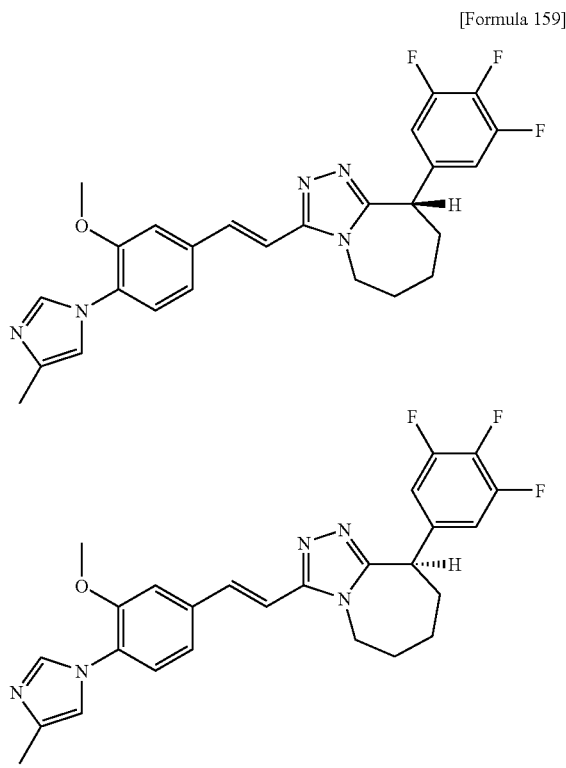

Synthesis of 2-[5-chloro-1-(3,4,5-trifluorophenyl)pentyl]-5-{(E)-2-[3-methoxy-4-(4-methyl-1H-imidazol-1-yl)phenyl]vinyl}[1,3,4]oxadiazole A solution of 4 N hydrogen chloride in ethyl acetate (30 mL) was added to tert-butyl N'-[6-chloro-2-(3,4,5-trifluorophenyl)hexanoyl]hydrazinecarboxylate synthesized according to the method described in Examples 112 and 113 (ESI-MS; m/z 417 [M⁺+Na], 2.08 g). The reaction solution was stirred at room temperature for one hour and then concentrated under reduced pressure to obtain 6-chloro-2-(3,4,5-trifluorophenyl)hexanoic acid hydrazide hydrochloride (1.81 g). IPEA (1.5 mL), (E)-3-[3-methoxy-4-(4-methylimi-dazol-1-yl)phenyl]acrylic acid (450 mg) and BOPCl (0.53 g) were added to a solution of 6-chloro-2-(3,4,5-trifluorophenyl)hexanoic acid hydrazide hydrochloride (612 mg) in methylene chloride (15 mL) at room temperature, and the reaction solution was stirred at room temperature for three hours. Water was added to the reaction solution, followed by extraction with chloroform. The resulting extract was washed with a saturated sodium chloride solution, dried over magnesium sulfate and then concentrated under reduced pressure. A solution of the resulting residue in phosphorus oxychloride (8 mL) was heated under reflux for three hours. The reaction solution was left to cool to room temperature and concentrated under reduced pressure. A saturated sodium bicarbonate solution was added to the resulting residue, followed by extraction with ethyl acetate. The resulting extract was dried over magnesium sulfate and then concentrated under reduced pressure. The residue was purified by silica gel column chromatography (elution solvent: heptane-ethyl acetate system) to obtain 430 mg of the title compound. The property value of the compound is as follows.

ESI-MS; m/z 517 [M⁺+H].

Synthesis of (S)-3-{(E)-2-[3-methoxy-4-(4-methyl-1H-imidazol-1-yl)phenyl]vinyl}-9-(3,4,5-trifluorophenyl)-6,7,8,9-tetrahydro-5H-[1,2,4]triazolo[4,3-a]azepine and (R)-3-{(E)-2-[3-methoxy-4-(4-methyl-1H-imidazol-1-yl)phenyl]vinyl}-9-(3,4,5-trifluorophenyl)-6,7,8,9-tetrahydro-5H-[1,2,4]triazolo[4,3-a]azepine Sodium azide (0.16 g) was added to a solution of 2-[5-chloro-1-(3,4,5-trifluorophenyl)pentyl]-5-{(E)-2-[3-methoxy-4-(4-methyl-1H-imidazol-1-yl)phenyl]vinyl}[1,3,4]oxadiazole (430 mg) in DMF (10 mL) at room temperature, and the reaction solution was stirred at 70° C. for six hours. The reaction solution was left to cool to room temperature. Then, ethyl acetate and a saturated sodium bicarbonate solution were added to the reaction solution, and the organic layer was separated. The resulting organic layer was washed with a saturated sodium chloride solution, dried over magnesium sulfate and then concentrated under reduced pressure. Triphenylphosphine (0.33 g) was added to a mixed solution of the resulting residue in THF (10 mL) and water (0.5 mL) at room temperature, and the reaction solution was stirred at 60° C. for two hours. The reaction solution was left to cool to room temperature and concentrated under reduced pressure. THF and toluene were added to the residue, and the solution was again concentrated under reduced pressure. A solution of the resulting residue in acetic acid (5 mL) was stirred at 150° C. for 18 hours. The reaction solution was left to cool to room temperature and concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system, then ethyl acetate-methanol system) to obtain 168 mg of the title compound as a racemate which was a mixture with by-products. The resulting title compound as a racemate (30 mg) was separated by CHIRALPAK™ IB manufactured by Daicel Chemical Industries, Ltd. (2 cm×25 cm; mobile phase: hexane:ethanol=4:1) and then by CHIRALPAK™ IA manufactured by Daicel Chemical Industries, Ltd. (2 cm×25 cm; mobile phase: hexane:ethanol=1:1) to obtain the title optically active compound with a retention time of 20 minutes (4.0 mg) and the title optically active compound with a retention time of 23 minutes (3.4 mg). The property values of the compounds are as follows.

ESI-MS; m/z 480 [M$^+$+H]. $^1$H-NMR (CDCl$_3$) δ (ppm): 1.81-2.15 (m, 5H), 2.23-2.35 (m, 1H), 2.31 (s, 3H), 3.87-3.98 (m, 1H), 3.92 (s, 3H), 4.03-4.13 (m, 1H), 4.49 (brd, J=8.0 Hz, 1H), 6.78-6.87 (m, 3H), 6.95 (s, 1H), 7.16 (s, 1H), 7.22-7.30 (m, 2H), 7.74 (brs, 1H), 7.77 (d, J=16.0 Hz, 1H).

Examples 169 and 170

Synthesis of (+)-2-{(E)-2-[3-methoxy-4-(4-methyl-1H-imidazol-1-yl)phenyl]vinyl}-9-(3,4,5-trifluorophenyl)-6,7,8,9-tetrahydro-5H-[1,2,4]triazolo[1,5-a]azepine and (−)-2-{(E)-2-[3-methoxy-4-(4-methyl-1H-imidazol-1-yl)phenyl]vinyl}-9-(3,4,5-trifluorophenyl)-6,7,8,9-tetrahydro-5H-[1,2,4]triazolo[1,5-a]azepine

[Formula 160]

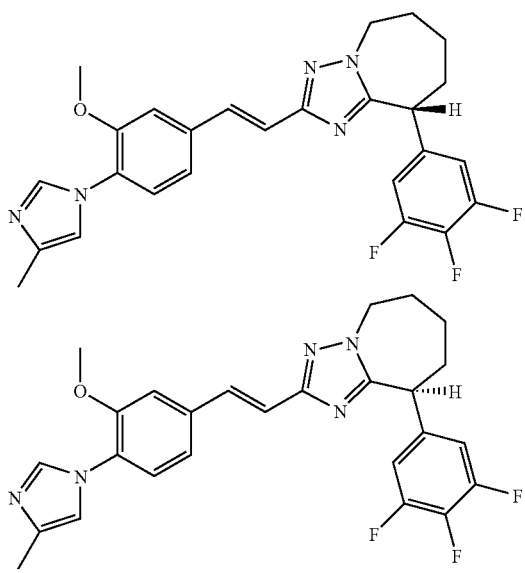

A solution of 6-chloro-2-(3,4,5-trifluorophenyl)hexanoic acid hydrazide hydrochloride (511 mg) and triethylamine (0.65 mL) in ethanol (7 mL) was added to a solution of ethyl(E)-3-[3-methoxy-4-(4-methyl-1H-imidazol-1-yl)phenyl]acrylimidate dihydrochloride (425 mg) and triethylamine (1 mL) in ethanol (7 mL) at room temperature, and the reaction solution was stirred at 80° C. for 24 hours. The reaction solution was left to cool to room temperature and concentrated under reduced pressure. Dioxane (15 mL) and IPEA (2 mL) were added to the resulting residue, and the reaction solution was stirred at 110° C. for 44 hours. The reaction solution was left to cool to room temperature and concentrated under reduced pressure. Water was added to the resulting residue, followed by extraction with chloroform. The resulting extract was dried over magnesium sulfate and then concentrated under reduced pressure. Sodium hydride (containing mineral oil at 40%, 48 mg) was added to a solution of the resulting residue in THF (20 mL) in a nitrogen atmosphere at 0° C., and the reaction solution was stirred at room temperature for five hours. Sodium hydride (containing mineral oil at 40%, 100 mg) was added to the reaction solution at room temperature, and the reaction solution was stirred at room temperature for three hours. An ammonium chloride solution was added to the reaction solution at 0° C., followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system, then ethyl acetate-methanol system) to obtain 63 mg of the title compound as a racemate which was a mixture with by-products. The resulting title compound as a racemate (63 mg) was separated by CHIRAL-PAK™ IB manufactured by Daicel Chemical Industries, Ltd. (2 cm×25 cm; mobile phase: hexane:ethanol=4:1) to obtain the title optically active compound with a retention time of 22 minutes and positive optical rotation (12 mg) and the title optically active compound with a retention time of 41 minutes and negative optical rotation (13 mg). The property values of the compounds are as follows.

ESI-MS; m/z 480 [M$^+$+H]. $^1$H-NMR (CDCl$_3$) δ (ppm): 1.84-1.98 (m, 4H), 2.05-2.12 (m, 1H), 2.16-2.27 (m, 1H), 2.29 (d, J=0.8 Hz, 3H), 3.87 (s, 3H), 4.18-4.26 (m, 1H), 4.28-4.41 (m, 2H), 6.75-6.84 (m, 2H), 6.89-6.93 (m, 1H), 7.01 (d, J=16.8 Hz, 1H), 7.12-7.17 (m, 2H), 7.22 (d, J=8.8 Hz, 1H), 7.46 (d, J=16.8 Hz, 1H), 7.70 (d, J=1.6 Hz, 1H).

Example 171

Synthesis of 3-(4-fluorophenyl)-8-{1-[3-methoxy-4-(4-methyl-1H-imidazol-1-yl)phenyl]-(E)-methylidene}-5,6,7,8-tetrahydro[1,2,4]triazolo[4,3-a]pyridine

[Formula 161]

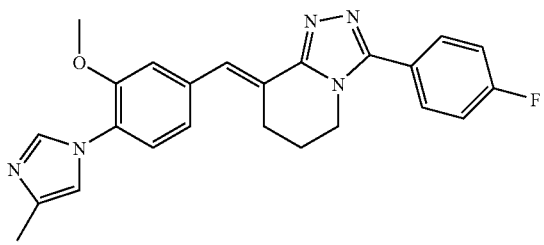

Synthesis of 2-{4-chloro-1-{1-[3-methoxy-4-(4-methyl-1H-imidazol-1-yl)phenyl]-(E)-methylidene}butyl}-5-(4-fluorophenyl)[1,3,4]oxadiazole IPEA (1.2 mL), EDC (0.89 g) and HOBT (0.62 g) were added to a suspension of 5-chloro-2-{1-[3-methoxy-4-(4-methyl-1H-imidazol-1-yl)phenyl]-(E)-methylidene}valeric acid trifluoroacetic acid salt (1.30 g) and 4-fluorobenzhydrazide (0.37 g) in DMF (25 mL) at room temperature, and the reaction solution was stirred at room temperature for two hours. A saturated sodium bicarbonate solution and ethyl acetate were added to the reaction solution, and the organic layer was separated. The organic layer was washed with a saturated sodium chloride solution, dried over magnesium sulfate and then concentrated under reduced pressure. A solution of the resulting residue in phosphorus oxychloride (6 mL) was heated under reflux for three hours. The reaction solution was left to cool to room temperature and concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system) to obtain 376 mg of the title compound. The property value of the compound is as follows.

ESI-MS; m/z 453 [M$^+$+H].

Synthesis of 3-(4-fluorophenyl)-8-{1-[3-methoxy-4-(4-methyl-1H-imidazol-1-yl)phenyl]-(E)-methylidene}-5,6,7,8-tetrahydro[1,2,4]triazolo[4,3-a]pyridine Sodium azide (0.15 g) was added to a solution of 2-{4-chloro-1-{1-[3-methoxy-4-(4-methyl-1H-imidazol-1-yl)phenyl]-(E)-methylidene}butyl}-5-(4-fluorophenyl)[1,3,4]oxadiazole (366 mg) in DMSO (10 mL) at room temperature, and the reaction solution was stirred at 70° C. for six hours. The reaction solution was left to cool to room temperature. Then, ethyl acetate and a saturated sodium bicarbonate solution were added to the reaction solution, and the organic layer was separated. The resulting organic layer was washed with a saturated sodium chloride solution, dried over magnesium sulfate and then concentrated under reduced pressure. Triphenylphosphine (0.33 g) was added to a mixed solution of the resulting residue in THF (10 mL) and water (0.5 mL) at room temperature, and the reaction solution was stirred at 60° C. for three hours. The reaction solution was left to cool to room temperature and concentrated under reduced pressure. THF and toluene were added to the residue, and the solution was again concentrated under reduced pressure. A solution of the resulting residue in acetic acid (5 mL) was stirred at 150° C. for 1.5 hours. The reaction solution was left to cool to room temperature and concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system, then ethyl acetate-methanol system), solidified with ethyl acetate and hexane and separated by filtration to obtain 188 mg of the title compound. The property values of the compound are as follows.

ESI-MS; m/z 416 [M$^+$+H]. $^1$H-NMR (CDCl$_3$) δ (ppm): 2.05-2.13 (m, 2H), 2.31 (d, J=0.8 Hz, 3H), 2.96-3.02 (m, 2H), 3.88 (s, 3H), 4.10-4.16 (m, 2H), 6.94 (s, 1H), 7.06-7.12 (m, 2H), 7.18-7.29 (m, 3H), 7.68-7.75 (m, 3H), 7.97 (brs, 1H).

Examples 172 and 173

Synthesis of (−)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine and (+)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine

[Formula 162]

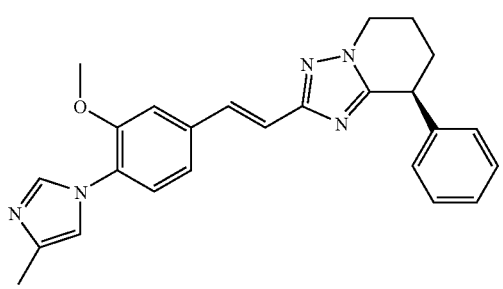

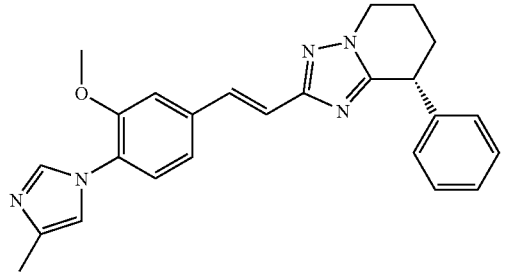

Synthesis of 5-chloro-2-phenylpentanoic acid hydrazide

A solution of methyl phenylacetate (2.0 g) in DMF (5 mL) was added to a solution of sodium hydride (containing mineral oil at 40%, 590 mg) in DMF (20 mL) under ice-cooling. The reaction solution was stirred for 10 minutes, further stirred at room temperature for 30 minutes and then ice-cooled again. A solution of 1-chloro-3-iodopropane (2.99 g) in DMF (5 mL) was added to the reaction mixture, and the reaction solution was stirred at room temperature overnight. Water and ethyl acetate were added to the reaction mixture, and the organic layer was separated. The resulting organic layer was washed with saturated aqueous sodium chloride, dried over anhydrous magnesium sulfate and then concentrated under reduced pressure to obtain a crude product of methyl 5-chloro-2-phenylpentanoate. Hydrazine monohydrate (8 mL) was added to a solution of the resulting crude methyl 5-chloro-2-phenylpentanoate (3.279 g) in ethanol (20 mL), and the reaction solution was stirred at room temperature overnight. The reaction solution was concentrated under reduced pressure. Saturated sodium bicarbonate water and ethyl acetate and were added to the residue, and the organic layer was separated. The resulting organic layer was washed with saturated aqueous sodium chloride, dried over anhydrous magnesium sulfate and then concentrated under reduced pressure. The resulting residue was purified by silica gel column chromatography (elution solvent: heptane-ethyl acetate system) to obtain 730 mg of the title compound. The property values of the compound are as follows.

$^1$H-NMR (CDCl$_3$) δ (ppm): 1.60-2.45 (m, 6H), 3.45-3.59 (m, 2H), 4.53 (t, J=7.6 Hz, 1H), 7.20-7.40 (m, 5H), 8.10 (brs, 1H).

Synthesis of (R)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine and (S)-2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine 32 mg of a racemate of the title compound was obtained from ethyl(E)-3-[3-methoxy-4-(4-methyl-1H-imidazol-1-yl)phenyl]acrylimidate dihydrochloride (250 mg) and 5-chloro-2-phenylpentanoic acid hydrazide (206 mg) by the same method as in Examples 150 and 151. The resulting racemate was separated by CHIRALPAK™ AD-H manufactured by Daicel Chemical Industries, Ltd. (2 cm×25 cm; mobile phase: ethanol, flow rate: 10 mL/min) to obtain the title optically active compound with a retention time of 21 minutes and negative optical rotation (11 mg) and the title optically active compound with a retention time of 25 minutes and positive optical rotation (12 mg).

The property values of the title optically active compound with a retention time of 21 minutes are as follows.

$^1$H-NMR (CDCl$_3$) δ (ppm): 2.06-2.12 (m, 2H), 2.16-2.24 (m, 1H), 2.29 (s, 3H), 2.33-2.40 (m, 1H), 3.85 (s, 3H), 4.21-4.37 (m, 3H), 6.91 (s, 1H), 7.07 (d, J=16.4 Hz, 1H), 7.13-7.15 (m, 3H), 7.21 (d, J=7.6 Hz, 1H), 7.26-7.29 (m, 2H), 7.32-7.36 (m, 2H), 7.52 (d, J=16.4 Hz, 1H), 7.69 (s, 1H).

The property values of the title optically active compound with a retention time of 25 minutes are as follows.

$^1$H-NMR (CDCl$_3$) δ (ppm): 2.06-2.12 (m, 2H), 2.16-2.24 (m, 1H), 2.29 (s, 3H), 2.33-2.40 (m, 1H), 3.85 (s, 3H), 4.21-4.37 (m, 3H), 6.91 (s, 1H), 7.07 (d, J=16.4 Hz, 1H), 7.13-7.15 (m, 3H), 7.21 (d, J=7.6 Hz, 1H), 7.26-7.29 (m, 2H), 7.32-7.36 (m, 2H), 7.52 (d, J=16.4 Hz, 1H), 7.69 (s, 1H).

Examples 174 and 175

Synthesis of (−)-8-(2-bromophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and (+)-8-(2-bromophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 163]

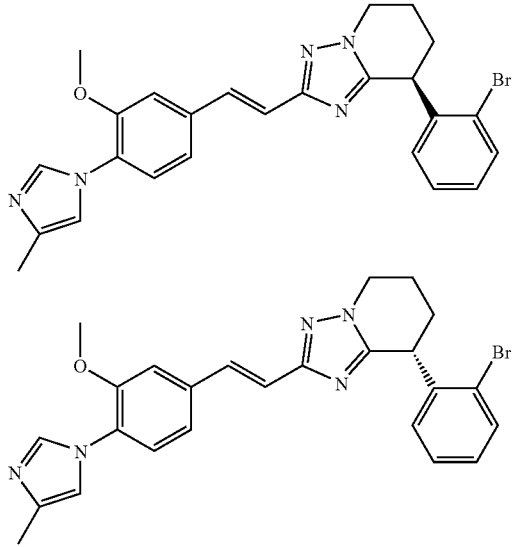

Synthesis of 1-amino-3-(2-bromophenyl)piperidin-2-one

A solution of methyl 2-bromophenylacetate (2.0 g) in DMF (5 mL) was added to a suspension of sodium hydride (containing mineral oil at 40%, 384 mg) in DMF (20 mL) under ice-cooling. The reaction solution was stirred for 10 minutes, further stirred at room temperature for 30 minutes and then ice-cooled again. A solution of 1-chloro-3-iodopropane (1.96 g) in DMF (5 mL) was added to the reaction mixture, and the reaction solution was stirred at room temperature overnight. Water and ethyl acetate were added to the reaction mixture, and the organic layer was separated. The resulting organic layer was washed with saturated aqueous sodium chloride, dried over anhydrous magnesium sulfate and then concentrated under reduced pressure to obtain a crude product of methyl 2-(2-bromophenyl)-5-chloropentanoate. Hydrazine monohydrate (4 mL) was added to a solution of the resulting crude methyl 2-(2-bromophenyl)-5-chloropentanoate (2.895 g) in ethanol (20 mL), and the reaction solution was stirred at room temperature for three hours. Hydrazine monohydrate (8 mL) was further added to the reaction solution, and the reaction solution was stirred at room temperature for two days. The reaction solution was concentrated under reduced pressure. Saturated sodium bicarbonate water and ethyl acetate and were added to the residue, and the organic layer was separated. The resulting organic layer was washed with saturated aqueous sodium chloride, dried over anhydrous magnesium sulfate and then concentrated under reduced pressure to obtain 1.504 g of the crude purified title compound. The property value of the compound is as follows.

ESI-MS; m/z 269, 271 [M$^+$+H].

Synthesis of (E)-N-[3-(2-bromophenyl)-2-oxopiperidin-1-yl]-3-[3-methoxy-4-(4-methyl-1H-imidazol-1-yl)phenyl]acrylamide BOPCl (1.48 g) was added to a suspension of (E)-3-[3-methoxy-4-(4-methyl-1H-imidazol-1-yl)phenyl]acrylic acid (1.0 g), 1-amino-3-(2-bromophenyl)piperidin-2-one (1.26 g) and TEA (1.1 mL) in DMF (20 mL), and the reaction solution was stirred at room temperature for three hours. Water and ethyl acetate were added to the reaction mixture, and the organic layer was separated. The resulting organic layer was washed with saturated aqueous sodium chloride, dried over anhydrous magnesium sulfate and then concentrated under reduced pressure. The resulting residue was purified by silica gel column chromatography (carrier: Chromatorex NH; elution solvent: ethyl acetate-methanol system) to obtain 1.130 g of the title compound. The property values of the compound are as follows.

$^1$H-NMR (CDCl$_3$) δ (ppm): 2.00-2.15 (m, 2H), 2.18-2.28 (m, 1H), 2.29 (s, 3H), 3.63-3.68 (m, 1H), 3.76-3.78 (m, 1H), 3.78 (s, 3H), 3.80-3.84 (m, 1H), 4.22-4.26 (m, 1H), 6.50 (d, J=16.0 Hz, 1H), 6.84-6.91 (m, 3H), 7.09 (d, J=8.4 Hz, 1H), 7.14 (dd, J=7.6, 1.2 Hz, 1H), 7.26-7.31 (m, 1H), 7.42 (d, J=16.0 Hz, 1H), 7.46 (dd, J=7.6, 1.2 Hz, 1H), 7.56 (dd, J=7.6, 1.2 Hz, 1H), 7.73 (d, J=1.2 Hz, 1H), 10.49 (s, 1H).

Synthesis of (R)-8-(2-bromophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and (S)-8-(2-bromophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine A solution of (E)-N-[3-(2-bromophenyl)-2-oxopiperidin-1-yl]-3-[3-methoxy-4-(4-methyl-1H-imidazol-1-yl)phenyl]acrylamide (1.130 g) in phosphorus oxychloride (7 mL) was heated under reflux for one hour. The reaction mixture was left to cool to room temperature and then concentrated under reduced pressure. Acetic acid (7 mL) and ammonium acetate (6 g) were added to the residue, and the reaction solution was stirred at 150° C. for one hour. The reaction solution was left to cool to room temperature and then concentrated under reduced pressure. Saturated sodium bicarbonate water and ethyl acetate and were added to the residue, and the organic layer was separated. The resulting organic layer was washed with saturated aqueous sodium chloride, dried over anhydrous magnesium sulfate and then concentrated under reduced pressure. The resulting residue was purified by silica gel column chromatography (carrier: Chromatorex NH; elution solvent: heptane-ethyl acetate system) to obtain 663 mg of a racemate of the title compound. The resulting racemate (55 mg) was separated by CHIRALPAK™ AD-H manufactured by Daicel Chemical Industries, Ltd. (2 cm×25 cm; mobile phase: ethanol, flow rate: 10 mL/min) to obtain the title optically active compound with a retention time of 18 minutes and negative optical rotation (20 mg) and the title optically active compound with a retention time of 24 minutes and positive optical rotation (20 mg).

The property values of the title optically active compound with a retention time of 18 minutes are as follows.

$^1$H-NMR (CDCl$_3$) δ (ppm): 2.03-2.20 (m, 2H), 2.30 (s, 3H), 2.35-2.42 (m, 1H), 3.70-3.75 (m, 1H), 3.86 (s, 3H), 4.25-4.35 (m, 2H), 4.76 (t, J=6.4 Hz, 1H), 6.86 (brd, J=7.6 Hz, 1H), 6.92 (s, 1H), 7.08 (d, J=16.4, 0.8 Hz, 1H), 7.13-7.17 (m, 3H), 7.21 (d, J=7.6 Hz, 1H), 7.26-7.27 (m, 2H), 7.51 (dd, J=7.6, 0.8 Hz, 1H), 7.69 (d, J=0.8 Hz, 1H).

The property values of the title optically active compound with a retention time of 24 minutes are as follows.

$^1$H-NMR (CDCl$_3$) δ (ppm): 2.03-2.20 (m, 2H), 2.30 (s, 3H), 2.35-2.42 (m, 1H), 3.70-3.75 (m, 1H), 3.86 (s, 3H), 4.25-4.35 (m, 2H), 4.76 (t, J=6.4 Hz, 1H), 6.86 (brd, J=7.6 Hz, 1H), 6.92 (s, 1H), 7.08 (d, J=16.4, 0.8 Hz, 1H), 7.13-7.17 (m, 3H), 7.21 (d, J=7.6 Hz, 1H), 7.26-7.27 (m, 2H), 7.51 (dd, J=7.6, 0.8 Hz, 1H), 7.69 (d, J=0.8 Hz, 1H).

Example 176

Synthesis of 8-(2-bromo-4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 164]

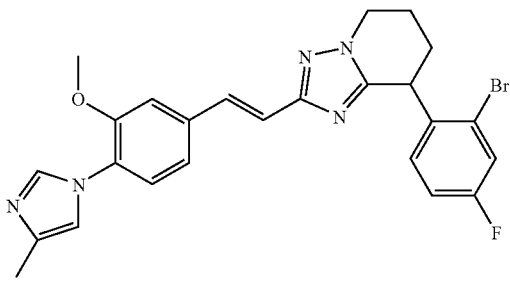

Synthesis of 1-amino-3-(2-bromo-4-fluorophenyl)piperidin-2-one

Thionyl chloride (6 mL) was added dropwise to a solution of 2-bromo-4-fluorophenylacetic acid (5.0 g) in methanol (50 mL), and the reaction solution was stirred at room temperature for one hour. The reaction mixture was concentrated under reduced pressure, and then the residue was dissolved in ethyl acetate. The solution was filtered through a silica gel pad (carrier: Chromatorex NH), and the filtrate was concentrated under reduced pressure to obtain methyl 2-bromo-4-fluorophenylacetate (5.53 g). A solution of methyl 2-bromo-4-fluorophenylacetate (2.0 g) in DMF (5 mL) was added to a suspension of sodium hydride (containing mineral oil at 40%, 356 mg) in DMF (20 mL) under ice-cooling. The reaction solution was stirred for 10 minutes, further stirred at room temperature for 30 minutes and then ice-cooled again. A solution of 1-chloro-3-iodopropane (1.82 g) in DMF (5 mL) was added to the reaction mixture, and the reaction solution was stirred at room temperature for three hours. Water and ethyl acetate were added to the reaction mixture, and the organic layer was separated. The resulting organic layer was washed with saturated aqueous sodium chloride, dried over anhydrous magnesium sulfate and then concentrated under reduced pressure. Hydrazine monohydrate (8 mL) was added to a solution of the resulting crude purified methyl 5-chloro-2-(2-bromo-4-fluoro)phenylpentanoate (2.75 g) in ethanol (20 mL), and the reaction solution was heated under reflux for 3.5 hours. The reaction solution was left to cool to room temperature and then concentrated under reduced pressure. Saturated sodium bicarbonate water and ethyl acetate and were added to the residue, and the organic layer was separated. The resulting organic layer was washed with saturated aqueous sodium chloride, dried over anhydrous magnesium sulfate and then concentrated under reduced pressure. The resulting residue was purified by silica gel column chromatography (elution solvent: ethyl acetate-methanol system) to obtain 1.157 g of the title compound. The property values of the compound are as follows.

$^1$H-NMR (CDCl$_3$) δ (ppm): 1.92-2.00 (m, 2H), 2.11-2.18 (m, 1H), 3.57-3.62 (m, 1H), 3.65-3.72 (m, 1H), 4.03-4.06 (m, 1H), 4.60 (brs, 2H), 6.98-7.02 (m, 1H), 7.15 (dd, J=8.4, 6.0 Hz, 1H), 7.32 (dd, J=8.4, 2.8 Hz, 1H).

Synthesis of (E)-N-[3-(2-bromo-4-fluorophenyl)-2-oxopiperidin-1-yl]-3-[3-methoxy-4-(4-methyl-1H-imidazol-1-yl)phenyl]acrylamide BOPCl (1.48 g) was added to a suspension of (E)-3-[3-methoxy-4-(4-methyl-1H-imidazol-1-yl)phenyl]acrylic acid (1.0 g), 1-amino-3-(2-bromo-4-fluorophenyl)piperidin-2-one (1.15 g) and TEA (1.1 mL) in DMF (20 mL), and the reaction solution was stirred at room temperature overnight. Water and ethyl acetate were added to the reaction mixture, and the organic layer was separated. The resulting organic layer was washed with saturated aqueous sodium chloride, dried over anhydrous magnesium sulfate and then concentrated under reduced pressure. The resulting residue was purified by silica gel column chromatography (carrier: Chromatorex NH; elution solvent: ethyl acetate-methanol system) to obtain 953 mg of the title compound. The property values of the compound are as follows.

$^1$H-NMR (CDCl$_3$) δ (ppm): 2.02-2.10 (m, 3H), 2.18-2.25 (m, 1H), 2.30 (s, 3H), 3.64-3.69 (m, 1H), 3.80 (s, 3H), 3.83-3.89 (m, 1H), 4.18-4.21 (m, 1H), 6.46 (d, J=15.6 Hz, 1H), 6.87-6.92 (m, 3H), 7.00-7.05 (m, 1H), 7.15 (d, J=8.4 Hz, 1H), 7.33 (dd, J=8.0, 2.8 Hz, 1H), 7.41-7.47 (m, 2H), 7.73 (d, J=1.2 Hz, 1H), 10.29 (s, 1H).

Synthesis of 8-(2-bromo-4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine A solution of (E)-N-[3-(2-bromo-4-fluorophenyl)-2-oxopiperidin-1-yl]-3-[3-methoxy-4-(4-methyl-1H-imidazol-1-yl)phenyl]acrylamide (953 mg) in phosphorus oxychloride (7 mL) was heated under reflux for one hour. The reaction mixture was left to cool to room temperature and then concentrated under reduced pressure. Acetic acid (7 mL) and ammonium acetate (6 g) were added to the residue, and the reaction solution was stirred at 150° C. for one hour. The reaction solution was left to cool to room temperature and then concentrated under reduced pressure. Saturated sodium bicarbonate water and ethyl acetate and were added to the residue, and the organic layer was separated. The resulting organic layer was washed with saturated aqueous sodium chloride, dried over anhydrous magnesium sulfate and then concentrated under reduced pressure. The resulting residue was purified by silica gel column chromatography (carrier: Chromatorex NH; elution solvent: heptane-ethyl acetate system) to obtain 559 mg of the title compound. The property values of the compound are as follows.

$^1$H-NMR (CDCl$_3$) δ (ppm): 1.98-2.20 (m, 3H), 2.30 (s, 3H), 2.35-2.42 (m, 1H), 3.86 (s, 3H), 4.28-4.31 (m, 2H), 4.71 (t, J=6.4 Hz, 1H), 6.87 (dd, J=8.4 Hz, 5.6 Hz, 1H), 6.92 (t, J=1.2 Hz, 1H), 6.96-7.01 (m, 1H), 7.07 (d, J=16.4 Hz, 1H), 7.14-7.16 (m, 2H), 7.22 (d, J=8.0 Hz, 1H), 7.36 (dd, J=8.0, 2.8 Hz, 1H), 7.51 (d, J=16.4 Hz, 1H), 7.70 (d, J=1.2 Hz, 1H).

Example 177

Synthesis of 8-(2-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

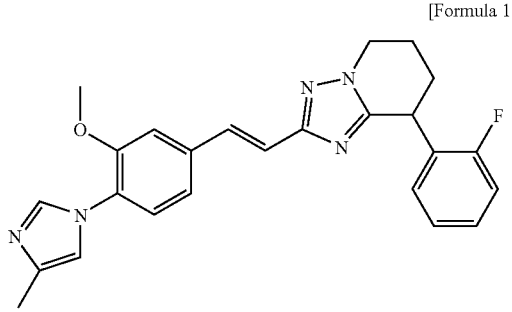

[Formula 165]

The title compound (468 mg) was obtained from (E)-N-[3-(2-fluorophenyl)-2-oxopiperidin-1-yl]-3-[3-methoxy-4-(4-methyl-1H-imidazol-1-yl)phenyl]acrylamide (761 mg) and 2-fluorophenylacetic acid as a starting material by the same method as in Example 176. The property values of the compound are as follows.

$^1$H-NMR (CDCl$_3$) δ (ppm): 2.03-2.24 (m, 3H), 2.29 (s, 3H), 2.33-2.39 (m, 1H), 3.85 (s, 3H), 4.27-4.30 (m, 2H), 4.58-4.61 (m, 1H), 6.91-6.92 (m, 1H), 6.93-6.98 (m, 1H), 7.05-7.15 (m, 5H), 7.21 (d, J=7.6 Hz, 1H), 7.24-7.30 (m, 1H), 7.51 (d, J=16.4 Hz, 1H), 7.69 (d, J=1.2 Hz, 1H).

Example 178

Synthesis of 2-{(E)-2-[3-methoxy-4-(4-methyl-1H-imidazol-1-yl)phenyl]vinyl}-8-(2-methoxyphenyl)-5,6,7,8-tetrahydro[1,2,4]triazolo[1,5-a]pyridine

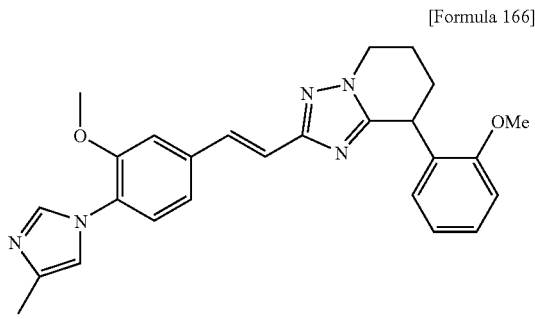

[Formula 166]

The title compound (371 mg) was obtained from (E)-3-[3-methoxy-4-(4-methyl-1H-imidazol-1-yl)phenyl]-N-[3-(2-methoxyphenyl)-2-oxopiperidin-1-yl]acrylamide (629 mg) and 2-methoxyphenylacetic acid as a starting material by the same method as in Example 176. The property values of the compound are as follows.

$^1$H-NMR (CDCl$_3$) δ (ppm): 2.00-2.29 (m, 4H), 2.29 (s, 3H), 3.81 (s, 3H), 3.85 (s, 3H), 4.22-4.32 (m, 2H), 4.66 (t, J=6.4 Hz, 1H), 6.82 (dd, J=7.6 Hz, 2.0 Hz, 1H), 6.87-6.92 (m, 3H), 7.07 (d, J=16.4 Hz, 1H), 7.12-7.16 (m, 2H), 7.21 (d, J=8.0 Hz, 1H), 7.23-7.28 (m, 1H), 7.51 (d, J=16.4 Hz, 1H), 7.69 (d, J=1.2 Hz, 1H).

Example 179

Synthesis of 8-(3-bromophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

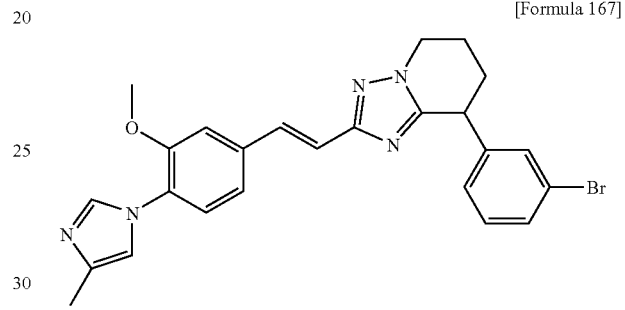

[Formula 167]

The title compound (935 mg) was obtained from (E)-N-[3-(3-bromophenyl)-2-oxopiperidin-1-yl]-3-[3-methoxy-4-(4-methyl-1H-imidazol-1-yl)phenyl]acrylamide (1.731 g) and 3-bromophenylacetic acid as a starting material by the same method as in Example 176. The property values of the compound are as follows.

$^1$H-NMR (CDCl$_3$) δ (ppm): 2.00-2.24 (m, 3H), 2.30 (s, 3H), 2.34-2.40 (m, 1H), 3.86 (s, 3H), 4.27-4.33 (m, 3H), 6.91-6.92 (m, 1H), 7.05-7.02 (m, 2H), 7.14-7.16 (m, 2H), 7.20-7.24 (m, 2H), 7.30 (t, J=2.0 Hz, 1H), 7.40-7.43 (m, 1H), 7.52 (d, J=16.4 Hz, 1H), 7.70 (d, J=1.2 Hz, 1H).

Example 180

Synthesis of 2-{(E)-2-[3-methoxy-4-(4-methyl-1H-imidazol-1-yl)phenyl]vinyl}-8-(2-nitrophenyl)-5,6,7,8-tetrahydro[1,2,4]triazolo[1,5-a]pyridine

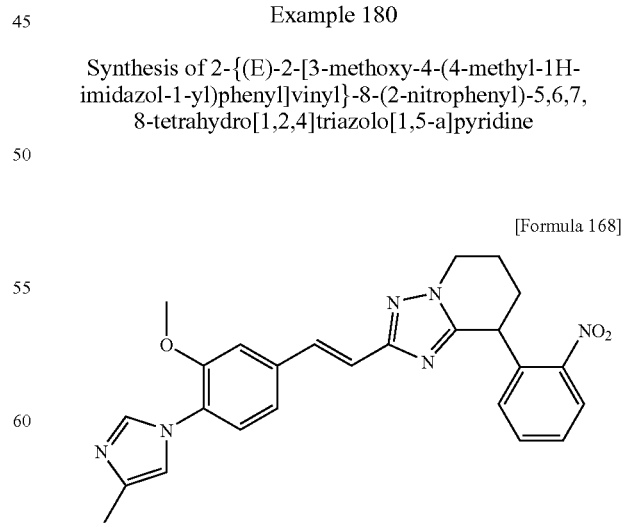

[Formula 168]

The title compound (920 mg) was obtained from (E)-3-[3-methoxy-4-(4-methyl-1H-imidazol-1-yl)phenyl]-N-[3-(2- nitrophenyl)-2-oxopiperidin-1-yl]acrylamide (1.279 g) and 2-nitrophenylacetic acid as a starting material by the same method as in Example 176. The property values of the compound are as follows.

$^1$H-NMR (CDCl$_3$) δ (ppm): 2.13-2.32 (m, 3H), 2.29 (s, 3H), 2.55-2.61 (m, 1H), 3.85 (s, 3H), 4.31-4.35 (m, 2H), 4.92-4.95 (m, 1H), 6.91-6.92 (m, 1H), 7.04 (d, J=16.4 Hz, 1H), 7.12-7.14 (m, 3H), 7.21 (d, J=7.6 Hz, 1H), 7.43-7.49 (m, 2H), 7.56-7.60 (m, 1H), 7.69 (d, J=1.6 Hz, 1H), 8.03 (dd, J=8.0, 1.6 Hz, 1H).

Test Example 1

Quantification of Aβ Peptide in Culture of Neurons from Rat Fetus Brain

The present inventors performed the following tests in order to exhibit utility of the compound of the general formula (I) of the present invention.

(1) Rat Primary Neuronal Culture

Primary neuronal cultures were prepared from the cerebral cortex of embryonic day 18 Wistar rats (Charles River Japan, Yokohama, Japan). Specifically, the embryos were aseptically removed from pregnant rats under ether anesthesia. The brain was isolated from the embryo and immersed in an ice-cold L-15 medium (Invitrogen Corp. Cat #11415-064, Carlsbad, Calif., USA, or SIGMA L1518, for example). The cerebral cortex was collected from the isolated brain under a stereoscopic microscope. The cerebral cortex fragments collected were enzymatically treated in an enzyme solution containing 0.25% trypsin (Invitrogen Corp. Cat #15050-065, Carlsbad, Calif., USA) and 0.01% DNase (Sigma D5025, St. Louis, Mo., USA) at 37° C. for 30 minutes to disperse the cells. Here, the enzymatic reaction was stopped by adding inactivated horse serum to the solution. The enzymatically treated solution was centrifuged at 1,500 rpm for five minutes to remove the supernatant. 5 to 10 ml of a medium was added to the resulting cell mass. Neurobasal medium (Invitrogen Corp. Cat #21103-049, Carlsbad, Calif., USA) supplemented with 2% B27 supplement (Invitrogen Corp. Cat #17504-044, Carlsbad, Calif., USA), 25 µM 2-mercaptoethanol (2-ME, WAKO Cat #139-06861, Osaka, Japan), 0.5 mM L-glutamine (Invitrogen Corp. Cat #25030-081, Carlsbad, Calif., USA), and Antibiotics-Antimycotics (Invitrogen Corp. Cat #15240-062, Carlsbad, Calif., USA) was used as the medium (Neurobasal/B27/2-ME). However, the above Neurobasal medium not supplemented with 2-ME (Neurobasal/B27) was used for the assay. The cells were redispersed by mild pipetting of the cell mass to which the medium was added. The cell dispersion was filtered through a 40-µm nylon mesh (Cell Strainer, Cat #35-2340, Becton Dickinson Labware, Franklin Lakes, N.J., USA) to remove the remaining cell mass, and thus a neuronal cell suspension was obtained. The neuronal cell suspension was diluted with the medium and then plated in a volume of 100 µl/well at an initial cell density of 5×10$^5$ cells/cm$^2$ in a 96-well polystyrene culture plate pre-coated with poly-L or D-lysine (Falcon Cat #35-3075, Becton Dickinson Labware, Franklin Lakes, N.J., USA coated with poly-L-lysine using the method shown below, or BIOCOAT™ cell environments Poly-D-lysine cell ware 96-well plate, Cat #35-6461, Becton Dickinson Labware, Franklin Lakes, N.J., USA). Poly-L-lysine coating was carried out as follows. 100 µg/ml of a poly-L-lysine (SIGMA P2636, St. Louis, Mo., USA) solution was aseptically prepared with a 0.15 M borate buffer (pH 8.5). 100 µl/well of the solution was added to the 96-well polystyrene culture plate and incubated at room temperature for one or more hours or at 4° C. overnight or longer. The coated 96-well polystyrene culture plate was washed with sterile water four or more times, and then dried or rinsed with, for example, sterile PBS or medium, and used for cell plating. The plated cells were cultured in the culture plate at 37° C. in 5% CO$_2$-95% air for one day. Then, the total amount of the medium was replaced with a fresh Neurobasal™/B27/2-ME medium, and then the cells were cultured for further three days.

Addition of Compounds

The drug was added to the culture plate on Day 4 of culture as follows. The total amount of the medium was removed from the wells, and 180 µl/well of Neurobasal medium not containing 2-ME and containing 2% B-27 (Neurobasal/B27) was added thereto. A solution of the test compound in dimethyl sulfoxide (hereinafter abbreviated as DMSO) was diluted with Neurobasal/B27 at 10-fold of the final concentration. 20 µl/well of the dilution was added to and sufficiently mixed with the medium. The final DMSO concentration was 1% or less. Only DMSO was added to the control group.

Sampling

The cells were cultured for three days after addition of the compound, and the total amount of the medium was collected. The resulting medium was used as an ELISA sample. The sample was not diluted for ELISA measurement of Aβx-42 and diluted to 5-fold with a diluent supplied with an ELISA kit for ELISA measurement of Aβx-40.

Evaluation of Cell Survival

Cell survival was evaluated by an MTT assay according to the following procedure. After collecting the medium, 100 µl/well of a pre-warmed medium was added to the wells. Further, 8 l/well of a solution of 8 mg/ml of MTT (SIGMA M2128, St. Louis, Mo., USA) in D-PBS(-) (Dulbecco's phosphate buffered Saline, SIGMA D8537, St. Louis, Mo., USA) was added to the wells. The 96-well polystyrene culture plate was incubated in an incubator at 37° C. in 5% CO$_2$-95% air for 20 minutes. 100 µl/well of an MTT lysis buffer was added thereto, and MTT formazan crystals were sufficiently dissolved in the buffer in the incubator at 37° C. in 5% CO$_2$-95% air. Then, the absorbance at 550 nm in each well was measured. The MTT lysis buffer was prepared as follows. 100 g of SDS (sodium dodecyl sulfate (sodium lauryl sulfate), WAKO 191-07145, Osaka, Japan) was dissolved in a mixed solution of 250 mL of N,N-dimethylformamide (WAKO 045-02916, Osaka, Japan) with 250 mL of distilled water. 350 µl each of concentrated hydrochloric acid and concentrated acetic acid were further added to the solution to allow the solution to have a final pH of about 4.7.

Upon measurement, wells having no cells plated and containing only the medium and MTT solution were set as background (bkg). The measured values were respectively applied to the following formula including subtracting bkg values from them. Thus, the proportion against the control group (group not treated with the drug, CTRL) (% of CTRL) was calculated to compare and evaluate cell survival activities.

% of CTRL=((*A*550_sample−*A*550_bkg)/ (*A*550_CTRL−*A*550_bkg))×100

(A550_sample: absorbance at 550 nm of sample well, A550_bkg: absorbance at 550 nm of background well, A550_CTRL: absorbance at 550 nm of control group well)

Aβ ELISA

For Aβ ELISA, Human/Rat β Amyloid (42) ELISA Kit Wako (#290-62601) and Human/Rat β Amyloid (40) ELISA Kit Wako (#294-62501) from Wako Pure Chemical Industries, Ltd., or Human Amyloid beta (1-42) Assay Kit (#27711) and Human Amyloid beta (1-40) Assay Kit (#27713) from Immuno-Biological Laboratories, Co., Ltd. (IBL Co., Ltd.) were used. Aβ ELISA was carried out according to the protocols recommended by the manufacturers (methods described in the attached documents). However, the Aβ calibration curve was created using beta-amyloid peptide 1-42, rat and beta-amyloid peptide 1-40, rat (Calbiochem, #171596 [Aβ$_{42}$], #171593 [Aβ$_{40}$]). The results are shown in Table 1 as percentage to the Aβ concentration in the medium of the control group (% of CTRL).

(2) The measurement results are shown in Tables 1 to 3 as percentage to the Aβ concentration in the medium of the control group (% of CTRL).

TABLE 1

| Test compound | Effect of reducing Aβ 42 production IC50 (nM) |
| --- | --- |
| Example 1 | 45 |
| Example 4 | 76 |
| Example 5 | 18 |
| Example 6 | 60 |
| Example 7 | 67 |
| Example 9 | 83 |
| Example 10 | 130 |
| Example 13 | 170 |
| Example 15 | 180 |
| Example 17 | 58 |
| Example 18 | 170 |
| Example 21 | 41 |
| Example 22 | 170 |
| Example 23 | 60 |
| Example 31 | 33 |
| Example 32 | 62 |

TABLE 2

| Test compound | Effect of reducing Aβ 42 production IC50 (nM) |
| --- | --- |
| Example 36 | 34 |
| Example 45 | 85 |
| Example 49 | 63 |
| Example 52 | 14 |
| Example 54 | 14 |
| Example 58 | 39 |
| Example 60 | 40 |
| Example 62 | 23 |
| Example 64 | 28 |
| Example 66 | 20 |
| Example 69 | 74 |
| Example 75 | 45 |
| Example 77 | 83 |

TABLE 3

| Test compound | Effect of reducing Aβ 42 production IC50 (nM) |
| --- | --- |
| Example 113 | 32 |
| Example 129 | 17 |
| Example 130 | 13 |
| Example 135 | 43 |
| Example 136 | 24 |
| Example 138 | 47 |
| Example 143 | 22 |
| Example 149 | 21 |
| Example 151 | 16 |
| Example 153 | 31 |
| Example 155 | 39 |
| Example 172 | 11 |
| Example 174 | 23 |

The results from Tables 1 to 3 confirmed that the compound of the present invention has an effect of reducing Aβ42 production.

Accordingly, the compound of the general formula (I) or pharmaceutically acceptable salt thereof according to the present invention have effect to reduce Aβ42 production. Thus, the present invention can particularly provide a prophylactic or therapeutic agent for a neurodegenerative disease caused by Aβ such as Alzheimer's disease or Down's syndrome.

The compound of the general formula (I) of the present invention has an effect of reducing Aβ40 and Aβ42 production, and thus is particularly useful as a prophylactic or therapeutic agent for a neurodegenerative disease caused by Aβ such as Alzheimer's disease or Down's syndrome.

The invention claimed is:

1. A compound represented by the formula

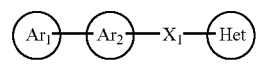

(I)

or a pharmacologically acceptable salt thereof, wherein
Ar1 represents an imidazolyl group that may be substituted with 1 to 3 substituents selected from Substituent Group A1,
Ar2 represents a phenyl group that may be substituted with 1 to 3 substituents selected from Substituent Group A2,
X1 represents —CR$^3$═CR$^4$— (wherein R$^3$ and R$^4$ are the same or different and each represent a substituent selected from Substituent Group A3), and
Het is a 5-membered aromatic heterocyclic group represented by the formula (II):

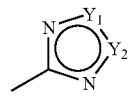

(II)

wherein Y1 and Y2 are the same or different and each represent a methine group or a carbon atom, an imino group or a nitrogen atom, an oxygen atom, or a sulfur atom,
which may be substituted with 1 to 3 substituents selected from the following Substituent Group A4:
Substituent Group A1: (1) a hydrogen atom, (2) a halogen atom, (3) a cyano group, (4) a nitro group, (5) a C3-8 cycloalkyl group, (6) a C2-6 alkenyl group, (7) a C2-6 alkynyl group, (8) a C1-6 alkoxy group, (9) a C3-8 cycloalkoxy group, (10) a formyl group, (11) a C1-6 alkylcarbonyl group and (12) a C1-6 alkyl group (wherein the C1-6 alkyl group may be substituted with 1 to 3 substituents selected from the group consisting of a halogen atom, a hydroxyl group, a cyano group, a C1-6 alkoxy group, a C3-8 cycloalkyl group and a C1-6 alkylcarbonyl group);
Substituent Group A2: (1) a hydrogen atom, (2) a halogen atom, (3) a hydroxyl group, (4) a cyano group, (5) a C1-6 alkoxy group (wherein the C1-6 alkoxy group may be substituted with 1 to 3 substituents selected from the group consisting of a halogen atom, a cyano group, a C1-6 alkyl group, a C2-6 alkenyl group, a C2-6 alkynyl group and a C3-8 cycloalkyl group), (6) a C3-8 cycloalkoxy group, (7) a C2-6 alkenyloxy group and (8) a C2-6 alkynyloxy group;

Substituent Group A3: (1) a hydrogen atom, (2) a halogen atom, (3) A* (wherein A* represents an aromatic hydrocarbon ring selected from selected from phenyl group, indenyl group, naphthyl group, azulenyl group, heptalenyl group, biphenyl group, fluorenyl group, phenalenyl group, phenanthrenyl group, anthracenyl group, an aromatic heterocycle selected from a pyrrolyl group, a pyridyl group, a pyridazinyl group, a pyrimidinyl group, a pyrazinyl group, a pyrazolinyl group, an imidazolyl group, an indolyl group, an isoindolyl group, an indolizinyl group, a purinyl group, an indazolyl group, a quinolyl group, an isoquinolyl group, a quinolizinyl group, a phthalazinyl group, a naphthyridinyl group, a quinoxalinyl group, a quinazolinyl group, a cinnolinyl group, a pteridinyl group, an imidazotriazinyl group, a pyrazinopyridazinyl group, an acridinyl group, a phenanthridinyl group, a carbazolyl group, a perimidinyl group, a phenanthrolinyl group, a thienyl group and a benzothienyl group, a furyl group, a pyranyl group, a cyclopentapyranyl group, a benzofuranyl group and an isobenzofuranyl group, a thiazolyl group, an isothiazolyl group, a benzothiazolinyl group, a benzothiadiazolyl group, a phenothiazinyl group, an isoxazolyl group, a furazanyl group, a phenoxazinyl group, a pyrazoloxazolyl group, an imidazothiazolyl group, a thienofuryl group, a furopyrrolyl group and a pyridooxazinyl group), that may be substituted with 1 to 3 substituents selected from Substituent Group A5, (4) a C1-6 alkyl group (wherein the C1-6 alkyl group may be substituted with 1 to 3 substituents selected from the group consisting of a formyl group, a halogen atom, a hydroxyl group, a hydroxyl group having a protecting group, a cyano group, a C2-6 alkenyl group, a C2-6 alkynyl group, a C3-8 cycloalkyl group, a C1-6 alkoxy group, a C1-6 alkylthio group, a C1-6 alkylsulfinyl group, a C1-6 alkylsulfonyl group, a C1-6 alkylcarbonyl group, an amino group (wherein the amino group may be substituted with 1 to 2 of a C1-6 alkyl group optionally having 1 to 3 halogen atoms), A* (wherein A* is as defined above) that may be substituted with 1 to 3 substituents selected from Substituent Group A5, a 6- to 14-membered non-aromatic hydrocarbon ring that may be substituted with 1 to 3 substituents selected from Substituent Group A5, a 5- to 14-membered non-aromatic heterocycle that may be substituted with 1 to 3 substituents selected from Substituent Group A5, and —X-A* (wherein X represents an imino group, —O— or —S—, and A* is as defined above that may be substituted with 1 to 3 substituents selected from Substituent Group A5)) and (5) a C1-6 alkoxy group that may be substituted with 1 to 3 halogen atoms;

Substituent Group A4: (1) a hydrogen atom, (2) a halogen atom, (3) a hydroxyl group, (4) a cyano group, (5) a nitro group, (6) a C3-8 cycloalkyl group, (7) a C2-6 alkenyl group that may be substituted with 1 to 3 substituents selected from Substituent Group A5, (8) a C2-6 alkynyl group that may be substituted with 1 to 3 substituents selected from Substituent Group A5, (9) a C3-8 cycloalkoxy group, (10) a C3-8 cycloalkylthio group, (11) a formyl group, (12) a C1-6 alkylcarbonyl group that may be substituted with 1 to 3 substituents selected from Substituent Group A5, (13) a C1-6 alkylthio group that may be substituted with 1 to 3 substituents selected from Substituent Group A5, (14) a C1-6 alkylsulfinyl group that may be substituted with 1 to 3 substituents selected from Substituent Group A5, (15) a C1-6 alkylsulfonyl group that may be substituted with 1 to 3 substituents selected from Substituent Group A5, (16) a hydroxyimino group, (17) a C1-6 alkoxyimino group, (18) a C1-6 alkyl group that may be substituted with 1 to 3 substituents selected from Substituent Group A5, (19) a C1-6 alkoxy group that may be substituted with 1 to 3 substituents selected from Substituent Group A5, (20) an amino group that may be substituted with 1 or 2 substituents selected from Substituent Group A5, (21) a carbamoyl group that may be substituted with 1 or 2 substituents selected from Substituent Group A5, (22) A* (wherein A* is as defined above) that may be substituted with 1 to 3 substituents selected from Substituent Group A5, (23) a 6- to 14-membered non-aromatic hydrocarbon ring that may be substituted with 1 to 3 substituents selected from Substituent Group A5, (24) a 5- to 14-membered non-aromatic heterocycle that may be substituted with 1 to 3 substituents selected from Substituent Group A5, (25) a C2-6 alkenyloxy group, (26) a C2-6 alkynyloxy group, (27) a C3-8 cycloalkylsulfinyl group, (28) a C3-8 cycloalkylsulfonyl group, (29) —X-A* (wherein X represents an imino group, —O— or —S—, and A* is as defined above that may be substituted with 1 to 3 substituents selected from Substituent Group A6), (30) —CO-A* (wherein A* is as defined above), (31) =CH-A* (wherein A* is as defined above), (32) a carboxyl group and (33) a C1-6 alkoxycarbonyl group;

Substituent Group A5: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group (wherein the C1-6 alkyl group may be substituted with 1 to 3 substituents selected from Substituent Group A6, A* (wherein A* is as defined above that may be substituted with 1 to 3 substituents selected from Substituent Group A6), (19) a C1-6 alkoxy group (wherein the C1-6 alkoxy group may be substituted with 1 to 3 substituents selected from Substituent Group A6, A* (wherein A* is as defined above that may be substituted with 1 to 3 substituents selected from Substituent Group A6), (20) an amino group that may be substituted with 1 or 2 C1-6 alkyl groups, (21) a carbamoyl group that may be substituted with 1 or 2 C1-6 alkyl groups, (22) A* (wherein A* is as defined above) that may be substituted with 1 to 3 substituents selected from Substituent Group A6, (23) a 6- to 14-membered non-aromatic hydrocarbon ring that may be substituted with 1 to 3 substituents selected from Substituent Group A6, (24) a 5- to 14-membered non-aromatic heterocycle that may be substituted with 1 to 3 substituents selected from Substituent Group A6, (25) a C2-6 alkenyloxy group, (26) a C2-6 alkynyloxy group, (27) a C3-8 cycloalkylsulfinyl group, (28) a C3-8 cycloalkylsulfonyl group, (29) —X-A* (wherein X represents an imino group, —O— or —S—, and A* is as defined above that may be substituted with 1 to 3 substituents that may be substituted with 1 to 3 substituents selected from Substituent Group A6), (30) —CO-A* (wherein A* is as defined above) and (31) =CH-A (wherein A* is as defined above);

Substituent Group A6: (1) a hydrogen atom, (2) a halogen atom, (3) a hydroxyl group, (4) a cyano group, (5) an amino group that may be substituted with 1 or 2 C1-6 alkyl groups, (6) a C1-6 alkyl group (wherein the C1-6 alkyl group may be substituted with 1 to 3 substituents selected from the group consisting of a halogen atom, a hydroxyl group, a cyano group, an amino group that may be substituted with 1 or 2 C1-6 alkyl groups) and (7) a C1-6 alkoxy group (wherein the C1-6 alkoxy group may be substituted with 1 to 3 substituents selected from the group consisting of a halogen atom, a hydroxyl group, a cyano group, an amino group that may be substituted with 1 or 2 C1-6 alkyl groups).

2. The compound or pharmacologically acceptable salt thereof according to claim 1, wherein Ar1 is substituted with 1 or 2 substituents selected from the group consisting of (1) a hydrogen atom, (2) a halogen atom, (3) a C3-8 cycloalkyl group, (4) a C2-6 alkenyl group, (5) a C2-6 alkynyl group and (6) a C1-6 alkyl group (wherein the C1-6 alkyl group may be substituted with 1 to 3 halogen atoms).

3. The compound or pharmacologically acceptable salt thereof according to claim 1, wherein Ar1 is substituted with a C1-6 alkyl group.

4. The compound or pharmacologically acceptable salt thereof according to claim 1, wherein Ar2 is substituted with 1 to 3 substituents selected from the group consisting of (1) a hydrogen atom, (2) a halogen atom, (3) a hydroxyl group, (4) a cyano group, (6) a C1-6 alkoxy group (wherein the C1-6 alkoxy group may be substituted with 1 to 3 substituents selected from the group consisting of a C1-6 alkyl group, a C2-6 alkenyl group, a C2-6 alkynyl group and a C3-8 cycloalkyl group), (7) a C2-6 alkenyloxy group and (8) a C2-6 alkynyloxy group.

5. The compound or pharmacologically acceptable salt thereof according to claim 1, wherein Ar2 is substituted with 1 to 3 substituents selected from the group consisting of (1) a hydrogen atom, (2) a halogen atom, (3) a cyano group and (4) a C1-6 alkoxy group.

6. The compound or pharmacologically acceptable salt thereof according to claim 1, wherein Ar2 is substituted with a C1-6 alkoxy group.

7. The compound or pharmacologically acceptable salt thereof according to claim 1, wherein X1 represents —CR$^3$=CR$^4$— (wherein R$^3$ and R$^4$ represent (1) a hydrogen atom, (2) a C1-6 alkyl group or (3) a C1-6 alkoxy group, or (4) a halogen atom).

8. The compound or pharmacologically acceptable salt thereof according to claim 1, wherein X1 is —CH=CH—.

9. The compound or pharmacologically acceptable salt thereof according to claim 1, wherein Het is an imidazolyl group, a tetrazolyl group or a triazolyl group which may be substituted with 1 to 3 substituents selected from Substituent Group A4.

10. The compound or pharmacologically acceptable salt thereof according to claim 1, wherein the compound is selected from the following group:
1) 4-(4-fluorophenyl)-2-{(E)-2-[3-methoxy-4-(4-methyl-1H-imidazol-1-yl)phenyl]vinyl}-1H-imidazole,
2) 4-(4-fluorophenyl)-2-{(E)-2-[3-methoxy-4-(4-methyl-1H-imidazol-1-yl)phenyl]vinyl}-1-methyl-1H-imidazole,
3) 2-{(E)-2-[3-methoxy-4-(4-methyl-1H-imidazol-1-yl)phenyl]vinyl}-1-methyl-5-phenyl-1H-imidazole,
4) 2-{(E)-2-[3-methoxy-4-(4-methyl-1H-imidazol-1-yl)phenyl]vinyl}-4-phenyl-1H-imidazole,
5) 2-{(E)-2-[3-methoxy-4-(4-methyl-1H-imidazol-1-yl)phenyl]vinyl}-1-methyl-4-phenyl-1H-imidazole,
6) methyl 5-(4-fluorophenyl)-2-{(E)-2-[3-methoxy-4-(4-methyl-1H-imidazol-1-yl)phenyl]vinyl}-1H-imidazole-4-carboxylate,
7) 5-(4-fluorophenyl)-2-{(E)-2-[3-methoxy-4-(4-methyl-1H-imidazol-1-yl)phenyl]vinyl}-(1H-imidazol-4-yl)methanol,
8) 5-(4-fluorophenyl)-2-{(E)-2-[3-methoxy-4-(4-methyl-1H-imidazol-1-yl)phenyl]vinyl}-1H-imidazole-4-carboxylic acid,
9) 5-(4-fluorophenyl)-2-{(E)-2-[3-methoxy-4-(4-methyl-1H-imidazol-1-yl)phenyl]vinyl}-1H-imidazole-4-carboxylic acid (2-chloroethyl)amide,
10) 2-{4-(4-fluorophenyl)-5-methoxymethyl-2-{(E)-2-[3-methoxy-4-(4-methyl-1H-imidazol-1-yl)phenyl]vinyl}imidazol-1-yl}ethanol,
11) 3-(3-fluorophenyl)-5-{(E)-2-[3-methoxy-4-(4-methyl-1H-imidazol-1-yl)phenyl]vinyl}-4H-[1,2,4]triazole,
12) 3-(4-fluorobenzyl)-5-{(E)-2-[3-methoxy-4-(4-methyl-1H-imidazol-1-yl)phenyl]vinyl}-4H-[1,2,4]triazole,
13) 1-(4-fluorobenzyl)-2-{(E)-2-[3-methoxy-4-(4-methyl-1H-imidazol-1-yl)phenyl]vinyl}-4,5-dimethyl-1H-imidazole,
14) 3-[1-(4-fluorophenyl)ethyl]-5-{(E)-2-[3-methoxy-4-(4-methyl-1H-imidazol-1-yl)phenyl]vinyl}-4H-[1,2,4]triazole,
15) 3-[2-(4-fluorophenyl)ethyl]-5-{(E)-2-[3-methoxy-4-(4-methyl-1H-imidazol-1-yl)phenyl]vinyl}-4H-[1,2,4]triazole,
16) 4-(4-fluorobenzyl)-2-{(E)-2-[3-methoxy-4-(4-methyl-1H-imidazol-1-yl)phenyl]vinyl}-1H-imidazole,
17) 5-(4-fluorobenzyl)-3-{(E)-2-[3-methoxy-4-(4-methyl-1H-imidazol-1-yl)phenyl]vinyl}-1-methyl-1H-[1,2,4]triazole,
18) 3-(4-fluorobenzyl)-5-{(E)-2-[3-methoxy-4-(4-methyl-1H-imidazol-1-yl)phenyl]vinyl}-1-methyl-1H-[1,2,4]triazole,
19) (+)-3-[1-(4-fluorophenyl)ethyl]-5-{(E)-2-[3-methoxy-4-(4-methyl-1H-imidazol-1-yl)phenyl]vinyl}-4H-[1,2,4]triazole,
20) (−)-3-[1-(4-fluorophenyl)ethyl]-5-{(E)-2-[3-methoxy-4-(4-methyl-1H-imidazol-1-yl)phenyl]vinyl}-4H-[1,2,4]triazole,
21) 5-[1-(4-fluorophenyl)ethyl]-3-{(E)-2-[3-methoxy-4-(4-methyl-1H-imidazol-1-yl)phenyl]vinyl}-1-methyl-1H-[1,2,4]triazole,
22) 3-[1-(4-fluorophenyl)ethyl]-5-{(E)-2-[3-methoxy-4-(4-methyl-1H-imidazol-1-yl)phenyl]vinyl}-1-methyl-1H-[1,2,4]triazole,
23) 5-[1-(4-fluorophenyl)ethyl]-3-{(E)-2-[3-methoxy-4-(4-methyl-1H-imidazol-1-yl)phenyl]vinyl}-1-methyl-1H-[1,2,4]triazole,
24) 3-[1-(4-fluorophenyl)ethyl]-5-{(E)-2-[3-methoxy-4-(4-methyl-1H-imidazol-1-yl)phenyl]vinyl}-1-methyl-1H-[1,2,4]triazole,
25) (+)-3-[1-(4-fluorophenyl)ethyl]-5-{(E)-2-[3-methoxy-4-(4-methyl-1H-imidazol-1-yl)phenyl]vinyl}-4-methyl-4H-[1,2,4]triazole,
26) (−)-3-[1-(4-fluorophenyl)ethyl]-5-{(E)-2-[3-methoxy-4-(4-methyl-1H-imidazol-1-yl)phenyl]vinyl}-4-methyl-4H-[1,2,4]triazole,
27) 3-{(E)-2-[3-methoxy-4-(4-methyl-1H-imidazol-1-yl)phenyl]vinyl}-5-(1-phenylethyl)-4H-[1,2,4]triazole,
28) 3-{(E)-2-[3-methoxy-4-(4-methyl-1H-imidazol-1-yl)phenyl]vinyl}-1-methyl-5-(1-phenylethyl)-1H-[1,2,4]triazole,
29) 5-{(E)-2-[3-methoxy-4-(4-methyl-1H-imidazol-1-yl)phenyl]vinyl}-1-methyl-3-(1-phenylethyl)-1H-[1,2,4]triazole, 30) 3-(4-fluorophenyl)-5-{(E)-2-[3-methoxy-4-(4-methyl-1H-imidazol-1-yl)phenyl]vinyl}-4H-[1,2,4]triazole,
31) 5-(4-fluorophenyl)-2-{(E)-2-[3-methoxy-4-(4-methyl-1H-imidazol-1-yl)phenyl]vinyl}-4-methyl-1H-imidazole,
32) 3-{(E)-2-[3-methoxy-4-(4-methyl-1H-imidazol-1-yl)phenyl]vinyl}-5-(1-methyl-1-phenylethyl)-4H-[1,2,4]triazole,
33) 3-{(E)-2-[3-methoxy-4-(4-methyl-1H-imidazol-1-yl)phenyl]vinyl}-5-((S)-1-phenylethyl)-4H-[1,2,4]triazole,
34) 3-{(E)-2-[3-methoxy-4-(4-methyl-1H-imidazol-1-yl)phenyl]vinyl}-5-((R)-1-phenylethyl)-4H-[1,2,4]triazole,
35) 5-[methoxy-(4-methoxyphenyl)methyl]-3-{(E)-2-[3-methoxy-4-(4-methyl-1H-imidazol-1-yl)phenyl]vinyl}-1H-[1,2,4]triazole,
36) 4-(4-fluorophenyl)-2-{(E)-2-[3-methoxy-4-(4-methyl-1H-imidazol-1-yl)phenyl]vinyl}-1-(tetrahydrofuran-2-ylmethyl)-1H-imidazole,
37) 4-{5-{(E)-2-[3-methoxy-4-(4-methyl-1H-imidazol-1-yl)phenyl]vinyl}-4H-[1,2,4]triazol-3-yl}-4-(3,4,5-trifluorophenyl)butan-1-ol,
38) 4-chloro-2-{(E)-2-[3-methoxy-4-(4-methyl-1H-imidazol-1-yl)phenyl]vinyl}-1H-imidazole,
39) 4-(4-methoxyphenyl)-2-{(E)-2-[3-methoxy-4-(4-methyl-1H-imidazol-1-yl)phenyl]vinyl}-1H-imidazole,
40) 4-(3-methoxyphenyl)-2-{(E)-2-[3-methoxy-4-(4-methyl-1H-imidazol-1-yl)phenyl]vinyl}-1H-imidazole,
41) 4-(2-methoxyphenyl)-2-{(E)-2-[3-methoxy-4-(4-methyl-1H-imidazol-1-yl)phenyl]vinyl}-1H-imidazole,
42) 4-(4-chlorophenyl)-2-{(E)-2-[3-methoxy-4-(4-methyl-1H-imidazol-1-yl)phenyl]vinyl}-1H-imidazole,
43) 4-(4-biphenyl)-2-{(E)-2-[3-methoxy-4-(4-methyl-1H-imidazol-1-yl)phenyl]vinyl}-1H-imidazole,
44) 4-(4-propyl)-2-{(E)-2-[3-methoxy-4-(4-methyl-1H-imidazol-1-yl)phenyl]vinyl}-1H-imidazole.

11. A pharmaceutical composition comprising the compound or pharmacologically acceptable salt thereof according to claim 1 as an active ingredient and a pharmaceutically acceptable carrier.

* * * * *